(12) United States Patent
Picataggio et al.

(10) Patent No.: US 8,728,798 B2
(45) Date of Patent: *May 20, 2014

(54) BIOLOGICAL METHODS FOR PREPARING ADIPIC ACID

(75) Inventors: Stephen Picataggio, Carlsbad, CA (US); Tom Beardslee, Carlsbad, CA (US)

(73) Assignee: Verdezyne, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,782

(22) Filed: Sep. 26, 2011

(65) Prior Publication Data

US 2012/0077237 A1    Mar. 29, 2012

Related U.S. Application Data

(60) Provisional application No. 61/482,160, filed on May 3, 2011.

(51) Int. Cl.
| | |
|---|---|
| *C12N 1/00* | (2006.01) |
| *C12N 9/00* | (2006.01) |
| *C12N 15/00* | (2006.01) |
| *C12N 15/74* | (2006.01) |
| *C12P 7/44* | (2006.01) |
| *C12P 21/06* | (2006.01) |
| *C07H 21/02* | (2006.01) |
| *C07H 21/04* | (2006.01) |

(52) U.S. Cl.
USPC ........... 435/254.22; 435/142; 435/254.11; 435/69.1; 435/320.1; 435/471; 435/476; 435/483; 435/183; 536/23.1; 536/23.2

(58) Field of Classification Search
None
See application file for complete search history.

(56) References Cited

U.S. PATENT DOCUMENTS

| | | | |
|---|---|---|---|
| 3,843,466 A | 10/1974 | Akabori et al. | |
| 3,912,586 A | 10/1975 | Kaneyuki et al. | |
| 4,400,468 A | 8/1983 | Faber | |
| 4,683,195 A | 7/1987 | Mullis et al. | |
| 4,683,202 A | 7/1987 | Mullis | |
| 4,725,542 A | 2/1988 | Barer et al. | |
| 4,965,188 A | 10/1990 | Mullis et al. | |
| 4,965,201 A | 10/1990 | Casey et al. | |
| 5,104,492 A | 4/1992 | King et al. | |
| 5,204,252 A | 4/1993 | Cregg et al. | |
| 5,232,841 A | 8/1993 | Hashimoto et al. | |
| 5,254,466 A | 10/1993 | Picataggio et al. | |
| 5,268,273 A | 12/1993 | Buckholz | |
| 5,296,639 A | 3/1994 | Klug et al. | |
| 5,349,084 A | 9/1994 | Shishikura et al. | |
| 5,389,529 A | 2/1995 | Panayotatos et al. | |
| 5,412,126 A | 5/1995 | King et al. | |
| 5,470,719 A | 11/1995 | Meng et al. | |
| 5,487,987 A | 1/1996 | Frost et al. | |
| 5,595,899 A | 1/1997 | Sato | |
| 5,620,878 A | 4/1997 | Picataggio et al. | |
| 5,635,369 A | 6/1997 | Pompon et al. | |
| 5,648,247 A | 7/1997 | Picataggio et al. | |
| 5,656,493 A | 8/1997 | Mullis et al. | |
| 5,712,114 A | 1/1998 | Mankovich et al. | |
| 5,766,891 A | 6/1998 | Shuman | |
| 5,846,818 A | 12/1998 | Robinson | |
| 5,888,732 A | 3/1999 | Hartley et al. | |
| 5,932,474 A | 8/1999 | Tsien et al. | |
| 5,962,285 A * | 10/1999 | Anderson et al. | 435/142 |
| 6,008,378 A | 12/1999 | Tsien et al. | |
| 6,054,271 A | 4/2000 | Tsien et al. | |
| 6,066,480 A | 5/2000 | Mobley et al. | |
| 6,087,527 A | 7/2000 | Niwa et al. | |
| 6,143,532 A | 11/2000 | Wenzel et al. | |
| 6,143,557 A | 11/2000 | Hartley et al. | |
| 6,171,861 B1 | 1/2001 | Hartley et al. | |
| 6,245,538 B1 | 6/2001 | Wenzel et al. | |
| 6,270,969 B1 | 8/2001 | Hartley et al. | |
| 6,277,608 B1 | 8/2001 | Hartley et al. | |
| 6,288,275 B1 | 9/2001 | Turner | |
| 6,288,302 B1 | 9/2001 | Yu et al. | |
| 6,331,420 B1 | 12/2001 | Wilson et al. | |
| 6,365,376 B1 | 4/2002 | Brzostowicz et al. | |
| 6,376,223 B1 | 4/2002 | Staley | |
| 6,440,688 B1 | 8/2002 | Bruce et al. | |
| 6,451,569 B1 | 9/2002 | Tsien et al. | |
| 6,465,224 B2 | 10/2002 | Brzonstowicz et al. | |
| 6,498,242 B1 | 12/2002 | Cheng et al. | |
| 6,503,734 B1 | 1/2003 | Craft et al. | |
| 6,569,670 B2 | 5/2003 | Anderson et al. | |
| 6,632,650 B1 | 10/2003 | Chen et al. | |
| 6,660,505 B2 | 12/2003 | Staley | |
| 6,673,613 B2 | 1/2004 | Craft et al. | |
| 6,720,140 B1 | 4/2004 | Hartley et al. | |

(Continued)

FOREIGN PATENT DOCUMENTS

| | | |
|---|---|---|
| EP | 1273663 | 1/2003 |
| RU | 2296743 | 4/2007 |

(Continued)

OTHER PUBLICATIONS

Picataggio et al. Bio/Technology, 10 (1992), pp. 894-898.*
Choi et al. JBC (1999), 274: 4671-4683.*
Office action mailed: Nov. 23, 2011 in U.S. Appl. No. 13/245,777, filed Sep. 26, 2011 and published as: 2012/0021474 on Jan. 26, 2012.
U.S. Appl. No. 60/587,583, filed Jul. 14, 2004, Wieslaw.
"Biosynthesis: Yeast yields plastic ingredient," Nature, Research Highlights, vol. 467, Iss. 7318, 887, Oct. 20, 2010.
"From field to plastic to biodiesel," Biodiesel Magazine, May 25, 2007.
"Latest Genomica Patents Enable Sustainable Nylon, Low-cost Chemicals," PR Newswire, Oct. 19, 2010.
Akbergenov et al., "ARC-1, a sequence element complementary to an internal 18S rRNA segment, enhances translation efficiency in plants when present in the leader or intercistronic region of mRNAs," Nucleic Acids Res. Jan. 12, 2004;32(1):239-47.

(Continued)

*Primary Examiner* — Iqbal H Chowdhury
(74) *Attorney, Agent, or Firm* — Wilson Sonsini Goodrich & Rosati, P.C.

(57) ABSTRACT

The technology relates in part to biological methods for producing adipic acid and engineered microorganisms capable of such production.

20 Claims, 63 Drawing Sheets

(56) References Cited

U.S. PATENT DOCUMENTS

| | | | |
|---|---|---|---|
| 6,777,213 | B2 | 8/2004 | Staley |
| 6,787,669 | B1 | 9/2004 | Costantini et al. |
| 6,790,640 | B2 | 9/2004 | Craft et al. |
| 6,790,645 | B2 | 9/2004 | Brzonstowicz et al. |
| 6,794,165 | B2 | 9/2004 | Cheng et al. |
| 6,797,500 | B2 | 9/2004 | Chen et al. |
| 7,018,829 | B1 | 3/2006 | Nielson et al. |
| 7,043,681 | B2 | 5/2006 | Kroeger |
| 7,049,112 | B2 | 5/2006 | Wilson et al. |
| 7,063,972 | B2 | 6/2006 | Wilson et al. |
| 7,083,960 | B2 | 8/2006 | Donnelly |
| 7,109,009 | B2 | 9/2006 | Wilson et al. |
| 7,157,237 | B2 | 1/2007 | Zhang et al. |
| 7,160,708 | B2 | 1/2007 | Eirich et al. |
| 7,226,768 | B2 | 6/2007 | Farinas et al. |
| 7,232,664 | B2 | 6/2007 | Van Hoek et al. |
| 7,270,947 | B2 | 9/2007 | Anderson et al. |
| 7,320,884 | B2 | 1/2008 | Anderson et al. |
| 7,326,829 | B1 | 2/2008 | Knerr |
| 7,388,084 | B2 | 6/2008 | Wilson et al. |
| 7,405,063 | B2 | 7/2008 | Eirich et al. |
| 7,670,823 | B1 | 3/2010 | Hartley et al. |
| 7,799,545 | B2 | 9/2010 | Burgard et al. |
| 8,133,704 | B2 | 3/2012 | Baynes et al. |
| 8,158,391 | B2 | 4/2012 | Gross |
| 8,241,879 | B2 | 8/2012 | Picataggio et al. |
| 8,343,752 | B2 | 1/2013 | Picataggio et al. |
| 2002/0007051 | A1 | 1/2002 | Cheo et al. |
| 2002/0061566 | A1 | 5/2002 | Eirich et al. |
| 2002/0127666 | A1 | 9/2002 | Brzonstowicz et al. |
| 2003/0049822 | A1 | 3/2003 | Wilson et al. |
| 2003/0083373 | A1 | 5/2003 | Tsien et al. |
| 2003/0087403 | A1 | 5/2003 | Cheng et al. |
| 2003/0113886 | A1 | 6/2003 | Brzostowicz et al. |
| 2003/0212946 | A1 | 11/2003 | Kroger |
| 2003/0215930 | A1 | 11/2003 | Chen et al. |
| 2004/0014198 | A1 | 1/2004 | Craft |
| 2004/0053412 | A1 | 3/2004 | Hartley et al. |
| 2004/0146999 | A1 | 7/2004 | Fallon et al. |
| 2004/0265980 | A1 | 12/2004 | Zhang et al. |
| 2005/0112590 | A1 | 5/2005 | Van Den Boom et al. |
| 2005/0146999 | A1 | 7/2005 | Yamada |
| 2005/0287592 | A1 | 12/2005 | Kless |
| 2009/0098626 | A1 | 4/2009 | Chang et al. |
| 2009/0305364 | A1 | 12/2009 | Burgard et al. |
| 2010/0167361 | A1 | 7/2010 | Craft et al. |
| 2010/0285545 | A1 | 11/2010 | Gross et al. |
| 2010/0291653 | A1* | 11/2010 | Ness et al. ............ 435/171 |
| 2011/0229945 | A1 | 9/2011 | Jansen et al. |
| 2012/0021474 | A1 | 1/2012 | Picataggio et al. |
| 2012/0077252 | A1 | 3/2012 | Picataggio et al. |

FOREIGN PATENT DOCUMENTS

| | | |
|---|---|---|
| WO | WO 91/14781 | 10/1991 |
| WO | WO 96/19497 | 6/1996 |
| WO | WO 97/04083 | 2/1997 |
| WO | WO 97/42307 | 11/1997 |
| WO | WO 99/04014 | 1/1999 |
| WO | WO 99/21013 | 4/1999 |
| WO | WO 00/20620 | 4/2000 |
| WO | WO 01/04337 | 1/2001 |
| WO | WO 01/21572 | 3/2001 |
| WO | WO 02/08412 | 1/2002 |
| WO | WO 03/057896 | 7/2003 |
| WO | WO 2004/013336 | 2/2004 |
| WO | WO 2007/044688 | 4/2007 |
| WO | WO 2007/107256 | 9/2007 |
| WO | WO 2009/113853 | 9/2009 |
| WO | WO 2010/003728 | 1/2010 |
| WO | WO 2010/085712 | 7/2010 |
| WO | WO 2011/003034 | 1/2011 |
| WO | WO 2012/094425 | 7/2012 |
| WO | WO 2013/006730 | 1/2013 |
| WO | WO 2013/006733 | 1/2013 |
| WO | WO 2013/048898 | 4/2013 |

OTHER PUBLICATIONS

Alani et al., "A method for gene disruption that allows repeated use of URA3 selection in the construction of multiply disrupted yeast strains", Genetics 116(4):541-545 Aug. 1987.

Beretta et al., "Optimization of *Candida tropicalis* cytochrom P450alk gene expression in *Saccharomyces cerevisiae* with continuous cultures.," Appl Microbiol Biotechnol. Oct. 1991; 36(1):48-60.

Bertrand et al., "NADPH-Cytochrome c Reductase of *Candida tropicalis* Grown on Alkane," Eur. J. Biochem. 93, 237-243 (1979).

Capone et al., "Amber, ochre and opal suppressor tRNA genes derived from a human serine tRNA gene," EMBO J. Jan. 1985;4(1):213-221.

Cheng et al., "Candida yeast long chain fatty alcohol oxidase is a c-type haemoprotein and plays and important role in long chain fatty acid metabolism," Biochim Biophys Acta, Aug. 15, 2005, 1735(3):192-203.

Craft et al., Identification and characterization of the CYP450 Family of *Candida tropicalis* ATCC 20336, Important for the Conversion of Fatty Acids and Alkanes to α, ω-dicarboxylic acids, Applied and Environmental Microbiology, 2003, 69(10):5983-5991.

Current Protocols in Molecular Biology, John Wiley & Sons, N.Y., 6.3.1-6.3.6 (1989).

Duppel et al., "Properties of a Yeast Cytochrome P-450-Containing Enzyme System which Catalyzes the Hydroxilation of Fatty Acids, Alkanes and Drugs," Eur J. Biochem, 36, 583-592 (1973).

Durrett, Russell, "NYU-Poly researcher makes bioplastics from yeast," A Yeast Grown in Brooklyn, http://russellDurrett.com, Dec. 18, 2010.

Eggertsson, et al., (1988) Microbiological Review 52(3):354-374.

Eirich et al., "Cloning and characterization of three fatty alcohol oxidase genes from *Candida tropicalis* strain ATCC 20336," Appl Environ Microbiol. Aug. 2004;70(8):4872-4879.

Eschenfeldt et al.,"Transformation of Fatty Acids Catalyzed by Cytochrome P450 Monooxygenase Enzymes of *Candida tropicalis*," Applied and Environmental Microbiology, Oct. 2003, 5992-5999.

Gallie, "The 5'-leader of tobacco mosaic virus promotes translation through enhanced recruitment of eIF4F," Nucleic Acids Research 30: 3401-3411 (2002).

Gallie, et al., "The 5'-leader sequence of tobacco mosaic virus RNA enhances the expression of foreign gene transcripts in vitro and in vivo," Nucleic Acids Res. Apr. 24, 1987;15(8):3257-3273.

Gilewicz et al., "Hyroxylase regulation in *Candida tropicalis* grown on alkanes," Can J Microbiol. Feb. 1979; 25(2):201-206.

Hill et al. "Studies on the formation of long-chain dicarboxylic acids from pure n-alkanes by mutant of *Candida tropicalis*," App Microbiol Biotechnol, 24:168-174 (1986).

Hill, Craig, "Automating nucleic acid amplification tests" IVD Technology Magazine, published Nov./Dec. 2000, downloaded from: http://www.devicelink.com/ivdt/archive/00/11/007.

Innis et al., "PCR Protocols: A Guide to Methods and Applications," eds, 1990.

Landy, A., "Mechanistic and structural complexity in the site-specific recombination pathways of Int and FLP," Curr Opin Genet Dev. Oct. 1993;3(5):699-707.

Lu et al., "Biosynthesis of Monomers for Plastics from Renewable Oils," JACS, 132, pp. 15451-15455, Oct. 11, 2010.

Masters, B.S.S., Williams, C.H., Kamin, H. (1967) Methods in Enzymology, X, 565-573).

Meyers & Miller, "Optimal alignments in linear space," CABIOS 4:11-17 (1989).

Mignone et al., "UTRdb and UTRsite: a collection of sequences and regulatory motifs of the untranslated regions of eukaryotic mRNAs," Nucleic Acids Research 33: D141-D146 (2005).

Mignone et al., Genome Biology 3(3): reviews 0004.1-0001.10 (2002).

Murakami et al., "Expression of Cloned Yeast NADPH-Cytochrome P450 Reductase Gene in *Saccharomyces cerevisiae*," J Biochem (1990) 108(5):859-865.

(56) References Cited

OTHER PUBLICATIONS

Nebert et al., "The P450 Superfamily: Recommended Nomenclature," DNA, vol. 6, No. 1, 1987, Mary Ann Liebert Inc Publishing, pp. 1-11.
Nebert et al., "The P450 Superfamily: Update on New Sequences, gene Mapping, and Recommended Nomenclature," DNA and Cell Biology, vol. 10, No. 1, 1991, Mary Ann Liebert, Inc. Publishers, pp. 1-14.
Nebert et al., "The P450 Superfamily: Updated Listing of All Genes and Reccomended Nomenclature for the Chromosomal Loci," DNA, vol. 8, No. 1, 1989, Mary Ann Liebert, Inc. Publishers, pp. 1-13.
Needleman & Wunsch, "A general method applicable to the search for similarities in the Amino Acid Sequence of two proteins." J. Mol. Biol. 48: 443-453 (1970).
Nelson et al., "Simultaneous detection of multiple nucleic acid targets in a homogeneous format," Biochemistry Jun. 25, 1996;35(25):8429-8438.
Ohkuma et al., "CYP52 (cytochrom P450alk) multigene family in Candida maltosa: molecular cloning and nucleotide sequence of the two tandemly arranged genes," DNA Cell Biol, May 1991; 10(4):271-282.
Osmundson et al., "Metabolic aspects of peroxisomal beta-oxidation," Biochim Biophis Acta, Sep. 11, 1991, 1085(2):141-158.
Papanikolaou, et al.,"Lipid production by Yarrowia lipolytica growing on industrial glycerol in a single-stage continuous culture," Bioresour. Technol. 82(1):43-49 (2002).
Paulous et al., "Comparison of the capacity of different viral internal ribosome entry segments to direct translation initiation in poly(A)-dependent reticulocyte lysates," Nucleic Acids Research 31: 722-733 (2003).
Picataggio et al., "Determination of Candida tropicalis Acyl Coenzyme A Oxidase Isoenzyme Function by Sequential Gene Disruption," Molecular and Cellular Biology, vol. 11, No. 9, Sep. 1991, pp. 4333-4339.
Sanglard et al., "Characterization of the alkane-inducable cytochrome P450 (P450alk) gene from the yeast Candida tropicalis: identification of a new P450 gene family," Gene Mar. 15, 1989;76(1):121-136.
Sanglard et al., "Heterogenity within the alkane-inducible cytochrome P450 gene of the yeast Candida tropicalis," FEB Letters, Oct. 1989, vol. 256, No. 1,2, 128-134.
Sanglard et al., "Isolation of the Alkane Inducible Cytochrome P450(P450alk) Gene From the Yeast Candida tropicalis," vol. 144, No. 1, Apr. 14, 1987, pp. 251-257.
Sanglard et al., "Metabolic Conditions Determining the Composition and Catalytic Activity of Cytochrom P-450 Monooxygenases in Candida tropicalis," Journal of Bacteriology, Jan. 1984, vol. 157, No. 1, p. 297-302.
Sanglard et al., "The distinction of different types of cytochromes P-450 from yeasts Candida tropicalis and Saccharomyces uvarum," Arch Biochem Biophys, Nov. 15, 1986, 251(1):276-286.
Sauer, B., "Site-specific recombination: developments and applications," Curr. Opin. Biotech. 5:521-527 (1994).
Seghezzi et al., "Characterization of a second alkane-inducible cytochrome P450-encoding gene, CYP52A2 from Candida tropicalis," Gene, Sep. 30, 1991;106(1):51-60.
Seghezzi et al., "Identification and characterization of additional members of the cytochrom p450 multigene family CYP52 of Candida tropicalis," DNA Cell Biol, Dec. 1992; 11(10):767-780.
Sekiguchi et al., "Requirements for noncovalent binding of vaccinia topoisomerase I to duplex DNA," Nucleic Acids Res. Dec. 11, 1994;22(24):5360-5365.
Shaloiko et al., "Effective non-viral leader for cap-independent translation in a eukaryotic cell-free system," Biotechnology and Bioengeneering, vol. 88, Iss. 6, pp. 730-739, Dec. 20, 2004.
Shimizu et al, "Enzymatic microdetermination of serum free fatty acids," Anal Biochem. Oct. 1, 1979;98(2):341-345.

Shuman, S., "Site-specific interaction of vaccinia virus topoisomerase I with duplex DNA. Minimal DNA substrate for strand cleavage in vitro," J Biol Chem. Jun. 15, 1991;266(17):11372-9.
Stahley et al., "Mechanism and specificity of DNA strand exchange catalyzed by vaccinia DNA topoisomerase type I." Biochemistry. Apr. 6, 2010;49(13):2786-95.
Stieglitz et al., "Novel microbial screen for detection of 1,4-butanediol, ethylene glycol, and adipic acid," Appl Environ Microbiol. Mar. 1985;49(3):593-8.
Sutter et al., "Isolation and Characterization of the Alkane-inducible NADPH-Cytochrome P-450 Oxidoreductase Gene from Candida tropicalis," The Journal of Biological Chemistry, vol. 265, No. 27, Sep. 27, 1990, pp. 16428-16436.
Tjalsma, et al., "Signal peptide-dependent protein transport in Bacillus subtilis: a genome-based survey of the secretome," Microbiol Mol Biol Rev. Sep. 2000;64(3):515-547.
Ueda et al., "Long-chain alcohol dehydrogenase of Candida yeast.," Methods Enzymol. 1990;188:171-175.
Ueda et al., "Long-chain aldehyde dehydrogenase of Candida yeast.," Methods Enzymol. 1990;188:176-178.
Vincent et al., "Helicase-dependent isothermal DNA amplification". EMBO reports 5 (8):795-800 (2004).
Wang, L., "Expanding the Genetic Code of Escherichia coli," Honorable Mention Essay from IUPAC Prize for Young Chemists, 2003.
Watanabe et al., "Initial characterization of a type I fatty acid synthase and polyketide synthase multienzyme complex NorS in the biosynthesis of aflatoxin B(1)," Chem Biol. Sep. 2002;9(9):981-8.
Yamada et al., "Assay of fatty acid omega-hydroxylation using high-performance liquid chromatography with fluorescence labeling reagent, 3-bromomethyl-7-methoxy-1,4-benzoxazin-2-one (BrMB)," 1991, Anal Biochem 199: 132-136.
Zimmer et al., "Mutual conversion of fatty-acid substrate specificity by a single amino-acid exchange at position 527 in P-450Cm2 and P-450Alk3A," Eur J. Biochem, 256, 398-403 (1998).
Zimmer et al., "Relationship between evolutionary distance and enzymatic distance and enzymatic properties among the members of the CYP52A subfamily of Candida maltosa," BiochemBiophys Res Commun, Oct. 9, 1989;251(1):244-247.
Zimmer et al., "The CYP450 multigene family of Candida maltosa encodes functionally diverse n-alkane-inducable cytochrome P450," Biochem Biophys Res Comm. Jul. 25, 1996;224(3)784-789.
Office action mailed: Mar. 14, 2012 in U.S. Appl. No. 13/245,780, filed Sep. 26, 2011 and published as: 2012/077252 on Mar. 29, 2012.
Office action mailed: Jun. 4, 2012 in U.S. Appl. No. 13/245,777, filed Sep. 26, 2011 and published as: 2012/0021474 on Jan. 26, 2012.
Office action mailed: Sep. 6, 2012 in U.S. Appl. No. 13/245,780, filed Sep. 26, 2011 and published as: 2012/077252 on Mar. 29, 2012.
International Search Report and Written Opinion dated: Aug. 30, 2012 in International Patent Application No: PCT/US2012/020230 filed, Jan. 4, 2012 and published as: WO/2012/094425 on: Jul. 20, 2012.
Genbank Accession No. AAA34362, Acyl-coenzyme A Oxidase II precursor [Candida tropicalis], Apr. 27, 1993, (http://www.ncbi.nlm.nih.gov/protein/AAA34362).
Extended European Search Report dated Nov. 7, 2012 in European Patent Application No. EP10794794 filed on: Jul. 1, 2010.
Thomas et al., "Biocatalysis applications and potentials for the chemical industry," Trends in Biotechnology, vol. 20, No. 6, Jun. 1, 2002, pp. 238-242.
Hitchman, "Hexanote Synthase, a Specialized Type I fatty Acid Synthase in Aflatoxin B1 Biosynthesis," Bioorganic Chemistry, vol. 20, No. 5, Oct. 1, 2001, pp. 293-307.
Coleman et al., "Biosynthesis of carbonic anhydrase in Chlamydomonas reinharditii during adaptation to low CO(2)" PNAS vol. 81, No. 19, Oct. 1, 1984 pp. 6049-6053.
Partial International Search Report dated: Nov. 6, 2012 in International Application No. PCT/US2012/045622 filed: Jul. 5, 2012.
Hara et al., "Repression of fatty-acyl-CoA oxidase-endoding gene expression is not necessarily a determinant of high-level production of dicarboxylic acids in industrial dicarboxylic-acid-producing Candida tropicalis," Applied Microbiology and Biotechnology, vol. 56, No. 3-4, ugust 1, 2001 pp. 478-485.

(56) References Cited

OTHER PUBLICATIONS

Nandy et al, "Medium-Long-Chain Chimeric Human Acyl-CoA Dehydrogenase" Medium-Chain Enzyme with the Active Center Base Arrangement of Long-Chain Acyl-CoA Dehydrogenase, Biochemistry, vol. 35, No. 38, Jan. 1, 1996, pp. 12402-12411.

Zeng et al., "Mutation of Tyr357 to Lys375 allows medium-chain acyl-CoA dehydrogenase to acquire acyl-CoA oxidase activity." Biochemica et Biophysica Acta (BBA) Proteins & Proteomics, Elsevier Netherlands, vol. 1774, No. 12, Dec. 1, 2007, pp. 1628-1634.

Arie et al., "Phylogenic identification of n-alkane assimilating *Candida* yeasts based on nucleotide divergence in the 59 end of Lsu rDNA gene," the Journal of General and Applied Microbiology, vol. 46, No. 5, Oct. 1, 2000, pp. 257-262.

Kim et al., "Acyl-CoA dehrdrogenase and acyl-CoA oxidases. Structural basis for mechanistic similarities and differences," European Journal of Biochemistry, vol. 271, No. 3, Feb. 1, 2004, pp. 483-493.

International Search Report and Written Opinion dated: Jan. 30, 2013 in International Patent Application No: PCT/US2012/045615 filed, Jul. 5, 2012 and published as: WO/2013/006730 on: Jan. 10, 2013.

International Search Report and Written Opinion dated: Feb. 8, 2013 in International Patent Application No: PCT/US2012/045622 filed, Jul. 5, 2012 and published as: WO/2013/006733 on: Jan. 10, 2013.

International Search Report and Written Opinion dated: Mar. 23, 2013 in International Patent Application No: PCT/US2012/056562 filed, Sep. 21, 2012 and published as: WO/2013/048898 on: Apr. 4, 2013.

\* cited by examiner

Plasmid diagram for inserting Aspergillus hexanoate synthase gene into C. tropicalis or Y. lipolytica.

Plasmid diagram for inserting heterologous cytochrome p450 gene into C. tropicalis or Y. lipolytica.

Plasmid diagram for inserting heterologous cytochrome p450 gene into
A. parasiticus or A. nidulans ble=bleomycin.

System for Biological Production of Adipic Acid

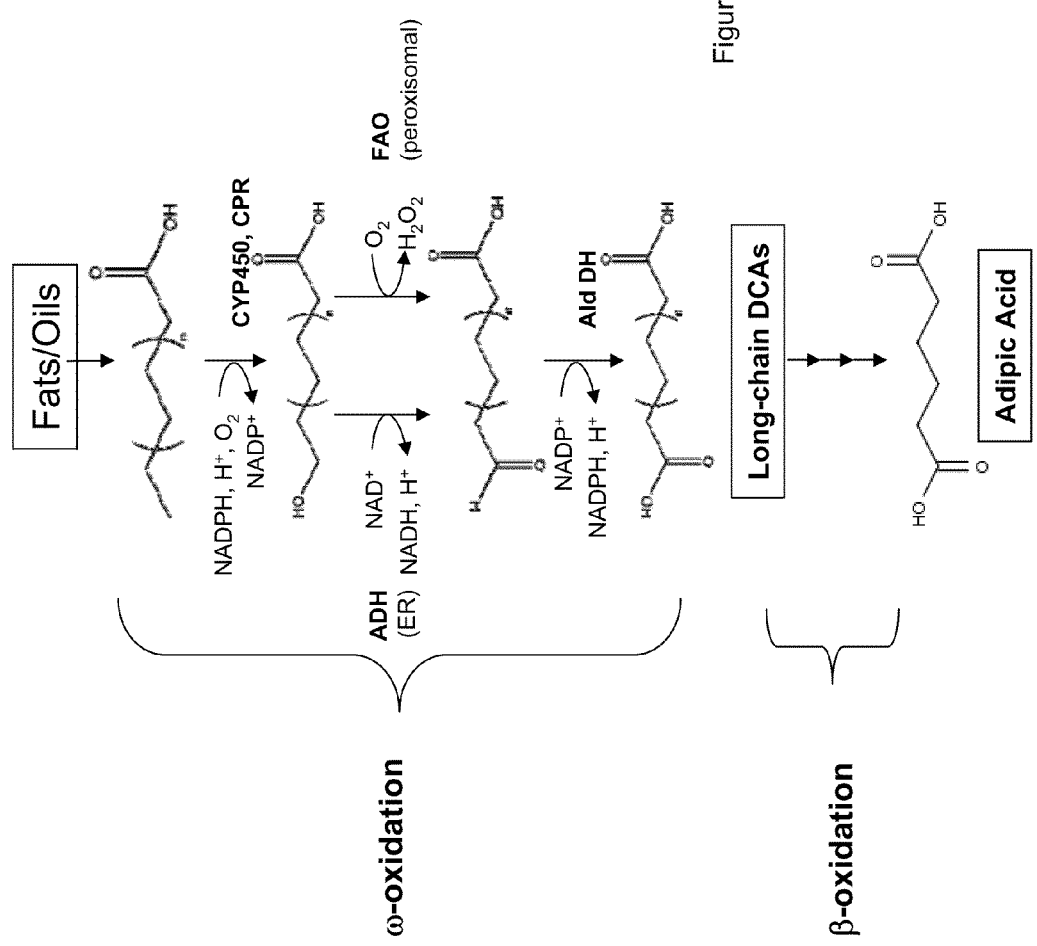

Full complement of POX genes,
Fatty acids utilized as energy and Carbon

BIOLOGICAL METHODS FOR PREPARING ADIPIC ACID

RELATED PATENT APPLICATIONS

This patent application claims the benefit of U.S. Provisional Patent Application No. 61/482,160, filed May 3, 2011, entitled BIOLOGICAL METHODS FOR PREPARING ADIPIC ACID, naming Stephen Picataggio and Tom Beardslee as inventors. The entire content of the foregoing patent application is incorporated herein by reference, including, without limitation, all text, tables and drawings.

SEQUENCE LISTING

The instant application contains a Sequence Listing which has been submitted in ASCII format via EFS-Web and is hereby incorporated by reference in its entirety. Said ASCII copy, created on Nov. 10, 2011, is named VRD10012.txt and is 350,653 bytes in size.

FIELD

The technology relates in part to biological methods for producing adipic acid and engineered microorganisms capable of such production.

BACKGROUND

Microorganisms employ various enzyme-driven biological pathways to support their own metabolism and growth. A cell synthesizes native proteins, including enzymes, in vivo from deoxyribonucleic acid (DNA). DNA first is transcribed into a complementary ribonucleic acid (RNA) that comprises a ribonucleotide sequence encoding the protein. RNA then directs translation of the encoded protein by interaction with various cellular components, such as ribosomes. The resulting enzymes participate as biological catalysts in pathways involved in production of molecules by the organism.

These pathways can be exploited for the harvesting of the naturally produced products. The pathways also can be altered to increase production or to produce different products that may be commercially valuable. Advances in recombinant molecular biology methodology allow researchers to isolate DNA from one organism and insert it into another organism, thus altering the cellular synthesis of enzymes or other proteins. Such genetic engineering can change the biological pathways within the host organism, causing it to produce a desired product. Microorganic industrial production can minimize the use of caustic chemicals and the production of toxic byproducts, thus providing a "clean" source for certain compounds.

SUMMARY

Provided herein are engineered microorganisms that produce six-carbon organic molecules such as adipic acid, methods for manufacturing such microorganisms and methods for using them to produce adipic acid and other six-carbon organic molecules. Also provided herein are engineered microorganisms including genetic alterations that direct carbon flux towards adipic acid through increased fatty acid production in conjunction with increased omega and beta oxidation activities, methods for manufacturing such organisms and methods for using them to produce adipic acid and other six-carbon organic molecules.

Thus, provided herein in some embodiments are engineered microorganisms capable of producing adipic acid, which microorganisms comprise one or more altered activities selected from the group consisting of aldehyde dehydrogenase activity (e.g., 6-oxohexanoic acid dehydrogenase activity, omega oxo fatty acid dehydrogenase activity), fatty alcohol oxidase activity (e.g., 6-hydroxyhexanoic acid dehydrogenase activity, omega hydroxyl fatty acid dehydrogenase activity), glucose-6-phosphate dehydrogenase activity, hexanoate synthase activity, lipase activity, fatty acid synthase activity, acetyl CoA carboxylase activity, acyl-CoA hydrolase (e.g., ACH; thioesterase) activity, acyl-CoA thioesterase (e.g., TESA) activity, acyl-CoA synthetase (e.g., ACS1) activity, long chain acyl-CoA synthetase (e.g., FAT1) activity, acyl-CoA sterol acyl transferase (e.g., ARE1, ARE2, or ARE1 and ARE2) activity, acyltransferase activity (e.g., diacyl-glycerol acyl transferase, DGA1, LRO1, or DGA1 and LRO1) activity and monooxygenase activity.

In certain embodiments, the microorganism comprises a genetic modification that adds or increases the aldehyde dehydrogenase activity (e.g., 6-oxohexanoic acid dehydrogenase activity, omega oxo fatty acid dehydrogenase activity), fatty alcohol oxidase activity (e.g., 6-hydroxyhexanoic acid dehydrogenase activity, omega hydroxyl fatty acid dehydrogenase activity), glucose-6-phosphate dehydrogenase activity, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, acyl-CoA hydrolase activity, acyl-CoA thioesterase activity and/or acetyl-CoA C-acyltransferase activity. Also provided in some embodiments, are engineered microorganisms that produce adipic acid, which microorganisms comprise an altered monooxygenase activity. Provided also herein in some embodiments are engineered microorganisms that include a genetic modification that reduces the acyl-CoA oxidase activity, acyl-CoA synthetase activity, long chain acyl-CoA synthetase activity, acyl-CoA sterol acyl transferase activity, and/or acyltransferase activity (e.g., diacyl-glycerol acyltransferase).

In some embodiments, an engineered microorganism includes a genetic modification that includes multiple copies of a polynucleotide that encodes a polypeptide having aldehyde dehydrogenase activity (e.g., 6-oxohexanoic acid dehydrogenase activity, omega oxo fatty acid dehydrogenase activity), fatty alcohol oxidase activity (e.g., 6-hydroxyhexanoic acid dehydrogenase activity, omega hydroxyl fatty acid dehydrogenase activity), glucose-6-phosphate dehydrogenase activity, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, acyl-CoA hydrolase activity, acyl-CoA thioesterase activity and/or acetyl-CoA C-acyltransferase activity. In some embodiments, 2, 3, 4, 5, 6, 7, 8, 9, 10, 15, 20, 25, 30, 35, 40, 45, 50 or more copies of the particular polynucleotide are present in the microbe. In certain embodiments, an engineered microorganism includes a heterologous promoter (and/or 5'UTR) in functional connection with a polynucleotide that encodes a polypeptide having aldehyde dehydrogenase activity (e.g., 6-oxohexanoic acid dehydrogenase activity, omega oxo fatty acid dehydrogenase activity), fatty alcohol oxidase activity (e.g., 6-hydroxyhexanoic acid dehydrogenase activity, omega hydroxyl fatty acid dehydrogenase activity), glucose-6-phosphate dehydrogenase activity, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, enoyl-CoA hydratase activity, 3-hydroxyacyl-CoA dehydrogenase activity, acyl-CoA hydrolase activity, acyl-CoA thioesterase activity and/or acetyl-CoA C-acyltransferase activity. In some embodiments, the promoter is a POX4 or POX5 promoter or monooxygenase promoter from a yeast (e.g., *Candida* yeast strain (e.g., *C. tropicalis* strain)), or other promoter. Examples of promoters that can be utilized are described herein. The promoter sometimes is exogenous or endogenous with respect to the microbe.

Also provided herein is an engineered microorganism that produces adipic acid, where the microorganism includes an altered monooxygenase activity. In certain embodiments, an engineered microorganism comprises a genetic modification that alters a monooxygenase activity. In some embodiments, an engineered microorganism includes a genetic modification that alters a monooxygenase activity selected from the group consisting of CYP52A12 activity, CYP52A13 activity, CYP52A14 activity, CYP52A15 activity, CYP52A16 activity, CYP52A17 activity, CYP52A18 activity, CYP52A19 activity, CYP52A20 activity, CYP52D2 activity, and/or BM3 activity (e.g., from *B. megaterium*). In certain embodiments, an engineered microorganism includes one or more genetically modified monooxygenase activities selected from the group consisting of CYP52A12 activity, CYP52A13 activity, CYP52A14 activity, CYP52A15 activity, CYP52A16 activity, CYP52A17 activity, CYP52A18 activity, CYP52A19 activity, CYP52A20 activity, CYP52D2 activity, and/or BM3 activity. In some embodiments, the monooxygenase activity is encoded by a CYP52A12 polynucleotide, a CYP52A13 polynucleotide, a CYP52A14 polynucleotide, a CYP52A15 polynucleotide, a CYP52A16 polynucleotide, a CYP52A17 polynucleotide, a CYP52A18 polynucleotide, a CYP52A19 polynucleotide, a CYP52A20 polynucleotide, a CYP52D2 polynucleotide, and/or a BM3 polynucleotide. In certain embodiments, an engineered microorganism includes one or more monooxygenase activities encoded by polynucleotides selected from the group consisting of a CYP52A12 polynucleotide, a CYP52A13 polynucleotide, a CYP52A14 polynucleotide, a CYP52A15 polynucleotide, a CYP52A16 polynucleotide, a CYP52A17 polynucleotide, a CYP52A18 polynucleotide, a CYP52A19 polynucleotide, a CYP52A20 polynucleotide, a CYP52D2 polynucleotide, and/or a BM3 polynucleotide. In some embodiments, the genetic modification increases monooxygenase activity. In certain embodiments, the genetic modification increases the copy number of an endogenous polynucleotide that encodes a polypeptide having the monooxygenase activity (e.g., 2, 3, 4, 5, 6, 7, 8, 9, 10, 15, 20, 25, 30, 35, 40, 45, 50 or more copies of the polynucleotide). In certain embodiments, an engineered microorganism comprises one or more polynucleotides that includes a promoter (e.g., promoter and/or 5'UTR) and encodes a polypeptide having a monooxygenase activity. The promoter may be exogenous or endogenous with respect to the microbe. An engineered microorganism in certain embodiments comprises one or more heterologous polynucleotides encoding a polypeptide having monooxygenase activity. In related embodiments, the heterologous polynucleotide is from a yeast, such as a *Candida* yeast in certain embodiments (e.g., *C. tropicalis*), or from a bacteria, such as *Bacillus* bacteria in some embodiments (e.g., *B. megaterium*).

In certain embodiments, an engineered microorganism comprises a genetic modification that alters monooxygenase reductase activity. In some embodiments, an engineered microorganism includes a genetic modification that alters a monooxygenase reductase activity selected from the group consisting of NADPH cytochrome P450 reductase (e.g., CPR, from *C. tropicalis* strain ATCC750), NADPH cytochrome P450 reductase A (e.g., CPRA, from *C. tropicalis* strain ATCC20336), NADPH cytochrome P450 reductase B (e.g., CPRB, from *C. tropicalis* strain ATCC20336) and/or cytochrome P450:NADPH P450 reductase (e.g., *B. megaterium*). In certain embodiments, an engineered microorganism includes one or more genetically modified monooxygenase reductase activities selected from the group consisting of NADPH cytochrome P450 reductase (e.g., CPR), NADPH cytochrome P450 reductase A (e.g., CPRA), NADPH cytochrome P450 reductase B (e.g., CPRB) and/or cytochrome P450:NADPH P450 reductase. In some embodiments, the genetic modification increases the copy number of an endogenous polynucleotide that encodes a polypeptide having monooxygenase reductase activity (e.g., 2, 3, 4, 5, 6, 7, 8, 9, 10, 15, 20, 25, 30, 35, 40, 45, 50 or more copies of the polynucleotide). In certain embodiments, an engineered microorganism comprises one or more polynucleotides that includes a promoter (e.g., promoter and/or 5'UTR) and encodes a polypeptide having a monooxygenase reductase activity. The promoter may be exogenous or endogenous with respect to the microbe. In some embodiments, the polynucleotide is from a yeast, and in certain embodiments the yeast is a *Candida* yeast (e.g., *C. tropicalis*). In some embodiments, the polynucleotide is from a bacteria, and in certain embodiments the bacteria is a *Bacillus* bacteria (e.g., *B. megaterium*).

An engineered microorganism in some embodiments comprises an altered thioesterase activity. In some embodiments, an engineered microorganism comprises a genetic modification that alters the thioesterase activity, and in certain embodiments, the engineered microorganism comprises a genetic alteration that adds or increases a thioesterase activity. In some embodiments, the engineered microorganism comprises a heterologous polynucleotide encoding a polypeptide having thioesterase activity. In certain embodiments, an engineered microorganism includes a genetic modification that alters a thioesterase activity selected from the group consisting of acyl-CoA hydrolase activity (e.g., ACHA, ACHB, ACHA and ACHB, from *C. tropicalis*), acyl-CoA thioesterase activity (e.g., TESA, from *E. coli*), and/or acyl-CoA hydrolase and acyl-CoA thioesterase activity. In some embodiments, the genetic modification increases the copy number of an endogenous polynucleotide that encodes a polypeptide having thioesterase activity (e.g., 2, 3, 4, 5, 6, 7, 8, 9, 10, 15, 20, 25, 30, 35, 40, 45, 50 or more copies of the polynucleotide). In certain embodiments, an engineered microorganism comprises one or more polynucleotides that includes a promoter (e.g., promoter and/or 5'UTR) and encodes a polypeptide having a thioesterase activity. The promoter may be exogenous or endogenous with respect to the microbe. In some embodiments, the polynucleotide is from a yeast, and in certain embodiments the yeast is a *Candida* yeast (e.g., *C. tropicalis*). In some embodiments, the polynucleotide is from a bacteria, and in certain embodiments the bacteria is an *Enteric* bacteria (e.g., *Eschericia coli*). Examples of polynucleotide sequences that encode peptides with thioesterase activity, and polypeptide sequences with thioesterase activity are provided herein (e.g., SEQ ID NOs: 42-47)

An engineered microorganism in some embodiments comprises an altered fatty alcohol oxidase activity. In some embodiments, an engineered microorganism comprises a genetic modification that alters the fatty alcohol oxidase activity, and in certain embodiments, the engineered microorganism comprises a genetic alteration that adds or increases a fatty alcohol oxidase activity. In some embodiments, the genetic modification increases the copy number of an endogenous polynucleotide that encodes a polypeptide having fatty alcohol oxidase activity (e.g., 2, 3, 4, 5, 6, 7, 8, 9, 10, 15, 20, 25, 30, 35, 40, 45, 50 or more copies of the polynucleotide). An engineered microorganism in certain embodiments comprises a heterologous promoter (e.g., endogenous or exogenous promoter with respect to the microbe) in functional connection with a polynucleotide that encodes a polypeptide having fatty alcohol oxidase activity. In some embodiments, the engineered microorganism comprises a heterologous polynucleotide encoding a polypeptide having fatty alcohol oxidase activity. In some embodiments, the polynucleotide is from a yeast, and in certain embodiments the yeast is *Candida* (e.g., a *C. tropicalis* strain).

An engineered microorganism in some embodiments comprises an altered 6-oxohexanoic acid dehydrogenase activity or an altered omega oxo fatty acid dehydrogenase activity. In some embodiments, an engineered microorganism comprises a genetic modification that adds or increases 6-oxohexanoic acid dehydrogenase activity or omega oxo fatty acid dehydrogenase activity, and in certain embodiments, an engineered microorganism comprises a heterologous polynucleotide encoding a polypeptide having 6-oxohexanoic acid dehydrogenase activity or omega oxo fatty acid dehydrogenase activity. In related embodiments, the heterologous polynucleotide sometimes is from a bacterium, such as an *Acinetobacter, Nocardia, Pseudomonas* or *Xanthobacter* bacterium in some embodiments.

An engineered microorganism in some embodiments comprises an altered 6-hydroxyhexanoic acid dehydrogenase activity or an altered omega hydroxyl fatty acid dehydrogenase activity. In some embodiments, an engineered microorganism comprises a genetic modification that adds or increases the 6-hydroxyhexanoic acid dehydrogenase activity or omega hydroxyl fatty acid dehydrogenase activity, and in certain embodiments, an engineered microorganism comprises a heterologous polynucleotide encoding a polypeptide having 6-hydroxyhexanoic acid dehydrogenase activity or omega hydroxyl fatty acid dehydrogenase activity. In related embodiments, the heterologous polynucleotide is from a bacterium, such as an *Acinetobacter, Nocardia, Pseudomonas* or *Xanthobacter* bacterium in some embodiments.

An engineered microorganism in some embodiments comprises an altered fatty acid synthase activity. In some embodiments, an engineered microorganism comprises a genetic modification that alters fatty acid synthase activity. In certain embodiments, an engineered microorganism includes a genetic alteration that adds or increases fatty acid synthase activity. In some embodiments, the genetic modification increases the copy number of endogenous polynucleotides that encode polypeptides having fatty acid synthase activity (e.g., 2, 3, 4, 5, 6, 7, 8, 9, 10, 15, 20, 25, 30, 35, 40, 45, 50 or more copies of a polynucleotide). An engineered microorganism in certain embodiments comprises a heterologous promoter (e.g., endogenous or exogenous promoter with respect to the microbe) in functional connection with a polynucleotide that encodes a polypeptide having fatty acid synthase activity. In some embodiments, the engineered microorganism comprises a heterologous polynucleotide encoding a polypeptide having fatty acid synthase activity. In certain embodiments, the fatty acid synthase activity is provided by one or more polypeptides having fatty acid synthase activity (e.g., a single subunit protein or multi subunit protein). In certain embodiments, the fatty acid synthase activity is provided by a polypeptide having fatty acid synthase subunit alpha (e.g., FAS2) activity, fatty acid synthase subunit beta (e.g., FAS1) activity, or fatty acid synthase subunit alpha activity and fatty acid synthase subunit beta activity. In some embodiments a fatty acid synthase activity comprises a hexanoate synthase activity. In certain embodiments, the polynucleotide is from a yeast, and in certain embodiments the yeast is a *Candida* yeast (e.g., *C. tropicalis*). Examples of polynucleotides that encode fatty acid synthase molecules (e.g., FAS1, FAS2) are provided herein (e.g., SEQ ID NOs: 31 and 32).

An engineered microorganism in some embodiments comprises an altered hexanoate synthase activity. In some embodiments, an engineered microorganism comprises a genetic modification that alters hexanoate synthase activity. In certain embodiments, an engineered microorganism includes a genetic alteration that adds or increases hexanoate synthase activity. In some embodiments, an engineered microorganism comprises a heterologous polynucleotide encoding a polypeptide having hexanoate synthase activity. In certain embodiments, the hexanoate synthase activity is provided by a polypeptide having hexanoate synthase activity. In certain embodiments, the hexanoate synthase activity is provided by a polypeptide having hexanoate synthase subunit A activity, hexanoate synthase subunit B activity, or hexanoate synthase subunit A activity and hexanoate synthase subunit B activity. In some embodiments, the heterologous polynucleotide is from a fungus, such as an *Aspergillus* fungus in certain embodiments (e.g., *A. parasiticus, A. nidulans*).

In certain embodiments, an engineered microorganism comprises a genetic modification that results in substantial (e.g., primary) hexanoate usage by monooxygenase activity. In related embodiments, the genetic modification reduces a polyketide synthase activity.

An engineered microorganism in some embodiments comprises an altered lipase activity. In certain embodiments, an engineered microorganism includes a genetic alteration that adds or increases a lipase activity. In some embodiments, the genetic modification increases the copy number of endogenous polynucleotides that encode polypeptides having lipase activity (e.g., 2, 3, 4, 5, 6, 7, 8, 9, 10, 15, 20, 25, 30, 35, 40, 45, 50 or more copies of a polynucleotide). An engineered microorganism in certain embodiments comprises a heterologous promoter (e.g., endogenous or exogenous promoter with respect to the microbe) in functional connection with a polynucleotide that encodes a polypeptide having lipase activity. In some embodiments, the engineered microorganism comprises a heterologous polynucleotide encoding a polypeptide having lipase activity. In certain embodiments, the lipase activity is provided by one or more polypeptides having lipase activity (e.g., a single subunit protein or multi subunit protein). In certain embodiments, the lipase activity is provided by a polypeptide comprising all or part of the amino acid sequence of SEQ ID NO: 28 or 29, and sometimes the polypeptide is encoded by a polynucleotide of SEQ ID NO: 27. In certain embodiments, the polynucleotide is from a yeast, and in certain embodiments the yeast is a *Candida* yeast (e.g., *C. tropicalis*).

An engineered microorganism in some embodiments comprises an altered acetyl-CoA carboxylase activity. In certain embodiments, an engineered microorganism includes a genetic alteration that adds or increases a acetyl-CoA carboxylase activity. In some embodiments, the genetic modification increases the copy number of endogenous polynucleotides that encode polypeptides having acetyl-CoA carboxylase activity (e.g., 2, 3, 4, 5, 6, 7, 8, 9, 10, 15, 20, 25, 30, 35, 40, 45, 50 or more copies of a polynucleotide). An engineered microorganism in certain embodiments comprises a heterologous promoter (e.g., endogenous or exogenous promoter with respect to the microbe) in functional connection with a polynucleotide that encodes a polypeptide having acetyl-CoA carboxylase activity. In some embodiments, the engineered microorganism comprises a heterologous polynucleotide encoding a polypeptide having acetyl-CoA carboxylase activity. In some embodiments, the engineered microorganism comprises a heterologous polynucleotide encoding a polypeptide having acetyl-CoA carboxylase activity. In some embodiments, the polynucleotide is from a yeast, and in certain embodiments the yeast is *Candida* (e.g., a *C. tropicalis* strain). In some embodiments an acetyl-CoA carboxylase polypeptide is encoded by a polynucleotide comprising the sequence of SEQ ID NO 30.

An engineered microorganism in some embodiments is a non-prokaryotic organism, and sometimes is a eukaryote. A eukaryote can be a yeast in some embodiments, such as a *Candida* yeast (e.g., *C. tropicalis*), for example. In certain embodiments a eukaryote is a fungus, such as a *Yarrowia* fungus (e.g., *Y. lipolytica*) or *Aspergillus* fungus (e.g., *A. parasiticus* or *A. nidulans*), for example.

In some embodiments, an engineered microorganism comprises a genetic modification that reduces 6-hydroxyhexanoic acid conversion. In related embodiments, the genetic modification reduces 6-hydroxyhexanoic acid dehydrogenase activity or omega hydroxyl fatty acid dehydrogenase activity.

In certain embodiments, an engineered microorganism comprises a genetic modification that reduces beta-oxidation activity, and in some embodiments, the genetic modification renders beta-oxidation activity undetectable (e.g., completely blocked beta-oxidation activity). In certain embodiments, the genetic modification partially reduces beta-oxidation activity.

A fatty acid-CoA derivative, or dicarboxylic acid-CoA derivative, can be converted to a trans-2,3-dehydroacyl-CoA derivative by the activity of acyl-CoA oxidase (e.g., also known as or referred to as acyl-CoA oxidoreductase and fatty acyl-coenzyme A oxidase), in many organisms. In some embodiments, an engineered microorganism comprises a genetic modification that alters the specificity of and/or reduces the activity of an acyl-CoA oxidase activity. In certain embodiments, the genetic modification disrupts an acyl-CoA oxidase activity. In some embodiments, the genetic modification includes disrupting a polynucleotide that encodes a polypeptide having an acyl-CoA oxidase activity. In certain embodiments, the genetic modification includes disrupting a promoter and/or 5'UTR in functional connection with a polynucleotide that encodes a polypeptide having the acyl-CoA oxidase activity. In some embodiments, the polypeptide having acyl-CoA activity is a POX polypeptide. In certain embodiments, the POX polypeptide is a POX4 polypeptide, a POX5 polypeptide, or a POX4 polypeptide and POX5 polypeptide. In certain embodiments, the genetic modification disrupts an acyl-CoA activity by disrupting a POX4 nucleotide sequence, a POX5 nucleotide sequence, or a POX4 and POX5 nucleotide sequence.

In some embodiments, an engineered microorganism comprises a genetic modification that increases beta-oxidation activity. In certain embodiments, the beta-oxidation increase in beta-oxidation activity is the result of an increase in activity in one or more activities involved in beta-oxidation. In some embodiments, the genetic modification increases the copy number of an endogenous polynucleotide that encodes a polypeptide having an activity involved in beta-oxidation (e.g., 2, 3, 4, 5, 6, 7, 8, 9, 10, 15, 20, 25, 30, 35, 40, 45, 50 or more copies of the polynucleotide). An engineered microorganism in certain embodiments comprises a heterologous promoter (e.g., endogenous or exogenous promoter with respect to the microbe) in functional connection with a polynucleotide that encodes a polynucleotide that encodes a polypeptide having an activity involved in beta-oxidation. In some embodiments, the engineered microorganism comprises a heterologous polynucleotide encoding a polynucleotide that encodes a polypeptide having an activity involved in beta-oxidation. In certain embodiments, beta oxidation activity that is increased is an acyl-CoA oxidase activity, and in some embodiments the acyl-CoA oxidase activity is an activity encoded by the POX5 gene. In some embodiments, the altered activity (e.g., increased activity) is provided by a polypeptide encoded by a polynucleotide native to the host organism (e.g., multiple copies of the native polynucleotide, promoter inserted in functional connection with the with the native polynucleotide). In certain embodiments, the polynucleotide is from a yeast, and in certain embodiments the yeast is *Candida* (e.g., a *C. tropicalis* strain).

In some embodiments, an engineered microorganism comprises a genetic modification that increases omega-oxidation activity. In some embodiments, an engineered microorganism comprises one or more genetic modifications that alter a reverse activity in a beta oxidation pathway, an omega oxidation pathway, or a beta oxidation and omega oxidation pathway, thereby increasing carbon flux through the respective pathways, due to the reduction in one or more reverse enzymatic activities.

An engineered microorganism can include a heterologous polynucleotide that encodes a polypeptide providing an activity described above, and the heterologous polynucleotide can be from any suitable microorganism. Examples of microorganisms are described herein (e.g., *Candida* yeast, *Saccharomyces* yeast, *Yarrowia* yeast, *Pseudomonas* bacteria, *Bacillus* bacteria, *Clostridium* bacteria, *Eubacterium* bacteria and others include *Megasphaera* bacteria.

Also provided herein are engineered microorganisms including genetic alterations that direct carbon flux (e.g., carbon metabolism) towards the production of adipic acid by increasing production and/or accumulation of fatty acids and increasing omega oxidation and beta oxidation activities. In certain embodiments, the genetic alterations are selected to maximize production of adipic acid from certain feedstocks (e.g., sugars, cellulose, triacylglycerides, fatty acids, the like and combinations thereof). In some embodiments, an engineered microorganism comprises a genetic modification that reduces activities associated with generation of biomass and/or carbon storage molecules (e.g., various storage triglycerides), or with utilization of fatty acids for energy via beta oxidation and in certain embodiments, the genetic modification renders the activities associated with generation of biomass and/or carbon storage molecules or utilization of fatty acids for energy undetectable. In some embodiments, the activity associated with generation of biomass and/or carbon storage molecules is an activity that generates phospholipids, triacylglycerides, and/or steryl esters. In certain embodiments, the activity associated with generation of biomass and/or carbon storage or utilization of fatty acids for energy is selected from acyl-CoA synthetase (e.g., ACS1) activity, long chain acyl-CoA synthetase (e.g., FAT1) activity, acyl-CoA sterol acyl transferase (e.g., ARE1, ARE2, or ARE1 and ARE2) activity, and/or diacyl-glycerol acyl transferase (e.g., DGA1, LRO1, or DGA1 and LRO1) activity.

In some embodiments, an engineered microorganism comprises a genetic modification that alters the specificity of and/or reduces the activity of an acyl-CoA synthetase activity. In certain embodiments, the genetic modification disrupts an acyl-CoA synthetase activity. In some embodiments, the genetic modification includes disrupting a polynucleotide that encodes a polypeptide having an acyl-CoA synthetase activity. In certain embodiments, the genetic modification includes disrupting a promoter and/or 5'UTR in functional connection with a polynucleotide that encodes a polypeptide having the acyl-CoA synthetase activity, and in some embodiments, the genetic modification includes disrupting a portion or all of the nucleotide sequence which encodes the polypeptide having acyl-CoA synthetase activity. In some embodiments, the polypeptide having acyl-CoA synthetase activity is an ACS polypeptide. In certain embodiments, the ACS polypeptide is an ACS1 polypeptide, an ACS2 polypeptide, or an ACS1 polypeptide and ACS2 polypeptide. In certain embodiments, the genetic modification disrupts an acyl-CoA synthetase activity by disrupting an ACS1 nucleotide sequence, an ACS2 nucleotide sequence, or an ACS1 and ACS2 nucleotide sequence. In some embodiments, an acyl-CoA synthetase activity is disrupted by disrupting an ACS1 nucleotide sequence substantially similar to the nucleotide sequence of SEQ ID No: 48. In certain embodiments involving disruption of an acyl-CoA synthetase activity, a polypeptide corresponding to SEQ ID NO: 49 is below the limits of detection using currently available detection methods (e.g., immunodetection, enzymatic assay, the like and combinations thereof), in a host organism.

In some embodiments, an engineered microorganism comprises a genetic modification that alters the specificity of and/or reduces the activity of a long chain acyl-CoA synthetase activity. In certain embodiments, the genetic modification disrupts a long chain acyl-CoA synthetase activity. In some embodiments, the genetic modification includes disrupting a polynucleotide that encodes a polypeptide having a long chain acyl-CoA synthetase activity. In certain embodiments, the genetic modification includes disrupting a promoter and/or 5'UTR in functional connection with a polynucleotide that encodes a polypeptide having the long chain acyl-CoA synthetase activity, and in some embodiments, the genetic modification includes disrupting a portion or all of the nucleotide sequence which encodes the polypeptide having long chain acyl-CoA synthetase activity. In some embodiments, the polypeptide having long chain acyl-CoA synthetase activity is a FAT1 polypeptide. In certain embodiments, the genetic modification disrupts a long chain acyl-CoA synthetase activity by disrupting a FAT1 nucleotide sequence. In some embodiments, a long chain acyl-CoA synthetase activity is disrupted by disrupting a FAT1 nucleotide sequence substantially similar to the nucleotide sequence of SEQ ID No: 50. In certain embodiments involving disruption of a long chain acyl-CoA synthetase activity, a polypeptide corresponding to SEQ ID NO: 51 is below the limits of detection using currently available detection methods (e.g., immunodetection, enzymatic assay, the like and combinations thereof), in a host organism.

In some embodiments, an engineered microorganism comprises a genetic modification that alters the specificity of and/or reduces the activity of an acyl-CoA sterol acyltransferase activity. In certain embodiments, the genetic modification disrupts an acyl-CoA sterol acyltransferase activity. In some embodiments, the genetic modification includes disrupting a polynucleotide that encodes a polypeptide having an acyl-CoA sterol acyltransferase activity. In certain embodiments, the genetic modification includes disrupting a promoter and/or 5'UTR in functional connection with a polynucleotide that encodes a polypeptide having the acyl-CoA sterol acyltransferase activity, and in some embodiments, the genetic modification includes disrupting a portion or all of the nucleotide sequence which encodes the polypeptide having acyl-CoA sterol acyltransferase activity. In some embodiments, the polypeptide having acyl-CoA sterol acyltransferase activity is an ARE polypeptide. In certain embodiments, the ARE polypeptide is an ARE1 polypeptide, an ARE2 polypeptide, or an ARE1 polypeptide and ARE2 polypeptide. In certain embodiments, the genetic modification disrupts an acyl-CoA sterol acyltransferase activity by disrupting an ARE1 nucleotide sequence, an ARE2 nucleotide sequence, or an ARE1 and ARE2 nucleotide sequence. In some embodiments, an acyl-CoA sterol acyltransferase activity is disrupted by disrupting an ARE nucleotide sequence substantially similar to a nucleotide sequence corresponding to SEQ ID NOs: 52 and/or 54. In certain embodiments involving disruption of an acyl-CoA sterol acyltransferase activity, a polypeptide substantially similar to an amino acid sequence corresponding to SEQ ID NOs: 53 and/or 55 is below the limits of detection using currently available detection methods (e.g., immunodetection, enzymatic assay, the like and combinations thereof), in a host organism.

In some embodiments, an engineered microorganism comprises a genetic modification that alters the specificity of and/or reduces the activity of a diacylglycerol acyltransferase activity. In certain embodiments, the genetic modification disrupts a diacylglycerol acyltransferase activity. In some embodiments, the genetic modification includes disrupting a polynucleotide that encodes a polypeptide having a diacylglycerol acyltransferase activity. In certain embodiments, the genetic modification includes disrupting a promoter and/or 5'UTR in functional connection with a polynucleotide that encodes a polypeptide having the diacylglycerol acyltransferase activity, and in some embodiments, the genetic modification includes disrupting a portion or all of the nucleotide sequence which encodes the polypeptide having a diacylglycerol acyltransferase activity. In some embodiments, the polypeptide having diacylglycerol acyltransferase activity is a DGA1 polypeptide. In certain embodiments, the genetic modification disrupts a diacylglycerol acyltransferase activity by disrupting a DGA1 nucleotide sequence. In some embodiments, a diacylglycerol acyltransferase activity is disrupted by disrupting a DGA1 nucleotide sequence substantially similar to the nucleotide sequence of SEQ ID No: 56. In certain embodiments involving disruption of a diacylglycerol acyltransferase activity, a polypeptide corresponding to SEQ ID NO: 57 is below the limits of detection using currently available detection methods (e.g., immunodetection, enzymatic assay, the like and combinations thereof), in a host organism.

In some embodiments, an engineered microorganism comprises a genetic modification that alters the specificity of and/or reduces the activity of an acyltransferase activity (e.g., LRO1). In certain embodiments, the genetic modification disrupts an acyltransferase activity. In some embodiments, the genetic modification includes disrupting a polynucleotide that encodes a polypeptide having an acyltransferase activity. In certain embodiments, the genetic modification includes disrupting a promoter and/or 5'UTR in functional connection with a polynucleotide that encodes a polypeptide having an acyltransferase activity, and in some embodiments, the genetic modification includes disrupting a portion or all of the nucleotide sequence which encodes the polypeptide having an acyltransferase activity. In some embodiments, the polypeptide having acyltransferase activity is a LRO1 polypeptide. In certain embodiments, the genetic modification disrupts an acyltransferase activity by disrupting a LRO1 nucleotide sequence. In some embodiments, an acyltransferase activity is disrupted by disrupting a LRO1 nucleotide sequence substantially similar to the nucleotide sequence of SEQ ID No: 58. In certain embodiments involving disruption of an acyltransferase activity, a polypeptide corresponding to SEQ ID NO: 59 is below the limits of detection using currently available detection methods (e.g., immunodetection, enzymatic assay, the like and combinations thereof), in a host organism.

Also provided in some embodiments are methods for manufacturing adipic acid, which comprise culturing an engineered microorganism described herein under culture conditions in which the cultured microorganism produces adipic acid. In some embodiments, the host microorganism from which the engineered microorganism is generated does not produce a detectable amount of adipic acid. In certain embodiments, the culture conditions comprise fermentation conditions, introduction of biomass, introduction of glucose, introduction of a paraffin (e.g., plant or petroleum based, such as hexane or coconut oil, for example) and/or combinations thereof. In some embodiments, the adipic acid is produced with a yield of greater than about 0.3 grams per gram of glucose added. In related embodiments, a method comprises purifying the adipic acid from the cultured microorganisms and or modifying the adipic acid, thereby producing modified adipic acid. In certain embodiments, a method comprises placing the cultured microorganisms, the adipic acid or the modified adipic acid in a container, and optionally, shipping the container.

Provided also in certain embodiments are methods for manufacturing 6-hydroxyhexanoic acid, which comprise culturing an engineered microorganism described herein under culture conditions in which the cultured microorganism produces 6-hydroxyhexanoic acid. In some embodiments, the host microorganism from which the engineered microorganism is generated does not produce a detectable amount of 6-hydroxyhexanoic acid. In certain embodiments, the culture conditions comprise fermentation conditions, introduction of biomass, introduction of glucose, and/or introduction of hexane. In some embodiments, the 6-hydroxyhexanoic acid is produced with a yield of greater than about 0.3 grams per gram of glucose added. In related embodiments, a method comprises purifying the 6-hydroxyhexanoic acid from the cultured microorganisms and or modifying the 6-hydroxyhexanoic acid, thereby producing modified 6-hydroxyhexanoic acid. In certain embodiments, a method comprises placing the cultured microorganisms, the 6-hydroxyhexanoic acid or the modified 6-hydroxyhexanoic acid in a container, and optionally, shipping the container.

Also provided in some embodiments are methods for preparing an engineered microorganism that produces adipic acid, which comprise: (a) introducing a genetic modification to a host organism that adds or increases monooxygenase activity, thereby producing engineered microorganisms having detectable and/or increased monooxygenase activity; and (b) selecting for engineered microorganisms that produce adipic acid. Provided also herein in some embodiments are methods for preparing an engineered microorganism that produces adipic acid, which comprise: (a) culturing a host organism with hexane as a nutrient source, thereby producing engineered microorganisms having detectable monooxygenase activity; and (b) selecting for engineered microorganisms that produce adipic acid. In some embodiments the monooxygenase activity is incorporation of a hydroxyl moiety into a six-carbon molecule, and in certain embodiments, the six-carbon molecule is hexanoate. In related embodiments, a method comprises selecting the engineered microorganisms that have a detectable amount of the monooxygenase activity. In some embodiments, a method comprises introducing a genetic modification that adds or increases a hexanoate synthase activity, thereby producing engineered microorganisms, and selecting for engineered microorganisms having detectable and/or increased hexanoate synthase activity. In related embodiments, the genetic modification encodes a polypeptide having a hexanoate synthase subunit A activity, a hexanoate synthase subunit B activity, or a hexanoate synthase subunit A activity and a hexanoate synthase subunit B activity.

In some embodiments, a method comprises introducing a genetic modification that adds or increases an aldehyde dehydrogenase activity (e.g., 6-oxohexanoic acid dehydrogenase activity, omega oxo fatty acid dehydrogenase), thereby producing engineered microorganisms, and selecting for engineered microorganisms having detectable and/or increased 6-oxohexanoic acid dehydrogenase activity or omega oxo fatty acid dehydrogenase relative to the host microorganism.

In certain embodiments, a method for preparing microorganisms that produce adipic acid includes selecting for engineered microorganisms having one or more detectable and/or increased activities selected from the group consisting of an aldehyde dehydrogenase activity (e.g., 6-oxohexanoic acid dehydrogenase activity, omega oxo fatty acid dehydrogenase), fatty alcohol oxidase activity (e.g., 6-hydroxyhexanoic acid dehydrogenase activity, omega hydroxyl-fatty acid dehydrogenase), glucose-6-phosphate dehydrogenase activity, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, acyl-CoA hydrolase, acyl-CoA thioesterase enoyl-CoA hydratase activity, 3-hydroxyacyl-CoA dehydrogenase activity, and/or acetyl-CoA C-acyltransferase activity.

In certain embodiments, a method comprises introducing a genetic modification that adds or increases a fatty alcohol oxidase activity (e.g., 6-hydroxyhexanoic acid dehydrogenase activity, omega hydroxyl fatty acid dehydrogenase activity) thereby producing engineered microorganisms, and selecting for engineered microorganisms having a detectable and/or increased 6-hydroxyhexanoic acid dehydrogenase activity or omega hydroxyl fatty acid dehydrogenase activity relative to the host microorganism. In some embodiments, a method comprises introducing a genetic modification that adds or increases a thioesterase activity, thereby producing engineered microorganisms, and selecting for engineered microorganisms having a detectable and/or increased thioesterase activity relative to the host microorganism.

In certain embodiments, a method comprises introducing a genetic modification that reduces 6-hydroxyhexanoic acid conversion, thereby producing engineered microorganisms, and selecting for engineered microorganisms having reduced 6-hydroxyhexanoic acid conversion relative to the host microorganism. In some embodiments, a method comprises introducing a genetic modification that reduces beta-oxidation activity, thereby producing engineered microorganisms, and selecting for engineered microorganisms having reduced beta-oxidation activity relative to the host microorganism. In certain embodiments, a method comprises introducing a genetic modification that reduces activities associated with generation of biomass and/or carbon storage molecules and/or utilization of fatty acids for energy, thereby producing engineered microorganisms, and selecting for engineered microorganisms having reduced activities associated with generation of biomass and/or carbon storage molecules and/or utilization of fatty acids for energy relative to the host microorganism. In certain embodiments, a method comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism. In some embodiments, a method comprises introducing a genetic modification that increases omega-oxidation activity, thereby producing engineered microorganisms, and selecting for engineered microorganisms having increased omega-oxidation activity relative to the host microorganism.

Provided also herein in certain embodiments are methods for preparing a microorganism that produces adipic acid, which comprise: (a) introducing one or more genetic modifications to a host organism that add or increase one or more activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase activity, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, acyl-CoA hydrolase activity, acyl-CoA thioesterase activity, enoyl-CoA hydratase activity, 3-hydroxyacyl-CoA dehydrogenase activity, and/or acetyl-CoA C-acyltransferase activity, thereby producing engineered microorganisms, and (b) selecting for engineered microorganisms that produce adipic acid. In some embodiments, a method comprises selecting for engineered microorganisms having one or more detectable and/or increased activities selected from the group consisting of 6-oxohexanoic acid dehydrogenase activity, 6-hydroxyhexanoic acid dehydrogenase activity, glucose-6-phosphate dehydrogenase activity, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, acyl-CoA hydrolase activity, acyl-CoA thioesterase activity, enoyl-CoA hydratase activity, 3-hydroxyacyl-CoA dehydrogenase activity, and/or acetyl-CoA C-acyltransferase activity, relative to the host microorganism.

In certain embodiments, a method comprises introducing a genetic modification that reduces 6-hydroxyhexanoic acid conversion, thereby producing engineered microorganisms, and selecting for engineered microorganisms having reduced 6-hydroxyhexanoic acid conversion relative to the host microorganism. In some embodiments, a method comprises introducing a genetic modification that reduces beta-oxidation activity, thereby producing engineered microorganisms, and selecting for engineered microorganisms having reduced beta-oxidation activity relative to the host microorganism. In certain embodiments, a method comprises introducing a genetic modification that reduces activities associated with generation of biomass and/or carbon storage molecules and/or utilization of fatty acids for energy, thereby producing engineered microorganisms, and selecting for engineered microorganisms having reduced activities associated with generation of biomass and/or carbon storage molecules and/or utilization of fatty acids for energy relative to the host microorganism. In certain embodiments, a method comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism.

Also provided in some embodiments are methods for preparing a microorganism that produces 6-hydroxyhexanoic acid, which comprise: (a) introducing one or more genetic modifications to a host organism that add or increase one or more activities selected from the group consisting of 6-oxohexanoic acid dehydrogenase activity, glucose-6-phosphate dehydrogenase activity, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, acyl-CoA hydrolase, acyl-CoA thioesterase enoyl-CoA hydratase activity, 3-hydroxyacyl-CoA dehydrogenase activity, and/or acetyl-CoA C-acyltransferase activity, thereby producing engineered microorganisms, (b) introducing a genetic modification to the host organism that reduces 6-hydroxyhexanoic acid conversion, and (c) selecting for engineered microorganisms that produce 6-hydroxyhexanoic acid. In certain embodiments, a method comprises selecting for engineered microorganisms having reduced 6-hydroxyhexanoic acid conversion relative to the host microorganism. In some embodiments, a method comprises selecting for engineered microorganisms having one or more detectable and/or increased activities selected from the group consisting of aldehyde dehydrogenase activity (e.g., 6-oxohexanoic acid dehydrogenase activity, omega oxo fatty acid dehydrogenase activity), fatty alcohol oxidase activity (e.g., 6-hydroxyhexanoic acid dehydrogenase activity, omega hydroxyl fatty acid dehydrogenase activity), glucose-6-phosphate dehydrogenase activity, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, acyl-CoA hydrolase, acyl-CoA thioesterase enoyl-CoA hydratase activity, 3-hydroxyacyl-CoA dehydrogenase activity, and/or acetyl-CoA C-acyltransferase activity, relative to the host microorganism. In certain embodiments, a method comprises introducing a genetic modification that reduces beta-oxidation activity, thereby producing engineered microorganisms, and selecting for engineered microorganisms having reduced beta-oxidation activity relative to the host microorganism. In some embodiments, a method comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism.

Also provided are methods that include contacting an engineered microorganism with a feedstock including one or more polysaccharides, wherein the engineered microorganism includes: (a) a genetic alteration that blocks beta oxidation activity, and (b) a genetic alteration that adds or increases a monooxygenase activity, a genetic alteration that adds or increases a fatty acid synthase activity, and/or a genetic alteration that adds or increases a hexanoate synthetase activity, and culturing the engineered microorganism under conditions in which adipic acid is produced. In some embodiments, the engineered microorganism comprises a genetic alteration that adds or increases fatty acid synthase activity and/or hexanoate synthetase activity. In certain embodiments, the engineered microorganism comprises a heterologous polynucleotide encoding a polypeptide having fatty acid synthase subunit alpha activity, and in some embodiments the engineered microorganism comprises a heterologous polynucleotide encoding a polypeptide having fatty acid synthase subunit beta activity. In certain embodiments, the engineered microorganism comprises a heterologous polynucleotide encoding a polypeptide having hexanoate synthase subunit A activity, and in some embodiments the engineered microorganism comprises a heterologous polynucleotide encoding a polypeptide having hexanoate synthase subunit B activity. In certain embodiments, the heterologous polynucleotide independently is selected from a fungus. In some embodiments, the fungus is an *Aspergillus* fungus, and in certain embodiments the *Aspergillus* fungus is *A. parasiticus*. In some embodiments, wherein the microorganism is a *Candida* yeast, and in certain embodiments, the microorganism is a *C. tropicalis* strain.

Provided also are methods that include contacting an engineered microorganism with a feedstock comprising one or more paraffins, wherein the engineered microorganism comprises a genetic alteration that partially blocks beta oxidation activity and culturing the engineered microorganism under conditions in which adipic acid is produced. In certain embodiments, the microorganism comprises a genetic alteration that increases a monooxygenase activity. In some embodiments, the microorganism is a *Candida* yeast, and in certain embodiments, the microorganism is a *C. tropicalis* strain.

In some embodiments, the genetic alteration that increases monooxygenase activity comprises a genetic alteration that increases monooxygenase (e.g., Cytochrome P450) reductase activity. In certain embodiments, the genetic alteration increases the number of copies of a polynucleotide that encodes a polypeptide having the Cytochrome P450 reductase activity. In some embodiments, the genetic alteration places a promoter and/or 5'UTR in functional connection with a polynucleotide that encodes a polypeptide having the Cytochrome P450 reductase activity. In certain embodiments the monooxygenase reductase activity is selected from the group consisting of cytochrome P450:NADPH P450 reductase (*B. megaterium*), NADPH cytochrome P450 reductase (CPR; *C. tropicalis* strain ATCC750), NADPH cytochrome P450 reductase A (e.g., CPRA; *C. tropicalis* strain ATCC20336), and NADPH cytochrome P450 reductase B (CPRB; *C. tropicalis* strain ATCC20336). In some embodiments the monooxygenase reductase activity is provided by a polypeptide encoded by a polynucleotide of any one of SEQ ID NOs: 23-26.

In certain embodiments, the genetic alteration that blocks beta oxidation activity disrupts acyl-CoA oxidase activity. In some embodiments, the genetic alteration disrupts POX4 and/or POX5 activity. In certain embodiments, the genetic alteration disrupts a polynucleotide that encodes a polypeptide having the acyl-CoA oxidase activity. In some embodiments, the genetic alteration disrupts a promoter and/or 5'UTR in functional connection with a polynucleotide that encodes a polypeptide having the acyl-CoA oxidase activity.

In some embodiments a genetic alteration that increases beta oxidation activity increases acyl-CoA oxidase activity. In certain embodiments, the genetic alteration that increases beta oxidation activity adds or increases the number of copies of a polynucleotide encoding an acyl-CoA oxidase activity. In some embodiments, the genetic alteration increases the activity of a promoter and/or 5'UTR in functional connection with a polynucleotide encoding an acyl-CoA oxidase activity. In certain embodiments, the genetic alteration adds or increases the number of copies of a polynucleotide encoding an acyl-CoA oxidase activity and/or increases the activity of a promoter and/or 5'UTR in functional connection with a polynucleotide encoding an acyl-CoA oxidase activity.

In some embodiments, the feedstock comprises a 6-carbon sugar. In certain embodiments, the feedstock comprises a 5-carbon sugar. In some embodiments, the feedstock comprises a fatty acid, and in certain embodiments the feedstock comprises a mixture of fatty acids. In some embodiments, the feedstock comprises a triacylglyceride. In certain embodiments, the adipic acid is produced at a level of about 80% or more of theoretical yield. In some embodiments, the amount of adipic acid produced is detected. In certain embodiments, the adipic acid produced is isolated (e.g., partially or completely purified). In some embodiments, the culture conditions comprise fermenting the engineered microorganism.

Provided also herein are engineered microorganisms in contact with a feedstock. In some embodiments, the feedstock includes a saccharide. In certain embodiments, the saccharide is a monosaccharide, polysaccharide, or a mixture of a monosaccharide and polysaccharide. In some embodiments, the feedstock includes a paraffin. In certain embodiments, the paraffin is a saturated paraffin, unsaturated paraffin, substituted paraffin, branched paraffin, linear paraffin, or combination thereof.

In some embodiments, the paraffin includes about 1 to about 60 carbon atoms (e.g., between about 1 carbon atom, about 2 carbon atoms, about 3 carbon atoms, about 4 carbon atoms, about 5 carbon atoms, about 6 carbon atoms, about 7 carbon atoms, about 8 carbon atoms, about 9 carbon atoms, about 10 carbon atoms, about 12 carbon atoms, about 14 carbon atoms, about 16 carbon atoms, about 18 carbon atoms, about 20 carbon atoms, about 22 carbon atoms, about 24 carbon atoms, about 26 carbon atoms, about 28 carbon atoms, about 30 carbon atoms, about 32 carbon atoms, about 34 carbon atoms, about 36 carbon atoms, about 38 carbon atoms, about 40 carbon atoms, about 42 carbon atoms, about 44 carbon atoms, about 46 carbon atoms, about 48 carbon atoms, about 50 carbon atoms, about 52 carbon atoms, about 54 carbon atoms, about 56 carbon atoms, about 58 carbon atoms and about 60 carbon atoms). In certain embodiments, the paraffin is in a mixture of paraffins. In some embodiments, the paraffins in the mixture of paraffins have a mean number of carbon atoms of about 8 carbon atoms to about 18 carbon atoms (e.g., about 8 carbon atoms, about 9 carbon atoms, about 10 carbon atoms, about 11 carbon atoms, about 12 carbon atoms, about 13 carbon atoms, about 14 carbon atoms, about 15 carbon atoms, about 16 carbon atoms, about 17 carbon atoms or about 18 carbon atoms). In certain embodiments, the paraffin is in a wax, and in some embodiments, the paraffin is in an oil. In some embodiments, the paraffin contains one or more fatty acids. In certain embodiments, the paraffin is from a petroleum product, and in some embodiments, the petroleum product is a petroleum distillate. In certain embodiments, the paraffin is from a plant or plant product.

Also provided herein, is an isolated polynucleotide selected from the group including a polynucleotide having a nucleotide sequence 96% or more (e.g., 96% or more, 97% or more, 98% or more, 99% or more, or 100%) identical to the nucleotide sequence of SEQ ID NO: 1, a polynucleotide having a nucleotide sequence that encodes a polypeptide of SEQ ID NO: 8, and a polynucleotide having a portion of a nucleotide sequence 96% or more identical to the nucleotide sequence of SEQ ID NO: 1 and encodes a polypeptide having fatty alcohol oxidase activity.

Also provided herein, is an isolated polynucleotide selected from the group including a polynucleotide having a nucleotide sequence 98% or more (e.g., 98% or more, 99% or more, or 100%) identical to the nucleotide sequence of SEQ ID NO: 2, a polynucleotide having a nucleotide sequence that encodes a polypeptide of SEQ ID NO:10, and a polynucleotide having a portion of a nucleotide sequence 98% or more identical to the nucleotide sequence of SEQ ID NO: 2 and encodes a polypeptide having fatty alcohol oxidase activity.

Also provided herein, is an isolated polynucleotide selected from the group including a polynucleotide having a nucleotide sequence 95% or more (e.g., 95% or more, 96% or more, 97% or more, 98% or more, 99% or more, or 100%) identical to the nucleotide sequence of SEQ ID NO: 3, a polynucleotide having a nucleotide sequence that encodes a polypeptide of SEQ ID NO: 9, and a polynucleotide having a portion of a nucleotide sequence 95% or more identical to the nucleotide sequence of SEQ ID NO: 3 and encodes a polypeptide having fatty alcohol oxidase activity.

Also provided herein, is an isolated polynucleotide selected from the group including a polynucleotide having a nucleotide sequence 83% or more (e.g., 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100%) identical to the nucleotide sequence of SEQ ID NO: 4, a polynucleotide having a nucleotide sequence that encodes a polypeptide of SEQ ID NO: 11, and a polynucleotide having a portion of a nucleotide sequence 83% or more identical to the nucleotide sequence of SEQ ID NO: 3 and encodes a polypeptide having fatty alcohol oxidase activity.

Also provided herein, is an isolated polynucleotide selected from the group including a polynucleotide having a nucleotide sequence 82% or more (e.g., 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, or 100%) identical to the nucleotide sequence of SEQ ID NO: 5, a polynucleotide having a nucleotide sequence that encodes a polypeptide of SEQ ID NO: 12, and a polynucleotide having a portion of a nucleotide sequence 82% or more identical to the nucleotide sequence of SEQ ID NO: 3 and encodes a polypeptide having fatty alcohol oxidase activity.

Also provided herein, is an isolated polynucleotide having a polynucleotide identical to the polynucleotide of SEQ ID NO: 13, or fragments thereof and encodes a polypeptide having monooxygenase activity. Also provided herein, is an isolated polynucleotide having a polynucleotide 96% or more identical to the polynucleotide of SEQ ID NO: 14 or 15, or fragments thereof and encodes a polypeptide having monooxygenase activity. Also provided herein, is an isolated polynucleotide having a polynucleotide 96% or more identical to the polynucleotide of SEQ ID NO 16 or 17, or fragments thereof and encodes a polypeptide having monooxygenase activity. Also provided herein, is an isolated polynucleotide having a polynucleotide 94% or more identical to the polynucleotide of SEQ ID NO 18 or 19, or fragments thereof and encodes a polypeptide having monooxygenase activity. Also provided herein, is an isolated polynucleotide having a polynucleotide 95% or more identical to the polynucleotide of SEQ ID NO 20 or 21, or fragments thereof and encodes a polypeptide having monooxygenase activity. Also provided herein, is an isolated polynucleotide comprising a nucleotide sequence of any one of SEQ ID NOs: 23 to 26, or fragment thereof that encodes a polypeptide having monooxygenase reductase activity.

Also provided herein, is an isolated polynucleotide (i) comprising a nucleotide sequence identical to the nucleotide sequence of SEQ ID NO: 27 or fragment thereof, that encodes a polypeptide, or (ii) a polynucleotide that encodes a polypeptide of SEQ ID NO: 28, the polypeptide having lipase activity. Also provided herein is a polypeptide having an amino acid sequence identical to the polypeptide of SEQ ID NO: 29, the polypeptide having lipase activity.

Also provided herein, is an isolated polynucleotide having a nucleotide sequence identical to the nucleotide sequence of SEQ ID NO: 30 or fragments thereof and encodes a polypeptide having acetyl-CoA carboxylase activity. Also provided herein, is an isolated polynucleotide selected from the group including polynucleotides having a nucleotide sequence identical to the nucleotide sequence of any one of SEQ ID NOs: 31 and 32, or fragments thereof and encodes a polypeptide having fatty acid synthase activity.

Also provided herein, is an isolated polynucleotide having a nucleotide sequence identical to the nucleotide sequence of SEQ ID NO: 33 or fragments thereof and encoding a polypeptide having glucose-6-phosphate dehydrogenase activity. Also provided herein is a polypeptide having an amino acid sequence identical to the polypeptide of SEQ ID NO: 34, the polypeptide having glucose-6-phosphate dehydrogenase activity.

Also provided herein, is an isolated polynucleotide selected from the group including a polynucleotide having a nucleotide sequence 96% or more (e.g., 96% or more, 97% or more, 98% or more, 99% or more, or 100%) identical to the nucleotide sequence of SEQ ID NO: 42 or 44, a polynucleotide having a nucleotide sequence that encodes a polypeptide having an amino acid sequence 98% or more (e.g., 98% or more, 99% or more, or 100%) identical to the amino acid sequence of SEQ ID NO: 43 or 45, and a polynucleotide having a portion of a nucleotide sequence 96% or more identical to the nucleotide sequence of SEQ ID NO: 42 or 44 and encodes a polypeptide having acyl-CoA hydrolase activity.

Also provided herein, is an isolated polynucleotide having a polynucleotide sequence identical to the polynucleotide sequence of SEQ ID NO: 45, or fragments thereof and encodes a polypeptide of SEQ ID NO:46 having acyl-CoA thioesterase activity.

Provided also herein, is an engineered microorganism capable of producing adipic acid, the microorganism including genetic alterations resulting in commitment of molecular pathways in directions for production of adipic acid, the pathways and directions include: (i) fatty acid synthesis pathway in the direction of acetyl CoA to long-chain fatty acids, and away from generation of biomass and/or carbon storage molecules (e.g., starch, lipids, triacylglycerides) and/or utilization of fatty acids for energy, (ii) omega oxidation pathway in the direction of long-chain fatty acids to diacids and (iii) beta oxidation pathway in the direction of diacids to adipic acid. Also provided herein, is an engineered microorganism capable of producing adipic acid, which microorganism comprises genetic alterations resulting in three or more increased activities, relative to the microorganism not containing the genetic alterations, selected from the group consisting of acetyl CoA carboxylase activity, fatty acid synthase activity, monooxygenase activity, monooxygenase reductase activity, acyl-CoA hydrolase activity, acyl-CoA thioesterase activity and acyl-CoA oxidase activity.

Also provided herein, is an engineered microorganism capable of producing adipic acid, the microorganism including genetic alterations resulting in commitment of molecular pathways in directions for production of adipic acid, the pathways and directions include: (i) hexanoic acid synthesis pathway in the direction of acetyl CoA to hexanoic acid, and (ii) omega oxidation pathway in the direction of hexanoic acid to adipic acid. Provided also herein, is an engineered microorganism capable of producing adipic acid, which microorganism comprises genetic alterations resulting in three or more increased activities, relative to the microorganism not containing the genetic alterations, selected from the group consisting of acetyl CoA carboxylase activity, acyl-CoA hydrolase activity, acyl-CoA thioesterase activity, hexanoate synthase activity, monooxygenase activity and monooxygenase reductase activity.

Provided also herein, is an engineered microorganism capable of producing adipic acid, the microorganism includes genetic alterations resulting in commitment of molecular pathways in directions for production of adipic acid, the pathways and directions include: (i) gluconeogenesis pathway in the direction of triacyl glycerides to 6-phosphoglucono-lactone and nicotinamide adenine dinucleotide phosphate (NADPH), (ii) omega oxidation pathway in the direction of fatty acids to diacids, (iii) beta oxidation pathway in the direction of diacids to adipic acid and (iv) fatty acid synthesis pathway in the direction of acetyl CoA to fatty acids. Also provided herein, is an engineered microorganism capable of producing adipic acid, which microorganism comprises genetic alterations resulting in three or more increased activities, relative to the microorganism not containing the genetic alterations, selected from the group consisting of lipase activity, glucose-6-phosphate dehydrogenase activity, fatty acid synthase activity, monooxygenase activity, monooxygenase reductase activity, acyl-CoA hydrolase activity, acyl-CoA thioesterase activity and acyl-CoA oxidase activity.

In some embodiments, an engineered microorganism includes an increased activity, relative to the microorganism not containing the genetic alterations, independently in each pathway. In certain embodiments, an engineered microorganism includes an increased acetyl CoA carboxylase activity in the fatty acid synthesis pathway. In some embodiments, an engineered microorganism includes an increased fatty acid synthase activity in the fatty acid synthesis pathway. In certain embodiments, an engineered microorganism includes an increased acyl-CoA hydrolase activity in the fatty acid synthesis pathway. In some embodiments, an engineered microorganism includes an increased acyl-CoA thioesterase activity in the fatty acid synthesis pathway. In certain embodiments, an engineered microorganism includes an increased monooxygenase activity. In some embodiments, an engineered microorganism includes an increased monooxygenase reductase activity. In certain embodiments, an engineered microorganism includes an increased acyl-CoA oxidase activity.

In certain embodiments, an engineered microorganism includes an increased acetyl CoA carboxylase activity in the hexanoic acid synthesis pathway. In some embodiments, an engineered microorganism includes increased hexanoate synthase activity in the hexanoic acid synthesis pathway. In certain embodiments, an engineered microorganism includes increased monooxygenase activity in the omega oxidation pathway. In some embodiments, an engineered microorganism includes increased monooxygenase reductase activity in the omega oxidation pathway.

In some embodiments, an engineered microorganism includes an increased lipase activity in the gluconeogenesis pathway. In certain embodiments, an engineered microorganism includes an increased glucose-6-phosphate dehydrogenase activity in the gluconeogenesis pathway. In some embodiments, an engineered microorganism includes an increased acyl-CoA oxidase activity in the beta oxidation pathway. In certain embodiments, an engineered microorganism includes an increased acyl-CoA hydrolase and/or an increased acyl-CoA thioesterase in the fatty acid synthesis pathway In some embodiments, one or more enzymes or proteins can provide an activity (e.g., single subunit protein, multi subunit protein). In certain embodiments, 2 or more activities can be provided by one or more enzymes or proteins (e.g., multifunction single protein, enzyme complex). In some embodiments, each of the increased activities independently is provided by an enzyme encoded by a gene endogenous to the microorganism. In certain embodiments, each of the increased activities independently is provided by an enzyme encoded by a gene exogenous to the microorganism. In some embodiments, each of the increased activities independently is provided by an increased amount of an enzyme from a yeast. In certain embodiments, the yeast is a *Candida* yeast, and in certain embodiments, the yeast is a *Candida tropicalis* yeast.

In some embodiments, each one of the increased activities independently results from increasing the copy number of a gene that encodes an enzyme that provides the activity. In certain embodiments, each one of the increased activities independently results from inserting a promoter in functional proximity to a gene that encodes an enzyme that provides the activity. In some embodiments, the gene is in plasmid nucleic acid, and in certain embodiments, the gene is in genomic nucleic acid of the microorganism.

In some embodiments, the acetyl CoA carboxylase activity is provided by an increased amount of an enzyme comprising (i) the amino acid sequence encoded by SEQ ID NO: 30, (ii) an amino acid sequence 90% or more identical to (i), or (iii) an amino acid sequence that includes 1 to 10 amino acid substitutions, insertions or deletions with respect to (i).

In certain embodiments, the fatty acid synthase activity is provided by an increased amount of a FAS1-encoded enzyme, a FAS2-encoded enzyme, or FAS1-encoded enzyme and FAS2-encoded enzyme. In some embodiments, the FAS1-encoded enzyme comprises (i) the amino acid sequence encoded by SEQ ID NO: 32, (ii) an amino acid sequence 90% or more identical to (i), or (iii) an amino acid sequence that includes 1 to 10 amino acid substitutions, insertions or deletions with respect to (i). In certain embodiments, the FAS2-encoded enzyme comprises (i) the amino acid sequence encoded by SEQ ID NO: 31, (ii) an amino acid sequence 90% or more identical to (i), or (iii) an amino acid sequence that includes 1 to 10 amino acid substitutions, insertions or deletions with respect to (i).

In some embodiments, the monooxygenase activity is provided by an increased amount of a cytochrome P450 enzyme. In certain embodiments, the monooxygenase activity is provided by an exogenous cytochrome P450 enzyme. In some embodiments, the exogenous cytochrome P450 enzyme is from *Bacillus megaterium*. In certain embodiments, the exogenous cytochrome P450 enzyme comprises (i) the amino acid sequence of SEQ ID NO: 41, (ii) an amino acid sequence 90% or more identical to (i), or (iii) an amino acid sequence that includes 1 to 10 amino acid substitutions, insertions or deletions with respect to (i).

In some embodiments, two or more endogenous cytochrome P450 enzymes are expressed in increased amounts. In certain embodiments, all endogenous cytochrome P450 enzymes are expressed in increased amounts. In some embodiments, the endogenous cytochrome P450 enzymes comprise (i) an amino acid sequence encoded by a polynucleotide selected from the group consisting of SEQ ID NO: 13, 14, 15, 16, 17, 18, 19, 20, 21, and 22, (ii) an amino acid sequence 90% or more identical to (i), or (iii) an amino acid sequence that includes 1 to 10 amino acid substitutions, insertions or deletions with respect to (i).

In certain embodiments, the monooxygenase reductase activity is provided by an increased amount of an enzyme comprising (i) the amino acid sequence encoded by any one of SEQ ID NOS: 23 to 26, (ii) an amino acid sequence 90% or more identical to (i), or (iii) an amino acid sequence that includes 1 to 10 amino acid substitutions, insertions or deletions with respect to (i). In some embodiments, the monooxygenase reductase activity is provided by an increased amount of a cytochrome P450:NADPH P450 reductase-encoded enzyme, a CPR-encoded enzyme, a CPRA-encoded enzyme, a CPRB-encoded enzyme, or a cytochrome P450:NADPH P450 reductase-encoded enzyme, a CPR-encoded enzyme, a CPRA-encoded enzyme, and/or a CPRB-encoded enzyme. In certain embodiments, the cytochrome P450:NADPH P450 reductase-encoded enzyme comprises (i) the amino acid sequence of SEQ ID NO: 41 (ii) an amino acid sequence 90% or more identical to (i), or (iii) an amino acid sequence that includes 1 to 10 amino acid substitutions, insertions or deletions with respect to (i). In some embodiments, the CPR-, CPRA and/or CPRB encoded enzymes comprise (i) an amino acid sequence encoded by any one of SEQ ID NOS: 24 to 26, (ii) an amino acid sequence 90% or more identical to (i), or (iii) an amino acid sequence that includes 1 to 10 amino acid substitutions, insertions or deletions with respect to (i).

In some embodiments, the acyl-CoA oxidase activity is provided by an increased amount of a POX4-encoded enzyme, a POX5-encoded enzyme, or a POX4-encoded enzyme and a POX5-encoded enzyme an enzyme. In certain embodiments, the POX4-encoded enzyme comprises (i) the amino acid sequence of SEQ ID NO: 39, (ii) an amino acid sequence 90% or more identical to (i), or (iii) an amino acid sequence that includes 1 to 10 amino acid substitutions, insertions or deletions with respect to (i). In some embodiments, the POX5-encoded enzyme comprises (i) the amino acid sequence of SEQ ID NO: 40, (ii) an amino acid sequence 90% or more identical to (i), or (iii) an amino acid sequence that includes 1 to 10 amino acid substitutions, insertions or deletions with respect to (i). In certain embodiments, the microorganism lacks an enzyme providing an acyl-CoA oxidase activity. In certain embodiments, the enzyme is a POX4-encoded enzyme or a POX5-encoded enzyme. In certain embodiments, the POX4 polynucleotide that encodes the POX4-encoded enzyme comprises (i) the polynucleotide of SEQ ID NO: 37, (ii) a polynucleotide 90% or more identical to (i), or (iii) polynucleotide that includes 1 to 10 nucleotide substitutions, insertions or deletions with respect to (i). In some embodiments, the POX5 polynucleotide that encodes the POX5-encoded enzyme comprises (i) the polynucleotide of SEQ ID NO: 38, (ii) a polynucleotide 90% or more identical to (i), or (iii) a polynucleotide that includes 1 to 10 amino acid substitutions, insertions or deletions with respect to (i). In certain embodiments, the microorganism lacks an enzyme providing an acyl-CoA oxidase activity, and sometimes lacks a POX4-encoded enzyme or a POX5-encoded enzyme.

In certain embodiments, the hexanoate synthase activity is provided by an increased amount of a HEXA-encoded protein, a HEXB-encoded protein, or HEXA-encoded protein and HEXB-encoded protein. In some embodiments, the HEXA-encoded protein comprises (i) the amino acid sequence encoded by SEQ ID NO: 35, (ii) an amino acid sequence 90% or more identical to (i), or (iii) an amino acid sequence that includes 1 to 10 amino acid substitutions, insertions or deletions with respect to (i). In certain embodiments, the HEXB-encoded protein comprises (i) the amino acid sequence encoded by SEQ ID NO: 36, (ii) an amino acid sequence 90% or more identical to (i), or (iii) an amino acid sequence that includes 1 to 10 amino acid substitutions, insertions or deletions with respect to (i).

In some embodiments, the lipase activity is provided by an increased amount of an enzyme comprising (i) the amino acid sequences of SEQ ID NO: 28 or 29, (ii) an amino acid sequence 90% or more identical to (i), or (iii) an amino acid sequence that includes 1 to 10 amino acid substitutions, insertions or deletions with respect to (i). In some embodiments, the lipase activity is provided by an increased amount of an enzyme encoded by a polynucleotide comprising (i) the polynucleotide of SEQ ID NO: 27, (ii) a polynucleotide 90% or more identical to (i), or (iii) a polynucleotide that includes 1 to 10 nucleotide substitutions, insertions or deletions with respect to (i).

In certain embodiments, the glucose-6-phosphate dehydrogenase activity is provided by an increased amount of an enzyme comprising (i) the amino acid sequence of SEQ ID NO: 34, (ii) an amino acid sequence 90% or more identical to (i), or (iii) an amino acid sequence that includes 1 to 10 amino acid substitutions, insertions or deletions with respect to (i). In some embodiments, the glucose-6-phosphate dehydrogenase activity is provided by an increased amount of an enzyme encoded by a polynucleotide comprising (i) the polynucleotide of SEQ ID NO: 33, (ii) a polynucleotide 90% or more identical to (i), or (iii) a polynucleotide that includes 1 to 10 nucleotide substitutions, insertions or deletions with respect to (i).

In some embodiments, the acyl-CoA hydrolase activity is provided by an increased amount of an enzyme comprising (i) the amino acid sequence encoded by SEQ ID NO: 43 or 45, (ii) an amino acid sequence 98% or more identical to (i), or (iii) an amino acid sequence that includes 1 to 10 amino acid substitutions, insertions or deletions with respect to (i).

In some embodiments, the acyl-CoA thioesterase activity is provided by an increased amount of an enzyme comprising (i) the amino acid sequence encoded by SEQ ID NO: 47, or (ii) an amino acid sequence that includes 1 to 10 amino acid substitutions, insertions or deletions with respect to (i).

In some embodiments, the microorganism is a yeast. In certain embodiments, the yeast is a *Candida* yeast. In some embodiments, the yeast is a *Candida tropicalis* yeast. In certain embodiments, the microorganism is a haploid and in some embodiments, the micro organism is a diploid In certain embodiments, an expression vector includes a polynucleotide sequence or expresses an amino acid sequence of any one of SEQ ID NOS: 1 to 59. In some embodiments, an integration vector includes a polynucleotide sequence or expresses an amino acid sequence of any one of SEQ ID NOS: 1 to 59. In certain embodiments, a microorganism includes an expression vector, an integration vector, or an expression vector and an integration vector that includes a polynucleotide sequence of SEQ ID NOS: 1 to 59. In some embodiments, a culture includes a microorganism that includes an expression vector, an integration vector, or an expression vector and an integration vector that includes a polynucleotide sequence or expresses an amino acid sequence of any one of SEQ ID NOS: 1 to 59. In certain embodiments, a fermentation device includes a microorganism that includes an expression vector, an integration vector, or an expression vector and an integration vector that includes a polynucleotide sequence or expresses an amino acid sequence of any one of SEQ ID NOS: 1 to 59. In some embodiments an integration vector is used to disrupt a polynucleotide sequence. Also provided herein is a polypeptide or a polypeptide encoded by a polynucleotide sequence of any one of SEQ ID NOS: 1 to 47 or produced by an expression vector that includes a polynucleotide sequence of, or expresses an amino acid sequence of any one of SEQ ID NOS: 1 to 47. Provided also herein is an antibody that specifically binds to a polypeptide of, or is encoded by a polynucleotide sequence or expresses an amino acid sequence of any one of SEQ ID NOS: 1 to 59 or produced by an expression vector that includes a polynucleotide sequence or expresses an amino acid sequence of any one of SEQ ID NOS: 1 to 59.

Also provided herein is a method for producing adipic acid, the method including culturing an engineered microorganism described herein under conditions in which adipic acid is produced. In some embodiments, the culture conditions include fermentation conditions. In certain embodiments, the culture conditions include introduction of biomass. In some embodiments, the culture conditions include introduction of a feedstock comprising glucose. In certain embodiments, the culture conditions include introduction of a feedstock comprising hexane. In some embodiments, the culture conditions include introduction of a feedstock comprising an oil.

In certain embodiments, adipic acid (and/or adipate) is produced with a yield of greater than about 0.15 grams per gram of the glucose, hexane or oil. In some embodiments, adipic acid (and/or adipate) is produced at between about 20% and about 100% of maximum theoretical yield of any introduced feedstock (e.g., about 25%, about 30%, about 35%, about 40%, about 45%, about 50%, about 55%, about 60%, about 65%, about 70%, about 75%, about 80%, about 85%, about 90%, about 95%, about 99%, or about 100% of theoretical maximum yield) for the feedstock utilized. In certain embodiments, adipic acid (and/or adipate) is produced in a concentration range of between about 1 g/L (grams per liter) to about 1,000 g/L of culture media, fermentation medium or fermentation broth (e.g., about 2 g/L, about 3 g/L, about 4 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, about 100 g/L, about 110 g/L, about 120 g/L, about 130 g/L, about 140 g/L, about 150 g/L, about 160 g/L, about 170 g/L, about 180 g/L, about 190 g/L, about 200 g/L, about 225 g/L, about 250 g/L, about 275 g/L, about 300 g/L, about 325 g/L, about 350 g/L, about 375 g/L, about 400 g/L, about 425 g/L, about 450 g/L, about 475 g/L, about 500 g/L, about 550 g/L, about 600 g/L, about 650 g/L, about 700 g/L, about 750 g/L, about 800 g/L, about 850 g/L, about 900 g/L, about 950 g/L, or about 1000 g/L).

In some embodiments, adipic acid (nad/or adipate) is produced at a rate of between about 0.5 g/L/hour to about 5 g/L/hour (e.g., about 0.5 g/L/hour, about 0.6 g/L/hour, about 0.7 g/L/hour, about 0.8 g/L/hour, about 0.9 g/L/hour, about 1.0 g/L/hour, about 1.1 g/L/hour, about 1.2 g/L/hour, about 1.3 g/L/hour, about 1.4 g/L/hour, about 1.5 g/L/hour, about 1.6 g/L/hour, about 1.7 g/L/hour, about 1.8 g/L/hour, about 1.9 g/L/hour, about 2.0 g/L/hour, about 2.25 g/L/hour, about 2.5 g/L/hour, about 2.75 g/L/hour, about 3.0 g/L/hour, about 3.25 g/L/hour, about 3.5 g/L/hour, about 3.75 g/L/hour, about 4.0 g/L/hour, about 4.25 g/L/hour, about 4.5 g/L/hour, about 4.75 g/L/hour, or about 5.0 g/L/hour.) In certain, embodiments, the engineered organism comprises between about a 5-fold to about a 500-fold increase in adipic acid production (and/or adipate production) when compared to wild-type or partially engineered organisms of the same strain, under identical fermentation conditions (e.g., about a 5-fold increase, about a 10-fold increase, about a 15-fold increase, about a 20-fold increase, about a 25-fold increase, about a 30-fold increase, about a 35-fold increase, about a 40-fold increase, about a 45-fold increase, about a 50-fold increase, about a 55-fold increase, about a 60-fold increase, about a 65-fold increase, about a 70-fold increase, about a 75-fold increase, about a 80-fold increase, about a 85-fold increase, about a 90-fold increase, about a 95-fold increase, about a 100-fold increase, about a 125-fold increase, about a 150-fold increase, about a 175-fold increase, about a 200-fold increase, about a 250-fold increase, about a 300-fold increase, about a 350-fold increase, about a 400-fold increase, about a 450-fold increase, or about a 500-fold increase).

In some embodiments, a method includes purifying the adipic acid from the cultured microorganisms. In certain embodiments, the method includes modifying the adipic acid, thereby producing modified adipic acid. In some embodiments, the method includes placing the cultured microorganisms, the adipic acid or the modified adipic acid in a container, and in certain embodiments, the method includes shipping the container.

In some embodiments, provided is a chimera exhibiting a fatty acid synthase and/or hexanoate synthase activity. In some embodiments, the chimera is encoded by a nucleotide sequence that includes a donor sequence in a base sequence. In certain embodiments, a donor sequence replaces a sequence earlier excised from the base sequence (excised sequence). There can be one or more donor sequences, and optionally one or more excised sequences, in a particular polynucleotide that encodes a chimera. In certain embodiments, the base sequence and donor sequence are from fatty acid synthase polynucleotides from different organisms. In some embodiments, each fatty acid synthase polynucleotide independently is obtained from a fungus or yeast (e.g., *Candida* yeast (e.g., *C. tropicalis*)). In certain embodiments, the donor sequence and/or base sequence is from a hexanoate synthase subunit A or B (e.g., HEXA, HEXB), such as a HEXA or HEXB sequence described herein. In some embodiments, the donor sequence or base sequence is from a fatty acid synthase gene of a fungus or yeast (e.g., *Candida* (e.g., *C. tropicalis*).

In certain chimera embodiments, the excised sequence and/or the donor sequence encodes a functional polypeptide, or portion thereof, that adds malonyl units to a growing fatty acid chain, and/or removes a grown fatty acid chain (e.g., palmitoyl fatty acid or derivative) from the polypeptide or portion thereof. In some embodiments, the donor sequence and/or excised sequence encodes a malonyl-palmitoyl transferase domain (MPT domain) from a hexanoate synthase gene or fatty acid synthase gene. In certain embodiments, the donor sequence and/or excised sequence encodes all or part of the functional polypeptide or domain described above, and optionally includes one or more additional nucleotides or stretches of contiguous polynucleotides. In some embodiments, the donor sequence or excised sequence is about 900 contiguous nucleotides to about 1500 contiguous nucleotides in length, and sometimes about 1200 contiguous nucleotides in length. In certain embodiments, the base sequence and/or donor sequence independently are (i) identical to a native sequence, (ii) 90% or more identical to a native sequence, or (iii) include 1 to 10 insertions, deletions or substitutions with respect to a native sequence. In some embodiments, the native donor sequence is from HEXB and the native base sequence is from FAS1. Examples of each of these sequences are provided herein.

In some chimera embodiments, the donor sequence and/or excised sequence encodes a ketoacyl synthase domain (KS domain) from a hexanoate synthase gene or fatty acid synthase gene. In certain embodiments, the donor sequence and/or or excised sequence encodes all or part of the domain described above, and optionally includes one or more additional nucleotides or stretches of contiguous polynucleotides. In some embodiments, the donor sequence or excised sequence is about 900 contiguous nucleotides to about 1700 contiguous nucleotides in length, and sometimes about 1350 contiguous nucleotides in length. In certain embodiments, the base sequence and/or donor sequence independently are (i)

identical to a native sequence, (ii) 90% or more identical to a native sequence, or (iii) include 1 to 10 insertions, deletions or substitutions with respect to a native sequence. In some embodiments, the native donor sequence is from HEXA and the native base sequence is from FAS2. Examples of each of these sequences are provided herein.

In certain chimera embodiments, donor sequences from FAS1 are used to fill in regions of a base HexB sequence that are not present in HexB. Donor sequences may be selected, in some embodiments, based upon an alignment of HexB and FAS1 sequences and identifying sequences present in FAS1 that do not align with, and/or appear to be inserted with respect to, HexB. In some embodiments, the donor sequence is about 100 contiguous nucleotides or less from FAS1. In certain embodiments, the base sequence and/or donor sequence independently are (i) identical to a native sequence from HexB and FAS1, respectively, (ii) 90% or more identical to the native sequence, or (iii) include 1 to 10 insertions, deletions or substitutions with respect to the native sequence.

Provided also herein are genetically modified microorganisms including one or more increased activities, with respect to the activity level in an unmodified or parental strain, which increased activities are chosen from: a monooxygenase activity, a monooxygenase reductase activity, an acyl-CoA oxidase activity, an acyl-CoA hydrolase activity, an acyl-CoA thioesterase activity and combinations of the forgoing. In some embodiments, the monooxygenase activity includes a cytochrome P450 A19 (e.g., CYP52A19) activity. In certain embodiments, the monooxygenase activity is a cytochrome P450 A19 (e.g., CYP52A19) activity. In some embodiments, the monooxygenase reductase activity includes one or more activities selected from CPR, CPRA, CPRB, and combinations of the foregoing.

In certain embodiments, the acyl-CoA oxidase activity includes a POX5 activity. In some embodiments, the acyl-CoA oxidase activity is a POX5 activity. In certain embodiments, the acyl-CoA hydrolase activity includes one or more activities selected from ACHA activity, ACHB activity, and ACHA activity and ACHB activity. In some embodiments, the acyl-CoA thioesterase activity includes a TESA activity.

In some embodiments, the one or more increased activities are three or more increased activities. In certain embodiments, the one or more increased activities are four or more increased activities, and in some embodiments, the one or more increased activities are five or more increased activities. In certain embodiments, the three or more increased activities include an increased monooxygenase activity, an increased monooxygenase reductase activity, and an increased acyl-CoA hydrolase activity. In some embodiments, the three or more increased activities include an increased monooxygenase activity, an increased monooxygenase reductase activity, and an increased acyl-CoA thioesterase activity. In certain embodiments, the four or more increased activities include an increased monooxygenase activity, an increased monooxygenase reductase activity, an increased acyl-CoA oxidase activity and an increased acyl-CoA hydrolase activity. In some embodiments, the four or more increased activities include an increased monooxygenase activity, an increased monooxygenase reductase activity, an increased acyl-CoA hydrolase activity and an increased acyl-CoA thioesterase activity. In certain embodiments, the five or more increased activities include an increased monooxygenase activity, an increased monooxygenase reductase activity, an increased acyl-CoA oxidase activity, and increased acyl-CoA thioesterase activity and an increased acyl-CoA hydrolase activity.

In some embodiments, genetically modified microorganisms further include one or more reduced activities, with respect to the activity level in an unmodified or parental strain, which reduced activities are chosen from: acyl-CoA synthetase activity, long chain acyl-CoA synthetase activity, acyl-CoA sterol acyl transferase activity, acyltransferase activity, and combinations of the foregoing. In certain embodiments, the acyl-CoA synthetase activity includes an ACS1 activity. In some embodiments, the long chain acyl-CoA synthetase activity includes a FAT1 activity. In certain embodiments, the acyl-CoA sterol acyl transferase activity includes one or more activities selected from an ARE1 activity, an ARE2 activity, and an ARE1 activity and an ARE2 activity. In some embodiments, the acyltransferase activity is a diacylglycerol acyltransferase activity, and in certain embodiments, the diacylglycerol acyltransferase activity includes one or more activities selected from a DGA1 activity, a LRO1 activity and a DGA1 activity and a LRO1 activity.

In certain embodiments, the one or more reduced activities is three or more reduced activities. In some embodiments, the three or more reduced activities are four or more reduced activities. In certain embodiments, the three or more reduced activities are five or more reduced activities. In some embodiments, genetically modified microorganisms include a reduced ACS1 activity, a reduced FAT1 activity, a reduced ARE1 activity, a reduced ARE2 activity, a reduced DGA1 activity and a reduced LRO1 activity.

Also provided herein, is a method for preparing a microorganism that produces adipic acid, which includes: (a) introducing one or more genetic modifications to a host organism that add or increase one or more activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, acyl-CoA hydrolase activity, acyl-CoA thioesterase activity, monooxygenase activity, and monooxygenase reductase activity, thereby producing engineered microorganisms, and (b) selecting for engineered microorganisms that produce adipic acid. In some embodiments a method for preparing a microorganism that produces adipic acid further includes selecting for engineered microorganisms having one or more detectable and/or increased activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, acyl-CoA hydrolase activity, acyl-CoA thioesterase activity, monooxygenase activity, and monooxygenase reductase activity, relative to the host microorganism. In certain embodiments, the method includes introducing a genetic modification that reduces one or more activities selected from acyl-CoA oxidase, acyl-CoA synthetase activity, long chain acyl-CoA synthetase activity, acyl-CoA sterol acyl transferase activity, acyltransferase activity, and 6-hydroxyhexanoic acid conversion activity, thereby producing engineered microorganisms, and selecting for engineered microorganisms having one or more reduced activities selected from acyl-CoA oxidase, acyl-CoA synthetase activity, long chain acyl-CoA synthetase activity, acyl-CoA sterol acyl transferase activity, acyltransferase activity, and 6-hydroxyhexanoic acid conversion activity relative to the host microorganism.

Provided also herein is a method for producing adipic acid, including: contacting an engineered microorganism with a feedstock including one or more sugars, cellulose, fatty acids, triacylglycerides or combinations of the forgoing, wherein the engineered microorganism includes: (a) a genetic alteration that partially blocks beta oxidation activity, (b) a genetic alteration that adds or increases a monooxygenase activity, (c) a genetic alteration that adds or increases a monooxygenase reductase activity, and (d) a genetic alteration that adds or increases an acyl-CoA hydrolase and/or an acyl-CoA thioesterase activity, and culturing the engineered microorganism under conditions in which adipic acid is produced. In some embodiments, the engineered microorganism further includes one or more genetic alterations that reduce an activity selected from an acyl-CoA oxidase activity, an acyl-CoA synthetase activity, a long chain acyl-CoA synthetase activity, an acyl-CoA sterol acyl transferase activity, and an acyltransferase activity.

In certain embodiments, the acyltransferase activity is a diacyl-glycerol acyltransferase activity. In some embodiments, the engineered microorganism includes a heterologous polynucleotide encoding a polypeptide having acyl-CoA thioesterase activity. In certain embodiments, the heterologous polynucleotide independently is selected from a bacterium. In some embodiments, the bacterium is an *Enteric* bacterium, and in certain embodiments, the *Enteric* bacterium is *E. coli*.

In some embodiments, the genetically modified microorganism is a yeast. In certain embodiments, the genetically modified microorganism is a *Candida* yeast. In some embodiments, the *Candida* yeast is *C. tropicalis*, and in certain embodiments, the *C. tropicalis* is *C. tropicalis* strain 20336.

In certain embodiments, the engineered microorganism includes a heterologous polynucleotide encoding a polypeptide having acyl-CoA thioesterase activity, and the polynucleotide sequence has been codon optimized for expression in *C. tropicalis*. In some embodiments, the genetic alteration that partially blocks beta oxidation activity reduces or eliminates POX4 activity. In certain embodiments, the genetic alteration that adds or increases monooxygenase activity, increases CYP52A19 activity. In some embodiments, the genetic alteration that adds or increases monooxygenase reductase activity increases a CPR activity, a CPRA activity, a CPRB activity, or combinations thereof.

In some embodiments, the genetic alteration that adds or increases acyl-CoA hydrolase activity increases an ACHA activity, an ACHB activity or an ACHA activity and an ACHB activity. In certain embodiments, the genetic alteration that adds or increases acyl-CoA thioesterase activity adds an *E. coli* derived TESA activity. In some embodiments, the genetic alteration that reduces an acyl-CoA synthetase activity, reduces or eliminates an ACS1 activity. In certain embodiments, the genetic alteration that reduces a long chain acyl-CoA synthetase activity, reduces or eliminates an FAT1 activity. In some embodiments, the genetic alteration that reduces an acyl-CoA sterol acyl transferase activity, reduces or eliminates an ARE1 activity, an ARE2 activity, or an ARE1 activity and an ARE2 activity. In certain embodiments, the genetic alteration that reduces an acyltransferase activity, reduces or eliminates a DGA1 activity, a LRO1 activity or a DGA1 activity and a LRO1 activity.

In certain embodiments, the maximum theoretical yield ($Y_{max}$) is about 0.6 grams of adipic acid produced per gram of coconut oil added, the percentage of $Y_{max}$ for the engineered microorganism under conditions in which adipic acid is produced is calculated as (% $Y_{max}$)=$Y_{p/s}$/$Y_{max}$*100, where ($Y_{p/s}$)=[adipic acid (g/L)*final volume of culture in flask (L)]/[feedstock added to flask (g)]. In some embodiments, the engineered microorganism produces adipic acid at about 10% to about 100% of maximum theoretical yield.

Also provided herein is an isolated polynucleotide selected from the group consisting of: a polynucleotide having a nucleotide sequence 96% or more identical to the nucleotide sequence of SEQ ID NO: 42 or 44: a polynucleotide having a nucleotide sequence that encodes a polypeptide having an amino acid sequence 98% or more identical to the amino acid sequence of SEQ ID NO: 43 or 45; and a polynucleotide having a portion of a nucleotide sequence 96% or more identical to the nucleotide sequence of SEQ ID NO: 42 or 44 and encodes a polypeptide having acyl-coA hydrolase activity. Provided also herein is an isolated polynucleotide selected from the group consisting of: a polynucleotide having a nucleotide sequence identical to the nucleotide sequence of SEQ ID NO: 46: a polynucleotide having a nucleotide sequence that encodes a polypeptide of SEQ ID NO: 47; and a polynucleotide having a portion of a nucleotide sequence identical to the nucleotide sequences of SEQ ID NO: 46 and encodes a polypeptide having acyl-CoA thioesterase activity. Also provided herein are expression vectors including a polynucleotide sequence 96% or more identical to the nucleotide sequence of SEQ ID NOS: 42 and 44. Provided also herein are expression vectors including a polynucleotide having the nucleotide sequence of SEQ ID NO: 46. Provided also herein are integration vectors including a polynucleotide sequence 96% or more identical to the polynucleotide sequence of SEQ ID NOS: 42 and 44. Provided also herein are integration vectors including a polynucleotide having the nucleotide sequence of SEQ ID NO: 46.

Also provided herein are microorganisms including an expression vector and/or an integration vector including a polynucleotide sequence 96% or more identical to the nucleotide sequence of SEQ ID NOS: 42 and 44. Provided also here are microorganisms including an expression vector and/or an integration vector including a polynucleotide having the nucleotide sequence of SEQ ID NO: 46. Provided also herein is a culture including a microorganism that includes an expression vector and/or integration described herein. Also provided herein is a fermentation device including a microorganism that includes an expression vector and/or integration described herein. Also provided in some embodiments are antibodies that specifically bind to a polypeptide produced from an expression vector described herein. Provided also in some embodiments are polypeptides encoded by a polynucleotide SEQ ID 42, 44, and 46, expressed by an engineered microorganism.

Also provided herein is an engineered microorganism capable of producing adipic acid, which microorganism includes genetic alterations resulting in one or more increased activities and further resulting in commitment of molecular pathways in directions for production of adipic acid, which pathways and directions include: (i) fatty acid synthesis pathway in the direction of acetyl CoA to long-chain fatty acids and away from synthesis or generation of biomass and/or carbon storage molecules, (ii) omega oxidation pathway in the direction of long-chain fatty acids to diacids and (iii) beta oxidation pathway in the direction of diacids to adipic acid. In some embodiments, carbon storage molecules include storage starches, storage lipids and combinations thereof. In certain embodiments, an engineered microorganism includes an increased activity, relative to the microorganism not containing the genetic alterations, independently in each pathway.

In some embodiments, an engineered microorganism includes an increased monooxygenase activity. In certain embodiments, an engineered microorganism includes an increased monooxygenase reductase activity. In some embodiments, an engineered microorganism includes an increased acyl-CoA oxidase activity. In certain embodiments, an engineered microorganism includes an increased acetyl CoA carboxylase activity in the fatty acid synthesis pathway. In some embodiments, an engineered microorganism includes an increased fatty acid synthase activity in the fatty acid synthesis pathway. In certain embodiments, an engineered microorganism includes an increased acyl-CoA hydrolase activity in the fatty acid synthesis pathway.

In some embodiments, the increased activities independently is provided by an enzyme encoded by a gene endogenous to the microorganism. In certain embodiments, each of the increased activities independently is provided by an increased amount of an enzyme from a yeast. In some embodiments, the yeast is a *Candida* yeast, and in certain embodiments, the yeast is a *Candida tropicalis* yeast.

In certain embodiments, an engineered microorganism includes an added acyl-CoA thioesterase activity in the fatty acid synthesis pathway. In some embodiments, the added activity independently is provided by an enzyme encoded by a gene exogenous to the microorganism. In certain embodiments an engineered microorganism further includes one or more reduced activities selected from an acyl-CoA oxidase activity, an acyl-CoA synthetase activity, a long chain acyl-CoA synthetase activity, an acyl-CoA sterol acyl transferase activity, and an acyltransferase activity. In some embodiments, the acyltransferase activity is a diacyl-glycerol acyl-transferase activity.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIGS. 11A and 11B depict omega and beta oxidation pathways useful for producing adipic acid from various carbon sources. Adipic acid can be produced from paraffins, fats, oils and intermediates of sugar metabolism, using omega oxidation, as shown in FIG. 11A. Adipic acid also can be produced from long chain fatty acids or dicarboxylic acids using beta oxidation, as shown in FIG. 11A. FIG. 11B shows a common intermediate from the metabolism of fats and sugars entering the omega oxidation pathway to ultimately produce adipic acid.

FIG. 16 depicts a plasmid diagram for inserting a heterologous HEXA gene into S. cerevisiae.

FIG. 17 depicts a plasmid diagram for inserting a heterologous HEXB gene into S. cerevisiae.

FIG. 18 depicts a plasmid diagram for inserting a heterologous HEXA-6×His gene ("6×His" disclosed as SEQ ID NO: 60) into S. cerevisiae.

FIG. 19 depicts a plasmid diagram for inserting a heterologous HEXB-6×His gene ("6×His" disclosed as SEQ ID NO: 60) into S. cerevisiae.

FIG. 20 depicts a plasmid diagram for inserting a heterologous STCJ gene into S. cerevisiae.

FIG. 21 depicts a plasmid diagram for inserting a heterologous STCK gene into S. cerevisiae.

FIG. 22 depicts a plasmid diagram for inserting a heterologous STCJ-6×His gene ("6×His" disclosed as SEQ ID NO: 60) into S. cerevisiae.

FIG. 23 depicts a plasmid diagram for inserting a heterologous STCK-6×His gene ("6×His" disclosed as SEQ ID NO: 60) into S. cerevisiae.

FIG. 24 depicts a plasmid diagram for inserting a heterologous alternative genetic code (AGC) HEXA gene into C. tropicalis.

FIG. 25 depicts a plasmid diagram for inserting a heterologous AGC-HEXB gene into C. tropicalis.

FIG. 26 depicts a plasmid diagram for inserting a heterologous AGC-HEXA-6×His gene ("6×His" disclosed as SEQ ID NO: 60) into C. tropicalis.

FIG. 27 depicts a plasmid diagram for inserting a heterologous AGC-HEXB-6×His gene ("6×His" disclosed as SEQ ID NO: 60) into C. tropicalis.

FIG. 28 depicts a diagram of a plasmid used for cloning the POX5 gene from C. tropicalis.

FIG. 29 depicts a diagram of a plasmid used for cloning the POX4 gene from C. tropicalis.

FIG. 30 illustrates a plasmid constructed for use of URA selection in C. tropicalis.

FIG. 31 depicts a plasmid containing the PGK promoter and terminator from C. tropicalis.

FIG. 32 depicts a plasmid used for integration of the CPR gene in C. tropicalis.

FIG. 33 depicts a plasmid used for integration of the CYP52A15 gene in C. tropicalis.

FIG. 34 depicts a plasmid used for integration of the CYP52A16 gene in C. tropicalis.

FIG. 40 discloses "6×HIS" as SEQ ID NO: 60.

DETAILED DESCRIPTION

Figure 1:
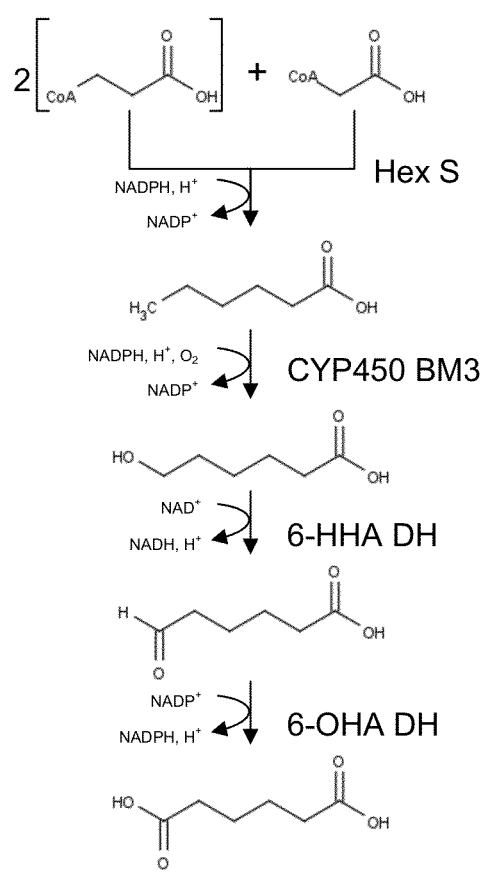
FIG. 1 depicts a metabolic pathway for making adipic acid. The pathway can be engineered into a eukaryotic microorganism to generate a microorganism capable of producing adipic acid.
Figure 2:
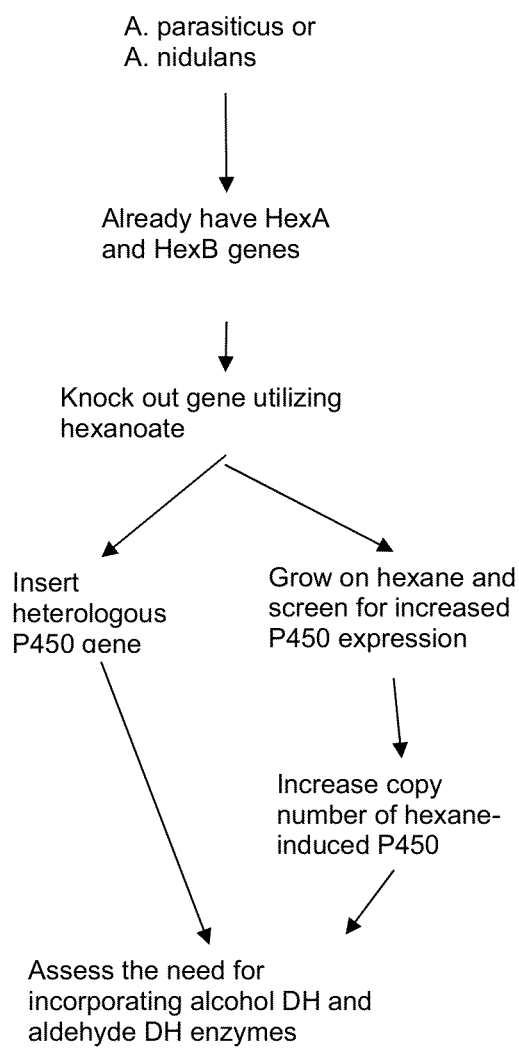
FIG. 2 depicts an embodiment for a method of generating an adipic acid producing microorganism. The method comprises expressing one or more genes catalyzing the omega oxidation of fatty acids to dicarboxylic acids in a host microorganism that produces hexanoate. In the method depicted, the host organism, for example *A. parasiticus* or *A. nidulans*, endogenously includes HEXA and HEXB (or STCJ and STCK) genes. In one embodiment the method comprises knocking out or otherwise disabling the gene coding for diversion of hexanoate into an endogenous pathway such as mycotoxin production. Certain embodiments of the method further comprise inserting a heterologous cytochrome P450 gene. Some embodiments of the method comprise growing the culture on hexane and screening for increased P450 expression. The copy number of hexanoate induced P450 may in certain embodiments be increased. In some embodiments the microorganism may be altered to increase the flux of six carbon substrate through the final two oxidation steps.
Figure 3:
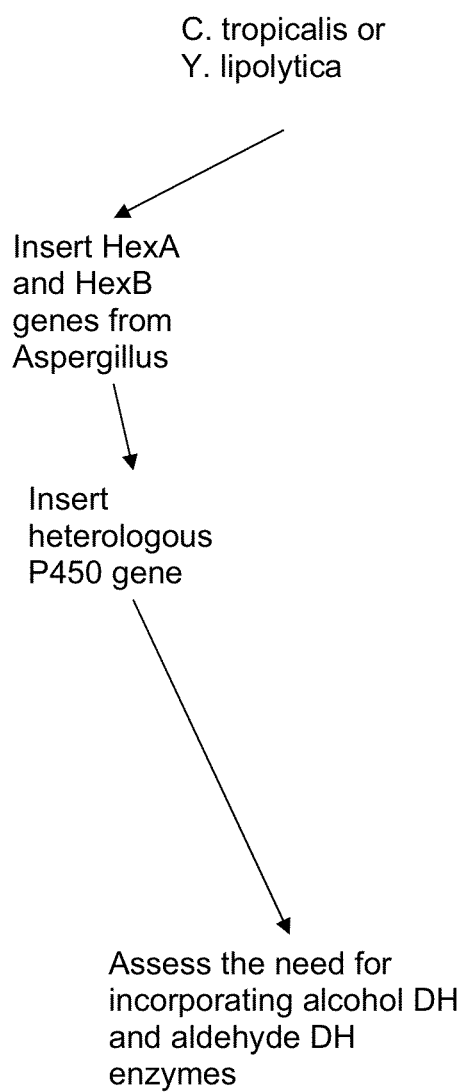
FIG. 3 depicts an embodiment for a method of generating an adipic acid producing organism. The method comprises expressing one or more genes encoding hexanoate synthase in a host microorganism that produces dicarboxylic acids via an omega-oxidation pathway. Such microorganisms may include, without limitation, *C. tropicalis* and *C. maltosa*. As depicted, the method comprises inserting HEXA and HEXB genes into the host microorganism. The genes may be isolated from *Aspergillus*, or another appropriate organism. In some embodiments, the genes are synthesized from an alternative sequence as described herein to produce the amino acid sequence of the donor mircroorganism enzyme through a non-standard translation mechanism of *C. tropicalis*. In some embodiments the method comprises inserting a heterologous cytochrome P450 gene into the host organism. In certain embodiments the microorganism may be altered to increase the flux of a six-carbon substrate through the final two oxidation steps.

Adipic acid is a six-carbon organic molecule that is a chemical intermediate in manufacturing processes used to make certain polyamides, polyurethanes and plasticizers, all of which have wide applications in producing items such as carpets, coatings, adhesives, elastomers, food packaging, and lubricants, for example. Some large-scale processes for making adipic acid include (i) liquid phase oxidation of ketone alcohol oil (KA oil); (ii) air oxidation/hydration of cyclohexane with boric acid to make cyclohexanol, followed by oxidation with nitric acid; and (iii) hydrocyanation of butadiene to a pentenenitrile mixture, followed by hydroisomerization of adiponitrile, followed by hydrogenation. Each of the latter processes requires use of noxious chemicals and/or solvents, some require high temperatures, and all require significant energy input. In addition, some of the processes emit toxic byproducts (such as nitrous oxide) and give rise to environmental concerns.

Provided herein are methods for producing adipic acid and other organic chemical intermediates using biological systems. Such production systems may have significantly less environmental impact and could be economically competitive with current manufacturing systems. Thus, provided herein are methods for manufacturing adipic acid by engineered microorganisms. In some embodiments microorganisms are engineered to contain at least one heterologous gene encoding an enzyme, where the enzyme is a member of a novel pathway engineered into the microorganism. In certain embodiments, an organism may be selected for elevated activity of a native enzyme.

Microorganisms

A microorganism selected often is suitable for genetic manipulation and often can be cultured at cell densities useful for industrial production of a target product. A microorganism selected often can be maintained in a fermentation device.

The term "engineered microorganism" as used herein refers to a modified microorganism that includes one or more activities distinct from an activity present in a microorganism utilized as a starting point (hereafter a "host microorganism"). An engineered microorganism includes a heterologous polynucleotide in some embodiments, and in certain embodiments, an engineered organism has been subjected to selective conditions that alter an activity, or introduce an activity, relative to the host microorganism. Thus, an engineered microorganism has been altered directly or indirectly by a human being. A host microorganism sometimes is a native microorganism, and at times is a microorganism that has been engineered to a certain point.

In some embodiments an engineered microorganism is a single cell organism, often capable of dividing and proliferating. A microorganism can include one or more of the following features: aerobe, anaerobe, filamentous, non-filamentous, monoploid, diploid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba).

Any suitable yeast may be selected as a host microorganism, engineered microorganism or source for a heterologous polynucleotide. Yeast include, but are not limited to, *Yarrowia* yeast (e.g., *Y. lipolytica* (formerly classified as *Candida lipolytica*)), *Candida* yeast (e.g., *C. revkaufi, C. pulcherrima, C. tropicalis, C. utilis*), *Rhodotorula* yeast (e.g., *R. glutinus, R. graminis*), *Rhodosporidium* yeast (e.g., *R. toruloides*), *Saccharomyces* yeast (e.g., *S. cerevisiae, S. bayanus, S. pastorianus, S. carlsbergensis*), *Cryptococcus* yeast, *Trichosporon* yeast (e.g., *T. pullans, T. cutaneum*), *Pichia* yeast (e.g., *P. pastoris*) and *Lipomyces* yeast (e.g., *L. starkeyii, L. lipoferus*). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *C. tropicalis* strain that includes, but is not limited to, ATCC20336, ATCC20913, SU-2 (ura3-/ura3-), ATCC20962, H5343 (beta oxidation blocked; U.S. Pat. No. 5,648,247) strains.

Any suitable fungus may be selected as a host microorganism, engineered microorganism or source for a heterologous polynucleotide. Non-limiting examples of fungi include, but are not limited to, *Aspergillus* fungi (e.g., *A. parasiticus, A. nidulans*), *Thraustochytrium* fungi, *Schizochytrium* fungi and *Rhizopus* fungi (e.g., *R. arrhizus, R. oryzae, R. nigricans*). In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium*), *Acinetobacter* bacteria, *Norcardia* bacteria, *Xanthobacter* bacteria, *Escherichia* bacteria (e.g., *E. coli* (e.g., strains DH10B, Stbl2, DH5-alpha, DB3, DB3.1), DB4, DB5, JDP682 and ccdA-over (e.g., U.S. application Ser. No. 09/518,188))), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), *Megasphaera* bacteria (e.g., *Megasphaera elsdenii*). Bacteria also include, but are not limited to, photosynthetic bacteria (e.g., green non-sulfur bacteria (e.g., *Choroflexus* bacteria (e.g., *C. aurantiacus*), *Chloronema* bacteria (e.g., *C. gigateum*)), green sulfur bacteria (e.g., *Chlorobium* bacteria (e.g., *C. limicola*), *Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and *Rhodomicrobium* bacteria (e.g., *R. vanellii*)).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

Microorganisms or cells used as host organisms or source for a heterologous polynucleotide are commercially available. Microorganisms and cells described herein, and other suitable microorganisms and cells are available, for example, from Invitrogen Corporation, (Carlsbad, Calif.), American Type Culture Collection (Manassas, Va.), and Agricultural Research Culture Collection (NRRL; Peoria, Ill.).

Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Carbon Processing Pathways and Activities

Figure 35:
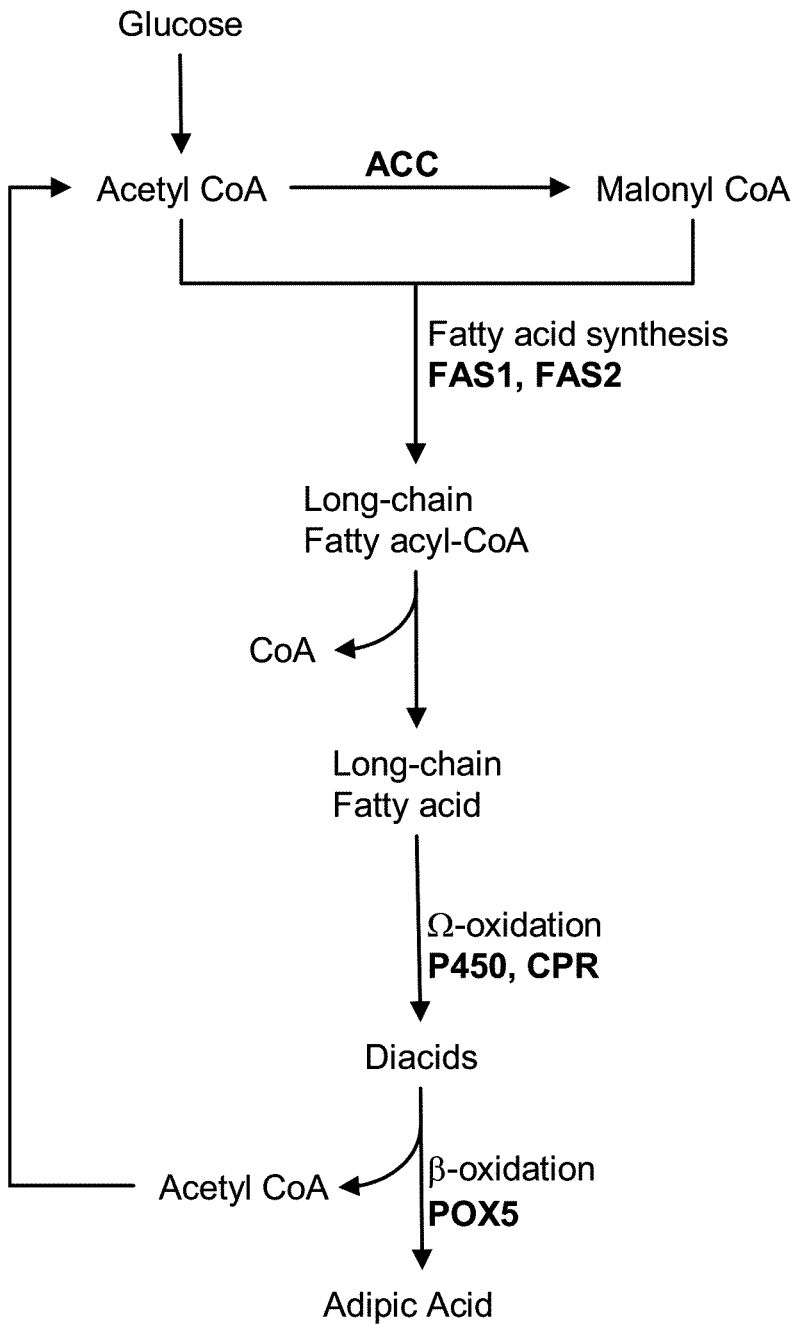
FIG. 35 depicts a metabolic pathway for making adipic acid from saccharide or polysaccharide carbon sources, similar to the pathways depicted in FIGS. 1 and 9, with additional activities that aid in metabolism of, or enhance metabolism of, pathway intermediates, thereby potentially increasing the yield of adipic acid. The additional activities are an acetyl-CoA carboxylase activity (ACC), a fatty acid synthase (FAS1, FAS2), a monooxygenase (P450) activity, a monooxygenase reductase activity (CPR) and an acyl-CoA oxidase activity (POX5). Part, or all, of the pathway can be engineered into a eukaryotic microorganism to generate a microorganism capable of producing adipic acid.
Figure 36:
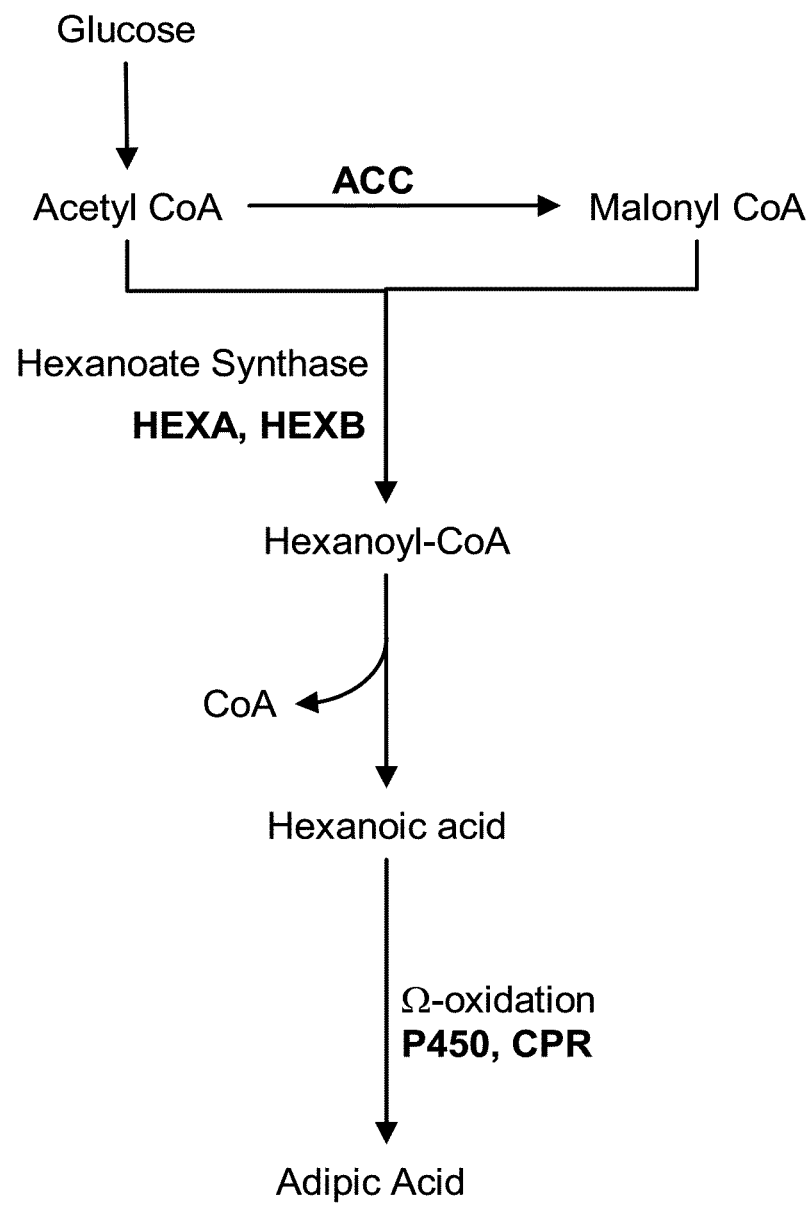
FIG. 36 depicts a metabolic pathway for making adipic acid from saccharide or polysaccharide carbon sources, similar to the pathways depicted in FIGS. 1 and 9, with additional activities that aid in metabolism of, or enhance metabolism of, pathway intermediates, thereby potentially increasing the yield of adipic acid. The additional activities are an acetyl-CoA carboxylase activity (ACC), a hexanoate synthase (HEXA, HEXB), a monooxygenase (P450) activity, and a monooxygenase reductase activity (CPR). Part, or all, of the pathway can be engineered into a eukaryotic microorganism to generate a microorganism capable of producing adipic acid.

FIGS. 1, 9, 35, 36, 42A and 42B depict embodiments of a biological pathways for making adipic acid, using a sugar as the carbon source starting material. Any suitable sugar can be used as the feedstock for the organism, (e.g., 6-carbon sugars (e.g., glucose, fructose), 5-carbon sugars (e.g., xylose), the like or combinations thereof). The sugars are initially metabolized using naturally occurring and/or engineered pathways to yield malonyl CoA, which is depicted as the molecule entering the omega oxidation pathway shown in FIG. 9. Malonyl-CoA sometimes is generated by the activity of an acyl-CoA carboxylase activity (e.g., ACC), as depicted in FIGS. 35 and 36, and sometimes is formed by the metabolism of sugars or paraffins, yielding Malonyl-CoA as a direct or indirect metabolic product.

An acetyl-CoA carboxylase activity (e.g., EC 6.4.1.2) catalyzes the irreversible carboxylation of acetyl-CoA to produce malonyl-CoA through its two catalytic activities, biotin carboxylase and carboxyltransferase. The reaction can be represented as;

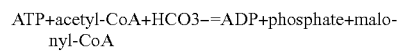

ATP+acetyl-CoA+HCO3-=ADP+phosphate+malonyl-CoA

Production of malonyl-CoA is the committed step in fatty acid biosynthesis. Acetyl-CoA carboxylase activity sometimes is present in a variety of organisms (e.g., prokaryotes, plants, algae) as a large multi-subunit protein, and often located in the endoplasmic reticulum of eukaryotes. Acetyl-CoA carboxylase activity in some plants also can carboxylate propanoyl-CoA and butanoyl-CoA. ACC sometimes is also referred to as "acetyl-CoA:carbon-dioxide ligase (ADP-forming)" and "acetyl coenzyme A carboxylase". The reverse activity (e.g., decarboxylation of malonyl-CoA) is carried out by a separate enzyme, malonyl-CoA decarboxylase. In some embodiments, to further increase carbon flux through a particular reaction or through a metabolic pathway, one or more reverse activities in the pathway can be altered to inhibit the back conversion of a desired product into its starting reactants. In certain embodiments, a malonyl-CoA decarboxylase activity is reduced or eliminated to further increase the carbon flux through an acetyl-CoA carboxylase activity in the direction of malonyl-CoA production.

An ACC activity in yeast may be amplified by over-expression of the ACC gene by any suitable method. Non-limiting examples of methods suitable to amplify or over express ACC include amplifying the number of ACC genes in yeast following transformation with a high-copy number plasmid (e.g., such as one containing a 2 u origin of replication), integration of multiple copies of ACC into the yeast genome, over-expression of the ACC gene directed by a strong promoter, the like or combinations thereof. The ACC gene may be native to *C. tropicalis*, or it may be obtained from a heterologous source.

A fatty acid synthase (e.g., FAS) activity catalyzes a series of decarboxylative Claisen condensation reactions from acetyl-CoA and malonyl-CoA. Without being limited by any theory, it is believed that following each round of elongation the beta keto group is reduced to the fully saturated carbon chain by the sequential action of a ketoreductase activity, a dehydratase activity, and an enol reductase activity. In the case of Type I FAS's, the growing fatty acid chain is carried between these active sites while attached covalently to the phosphopantetheine prosthetic group of an acyl carrier protein (ACP), and is released by the action of a thioesterase (TE) upon reaching a carbon chain length of 16 (e.g., palmitic acid). Thus, a fatty acid synthase activity comprises a collection of activities (e.g., an enzymatic system) that perform functions associated with the production of fatty acids. Therefore, the terms "fatty acid synthase activity", "fatty acid synthase", "FAS", and "FAS activity", as used herein refer to a collection of activities, or an enzymatic system, that perform functions associated with the production of fatty acids. In some embodiments, the collection of activities is found in a multifunctional, multi-subunit protein complex (e.g., Type I FAS activity).

Fatty acid synthases typically produce fatty acids with longer chain carbon chain lengths, however fatty acids with carbon chain lengths of 6C or 8C often are found in organisms. In some instances, the shorter fatty acids are the result of metabolic activities (e.g., beta-oxidation) that shorten the carbon chain length to a desired shorter number of carbon units. However, in certain instances, shorter chain fatty acids are produced directly by the activity of a specialized fatty acid synthase activity, hexanoate synthase.

Figure 9:
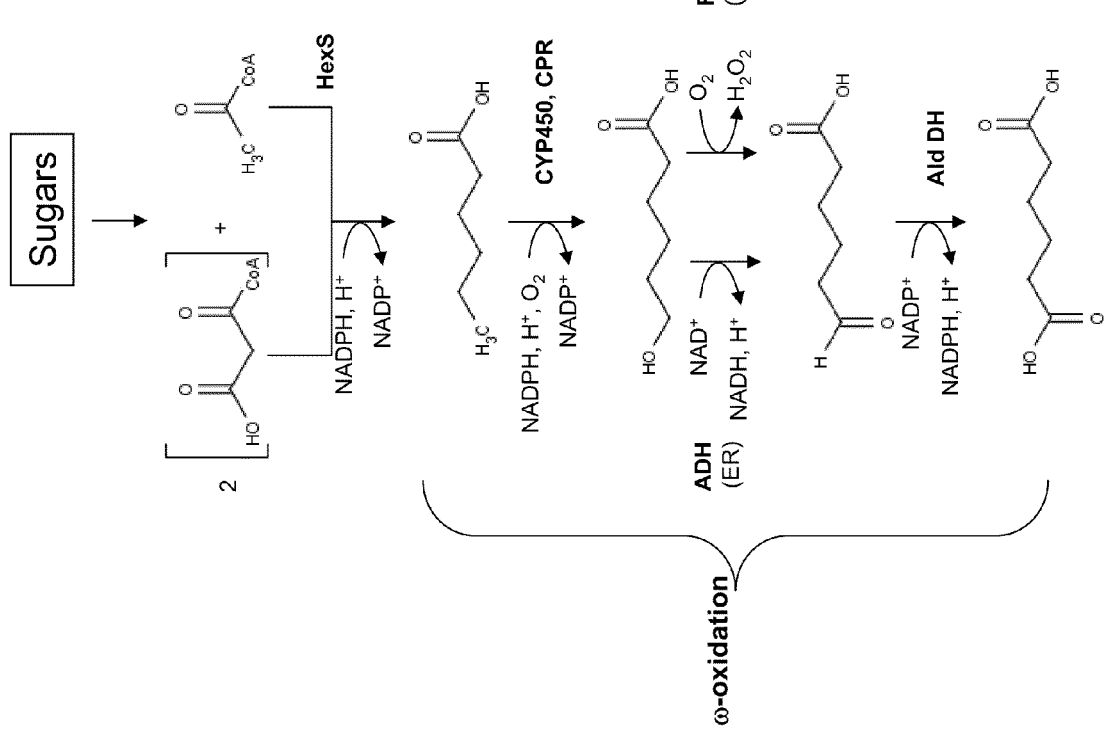
FIG. 9 depicts a metabolic pathway for making adipic acid from saccharide or polysaccharide carbon sources, similar to the pathway depicted in FIG. 1, with additional activities that aid in metabolism of, or enhance metabolism of, pathway intermediates, thereby potentially increasing the yield of adipic acid. The additional activities are a monooxygenase reductase activity (cytochrome P450 reductase or CPR) and a fatty alcohol oxidase activity (FAO). Part, or all, of the pathway can be engineered into a eukaryotic microorganism to generate a microorganism capable of producing adipic acid.

As depicted in FIGS. 1, 9, and 36, the enzyme hexanoate synthase converts two molecules of malonyl-CoA and one molecule of acetyl-CoA to one molecule of hexanoic acid. As depicted in FIG. 36, fatty acid synthase converts malonyl-CoA to a long chain fatty acyl-CoA by repeated condensation with acetyl-CoA. In some embodiments a cytochrome P450 enzyme converts hexanoic acid to 6-hydroxyhexanoic acid, which may be oxidized to 6-oxohexanoic acid via 6-hydroxyhexanoic acid dehydrogenase, or fatty alcohol oxidase. 6-oxohexanoic acid may be converted to adipic acid by 6-oxohexanoic acid dehydrogenase. In certain embodiments, a cytochrome P450 enzyme converts medium-, or long-chain fatty acids to dicarboxylic acids (e.g., diacids), which may be further metabolized by natural or engineered pathways described herein to yield adipic acid.

A fatty acid synthase enzyme (FAS) is coded by fatty acid synthase subunit alpha (FAS2) and fatty acid synthase subunit beta (FAS1) genes. In some embodiments, the FAS enzyme is endogenous to the host microorganism. Fatty acid synthase activity in yeast may be amplified by over-expression of the FAS2 and FAS1 genes by any suitable method. Non-limiting examples of methods suitable to amplify or over express FAS2 and FAS1 genes include amplifying the number of FAS2 and FAS1 genes in yeast following transformation with a high-copy number plasmid (e.g., such as one containing a 2 u origin of replication), integration of multiple copies of FAS2 and FAS1 genes into the yeast genome, over-expression of the FAS2 and FAS1 genes directed by a strong promoter, the like or combinations thereof. The FAS2 and FAS1 genes may be native to *C. tropicalis*, or they may be obtained from a heterologous source.

A specialized fatty acid synthase enzyme, hexanoate synthase (HexS) is coded by hexonate synthase subunit alpha (HEXA) and hexanoate synthase subunit beta (HEXB) genes. In some embodiments, the HexS enzyme is endogenous to the host microorganism. In certain embodiments, HEXA and HEXB genes may be isolated from a suitable organism (e.g., *Aspergillus parasiticus*). In some embodiments, HEXA and HEXB orthologs, such as STCJ and STCK, also may be isolated from suitable organisms (e.g., *Aspergillus nidulans*).

Hexanoate is omega-hydroxylated by the activity of cytochrome P450 enzymes, thereby generating a six carbon alcohol, in some embodiments. In certain embodiments, a cytochrome P450 activity can be increased by increasing the number of copies of a cytochrome P450 gene (e.g., 2, 3, 4, 5, 6, 7, 8, 9, 10, 15, 20, 25 or more copies of the gene), by increasing the activity of a promoter that regulates transcription of a cytochrome P450 gene, or by increasing the number of copies of a cytochrome P450 gene and increasing the activity of a promoter that regulates transcription of a cytochrome P450 gene, thereby increasing the production of target product (e.g., adipic acid) via increased activity of one or more cytochrome P450 enzymes. In some embodiments, a cytochrome P450 enzyme is endogenous to the host microorganism. In certain embodiments, the cytochrome P450 gene is isolated from *Bacillus megaterium* and codes for a single subunit, soluble, cytoplasmic enzyme. Soluble or membrane bound cytochrome P450 from certain host organisms is specific for 6-carbon substrates and may be used in some embodiments. Cytochrome P450 is reduced by the activity of cytochrome P450 reductase (CPR), thereby recycling cytochrome P450 to allow further enzymatic activity. In certain embodiments, the CPR enzyme is endogenous to the host microorganism. In some embodiments, host CPR activity can be increased by increasing the number of copies of a CPR gene (e.g., 2, 3, 4, 5, 6, 7, 8, 9, 10, 15, 20, 25 or more copies of the gene), by increasing the activity of a promoter that regulates transcription of a CPR gene, or by increasing the number of copies of a CPR gene and increasing the activity of a promoter that regulates transcription of a CPR gene, thereby increasing the production of target product (e.g., adipic acid) via increased recycling of cytochrome P450. In certain embodiments, the promoter can be a heterologous promoter (e.g., endogenous or exogenous promoter). In some embodiments, the CPR gene is heterologous and exogenous and can be isolated from any suitable organism. Non-limiting examples of organisms from which a CPR gene can be isolated include *C. tropicalis, S. cerevisiae* and *Bacillus megaterium*.

Oxidation of the alcohol to an aldehyde may be performed by an enzyme in the fatty alcohol oxidase family (e.g., 6-hydroxyhexanoic acid dehydrogenase, omega hydroxyl fatty acid dehydrogenase), or an enzyme in the aldehyde dehydrogenase family (e.g., 6-oxohexanoic acid dehydrogenase, omega oxo fatty acid dehydrogenase). The enzyme 6-oxohexanoic acid dehydrogenase or omega oxo fatty acid dehydrogenase may oxidize the aldehyde to the carboxylic acid adipic acid. In some embodiments, the enzymes 6-hydroxyhexanoic acid dehydrogenase, omega hydroxyl fatty acid dehydrogenase, fatty alcohol oxidase, 6-oxohexanoic acid dehydrogenase, or omega oxo fatty acid dehydrogenase, exist in a host organism. Flux through these two steps may sometimes be augmented by increasing the copy number of the enzymes, or by increasing the activity of the promoter transcribing the genes. In some embodiments alcohol and aldehyde dehydrogenases specific for six carbon substrates may be isolated from another organism, for example *Acinetobacter, Candida, Saccharomyces* or *Pseudomonas* and inserted into the host organism.

Figure 10:
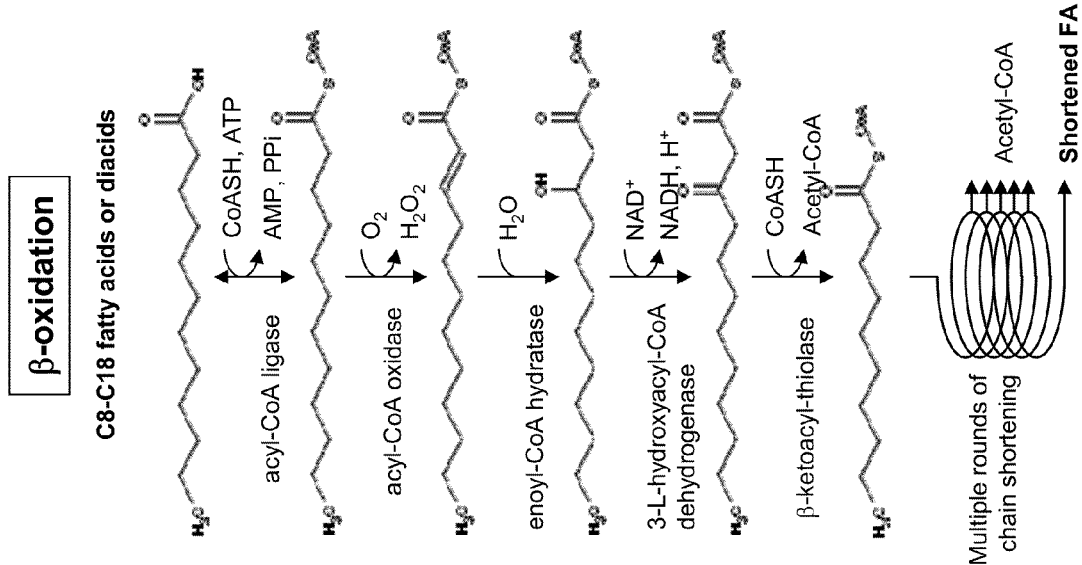
FIG. 10 depicts a non-limiting example of a metabolic pathway for making adipic acid from paraffins, fats, oils, fatty acids or dicarboxylic acids, as described in FIG. 2. Part, or all, of the pathway can be engineered (e.g., added, altered to increase or decrease copy number, or increase or decrease promoter activity, depending on the desired effect) into a microorganism, depending on the activities already present in the host organism, to generate a microorganism capable of producing adipic acid.
Figure 37:
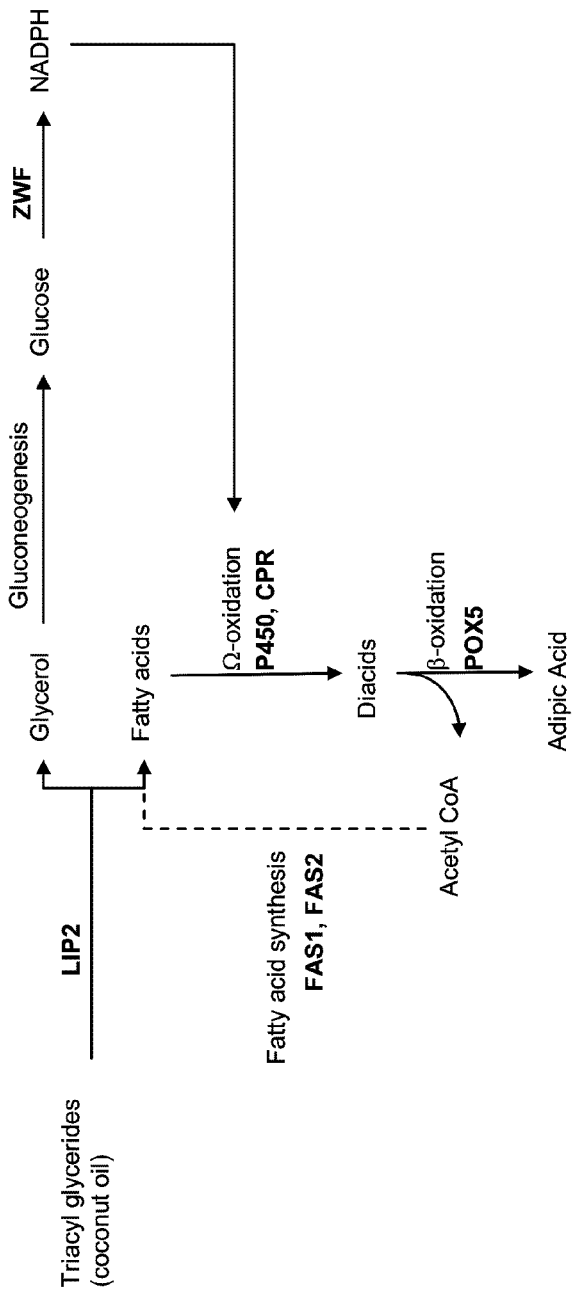
FIG. 37 depicts a non-limiting example of a metabolic pathway for making adipic acid from paraffins, fats, oils, fatty acids or dicarboxylic acids, as described in FIGS. 2 and 10, with additional activities that aid in metabolism of, or enhance metabolism of, pathway intermediates, thereby potentially increasing the yield of adipic acid. The additional activities are a lipase, a fatty acid synthase, a glucose-6-phosphate dehydrogenase (ZWF1), a monooxygenase (P450) activity, and a monooxygenase reductase activity (CPR). Part, or all, of the pathway can be engineered (e.g., added, altered to increase or decrease copy number, or increase or decrease promoter activity, depending on the desired effect) into a microorganism, depending on the activities already present in the host organism, to generate a microorganism capable of producing adipic acid.

FIGS. 10 and 37 depict embodiments of biological pathways for making adipic acid, using fats, oils, dicarboxylic acids, paraffins (e.g., linear, branched, substituted, saturated, unsaturated, the like and combinations thereof), fatty alcohols, fatty acids, or the like, as the carbon source starting material. Any suitable fatty alcohol, fatty acid, paraffin, dicarboxylic acid, fat or oil can be used as the feedstock for the organism, (e.g., hexane, hexanoic acid, oleic acid, coconut oil, the like or combinations thereof). Carbon sources with longer chain lengths (e.g., 8 carbons or greater in length) can be metabolized using naturally occurring and/or engineered pathways to yield molecules that can be further metabolized using the beta oxidation pathway shown in FIG. 10 and the lower portion of FIGS. 11A and 37. In some embodiments, the activities in the pathway shown in FIGS. 10 and 37 also can be engineered (e.g., as described herein) to enhance metabolism and target product formation.

In certain embodiments, one or more activities in one or more metabolic pathways can be engineered to increase carbon flux through the engineered pathways to produce a desired product (e.g., adipic acid). The engineered activities can be chosen to allow increased production of metabolic intermediates that can be utilized in one or more other engineered pathways to achieve increased production of a desired product with respect to the unmodified host organism. This "carbon flux management" can be optimized for any chosen feedstock, by engineering the appropriate activities in the appropriate pathways. A non-limiting example is given herein using an oil (e.g. coconut oil) based feedstock (see FIG. 37). The engineered activities increase the production of adipic acid through the increased activities in a number of pathways (e.g., fatty acid degradation, fatty acid synthesis, gluconeogenesis, pentose phosphate pathway, beta oxidation, omega oxidation). The pathways utilized in the non-limiting examples presented herein were chosen to maximize the production of adipic acid by regenerating or utilizing metabolic byproducts to internally generate additional carbon sources that can be further metabolized to produce adipic acid. The process of "carbon flux management" through engineered pathways produces adipic acid at a level and rate closer to the calculated maximum theoretical yield for any given feedstock, in certain embodiments. The terms "theoretical yield" or "maximum theoretical yield" as used herein refer to the yield of product of a chemical or biological reaction that would be formed if the reaction went to completion. Theoretical yield is based on the stoichiometry of the reaction and ideal conditions in which starting material is completely consumed, undesired side reactions do not occur, the reverse reaction does not occur, and there no losses in the work-up procedure. The overall yield of product depends on the limiting reagent. In the embodiment depicted in FIG. 37, carbon flux management is achieved by the production of adipic acid from fatty acids liberated from triacylglycerides, and synthesis of glucose through gluconeogenesis which is subsequently converted to adipic acid through the engineered pentose phosphate pathway, omega oxidation pathway and beta oxidation pathway, as described herein.

Fats, oils, paraffins and the like frequently contain triacylglycerides that can be converted into one or more products useful for producing adipic acid utilizing engineered microorganisms described herein. Triacylglycerides can be converted into glycerol and fatty acids by a lipase activity, as shown in FIG. 37. Lipases catalyze the hydrolysis of ester chemical bonds in water-insoluble lipid (e.g., fats, oils, paraffins) substrates. The generalized reaction can be represented by;

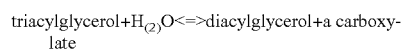

triacylglycerol+H$_{(2)}$O<=>diacylglycerol+a carboxylate

Lipase activity often is associated with activation of other activities or pathways, by its involvement with protein lipoylation. Certain lipases are involved in the modification of mitochondrial enzymes. Increasing lipase activity in an engineered microorganism can enhance the utilization of fats, oils, paraffins and the like as feedstocks for production of adipic acid by increasing overall carbon flux through the native and engineered pathways of a host microorganism.

Fatty acids cleaved from a glycerol backbone can be further metabolized directly, or indirectly via utilization in synthesis pathways that yield products that subsequently can be metabolized, by native and/or engineered (i) omega oxidation pathways, (ii) beta oxidation pathways, (iii) fatty acid synthase pathways, (iv) hexanoate synthase pathways, or (v) combinations thereof, described herein and shown in FIG. 37. In some embodiments, the pathway by which a fatty acid is further directly or indirectly metabolized into adipic acid, is determined by fatty acid chain length.

The glycerol backbone also can be further metabolized (e.g., directly and/or indirectly) to yield adipic acid, by entry into the gluconeogenesis pathway to yield glucose. To further increase production of adipic acid, metabolism of the increased carbon flux through gluconeogenesis can be enhanced by increasing glucose-6-phosphate dehydrogenase activity. Glucose-6-phosphate dehydrogenase (EC 1.1.1.49) catalyzes the first step of the pentose phosphate pathway, and is encoded by the *C. tropicalis* gene, ZWF. The reaction for the first step in the PPP pathway is;

D-glucose 6-phosphate+NADP+=D-glucono-1,5-lactone 6-phosphate+NADPH+H+

This reaction is irreversible and rate-limiting for efficient fermentation of sugar via the Entner-Doudoroff pathway. The enzyme regenerates NADPH from NADP+ and is important both for maintaining cytosolic levels of NADPH and protecting yeast against oxidative stress. Glucoses-6-phosphate expression in yeast is constitutive, and the activity is inhibited by NADPH such that processes that decrease the cytosolic levels of NADPH stimulate the oxidative branch of the pentose phosphate pathway. Amplification of glucose-6-phosphate dehydrogenase activity in yeast may be desirable to increase the proportion of glucose-6-phosphate converted to 6-phosphoglucono-lactone and thereby improve conversion of sugar (e.g., glucose) to adipic acid via metabolism into products that can be further metabolized by native and/or engineered (i) omega oxidation pathways, (ii) beta oxidation pathways, (iii) fatty acid synthase pathways, (iv) hexanoate synthase pathways, or (v) combinations thereof, described herein, and shown in FIG. 37.

Glucose-6-phosphate dehydrogenase (EC 1.1.1.49) activity in yeast may be amplified by over-expression of the ZWF gene by any suitable method. Non-limiting examples of methods suitable to amplify or over express ZWF include amplifying the number of ZWF genes in yeast following transformation with a high-copy number plasmid (e.g., such as one containing a 2 u origin of replication), integration of multiple copies of ZWF into the yeast genome, over-expression of the ZWF gene directed by a strong promoter, the like or combinations thereof. The ZWF gene may be native to *C. tropicalis*, or it may be obtained from a heterologous source.

Depicted in the first step of the reaction in FIG. 10, the enzyme acyl-CoA ligase converts a long chain fatty alcohol, fatty acid or dicarboxylic acid and 1 molecule of acetyl-CoA into an acyl-CoA derivative of the long chain fatty alcohol, fatty acid or dicarboxylic acid with the conversion of ATP to AMP and inorganic phosphate. The term "beta oxidation pathway" as used herein, refers to a series of enzymatic activities utilized to metabolize fatty alcohols, fatty acids, or dicarboxylic acids.

The activities utilized to metabolize fatty alcohols, fatty acids, or dicarboxylic acids include, but are not limited to, acyl-CoA ligase activity, acyl-CoA oxidase activity, acyl-CoA hydrolase, acyl-CoA thioesterase enoyl-CoA hydratase activity, 3-hydroxyacyl-CoA dehydrogenase activity and acetyl-CoA C-acyltransferase activity. The term "beta oxidation activity" refers to any of the activities in the beta oxidation pathway utilized to metabolize fatty alcohols, fatty acids or dicarboxylic acids. The term "omega oxidation activity" refers to any of the activities in the omega oxidation pathway utilized to metabolize fatty alcohols, fatty acids, dicarboxylic acids, or sugars.

In certain embodiments, an acyl-CoA ligase enzyme converts a long chain fatty alcohol, fatty acid or dicarboxylic acid into the acyl-CoA derivative, which may be oxidized to yield a trans-2,3-dehydroacyl-CoA derivative, by the activity of Acyl CoA oxidase (e.g., also known as acyl-CoA oxidoreductase and fatty acyl-coenzyme A oxidase). The trans-2,3-dehydroacyl-CoA derivative long chain fatty alcohol, fatty acid or dicarboxylic acid may be further converted to 3-hydroxyacyl-CoA by the activity of enoyl-CoA hydratase. 3-hydroxyacyl-CoA can be converted to 3-oxoacyl-CoA by the activity of 3-hydroxyacyl-CoA dehydrogenase. 3-oxoacyl-CoA may be converted to an acyl-CoA molecule, shortened by 2 carbons and an acetyl-CoA, by the activity of Acetyl-CoA C-acyltransferase (e.g., also known as beta-ketothiolase and -ketothiolase). In some embodiments, acyl-CoA molecules may be repeatedly shortened by beta oxidation until a desired carbon chain length is generated (e.g., 6 carbons, adipic acid). The shortened fatty acid can be further processed using omega oxidation to yield adipic acid.

An acyl-CoA ligase enzyme sometimes is encoded by the host organism and can be added to generate an engineered organism. In some embodiments, host acyl-CoA ligase activity can be increased by increasing the number of copies of an acyl-CoA ligase gene, by increasing the activity of a promoter that regulates transcription of an acyl-CoA ligase gene, or by increasing the number copies of the gene and by increasing the activity of a promoter that regulates transcription of the gene, thereby increasing production of target product (e.g., adipic acid) due to increased carbon flux through the pathway. In certain embodiments, the acyl-CoA ligase gene can be isolated from any suitable organism. Non-limiting examples of organisms that include, or can be used as donors for, acyl-CoA ligase enzymes include *Candida, Saccharomyces*, or *Yarrowia*.

An enoyl-CoA hydratase enzyme catalyzes the addition of a hydroxyl group and a proton to the unsaturated β-carbon on a fatty-acyl CoA and sometimes is encoded by the host organism and sometimes can be added to generate an engineered organism. In certain embodiments, the enoyl-CoA hydratase activity is unchanged in a host or engineered organism. In some embodiments, the host enoyl-CoA hydratase activity can be increased by increasing the number of copies of an enoyl-CoA hydratase gene, by increasing the activity of a promoter that regulates transcription of an enoyl-CoA hydratase gene, or by increasing the number copies of the gene and by increasing the activity of a promoter that regulates transcription of the gene, thereby increasing the production of target product (e.g., adipic acid) due to increased carbon flux through the pathway. In certain embodiments, the enoyl-CoA hydratase gene can be isolated from any suitable organism. Non-limiting examples of organisms that include, or can be used as donors for, enoyl-CoA hydratase enzymes include *Candida, Saccharomyces*, or *Yarrowia*.

3-hydroxyacyl-CoA dehydrogenase enzyme catalyzes the formation of a 3-ketoacyl-CoA by removal of a hydrogen from the newly formed hydroxyl group created by the activity of enoyl-CoA hydratase. In some embodiments, the activity is encoded by the host organism and sometimes can be added or increased to generate an engineered organism. In certain embodiments, the 3-hydroxyacyl-CoA activity is unchanged in a host or engineered organism. In some embodiments, the host 3-hydroxyacyl-CoA dehydrogenase activity can be increased by increasing the number of copies of a 3-hydroxyacyl-CoA dehydrogenase gene, by increasing the activity of a promoter that regulates transcription of a 3-hydroxyacyl-CoA dehydrogenase gene, or by increasing the number copies of the gene and by increasing the activity of a promoter that regulates transcription of the gene, thereby increasing production of target product (e.g., adipic acid) due to increased carbon flux through the pathway. In certain embodiments, the 3-hydroxyacyl-CoA dehydrogenase gene can be isolated from any suitable organism. Non-limiting examples of organisms that include, or can be used as donors for, 3-hydroxyacyl-CoA dehydrogenase enzymes include *Candida, Saccharomyces*, or *Yarrowia*.

An Acetyl-CoA C-acyltransferase (e.g., -ketothiolase) enzyme catalyzes the formation of a fatty acyl-CoA shortened by 2 carbons by cleavage of the 3-ketoacyl-CoA by the thiol group of another molecule of CoA. The thiol is inserted between C-2 and C-3, which yields an acetyl CoA molecule and an acyl CoA molecule that is two carbons shorter. An Acetyl-CoA C-acyltransferase sometimes is encoded by the host organism and sometimes can be added to generate an engineered organism. In certain embodiments, the acetyl-CoA C-acyltransferase activity is unchanged in a host or engineered organism. In some embodiments, the host acetyl-CoA C-acyltransferase activity can be increased by increasing the number of copies of an acetyl-CoA C-acyltransferase gene, or by increasing the activity of a promoter that regulates transcription of an acetyl-CoA C-acyltransferase gene, thereby increasing the production of target product (e.g., adipic acid) due to increased carbon flux through the pathway. In certain embodiments, the acetyl-CoA C-acyltransferase gene can be isolated from any suitable organism. Non-limiting examples of organisms that include, or can be used as donors for, acetyl-CoA C-acyltransferase enzymes include *Candida, Saccharomyces*, or *Yarrowia*.

Figure 42A:
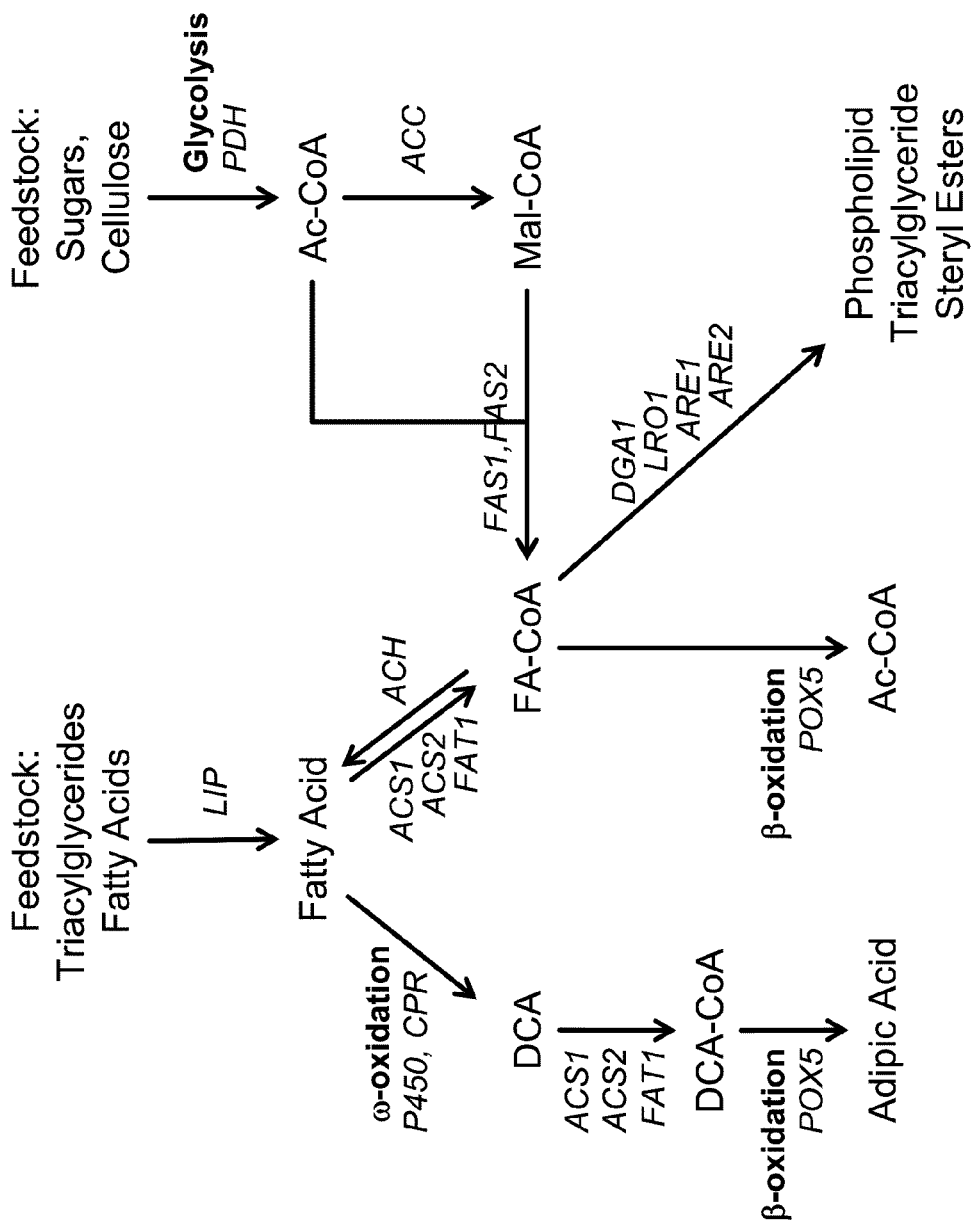
FIG. 42A depicts naturally occurring metabolic pathways which together combine to produce adipic acid, acetyl-CoA, and phospholipids, triacylglycerides and steryl esters from a number of different feedstocks (e.g., triacylglycerides, fatty acids, sugars, cellulose). Production of adipic acid is accompanied by the production of energy and carbon dioxide. Production of acetyl-CoA is accompanied by the production of biomass, energy and carbon dioxide. Production of phospholipids, triacylglycerides and steryl esters is accompanied by the production of biomass and carbon storage moieties (e.g., triacylglycerides and steryl esters).
Figure 42B:
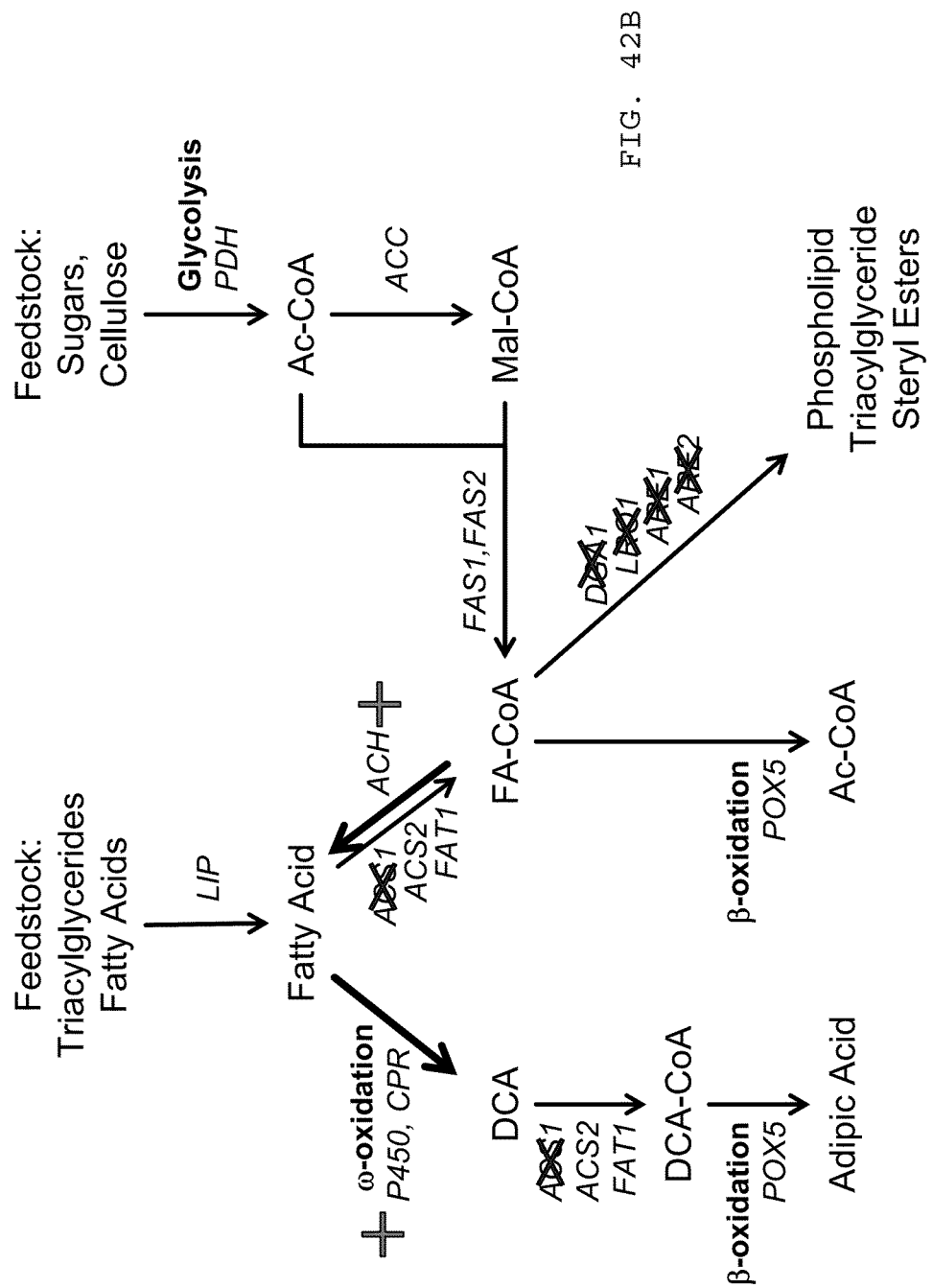
FIG. 42B depicts modifications to the various metabolic pathways, illustrated in FIG. 42A, which alter the host organism's carbon flux towards the production of adipic acid through increased fatty acid production, increased omega oxidation and increased beta oxidation. The altered activities are highlighted by a + for activities that are added or increased and by an X for activities that are reduced or eliminated.

FIGS. 42A and 42B illustrate pathways that can be manipulated to produce adipic acid from sugars, cellulose, triacylglycerides and fatty acids. Illustrated in FIG. 42A are various activities normally active in a host organism, whereas FIG. 42B illustrates activities, that when manipulated, direct the flow of carbon in the host organism towards the production of adipic acid through increased fatty acid production and increased omega and beta oxidation activities. As shown in FIG. 42B, activities that are increased or added are shown with a "+" and activities that are reduced or eliminated are shown with a "X". In addition to directing the flow of carbon towards the production of adipic acid through increased fatty acid production and increased omega and beta oxidation activities, the altered activities in the pathways illustrated in FIGS. 42A and 42B direct the flow of carbon away from the production of biomass and carbon storage molecules (e.g., starch, lipids, triacylglycerides, the like, combinations thereof) and away from the utilization of fatty acids for energy. Increased activities shown in FIGS. 42A and 42B (e.g., monooxygenase (e.g., P450), monooxygenase reductase (e.g., CPR), and thioesterase (e.g., ACH and TESA)) are described herein.

A microorganism may be modified and engineered to include or regulate one or more activities in an adipic acid pathway. The term "activity" as used herein refers to the functioning of a microorganism's natural or engineered biological pathways to yield various products including adipic acid and its precursors. Adipic acid producing activity can be provided by any non-mammalian source in certain embodiments. Such sources include, without limitation, eukaryotes such as yeast and fungi and prokaryotes such as bacteria. In some embodiments, a reverse activity in a pathway described herein can be altered (e.g., disrupted, reduced) to increase carbon flux through a beta oxidation pathway, an omega oxidation pathway, or a beta oxidation and omega oxidation pathway, towards the production of target product (e.g., adipic acid). In some embodiments, a genetic modification disrupts an activity in the beta oxidation pathway, or disrupts a polynucleotide that encodes a polypeptide that carries out a forward reaction in the beta oxidation pathway, which renders beta oxidation activity undetectable. The term "undetectable" as used herein refers to an amount of an analyte that is below the limits of detection, using detection methods or assays known (e.g., described herein). In certain embodiments, the genetic modification partially reduces beta oxidation activity. The term "partially reduces beta oxidation activity" as used here refers to a level of activity in an engineered organism that is lower than the level of activity found in the host or starting organism.

An activity within an engineered microorganism provided herein can include one or more (e.g., 1, 2, 3, 4, 5, 6, 7, 8, 9, 10, 11, 12, 13, 14 or all) of the following activities: 6-oxohexanoic acid dehydrogenase activity; 6-hydroxyhexanoic acid dehydrogenase activity; hexanoate synthase activity; cytochrome P450 activity; cytochrome P450 reductase activity; fatty alcohol oxidase activity; acyl-CoA ligase activity, acyl-CoA oxidase activity; enoyl-CoA hydratase activity, 3-hydroxyacyl-CoA dehydrogenase activity, fatty acid synthase activity, lipase activity, acyl-CoA carboxylase activity, glucose-6-phosphate dehydrogenase, and thioesterase activity (e.g., acyl-CoA hydrolase, acyl-CoA thioesterase, acetyl-CoA C-acyltransferase, beta-ketothiolase). In certain embodiments, one or more (e.g., 1, 2, 3, 4, 5, 6, 7, 8, 9, 10 or all) of the foregoing activities is altered by way of a genetic modification. In some embodiments, one or more (e.g., 1, 2, 3, 4, 5, 6, 7, 8, 9, 10, 11, 12, 13, 14 or all) of the foregoing activities is altered by way of (i) adding a heterologous polynucleotide that encodes a polypeptide having the activity, and/or (ii) altering or adding a regulatory sequence that regulates the expression of a polypeptide having the activity.

The term "6-oxohexanoic acid dehydrogenase activity" as used herein refers to conversion of 6-oxohexanoic acid to adipic acid. The 6-oxohexanoic acid dehydrogenase activity can be provided by a polypeptide. In some embodiments, the polypeptide is encoded by a heterologous nucleotide sequence introduced to a host microorganism. In certain embodiments, an endogenous polypeptide having the 6-oxohexanoic acid dehydrogenase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Nucleic acid sequences conferring 6-oxohexanoic acid dehydrogenase activity can be obtained from a number of sources, including *Actinobacter, Norcardia, Pseudomonas* and *Xanthobacter* bacteria. Examples of an amino acid sequence of a polypeptide having 6-oxohexanoic acid dehyrdogenase activity, and a nucleotide sequence of a polynucleotide that encodes the polypeptide, are presented herein. Presence, absence or amount of 6-oxohexanoic acid dehydrogenase activity can be detected by any suitable method known in the art. For an example of a detection method for alcohol oxidase or alcohol dehydrogenase activity (see Appl Environ Microbiol 70: 4872). In some embodiments, 6-oxohexanoic acid dehydrogenase activity is not altered in a host microorganism, and in certain embodiments, the activity is added or increased in the engineered microorganism relative to the host microorganism.

The term "omega oxo fatty acid dehydrogenase activity" as used herein refers to conversion of an omega oxo fatty acid to a dicarboxylic acid. The omega oxo fatty acid dehydrogenase activity can be provided by a polypeptide. In some embodiments, the polypeptide is encoded by a heterologous nucleotide sequence introduced to a host microorganism. In certain embodiments, an endogenous polypeptide having the omega oxo fatty acid dehydrogenase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Nucleic acid sequences conferring omega oxo fatty acid dehydrogenase activity can be obtained from a number of sources, including *Actinobacter, Norcardia, Pseudomonas* and *Xanthobacter* bacteria. Examples of an amino acid sequence of a polypeptide having omega oxo fatty acid dehydrogenase activity and a nucleotide sequence of a polynucleotide that encodes the polypeptide, are presented herein. Presence, absence or amount of omega oxo fatty acid dehydrogenase activity can be detected by any suitable method known in the art. In some embodiments, omega oxo fatty acid dehydrogenase activity is not altered in a host microorganism, and in certain embodiments, the activity is added or increased in the engineered microorganism relative to the host microorganism.

The term "6-hydroxyhexanoic acid dehydrogenase activity" as used herein refers to conversion of 6-hydroxyhexanoic acid to 6-oxohexanoic acid. The 6-hydroxyhexanoic acid dehydrogenase activity can be provided by a polypeptide. In some embodiments, the polypeptide is encoded by a heterologous nucleotide sequence introduced to a host microorganism. In certain embodiments, an endogenous polypeptide having the 6-hydroxyhexanoic acid dehydrogenase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Nucleic acid sequences conferring 6-hydroxohexanoic acid dehydrogenase activity can be obtained from a number of sources, including *Actinobacter, Norcardia, Pseudomonas*, and *Xanthobacter*. Examples of an amino acid sequence of a polypeptide having 6-hydroxyhexanoic acid dehydrogenase activity, and a nucleotide sequence of a polynucleotide that encodes the polypeptide, are presented herein. Presence, absence or amount of 6-hydroxyhexanoic acid dehydrogenase activity can be detected by any suitable method known in the art. An example of such a method is described in Methods in Enzymology, 188: 176. In some embodiments, 6-hydroxyhexanoic acid dehydrogenase activity is not altered in a host microorganism, and in certain embodiments, the activity is added or increased in the engineered microorganism relative to the host microorganism.

The term "omega hydroxyl fatty acid dehydrogenase activity" as used herein refers to conversion of an omega hydroxyl fatty acid to an omega oxo fatty acid. The omega hydroxyl fatty acid dehydrogenase activity can be provided by a polypeptide. In some embodiments, the polypeptide is encoded by a heterologous nucleotide sequence introduced to a host microorganism. In certain embodiments, an endogenous polypeptide having the omega hydroxyl fatty acid dehydrogenase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Nucleic acid sequences conferring omega hydroxyl fatty acid dehydrogenase activity can be obtained from a number of sources, including *Actinobacter, Norcardia, Pseudomonas* and *Xanthobacter* bacteria. Examples of an amino acid sequence of a polypeptide having omega hydroxyl fatty acid dehydrogenase activity and a nucleotide sequence of a polynucleotide that encodes the polypeptide, are presented herein. Presence, absence or amount of omega hydroxyl fatty acid dehydrogenase activity can be detected by any suitable method known in the art. In some embodiments, omega hydroxyl fatty acid dehydrogenase activity is not altered in a host microorganism, and in certain embodiments, the activity is added or increased in the engineered microorganism relative to the host microorganism.

The term "lipase activity" as used herein refers to the hydrolysis of triacylglycerol to produce a diacylglycerol and a fatty acid anion. The lipase activity can be provided by a polypeptide. In certain embodiments, an endogenous polypeptide having the lipase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Examples of a nucleotide sequence of a polynucleotide that encodes a polypeptide having lipase activity, and amino acid sequences that code a lipase activity are presented herein. In some embodiments, lipase activity is not altered in a host microorganism, and in certain embodiments, the activity is added or increased in the engineered microorganism relative to the host microorganism. Presence, absence or amount of lipase activity can be detected by any suitable method known in the art, including western blot analysis.

The term "glucose-6-phosphate dehydrogenase activity" as used herein refers to the conversion of D-glucose 6-phosphate into D-glucono-1,5-lactone 6-phosphate. Glucose-6-phosphate dehydrogenase is an activity that forms part of the pentose phosphate pathway. Glycerol backbones liberated from fatty acids by a lipase activity can ultimately be converted to glucose by the action of the gluconeogenesis pathway, where glycerol is first converted to dihydroxyacetone phosphate. Glucose can be preferentially metabolized by the pentose phosphate pathway by increasing one or more activities in the pentose phosphate pathway (e.g., glucose-6-phosphate dehydrogenase). In addition to increasing the conversion of D-glucose 6-phosphate into D-glucono-1,5-lactone 6-phosphate, increasing the level of glucose-6-phosphate dehydrogenase activity also may yield advantageous benefits due to the additional reducing power generated by the increased activity of glucose-6-phosphate dehydrogenase. In some embodiments, increasing the activity of glucose-6-phosphate dehydrogenase increases the activity of a gluconeogenesis pathway, a pentose phosphate pathway or a gluconeogenesis pathway and a pentose phosphate pathway due to a forward biased increased carbon flux through the pathways.

A glucose-6-phosphate dehydrogenase (G6PD) activity may be provided by an enzyme. The glucose-6-phosphate dehydrogenase activity can be provided by a polypeptide. In certain embodiments, an endogenous polypeptide having the glucose-6-phosphate dehydrogenase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Examples of a nucleotide sequence of a polynucleotide that encodes a polypeptide having glucose-6-phosphate dehydrogenase activity, is presented herein. In some embodiments, glucose-6-phosphate dehydrogenase activity is not altered in a host microorganism, and in certain embodiments, the activity is added or increased in the engineered microorganism relative to the host microorganism. Presence, absence or amount of glucose-6-phosphate dehydrogenase activity can be detected by any suitable method known in the art including western blot analysis The term "acetyl-CoA carboxylase activity" as used herein refers to the irreversible carboxylation of acetyl-CoA to produce malonyl-CoA. Acetyl-CoA carboxylase activity may be provided by an enzyme that includes one or two subunits, depending on the source organism. The acetyl-CoA carboxylase synthase activity can be provided by a polypeptide. In certain embodiments, an endogenous polypeptide having the acetyl-CoA carboxylase activity is identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). An example of a nucleotide sequence of a polynucleotide that encodes a polypeptide having acetyl-CoA carboxylase activity, is presented herein. In some embodiments, acetyl-CoA carboxylase activity is not altered in a host microorganism, and in certain embodiments, the activity is added or increased in the engineered microorganism relative to the host microorganism. Presence, absence or amount of acetyl-CoA carboxylase activity can be detected by any suitable method known in the art including western blot analysis The term "fatty acid synthase activity" as used herein refers to conversion of acetyl-CoA and malonyl-CoA to fatty acids. Fatty acid synthase activity may be provided by an enzyme that includes one or two subunits (referred to hereafter as "subunit alpha" and/or "subunit beta"). The fatty acid synthase activity can be provided by a polypeptide. In certain embodiments, endogenous polypeptides having the fatty acid synthase activity are identified in the host microorganism, and the host microorganism is genetically altered to increase the amount of the polypeptide produced (e.g., a heterologous promoter is introduced in operable linkage with a polynucleotide that encodes the polypeptide; the copy number of a polynucleotide that encodes the polypeptide is increased (e.g., by introducing a plasmid that includes the polynucleotide)). Examples of a nucleotide sequence of a polynucleotide that encodes a polypeptide having fatty acid synthase activity, is presented herein. In some embodiments, fatty acid synthase activity is not altered in a host microorganism, and in certain embodiments, the activity is added or increased in the engineered microorganism relative to the host microorganism. Presence, absence or amount of fatty acid synthase activity can be detected by any suitable method known in the art, including western blot analysis.

The term "hexanoate synthase activity" as used herein refers to conversion of acetyl-CoA and malonyl-CoA to hexanoic acid. Hexanoate synthase activity may be provided by an enzyme that includes one or two subunits (referred to hereafter as "subunit A" and/or "subunit B"). The hexanoate synthase activity can be provided by a polypeptide. In some embodiments, the polypeptide is encoded by a heterologous nucleotide sequence introduced to a host microorganism. Nucleic acid sequences conferring hexonate synthase activity can be obtained from a number of sources, including *Aspergillus parisiticus*, for example. Examples of an amino acid sequence of a polypeptide having hexanoate synthase activity, and a nucleotide sequence of a polynucleotide that encodes the polypeptide, are presented herein. In some embodiments, hexanoate synthase activity is not altered in a host microorganism, and in certain embodiments, the activity is added or increased in the engineered microorganism relative to the host microorganism.

Presence, absence or amount of hexanoate synthase activity can be detected by any suitable method known in the art. An example of such a method is described in Hexanoate synthase+thioesterase (Chemistry and Biology 9: 981-988). Briefly, an indicator strain may be prepared. An indicator strain may be *Bacillus subtilis* containing a reporter gene (beta-galactosidase, green fluorescent protein, etc.) under control of the promoter regulated by LiaR, for example. An indicator strain also may be *Candida tropicalis* containing either the LiaR regulatable promoter from *Bacillus subtilis* or the alkane inducible promoter for the native gene for the peroxisomal 3-ketoacyl coenzyme A thiolase gene (CT-T3A), for example. Mutants with an improved functionality of HexS, thereby producing more hexanoic acid, can be plated onto a lawn of indicator strain. Upon incubation and growth of both the test mutant and the indicator strain, the appearance of a larger halo, which correlates to the induction of the reporter strain compared to control strains, indicates a mutant with improved activity. In alternative approach, mutants are grown in conditions favoring production of hexanoyl CoA or hexanoic acid and lysed. Cell lysates are treated with proteases which may release hexanoic acid from the PKS. Clarified lysates may be spotted onto lawns of indicator strains to assess improved production. In another alternative approach, indicator strains are grown under conditions suitable to support expression of the reporter gene when induced by hexanoic acid. Dilutions of a known concentration of hexanoic acid are used to determine a standard curve. Lysates of the test strain grown under conditions favoring production of hexanoic acid are prepared and dilutions of the lysate added to the indicator strain. Indicator strains with lysates are placed under identical conditions as used to determine the standard curve. The lysate dilutions that minimally support induction can be used to determine, quantitatively, the amount produced when compared to the standard curve.

The term "monooxygenase activity" as used herein refers to inserting one atom of oxygen from $O_2$ into an organic substrate (RH) and reducing the other oxygen atom to water. In some embodiments, monooxygenase activity refers to incorporation of an oxygen atom onto a six-carbon organic substrate. In certain embodiments, monooxygenase activity refers to conversion of hexanoate to 6-hydroxyhexanoic acid. Monooxygenase activity can be provided by any suitable polypeptide, such as a cytochrome P450 polypeptide (hereafter "CYP450") in certain embodiments. Nucleic acid sequences conferring CYP450 activity can be obtained from a number of sources, including *Bacillus megaterium* and may be induced in organisms including but not limited to *Candida tropicalis*, *Yarrowia lipolytica*, *Aspergillus nidulans*, and *Aspergillus parasiticus*. Examples of oligonucleotide sequences utilized to isolate a polynucleotide sequence encoding a polypeptide having CYP450 activity (e.g., CYP52A12 polynucleotide, a CYP52A13 polynucleotide, a CYP52A14 polynucleotide, a CYP52A15 polynucleotide, a CYP52A16 polynucleotide, a CYP52A17 polynucleotide, a CYP52A18 polynucleotide, a CYP52A19 polynucleotide, a CYP52A20 polynucleotide, a CYP52D2 polynucleotide, and/or a BM3 polynucleotide) are presented herein. In some embodiments, monooxygenase activity is not altered in a host microorganism, and in certain embodiments, the activity is added or increased in the engineered microorganism relative to the host microorganism. In some embodiments, the altered monooxygenase activity is an endogenous activity, and in certain embodiments, the altered monooxygenase activity is an exogenous activity. In some embodiments, the exogenous activity is a single polypeptide with both monooxygenase and monooxygenase reductase activities (e.g., *B. megaterium* cytochrome P450:NADPH P450 reductase).

Presence, absence or amount of cytochrome P450 activity can be detected by any suitable method known in the art. For example, detection can be performed by assaying a reaction containing cytochrome P450 (CYP52A family) and NADPH-cytochrome P450 reductase (see Appl Environ Microbiol 69: 5983 and 5992). Briefly, cells are grown under standard conditions and harvested for production of microsomes, which are used to detect CYP activity. Microsomes are prepared by lysing cells in Tris-buffered sucrose (10 mM Tris-HCl pH 7.5, 1 mM EDTA, 0.25M sucrose). Differential centrifugation is performed first at 25,000×g then at 100,000×g to pellet cell debris then microsomes, respectively. The microsome pellet is resuspended in 0.1M phosphate buffer (pH 7.5), 1 mM EDTA to a final concentration of approximately 10 mg protein/mL. A reaction mixture containing approximately 0.3 mg microsomes, 0.1 mM sodium hexanoate, 0.7 mM NADPH, 50 mM Tris-HCl pH 7.5 in 1 mL is initiated by the addition of NADPH and incubated at 37° C. for 10 minutes. The reaction is terminated by addition of 0.25 mL 5M HCl and 0.25 mL 2.5 ug/mL 10-hydroxydecanoic acid is added as an internal standard (3.3 nmol). The mixture is extracted with 4.5 mL diethyl ether under NaCl-saturated conditions. The organic phase is transferred to a new tube and evaporated to dryness. The residue is dissolved in acetonitrile containing 10 mM 3-bromomethyl-7-methoxy-1,4-benzoxazin-2-one (BrMB) and 0.1 mL of 15 mg/mL 18-crown-6 in acetonitril saturated with $K_2CO_3$. The solution is incubated at 40° C. for 30 minutes before addition of 0.05 mL 2% acetic acid. The fluorescently labeled omega-hydroxy fatty acids are resolved via HPLC with detection at 430 nm and excitation at 355 nm (Yamada et al., 1991, AnalBiochem 199: 132-136). Optionally, specifically induced CYP gene(s) may be detected by Northern blotting and/or quantitative RT-PCR. (Craft et al., 2003, AppEnvironMicro 69: 5983-5991).

The term "monooxygenase reductase activity" as used herein refers to the transfer of an electron from NAD(P)H, FMN, or FAD by way of an electron transfer chain, reducing the ferric heme iron of cytochrome P450 to the ferrous state. The term "monooxygenase reductase activity" as used herein also can refer to the transfer of a second electron via the electron transport system, reducing a dioxygen adduct to a negatively charged peroxo group. In some embodiments, a monooxygenase activity can donate electrons from the two-electron donor NAD(P)H to the heme of cytochrome P450 (e.g., monooxygenase activity) in a coupled two-step reaction in which NAD(P)H can bind to the NAD(P)H-binding domain of the polypeptide having the monooxygenase reductase activity and electrons are shuttled from NAD(P)H through FAD and FMN to the heme of the monooxygenase activity, thereby regenerating an active monooxygenase activity (e.g., cytochrome P450). Monooxygenase reductase activity can be provided by any suitable polypeptide, such as a cytochrome P450 reductase polypeptide (hereafter "CPR") in certain embodiments. Nucleic acid sequences conferring CPR activity can be obtained from and/or induced in a number of sources, including but not limited to *Bacillus megaterium*, *Candida tropicalis*, *Yarrowia lipolytica*, *Aspergillus nidulans*, and *Aspergillus parasiticus*. Examples of oligonucleotide sequences utilized to isolate a polynucleotide sequence encoding a polypeptide having CPR activity are presented herein. In some embodiments, monooxygenase reductase activity is not altered in a host microorganism, and in certain embodiments, the activity is added or increased in the engineered microorganism relative to the host microorganism. In some embodiments, the altered monooxygenase reductase activity is an endogenous activity, and in certain embodiments, the altered monooxygenase reductase activity is an exogenous activity. In some embodiments, the exogenous activity is a single polypeptide with both monooxygenase and monooxygenase reductase activities (e.g., *B. megaterium* cytochrome P450:NADPH P450 reductase).

Presence, absence or amount of CPR activity can be detected by any suitable method known in the art. For example, an engineered microorganism having an increased number of genes encoding a CPR activity, relative to the host microorganism, could be detected using quantitative nucleic acid detection methods (e.g., southern blotting, PCR, primer extension, the like and combinations thereof). An engineered microorganism having increased expression of genes encoding a CPR activity, relative to the host microorganism, could be detected using quantitative expression based analysis (e.g., RT-PCR, western blot analysis, northern blot analysis, the like and combinations thereof). Alternately, an enzymatic assay can be used to detect Cytochrome P450 reductase activity, where the enzyme activity alters the optical absorbance at 550 nanometers of a substrate solution (Masters, B. S. S., Williams, C. H., Kamin, H. (1967) Methods in Enzymology, X, 565-573).

The term "fatty alcohol oxidase activity" as used herein refers to inserting one atom of oxygen from $O_2$ into an organic substrate and reducing the other oxygen atom to peroxide. Fatty alcohol oxidase activity sometimes also is referred to as "long-chain-alcohol oxidase activity", "long-chain-alcohol: oxygen oxidoreductase activity", "fatty alcohol:oxygen oxidoreductase activity" and "long-chain fatty acid oxidase activity". In some embodiments, fatty alcohol oxidase activity refers to incorporation of an oxygen atom onto a six-carbon organic substrate. In certain embodiments, fatty alcohol oxidase activity refers to the conversion of 6-hydroxyhexanoic acid into 6-oxohexanoic acid. In some embodiments, fatty alcohol oxidase activity refers to the conversion of an omega hydroxyl fatty acid into an omega oxo fatty acid. A Fatty alcohol oxidase (FAO) activity can be provided by any suitable polypeptide, such as a fatty alcohol oxidase peptide, a long-chain-alcohol oxidase peptide, a long-chain-alcohol:oxygen oxidoreductase peptide, a fatty alcohol:oxygen oxidoreductase peptide and a long-chain fatty acid oxidase peptide. Nucleic acid sequences conferring FAO activity can be obtained from a number of sources, including but not limited to *Candida tropicalis*, *Candida cloacae*, *Yarrowia lipolytica*, and *Arabidopsis thaliana*. Examples of amino acid sequences of polypeptides having FAO activity, and nucleotide sequences of polynucleotides that encode the polypeptides, are presented herein. In some embodiments, fatty alcohol oxidase activity is not altered in a host microorganism, and in certain embodiments, the activity is added or increased in the engineered microorganism relative to the host microorganism. Presence, absence or amount of FAO activity can be detected by any suitable method known in the art. For example, an engineered microorganism having an increased number of genes encoding an FAO activity, relative to the host microorganism, could be detected using quantitative nucleic acid detection methods (e.g., southern blotting, PCR, primer extension, the like and combinations thereof). An engineered microorganism having increased expression of genes encoding an FAO activity, relative to the host microorganism, could be detected using quantitative expression based analysis (e.g., RT-PCR, western blot analysis, northern blot analysis, the like and combinations thereof). Alternately, an enzymatic assay can be used to detect fatty alcohol oxidase activity as described in Eirich et al, 2004, or as modified in the Examples herein.

The term "acyl-CoA oxidase activity" as used herein refers to the oxidation of a long chain fatty-acyl-CoA to a trans-2, 3-dehydroacyl-CoA fatty alcohol. In some embodiments, the acyl-CoA activity is from a peroxisome. In certain embodiments, the acyl-CoA oxidase activity is a peroxisomal acyl-CoA oxidase (POX) activity, carried out by a POX polypeptide. In some embodiments the acyl-CoA oxidase activity is encoded by the host organism and sometimes can be altered to generate an engineered organism. Acyl-CoA oxidase activity is encoded by the POX4 and POX5 genes of *C. tropicalis*. In certain embodiments, endogenous acyl-CoA oxidase activity can be increased. In some embodiments, acyl-CoA oxidase activity of the POX4 polypeptide or the POX5 polypeptide can be altered independently of each other (e.g., increase activity of POX4 alone, POX5 alone, increase one and disrupt the other, and the like). Increasing the activity of one POX activity, while disrupting the activity of another POX activity, may alter the specific activity of acyl-CoA oxidase with respect to carbon chain length, while maintaining or increasing overall flux through the beta oxidation pathway, in certain embodiments.

Figure 15A:
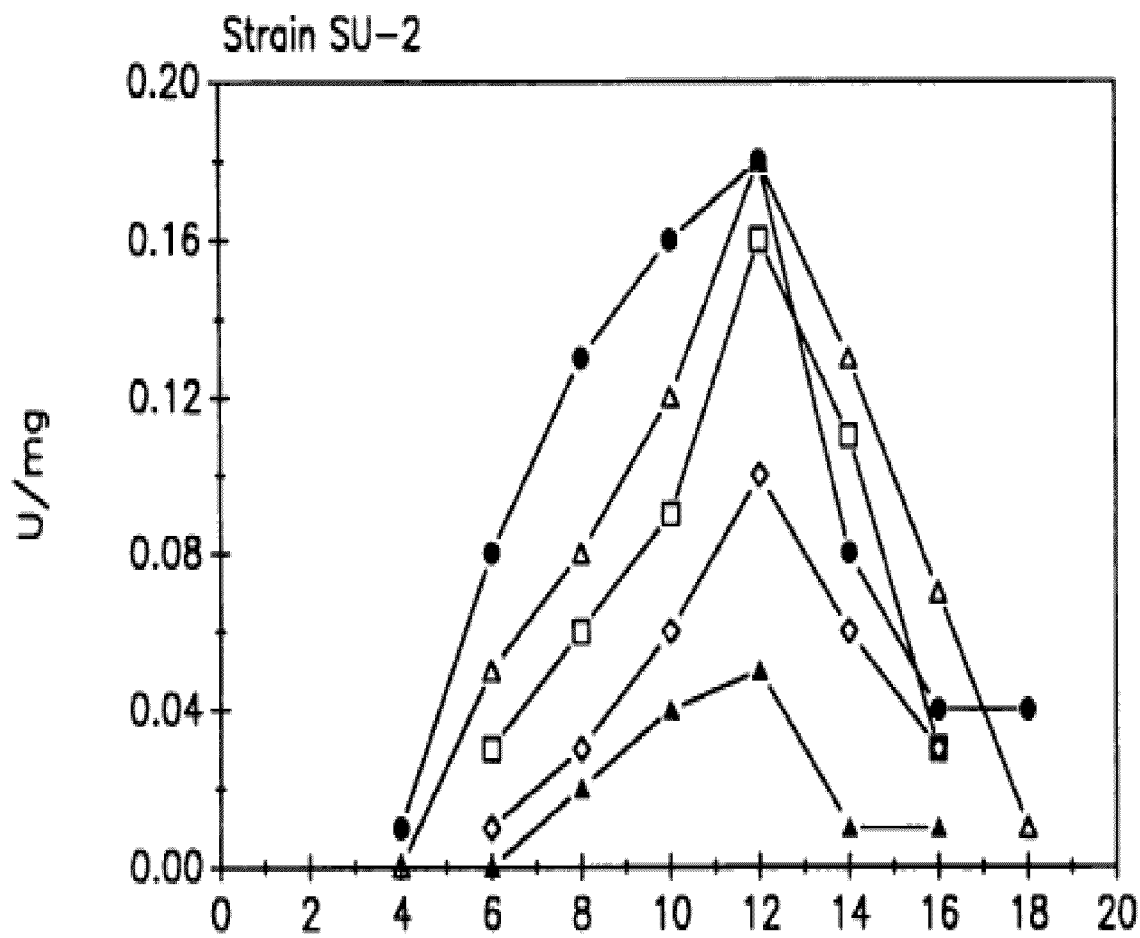
FIGS. 15A-15C illustrate results of acyl-CoA oxidase (POX) enzymatic activity assays on substrates of various carbon lengths, using acyl-CoA enzyme preparations from Candida tropicalis strains with no POX genes disrupted (see FIG. 15A), POX4 genes disrupted (see FIG. 15C) or POX5 genes disrupted (see FIG. 15B). Experimental results and conditions are given in the Detailed Description and Examples sections.
Figure 15B:
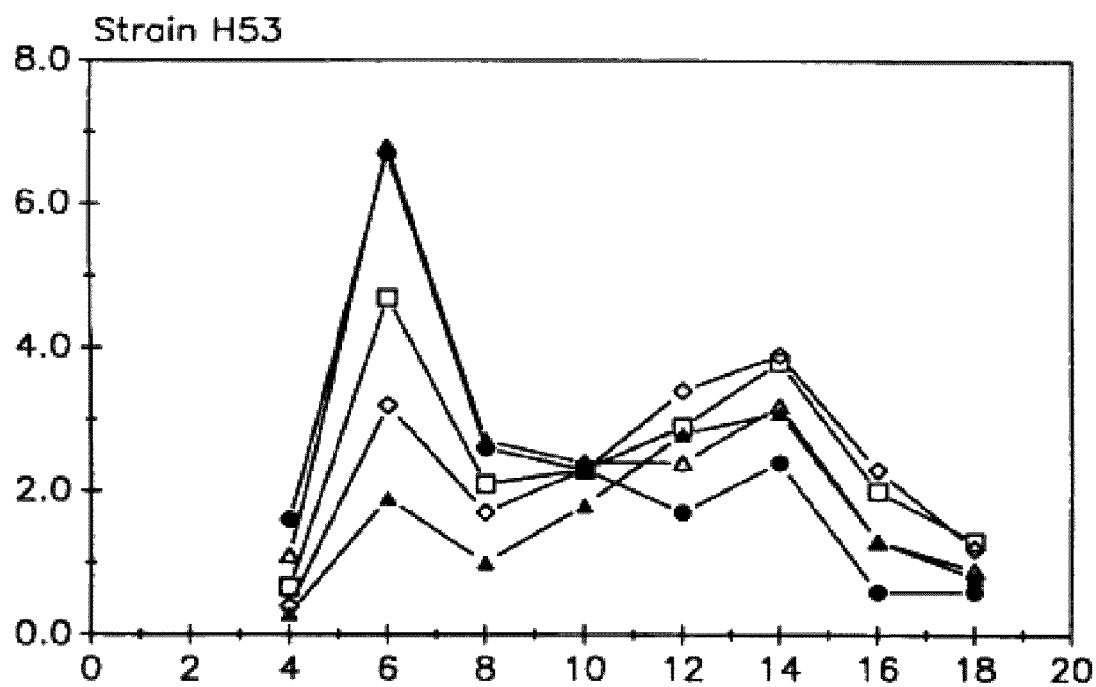
Figure 15C:
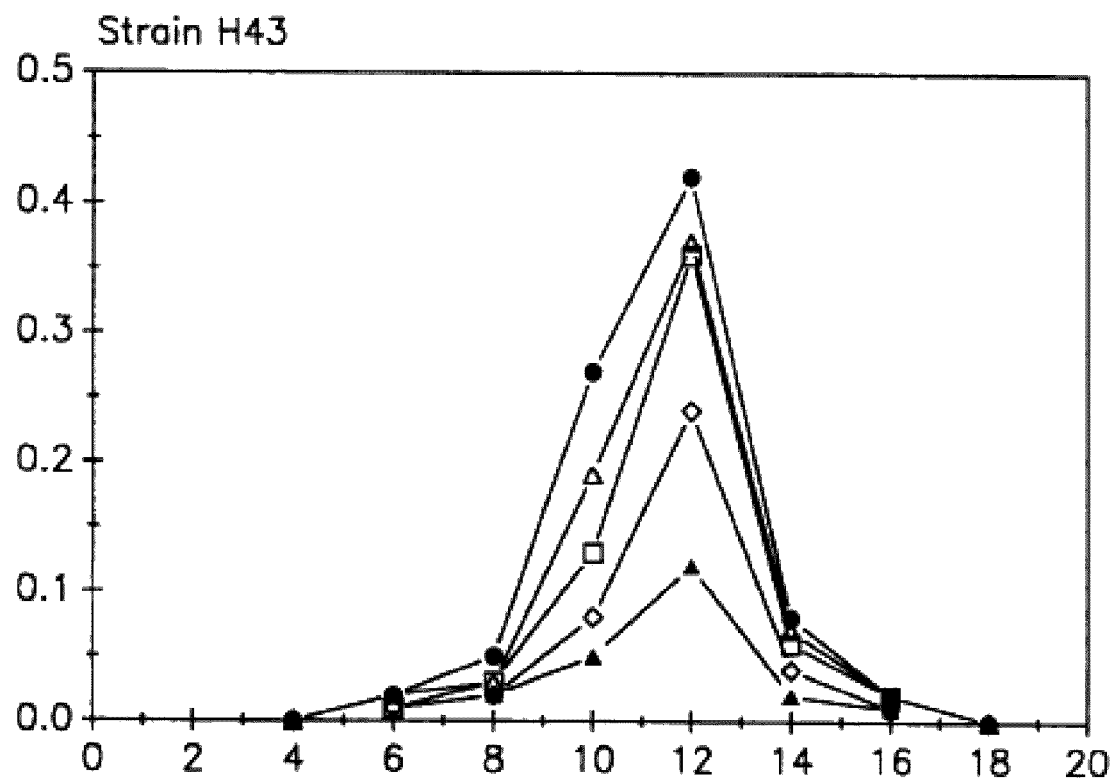
Figure 16:
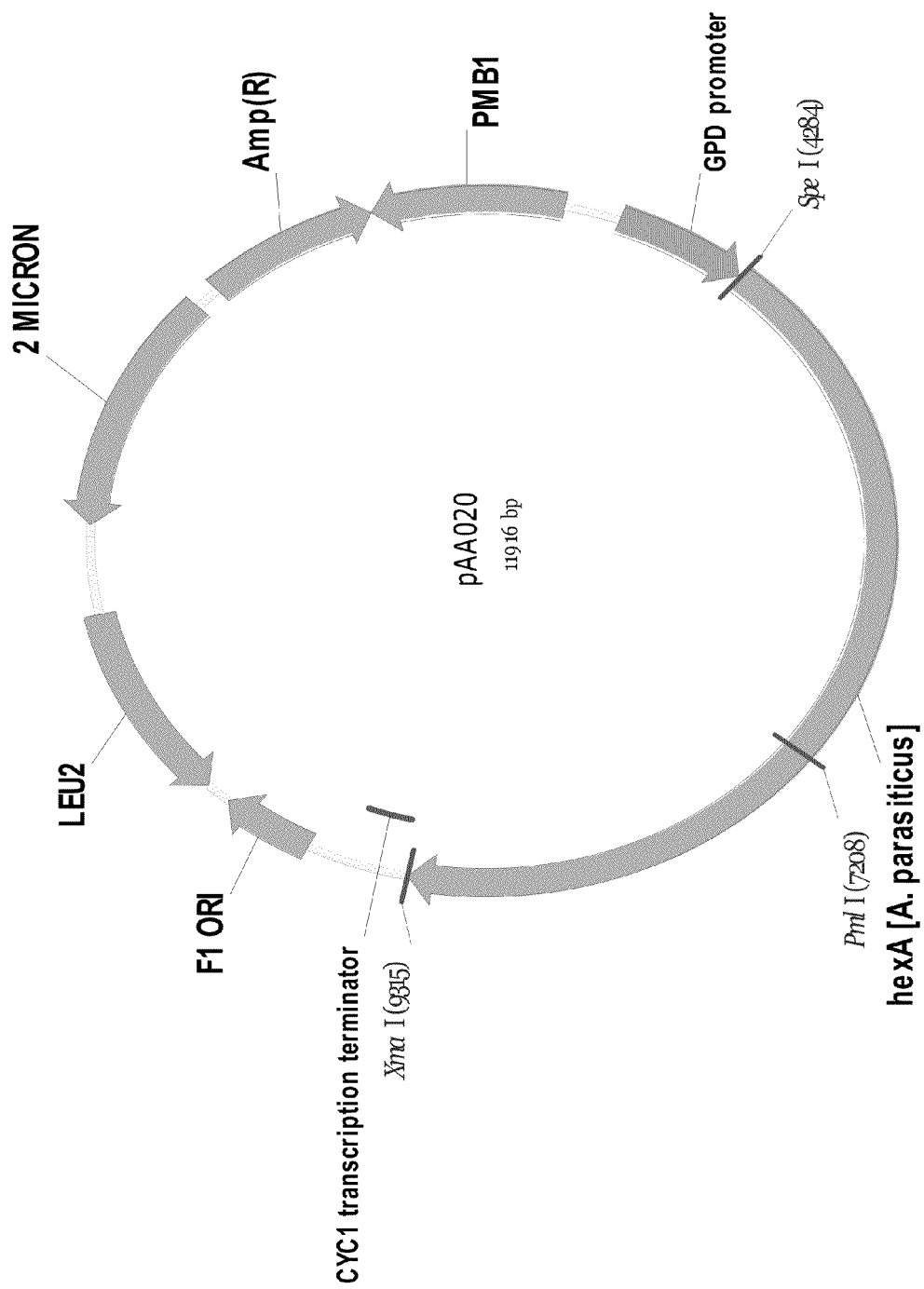
FIGS. 16-34 illustrate various plasmids for cloning, expression, or integration of various activities described herein, into a host organism or engineered organism.
Figure 17:
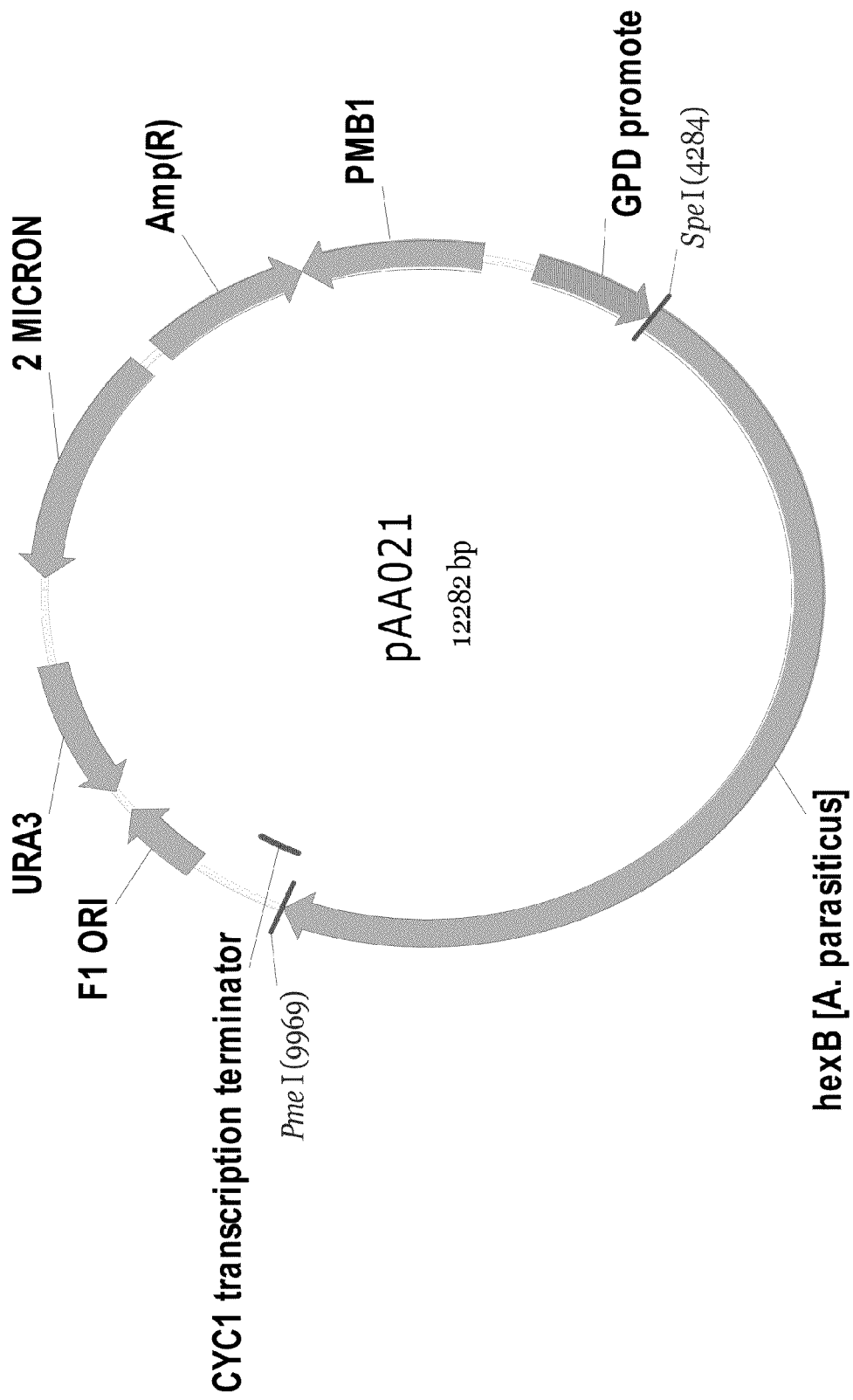
Figure 18:
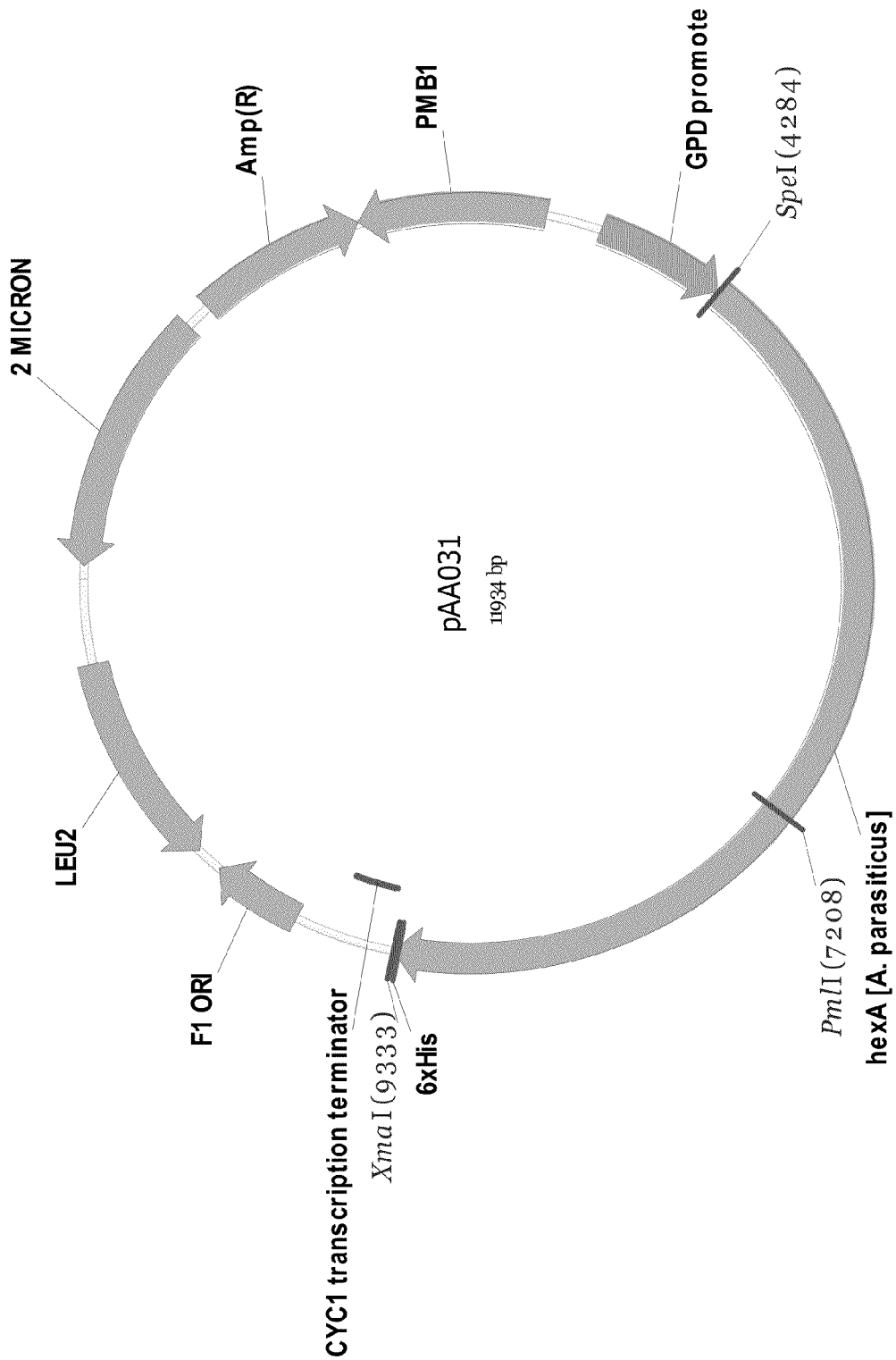
Figure 19:
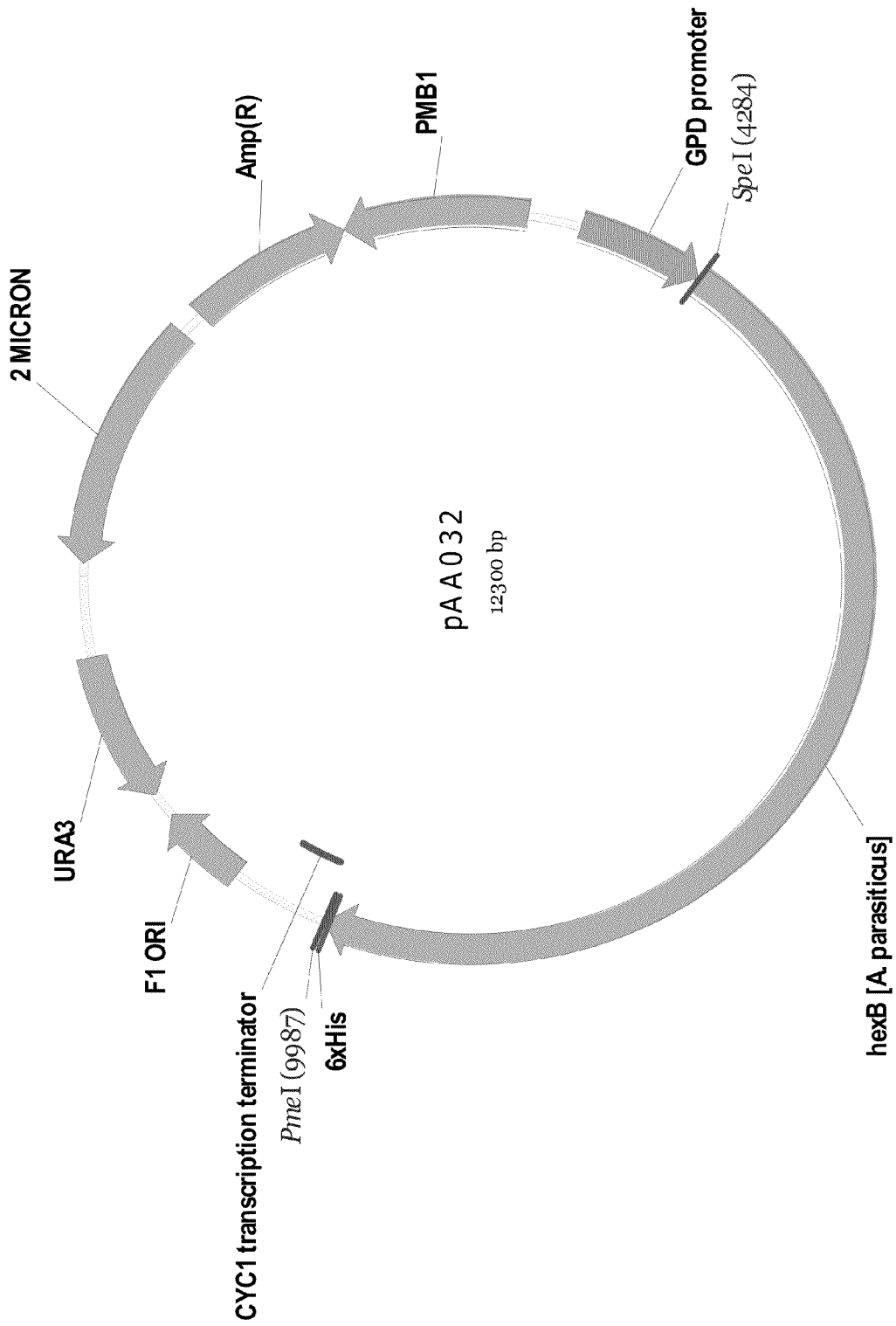
Figure 20:
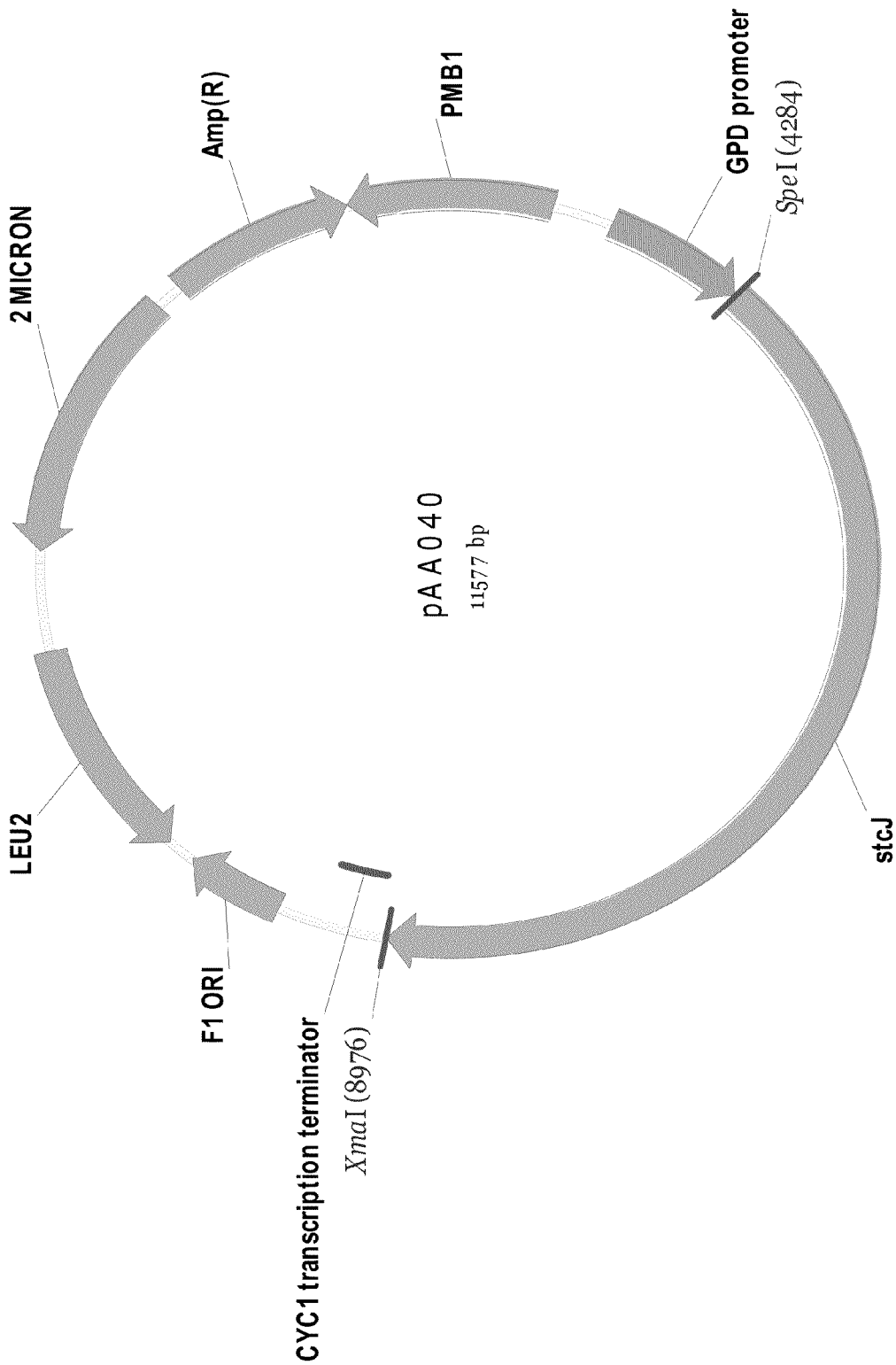
Figure 21:
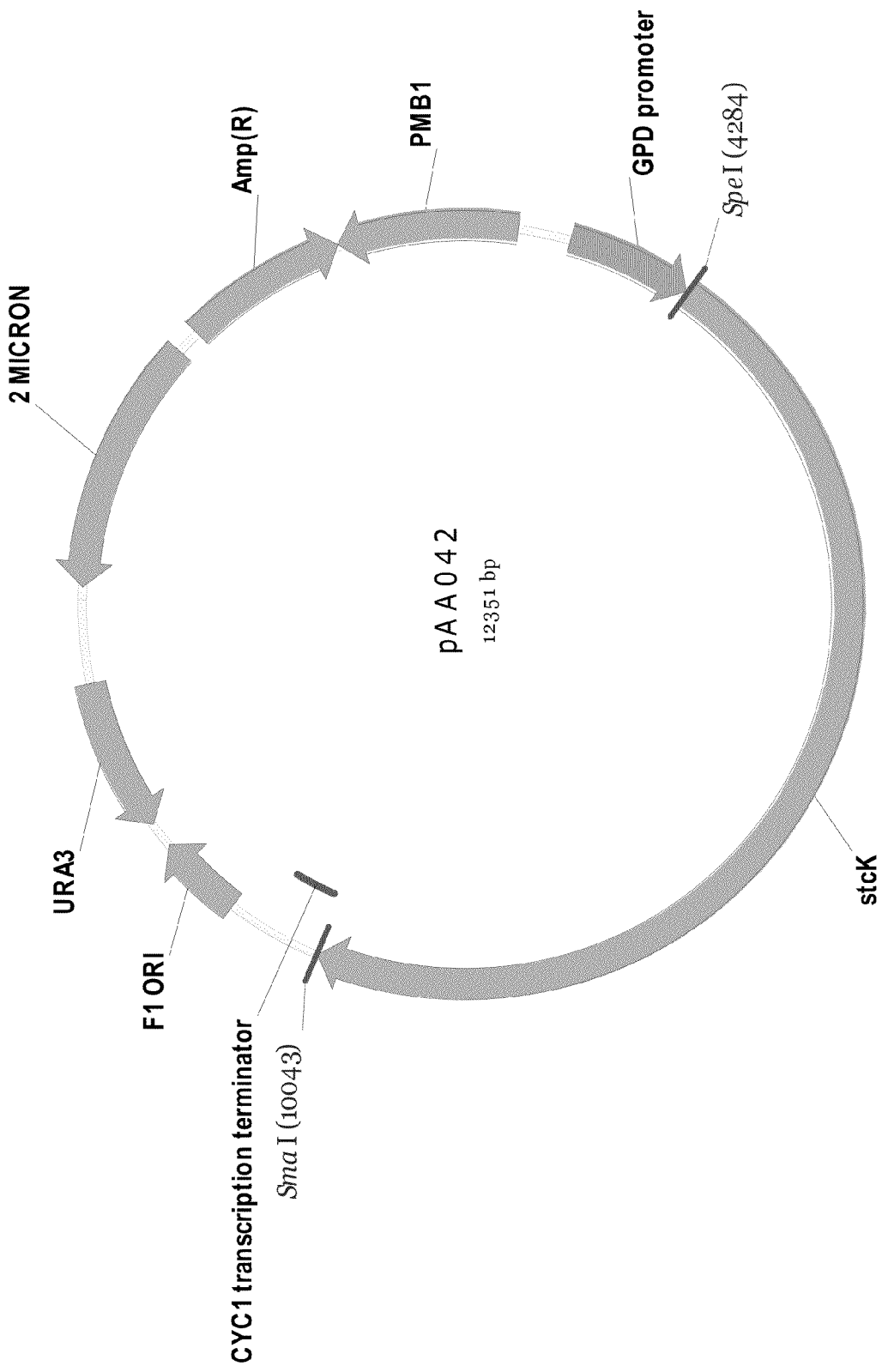
Figure 22:
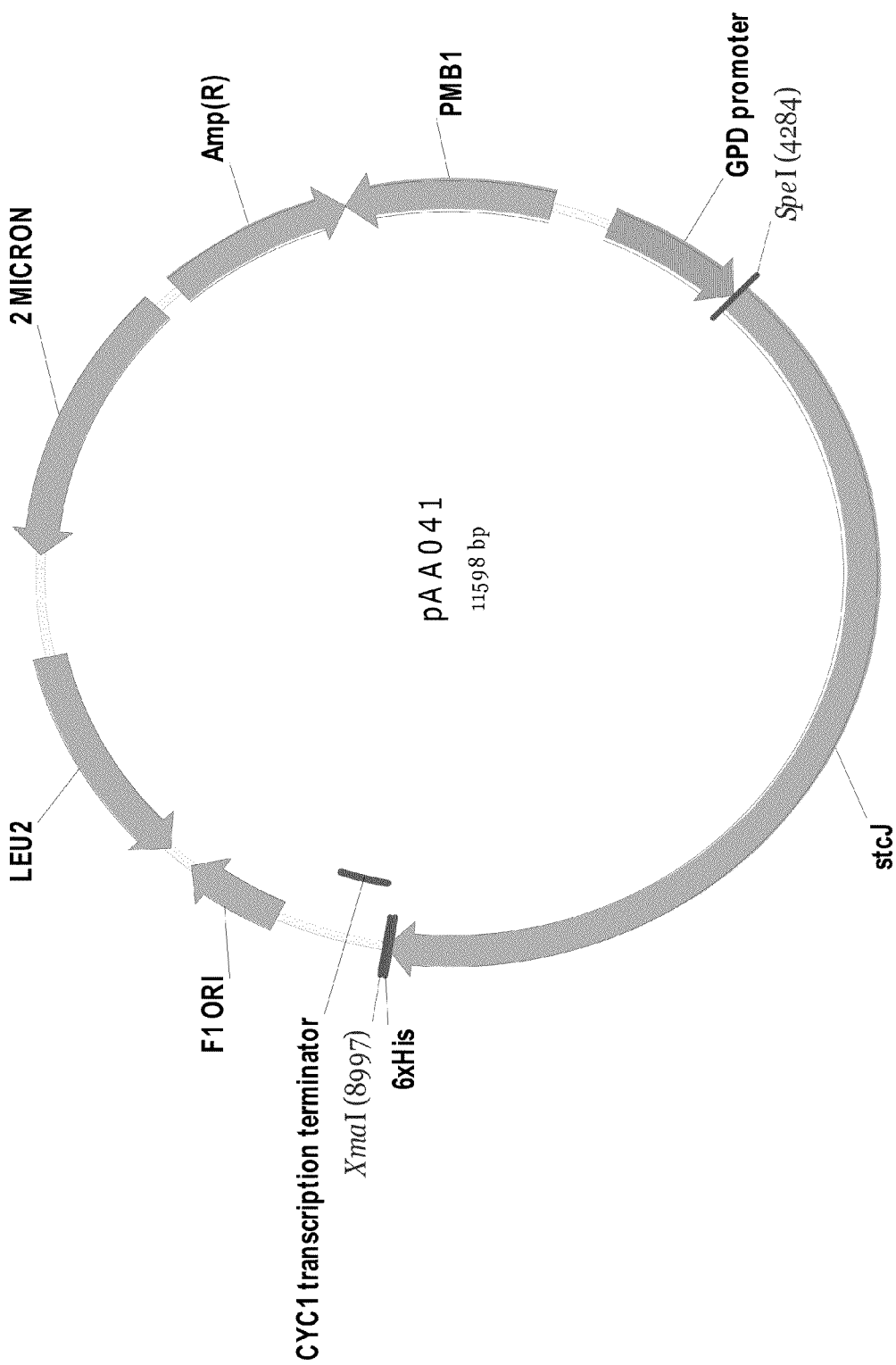
Figure 23:
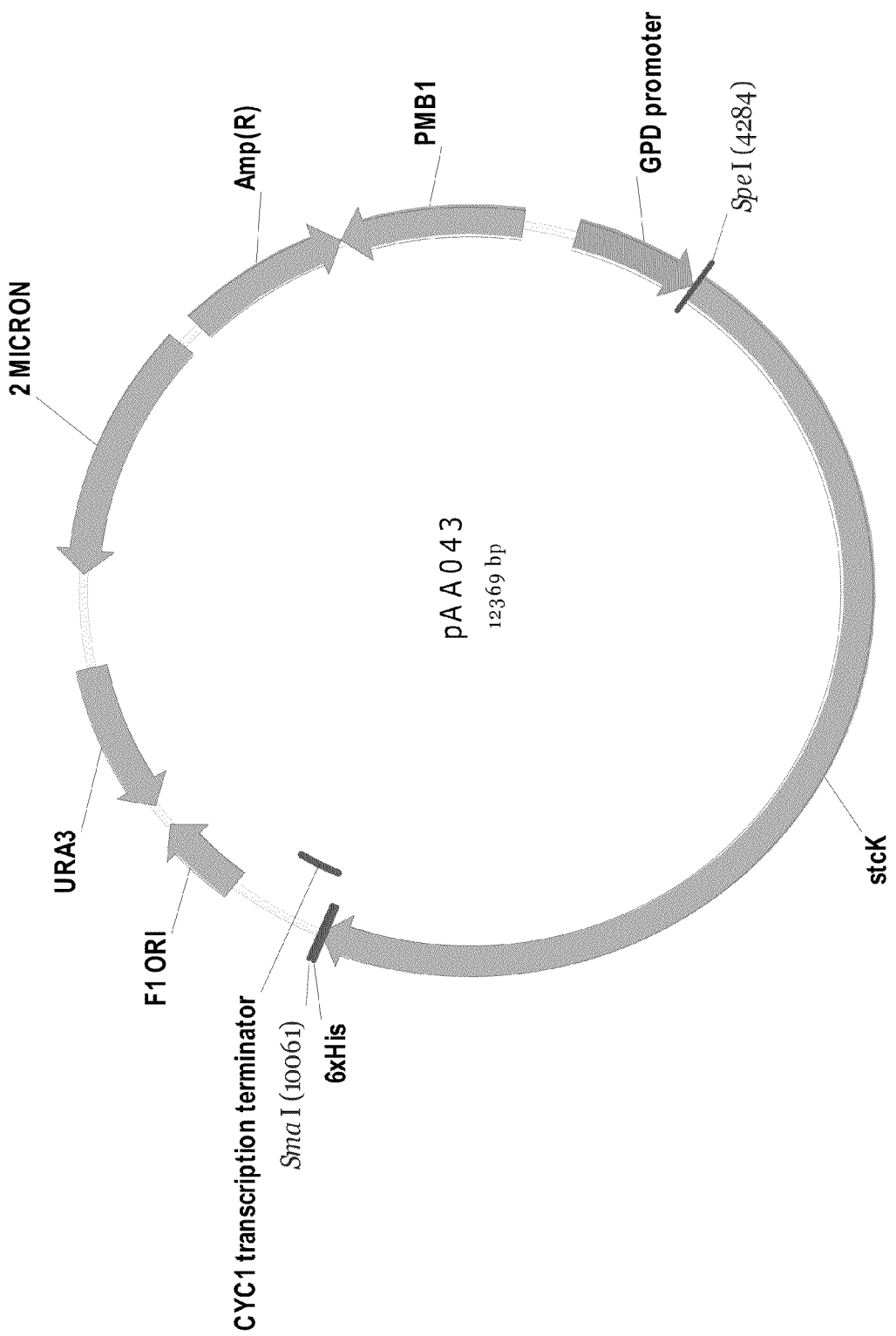
Figure 24:
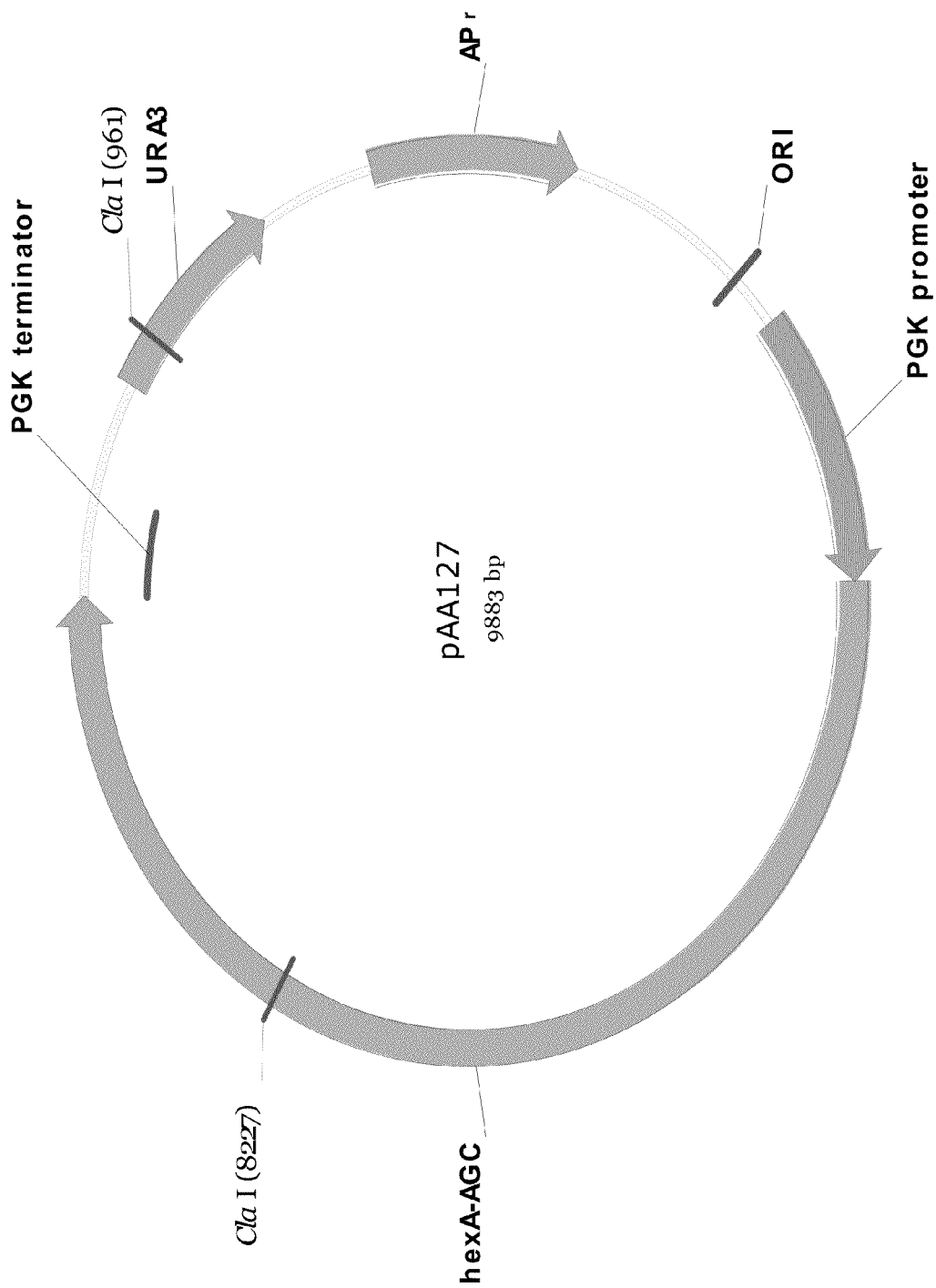
Figure 25:
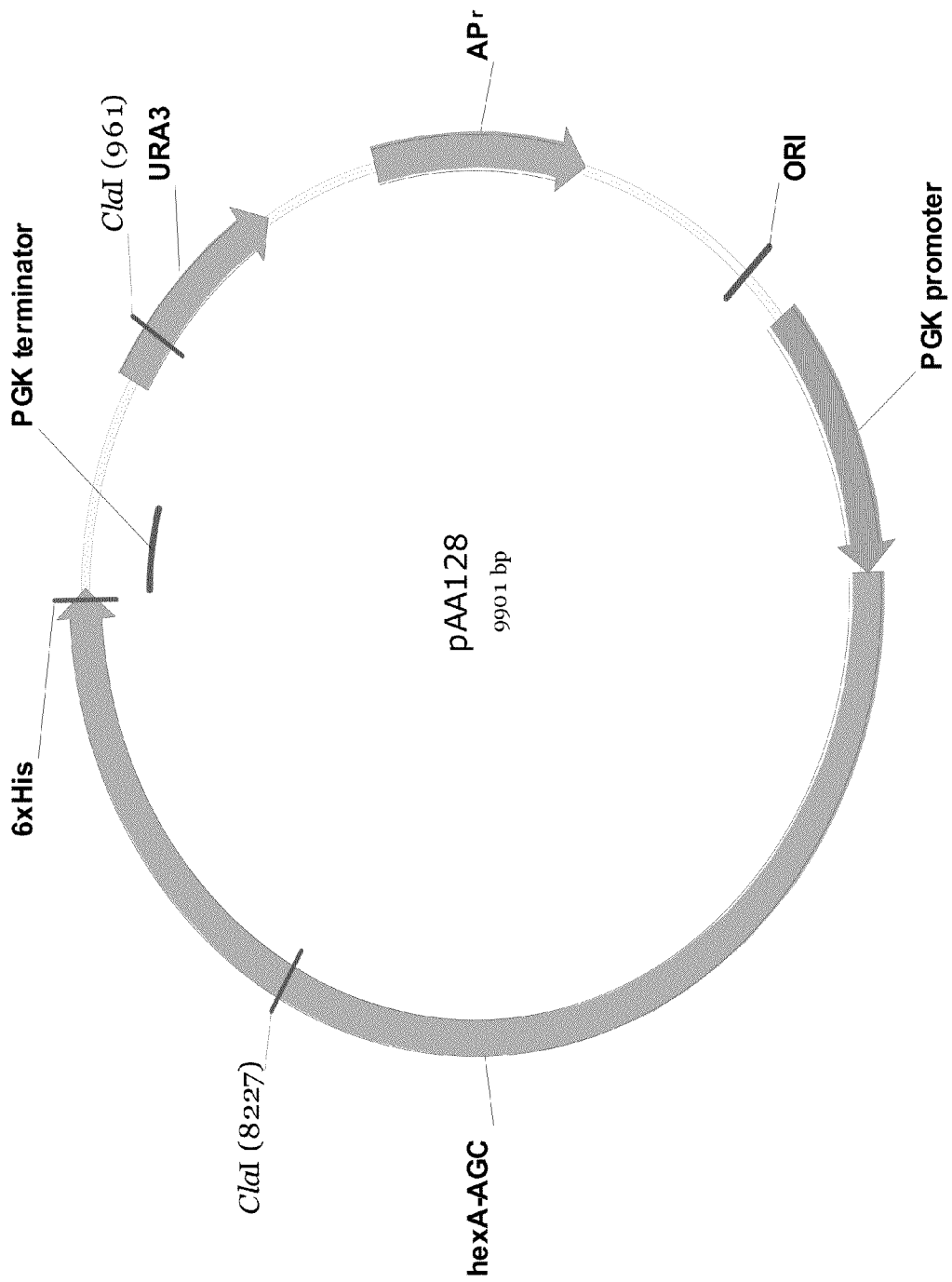
Figure 26:
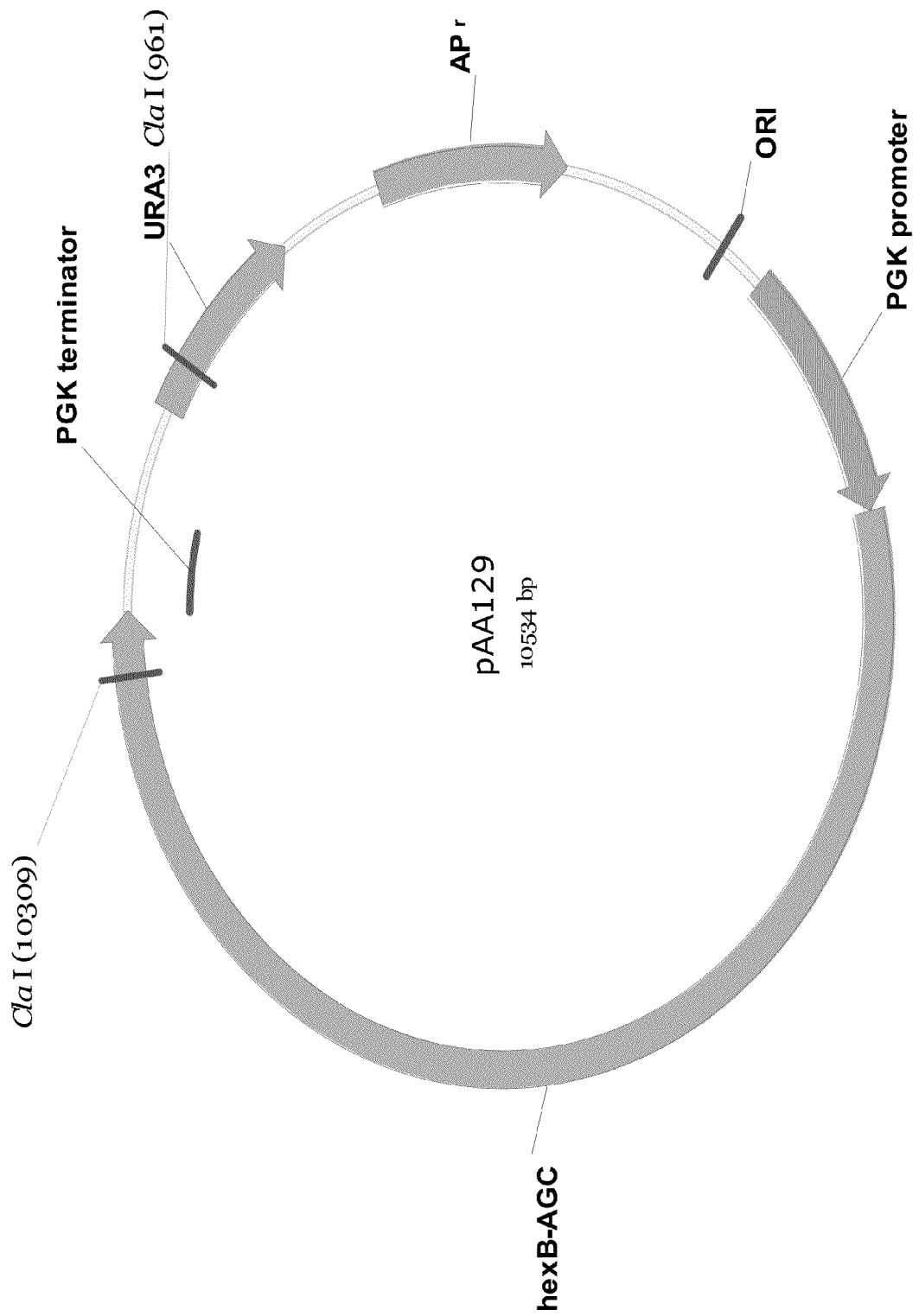
Figure 27:
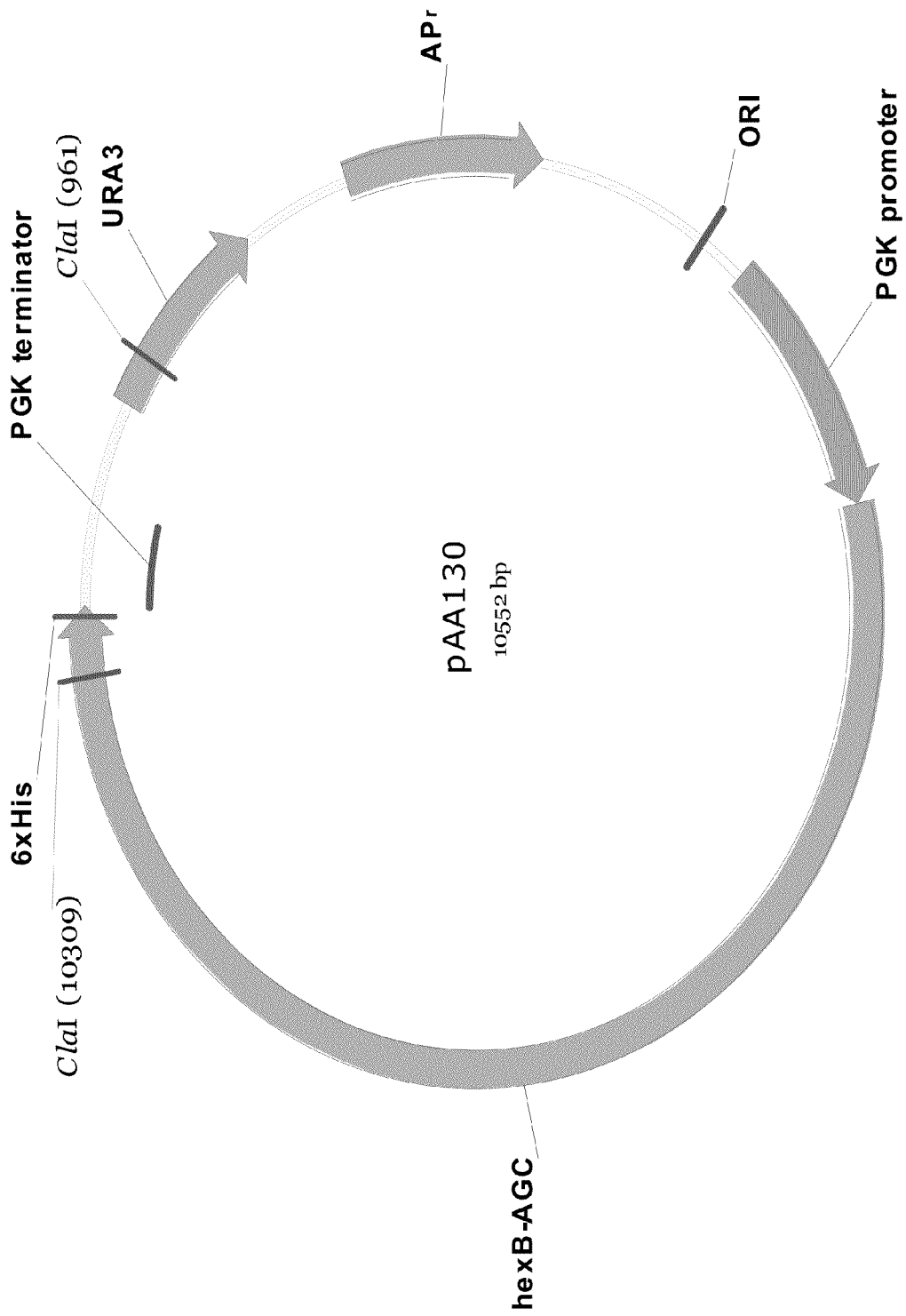

FIGS. 15A-15C graphically illustrate the units of acyl-CoA oxidase activity expressed as units (U) per milligram of protein (Y axis) in various strains of *Candida tropicalis* induced by feedstocks of specific chain length (Picataggio et al. 1991 Molecular and Cellular Biology 11: 4333-4339). Isolated protein was assayed for acyl-CoA oxidase activity using carbon chains of various length (X axis). The X and Y axes in FIGS. 15A-15C represent substantially similar data. FIG. 15A illustrates acyl-CoA oxidase activity as measured in a strain having a full complement of POX genes (e.g., POX4 and POX5 are active). FIG. 15B illustrates acyl-CoA oxidase activity as measured in a strain having a disrupted POX5 gene. The activity encoded by the functional POX4 gene exhibits a higher specific activity for acyl-CoA molecules with shorter carbon chain lengths (e.g., less than 10 carbons). The results of the POX5 disrupted strain also are presented numerically in the table in FIG. 15B. FIG. 15C illustrates acyl-CoA oxidase activity as measured in a strain having a disrupted POX4 gene. The activity encoded by the functional POX5 gene exhibits a narrow peak of high specific activity for acyl-CoA molecules 12 carbons in length, with a lower specific activity for molecules 10 carbons in length. The results of the POX4 disrupted strain are presented numerically in the table in FIG. 15C.

In certain embodiments, host acyl-CoA oxidase activity of one of the POX genes can be increased by genetically altering (e.g., increasing) the amount of the polypeptide produced (e.g., a strongly transcribed or constitutively expressed heterologous promoter is introduced in operable linkage with a polynucleotide that encodes the polypeptide; the copy number of a polynucleotide that encodes the polypeptide is increased (e.g., by introducing a plasmid that includes the polynucleotide, integration of additional copies in the host genome)). In some embodiments, the host acyl-CoA oxidase activity can be decreased by disruption (e.g., knockout, insertion mutagenesis, the like and combinations thereof) of an acyl-CoA oxidase gene, or by decreasing the activity of the promoter (e.g., addition of repressor sequences to the promoter or 5'UTR) which transcribes an acyl-CoA oxidase gene.

A noted above, disruption of nucleotide sequences encoding POX4, POX 5, or POX4 and POX5 sometimes can alter pathway efficiency, specificity and/or specific activity with respect to metabolism of carbon chains of different lengths (e.g., carbon chains including fatty alcohols, fatty acids, paraffins, dicarboxylic acids of between about 1 and about 60 carbons in length). In some embodiments, the nucleotide sequence of POX4, POX5, or POX4 and POX5 is disrupted with a URA3 nucleotide sequence encoding a selectable marker, and introduced to a host microorganism, thereby generating an engineered organism deficient in POX4, POX5 or POX4 and POX5 activity. Nucleic acid sequences encoding POX4 and POX5 can be obtained from a number of sources, including *Candida tropicalis*, for example. Examples of POX4 and POX5 amino acid sequences and nucleotide sequences of polynucleotides that encode the polypeptides, are presented herein. Example 32 describes experiments conducted to amplify the activity encoded by the POX5 gene.

Presence, absence or amount of POX4 and/or POX5 activity can be detected by any suitable method known in the art. For example, using enzymatic assays as described in Shimizu et al, 1979, and as described herein in the Examples. Alternatively, nucleic acid sequences representing native and/or disrupted POX4 and POX5 sequences also can be detected using nucleic acid detection methods (e.g., PCR, primer extension, nucleic acid hybridization, the like and combinations thereof), or quantitative expression based analysis (e.g., RT-PCR, western blot analysis, northern blot analysis, the like and combinations thereof), where the engineered organism exhibits decreased RNA and/or polypeptide levels as compared to the host organism.

The term "a genetic modification that results in increased fatty acid synthesis" as used herein refers to a genetic alteration of a host microorganism that increases an endogenous activity and/or adds a heterologous activity that metabolically synthesizes fatty acids and/or imports fatty acids into the microorganism from an external source (e.g., a feedstock, culture medium, environment, the like and combinations thereof). In some embodiments, an endogenous activity that converts fatty acyl-CoA to fatty acid is increased. In certain embodiments, a thioesterase activity is added or increased. Such alterations can advantageously increase yields of end products, such as adipic acid.

The term "thioesterase activity" as used herein refers to removal of Coenzyme A from hexanoate. The term "thioesterase activity" as used herein also refers to the removal of Coenzyme A from an activated fatty acid (e.g., fatty-acyl-CoA). A Non-limiting example of an enzyme with thioesterase activity includes acyl-CoA hydrolase (e.g., EC 3.1.2.20; also referred to as acyl coenzyme A thioesterase, acyl-CoA thioesterase, acyl coenzyme A hydrolase, thioesterase B, thioesterase II, lecithinase B, lysophospholipase L1, acyl-CoA thioesterase 1, and acyl-CoA thioesterase). Thioesterases that remove Coenzyme A from fatty-acyl-CoA molecules catalyze the reaction,

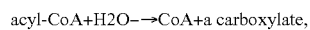

acyl-CoA+H2O-→CoA+a carboxylate, where the carboxylate often is a fatty acid. The released Coenzyme A can then be reused for other cellular activities.

The thioesterase activity can be provided by a polypeptide. In certain embodiments, the polypeptide is an endogenous nucleotide sequence that is increased in copy number, operably linked to a heterologous and/or endogenous promoter, or increased in copy number and operably linked to a heterologous and/or endogenous promoter. In some embodiments, the polypeptide is encoded by a heterologous nucleotide sequence introduced to a host microorganism. Nucleic acid sequences conferring thioesterase activity can be obtained from a number of sources, including *C. tropicalis* (e.g., see SEQ ID NOS: 42 and 44), *E. coli* (e.g., see SEQ ID NO: 46) and *Cuphea lanceolata*. Examples of such polypeptides include, without limitation, acyl-CoA hydrolase (e.g., ACHA and ACHB, see SEQ ID NOS: 43 and 45)) from *C. tropicalis*, acyl-CoA thioesterase (e.g., TESA, see SEQ ID NO: 47) from *E. coli*, and acyl-(ACP) thioesterase type B from *Cuphea lanceolata*, encoded by the nucleotide sequences referenced by accession number CAB60830 at the World Wide Web Uniform Resource Locator (URL) ncbi.nlm.nih.gov of the National Center for Biotechnology Information (NCBI).

Presence, absence or amount of thioesterase activity can be detected by any suitable method known in the art. An example of such a method is described Chemistry and Biology 9: 981-988. In some embodiments, thioesterase activity is not altered in a host microorganism, and in certain embodiments, the activity is added or increased in the engineered microorganism relative to the host microorganism. In some embodiments, a polypeptide having thioesterase activity is linked to another polypeptide (e.g., a hexanoate synthase A or hexanoate synthase B polypeptide). A non-limiting example of an amino acid sequence (one letter code sequence) for a polypeptide having thioesterase activity is provided hereafter:

(SEQ ID NO: 61)
MVAAAATSAFFPVPAPGTSPKPGKSGNWPSSLSPTFKPKSIPNAG

FQVKANASAHPKANGSAVNLKSGSLNTQEDTSSSPPPRAFLNQLP

```
DWSMLLTAITTVFVAAEKQWTMLDRKSKRPDMLVDSVGLKSIVRD

GLVSRQSFLIRSYEIGADRTASIETLMNHLQETSINHCKSLGLLNDG

FGRTPGMCKNDLIWVLTKMQIMVNRYPTWGDTVEINTWFSQSGKI

GMASDWLISDCNTGEILIRATSVWAMMNQKTRRFSRLPYEVRQEL

TPHFVDSPHVIEDNDQKLHKFDVKTGDSIRKGLTPRWNDLDVNQH

VSNVKYIGWILESMPIEVLETQELCSLTVEYRRECGMDSVLESVTAV

DPSENGGRSQYKHLLRLEDGTDIVKSRTEWRPKNAGTNGAISTST

AKTSNGNSAS
```

Additional examples of polynucleotide sequences encoding thioesterase activities, and polypeptides having thioesterase activity are provided in Example 51 (see SEQ ID NOS: 42-47).

The term "a genetic modification that results in substantial hexanoate usage by monooxygenase activity" as used herein refers to a genetic alteration of a host microorganism that reduces an endogenous activity that converts hexanoate to another product. In some embodiments, an endogenous activity that converts hexanoate to a toxin (e.g., in fungus) is reduced. In certain embodiments, a polyketide synthase activity is reduced. Such alterations can advantageously increase yields of end products, such as adipic acid.

The term "polyketide synthase activity" as used herein refers to the alteration of hexanoic acid by the polyketide synthase enzyme (PKS) as a step in the production of other products including mycotoxin. The PKS activity can be provided by a polypeptide. Examples of such polypeptides include, without limitation, an *Aspergillus parasiticus* enzyme referenced by accession number AAS66004 at the World Wide Web Uniform Resource Locator (URL) ncbi.nlm.nih.gov of the National Center for Biotechnology Information (NCBI). In certain embodiments, a PKS enzyme uses hexanoic acid generated by hexanoate synthase as a substrate and a component of the *Aspergillus* N or S multienzyme complex, a closely associated gene cluster involved in the synthesis of various products including mytoxin. Accordingly, a PKS activity sometimes is altered to free hexanoic acid for an engineered adipic acid pathway. In some embodiments PKS activity is diminished or blocked. In certain embodiments the PKS enzyme is engineered to substitute thioesterase activity for PKS activity. Presence, absence, or amount of PKS activity can be detected by any suitable method known in the art, such as that described in Watanabe C and Townsend C (2002) Initial characterization of a type I fatty acid synthase and polyketide synthase multienzyme complex N or S in the biosynthesis of aflatoxin B1. Chemistry and Biology 9: 981-988. A non-limiting example of an amino acid sequence (one letter code sequence) of a polypeptide having polyketide synthase activity is provided hereafter:

```
                                       (SEQ ID NO: 62)
MAQSRQLFLFGDQTADFVPKLRSLLSVQDSPILAAFLDQSHYVVRA

QMLQSMNTVDHKLARTADLRQMVQKYVDGKLTPAFRTALVCLCQL

GCFIREYEESGNMYPQPSDSYVLGFCMGSLAAVAVSCSRSLSELL

PIAVQTVLIAFRLGLCALEMRDRVDGCSDDRGDPWSTIVWGLDPQ

QARDQIEVFCRTTNVPQTRRPWISCISKNAITLSGSPSTLRAFCAMP

QMAQHRTAPIPICLPAHNGALFTQADITTILDTTPTTPWEQLPGQIPY

ISHVTGNVVQTSNYRDLIEVALSETLLEQVRLDLVETGLPRLLQSRQ

VKSVTIVPFLTRMNETMSNILPDSFISTETRTDTGRAIPASGRPGAG

KCKLAIVSMSGRFPESPTTESFWDLLYKGLDVCKEVPRRRWDINTH

VDPSGKARNKGATKWGCWLDFSGDFDPRFFGISPKEAPQMDPAQ

RMALMSTYEAMERAGLVPDTTPSTQRDRIGVFHGVTSNDWMETN

TAQNIDTYFITGGNRGFIPGRINFCFEFAGPSYTNDTACSSSLAAIHL

ACNSLWRGDCDTAVAGGTNMIYTPDGHTGLDKGFFLSRTGNCKP

YDDKADGYCRAEGVGTVFIKRLEDALADNDPILGVILDAKTNHSAM

SESMTRPHVGAQIDNMTAALNTTGLHPNDFSYIEMHGTGTQVGDA

VEMESVLSVFAPSETARKADQPLFVGSAKANVGHGEGVSGVTSLI

KVLMMMQHDTIPPHCGIKPGSKINRNFPDLGARNVHIAFEPKPWPR

THTPRRVLINNFSAAGGNTALIVEDAPERHWPTEKDPRSSHIVALSA

HVGASMKTNLERLHQYLLKNPHTDLAQLSYTTTARRWHYLHRVSV

TGASVEEVTRKLEMAIQNGDGVSRPKSKPKILFAFTGQGSQYATM

GKQVYDAYPSFREDLEKFDRLAQSHGFPSFLHVCTSPKGDVEEMA

PVVVQLAITCLQMALTNLMTSFGIRPDVTVGHSLGEFAALYAAGVLS

ASDVVYLVGQRAELLQERCQRGTHAMLAVKATPEALSQWIQDHDC

EVACINGPEDTVLSGTTKNVAEVQRAMTDNGIKCTLLKLPFAFHSA

QVQPILDDFEALAQGATFAKPQLLILSPLLRTEIHEQGVVTPSYVAQ

HCRHTVDMAQALRSAREKGLIDDKTLVIELGPKPLISGMVKMTLGD

KISTLPTLAPNKAIWPSLQKILTSVYTGGWDINWKKYHAPFASSQKV

VDLPSYGWDLKDYYIPYQGDWCLHRHQQDCKCAAPGHEIKTADY

QVPPESTPHRPSKLDPSKEAFPEIKTTTTLHRVVEETTKPLGATLVV

ETDISRKDVNGLARGHLVDGIPLCTPSFYADIAMQVGQYSMQRLRA

GHPGAGAIDGLVDVSDMVVDKALVPHGKGPQLLRTTLTMEWPPKA

AATTRSAKVKFATYFADGKLDTEHASCTVRFTSDAQLKSLRRSVSE

YKTHIRQLHDGHAKGQFMRYNRKTGYKLMSSMARFNPDYMLLDYL

VLNEAENEAASGVDFSLGSSEGTFAAHPAHVDAITQVAGFAMNAN

DNVDIEKQVYVNHGWDSFQIYQPLDNSKSYQVYTKMGQAKENDLV

HGDVVVLDGEQIVAFFRGLTLRSVPRGALRVVLQTTVKKADRQLGF

KTMPSPPPPTTTMPISPYKPANTQVSSQAIPAEATHSHTPPQPKHS

PVPETAGSAPAAKGVGVSNEKLDAVMRVVSEESGIALEELTDDSNF

ADMGIDSLSSMVIGSRFREDLGLDLGPEFSLFIDCTTVRALKDFMLG

SGDAGSGSNVEDPPPSATPGINPETDWSSSASDSIFASEDHGHSS

ESGADTGSPPALDLKPYCRPSTSVVLQGLPMVARKTLFMLPDGGG

SAFSYASLPRLKSDTAVVGLNCPYARDPENMNCTHGAMIESFCNEI

RRRQPRGPYHLGGWSSGGAFAYVVAEALVNQGEEVHSLIIIDAPIP

QAMEQLPRAFYEHCNSIGLFATQPGASPDGSTEPPSYLIPHFTAVV

DVMLDYKLAPLHARRMPKVGIVWAADTVMDERDAPKMKGMHFMI

QKRTEFGPDGWDTIMPGASFDIVRADGANHFTLMQKEHVSIISDLID

RVMA
```

The terms "a genetic modification that reduces 6-hydroxyhexanoic acid conversion" or "a genetic modification that reduces omega hydroxyl fatty acid conversion" as used herein refer to genetic alterations of a host microorganism that reduce an endogenous activity that converts 6-hydroxyhexanoic acid to another product. In some embodiments, an endogenous 6-hydroxyhexanoic acid dehydrogenase activity is reduced. Such alterations can advantageously increase the amount of 6-hydroxyhexanoic acid, which can be purified and further processed.

The term "a genetic modification that reduces beta-oxidation activity" as used herein refers to a genetic alteration of a host microorganism that reduces an endogenous activity that oxidizes a beta carbon of carboxylic acid containing organic molecules. In certain embodiments, the organic molecule is a six carbon molecule, and sometimes contains one or two carboxylic acid moieties located at a terminus of the molecule (e.g., adipic acid). Such alterations can advantageously increase yields of end products, such as adipic acid.

The term "a genetic modification that results in increased fatty acid synthesis" as used herein also refers to a genetic alteration of a host microorganism that reduces an endogenous activity that converts fatty acids into fatty-acyl-CoA intermediates. In some embodiments, an endogenous activity that converts fatty acids into fatty-acyl-CoA intermediates is reduced. In certain embodiments, an acyl-CoA synthetase activity is reduced. Such alterations can advantageously increase yields of end products, such as adipic acid.

Fatty acids can be converted into fatty-acyl-CoA intermediates by the activity of an acyl-CoA synthetase (e.g., ACS1, ACS2; EC 6.2.1.3; also referred to as acyl-CoA synthetase, acyl-CoA ligase), in many organisms. Acyl-CoA synthetase has two isoforms encoded by ACS1 and ACS2, respectively, in *C. tropicalis* (e.g., homologous to FAA1, FAA2, FAA3 and FAA4 in *S. cerevisiae*). Acyl-CoA synthetase is a member of the ligase class of enzymes and catalyzes the reaction,

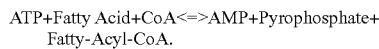
ATP+Fatty Acid+CoA<=>AMP+Pyrophosphate+
Fatty-Acyl-CoA.

Fatty acids and Coenzyme A often are utilized in the activation of fatty acids to fatty-acyl-CoA intermediates for entry into various cellular processes. Without being limited by theory, it is believed that reduction in the amount of fatty-acyl-CoA available for various cellular processes can increase the amount of fatty acids available for conversion into adipic acid by other engineered pathways in the same host organism (e.g., omega oxidation pathway, beta oxidation pathway, omega oxidation pathway and beta oxidation pathway). Acyl-CoA synthetase can be inactivated by any suitable means. Described herein are gene knockout methods suitable for use to disrupt the nucleotide sequence that encodes a polypeptide having ACS1 activity. A nucleotide sequence of ACS1 is provided in Example 51, SEQ ID NO: 48. An example of an integration/disruption construct, configured to generate a deletion mutant for ACS1 is described in Example 43.

The presence, absence or amount of acyl-CoA synthetase activity can be detected by any suitable method known in the art. Non-limiting examples of suitable detection methods include enzymatic assays (e.g., Lageweg et al "A Fluorimetric Assay for Acyl-CoA Synthetase Activity", Analytical Biochemistry, 197(2):384-388 (1991)), PCR based assays (e.g., qPCR, RTPCR), immunological detection methods (e.g., antibodies specific for acyl-CoA synthetase), the like and combinations thereof.

The term "a genetic modification that results in increased fatty acid synthesis" as used herein also refers to a genetic alteration of a host microorganism that reduces an endogenous activity that converts long chain and very long chain fatty acids into activated fatty-acyl-CoA intermediates. In some embodiments, an endogenous activity that converts long chain and very long chain fatty acids into activated fatty-acyl-CoA intermediates is reduced. In certain embodiments, a long chain acyl-coA synthetase activity is reduced. Such alterations can advantageously increase yields of end products, such as adipic acid.

Long chain fatty acids (e.g., C12-C18 chain lengths) and very long chain fatty acids (e.g., C20-C26) often are activated and/or transported by the thiioesterification activity of a long-chain acyl-CoA synthetase (e.g., FAT1; EC EC 6.2.1.3; also referred to as long-chain fatty acid-CoA ligase, acyl-CoA synthetase; fatty acid thiokinase (long chain); acyl-activating enzyme; palmitoyl-CoA synthase; lignoceroyl-CoA synthase; arachidonyl-CoA synthetase; acyl coenzyme A synthetase; acyl-CoA ligase; palmitoyl coenzyme A synthetase; thiokinase; palmitoyl-CoA ligase; acyl-coenzyme A ligase; fatty acid CoA ligase; long-chain fatty acyl coenzyme A synthetase; oleoyl-CoA synthetase; stearoyl-CoA synthetase; long chain fatty acyl-CoA synthetase; long-chain acyl CoA synthetase; fatty acid elongase; LCFA synthetase; pristanoyl-CoA synthetase; ACS3; long-chain acyl-CoA synthetase I; long-chain acyl-CoA synthetase II; fatty acyl-coenzyme A synthetase; long-chain acyl-coenzyme A synthetase; and acid:CoA ligase (AMP-forming)), in some organisms.

Fatty acids also can be transported into the host organism from feedstocks by the activity of long chain acyl-CoA synthetase.

Long-chain acyl-CoA synthetase catalyzes the reaction,

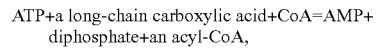
ATP+a long-chain carboxylic acid+CoA=AMP+
diphosphate+an acyl-CoA, where "an acyl-CoA" refers to a fatty-acyl-CoA molecule. As noted herein, activation of fatty acids is often necessary for entry of fatty acids into various cellular processes (e.g., as an energy source, as a component for membrane formation and/or remodeling, as carbon storage molecules). Deletion mutants of FAT1 have been shown to accumulate very long chain fatty acids and exhibit decreased activation of these fatty acids. Without being limited by theory, it is believed that reduction in the activity of long-chain acyl-CoA synthetase may reduce the amount of long chain fatty acids converted into fatty-acyl-CoA intermediates, thereby increasing the amount of fatty acids available for conversion into adipic acid by other engineered pathways in the same host organism (e.g., omega oxidation pathway, beta oxidation pathway, omega oxidation pathway and beta oxidation pathway). Long-chain-acyl-CoA synthetase activity can be reduced or inactivated by any suitable means. Described herein are gene knockout methods suitable for disrupting the nucleotide sequence that encodes the polypeptide having FAT1 activity. The nucleotide sequence of FAT1 is provided in Example 51, SEQ ID NO: 50. DNA vectors suitable for use in constructing "knockout" constructs are described herein.

The presence, absence or amount of long-chain-acyl-CoA synthetase activity can be detected by any suitable method known in the art. Non-limiting examples of suitable detection methods include enzymatic assays, binding assays (e.g., Erland et al, Analytical Biochemistry 295(1):38-44 (2001)), PCR based assays (e.g., qPCR, RTPCR), immunological detection methods (e.g., antibodies specific for long-chain-acyl-CoA synthetase), the like and combinations thereof.

The term "a genetic modification that results in increased fatty acid synthesis" as used herein also refers to a genetic alteration of a host microorganism that reduces an endogenous activity that converts cholesterol into cholesterol esters. In some embodiments, an endogenous activity that converts cholesterol into cholesterol esters is reduced. In certain embodiments, an acyl-CoA sterol acyltransferase activity is reduced. Such alterations can advantageously increase yields of end products, such as adipic acid.

Cholesterol can be converted into a cholesterol-ester by the activity of acyl-CoA sterol acyltransferase (e.g., ARE1, ARE2; EC 2.3.1.26; also referred to as sterol O-acyltransferase; cholesterol acyltransferase; sterol-ester synthase; sterol-ester synthetase; sterol-ester synthase; acyl coenzyme A-cholesterol-O-acyltransferase; acyl-CoA:cholesterol acyltransferase; ACAT; acylcoenzyme A:cholesterol O-acyltransferase; cholesterol ester synthase; cholesterol ester synthetase; and cholesteryl ester synthetase), in many organisms. Without being limited by any theory, cholesterol esterification may be involved in directing cholesterol away from incorporation into cell membranes and towards storage forms of lipids. Acyl-CoA sterol acyltransferase catalyzes the reaction,

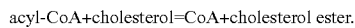

acyl-CoA+cholesterol=CoA+cholesterol ester.

The esterification of cholesterol is believed to limit its solubility in cell membrane lipids and thus promotes accumulation of cholesterol ester in the fat droplets (e.g., a form of carbon storage molecule) within cytoplasm. Therefore, without being limited by any theory esterification of cholesterol may cause the accumulation of lipid storage molecules, and disruption of the activity of acyl-CoA sterol acyltransferase may cause an increase in acyl-CoA levels that can be converted into adipic acid by other engineered pathways in the same host organism (e.g., omega oxidation pathway, beta oxidation pathway, omega oxidation pathway and beta oxidation pathway). Acyl-CoA sterol acyltransferase can be inactivated by any suitable means. Described herein are gene knockout methods suitable for disrupting nucleotide sequences that encode polypeptides having ARE1 activity, ARE2 activity or ARE1 activity and ARE2 activity. The nucleotide sequences of ARE1 and ARE2 are provided in Example 51, SEQ ID NOS: 52 and 54. DNA vectors suitable for use in constructing "knockout" constructs are described herein.

The presence, absence or amount of acyl-CoA sterol acyltransferase activity can be detected by any suitable method known in the art. Non-limiting examples of suitable detection methods include enzymatic assays (e.g., Chen et al, Plant Physiology 145:974-984 (2007)), binding assays, PCR based assays (e.g., qPCR, RTPCR), immunological detection methods (e.g., antibodies specific for long-chain-acyl-CoA synthetase), the like and combinations thereof.

The term "a genetic modification that results in increased fatty acid synthesis" as used herein also refers to a genetic alteration of a host microorganism that reduces an endogenous activity that catalyzes diacylglycerol esterification (e.g., addition of acyl group to a diacylglycerol to form a triacylglycerol). In some embodiments, an endogenous activity that converts diacylglycerol into triacylglycerol is reduced. In certain embodiments, an acyltransferase activity is reduced. In some embodiments a diacylglycerol acyltransferase activity is reduced. In some embodiments a diacylglycerol acyltransferase (e.g., DGA1) activity and an acyltransferase (e.g., LRO1) activity are reduced. Such alterations can advantageously increase yields of end products, such as adipic acid.

Diacylglycerol can be converted into triacylglycerol by the activity of diacylglycerol acyltransferase (e.g., DGA1; EC2.3.1.20; also referred to as diglyceride acyltransferase; 1,2-diacylglycerol acyltransferase; diacylglycerol acyltransferase; diglyceride O-acyltransferase; palmitoyl-CoA-sn-1,2-diacylglycerol acyltransferase; acyl-CoA:1,2-diacylglycerol O-acyltransferase and acyl-CoA:1,2-diacyl-sn-glycerol O-acyltransferase), in many organisms. Diacylglycerol acyltransferase catalyzes the reaction,

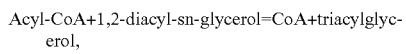

Acyl-CoA+1,2-diacyl-sn-glycerol=CoA+triacylglycerol, and is generally considered the terminal and only committed step in triglyceride synthesis. The product of the DGA1 gene in yeast normally is localized to lipid particles.

In addition to the diacylglycerol esterification activity described for DGA1, many organisms also can generate triglycerides by the activity of other acyltransferase activities, non-limiting examples of which include lecithin-cholesterol acyltransferase activity (e.g., LRO1; EC 2.3.1.43; also referred to as phosphatidylcholine-sterol O-acyltransferase activity; lecithin-cholesterol acyltransferase activity; phospholipid-cholesterol acyltransferase activity; LCAT (lecithin-cholesterol acyltransferase) activity; lecithin:cholesterol acyltransferase activity; and lysolecithin acyltransferase activity) and phospholipid:diacylglycerol acyltransferase (e.g., EC 2.3.1.158; also referred to as PDAT activity and phospholipid:1,2-diacyl-sn-glycerol O-acyltransferase activity). Acyltransferases of the families EC 2.3.1.43 and EC 2.3.1.58 catalyze the general reaction,

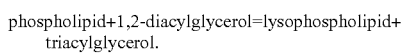

phospholipid+1,2-diacylglycerol=lysophospholipid+triacylglycerol.

Triacylglycerides often are utilized as carbon (e.g., fatty acid or lipid) storage molecules. Without being limited by any theory, it is believe that reducing the activity of acyltransferases may reduce the conversion of diacylglycerol to triacylglycerol, which may cause increased accumulation of fatty acid, in conjunction with additional genetic modifications (e.g., lipase to further remove fatty acids from the glycerol backbone) that can be converted into adipic acid by other engineered pathways in the same host organism (e.g., omega oxidation pathway, beta oxidation pathway, omega oxidation pathway and beta oxidation pathway). Acyltransferases can be inactivated by any suitable means. Described herein are gene knockout methods suitable for disrupting nucleotide sequences that encode polypeptides having DGA1 activity, LRO1 activity or DGA1 activity and LRO1 activity. The nucleotide sequence of DGA1 is provided in Example 51, SEQ ID NO: 56. The nucleotide sequence of LRO1 is provided in Example 51, SEQ ID NO: 58. DNA vectors suitable for use in constructing "knockout" constructs are described herein.

The presence, absence or amount of acyltransferase activity can be detected by any suitable method known in the art. Non-limiting examples of suitable detection methods include enzymatic assays (e.g., Geelen, Analytical Biochemistry 322 (2):264-268 (2003), Dahlqvist et al, PNAS 97(12):6487-6492 (2000)), binding assays, PCR based assays (e.g., qPCR, RTPCR), immunological detection methods (e.g., antibodies specific for a DGA1 or LRO1 acyltransferase), the like and combinations thereof.

Polynucleotides and Polypeptides

A nucleic acid (e.g., also referred to herein as nucleic acid reagent, target nucleic acid, target nucleotide sequence, nucleic acid sequence of interest or nucleic acid region of interest) can be from any source or composition, such as DNA, cDNA, gDNA (genomic DNA), RNA, siRNA (short inhibitory RNA), RNAi, tRNA or mRNA, for example, and can be in any form (e.g., linear, circular, supercoiled, single-stranded, double-stranded, and the like). A nucleic acid can also comprise DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Deoxyribonucleotides include deoxyadenosine, deoxycytidine, deoxyguanosine and deoxythymidine. For RNA, the uracil base is uridine.

A nucleic acid sometimes is a plasmid, phage, autonomously replicating sequence (ARS), centromere, artificial chromosome, yeast artificial chromosome (e.g., YAC) or other nucleic acid able to replicate or be replicated in a host cell. In certain embodiments a nucleic acid can be from a library or can be obtained from enzymatically digested, sheared or sonicated genomic DNA (e.g., fragmented) from an organism of interest. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method in the art, and the average, mean or nominal length of nucleic acid fragments can be controlled by selecting an appropriate fragment-generating procedure by the person of ordinary skill. In some embodiments, the fragmented DNA can be size selected to obtain nucleic acid fragments of a particular size range.

Nucleic acid can be fragmented by various methods known to the person of ordinary skill, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Nucleic acid may be specifically cleaved by contacting the nucleic acid with one or more specific cleavage agents. The term "specific cleavage agent" as used herein refers to an agent, sometimes a chemical or an enzyme that can cleave a nucleic acid at one or more specific sites. Specific cleavage agents often will cleave specifically according to a particular nucleotide sequence at a particular site. Examples of enzymic specific cleavage agents include without limitation endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I, Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acids of interest may be treated with one or more specific cleavage agents (e.g., 1, 2, 3, 4, 5, 6, 7, 8, 9, 10 or more specific cleavage agents) in one or more reaction vessels (e.g., nucleic acid of interest is treated with each specific cleavage agent in a separate vessel).

A nucleic acid suitable for use in the embodiments described herein sometimes is amplified by any amplification process known in the art (e.g., PCR, RT-PCR and the like). Nucleic acid amplification may be particularly beneficial when using organisms that are typically difficult to culture (e.g., slow growing, require specialize culture conditions and the like). The terms "amplify", "amplification", "amplification reaction", or "amplifying" as used herein refer to any in vitro processes for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step. In some embodiments, a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions.

In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids). As described herein, the term "native sequence" refers to an unmodified nucleotide sequence as found in its natural setting (e.g., a nucleotide sequence as found in an organism).

A nucleic acid or nucleic acid reagent can comprise certain elements often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments. In some embodiments, a promoter element can be isolated from a gene or organism and inserted in functional connection with a polynucleotide sequence to allow altered and/or regulated expression. A non-native promoter (e.g., promoter not normally associated with a given nucleic acid sequence) used for expression of a nucleic acid often is referred to as a heterologous promoter. In certain embodiments, a heterologous promoter and/or a 5'UTR can be inserted in functional connection with a polynucleotide that encodes a polypeptide having a desired activity as described herein. The terms "operably linked" and "in functional connection with" as used herein with respect to promoters, refer to a relationship between a coding sequence and a promoter element. The promoter is operably linked or in functional connection with the coding sequence when expression from the coding sequence via transcription is regulated, or controlled by, the promoter element. The terms "operably linked" and "in functional connection with" are utilized interchangeably herein with respect to promoter elements.

A promoter often interacts with a RNA polymerase. A polymerase is an enzyme that catalyses synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that can influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermentor, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

In some embodiments the activity can be altered using recombinant DNA and genetic techniques known to the artisan. Methods for engineering microorganisms are further described herein. Tables herein provide non-limiting lists of yeast promoters that are up-regulated by oxygen, yeast promoters that are down-regulated by oxygen, yeast transcriptional repressors and their associated genes, DNA binding motifs as determined using the MEME sequence analysis software. Potential regulator binding motifs can be identified using the program MEME to search intergenic regions bound by regulators for overrepresented sequences. For each regulator, the sequences of intergenic regions bound with p-values less than 0.001 were extracted to use as input for motif discovery. The MEME software was run using the following settings: a motif width ranging from 6 to 18 bases, the "zoops" distribution model, a $6^{th}$ order Markov background model and a discovery limit of 20 motifs. The discovered sequence motifs were scored for significance by two criteria: an E-value calculated by MEME and a specificity score. The motif with the best score using each metric is shown for each regulator. All motifs presented are derived from datasets generated in rich growth conditions with the exception of a previously published dataset for epitope-tagged Gal4 grown in galactose.

In some embodiments, the altered activity can be found by screening the organism under conditions that select for the desired change in activity. For example, certain microorganisms can be adapted to increase or decrease an activity by selecting or screening the organism in question on a media containing substances that are poorly metabolized or even toxic. An increase in the ability of an organism to grow a substance that is normally poorly metabolized would result in an increase in the growth rate on that substance, for example. A decrease in the sensitivity to a toxic substance might be manifested by growth on higher concentrations of the toxic substance, for example. Genetic modifications that are identified in this manner sometimes are referred to as naturally occurring mutations or the organisms that carry them can sometimes be referred to as naturally occurring mutants. Modifications obtained in this manner are not limited to alterations in promoter sequences. That is, screening microorganisms by selective pressure, as described above, can yield genetic alterations that can occur in non-promoter sequences, and sometimes also can occur in sequences that are not in the nucleotide sequence of interest, but in a related nucleotide sequences (e.g., a gene involved in a different step of the same pathway, a transport gene, and the like). Naturally occurring mutants sometimes can be found by isolating naturally occurring variants from unique environments, in some embodiments.

In addition to the regulated promoter sequences, regulatory sequences, and coding polynucleotides provided herein, a nucleic acid reagent may include a polynucleotide sequence 80% or more identical to the foregoing (or to the complementary sequences). That is, a nucleotide sequence that is at least 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to a nucleotide sequence described herein can be utilized. The term "identical" as used herein refers to two or more nucleotide sequences having substantially the same nucleotide sequence when compared to each other. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the http address www.gcg.com), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at http address www.gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Sequence identity can also be determined by hybridization assays conducted under stringent conditions. As use herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

As noted above, nucleic acid reagents may also comprise one or more 5' UTR's, and one or more 3'UTR's. A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, −35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5' UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., http address www.interscience.wiley.com, DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR can be used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

A nucleotide reagent sometimes can comprise a target nucleotide sequence. A "target nucleotide sequence" as used herein encodes a nucleic acid, peptide, polypeptide or protein of interest, and may be a ribonucleotide sequence or a deoxyribonucleotide sequence. A target nucleic acid sometimes is an untranslated ribonucleic acid and sometimes is a translated ribonucleic acid. An untranslated ribonucleic acid may include, but is not limited to, a small interfering ribonucleic acid (siRNA), a short hairpin ribonucleic acid (shRNA), other ribonucleic acid capable of RNA interference (RNAi), an antisense ribonucleic acid, or a ribozyme. A translatable target nucleotide sequence (e.g., a target ribonucleotide sequence) sometimes encodes a peptide, polypeptide or protein, which are sometimes referred to herein as "target peptides," "target polypeptides" or "target proteins."

Any peptides, polypeptides or proteins, or an activity catalyzed by one or more peptides, polypeptides or proteins may be encoded by a target nucleotide sequence and may be selected by a user. Representative proteins include enzymes (e.g., glucose-6-phosphate dehydrogenase, lipase, fatty acid synthase acetyl-CoA carboxylase, acyl-CoA oxidase, hexanoate synthase, thioesterase, monooxygenase, monooxygenase reductase, fatty alcohol oxidase, 6-oxohexanoic acid dehydrogenase, 6-hydroxyhexanoic acid dehydrogenase and the like, for example), antibodies, serum proteins (e.g., albumin), membrane bound proteins, hormones (e.g., growth hormone, erythropoietin, insulin, etc.), cytokines, etc., and include both naturally occurring and exogenously expressed polypeptides. Representative activities (e.g., enzymes or combinations of enzymes which are functionally associated to provide an activity) include hexanoate synthase activity, thioesterase activity, monooxygenase activity, 6-oxohexanoic acid dehydrogenase activity, 6-hydroxyhexanoic acid dehydrogenase activity, beta-oxidation activity and the like, for example. The term "enzyme" as used herein refers to a protein which can act as a catalyst to induce a chemical change in other compounds, thereby producing one or more products from one or more substrates.

Specific polypeptides (e.g., enzymes) useful for embodiments described herein are listed herein. The term "protein" as used herein refers to a molecule having a sequence of amino acids linked by peptide bonds. This term includes fusion proteins, oligopeptides, peptides, cyclic peptides, polypeptides and polypeptide derivatives, whether native or recombinant, and also includes fragments, derivatives, homologs, and variants thereof. A protein or polypeptide sometimes is of intracellular origin (e.g., located in the nucleus, cytosol, or interstitial space of host cells in vivo) and sometimes is a cell membrane protein in vivo. In some embodiments (described above, and in further detail hereafter in Engineering and Alteration Methods), a genetic modification can result in a modification (e.g., increase, substantially increase, decrease or substantially decrease) of a target activity.

A translatable nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). A translatable nucleotide sequence (e.g., ORF) sometimes is encoded differently in one organism (e.g., most organisms encode CTG as leucine) than in another organism (e.g., C. tropicalis encodes CTG as serine). In some embodiments, a translatable nucleotide sequence is altered to correct alternate genetic code (e.g., codon usage) differences between a nucleotide donor organism and an nucleotide recipient organism (e.g., engineered organism). In certain embodiments, a translatable nucleotide sequence is altered to improve; (i) codon usage, (ii) transcriptional efficiency, (iii) translational efficiency, (iv) the like, and combinations thereof.

A nucleic acid reagent sometimes comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A tag sometimes specifically binds a molecule or moiety of a solid phase or a detectable label, for example, thereby having utility for isolating, purifying and/or detecting a protein or peptide encoded by the ORF. In some embodiments, a tag comprises one or more of the following elements: FLAG (e.g., DYKDDDDKG (SEQ ID NO: 63)), V5 (e.g., GKPIPNPLLGLDST (SEQ ID NO: 64)), c-MYC (e.g., EQKLISEEDL (SEQ ID NO: 65)), HSV (e.g., QPELAPEDPED (SEQ ID NO: 66)), influenza hemaglutinin, HA (e.g., YPYDVPDYA (SEQ ID NO: 67)), VSV-G (e.g., YTDIEMNRLGK (SEQ ID NO: 68)), bacterial glutathione-S-transferase, maltose binding protein, a streptavidin- or avidin-binding tag (e.g., pcDNA™6 BioEase™ Gateway® Biotinylation System (Invitrogen)), thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6 (SEQ ID NO: 60)) or other sequence that chelates a metal (e.g., cobalt, zinc, copper), and/or a cysteine-rich sequence that binds to an arsenic-containing molecule. In certain embodiments, a cysteine-rich tag comprises the amino acid sequence CC-Xn-CC (SEQ ID NO: 69), wherein X is any amino acid and n is 1 to 3, and the cysteine-rich sequence sometimes is CCPGCC (SEQ ID NO: 70). In certain embodiments, the tag comprises a cysteine-rich element and a polyhistidine element (e.g., CCPGCC (SEQ ID NO: 70) and His6 (SEQ ID NO: 60)).

A tag often conveniently binds to a binding partner. For example, some tags bind to an antibody (e.g., FLAG) and sometimes specifically bind to a small molecule. For example, a polyhistidine tag specifically chelates a bivalent metal, such as copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ (EDT2[4',5'-bis(1,3,2-dithioarsolan-2-yl)fluorescein-(1,2-ethanedithiol)2]) and ReAsH reagents (e.g., U.S. Pat. No. 5,932,474 to Tsien et al., entitled "Target Sequences for Synthetic Molecules;" U.S. Pat. No. 6,054,271 to Tsien et al., entitled "Methods of Using Synthetic Molecules and Target Sequences;" U.S. Pat. Nos. 6,451,569 and 6,008,378; published U.S. Patent Application 2003/0083373, and published PCT Patent Application WO 99/21013, all to Tsien et al. and all entitled "Synthetic Molecules that Specifically React with Target Sequences"). Such antibodies and small molecules sometimes are linked to a solid phase for convenient isolation of the target protein or target peptide.

A tag sometimes comprises a sequence that localizes a translated protein or peptide to a component in a system, which is referred to as a "signal sequence" or "localization signal sequence" herein. A signal sequence often is incorporated at the N-terminus of a target protein or target peptide, and sometimes is incorporated at the C-terminus. Examples of signal sequences are known to the artisan, are readily incorporated into a nucleic acid reagent, and often are selected according to the organism in which expression of the nucleic acid reagent is performed. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondrial targeting signal (e.g., amino acid sequence that forms an amphipathic helix); peroxisome targeting signal (e.g., C-terminal sequence in YFG from *S. cerevisiae*); and a secretion signal (e.g., N-terminal sequences from invertase, mating factor alpha, PHO5 and SUC2 in *S. cerevisiae*; multiple N-terminal sequences of *B. subtilis* proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470,719); lam beta signal sequence (e.g., U.S. Pat. No. 5,389,529); *B. brevis* signal sequence (e.g., U.S. Pat. No. 5,232,841); and *P. pastoris* signal sequence (e.g., U.S. Pat. No. 5,268,273)).

A tag sometimes is directly adjacent to the amino acid sequence encoded by an ORF (i.e., there is no intervening sequence) and sometimes a tag is substantially adjacent to an ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I (E/D)GR), thrombin (e.g., recognition site LVPRGS (SEQ ID NO: 71)), enterokinase (e.g., recognition site DDDDK (SEQ ID NO: 72)), TEV protease (e.g., recognition site ENLYFQG (SEQ ID NO: 73)) or PreScission™ protease (e.g., recognition site LEVLFQGP (SEQ ID NO: 74)), for example.

An intervening sequence sometimes is referred to herein as a "linker sequence," and may be of any suitable length selected by the artisan. A linker sequence sometimes is about 1 to about 20 amino acids in length, and sometimes about 5 to about 10 amino acids in length. The artisan may select the linker length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and to enhance interaction of a tag/target protein product with a solid phase. A linker can be of any suitable amino acid content, and often comprises a higher proportion of amino acids having relatively short side chains (e.g., glycine, alanine, serine and threonine).

A nucleic acid reagent sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons (e.g., U.S. Patent Application No. 60/587,583, filed Jul. 14, 2004, entitled "Production of Fusion Proteins by Cell-Free Protein Synthesis,"; Eggertsson, et al., (1988) Microbiological Review 52(3):354-374, and Engleerg-Kukla, et al. (1996) in *Escherichia coli* and *Salmonella* Cellular and Molecular Biology, Chapter 60, pps 909-921, Neidhardt, et al. eds., ASM Press, Washington, D.C.). A number of suppressor tRNAs are known, including but not limited to, supE, supP, supD, supF and supZ suppressors, which suppress the termination of translation of the amber stop codon; supB, glT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. Mutations that enhance the efficiency of termination suppressors (i.e., increase stop codon read-through) have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rplL gene.

Thus, a nucleic acid reagent comprising a stop codon located between an ORF and a tag can yield a translated ORF alone when no suppressor tRNA is present in the translation system, and can yield a translated ORF-tag fusion when a suppressor tRNA is present in the system. Suppressor tRNA can be generated in cells transfected with a nucleic acid encoding the tRNA (e.g., a replication incompetent adenovirus containing the human tRNA-Ser suppressor gene can be transfected into cells, or a YAC containing a yeast or bacterial tRNA suppressor gene can be transfected into yeast cells, for example). Vectors for synthesizing suppressor tRNA and for translating ORFs with or without a tag are available to the artisan (e.g., Tag-On-Demand™ kit (Invitrogen Corporation, California); Tag-On-Demand™ Suppressor Supernatant Instruction Manual, Version B, 6 Jun. 2003, at http address www.invitrogen.com/content/sfs/manuals/tagondemand_supernatant_man.pdf; Tag-On-Demand™ Gateway® Vector Instruction Manual, Version B, 20 Jun. 2003 at http address www.invitrogen.com/content/sfs/manuals/tagondemand-_vectors_man.pdf; and Capone et al., Amber, ochre and opal suppressor tRNA genes derived from a human serine tRNA gene. EMBO J. 4:213, 1985).

Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described herein. In some embodiments, a cloning strategy can be combined with genetic manipulation such as recombination (e.g., recombination of a nucleic acid reagent with a nucleic acid sequence of interest into the genome of the organism to be modified, as described further herein). In some embodiments, the cloned ORF(s) can produce (directly or indirectly) adipic acid, by engineering a microorganism with one or more ORFs of interest, which microorganism comprises one or more altered activities selected from the group consisting of 6-oxohexanoic acid dehydrogenase activity, 6-hydroxyhexanoic acid dehydrogenase activity, glucose-6-phosphate dehydrogenase activity, hexanoate synthase activity, lipase activity, fatty acid synthase activity, acetyl CoA carboxylase activity, monooxygenase activity and monooxygenase reductase activity.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., FIG. 1 of Sauer, B., Curr. Opin. Biotech. 5:521-527 (1994)). Other examples of recombination sites include attB, attP, attL, and attR sequences, and mutants, fragments, variants and derivatives thereof, which are recognized by the recombination protein λ Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. No. 09/517,466, filed Mar. 2, 2000, and 09/732,914, filed Aug. 14, 2003, and in U.S. patent publication no. 2002-0007051-A1; Landy, Curr. Opin. Biotech. 3:699-707 (1993)).

Examples of recombinase cloning nucleic acids are in Gateway® systems (Invitrogen, California), which include at least one recombination site for cloning a desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and sub-cloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A recombination system useful for engineering yeast is outlined briefly. The system makes use of the URA3 gene (e.g., for *S. cerevisieae* and *C. albicans*, for example) or URA4 and URA5 genes (e.g., for *S. pombe*, for example) and toxicity of the nucleotide analogue 5-Fluoroorotic acid (5-FOA). The URA3 or URA4 and URA5 genes encode orotine-5'-monophosphate (OMP) dicarboxylase. Yeast with an active URA3 or URA4 and URA5 gene (phenotypically Ura+) convert 5-FOA to fluorodeoxyuridine, which is toxic to yeast cells. Yeast carrying a mutation in the appropriate gene(s) or having a knock out of the appropriate gene(s) can grow in the presence of 5-FOA, if the media is also supplemented with uracil.

A nucleic acid engineering construct can be made which may comprise the URA3 gene or cassette (for *S. cerevisieae*), flanked on either side by the same nucleotide sequence in the same orientation. The URA3 cassette comprises a promoter, the URA3 gene and a functional transcription terminator. Target sequences which direct the construct to a particular nucleic acid region of interest in the organism to be engineered are added such that the target sequences are adjacent to and abut the flanking sequences on either side of the URA3 cassette. Yeast can be transformed with the engineering construct and plated on minimal media without uracil. Colonies can be screened by PCR to determine those transformants that have the engineering construct inserted in the proper location in the genome. Checking insertion location prior to selecting for recombination of the ura3 cassette may reduce the number of incorrect clones carried through to later stages of the procedure. Correctly inserted transformants can then be replica plated on minimal media containing 5-FOA to select for recombination of the URA3 cassette out of the construct, leaving a disrupted gene and an identifiable footprint (e.g., nucleic acid sequence) that can be use to verify the presence of the disrupted gene. The technique described is useful for disrupting or "knocking out" gene function, but also can be used to insert genes or constructs into a host organisms genome in a targeted, sequence specific manner.

In certain embodiments, a nucleic acid reagent includes one or more topoisomerase insertion sites. A topoisomerase insertion site is a defined nucleotide sequence recognized and bound by a site-specific topoisomerase. For example, the nucleotide sequence 5'-(C/T)CCTT-3' is a topoisomerase recognition site bound specifically by most poxvirus topoisomerases, including vaccinia virus DNA topoisomerase I. After binding to the recognition sequence, the topoisomerase cleaves the strand at the 3'-most thymidine of the recognition site to produce a nucleotide sequence comprising 5'-(C/T) CCTT-PO4-TOPO, a complex of the topoisomerase covalently bound to the 3' phosphate via a tyrosine in the topoisomerase (e.g., Shuman, J. Biol. Chem. 266:11372-11379, 1991; Sekiguchi and Shuman, Nucl. Acids Res. 22:5360-5365, 1994; U.S. Pat. No. 5,766,891; PCT/US95/16099; and PCT/US98/12372). In comparison, the nucleotide sequence 5'-GCAACTT-3' is a topoisomerase recognition site for type IA *E. coli* topoisomerase III. An element to be inserted often is combined with topoisomerase-reacted template and thereby incorporated into the nucleic acid reagent (e.g., World Wide Web URL invitrogen.com/downloads/F-13512_Topo_Flyer.pdf; World Wide Web URL invitrogen.com/content/sfs/brochures/710_021849%20_B_TO-POCloning_bro.pdf; TOPO TA Cloning® Kit and Zero Blunt® TOPO® Cloning Kit product information).

A nucleic acid reagent sometimes contains one or more origin of replication (ORI) elements. In some embodiments, a template comprises two or more ORIs, where one functions efficiently in one organism (e.g., a bacterium) and another functions efficiently in another organism (e.g., a eukaryote, like yeast for example). In some embodiments, an ORI may function efficiently in one species (e.g., *S. cerevisieae*, for example) and another ORI may function efficiently in a different species (e.g., *S. pombe*, for example). A nucleic acid reagent also sometimes includes one or more transcription regulation sites.

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent is of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (see, e.g., Biochemistry 1996 Jun. 25; 35(25):8429-38 and http address www.devicelink.com/ivdt/archive/00/11/007.html). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95 C for 5 minutes; repeating forty-five cycles of 95 C for 1 minute, 59 C for 1 minute, 10 seconds, and 72 C for 1 minute 30 seconds; and then treating the sample at 72 C for 5 minutes. Multiple cycles frequently are performed using a commercially available thermal cycler. PCR amplification products sometimes are stored for a time at a lower temperature (e.g., at 4 C) and sometimes are frozen (e.g., at −20 C) before analysis.

In some embodiments, a nucleic acid reagent, protein reagent, protein fragment reagent or other reagent described herein is isolated or purified. The term "isolated" as used herein refers to material removed from its original environment (e.g., the natural environment if it is naturally occurring, or a host cell if expressed exogenously), and thus is altered "by the hand of man" from its original environment. The term "purified" as used herein with reference to molecules does not refer to absolute purity. Rather, "purified" refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated. Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition.

Engineering and Alteration Methods

Methods and compositions (e.g., nucleic acid reagents) described herein can be used to generate engineered microorganisms. As noted above, the term "engineered microorganism" as used herein refers to a modified organism that includes one or more activities distinct from an activity present in a microorganism utilized as a starting point for modification (e.g., host microorganism or unmodified organism). Engineered microorganisms typically arise as a result of a genetic modification, usually introduced or selected for, by one of skill in the art using readily available techniques. Non-limiting examples of methods useful for generating an altered activity include, introducing a heterologous polynucleotide (e.g., nucleic acid or gene integration, also referred to as "knock in"), removing an endogenous polynucleotide, altering the sequence of an existing endogenous nucleic acid sequence (e.g., site-directed mutagenesis), disruption of an existing endogenous nucleic acid sequence (e.g., knock outs and transposon or insertion element mediated mutagenesis), selection for an altered activity where the selection causes a change in a naturally occurring activity that can be stably inherited (e.g., causes a change in a nucleic acid sequence in the genome of the organism or in an epigenetic nucleic acid that is replicated and passed on to daughter cells), PCR-based mutagenesis, and the like. The term "mutagenesis" as used herein refers to any modification to a nucleic acid (e.g., nucleic acid reagent, or host chromosome, for example) that is subsequently used to generate a product in a host or modified organism. Non-limiting examples of mutagenesis include, deletion, insertion, substitution, rearrangement, point mutations, suppressor mutations and the like. Mutagenesis methods are known in the art and are readily available to the artisan. Non-limiting examples of mutagenesis methods are described herein and can also be found in Maniatis, T., E. F. Fritsch and J. Sambrook (1982) *Molecular Cloning: a Laboratory Manual*; Cold Spring Harbor Laboratory, Cold Spring Harbor, N.Y. Another non-limiting example of mutagenesis can be conducted using a Stratagene (San Diego, Calif.) "QuickChange" kit according to the manufacturer's instructions.

The term "genetic modification" as used herein refers to any suitable nucleic acid addition, removal or alteration that facilitates production of a target product (e.g., adipic acid, 6-hydroxyhexanoic acid) in an engineered microorganism. Genetic modifications include, without limitation, insertion of one or more nucleotides in a native nucleic acid of a host organism in one or more locations, deletion of one or more nucleotides in a native nucleic acid of a host organism in one or more locations, modification or substitution of one or more nucleotides in a native nucleic acid of a host organism in one or more locations, insertion of a non-native nucleic acid into a host organism (e.g., insertion of an autonomously replicating vector), and removal of a non-native nucleic acid in a host organism (e.g., removal of a vector).

The term "heterologous polynucleotide" as used herein refers to a nucleotide sequence not present in a host microorganism in some embodiments. In certain embodiments, a heterologous polynucleotide is present in a different amount (e.g., different copy number) than in a host microorganism, which can be accomplished, for example, by introducing more copies of a particular nucleotide sequence to a host microorganism (e.g., the particular nucleotide sequence may be in a nucleic acid autonomous of the host chromosome or may be inserted into a chromosome). A heterologous polynucleotide is from a different organism in some embodiments, and in certain embodiments, is from the same type of organism but from an outside source (e.g., a recombinant source).

In some embodiments, an organism engineered using the methods and nucleic acid reagents described herein can produce adipic acid. In certain embodiments, an engineered microorganism described herein that produces adipic acid may comprise one or more altered activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, hexanoate synthase activity, lipase activity, fatty acid synthase activity, acetyl CoA carboxylase activity, monooxygenase activity and monooxygenase reductase activity. In some embodiments, an engineered microorganism as described herein may comprise a genetic modification that adds or increases the 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, monooxygenase activity and monooxygenase reductase activity.

In certain embodiments, an engineered microorganism described herein can comprise an altered thioesterase activity. In some embodiments, the engineered microorganism may comprise a genetic alteration that adds or increases a thioesterase activity. In some embodiments, the engineered microorganism comprising a genetic alteration that adds or increases a thioesterase activity, may further comprise a heterologous polynucleotide encoding a polypeptide having thioesterase activity.

The term "altered activity" as used herein refers to an activity in an engineered microorganism that is added or modified relative to the host microorganism (e.g., added, increased, reduced, inhibited or removed activity). An activity can be altered by introducing a genetic modification to a host microorganism that yields an engineered microorganism having added, increased, reduced, inhibited or removed activity.

An added activity often is an activity not detectable in a host microorganism. An increased activity generally is an activity detectable in a host microorganism that has been increased in an engineered microorganism. An activity can be increased to any suitable level for production of a target product (e.g., adipic acid, 6-hydroxyhexanoic acid), including but not limited to less than 2-fold (e.g., about 10% increase to about 99% increase; about 20%, 30%, 40%, 50%, 60%, 70%, 80%, 90% increase), 2-fold, 3-fold, 4-fold, 5-fold, 6-fold, 7-fold, 8-fold, 9-fold, of 10-fold increase, or greater than about 10-fold increase. A reduced or inhibited activity generally is an activity detectable in a host microorganism that has been reduced or inhibited in an engineered microorganism. An activity can be reduced to undetectable levels in some embodiments, or detectable levels in certain embodiments. An activity can be decreased to any suitable level for production of a target product (e.g., adipic acid, 6-hydroxyhexanoic acid), including but not limited to less than 2-fold (e.g., about 10% decrease to about 99% decrease; about 20%, 30%, 40%, 50%, 60%, 70%, 80%, 90% decrease), 2-fold, 3-fold, 4-fold, 5-fold, 6-fold, 7-fold, 8-fold, 9-fold, of 10-fold decrease, or greater than about 10-fold decrease.

An altered activity sometimes is an activity not detectable in a host organism and is added to an engineered organism. An altered activity also may be an activity detectable in a host organism and is increased in an engineered organism. An activity may be added or increased by increasing the number of copies of a polynucleotide that encodes a polypeptide having a target activity, in some embodiments. In certain embodiments an activity can be added or increased by inserting into a host microorganism a heterologous polynucleotide that encodes a polypeptide having the added activity. In certain embodiments, an activity can be added or increased by inserting into a host microorganism a heterologous polynucleotide that is (i) operably linked to another polynucleotide that encodes a polypeptide having the added activity, and (ii) up regulates production of the polynucleotide. Thus, an activity can be added or increased by inserting or modifying a regulatory polynucleotide operably linked to another polynucleotide that encodes a polypeptide having the target activity. In certain embodiments, an activity can be added or increased by subjecting a host microorganism to a selective environment and screening for microorganisms that have a detectable level of the target activity. Examples of a selective environment include, without limitation, a medium containing a substrate that a host organism can process and a medium lacking a substrate that a host organism can process.

An altered activity sometimes is an activity detectable in a host organism and is reduced, inhibited or removed (i.e., not detectable) in an engineered organism. An activity may be reduced or removed by decreasing the number of copies of a polynucleotide that encodes a polypeptide having a target activity, in some embodiments. In some embodiments, an activity can be reduced or removed by (i) inserting a polynucleotide within a polynucleotide that encodes a polypeptide having the target activity (disruptive insertion), and/or (ii) removing a portion of or all of a polynucleotide that encodes a polypeptide having the target activity (deletion or knock out, respectively). In certain embodiments, an activity can be reduced or removed by inserting into a host microorganism a heterologous polynucleotide that is (i) operably linked to another polynucleotide that encodes a polypeptide having the target activity, and (ii) down regulates production of the polynucleotide. Thus, an activity can be reduced or removed by inserting or modifying a regulatory polynucleotide operably linked to another polynucleotide that encodes a polypeptide having the target activity.

An activity also can be reduced or removed by (i) inhibiting a polynucleotide that encodes a polypeptide having the activity or (ii) inhibiting a polynucleotide operably linked to another polynucleotide that encodes a polypeptide having the activity. A polynucleotide can be inhibited by a suitable technique known in the art, such as by contacting an RNA encoded by the polynucleotide with a specific inhibitory RNA (e.g., RNAi, siRNA, ribozyme). An activity also can be reduced or removed by contacting a polypeptide having the activity with a molecule that specifically inhibits the activity (e.g., enzyme inhibitor, antibody). In certain embodiments, an activity can be reduced or removed by subjecting a host microorganism to a selective environment and screening for microorganisms that have a reduced level or removal of the target activity.

In some embodiments, an untranslated ribonucleic acid, or a cDNA can be used to reduce the expression of a particular activity or enzyme. For example, a microorganism can be engineered by genetic modification to express a nucleic acid reagent that reduces the expression of an activity by producing an RNA molecule that is partially or substantially homologous to a nucleic acid sequence of interest which encodes the activity of interest. The RNA molecule can bind to the nucleic acid sequence of interest and inhibit the nucleic acid sequence from performing its natural function, in certain embodiments. In some embodiments, the RNA may alter the nucleic acid sequence of interest which encodes the activity of interest in a manner that the nucleic acid sequence of interest is no longer capable of performing its natural function (e.g., the action of a ribozyme for example).

In certain embodiments, nucleotide sequences sometimes are added to, modified or removed from one or more of the nucleic acid reagent elements, such as the promoter, 5'UTR, target sequence, or 3'UTR elements, to enhance, potentially enhance, reduce, or potentially reduce transcription and/or translation before or after such elements are incorporated in a nucleic acid reagent. In some embodiments, one or more of the following sequences may be modified or removed if they are present in a 5'UTR: a sequence that forms a stable secondary structure (e.g., quadruplex structure or stem loop stem structure (e.g., EMBL sequences X12949, AF274954, AF139980, AF152961, S95936, U194144, AF116649 or substantially identical sequences that form such stem loop stem structures)); a translation initiation codon upstream of the target nucleotide sequence start codon; a stop codon upstream of the target nucleotide sequence translation initiation codon; an ORF upstream of the target nucleotide sequence translation initiation codon; an iron responsive element (IRE) or like sequence; and a 5' terminal oligopyrimidine tract (TOP, e.g., consisting of 5-15 pyrimidines adjacent to the cap). A translational enhancer sequence and/or an internal ribosome entry site (IRES) sometimes is inserted into a 5'UTR (e.g., EMBL nucleotide sequences J04513, X87949, M95825, M12783, AF025841, AF013263, AF006822, M17169, M13440, M22427, D14838 and M17446 and substantially identical nucleotide sequences). An AU-rich element (ARE, e.g., AUUUA repeats) and/or splicing junction that follows a nonsense codon sometimes is removed from or modified in a 3'UTR. A polyadenosine tail sometimes is inserted into a 3'UTR if none is present, sometimes is removed if it is present, and adenosine moieties sometimes are added to or removed from a polyadenosine tail present in a 3'UTR. Thus, some embodiments are directed to a process comprising: determining whether any nucleotide sequences that increase, potentially increase, reduce or potentially reduce translation efficiency are present in the elements, and adding, removing or modifying one or more of such sequences if they are identified. Certain embodiments are directed to a process comprising: determining whether any nucleotide sequences that increase or potentially increase translation efficiency are not present in the elements, and incorporating such sequences into the nucleic acid reagent.

In some embodiments, an activity can be altered by modifying the nucleotide sequence of an ORF. An ORF sometimes is mutated or modified (for example, by point mutation, deletion mutation, insertion mutation, PCR based mutagenesis and the like) to alter, enhance or increase, reduce, substantially reduce or eliminate the activity of the encoded protein or peptide. The protein or peptide encoded by a modified ORF sometimes is produced in a lower amount or may not be produced at detectable levels, and in other embodiments, the product or protein encoded by the modified ORF is produced at a higher level (e.g., codons sometimes are modified so they are compatible with tRNA's preferentially used in the host organism or engineered organism). To determine the relative activity, the activity from the product of the mutated ORF (or cell containing it) can be compared to the activity of the product or protein encoded by the unmodified ORF (or cell containing it).

In some embodiments, an ORF nucleotide sequence sometimes is mutated or modified to alter the triplet nucleotide sequences used to encode amino acids (e.g., amino acid codon triplets, for example). Modification of the nucleotide sequence of an ORF to alter codon triplets sometimes is used to change the codon found in the original sequence to better match the preferred codon usage of the organism in which the ORF or nucleic acid reagent will be expressed. The codon usage, and therefore the codon triplets encoded by a nucleic acid sequence, in bacteria may be different from the preferred codon usage in eukaryotes, like yeast or plants for example. Preferred codon usage also may be different between bacterial species. In certain embodiments an ORF nucleotide sequences sometimes is modified to eliminate codon pairs and/or eliminate mRNA secondary structures that can cause pauses during translation of the mRNA encoded by the ORF nucleotide sequence. Translational pausing sometimes occurs when nucleic acid secondary structures exist in an mRNA, and sometimes occurs due to the presence of codon pairs that slow the rate of translation by causing ribosomes to pause. In some embodiments, the use of lower abundance codon triplets can reduce translational pausing due to a decrease in the pause time needed to load a charged tRNA into the ribosome translation machinery. Therefore, to increase transcriptional and translational efficiency in bacteria (e.g., where transcription and translation are concurrent, for example) or to increase translational efficiency in eukaryotes (e.g., where transcription and translation are functionally separated), the nucleotide sequence of a nucleotide sequence of interest can be altered to better suit the transcription and/or translational machinery of the host and/or genetically modified microorganism. In certain embodiments, slowing the rate of translation by the use of lower abundance codons, which slow or pause the ribosome, can lead to higher yields of the desired product due to an increase in correctly folded proteins and a reduction in the formation of inclusion bodies.

Codons can be altered and optimized according to the preferred usage by a given organism by determining the codon distribution of the nucleotide sequence donor organism and comparing the distribution of codons to the distribution of codons in the recipient or host organism. Techniques described herein (e.g., site directed mutagenesis and the like)

can then be used to alter the codons accordingly. Comparisons of codon usage can be done by hand, or using nucleic acid analysis software commercially available to the artisan.

Modification of the nucleotide sequence of an ORF also can be used to correct codon triplet sequences that have diverged in different organisms. For example, certain yeast (e.g., *C. tropicalis* and *C. maltosa*) use the amino acid triplet CUG (e.g., CTG in the DNA sequence) to encode serine. CUG typically encodes leucine in most organisms. In order to maintain the correct amino acid in the resultant polypeptide or protein, the CUG codon must be altered to reflect the organism in which the nucleic acid reagent will be expressed. Thus, if an ORF from a bacterial donor is to be expressed in either *Candida* yeast strain mentioned above, the heterologous nucleotide sequence must first be altered or modified to the appropriate leucine codon. Therefore, in some embodiments, the nucleotide sequence of an ORF sometimes is altered or modified to correct for differences that have occurred in the evolution of the amino acid codon triplets between different organisms. In some embodiments, the nucleotide sequence can be left unchanged at a particular amino acid codon, if the amino acid encoded is a conservative or neutral change in amino acid when compared to the originally encoded amino acid.

In some embodiments, an activity can be altered by modifying translational regulation signals, like a stop codon for example. A stop codon at the end of an ORF sometimes is modified to another stop codon, such as an amber stop codon described above. In some embodiments, a stop codon is introduced within an ORF, sometimes by insertion or mutation of an existing codon. An ORF comprising a modified terminal stop codon and/or internal stop codon often is translated in a system comprising a suppressor tRNA that recognizes the stop codon. An ORF comprising a stop codon sometimes is translated in a system comprising a suppressor tRNA that incorporates an unnatural amino acid during translation of the target protein or target peptide. Methods for incorporating unnatural amino acids into a target protein or peptide are known, which include, for example, processes utilizing a heterologous tRNA/synthetase pair, where the tRNA recognizes an amber stop codon and is loaded with an unnatural amino acid (e.g., World Wide Web URL iupac.org/news/prize/2003/wang.pdf).

Depending on the portion of a nucleic acid reagent (e.g., Promoter, 5' or 3' UTR, ORI, ORF, and the like) chosen for alteration (e.g., by mutagenesis, introduction or deletion, for example) the modifications described above can alter a given activity by (i) increasing or decreasing feedback inhibition mechanisms, (ii) increasing or decreasing promoter initiation, (iii) increasing or decreasing translation initiation, (iv) increasing or decreasing translational efficiency, (v) modifying localization of peptides or products expressed from nucleic acid reagents described herein, or (vi) increasing or decreasing the copy number of a nucleotide sequence of interest, (vii) expression of an anti-sense RNA, RNAi, siRNA, ribozyme and the like. In some embodiments, alteration of a nucleic acid reagent or nucleotide sequence can alter a region involved in feedback inhibition (e.g., 5' UTR, promoter and the like). A modification sometimes is made that can add or enhance binding of a feedback regulator and sometimes a modification is made that can reduce, inhibit or eliminate binding of a feedback regulator.

In certain embodiments, alteration of a nucleic acid reagent or nucleotide sequence can alter sequences involved in transcription initiation (e.g., promoters, 5' UTR, and the like). A modification sometimes can be made that can enhance or increase initiation from an endogenous or heterologous promoter element. A modification sometimes can be made that removes or disrupts sequences that increase or enhance transcription initiation, resulting in a decrease or elimination of transcription from an endogenous or heterologous promoter element.

In some embodiments, alteration of a nucleic acid reagent or nucleotide sequence can alter sequences involved in translational initiation or translational efficiency (e.g., 5' UTR, 3' UTR, codon triplets of higher or lower abundance, translational terminator sequences and the like, for example). A modification sometimes can be made that can increase or decrease translational initiation, modifying a ribosome binding site for example. A modification sometimes can be made that can increase or decrease translational efficiency. Removing or adding sequences that form hairpins and changing codon triplets to a more or less preferred codon are non-limiting examples of genetic modifications that can be made to alter translation initiation and translation efficiency.

In certain embodiments, alteration of a nucleic acid reagent or nucleotide sequence can alter sequences involved in localization of peptides, proteins or other desired products (e.g., adipic acid, for example). A modification sometimes can be made that can alter, add or remove sequences responsible for targeting a polypeptide, protein or product to an intracellular organelle, the periplasm, cellular membranes, or extracellularly. Transport of a heterologous product to a different intracellular space or extracellularly sometimes can reduce or eliminate the formation of inclusion bodies (e.g., insoluble aggregates of the desired product).

In some embodiments, alteration of a nucleic acid reagent or nucleotide sequence can alter sequences involved in increasing or decreasing the copy number of a nucleotide sequence of interest. A modification sometimes can be made that increases or decreases the number of copies of an ORF stably integrated into the genome of an organism or on an epigenetic nucleic acid reagent. Non-limiting examples of alterations that can increase the number of copies of a sequence of interest include, adding copies of the sequence of interest by duplication of regions in the genome (e.g., adding additional copies by recombination or by causing gene amplification of the host genome, for example), cloning additional copies of a sequence onto a nucleic acid reagent, or altering an ORI to increase the number of copies of an epigenetic nucleic acid reagent. Non-limiting examples of alterations that can decrease the number of copies of a sequence of interest include, removing copies of the sequence of interest by deletion or disruption of regions in the genome, removing additional copies of the sequence from epigenetic nucleic acid reagents, or altering an ORI to decrease the number of copies of an epigenetic nucleic acid reagent.

In certain embodiments, increasing or decreasing the expression of a nucleotide sequence of interest can also be accomplished by altering, adding or removing sequences involved in the expression of an anti-sense RNA, RNAi, siRNA, ribozyme and the like. The methods described above can be used to modify expression of anti-sense RNA, RNAi, siRNA, ribozyme and the like.

The methods and nucleic acid reagents described herein can be used to generate genetically modified microorganisms with altered activities in cellular processes involved in adipic acid synthesis. In some embodiments, an engineered microorganism described herein may comprise a heterologous polynucleotide encoding a polypeptide having 6-oxohexanoic acid dehydrogenase activity, and in certain embodiments, an engineered microorganism described herein may comprise a heterologous polynucleotide encoding a polypeptide having omega oxo fatty acid dehydrogenase activity. In some embodiments, an engineered microorganism described herein may comprise a heterologous polynucleotide encoding a polypeptide having 6-hydroxyhexanoic acid dehydrogenase activity, and in certain embodiments, an engineered microorganism described herein may comprise a heterologous polynucleotide encoding a polypeptide having omega hydroxyl fatty acid dehydrogenase activity. In some embodiments, the heterologous polynucleotide can be from a bacterium. In some embodiments, the bacterium can be an *Acinetobacter, Nocardia, Pseudomonas* or *Xanthobacter* bacterium.

In certain embodiments, an engineered microorganism described herein may comprise a heterologous polynucleotide encoding a polypeptide having hexanoate synthase subunit A activity. In some embodiments, an engineered microorganism described herein may comprise a heterologous polynucleotide encoding a polypeptide having hexanoate synthase subunit B activity. In certain embodiments, the heterologous polynucleotide independently is selected from a fungus. In some embodiments, the fungus can be an *Aspergillus* fungus. In certain embodiments, the *Aspergillus* fungus is *A. parasiticus*.

In some embodiments, an engineered microorganism described herein may comprise a heterologous polynucleotide encoding a polypeptide having monooxygenase activity. In certain embodiments, the heterologous polynucleotide can be from a bacterium. In some embodiments, the bacterium can be a *Bacillus* bacterium. In certain embodiments, the *Bacillus* bacterium is *B. megaterium*.

In some embodiments, an engineered microorganism described herein may comprise a genetic modification that results in primary hexanoate usage by monooxygenase activity. In certain embodiments, the genetic modification can reduce a polyketide synthase activity. In some embodiments, the engineered microorganism can be a eukaryote. In certain embodiments, the eukaryote can be a yeast. In some embodiments, the eukaryote may be a fungus. In certain embodiments, the yeast can be a *Candida* yeast. In some embodiments, the *Candida* yeast may be *C. troplicalis*. In certain embodiments, the fungus can be a *Yarrowia* fungus. In some embodiments the *Yarrowia* fungus may be *Y. lipolytica*. In certain embodiments, the fungus can be an *Aspergillus* fungus. In some embodiments, the *Aspergillus* fungus may be *A. parasiticus* or *A. nidulans*.

In certain embodiments, an engineered microorganism described herein may comprise a genetic modification that reduces 6-hydroxyhexanoic acid conversion. In some embodiments, the genetic modification can reduce 6-hydroxyhexanoic acid dehydrogenase activity. In certain embodiments, an engineered microorganism described herein may comprise a genetic modification that reduces beta-oxidation activity. In some embodiments, the genetic modification can reduce a target activity described herein.

Engineered microorganisms that produce adipic acid, as described herein, can comprise an altered monooxygenase activity, in certain embodiments. In some embodiments, the engineered microorganism described herein may comprise a genetic modification that alters the monooxygenase activity. In certain embodiments, the genetic modification can result in substantial hexanoate usage by the monooxygenase activity. In some embodiments, the genetic modification can reduce a polyketide synthase activity. In certain embodiments, the engineered microorganism described herein can comprise a heterologous polynucleotide encoding a polypeptide having monooxygenase activity. In certain embodiments, the heterologous polynucleotide can be from a bacterium. In some embodiments, the bacterium can be a *Bacillus* bacterium. In certain embodiments, the *Bacillus* bacterium is *B. megaterium*.

In some embodiments, the engineered microorganism described herein may comprise an altered hexanoate synthase activity. In certain embodiments, the altered hexanoate synthase activity is an altered hexanoate synthase subunit A activity, altered hexanoate synthase subunit B activity, or altered hexanoate synthase subunit A activity and altered hexanoate synthase subunit B activity. In some embodiments, the engineered microorganism may comprise a genetic alteration that adds or increases hexanoate synthase activity. In certain embodiments, the engineered microorganism may comprise a heterologous polynucleotide encoding a polypeptide having hexanoate synthase activity. In some embodiments, the heterologous polynucleotide can be from a fungus. In certain embodiments, the fungus can be an *Aspergillus* fungus. In some embodiments, the *Aspergillus* fungus is *A. parasiticus*.

Engineered microorganisms that produce adipic acid, as described herein, can comprise an altered thioesterase activity, in certain embodiments. In some embodiments, the engineered microorganism may comprise a genetic modification that adds or increases the thioesterase activity. In certain embodiments, the engineered microorganism may comprise a heterologous polynucleotide encoding a polypeptide having thioesterase activity.

In some embodiments, the engineered microorganism with an altered thioesterase activity may comprise an altered 6-oxohexanoic acid dehydrogenase activity, or an altered omega oxo fatty acid dehydrogenase activity. In certain embodiments, the engineered microorganism with an altered thioesterase activity may comprise a genetic modification that adds or increases 6-oxohexanoic acid dehydrogenase activity, or a genetic modification that adds or increases omega oxo fatty acid dehydrogenase activity. In some embodiments, the engineered microorganism may comprise a heterologous polynucleotide encoding a polypeptide having altered 6-oxohexanoic acid dehydrogenase activity, and in some embodiments, the engineered microorganism may comprise a heterologous polynucleotide encoding a polypeptide having altered omega oxo fatty acid dehydrogenase activity. In certain embodiments, the heterologous polynucleotide can be from a bacterium. In some embodiments, the bacterium can be an *Acinetobacter, Nocardia, Pseudomonas* or *Xanthobacter* bacterium.

Engineered microorganisms that produce adipic acid, as described herein, can comprise an altered 6-hydroxyhexanoic acid dehydrogenase activity, in certain embodiments, and in some embodiments, can comprise an altered omega hydroxyl fatty acid dehydrogenase activity. In certain embodiments, the engineered microorganism may comprise a genetic modification that adds or increases the 6-hydroxyhexanoic acid dehydrogenase activity and in some embodiments the engineered microorganism may comprise a genetic modification that adds or increases the omega hydroxyl fatty acid dehydrogenase activity. In certain embodiments, the engineered microorganism may comprise a heterologous polynucleotide encoding a polypeptide having altered 6-hydroxyhexanoic acid dehydrogenase activity, and in some embodiments, the engineered microorganism may comprise a heterologous polynucleotide encoding a polypeptide having altered omega hydroxyl fatty acid dehydrogenase activity. In some embodiments, the heterologous polynucleotide is from a bacterium. In certain embodiments, the bacterium can be an *Acinetobacter, Nocardia, Pseudomonas* or *Xanthobacter* bacterium. In some embodiments, the engineered microorganism can be a eukaryote. In certain embodiments, the eukaryote can be a yeast. In some embodiments, the eukaryote may be a fungus. In certain embodiments, the yeast can be a *Candida* yeast. In some embodiments, the *Candida* yeast may be *C. troplicalis*. In certain embodiments, the fungus can be a *Yarrowia* fungus. In some embodiments the *Yarrowia* fungus may be *Y. lipolytica*. In certain embodiments, the fungus can be an *Aspergillus* fungus. In some embodiments, the *Aspergillus* fungus may be *A. parasiticus* or *A. nidulans*.

In some embodiments, an engineered microorganism as described above may comprise a genetic modification that reduces 6-hydroxyhexanoic acid conversion. In certain embodiments, the genetic modification can reduce 6-hydroxyhexanoic acid dehydrogenase activity. In some embodiments the genetic may reduce beta-oxidation activity. In certain embodiments, the genetic modification may reduce a target activity described herein.

Engineered microorganisms can be prepared by altering, introducing or removing nucleotide sequences in the host genome or in stably maintained epigenetic nucleic acid reagents, as noted above. The nucleic acid reagents use to alter, introduce or remove nucleotide sequences in the host genome or epigenetic nucleic acids can be prepared using the methods described herein or available to the artisan.

Nucleic acid sequences having a desired activity can be isolated from cells of a suitable organism using lysis and nucleic acid purification procedures described in a known reference manual (e.g., Maniatis, T., E. F. Fritsch and J. Sambrook (1982) *Molecular Cloning: a Laboratory Manual*; Cold Spring Harbor Laboratory, Cold Spring Harbor, N.Y.) or using commercially available cell lysis and DNA purification reagents and kits. In some embodiments, nucleic acids used to engineer microorganisms can be provided for conducting methods described herein after processing of the organism containing the nucleic acid. For example, the nucleic acid of interest may be extracted, isolated, purified or amplified from a sample (e.g., from an organism of interest or culture containing a plurality of organisms of interest, like yeast or bacteria for example). The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated sample nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to sample nucleic acid provided that contains fewer nucleic acid species than in the sample source from which the sample nucleic acid is derived. A composition comprising sample nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a cell, organism or sample to a process that linearly or exponentially generates amplicon nucleic acids having the same or substantially the same nucleotide sequence as the nucleotide sequence of the nucleic acid in the sample, or portion thereof. As noted above, the nucleic acids used to prepare nucleic acid reagents as described herein can be subjected to fragmentation or cleavage.

Amplification of nucleic acids is sometimes necessary when dealing with organisms that are difficult to culture. Where amplification may be desired, any suitable amplification technique can be utilized. Non-limiting examples of methods for amplification of polynucleotides include, polymerase chain reaction (PCR); ligation amplification (or ligase chain reaction (LCR)); amplification methods based on the use of Q-beta replicase or template-dependent polymerase (see US Patent Publication Number US20050287592); helicase-dependant isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR(RT-PCR), Real Time PCR, Single cell PCR, Solid phase PCR, combinations thereof, and the like. Reagents and hardware for conducting PCR are commercially available.

Protocols for conducting the various type of PCR listed above are readily available to the artisan. PCR conditions can be dependent upon primer sequences, target abundance, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. PCR often is carried out as an automated process with a thermostable enzyme. In this process, the temperature of the reaction mixture is cycled through a denaturing region, a primer-annealing region, and an extension reaction region automatically. Machines specifically adapted for this purpose are commercially available. A non-limiting example of a PCR protocol that may be suitable for embodiments described herein is, treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Additional PCR protocols are described in the example section. Multiple cycles frequently are performed using a commercially available thermal cycler. Suitable isothermal amplification processes known and selected by the person of ordinary skill in the art also may be applied, in certain embodiments. In some embodiments, nucleic acids encoding polypeptides with a desired activity can be isolated by amplifying the desired sequence from an organism having the desired activity using oligonucleotides or primers designed based on sequences described herein.

Amplified, isolated and/or purified nucleic acids can be cloned into the recombinant DNA vectors described in Figures herein or into suitable commercially available recombinant DNA vectors. Cloning of nucleic acid sequences of interest into recombinant DNA vectors can facilitate further manipulations of the nucleic acids for preparation of nucleic acid reagents, (e.g., alteration of nucleotide sequences by mutagenesis, homologous recombination, amplification and the like, for example). Standard cloning procedures (e.g., enzymic digestion, ligation, and the like) are known (e.g., described in Maniatis, T., E. F. Fritsch and J. Sambrook (1982) *Molecular Cloning: a Laboratory Manual*; Cold Spring Harbor Laboratory, Cold Spring Harbor, N.Y.).

In some embodiments, nucleic acid sequences prepared by isolation or amplification can be used, without any further modification, to add an activity to a microorganism and thereby create a genetically modified or engineered microorganism. In certain embodiments, nucleic acid sequences prepared by isolation or amplification can be genetically modified to alter (e.g., increase or decrease, for example) a desired activity. In some embodiments, nucleic acids, used to add an activity to an organism, sometimes are genetically modified to optimize the heterologous polynucleotide sequence encoding the desired activity (e.g., polypeptide or protein, for example). The term "optimize" as used herein can refer to alteration to increase or enhance expression by preferred codon usage. The term optimize can also refer to modifications to the amino acid sequence to increase the activity of a polypeptide or protein, such that the activity exhibits a higher catalytic activity as compared to the "natural" version of the polypeptide or protein.

Nucleic acid sequences of interest can be genetically modified using methods known in the art. Mutagenesis techniques are particularly useful for small scale (e.g., 1, 2, 5, 10 or more nucleotides) or large scale (e.g., 50, 100, 150, 200, 500, or more nucleotides) genetic modification. Mutagenesis allows the artisan to alter the genetic information of an organism in a stable manner, either naturally (e.g., isolation using selection and screening) or experimentally by the use of chemicals, radiation or inaccurate DNA replication (e.g., PCR mutagenesis). In some embodiments, genetic modification can be performed by whole scale synthetic synthesis of nucleic acids, using a native nucleotide sequence as the reference sequence, and modifying nucleotides that can result in the desired alteration of activity. Mutagenesis methods sometimes are specific or targeted to specific regions or nucleotides (e.g., site-directed mutagenesis, PCR-based site-directed mutagenesis, and in vitro mutagenesis techniques such as transplacement and in vivo oligonucleotide site-directed mutagenesis, for example). Mutagenesis methods sometimes are non-specific or random with respect to the placement of genetic modifications (e.g., chemical mutagenesis, insertion element (e.g., insertion or transposon elements) and inaccurate PCR based methods, for example).

Site directed mutagenesis is a procedure in which a specific nucleotide or specific nucleotides in a DNA molecule are mutated or altered. Site directed mutagenesis typically is performed using a nucleic acid sequence of interest cloned into a circular plasmid vector. Site-directed mutagenesis requires that the wild type sequence be known and used a platform for the genetic alteration. Site-directed mutagenesis sometimes is referred to as oligonucleotide-directed mutagenesis because the technique can be performed using oligonucleotides which have the desired genetic modification incorporated into the complement a nucleotide sequence of interest. The wild type sequence and the altered nucleotide are allowed to hybridize and the hybridized nucleic acids are extended and replicated using a DNA polymerase. The double stranded nucleic acids are introduced into a host (e.g., E. coli, for example) and further rounds of replication are carried out in vivo. The transformed cells carrying the mutated nucleic acid sequence are then selected and/or screened for those cells carrying the correctly mutagenized sequence. Cassette mutagenesis and PCR-based site-directed mutagenesis are further modifications of the site-directed mutagenesis technique. Site-directed mutagenesis can also be performed in vivo (e.g., transplacement "pop-in pop-out", In vivo site-directed mutagenesis with synthetic oligonucleotides and the like, for example).

PCR-based mutagenesis can be performed using PCR with oligonucleotide primers that contain the desired mutation or mutations. The technique functions in a manner similar to standard site-directed mutagenesis, with the exception that a thermocycler and PCR conditions are used to replace replication and selection of the clones in a microorganism host. As PCR-based mutagenesis also uses a circular plasmid vector, the amplified fragment (e.g., linear nucleic acid molecule) containing the incorporated genetic modifications can be separated from the plasmid containing the template sequence after a sufficient number of rounds of thermocycler amplification, using standard electrophorectic procedures. A modification of this method uses linear amplification methods and a pair of mutagenic primers that amplify the entire plasmid. The procedure takes advantage of the E. coli Dam methylase system which causes DNA replicated in vivo to be sensitive to the restriction endonucleases Dpnl. PCR synthesized DNA is not methylated and is therefore resistant to Dpnl. This approach allows the template plasmid to be digested, leaving the genetically modified, PCR synthesized plasmids to be isolated and transformed into a host bacteria for DNA repair and replication, thereby facilitating subsequent cloning and identification steps. A certain amount of randomness can be added to PCR-based sited directed mutagenesis by using partially degenerate primers.

Recombination sometimes can be used as a tool for mutagenesis. Homologous recombination allows the artisan to specifically target regions of known sequence for insertion of heterologous nucleotide sequences using the host organisms natural DNA replication and repair enzymes. Homologous recombination methods sometimes are referred to as "pop in pop out" mutagenesis, transplacement, knock out mutagenesis or knock in mutagenesis. Integration of a nucleic acid sequence into a host genome is a single cross over event, which inserts the entire nucleic acid reagent (e.g., pop in). A second cross over event excises all but a portion of the nucleic acid reagent, leaving behind a heterologous sequence, often referred to as a "footprint" (e.g., pop out). Mutagenesis by insertion (e.g., knock in) or by double recombination leaving behind a disrupting heterologous nucleic acid (e.g., knock out) both server to disrupt or "knock out" the function of the gene or nucleic acid sequence in which insertion occurs. By combining selectable markers and/or auxotrophic markers with nucleic acid reagents designed to provide the appropriate nucleic acid target sequences, the artisan can target a selectable nucleic acid reagent to a specific region, and then select for recombination events that "pop out" a portion of the inserted (e.g., "pop in") nucleic acid reagent.

Such methods take advantage of nucleic acid reagents that have been specifically designed with known target nucleic acid sequences at or near a nucleic acid or genomic region of interest. Popping out typically leaves a "foot print" of left over sequences that remain after the recombination event. The left over sequence can disrupt a gene and thereby reduce or eliminate expression of that gene. In some embodiments, the method can be used to insert sequences, upstream or downstream of genes that can result in an enhancement or reduction in expression of the gene. In certain embodiments, new genes can be introduced into the genome of a host organism using similar recombination or "pop in" methods. An example of a yeast recombination system using the ura3 gene and 5-FOA were described briefly above and further detail is presented herein.

A method for modification is described in Alani et al., "A method for gene disruption that allows repeated use of URA3 selection in the construction of multiply disrupted yeast strains", Genetics 116(4):541-545 August 1987. The original method uses a Ura3 cassette with 1000 base pairs (bp) of the same nucleotide sequence cloned in the same orientation on either side of the URA3 cassette. Targeting sequences of about 50 bp are added to each side of the construct. The double stranded targeting sequences are complementary to sequences in the genome of the host organism. The targeting sequences allow site-specific recombination in a region of interest. The modification of the original technique replaces the two 1000 bp sequence direct repeats with two 200 bp direct repeats. The modified method also uses 50 bp targeting sequences. The modification reduces or eliminates recombination of a second knock out into the 1000 bp repeat left behind in a first mutagenesis, therefore allowing multiply knocked out yeast. Additionally, the 200 bp sequences used herein are uniquely designed, self-assembling sequences that leave behind identifiable footprints. The technique used to design the sequences incorporate design features such as low identity to the yeast genome, and low identity to each other. Therefore a library of the self-assembling sequences can be generated to allow multiple knockouts in the same organism, while reducing or eliminating the potential for integration into a previous knockout.

As noted above, the URA3 cassette makes use of the toxicity of 5-FOA in yeast carrying a functional URA3 gene. Uracil synthesis deficient yeast are transformed with the modified URA3 cassette, using standard yeast transformation protocols, and the transformed cells are plated on minimal media minus uracil. In some embodiments, PCR can be used to verify correct insertion into the region of interest in the host genome, and certain embodiments the PCR step can be omitted. Inclusion of the PCR step can reduce the number of transformants that need to be counter selected to "pop out" the URA3 cassette. The transformants (e.g., all or the ones determined to be correct by PCR, for example) can then be counter-selected on media containing 5-FOA, which will select for recombination out (e.g., popping out) of the URA3 cassette, thus rendering the yeast ura3 deficient again, and resistant to 5-FOA toxicity. Targeting sequences used to direct recombination events to specific regions are presented herein. A modification of the method described above can be used to integrate genes in to the chromosome, where after recombination a functional gene is left in the chromosome next to the 200 bp footprint.

In some embodiments, other auxotrophic or dominant selection markers can be used in place of URA3 (e.g., an auxotrophic selectable marker), with the appropriate change in selection media and selection agents. Auxotrophic selectable markers are used in strains deficient for synthesis of a required biological molecule (e.g., amino acid or nucleoside, for example). Non-limiting examples of additional auxotrophic markers include; HIS3, TRP1, LEU2, LEU2-d, and LYS2. Certain auxotrophic markers (e.g., URA3 and LYS2) allow counter selection to select for the second recombination event that pops out all but one of the direct repeats of the recombination construct. HIS3 encodes an activity involved in histidine synthesis. TRP1 encodes an activity involved in tryptophan synthesis. LEU2 encodes an activity involved in leucine synthesis. LEU2-d is a low expression version of LEU2 that selects for increased copy number (e.g., gene or plasmid copy number, for example) to allow survival on minimal media without leucine. LYS2 encodes an activity involved in lysine synthesis, and allows counter selection for recombination out of the LYS2 gene using alpha-amino adipate (-amino adipate).

Dominant selectable markers are useful because they also allow industrial and/or prototrophic strains to be used for genetic manipulations. Additionally, dominant selectable markers provide the advantage that rich medium can be used for plating and culture growth, and thus growth rates are markedly increased. Non-limiting examples of dominant selectable markers include; Tn903 kan$^r$, Cm$^r$, Hyg$^r$, CUP1, and DHFR. Tn903 kan$^r$ encodes an activity involved in kanamycin antibiotic resistance (e.g., typically neomycin phosphotransferase II or NPTII, for example). Cm$^r$ encodes an activity involved in chloramphenicol antibiotic resistance (e.g., typically chloramphenicol acetyl transferase or CAT, for example). Hyg$^r$ encodes an activity involved in hygromycin resistance by phosphorylation of hygromycin B (e.g., hygromycin phosphotransferase, or HPT). CUP1 encodes an activity involved in resistance to heavy metal (e.g., copper, for example) toxicity. DHFR encodes a dihydrofolate reductase activity which confers resistance to methotrexate and sulfanilamide compounds.

In contrast to site-directed or specific mutagenesis, random mutagenesis does not require any sequence information and can be accomplished by a number of widely different methods. Random mutagenesis often is used to create mutant libraries that can be used to screen for the desired genotype or phenotype. Non-limiting examples of random mutagenesis include; chemical mutagenesis, UV-induced mutagenesis, insertion element or transposon-mediated mutagenesis, DNA shuffling, error-prone PCR mutagenesis, and the like.

Chemical mutagenesis often involves chemicals like ethyl methanesulfonate (EMS), nitrous acid, mitomycin C, N-methyl-N-nitrosourea (MNU), diepoxybutane (DEB), 1,2,7,8-diepoxyoctane (DEO), methyl methane sulfonate (MMS), N-methyl-N'-nitro-N-nitrosoguanidine (MNNG), 4-nitroquinoline 1-oxide (4-NQO), 2-methyloxy-6-chloro-9(3-[ethyl-2-chloroethyl]-aminopropylamino)-acridinedihydrochloride (ICR-170), 2-amino purine (2AP), and hydroxylamine (HA), provided herein as non-limiting examples. These chemicals can cause base-pair substitutions, frameshift mutations, deletions, transversion mutations, transition mutations, incorrect replication, and the like. In some embodiments, the mutagenesis can be carried out in vivo. Sometimes the mutagenic process involves the use of the host organisms DNA replication and repair mechanisms to incorporate and replicate the mutagenized base or bases.

Another type of chemical mutagenesis involves the use of base-analogs. The use of base-analogs cause incorrect base pairing which in the following round of replication is corrected to a mismatched nucleotide when compared to the starting sequence. Base analog mutagenesis introduces a small amount of non-randomness to random mutagenesis, because specific base analogs can be chose which can be incorporated at certain nucleotides in the starting sequence. Correction of the mispairing typically yields a known substitution. For example, Bromo-deoxyuridine (BrdU) can be incorporated into DNA and replaces T in the sequence. The host DNA repair and replication machinery can sometime correct the defect, but sometimes will mispair the BrdU with a G. The next round of replication then causes a G-C transversion from the original A-T in the native sequence.

Ultra violet (UV) induced mutagenesis is caused by the formation of thymidine dimers when UV light irradiates chemical bonds between two adjacent thymine residues. Excision repair mechanism of the host organism correct the lesion in the DNA, but occasionally the lesion is incorrectly repaired typically resulting in a C to T transition.

Insertion element or transposon-mediated mutagenesis makes use of naturally occurring or modified naturally occurring mobile genetic elements. Transposons often encode accessory activities in addition to the activities necessary for transposition (e.g., movement using a transposase activity, for example). In many examples, transposon accessory activities are antibiotic resistance markers (e.g., see Tn903 kan$^r$ described above, for example). Insertion elements typically only encode the activities necessary for movement of the nucleic acid sequence. Insertion element and transposon mediated mutagenesis often can occur randomly, however specific target sequences are known for some transposons. Mobile genetic elements like IS elements or Transposons (Tn) often have inverted repeats, direct repeats or both inverted and direct repeats flanking the region coding for the transposition genes. Recombination events catalyzed by the transposase cause the element to remove itself from the genome and move to a new location, leaving behind a portion of an inverted or direct repeat. Classic examples of transposons are the "mobile genetic elements" discovered in maize. Transposon mutagenesis kits are commercially available which are designed to leave behind a 5 codon insert (e.g., Mutation Generation System kit, Finnzymes, World Wide Web URL finnzymes.us, for example). This allows the artisan to identify the insertion site, without fully disrupting the function of most genes.

DNA shuffling is a method which uses DNA fragments from members of a mutant library and reshuffles the fragments randomly to generate new mutant sequence combinations. The fragments are typically generated using DNaseI, followed by random annealing and re-joining using self priming PCR. The DNA overhanging ends, from annealing of random fragments, provide "primer" sequences for the PCR process. Shuffling can be applied to libraries generated by any of the above mutagenesis methods.

Error prone PCR and its derivative rolling circle error prone PCR uses increased magnesium and manganese concentrations in conjunction with limiting amounts of one or two nucleotides to reduce the fidelity of the Taq polymerase. The error rate can be as high as 2% under appropriate conditions, when the resultant mutant sequence is compared to the wild type starting sequence. After amplification, the library of mutant coding sequences must be cloned into a suitable plasmid. Although point mutations are the most common types of mutation in error prone PCR, deletions and frameshift mutations are also possible. There are a number of commercial error-prone PCR kits available, including those from Stratagene and Clontech (e.g., World Wide Web URL stratagene.com and World Wide Web URL clontech.com, respectively, for example). Rolling circle error-prone PCR is a variant of error-prone PCR in which wild-type sequence is first cloned into a plasmid, then the whole plasmid is amplified under error-prone conditions.

As noted above, organisms with altered activities can also be isolated using genetic selection and screening of organisms challenged on selective media or by identifying naturally occurring variants from unique environments. For example, 2-Deoxy-D-glucose is a toxic glucose analog. Growth of yeast on this substance yields mutants that are glucose-deregulated. A number of mutants have been isolated using 2-Deoxy-D-glucose including transport mutants, and mutants that ferment glucose and galactose simultaneously instead of glucose first then galactose when glucose is depleted. Similar techniques have been used to isolate mutant microorganisms that can metabolize plastics (e.g., from landfills), petrochemicals (e.g., from oil spills), and the like, either in a laboratory setting or from unique environments.

Similar methods can be used to isolate naturally occurring mutations in a desired activity when the activity exists at a relatively low or nearly undetectable level in the organism of choice, in some embodiments. The method generally consists of growing the organism to a specific density in liquid culture, concentrating the cells, and plating the cells on various concentrations of the substance to which an increase in metabolic activity is desired. The cells are incubated at a moderate growth temperature, for 5 to 10 days. To enhance the selection process, the plates can be stored for another 5 to 10 days at a low temperature. The low temperature sometimes can allow strains that have gained or increased an activity to continue growing while other strains are inhibited for growth at the low temperature. Following the initial selection and secondary growth at low temperature, the plates can be replica plated on higher or lower concentrations of the selection substance to further select for the desired activity.

A native, heterologous or mutagenized polynucleotide can be introduced into a nucleic acid reagent for introduction into a host organism, thereby generating an engineered microorganism. Standard recombinant DNA techniques (restriction enzyme digests, ligation, and the like) can be used by the artisan to combine the mutagenized nucleic acid of interest into a suitable nucleic acid reagent capable of (i) being stably maintained by selection in the host organism, or (ii) being integrating into the genome of the host organism. As noted above, sometimes nucleic acid reagents comprise two replication origins to allow the same nucleic acid reagent to be manipulated in bacterial before final introduction of the final product into the host organism (e.g., yeast or fungus for example). Standard molecular biology and recombinant DNA methods are known (e.g., described in Maniatis, T., E. F. Fritsch and J. Sambrook (1982) *Molecular Cloning: a Laboratory Manual*; Cold Spring Harbor Laboratory, Cold Spring Harbor, N.Y.).

Nucleic acid reagents can be introduced into microorganisms using various techniques. Non-limiting examples of methods used to introduce heterologous nucleic acids into various organisms include; transformation, transfection, transduction, electroporation, ultrasound-mediated transformation, particle bombardment and the like. In some instances the addition of carrier molecules (e.g., bis-benzimidazolyl compounds, for example, see U.S. Pat. No. 5,595,899) can increase the uptake of DNA in cells typically though to be difficult to transform by conventional methods. Conventional methods of transformation are known (e.g., described in Maniatis, T., E. F. Fritsch and J. Sambrook (1982) *Molecular Cloning: a Laboratory Manual*; Cold Spring Harbor Laboratory, Cold Spring Harbor, N.Y.).

Culture, Production and Process Methods

Engineered microorganisms often are cultured under conditions that optimize yield of a target molecule (e.g., six-carbon target molecule). Non-limiting examples of such target molecules are adipic acid and 6-hydroxyhexanoic acid. Culture conditions often optimize activity of one or more of the following activities: 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase activity, hexanoate synthase activity, lipase activity, fatty acid synthase activity, acetyl CoA carboxylase activity, monooxygenase activity, monooxygenase reductase activity, fatty alcohol oxidase, acyl-CoA ligase, acyl-CoA oxidase, enoyl-CoA hydratase, 3-hydroxyacyl-CoA dehydrogenase, and/or acetyl-CoA C-acyltransferase activities. In general, non-limiting examples of conditions that may be optimized include the type and amount of carbon source, the type and amount of nitrogen source, the carbon-to-nitrogen ratio, the oxygen level, growth temperature, pH, length of the biomass production phase, length of target product accumulation phase, and time of cell harvest.

Culture media generally contain a suitable carbon source. Carbon sources useful for culturing microorganisms and/or fermentation processes sometimes are referred to as feedstocks. The term "feedstock" as used herein refers to a composition containing a carbon source that is provided to an organism, which is used by the organism to produce energy and metabolic products useful for growth. A feedstock may be a natural substance, a "man-made substance," a purified or isolated substance, a mixture of purified substances, a mixture of unpurified substances or combinations thereof. A feedstock often is prepared by and/or provided to an organism by a person, and a feedstock often is formulated prior to administration to the organism. A carbon source may include, but is not limited to including, one or more of the following substances: monosaccharides (e.g., also referred to as "saccharides," which include 6-carbon sugars (e.g., glucose, fructose), 5-carbon sugars (e.g., xylose and other pentoses) and the like), disaccharides (e.g., lactose, sucrose), oligosaccharides (e.g., glycans, homopolymers of a monosaccharide), polysaccharides (e.g., starch, cellulose, heteropolymers of monosaccharides or mixtures thereof), sugar alcohols (e.g., glycerol), and renewable feedstocks (e.g., cheese whey permeate, cornsteep liquor, sugar beet molasses, barley malt).

A carbon source also may include a metabolic product that can be used directly as a metabolic substrate in an engineered pathway described herein, or indirectly via conversion to a different molecule using engineered or native biosynthetic pathways in an engineered microorganism. In some embodiments, a carbon source may include glycerol backbones generated by the action of an engineered pathway including at least a lipase activity. In certain embodiments, metabolic pathways can be preferentially biased towards production of a desired product by increasing the levels of one or more activities in one or more metabolic pathways having and/or generating at least one common metabolic and/or synthetic substrate. In some embodiments, a metabolic byproduct (e.g., glycerol) of an engineered activity (e.g., lipase activity) can be used in one or more metabolic pathways selected from gluconeogenesis, pentose phosphate pathway, glycolysis, fatty acid synthesis, beta oxidation, and omega oxidation, to generate a carbon source that can be converted to adipic acid.

Carbon sources also can be selected from one or more of the following non-limiting examples: paraffin (e.g., saturated paraffin, unsaturated paraffin, substituted paraffin, linear paraffin, branched paraffin, or combinations thereof); alkanes (e.g., hexane), alkenes or alkynes, each of which may be linear, branched, saturated, unsaturated, substituted or combinations thereof (described in greater detail below); linear or branched alcohols (e.g., hexanol); saturated and/or unsaturated fatty acids (e.g., each fatty acid is about 1 carbon to about 60 carbons with 0 to 10 unsaturations, including free fatty acids, mixed fatty acids, single fatty acid, purified fatty acids (e.g., single fatty acid or mixture of fatty acids) fatty acid distillates, soap stocks, the like and combinations thereof); esters of fatty acids; monoglycerides; diglycerides; triglycerides; and phospholipids. Non-limiting commercial sources of products for preparing feedstocks include plants or plant products (e.g., vegetable oils (e.g., almond oil, canola oil, cocoa butter, coconut oil, corn oil, cottonseed oil, flaxseed oil, grape seed oil, illipe, olive oil, palm oil, palm olein, palm kernel oil, safflower oil, peanut oil, soybean oil, sesame oil, shea nut oil, sunflower oil walnut oil, oleic acid, the like and combinations thereof), vegetable oil products and purified fatty acids (e.g., myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid), and animal fats (e.g., beef tallow, butterfat, lard, cod liver oil)). A carbon source may include a petroleum product and/or a petroleum distillate (e.g., diesel, fuel oils, gasoline, kerosene, paraffin wax, paraffin oil, petrochemicals).

The term "paraffin" as used herein refers to the common name for alkane hydrocarbons, independent of the source (e.g., plant derived, petroleum derived, chemically synthesized, fermented by a microorganism), or carbon chain length. A carbon source sometimes comprises a paraffin, and in some embodiments, a paraffin is predominant in a carbon source (e.g., about 75%, 80%, 85%, 90% or 95% paraffin). A paraffin sometimes is saturated (e.g., fully saturated), sometimes includes one or more unsaturations (e.g., about 1, 2, 3, 4, 5, 6, 7, 8, 9, 10 unsaturations) and sometimes is substituted with one or more non-hydrogen substituents. Non-limiting examples of non-hydrogen substituents include halo, acetyl, =O, =N—CN, =N—OR, =NR, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, where each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, where each R' is independently H, C1-C8 alkyl, C2-C8 heteroalkyl, C1-C8 acyl, C2-C8 heteroacyl, C6-C10 aryl or C5-C10 heteroaryl.

In some embodiments a feedstock is selected according to the genotype and/or phenotype of the engineered microorganism to be cultured. For example, a feedstock rich in 12-carbon fatty acids, 12-carbon dicarboxylic acids or 12-carbon paraffins, or a mixture of 10-carbon and 12-carbon compounds can be useful for culturing yeast strains harboring an alteration that partially blocks beta oxidation by disrupting POX4 activity, as described herein. Non-limiting examples of carbon sources having 10 and/or 12 carbons include fats (e.g., coconut oil, palm kernel oil), paraffins (e.g., alkanes, alkenes, or alkynes) having 10 or 12 carbons, (e.g., decane, dodecane (also referred to as adakane12, bihexyl, dihexyl and duodecane), alkene and alkyne derivatives), fatty acids (decanoic acid, dodecanoic acid), fatty alcohols (decanol, dodecanol), the like, non-toxic substituted derivatives or combinations thereof.

A carbon source sometimes comprises an alkyl, alkenyl or alkynyl compound or molecule (e.g., a compound that includes an alkyl, alkenyl or alkynyl moiety (e.g., alkane, alkene, alkyne)). In certain embodiments, an alkyl, alkenyl or alkynyl molecule, or combination thereof, is predominant in a carbon source (e.g., about 75%, 80%, 85%, 90% or 95% of such molecules). As used herein, the terms "alkyl," "alkenyl" and "alkynyl" include straight-chain (referred to herein as "linear"), branched-chain (referred to herein as "non-linear"), cyclic monovalent hydrocarbyl radicals, and combinations of these, which contain only C and H atoms when they are unsubstituted. Non-limiting examples of alkyl moieties include methyl, ethyl, isobutyl, cyclohexyl, cyclopentylethyl, 2-propenyl, 3-butynyl, and the like. An alkyl that contains only C and H atoms and is unsubstituted sometimes is referred to as "saturated." An alkenyl or alkynyl generally is "unsaturated" as it contains one or more double bonds or triple bonds, respectively. An alkenyl can include any number of double bonds, such as 1, 2, 3, 4 or 5 double bonds, for example. An alkynyl can include any number of triple bonds, such as 1, 2, 3, 4 or 5 triple bonds, for example. Alkyl, alkenyl and alkynyl molecules sometimes contain between about 2 to about 60 carbon atoms (C). For example, an alkyl, alkenyl and alkynyl molecule can include about 1 carbon atom, about 2 carbon atoms, about 3 carbon atoms, about 4 carbon atoms, about 5 carbon atoms, about 6 carbon atoms, about 7 carbon atoms, about 8 carbon atoms, about 9 carbon atoms, about 10 carbon atoms, about 12 carbon atoms, about 14 carbon atoms, about 16 carbon atoms, about 18 carbon atoms, about 20 carbon atoms, about 22 carbon atoms, about 24 carbon atoms, about 26 carbon atoms, about 28 carbon atoms, about 30 carbon atoms, about 32 carbon atoms, about 34 carbon atoms, about 36 carbon atoms, about 38 carbon atoms, about 40 carbon atoms, about 42 carbon atoms, about 44 carbon atoms, about 46 carbon atoms, about 48 carbon atoms, about 50 carbon atoms, about 52 carbon atoms, about 54 carbon atoms, about 56 carbon atoms, about 58 carbon atoms or about 60 carbon atoms. In some embodiments, paraffins can have a mean number of carbon atoms of between about 8 to about 18 carbon atoms (e.g., about 8 carbon atoms, about 9 carbon atoms, about 10 carbon atoms, about 11 carbon atoms, about 12 carbon atoms, about 13 carbon atoms, about 14 carbon atoms, about 15 carbon atoms, about 16 carbon atoms, about 17 carbon atoms and about 18 carbon atoms). A single group can include more than one type of multiple bond, or more than one multiple bond. Such groups are included within the definition of the term "alkenyl" when they contain at least one carbon-carbon double bond, and are included within the term "alkynyl" when they contain at least one carbon-carbon triple bond. Alkyl, alkenyl and alkynyl molecules include molecules that comprise an alkyl, alkenyl and/or alkynyl moiety, and include molecules that consist of an alkyl, alkenyl or alkynyl moiety (i.e., alkane, alkene and alkyne molecules).

Alkyl, alkenyl and alkynyl substituents sometimes contain 1-20C (alkyl) or 2-20C (alkenyl or alkynyl). They can contain about 8-14C or about 10-14C in some embodiments. A single group can include more than one type of multiple bond, or more than one multiple bond. Such groups are included within the definition of the term "alkenyl" when they contain at least one carbon-carbon double bond, and are included within the term "alkynyl" when they contain at least one carbon-carbon triple bond.

Alkyl, alkenyl and alkynyl groups or compounds sometimes are substituted to the extent that such substitution can be synthesized and can exist. Typical substituents include, but are not limited to, halo, acetyl, =O, =N—CN, =N—OR, =NR, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, where each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C11 aryl, or C5-C11 heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, where each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Acetylene" or "acetyl" substituents are 2-10C alkynyl groups that are optionally substituted, and are of the formula —C≡C-Ri, where Ri is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and each Ri group is optionally substituted with one or more substituents selected from halo, =O, =N—CN, =N—OR', =NR', OR', NR'2, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, where each R' is independently H, C1-C6 alkyl, C2-C6 heteroalkyl, C1-C6 acyl, C2-C6 heteroacyl, C6-C10 aryl, C5-C10 heteroaryl, C7-C12 arylalkyl, or C6-C12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and where two R' can be linked to form a 3-7 membered ring optionally containing up to three heteroatoms selected from N, O and S. In some embodiments, Ri of —C≡C-Ri is H or Me.

A carbon source sometimes comprises a heteroalkyl, heteroalkenyl and/or heteroalkynyl molecule or compound (e.g., comprises heteroalkyl, heteroalkenyl and/or heteroalkynyl moiety (e.g., heteroalkane, heteroalkene or heteroalkyne)). "Heteroalkyl", "heteroalkenyl", and "heteroalkynyl" and the like are defined similarly to the corresponding hydrocarbyl (alkyl, alkenyl and alkynyl) groups, but the 'tetero' terms refer to groups that contain one to three O, S or N heteroatoms or combinations thereof within the backbone; thus at least one carbon atom of a corresponding alkyl, alkenyl, or alkynyl group is replaced by one of the specified heteroatoms to form a heteroalkyl, heteroalkenyl, or heteroalkynyl group. The typical and sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

The term "alkyl" as used herein includes cycloalkyl and cycloalkylalkyl groups and compounds, the term "cycloalkyl" may be used herein to describe a carbocyclic non-aromatic compound or group that is connected via a ring carbon atom, and "cycloalkylalkyl" may be used to describe a carbocyclic non-aromatic compound or group that is connected to a molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

A carbon source sometimes comprises an acyl compound or moiety (e.g., compound comprising an acyl moiety). As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups where at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

A carbon source sometimes comprises one or more aromatic moieties and/or heteroaromatic moieties. "Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5 membered rings as well as 6 membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. The monocyclic heteroaryls sometimes contain 5-6 ring members, and the bicyclic heteroaryls sometimes contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, where each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may be further substituted with the groups described herein as suitable for each type of such substituents or for each component of the substituent. Thus, for example, an arylalkyl substituent may be substituted on the aryl portion with substituents typical for aryl groups, and it may be further substituted on the alkyl portion with substituents as typical or suitable for alkyl groups.

Similarly, "arylalkyl" and "heteroarylalkyl" refer to aromatic and heteroaromatic ring systems, which are stand-alone molecules (e.g., benzene or substituted benzene, pyridine or substituted pyridine), or which are bonded to an attachment point through a linking group such as an alkylene, including substituted or unsubstituted, saturated or unsaturated, cyclic or acyclic linkers. A linker often is C1-C8 alkyl or a hetero form thereof. These linkers also may include a carbonyl group, thus making them able to provide substituents as an acyl or heteroacyl moiety. An aryl or heteroaryl ring in an arylalkyl or heteroarylalkyl group may be substituted with the same substituents described above for aryl groups. An arylalkyl group sometimes includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group often includes a C5-C6 monocyclic heteroaryl group optionally substituted with one or more of the groups described above as substituents typical on aryl groups and a C1-C4 alkylene that is unsubstituted. A heteroarylalkyl group sometimes is substituted with one or two C1-C4 alkyl groups or heteroalkyl groups, or includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on the alkyl or heteroalkyl portion or on the aryl or heteroaryl portion of the group. The substituents optionally present on the alkyl or heteroalkyl portion sometimes are the same as those described above for alkyl groups, and the substituents optionally present on the aryl or heteroaryl portion often are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl includes pyridylmethyl, phenoxy, and N-pyrrolylmethoxy.

"Alkylene" as used herein refers to a divalent hydrocarbyl group. Because an alkylene is divalent, it can link two other groups together. An alkylene often is referred to as —$(CH_2)_n$— where n can be 1-20, 1-10, 1-8, or 1-4, though where specified, an alkylene can also be substituted by other groups, and can be of other lengths, and the open valences need not be at opposite ends of a chain. Thus —CH(Me)- and —$C(Me)_2$- may also be referred to as alkylenes, as can a cyclic group such as cyclopropan-1,1-diyl. Where an alkylene group is substituted, the substituents include those typically present on alkyl groups as described herein.

In some embodiments, a feedstock includes a mixture of carbon sources, where each carbon source in the feedstock is selected based on the genotype of the engineered microorganism. In certain embodiments, a mixed carbon source feedstock includes one or more carbon sources selected from sugars, cellulose, fatty acids, triacylglycerides, paraffins, the like and combinations thereof.

Nitrogen may be supplied from an inorganic (e.g., $(NH_4)_2SO_4$) or organic source (e.g., urea or glutamate). In addition to appropriate carbon and nitrogen sources, culture media also can contain suitable minerals, salts, cofactors, buffers, vitamins, metal ions (e.g., $Mn^{+2}$, $Co^{+2}$, $Zn^{+2}$, $Mg^{+2}$) and other components suitable for culture of microorganisms.

Engineered microorganisms sometimes are cultured in complex media (e.g., yeast extract-peptone-dextrose broth (YPD)). In some embodiments, engineered microorganisms are cultured in a defined minimal media that lacks a component necessary for growth and thereby forces selection of a desired expression cassette (e.g., Yeast Nitrogen Base (DIFCO Laboratories, Detroit, Mich.)). Culture media in some embodiments are common commercially prepared media, such as Yeast Nitrogen Base (DIFCO Laboratories, Detroit, Mich.). Other defined or synthetic growth media may also be used and the appropriate medium for growth of the particular microorganism are known. A variety of host organisms can be selected for the production of engineered microorganisms. Non-limiting examples include yeast (e.g., *Candida tropicalis* (e.g., ATCC20336, ATCC20913, ATCC20962), *Yarrowia lipolytica* (e.g., ATCC20228)) and filamentous fungi (e.g., *Aspergillus nidulans* (e.g., ATCC38164) and *Aspergillus parasiticus* (e.g., ATCC 24690)). In specific embodiments, yeast are cultured in YPD media (10 g/L Bacto Yeast Extract, 20 g/L Bacto Peptone, and 20 g/L Dextrose). Filamentous fungi, in particular embodiments, are grown in CM (Complete Medium) containing 10 g/L Dextrose, 2 g/L Bacto Peptone, 1 g/L Bacto Yeast Extract, 1 g/L Casamino acids, 50 mL/L 20× Nitrate Salts (120 g/L $NaNO_3$, 10.4 g/L KCl, 10.4 g/L $MgSO_4.7H_2O$), 1 mL/L 1000× Trace Elements (22 g/L $ZnSO_4.7H_2O$, 11 g/L $H_3BO_3$, 5 g/L $MnCl_2.7H_2O$, 5 g/L $FeSO_4.7H_2O$, 1.7 g/L $CoCl_2.6H_2O$, 1.6 g/L $CuSO_4.5H_2O$, 1.5 g/L $Na_2MoO_4.2H_2O$, and 50 g/L $Na_4EDTA$), and 1 mL/L Vitamin Solution (100 mg each of Biotin, pyridoxine, thiamine, riboflavin, p-aminobenzoic acid, and nicotinic acid in 100 mL water).

A suitable pH range for the fermentation often is between about pH 4.0 to about pH 8.0, where a pH in the range of about pH 5.5 to about pH 7.0 sometimes is utilized for initial culture conditions. Depending on the host organism, culturing may be conducted under aerobic or anaerobic conditions, where microaerobic conditions sometimes are maintained. A two-stage process may be utilized, where one stage promotes microorganism proliferation and another state promotes production of target molecule. In a two-stage process, the first stage may be conducted under aerobic conditions (e.g., introduction of air and/or oxygen) and the second stage may be conducted under anaerobic conditions (e.g., air or oxygen are not introduced to the culture conditions). In some embodiments, the first stage may be conducted under anaerobic conditions and the second stage may be conducted under aerobic conditions. In certain embodiments, a two-stage process may include two more organisms, where one organism generates an intermediate product (e.g., hexanoic acid produced by *Megasphera* spp.) in one stage and another organism processes the intermediate product into a target product (e.g., adipic acid) in another stage, for example.

A variety of fermentation processes may be applied for commercial biological production of a target product. In some embodiments, commercial production of a target product from a recombinant microbial host is conducted using a batch, fed-batch or continuous fermentation process, for example.

A batch fermentation process often is a closed system where the media composition is fixed at the beginning of the process and not subject to further additions beyond those required for maintenance of pH and oxygen level during the process. At the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high-growth log phase and finally to a stationary phase, wherein the growth rate is diminished or halted. Left untreated, cells in the stationary phase will eventually die.

A variation of the standard batch process is the fed-batch process, where the carbon source is continually added to the fermentor over the course of the fermentation process. Fed-batch processes are useful when catabolite repression is apt to inhibit the metabolism of the cells or where it is desirable to have limited amounts of carbon source in the media at any one time. Measurement of the carbon source concentration in fed-batch systems may be estimated on the basis of the changes of measurable factors such as pH, dissolved oxygen and the partial pressure of waste gases (e.g., CO.sub.2).

Batch and fed-batch culturing methods are known in the art. Examples of such methods may be found in Thomas D. Brock in Biotechnology: A Textbook of Industrial Microbiology, 2.sup.nd ed., (1989) Sinauer Associates Sunderland, Mass. and Deshpande, Mukund V., Appl. Biochem. Biotechnol., 36:227 (1992).

In continuous fermentation process a defined media often is continuously added to a bioreactor while an equal amount of culture volume is removed simultaneously for product recovery. Continuous cultures generally maintain cells in the log phase of growth at a constant cell density. Continuous or semi-continuous culture methods permit the modulation of one factor or any number of factors that affect cell growth or end product concentration. For example, an approach may limit the carbon source and allow all other parameters to moderate metabolism. In some systems, a number of factors affecting growth may be altered continuously while the cell concentration, measured by media turbidity, is kept constant. Continuous systems often maintain steady state growth and thus the cell growth rate often is balanced against cell loss due to media being drawn off the culture. Methods of modulating nutrients and growth factors for continuous culture processes, as well as techniques for maximizing the rate of product formation, are known and a variety of methods are detailed by Brock, supra.

In some embodiments involving fermentation, the fermentation can be carried out using two or more microorganisms (e.g., host microorganism, engineered microorganism, isolated naturally occurring microorganism, the like and combinations thereof), where a feedstock is partially or completely utilized by one or more organisms in the fermentation (e.g., mixed fermentation), and the products of cellular respiration or metabolism of one or more organisms can be further metabolized by one or more other organisms to produce a desired target product (e.g., adipic acid, hexanoic acid). In certain embodiments, each organism can be fermented independently and the products of cellular respiration or metabolism purified and contacted with another organism to produce a desired target product. In some embodiments, one or more organisms are partially or completely blocked in a metabolic pathway (e.g., beta oxidation, omega oxidation, the like or combinations thereof), thereby producing a desired product that can be used as a feedstock for one or more other organisms. Any suitable combination of microorganisms can be utilized to carry out mixed fermentation or sequential fermentation. A non-limiting example of an organism combination and feedstock suitable for use in mixed fermentations or sequential fermentations where the fermented media from a first organism is used as a feedstock for a second organism is the use of long chain dicarboxylic acids as a fermentation media for *Megasphaera elsdenii* to produce hexanoic acid, and *Candida tropicalis* engineered as described herein to produce adipic acid from the hexanoic acid produced by *Megasphaera elsdenii*. *Megasphaera elsdenii* is a facultative anaerobe. Without being limited by theory, it is believe that *Megasphaera elsdenii* naturally accumulates hexanoic acid as a result of anaerobic respiration. *Candida tropicalis* can grow aerobically and anaerobically. In some embodiments, the hexanoic acid produced by *Megasphaera elsdenii* can be utilized as a feedstock for *Candida tropicalis* to produce adipic acid. In certain embodiments, the *Megasphaera* produced hexanoic acid is purified (e.g., partially, completely) prior to being used as a feedstock for *C. tropicalis*.

In various embodiments adipic acid is isolated or purified from the culture media or extracted from the engineered microorganisms. In some embodiments, fermentation of feedstocks by methods described herein can produce a target product (e.g., adipic acid) at a level of about 80% or more of theoretical yield (e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more of theoretical yield). The term "theoretical yield" as used herein refers to the amount of product that could be made from a starting material if the reaction is 100% complete. Theoretical yield is based on the stoichiometry of a reaction and ideal conditions in which starting material is completely consumed, undesired side reactions do not occur, the reverse reaction does not occur, and there are no losses in the work-up procedure. Culture media may be tested for target product (e.g., adipic acid) concentration and drawn off when the concentration reaches a predetermined level. Detection methods are known in the art, including but not limited to those set forth in B Stieglitz and P J Weimer, Novel microbial screen for detection of 1,4-butanediol, ethylene glycol, and adipic acid, Appl Environ Microbiol. 198. Target product (e.g., adipic acid) may be present at a range of levels as described herein.

A target product sometimes is retained within an engineered microorganism after a culture process is completed, and in certain embodiments, the target product is secreted out of the microorganism into the culture medium. For the latter embodiments, (i) culture media may be drawn from the culture system and fresh medium may be supplemented, and/or (ii) target product may be extracted from the culture media during or after the culture process is completed. Engineered microorganisms may be cultured on or in solid, semi-solid or liquid media. In some embodiments media is drained from cells adhering to a plate. In certain embodiments, a liquid-cell mixture is centrifuged at a speed sufficient to pellet the cells but not disrupt the cells and allow extraction of the media, as known in the art. The cells may then be resuspended in fresh media. Target product may be purified from culture media according to known methods, such as those described in U.S. Pat. No. 6,787,669 and U.S. Pat. No. 5,296,639, for example.

In certain embodiments, target product is extracted from the cultured engineered microorganisms. The microorganism cells may be concentrated through centrifugation at a speed sufficient to shear the cell membranes. In some embodiments, the cells may be physically disrupted (e.g., shear force, sonication) or chemically disrupted (e.g., contacted with detergent or other lysing agent). The phases may be separated by centrifugation or other method known in the art and target product may be isolated according to known methods.

Commercial grade target product sometimes is provided in substantially pure form (e.g., 90% pure or greater, 95% pure or greater, 99% pure or greater or 99.5% pure or greater). In some embodiments, target product may be modified into any one of a number of downstream products. For example, adipic acid may be polycondensed with hexamethylenediamine to produce nylon. Nylon may be further processed into fibers for applications in carpeting, automobile tire cord and clothing. Adipic acid is also used for manufacturing plasticizers, lubricant components and polyester polyols for polyurethane systems. Food grade adipic acid is used as a gelling aid, acidulant, leavening and buffering agent. Adipic acid has two carboxylic acid (—COOH) groups, which can yield two kinds of salts. Its derivatives, acyl halides, anhydrides, esters, amides and nitriles, are used in making downstream products such as flavoring agents, internal plasticizers, pesticides, dyes, textile treatment agents, fungicides, and pharmaceuticals through further reactions of substitution, catalytic reduction, metal hydride reduction, diborane reduction, keto formation with organometallic reagents, electrophile bonding at oxygen, and condensation.

Target product may be provided within cultured microbes containing target product, and cultured microbes may be supplied fresh or frozen in a liquid media or dried. Fresh or frozen microbes may be contained in appropriate moisture-proof containers that may also be temperature controlled as necessary. Target product sometimes is provided in culture medium that is substantially cell-free. In some embodiments target product or modified target product purified from microbes is provided, and target product sometimes is provided in substantially pure form. In certain embodiments crystallized or powdered target product is provided. Crystalline adipic acid is a white powder with a melting point of 360° F. and may be transported in a variety of containers including one ton cartons, drums, 50 pound bags and the like.

In certain embodiments, a target product (e.g., adipic acid, 6-hydroxyhexanoic acid) is produced with a yield of about 0.30 grams of target product, or greater, per gram of glucose added during a fermentation process (e.g., about 0.31 grams of target product per gram of glucose added, or greater; about 0.32 grams of target product per gram of glucose added, or greater; about 0.33 grams of target product per gram of glucose added, or greater; about 0.34 grams of target product per gram of glucose added, or greater; about 0.35 grams of target product per gram of glucose added, or greater; about 0.36 grams of target product per gram of glucose added, or greater; about 0.37 grams of target product per gram of glucose added, or greater; about 0.38 grams of target product per gram of glucose added, or greater; about 0.39 grams of target product per gram of glucose added, or greater; about 0.40 grams of target product per gram of glucose added, or greater; about 0.41 grams of target product per gram of glucose added, or greater; 0.42 grams of target product per gram of glucose added, or greater; 0.43 grams of target product per gram of glucose added, or greater; 0.44 grams of target product per gram of glucose added, or greater; 0.45 grams of target product per gram of glucose added, or greater; 0.46 grams of target product per gram of glucose added, or greater; 0.47 grams of target product per gram of glucose added, or greater; 0.48 grams of target product per gram of glucose added, or greater; 0.49 grams of target product per gram of glucose added, or greater; 0.50 grams of target product per gram of glucose added, or greater; 0.51 grams of target product per gram of glucose added, or greater; 0.52 grams of target product per gram of glucose added, or greater; 0.53 grams of target product per gram of glucose added, or greater; 0.54 grams of target product per gram of glucose added, or greater; 0.55 grams of target product per gram of glucose added, or greater; 0.56 grams of target product per gram of glucose added, or greater; 0.57 grams of target product per gram of glucose added, or greater; 0.58 grams of target product per gram of glucose added, or greater; 0.59 grams of target product per gram of glucose added, or greater; 0.60 grams of target product per gram of glucose added, or greater; 0.61 grams of target product per gram of glucose added, or greater; 0.62 grams of target product per gram of glucose added, or greater; 0.63 grams of target product per gram of glucose added, or greater; 0.64 grams of target product per gram of glucose added, or greater; 0.65 grams of target product per gram of glucose added, or greater; 0.66 grams of target product per gram of glucose added, or greater; 0.67 grams of target product per gram of glucose added, or greater; 0.68 grams of target product per gram of glucose added, or greater; 0.69 or 0.70 grams of target product per gram of glucose added or greater).

EXAMPLES

The examples set forth below illustrate certain embodiments and do not limit the technology. Certain examples set forth below utilize standard recombinant DNA and other biotechnology protocols known in the art. Many such techniques are described in detail in Maniatis, T., E. F. Fritsch and J. Sambrook (1982) *Molecular Cloning: a Laboratory Manual*; Cold Spring Harbor Laboratory, Cold Spring Harbor, N.Y. DNA mutagenesis can be accomplished using the Stratagene (San Diego, Calif.) "QuickChange" kit according to the manufacturer's instructions.

Example 1

Cloning Hexanoate Synthase ("HexS") Subunit Genes

Total RNA from *Aspergillus parasiticus* was prepared using the RiboPure™ (Ambion, Austin, Tex.) kit for yeast. The genes encoding the two subunits of hexanoate synthase (referred to as "hexA" and "hex B" were isolated from this total RNA using the 2-step RT-PCR method with Superscript III reverse transcriptase (Life Technologies, Carlsbad, Calif.) and the fragments were gel purified. The primers used for each RT-PCR reaction are as follows:

```
HexA Aspergillus parasiticus primers (SEQ ID NOS
75-84, respectively, in order of appearance)
SP_HexA_Apar_1_1149
ATGGTCATCCAAGGGAAGAGATTGGCCGCCTCCTCTATTCAGC ASP_HexA_Apar_1_1149
GTAGGCGTCACAGGAAAGACTGCGTACCA SP_HexA_Apar_941_2270
TATCACCAATGCTGGATGTAAAGAAGTCGCG ASP_HexA_Apar_941_2270
AATTGGGCTAGGAAACCGGGGATGC SP_HexA_Apar_2067_3016
CGGTCTAATGACGGCGCATGATATCATAGCCGAAACGGTCGAG ASP_HexA_Apar_2067_3016
ACTTGGCTGGAGTCCATCCCTTCGGCA SP_HexA_Apar_2812_4181
CTGCCCGAGTTTGAAGTATCTCAACTTACCGCCGACGCCATG ASP_HexA_Apar_2812_4181
TGAGACGCGCTGCGCAGGGC SP_HexA_Apar_3975_5016
CGAGGTGATCGAGACGCAGATGC ASP_HexA_Apar_3975_5016
TTATGAAGCACCAGACATCAGCCCCAGC HexB Aspergillus parasiticus primers (SEQ ID NOS
85-94, respectively, in order of appearance)
SP_HexB_Apar_1_1166
ATGGGTTCCGTTAGTAGGGAACATGAGTCAATC ASP_HexB_Apar_1_1166
GTTCCTTGTGTGAGCTCCTGAATAAGACTGCATG SP_HexB_Apar_962_2042
CCATCAAAATCCCCCTCTATCACACGGGCACTGGGAGCAAC ASP_HexB_Apar_962_2042
CCCACGCCTTGCGCATCTATAATCAGG SP_HexB_Apar_1837_3527
TGTCCGAATATTCTCCTCGTTGTAGGTAGTGGATT ASP_HexB_Apar_1837_3527
GCAGTAGTCGATAGGTACACATCCTTGGGGGTTCCATGACTGC SP_HexB_Apar_3322_4460
AGAGGATCAAGGCATTATACATGAGTCTGTGGAACTTGGGCTTTCC ASP_HexB_Apar_3322_4460
TTCCCCGTCCTCCATGGCCTTATGC SP_HexB_Apar_4256_5667
GGCCTTTGCGCGATACGCTGGTCTCTCGGGTCCCAT ASP_HexB_Apar_4256_5667
TCACGCCATTTGTTGAAGCAGGGAATG
```

Each of the fragments was inserted separately into the plasmid pCRBlunt II (Life Technologies, Carlsbad, Calif.) such that there were four hexA plasmids, each with a different hexA gene fragment, and five hex B plasmids each with a different hexB gene fragment. Each hexA and hexB fragment was sequence verified, after which the fragments were PCR cloned from each plasmid. Overlap PCR was then used to create the full length hexA and hexB genes. The hexA gene was inserted into the vector p425GPD which has a LEU2 selectable marker and a glyceraldehyde 3-phosphate dehydrogenase promoter (American Type Culture Collection) and the hexB full length gene was inserted into p426GPD which has a URA3 selectable marker and a glyceraldehyde 3-phosphate dehydrogenase promoter (American Type Culture Collection).

Example 2

Transformation of *Saccharomyces cerevisiae* with HexA and HexB Genes

*Saccharomyces cereviseae* cells (strain BY4742, ATCC Accession Number 201389) were grown in standard YPD (10 g Yeast Extract, 20 g Bacto-Peptone, 20 g Glucose, 1 L total) media at about 30 degrees Celsius for about 3 days. The plasmids containing the hexA and hexB genes were co-transformed into the *Saccharomyces cerevisiae*. Transformation was accomplished using the Zymo kit (Catalog number T2001; Zymo Research Corp., Orange, Calif. 92867) using 1 µg plasmid DNA and cultured on SC drop out media with glucose (minus uracil and minus leucine) (20 g glucose; 2.21 g SC (-URA,-LEU) dry mix, 6.7 g Yeast Nitrogen Base, 1 L total) for 2-3 days at about 30° C.

SC(-URA) mix contains:

0.4 g Adenine hemisulfate 3.5 g Arginine 1 g Glutamic Acid
0.433 g Histidine
0.4 g Myo-Inositol
5.2 g Isoleucine
0.9 g Lysine
1.5 g Methionine
0.8 g Phenylalanine
1.1 g Serine
1.2 g Threonine
0.8 g Tryptophan
0.2 g Tyrosine
1.2 g Valine
When needed:
0.263 g Leucine
0.2 g Uracil Co-transformants were selected and established as liquid cultures in YPD media under standard conditions.

Example 3

Production of Synthetic HexA and HexB Genes

Synthetic hexaonoate synthase subunit genes were designed for use in *Candida tropicalis*. This organism uses an alternate genetic code in which the codon "CTG" encodes serine instead of leucine. Therefore, all "CTG" codons were replaced with the codon "TTG" to ensure that these genes, when translated by *C. tropicalis*, would generate polypeptides with amino acid sequences identical to the wild type polypeptides found in *A. parasiticus*. Due to the large size of each subunit, each was synthesized as four fragments, and each fragment was inserted into the vector pUC57. PCR was used to clone each fragment, and overlap extension PCR was then used to generate each full length gene.

The sequence of the synthetic gene for each hexanoate synthase subunit is set forth below. The synthetic gene encoding the hexA subunit is referred to as hexA-AGC ("Alternate Genetic Code") and the synthetic gene encoding the hexB subunit is referred to as hexB-AGC.

hexA-AGC for *Candida tropicalis*

SEQ ID NO: 35

```
atggtcatccaagggaagagattggccgcctcctctattcagcttctcgcaagctcgttagacgc gaagaagctttgttatgagtatgacgagaggcaagccccaggtgtaacccaaatcaccgagg aggcgcctacagagcaaccgcctctctctacccctccctcgctaccccaaacgcccaatatttc gcctataagtgcttcaaagatcgtgatcgacgatgtggcgctatctcgagtgcaaattgttcagg ctcttgttgccagaaagttgaagacggcaattgctcagcttcctacatcaaagtcaatcaaaga gttgtcgggtggtcggtcttctttgcagaacgagctcgtgggggatatacacaacgagttcagct ccatcccggatgcaccagagcagatcttgttgcgggactttggcgacgccaacccaacagtg caattggggaaaacgtcctccgcggcagttgccaaactaatctcgtccaagatgcctagtgact tcaacgccaacgctattcgagcccacctagcaaacaagtggggtctaggacccttgcgacaa acagcggtgttgctctacgccattgcgtcagaacccccatcgcgtttagcttcatcgagcgcagc ggaagagtactgggacaacgtgtcatccatgtacgccgaatcgtgtggcatcaccctccgccc gagacaagacactatgaatgaagatgctatggcatcgtcggcgattgatccggctgtggtagc cgagttttccaaggggcaccgtaggctcggagttcaacagttccaagcgctagcagaatactt acaaattgatttgtcggggtctcaagcctctcagtcggatgctttggtggcggaacttcagcaga aagtcgatctctggacggccgaaatgacccccgagtttctcgccgggatatcaccaatgttgga tgtaaagaagtcgcgacgctatggctcgtggtggaacatggcacggcaggatgtcttggccttc tatcgccgtccttcctacagtgaattcgtggacgacgccttggccttcaaagtttttctcaatcgtct ctgtaaccgagctgatgaggccctcctcaacatggtacgcagtctttcctgtgacgcctacttca agcaaggttctttgcccggatatcatgccgcctcgcgactccttgagcaggccatcacatccac agtggcggattgcccgaaggcacgcctcattctcccggcggtgggcccccacaccaccatta caaaggacggcacgattgaatacgcggaggcaccgcgccagggagtgagtggtcccactg cgtacatccagtctctccgccaaggcgcatctttcattggtctcaagtcagccgacgtcgatactc agagcaacttgaccgacgctttgcttgacgccatgtgcttagcactccataatggaatctcgtttgt tggtaaaacctttttggtgacgggagcgggtcaggggtcaataggagcgggagtggtgcgtct attgttagagggaggagcccgagtattggtgacgacgagcagggagccggcgacgacatcc agatacttccagcagatgtacgataatcacggtgcgaagttctccgagttgcgggtagttccttg caatctagccagcgcccaagattgcgaagggttgatccggcacgtctacgatccccgtgggct
```

-continued aaattgggatttggatgccatccttccttcgctgccgcgtccgactacagcaccgagatgcatg acattcggggacagagcgagttgggccaccggctaatgttggtcaatgtcttccgcgtgttggg gcatatcgtccactgtaaacgagatgccggggttgactgccatccgacgcaggtgttgttgccat tgtcgccaaatcacggcatcttcggtggcgatgggatgtatccggagtcaaagctagcccttga gagcttgttccatcgcatccgatcagagtcttggtcagaccagttatctatatgcggcgttcgtatc ggttggacccggtcgaccggtctaatgacggcgcatgatatcatagccgaaacggtcgagga acacggaatacgcacattttccgtggccgagatggcactcaacatagccatgttgttaaccccc gactttgtggcccattgtgaagatggacctttggatgccgatttcaccggcagcttgggaacattg ggtagcatccccggtttcctagcccaattgcaccagaaagtccagttggcagccgaggtgatc cgtgccgtgcaggccgaggatgagcatgagagattcttgtctccgggaacaaaacctaccttg caagcacccgtggcccaatgcaccccgcagtagccttcgtgtaggctatcccgtctcccc gattatgagcaagagattcgcccgttgtccccacggttggaaaggttgcaagatccggccaat gctgtggtggtggtcgggtactcggagttggggccatggggtagcgcgcgattacggtgggaa atagagagccagggccagtggacttcagccggttatgtcgaacttgcctggttgatgaacctca tccgccacgtcaacgatgaatcctacgtcggctgggtggatactcagaccggaaagccagtg cgggatggcgagatccaggcattgtacggggaccacattgacaaccacaccggtatccgtcc tatccagtccacctcgtacaacccagagcgcatggaggtcttgcaggaggtcgctgtcgagga ggatttgcccgagtttgaagtatctcaacttaccgccgacgccatgcgtctccgccatggagcta acgtttccatccgcccagtggaaatcccgacgcatgccacgtgaagcttaaacgaggcgct gttatccttgttcccaagacagttccctttgtttggggatcgtgtgccggtgagttgccgaagggat ggactccagccaagtacggcatccctgagaacctaattcatcaggtcgaccccgtcacgctct atacaatttgctgcgtggcggaggcattttacagtgccggtataactcaccctcttgaggtcttcg acacattcacctctcggaactaggcaacttttatcggatcctccatgggtgggccgacgaagact cgtcagctctaccgagatgtctacttcgaccatgagattccgtcggatgttttgcaagacacttatc tcaacacacctgctgcctgggttaatatgctactccttggctgcacggggccgatcaaaactccc gtcggcgcatgtgccaccggggtcgagtcgatcgattccggctacgagtcaatcatggcgggc aagacaaagatgtgtcttgtgggtggctacgacgatttgcaggaggaggcatcgtatggattcg cacaacttaaggccacggtcaacgttgaagaggagatcgcctgcggtcgacagccctcgga gatgtcgcgcccatggctgagagtcgtgctggctttgtcgaggcgcatggctgcggtgtacag ttgttgtgtcgaggtgacatcgccttgcaaatgggtcttcctatctatgcggtcattgccagctcagc catggccgcgacaagatcggttcctcggtgccagcaccgggccagggcattctaagcttctc ccgtgagcgcgctcgatccagtatgatatccgtcacgtcgcgcccgagtagccgtagcagcac atcatctgaagtctcggacaaatcatccttgacctcaatcacctcaatcagcaatcccgctcctc gtgcacaacgcgcccgatccaccactgatatggctccgttgcgagcagcgcttgcgacttggg ggttgactatcgacgacttggatgtggcctcattgcacggcacctcgacgcgcggtaacgatct caatgagcccgaggtgatcgagacgcagatgcgccatttaggtcgcactcctggccgcccctt gtgggccatctgccaaaagtcagtgacgggacaccctaaagcccagcggccgcatggatg ctcaatggatgcttgcaagtattggactcggggttggtgccgggcaaccgcaatcttgacacgtt ggacgaggcttgcgcagcgcgtctcatctctgcttccctacgcgcaccgtgcagctacgtgag gtcaaggcattcttgttgacctcatttggcttcggacagaagggggggccaagtcgtcggcgttgc -continued ccccaagtacttctttgctacgctcccccgccccgaggttgagggctactatcgcaaggtgagg gttcgaaccgaggcgggtgatcgcgcctacgccgcggcggtcatgtcgcaggcggtggtgaa gatccagacgcaaaacccgtacgacgagccggatgccccccgcattttctcgatcccttggc acgtatctcccaggatccgtcgacgggccagtatcggtttcgttccgatgccactcccgccctcg atgatgatgctttgccacctcccggcgaacccaccgagctagtgaagggcatctcctccgcctg gatcgaggagaaggtgcgaccgcatatgtctcccggcggcacggtgggcgtggacttggttc ctctcgcctccttcgacgcatacaagaatgccatctttgttgagcgcaattatacggtaagggag cgcgattgggctgaaaagagtgcggatgtgcgcgcggcctatgccagtcggtggtgtgcaaa agaggcggtgttcaaatgtctccagacacattcacagggcgcgggggcagccatgaaagag attgagatcgagcatggaggtaacggcgcaccgaaagtcaagctccggggtgctgcgcaaa cagcggcgcggcaacgaggattggaaggagtgcaattgagcatcagctatggcgacgatgc ggtgatagcggtggcgttggggttgatgtctggtgcttcataa hexB-AGC for *Candida tropicalis*

SEQ ID NO: 36 atgggttccgttagtagggaacatgagtcaatccccatccaggccgcccagagaggcgctgc ccggatctgcgctgcttttggaggtcaagggtctaacaatttggacgtgttaaaaggtctattgga gttatacaagcggtatggcccagatttggatgagctactagacgtggcatccaacacgctttcg cagttggcatcttcccctgctgcaatagacgtccacgaaccctgggtttcgacctccgacaatg gttgaccacaccggaggttgctcctagcaaagaaattcttgccttgccaccacgaagctttccct taaatacgttacttagcttggcgctctattgtgcaacttgtcgagagcttgaacttgatcctgggca atttcgatccctccttcatagttccacggggcattcccaaggcatattggcggcggtggccatca cccaagccgagagctggccaaccttttatgacgcctgcaggacggtgctccagatctctttctg gattggactcgaggcttacctcttcactccatcctccgccgcctcggatgccatgatccaagattg catcgaacatggcgagggccttcttcctcaatgctaagtgtctccgggctctcccgctcccaagt tgagcgagtaattgagcacgtcaataaagggctcggagaatgcaaccgatgggttcacttggc cttggttaactcccacgaaaagttcgtcttagcgggaccacctcaatccttatgggccgtttgtctt catgtccgacggatcagagcagacaatgacctcgaccagtcgcgtatcttgttccgcaaccga aagcctatagtggatatattatttcttcccatatccgcaccatttcacacaccgtacttggacggtgt tcaagatcgcgttatcgaggctttgagctctgcttcgttggctctccattccatcaaaatccccctct atcacacgggcactgggagcaacctacaagaactacaaccacatcagctaatcccgactctt atccgcgccattaccgtggaccaattggactggccgttggtttgccggggcttgaacgcaacgc acgtgttggactttggacctggacaaacatgcagtcttattcaggagctcacacaaggaacag gtgtatcagtgatccagttgactactcaatcgggaccaaaacccgttggaggccatttggcggc agtgaactgggaggccgagtttggcttacgacttcatgccaatgtccacggtgcagctaaattg cacaaccgtatgacaacattgcttgggaagcctcctgtgatggtagccggaatgacacctacta cggtgcgctgggactttgtcgctgccgttgctcaagctggataccacgtcgaattggctggtggt ggctaccacgcagagcgccagttcgaggccgagattcggcgcttggcaactgccatcccagc agatcatggcatcacctgcaatctcctctacgccaagcctacgactttttcctggcagatctctgtc atcaaggatttggtgcgccaggagttcccgtggaaggaatcaccatcggcgccggcatccct tctccggaggtcgtccaagaatgtgtacagtccatcggactcaagcacatctcattcaagcctg -continued

```
ggtctttcgaagccattcaccaagtcatacagatcgcgcgtacccatcctaactttttgatcgggtt
gcaatggaccgcaggacgagggggaggacatcattcctgggaagacttccatggacctatttt
ggcaacctacgctcaaatccgatcatgtccgaatattctcctcgttgtaggtagtggattcggtgg
aggcccggacacgtttccctacctcacgggccaatgggcccaggcctttggctatccatgcatg
cccttcgacggagtgttgctcggcagtcgcatgatggtggctcgggaagcccatacgtcagcc
caggcaaaacgcttgattatagatgcgcaaggcgtgggagatgcagattggcacaagtcttc
gatgagcctaccggcggcgtagtgacggtcaactcggaattcggtcaacctatccacgttctag
ctactcgcggagtgatgttgtggaaagaactcgacaacccgggtcttttcaatcaaagacacttct
aagcgcttagaatatttgcgcaaccaccggcaagaaattgtgagccgtcttaacgcagactttg
cccgtccctggtttgccgttgacggacacggacagaatgtggagttggaggacatgacctacct
cgaggttctccgccgtttgtgcgatctcacgtatgtttcccaccagaagcgatgggtagatccatc
atatcgaatattattgttggacttcgttcatttgcttcgagaacgattccaatgcgctattgacaacc
ccggcgaatatccactcgacatcatcgtccgggtggaagagagcttgaaggataaagcatac
cgcacgctttatccagaagatgtctctcttctaatgcatttgttcagccgacgtgacatcaagccc
gtaccattcatccccaggttggatgagcgttttgagacctggtttaaaaaagactcattgtggcaa
tccgaagatgtggaggcggtaattggacaggacgtccagcgaatcttcatcattcaagggcct
atggccgttcagtactcaatatccgacgatgagtctgttaaagacattttacacaatatttgtaatc
attacgtggaggctctacaggctgattcaagagaaacttctatcggcgatgtacactcgatcac
gcaaaaacctctcagcgcgtttcctgggctcaaagtgacgacaaatagggtccaagggctcta
taagttcgagaaagtaggagcagtccccgaaatggacgttcttttttgagcatattgtcggattgtc
gaagtcatgggctcggacatgtttgatgagtaaatcggtctttagggacggttctcgtttgcataa
ccccattcgcgccgcactccagctccagcgcggcgacaccatcgaggtgcttttaacagcag
actcggaaattcgcaagattcgacttatttcacccacggggatggtggatccacttctaaggtc
gtattagagatagtctctaacgacggacaaagagttttcgccaccttggcccctaacatcccact
cagccccgagcccagcgtcgtcttttgcttcaaggtcgaccagaagccgaatgagtggaccct
tgaggaggatgcgtctggccgggcagagaggatcaaggcattatacatgagtttgtggaactt
gggctttccgaacaaggcctctgttttgggtcttaattcgcaattcacgggagaagaattgatgat
cacaacggacaagattcgtgatttcgaaagggtattgcggcaaaccagtcctcttcagttgcag
tcatggaaccccaaggatgtgtacctatcgactactgcgtggtcatcgcctggtctgctcttacc
aagcctttgatggtctcctctttgaaatgcgacctcttggatttgctccacagcgctataagcttcca
ctatgctccatctgtcaaaccattgcgggtgggcgatattgtcaaaacctcatcccgtatcctagc
ggtctcggtgagacctaggggaactatgttgacggtgtcggcggacattcagcgccagggac
aacatgtagtcactgtcaaatcagattttctttctcggaggccccgttttggcatgtgaaaccccttc
gaactcactgaggagcctgaaatggttgtccatgtcgactctgaagtgcgccgtgctatttaca
cagccgcaagtggctcatgcgagaagatcgcgcgctagatttgctagggaggcagctcctctt
cagattaaagagcgaaaaattgttcaggccagacggccagctagcattgttacaggtaacag
gttccgtgttcagctacagccccgatgggtcaacgacagcattcggtcgcgtatacttcgaaag
cgagtcttgtacagggaacgtggtgatggacttcttgcaccgctacggtgcacctcgggcgcag
ttgttggagttgcaacatcccgggtggacgggcacctctactgtggcagtaagaggtcctcgac
gcagccaatcctacgcacgcgtctccctcgatcataatcccatccatgtttgtccggcctttgcgc
```

-continued
```
gatacgctggtctctcgggtcccattgtccatgggatggaaacctctgccatgatgcgcagaatt gccgaatgggccatcggagatgcagaccggtctcggttccggagctggcatatcaccttgcaa gcacccgtccacccaacgaccctttgcgggtggagttgcagcataaggccatggaggacg gggaaatggttttgaaagtacaagcatttaacgaaaggacggaagaacgcgtagcggaggc agatgcccatgttgagcaggaaactacggcttacgtcttctgtggccagggcagtcaacgaca ggggatgggaatggacttgtacgtcaactgtccggaggctaaagcgttgtgggctcgcgccga caagcatttgtgggagaaatatgggttctccatcttgcacattgtgcaaaacaaccctccagccc tcactgttcactttggcagccagcgagggcgccgtattcgtgccaactatttgcgcatgatggga cagccaccgatagatggtagacatccgcccatattgaagggattgacgcggaattcgacctcg tacaccttctcctattcccagggggttgttgatgtccacccagttcgcccagcccgcattggcgttga tggaaatggctcagttcgaatggctcaaagcccagggagtcgttcagaagggtgcgcggttcg cgggacattcgttgggagaatatgccgcccttggagcttgtgcttccttcctctcatttgaagatctc atatctctcatcttttatcggggcttgaagatgcagaatgcgttgccgcgcgatgccaacggcca caccgactatggaatgttggctgccgatccatcgcggataggaaaaggtttcgaggaagcga gtttgaaatgtcttgtccatatcattcaacaggagaccggctggttcgtggaagtcgtcaactaca acatcaactcgcagcaatacgtctgtgcaggccatttccgagcccttggatgttgggtaagata tgcgatgacctttcatgccaccctcaaccggagactgttgaaggccaagagctacgggccatg gtctggaagcatgtcccgacggtggagcaggtgcccgcgaggatcgcatggaacgaggtc gagcgaccattccgttgccggggatcgatatcccataccattcgaccatgttacgaggggagat tgagccttatcgtgaatatttgtctgaacgtatcaaggtgggggatgtgaagccgtgcgaattggt gggacgctggatccctaatgttgttggccagcctttctccgtcgataagtcttacgttcagttggtgc acggcatcacaggtagtcctcggcttcattccttgcttcaacaaatggcgtga
```

Example 4

Transformation of C. tropicalis with the Synthetic Hexanoate Synthase Subunit Genes Candida tropicalis cells (ATCC number 20962) and cultured under standard conditions in YPD medium at 30 degrees Celsius. The synthetic genes encoding hexA and hexB are amplified using standard PCR amplification techniques. A linear DNA construct comprising, from 5' to 3', the TEF (transcription elongation factor) promoter, the hexA-AGC gene, the TEF promoter, the hexB-AGC gene, and the URA3 marker. Each end of this construct is designed to contain a mini-URA-Blaster for integration of the construct into C. tropicalis genomic DNA (Alani E, Cao L, Kleckner N. A method for gene disruption that allows repeated use of URA3 selection in the construction of multiply disrupted yeast strains. Genetics. 1987 August; 116 (4):541-545).

The construct is amplified using standard techniques. Transformation of C. tropicalis cells with this linear construct is accomplished using standard electroporation techniques such as those set forth in U.S. Pat. No. 5,648,247 or U.S. Pat. No. 5,204,252. Transformants are selected by plating and growing the transformed cells on SC-URA media as described above in which only transformants will survive. To remove the URA cassette, the confirmed strain is then replated onto SC complete media containing 5-Fluoroorotic Acid (5-FOA) and confirmed for the loss of the URA cassette.

Example 5

Assay of Cytochrome P450 with Activity on Six Carbon Chains in C. tropicalis

Cultures of C. tropicalis are cultured in YPD media to late log phase and then exposed to hexane exposed to various concentrations of hexane up to about 0.1 percent (v/v) induce the expression of the cytochrome p450 gene having activity specific for six carbon substrates. After about 2 hours exposure to the hexane solution, cells were harvested and RNA isolated using techniques described above. The specifically induced gene may be detected by Northern blotting and/or quantitative RT-PCR.

Cells to be analyzed for cytochrome P450 activity are grown under standard conditions and harvested for the production of microsomes. Microsomes were prepared by lysing cells in Tris-buffered sucrose (10 mM Tris-HCl pH 7.5, 1 mM EDTA, 0.25M sucrose). Differential centrifugation is performed first at 25,000×g then at 100,000×g to pellet cell debris then microsomes, respectively. The microsome pellet is resuspended in 0.1M phosphate buffer (pH 7.5), 1 mM EDTA to a final concentration of approximately 10 mg protein/mL.

A reaction mixture containing approximately 0.3 mg microsomes, 0.1 mM sodium hexanoate, 0.7 mM NADPH, 50 mM Tris-HCl pH 7.5 in 1 mL is initiated by the addition of NADPH and incubated at 37° C. for 10 minutes. The reaction is terminated by addition of 0.25 mL 5M HCl and 0.25 mL 2.5 ug/mL 10-hydroxydecanoic acid is added as an internal standard (3.3 nmol). The mixture is extracted with 4.5 mL diethyl ether under NaCl-saturated conditions. The organic phase is transferred to a new tube and evaporated to dryness. The residue is dissolved in acetonitrile containing 10 mM 3-bromomethyl-7-methoxy-1,4-benzoxazin-2-one (BrMB) and 0.1 mL of 15 mg/mL 18-crown-6 in acetonitril saturated with $K_2CO_3$. The solution is incubated at 40° C. for 30 minutes before addition of 0.05 mL 2% acetic acid. The fluorescently labeled omega-hydroxy fatty acids are resolved via HPLC with detection at 430 nm and excitation at 355 nm.

Example 6

Examples of Polynucleotide Regulators

Provided in the tables hereafter are non-limiting examples of regulator polynucleotides that can be utilized in embodiments herein. Such polynucleotides may be utilized in native form or may be modified for use herein. Examples of regulatory polynucleotides include those that are regulated by oxygen levels in a system (e.g., upregulated or downregulated by relatively high oxygen levels or relatively low oxygen levels).

| Regulated Yeast Promoters - Up-regulated by oxygen | | | | |
|---|---|---|---|---|
| ORF name | Gene name | Relative mRNA level (Aerobic) | Relative mRNA level (Anaerobic) | Ratio |
| YPL275W | | 4389 | 30 | 219.5 |
| YPL276W | | 2368 | 30 | 118.4 |
| YDR256C | CTA1 | 2076 | 30 | 103.8 |
| YHR096C | HXT5 | 1846 | 30 | 72.4 |
| YDL218W | | 1189 | 30 | 59.4 |
| YCR010C | | 1489 | 30 | 48.8 |
| YOR161C | | 599 | 30 | 29.9 |
| YPL200W | | 589 | 30 | 29.5 |
| YGR110W | | 1497 | 30 | 27 |
| YNL237W | YTP1 | 505 | 30 | 25.2 |
| YBR116C | | 458 | 30 | 22.9 |
| YOR348C | PUT4 | 451 | 30 | 22.6 |
| YBR117C | TKL2 | 418 | 30 | 20.9 |
| YLL052C | | 635 | 30 | 20 |
| YNL195C | | 1578 | 30 | 19.4 |
| YPR193C | | 697 | 30 | 15.7 |
| YDL222C | | 301 | 30 | 15 |
| YNL335W | | 294 | 30 | 14.6 |
| YPL036W | PMA2 | 487 | 30 | 12.8 |
| YML122C | | 206 | 30 | 10.3 |
| YGR067C | | 236 | 30 | 10.2 |
| YPR192W | | 204 | 30 | 10.2 |
| YNL014W | | 828 | 30 | 9.8 |
| YFL061W | | 256 | 30 | 9.1 |
| YNR056C | | 163 | 30 | 8.1 |
| YOR186W | | 153 | 30 | 7.6 |
| YDR222W | | 196 | 30 | 6.5 |
| YOR338W | | 240 | 30 | 6.3 |
| YPR200C | | 113 | 30 | 5.7 |
| YMR018W | | 778 | 30 | 5.2 |
| YOR364W | | 123 | 30 | 5.1 |
| YNL234W | | 93 | 30 | 4.7 |
| YNR064C | | 85 | 30 | 4.2 |
| YGR213C | RTA1 | 104 | 30 | 4 |
| YCL064C | CHA1 | 80 | 30 | 4 |
| YOL154W | | 302 | 30 | 3.9 |
| YPR150W | | 79 | 30 | 3.9 |
| YPR196W | MAL63 | 30 | 30 | 3.6 |
| YDR420W | HKR1 | 221 | 30 | 3.5 |
| YJL216C | | 115 | 30 | 3.5 |
| YNL270C | ALP1 | 67 | 30 | 3.3 |
| YHL016C | DUR3 | 224 | 30 | 3.2 |
| YOL131W | | 230 | 30 | 3 |
| YOR077W | RTS2 | 210 | 30 | 3 |
| YDR536W | STL1 | 55 | 30 | 2.7 |
| YNL150W | | 78 | 30 | 2.6 |
| YHR212C | | 149 | 30 | 2.4 |
| YJL108C | | 106 | 30 | 2.4 |
| YGR069W | | 49 | 30 | 2.4 |
| YDR106W | | 60 | 30 | 2.3 |
| YNR034W | SOL1 | 197 | 30 | 2.2 |
| YEL073C | | 104 | 30 | 2.1 |
| YOL141W | | 81 | 30 | 1.8 |

| Regulated Yeast Promoters - Down-regulated by oxygen | | | | |
|---|---|---|---|---|
| ORF name | Gene name | Relative mRNA level (Aerobic) | Relative mRNA level (Anaerobic) | Ratio |
| YJR047C | ANB1 | 30 | 4901 | 231.1 |
| YMR319C | FET4 | 30 | 1159 | 58 |
| YPR194C | | 30 | 982 | 49.1 |
| YIR019C | STA1 | 30 | 981 | 22.8 |
| YHL042W | | 30 | 608 | 12 |
| YHR210C | | 30 | 552 | 27.6 |
| YHR079B | SAE3 | 30 | 401 | 2.7 |
| YGL162W | STO1 | 30 | 371 | 9.6 |
| YHL044W | | 30 | 334 | 16.7 |
| YOL015W | | 30 | 320 | 6.1 |
| YCLX07W | | 30 | 292 | 4.2 |
| YIL013C | PDR11 | 30 | 266 | 10.6 |
| YDR046C | | 30 | 263 | 13.2 |
| YBR040W | FIG1 | 30 | 257 | 12.8 |
| YLR040C | | 30 | 234 | 2.9 |
| YOR255W | | 30 | 231 | 11.6 |
| YOL014W | | 30 | 229 | 11.4 |
| YAR028W | | 30 | 212 | 7.5 |
| YER089C | | 30 | 201 | 6.2 |
| YFL012W | | 30 | 193 | 9.7 |
| YDR539W | | 30 | 187 | 3.4 |
| YHL043W | | 30 | 179 | 8.9 |
| YJR162C | | 30 | 173 | 6 |
| YMR165C | SMP2 | 30 | 147 | 3.5 |
| YER106W | | 30 | 145 | 7.3 |
| YDR541C | | 30 | 140 | 7 |
| YCRX07W | | 30 | 138 | 3.3 |
| YHR048W | | 30 | 137 | 6.9 |
| YCL021W | | 30 | 136 | 6.8 |
| YOL160W | | 30 | 136 | 6.8 |
| YCRX08W | | 30 | 132 | 6.6 |
| YMR057C | | 30 | 109 | 5.5 |
| YDR540C | | 30 | 83 | 4.2 |
| YOR378W | | 30 | 78 | 3.9 |
| YBR085W | AAC3 | 45 | 1281 | 28.3 |
| YER188W | | 47 | 746 | 15.8 |
| YLL065W | GIN11 | 50 | 175 | 3.5 |
| YDL241W | | 58 | 645 | 11.1 |
| YBR238C | | 59 | 274 | 4.6 |
| YCR048W | ARE1 | 60 | 527 | 8.7 |
| YOL165C | | 60 | 306 | 5.1 |
| YNR075W | | 60 | 251 | 4.2 |
| YJL213W | | 60 | 250 | 4.2 |
| YPL265W | DIP5 | 61 | 772 | 12.7 |
| YDL093W | PMT5 | 62 | 353 | 5.7 |
| YKR034W | DAL80 | 63 | 345 | 5.4 |
| YKR053C | | 66 | 1268 | 19.3 |
| YJR147W | | 68 | 281 | 4.1 |

| Known and putative DNA binding motifs | | |
|---|---|---|
| Regulator | Known Consensus Motif | SEQ ID NO: |
| Abf1 | TCRNNNNNNACG | 95 |
| Cbf1 | RTCACRTG | |
| Gal4 | CGGNNNNNNNNNNNCCG | 96 |
| Gcn4 | TGACTCA | |
| Gcr1 | CTTCC | |
| Hap2 | CCAATNA | |
| Hap3 | CCAATNA | |
| Hap4 | CCAATNA | |
| Hsf1 | GAANNTTCNNGAA | 97 |
| Ino2 | ATGTGAAA | |
| Mata(A1) | TGATGTANNT | 98 |
| Mcm1 | CCNNNWWRGG | 99 |
| Mig1 | WWWWSYGGGG | 100 |
| Pho4 | CACGTG | |
| Rap1 | RMACCCANNCAYY | 101 |
| Reb1 | CGGGTRR | |
| Ste12 | TGAAACA | |
| Swi4 | CACGAAA | |
| Swi6 | CACGAAA | |
| Yap1 | TTACTAA | |

| Putative DNA Binding Motifs Regulator | Best Motif (scored by E-value) | SEQ ID NO: | Best Motif (scored by Hypergeometric) | SEQ ID NO: |
|---|---|---|---|---|
| Abf1 | TYCGT--R-ARTGAYA | 102 | TYCGT--R-ARTGAYA | 196 |
| Ace2 | RRRAARARAA-A-RARAA | 103 | GTGTGTGTGTGTGTG | 197 |
| Adr1 | A-AG-GAGAGAG-GGCAG | 104 | YTSTYSTT-TTGYTWTT | 198 |
| Arg80 | T--CCW-TTTKTTTC | 105 | GCATGACCATCCACG | 199 |
| Arg81 | AAAAARARAAAARMA | 106 | GSGAYARMGGAMAAAAA | 200 |
| Aro80 | YKYTYTTYTT----KY | 107 | TRCCGAGRYW-SSSGCGS | 201 |
| Ash1 | CGTCCGGCGC | 108 | CGTCCGGCGC | 202 |
| Azf1 | GAAAAAGMAAAAAAA | 109 | AARWTSGARG-A--CSAA | 203 |
| Bas1 | TTTTYYTTYTTKY-TY-T | 110 | CS-CCAATGK--CS | 204 |
| Cad1 | CATKYTTTTTTKYTY | 111 | GCT-ACTAAT | 205 |
| Cbf1 | CACGTGACYA | 112 | CACGTGACYA | 206 |
| Cha4 | CA---ACACASA-A | 113 | CAYAMRTGY-C | 207 |
| Cin5 | none | | none | |
| Crz1 | GG-A-A--AR-ARGGC- | 114 | TSGYGRGASA | 208 |
| Cup9 | TTTKYTKTTY-YTTTKTY | 115 | K-C-C---SCGCTACKGC | 209 |

-continued

| Known and putative DNA binding motifs | | | | | |
|---|---|---|---|---|---|
| Dal81 | WTTKTTTTYTTTTT-T | 116 | SR-GGCMCGGC-SSG | 210 |
| Dal82 | TTKTTTTYTTC | 117 | TACYACA-CACAWGA | 211 |
| Dig1 | AAA--RAA-GARRAA-AR | 118 | CCYTG-AYTTCW-CTTC | 212 |
| Dot6 | GTGMAK-MGRA-G-G | 119 | GTGMAK-MGRA-G-G | 213 |
| Fhl1 | -TTWACAYCCRTACAY-Y | 120 | -TTWACAYCCRTACAY-Y | 214 |
| Fkh1 | TTT-CTTTKYTT-YTTTT | 121 | AAW-RTAAAYARG | 215 |
| Fkh2 | AAARA-RAAA-AAAR-AA | 122 | GG-AAWA-GTAAACAA | 216 |
| Fzf1 | CACACACACACACAC | 123 | SASTKCWCTCKTCGT | 217 |
| Gal4 | TTGCTTGAACGSATGCCA | 124 | TTGCTTGAACGSATGCCA | 218 |
| Gal4 (Gal) | YCTTTTTTTTYTTYYKG | 125 | CGGM---CW-Y--CCCG | 219 |
| Gat1 | none | | none | |
| Gat3 | RRSCCGMCGMGRCGCGCS | 126 | RGARGTSACGCAKRTTCT | 220 |
| Gcn4 | AAA-ARAR-RAAAARRAR | 127 | TGAGTCAY | |
| Gcr1 | GGAAGCTGAAACGYMWRR | 128 | GGAAGCTGAAACGYMWRR | 221 |
| Gcr2 | GGAGAGGCATGATGGGGG | 129 | AGGTGATGGAGTGCTCAG | 222 |
| Gln3 | CT-CCTTTCT | 130 | GKCTRR-RGGAGA-GM | 223 |
| Grf10 | GAAARRAAAAAAMRMARA | 131 | -GGGSG-T-SYGT-CGA | 224 |
| Gts1 | G-GCCRS--TM | 132 | AG-AWGTTTTGWCAAMA | 225 |
| Haa1 | none | | none | |
| Hal9 | TTTTTTYTTTTY-KTTTT | 133 | KCKSGCAGGCWTTKYTCT | 226 |
| Hap2 | YTTCTTTTYT-Y-C-KT- | 134 | G-CCSART-GC | 227 |
| Hap3 | T-SYKCTTTTCYTTY | 135 | SGCGMGGG--CC-GACCG | 228 |
| Hap4 | STT-YTTTY-TTYTYYYY | 136 | YCT-ATTSG-C-GS | 229 |
| Hap5 | YK-TTTWYYTC | 137 | T-TTSMTT-YTTTCCK-C | 230 |
| Hir1 | AAAA-A-AARAR-AG | 138 | CCACKTKSGSCCT-S | 231 |
| Hir2 | WAAAAAGAAAA-AAAAR | 139 | CRSGCYWGKGC | 232 |
| Hms1 | AAA-GG-ARAM | 140 | -AARAAGC-GGGCAC-C | 233 |
| Hsf1 | TYTTCYAGAA--TTCY | 141 | TYTTCYAGAA--TTCY | 234 |
| Ime4 | CACACACACACACACA | 142 | CACACACACACACACA | 235 |
| Ino2 | TTTYCACATGC | 143 | SCKKCGCKSTSSTTYAA | 236 |
| Ino4 | G--GCATGTGAAAA | 144 | G--GCATGTGAAAA | 237 |
| Ixr1 | GAAAA-AAAAAAAARA-A | 145 | CTTTTTTTYYTSGCC | 238 |
| Leu3 | GAAAAARAARAA-AA | 146 | GCCGGTMMCGSYC-- | 239 |
| Mac1 | YTTKT--TTTTTYTYTTT | 147 | A--TTTTTYTTKYGC | 240 |
| Mal13 | GCAG-GCAGG | 148 | AAAC-TTTATA-ATACA | 241 |
| Mal33 | none | | none | |
| Mata1 | GCCC-C | | CAAT-TCT-CK | 242 |
| Mbp1 | TTTYTYKTTT-YYTTTTT | 149 | G-RR-A-ACGCGT-R | 243 |
| Mcm1 | TTTCC-AAW-RGGAAA | 150 | TTTCC-AAW-RGGAAA | 244 |

-continued

Known and putative DNA binding motifs

| Met31 | YTTYYTTYTTTTYTYTTC | 151 |
| Met4 | MTTTTTYTYTYTTC | 152 |
| Mig1 | TATACA-AGMKRTATATG | 153 |
| Mot3 | TMTTT-TY-CTT-TTTWK | 154 |
| Msn1 | KT--TTWTTATTCC-C | 155 |
| Msn2 | ACCACC | |
| Msn4 | R--AAAA-RA-AARAAAT | 156 |
| MSS11 | TTTTTTTTCWCTTTKYC | 157 |
| Ndd1 | TTTY-YTKTTTY-YTTYT | 158 |
| Nrg1 | TTY--TTYTT-YTTTYYY | 159 |
| Pdr1 | T-YGTGKRYGT-YG | 160 |
| Phd1 | TTYYYTTTTTYTTTTYTT | 161 |
| Pho4 | GAMAAAAARAAAAR | 162 |
| Put3 | CYCGGGAAGCSAMM-CCG | 163 |
| Rap1 | GRTGYAYGGRTGY | 164 |
| Rcs1 | KMAARAAAARAAR | 165 |
| Reb1 | RTTACCCGS | |
| Rfx1 | AYGRAAARARAAARAA | 166 |
| Rgm1 | GGAKSCC-TTTY-GMRTA | 167 |
| Rgt1 | CCCTCC | |
| Rim101 | GCGCCGC | |
| Rlm1 | TTTTC-KTTTYTTTTC | 168 |
| Rme1 | ARAAGMAGAAARRAA | 169 |
| Rox1 | YTTTTCTTTTY-TTTTT | 170 |
| Rph1 | ARRARAAAGG- | 171 |
| Rtg1 | YST-YK-TYTT-CTCCCM | 172 |
| Rtg3 | GARA-AAAAR-RAARAAA | 173 |
| Sfl1 | CY--GGSSA-C | 174 |
| Sfp1 | CACACACACACACAYA | 175 |
| Sip4 | CTTYTWTTKTTKTSA | 176 |
| Skn7 | YTTYYYTYTTTYTYYTTT | 177 |
| Sko1 | none | |
| Smp1 | AMAAAAARAARWARA-AA | 178 |
| Sok2 | ARAAAARRAAAAAG-RAA | 179 |
| Stb1 | RAARAAAARCMRSRAAA | 180 |
| Ste12 | TTYTKTYTY-TYYKTTTY | 181 |
| Stp1 | GAAAAMAA-AAAAA-AAA | 182 |
| Stp2 | YAA-ARAARAAAA-AAM | 183 |
| Sum1 | TY-TTTTTYTTTTT-TK | 184 |

Known and putative DNA binding motifs

| | | |
|---|---|---|
| Swi4 | RAARAARAAA-AA-R-AA | 185 |
| Swi5 | CACACACACACACACACA | 186 |
| Swi6 | RAARRRAAAAA-AAAMAA | 187 |
| Thi2 | GCCAGACCTAC | 188 |
| Uga3 | GG-GGCT | |
| Yap1 | TTYTTYTTYTTTY-YTYT | 189 |
| Yap3 | none | |
| Yap5 | YKSGCGCGYCKCGKCGGS | 190 |
| Yap6 | TTTTYYTTTTYYYYKTT | 191 |
| Yap7 | none | |
| Yfl044c | TTCTTKTYYTTTT | 192 |
| Yjl206c | TTYTTTTYTYYTTTYTTT | 193 |
| Zap1 | TTGCTTGAACGGATGCCA | 194 |
| Zms1 | MG-MCAAAAATAAAAS | 195 |

Transcriptional repressors

| Associated Gene(s) | Description(s) |
|---|---|
| WHI5 | Repressor of G1 transcription that binds to SCB binding factor (SBF) at SCB target promoters in early G1; phosphorylation of Whi5p by the CDK, Cln3p/Cdc28p relieves repression and promoter binding by Whi5; periodically expressed in G1 |
| TUP1 | General repressor of transcription, forms complex with Cyc8p, involved in the establishment of repressive chromatin structure through interactions with histones H3 and H4, appears to enhance expression of some genes |
| ROX1 | Heme-dependent repressor of hypoxic genes; contains an HMG domain that is responsible for DNA bending activity |
| SFL1 | Transcriptional repressor and activator; involved in repression of flocculation-related genes, and activation of stress responsive genes; negatively regulated by cAMP-dependent protein kinase A subunit Tpk2p |
| RIM101 | Transcriptional repressor involved in response to pH and in cell wall construction; required for alkaline pH-stimulated haploid invasive growth and sporulation; activated by proteolytic processing; similar to *A. nidulans* PacC |
| RDR1 | Transcriptional repressor involved in the control of multidrug resistance; negatively regulates expression of the PDR5 gene; member of the Gal4p family of zinc cluster proteins |
| SUM1 | Transcriptional repressor required for mitotic repression of middle sporulation-specific genes; also acts as general replication initiation factor; involved in telomere maintenance, chromatin silencing; regulated by pachytene checkpoint |
| XBP1 | Transcriptional repressor that binds to promoter sequences of the cyclin genes, CYS3, and SMF2; expression is induced by stress or starvation during mitosis, and late in meiosis; member of the Swi4p/Mbp1p family; potential Cdc28p substrate |
| NRG2 | Transcriptional repressor that mediates glucose repression and negatively regulates filamentous growth; has similarity to Nrg1p |
| NRG1 | Transcriptional repressor that recruits the Cyc8p-Tup1p complex to promoters; mediates glucose repression and negatively regulates a variety of processes including filamentous growth and alkaline pH response |
| CUP9 | Homeodomain-containing transcriptional repressor of PTR2, which encodes a major peptide transporter; imported |

-continued

Transcriptional repressors

| Associated Gene(s) | Description(s) |
|---|---|
| | peptides activate ubiquitin-dependent proteolysis, resulting in degradation of Cup9p and de-repression of PTR2 transcription |
| YOX1 | Homeodomain-containing transcriptional repressor, binds to Mcm1p and to early cell cycle boxes (ECBs) in the promoters of cell cycle-regulated genes expressed in M/G1 phase; expression is cell cycle-regulated; potential Cdc28p substrate |
| RFX1 | Major transcriptional repressor of DNA-damage-regulated genes, recruits repressors Tup1p and Cyc8p to their promoters; involved in DNA damage and replication checkpoint pathway; similar to a family of mammalian DNA binding RFX1-4 proteins |
| MIG3 | Probable transcriptional repressor involved in response to toxic agents such as hydroxyurea that inhibit ribonucleotide reductase; phosphorylation by Snf1p or the Mec1p pathway inactivates Mig3p, allowing induction of damage response genes |
| RGM1 | Putative transcriptional repressor with proline-rich zinc fingers; overproduction impairs cell growth |
| YHP1 | One of two homeobox transcriptional repressors (see also Yox1p), that bind to Mcm1p and to early cell cycle box (ECB) elements of cell cycle regulated genes, thereby restricting ECB-mediated transcription to the M/G1 interval |
| HOS4 | Subunit of the Set3 complex, which is a meiotic-specific repressor of sporulation specific genes that contains deacetylase activity; potential Cdc28p substrate |
| CAF20 | Phosphoprotein of the mRNA cap-binding complex involved in translational control, repressor of cap-dependent translation initiation, competes with eIF4G for binding to eIF4E |
| SAP1 | Putative ATPase of the AAA family, interacts with the Sin1p transcriptional repressor in the two-hybrid system |
| SET3 | Defining member of the SET3 histone deacetylase complex which is a meiosis-specific repressor of sporulation genes; necessary for efficient transcription by RNAPII; one of two yeast proteins that contains both SET and PHD domains |
| RPH1 | JmjC domain-containing histone demethylase which can specifically demethylate H3K36 tri- and dimethyl modification states; transcriptional repressor of PHR1; Rph1p phosphorylation during DNA damage is under control of the MEC1-RAD53 pathway |
| YMR181C | Protein of unknown function; mRNA transcribed as part of a bicistronic transcript with a predicted transcriptional repressor RGM1/YMR182C; mRNA is destroyed by nonsense-mediated decay (NMD); YMR181C is not an essential gene |
| YLR345W | Similar to 6-phosphofructo-2-kinase/fructose-2,6-bisphosphatase enzymes responsible for the metabolism of fructoso-2,6-bisphosphate; mRNA expression is repressed by the Rfx1p-Tup1p-Ssn6p repressor complex; YLR345W is not an essential gene |
| MCM1 | Transcription factor involved in cell-type-specific transcription and pheromone response; plays a central role in the formation of both repressor and activator complexes |
| PHR1 | DNA photolyase involved in photoreactivation, repairs pyrimidine dimers in the presence of visible light; induced by DNA damage; regulated by transcriptional repressor Rph1p |
| HOS2 | Histone deacetylase required for gene activation via specific deacetylation of lysines in H3 and H4 histone tails; subunit of the Set3 complex, a meiotic-specific repressor of sporulation specific genes that contains deacetylase activity |
| RGT1 | Glucose-responsive transcription factor that regulates expression of several glucose transporter (HXT) genes in response to glucose; binds to promoters and acts both as a transcriptional activator and repressor |
| SRB7 | Subunit of the RNA polymerase II mediator complex; associates with core polymerase subunits to form the RNA polymerase II holoenzyme; essential for transcriptional regulation; target of the global repressor Tup1p |
| GAL11 | Subunit of the RNA polymerase II mediator complex; associates with core polymerase subunits to form the RNA polymerase II holoenzyme; affects transcription by acting as target of activators and repressors |

| Transcriptional activators | |
|---|---|
| Associated Gene(s) | Description(s) |
| SKT5 | Activator of Chs3p (chitin synthase III), recruits Chs3p to the bud neck via interaction with Bni4p; has similarity to Shc1p, which activates Chs3p during sporulation |
| MSA1 | Activator of G1-specific transcription factors, MBF and SBF, that regulates both the timing of G1-specific gene transcription, and cell cycle initiation; potential Cdc28p substrate |
| AMA1 | Activator of meiotic anaphase promoting complex (APC/C); Cdc20p family member; required for initiation of spore wall assembly; required for Clb1p degradation during meiosis |
| STB5 | Activator of multidrug resistance genes, forms a heterodimer with Pdr1p; contains a Zn(II)2Cys6 zinc finger domain that interacts with a PDRE (pleotropic drug resistance element) in vitro; binds Sin3p in a two-hybrid assay |
| RRD2 | Activator of the phosphotyrosyl phosphatase activity of PP2A, peptidyl-prolyl cis/trans-isomerase; regulates G1 phase progression, the osmoresponse, microtubule dynamics; subunit of the Tap42p-Pph21p-Rrd2p complex |
| BLM10 | Proteasome activator subunit; found in association with core particles, with and without the 19S regulatory particle; required for resistance to bleomycin, may be involved in protecting against oxidative damage; similar to mammalian PA200 |
| SHC1 | Sporulation-specific activator of Chs3p (chitin synthase III), required for the synthesis of the chitosan layer of ascospores; has similarity to Skt5p, which activates Chs3p during vegetative growth; transcriptionally induced at alkaline pH |
| NDD1 | Transcriptional activator essential for nuclear division; localized to the nucleus; essential component of the mechanism that activates the expression of a set of late-S-phase-specific genes |
| IMP2' | Transcriptional activator involved in maintenance of ion homeostasis and protection against DNA damage caused by bleomycin and other oxidants, contains a C-terminal leucine-rich repeat |
| LYS14 | Transcriptional activator involved in regulation of genes of the lysine biosynthesis pathway; requires 2-aminoadipate semialdehyde as co-inducer |
| MSN1 | Transcriptional activator involved in regulation of invertase and glucoamylase expression, invasive growth and pseudohyphal differentiation, iron uptake, chromium accumulation, and response to osmotic stress; localizes to the nucleus |
| HAA1 | Transcriptional activator involved in the transcription of TPO2, YRO2, and other genes putatively encoding membrane stress proteins; involved in adaptation to weak acid stress |
| UGA3 | Transcriptional activator necessary for gamma-aminobutyrate (GABA)-dependent induction of GABA genes (such as UGA1, UGA2, UGA4); zinc-finger transcription factor of the Zn(2)-Cys(6) binuclear cluster domain type; localized to the nucleus |
| GCR1 | Transcriptional activator of genes involved in glycolysis; DNA-binding protein that interacts and functions with the transcriptional activator Gcr2p |
| GCR2 | Transcriptional activator of genes involved in glycolysis; interacts and functions with the DNA-binding protein Gcr1p |
| GAT1 | Transcriptional activator of genes involved in nitrogen catabolite repression; contains a GATA-1-type zinc finger DNA-binding motif; activity and localization regulated by nitrogen limitation and Ure2p |
| GLN3 | Transcriptional activator of genes regulated by nitrogen catabolite repression (NCR), localization and activity regulated by quality of nitrogen source |
| PUT3 | Transcriptional activator of proline utilization genes, constitutively binds PUT1 and PUT2 promoter sequences and undergoes a conformational change to form the active state; has a Zn(2)-Cys(6) binuclear cluster domain |
| ARR1 | Transcriptional activator of the basic leucine zipper (bZIP) family, required for transcription of genes involved in resistance to arsenic compounds |
| PDR3 | Transcriptional activator of the pleiotropic drug resistance network, regulates expression of ATP-binding cassette (ABC) transporters through binding to cis-acting sites known as PDREs (PDR responsive elements) |
| MSN4 | Transcriptional activator related to Msn2p; activated in stress conditions, which results in translocation from the cytoplasm to the nucleus; binds DNA at stress response elements of responsive genes, inducing gene expression |
| MSN2 | Transcriptional activator related to Msn4p; activated in stress conditions, which results in translocation from the cytoplasm to the nucleus; binds DNA at stress response elements of responsive genes, inducing gene expression |

-continued

Transcriptional activators

| Associated Gene(s) | Description(s) |
|---|---|
| PHD1 | Transcriptional activator that enhances pseudohyphal growth; regulates expression of FLO11, an adhesin required for pseudohyphal filament formation; similar to StuA, an *A. nidulans* developmental regulator; potential Cdc28p substrate |
| FHL1 | Transcriptional activator with similarity to DNA-binding domain of Drosophila forkhead but unable to bind DNA in vitro; required for rRNA processing; isolated as a suppressor of splicing factor prp4 |
| VHR1 | Transcriptional activator, required for the vitamin H-responsive element (VHRE) mediated induction of VHT1 (Vitamin H transporter) and BIO5 (biotin biosynthesis intermediate transporter) in response to low biotin concentrations |
| CDC20 | Cell-cycle regulated activator of anaphase-promoting complex/cyclosome (APC/C), which is required for metaphase/anaphase transition; directs ubiquitination of mitotic cyclins, Pds1p, and other anaphase inhibitors; potential Cdc28p substrate |
| CDH1 | Cell-cycle regulated activator of the anaphase-promoting complex/cyclosome (APC/C), which directs ubiquitination of cyclins resulting in mitotic exit; targets the APC/C to specific substrates including Cdc20p, Ase1p, Cin8p and Fin1p |
| AFT2 | Iron-regulated transcriptional activator; activates genes involved in intracellular iron use and required for iron homeostasis and resistance to oxidative stress; similar to Aft1p |
| MET4 | Leucine-zipper transcriptional activator, responsible for the regulation of the sulfur amino acid pathway, requires different combinations of the auxiliary factors Cbf1p, Met28p, Met31p and Met32p |
| CBS2 | Mitochondrial translational activator of the COB mRNA; interacts with translating ribosomes, acts on the COB mRNA 5'-untranslated leader |
| CBS1 | Mitochondrial translational activator of the COB mRNA; membrane protein that interacts with translating ribosomes, acts on the COB mRNA 5'-untranslated leader |
| CBP6 | Mitochondrial translational activator of the COB mRNA; phosphorylated |
| PET111 | Mitochondrial translational activator specific for the COX2 mRNA; located in the mitochondrial inner membrane |
| PET494 | Mitochondrial translational activator specific for the COX3 mRNA, acts together with Pet54p and Pet122p; located in the mitochondrial inner membrane |
| PET122 | Mitochondrial translational activator specific for the COX3 mRNA, acts together with Pet54p and Pet494p; located in the mitochondrial inner membrane |
| RRD1 | Peptidyl-prolyl cis/trans-isomerase, activator of the phosphotyrosyl phosphatase activity of PP2A; involved in G1 phase progression, microtubule dynamics, bud morphogenesis and DNA repair; subunit of the Tap42p-Sit4p-Rrd1p complex |
| YPR196W | Putative maltose activator |
| POG1 | Putative transcriptional activator that promotes recovery from pheromone induced arrest; inhibits both alpha-factor induced G1 arrest and repression of CLN1 and CLN2 via SCB/MCB promoter elements; potential Cdc28p substrate; SBF regulated |
| MSA2 | Putative transcriptional activator, that interacts with G1-specific transcription factor, MBF and G1-specific promoters; ortholog of Msa2p, an MBF and SBF activator that regulates G1-specific transcription and cell cycle initiation |
| PET309 | Specific translational activator for the COX1 mRNA, also influences stability of intron-containing COX1 primary transcripts; localizes to the mitochondrial inner membrane; contains seven pentatricopeptide repeats (PPRs) |
| TEA1 | Ty1 enhancer activator required for full levels of Ty enhancer-mediated transcription; C6 zinc cluster DNA-binding protein |
| PIP2 | Autoregulatory oleate-specific transcriptional activator of peroxisome proliferation, contains Zn(2)-Cys(6) cluster domain, forms heterodimer with Oaf1p, binds oleate response elements (OREs), activates beta-oxidation genes |
| CHA4 | DNA binding transcriptional activator, mediates serine/threonine activation of the catabolic L-serine (L-threonine) deaminase (CHA1); Zinc-finger protein with Zn[2]-Cys[6] fungal-type binuclear cluster domain |
| SFL1 | Transcriptional repressor and activator; involved in repression of flocculation-related genes, and activation of stress responsive genes; negatively regulated by cAMP-dependent protein kinase A subunit Tpk2p |
| RDS2 | Zinc cluster transcriptional activator involved in conferring resistance to ketoconazole |

Transcriptional activators

| Associated Gene(s) | Description(s) |
|---|---|
| CAT8 | Zinc cluster transcriptional activator necessary for derepression of a variety of genes under non-fermentative growth conditions, active after diauxic shift, binds carbon source responsive elements |
| ARO80 | Zinc finger transcriptional activator of the Zn2Cys6 family; activates transcription of aromatic amino acid catabolic genes in the presence of aromatic amino acids |
| SIP4 | C6 zinc cluster transcriptional activator that binds to the carbon source-responsive element (CSRE) of gluconeogenic genes; involved in the positive regulation of gluconeogenesis; regulated by Snf1p protein kinase; localized to the nucleus |
| SPT10 | Putative histone acetylase, sequence-specific activator of histone genes, binds specifically and highly cooperatively to pairs of UAS elements in core histone promoters, functions at or near the TATA box |
| MET28 | Basic leucine zipper (bZIP) transcriptional activator in the Cbf1p-Met4p-Met28p complex, participates in the regulation of sulfur metabolism |
| GCN4 | Basic leucine zipper (bZIP) transcriptional activator of amino acid biosynthetic genes in response to amino acid starvation; expression is tightly regulated at both the transcriptional and translational levels |
| CAD1 | AP-1-like basic leucine zipper (bZIP) transcriptional activator involved in stress responses, iron metabolism, and pleiotropic drug resistance; controls a set of genes involved in stabilizing proteins; binds consensus sequence TTACTAA |
| INO2 | Component of the heteromeric Ino2p/Ino4p basic helix-loop-helix transcription activator that binds inositol/choline-responsive elements (ICREs), required for derepression of phospholipid biosynthetic genes in response to inositol depletion |
| THI2 | Zinc finger protein of the Zn(II)2Cys6 type, probable transcriptional activator of thiamine biosynthetic genes |
| SWI4 | DNA binding component of the SBF complex (Swi4p-Swi6p), a transcriptional activator that in concert with MBF (Mbp1-Swi6p) regulates late G1-specific transcription of targets including cyclins and genes required for DNA synthesis and repair |
| HAP5 | Subunit of the heme-activated, glucose-repressed Hap2/3/4/5 CCAAT-binding complex, a transcriptional activator and global regulator of respiratory gene expression; required for assembly and DNA binding activity of the complex |
| HAP3 | Subunit of the heme-activated, glucose-repressed Hap2p/3p/4p/5p CCAAT-binding complex, a transcriptional activator and global regulator of respiratory gene expression; contains sequences contributing to both complex assembly and DNA binding |
| HAP2 | Subunit of the heme-activated, glucose-repressed Hap2p/3p/4p/5p CCAAT-binding complex, a transcriptional activator and global regulator of respiratory gene expression; contains sequences sufficient for both complex assembly and DNA binding |
| HAP4 | Subunit of the heme-activated, glucose-repressed Hap2p/3p/4p/5p CCAAT-binding complex, a transcriptional activator and global regulator of respiratory gene expression; provides the principal activation function of the complex |
| YML037C | Putative protein of unknown function with some characteristics of a transcriptional activator; may be a target of Dbf2p-Mob1p kinase; GFP-fusion protein co-localizes with clathrin-coated vesicles; YML037C is not an essential gene |
| TRA1 | Subunit of SAGA and NuA4 histone acetyltransferase complexes; interacts with acidic activators (e.g., Gal4p) which leads to transcription activation; similar to human TRRAP, which is a cofactor for c-Myc mediated oncogenic transformation |
| YLL054C | Putative protein of unknown function with similarity to Pip2p, an oleate-specific transcriptional activator of peroxisome proliferation; YLL054C is not an essential gene |
| RTG2 | Sensor of mitochondrial dysfunction; regulates the subcellular location of Rtg1p and Rtg3p, transcriptional activators of the retrograde (RTG) and TOR pathways; Rtg2p is inhibited by the phosphorylated form of Mks1p |
| YBR012C | Dubious open reading frame, unlikely to encode a functional protein; expression induced by iron-regulated transcriptional activator Aft2p |
| JEN1 | Lactate transporter, required for uptake of lactate and pyruvate; phosphorylated; expression is derepressed by transcriptional activator Cat8p during respiratory growth, and repressed in the presence of glucose, fructose, and mannose |
| MRP1 | Mitochondrial ribosomal protein of the small subunit; MRP1 exhibits genetic interactions with PET122, encoding a COX3- |

-continued

Transcriptional activators

Figure 4:
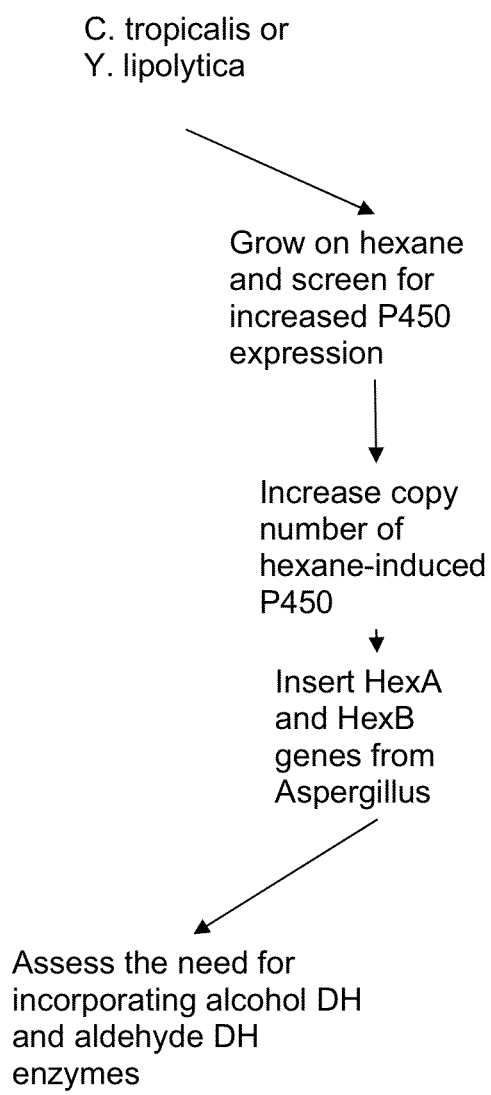
FIG. 4 depicts an embodiment of a method for generating an adipic acid producing organism. The method comprises expressing one or more genes encoding hexanoate synthase in a host microorganism that produces dicarboxylic acids via an omega-oxidation pathway. The microorganisms can include, without limitation, *C. tropicalis* and *C. maltosa*. In some embodiments, the method comprises growing a host microorganism on hexane and screening for increased P450 expression. In certain embodiments, copy number of hexane-induced P450 may be increased. HEXA and HEXB genes may be inserted into the host microorganism. In certain embodiments, the host microorganism may be altered to increase the flux of a six-carbon substrate through the final two oxidation steps.
Figure 5:
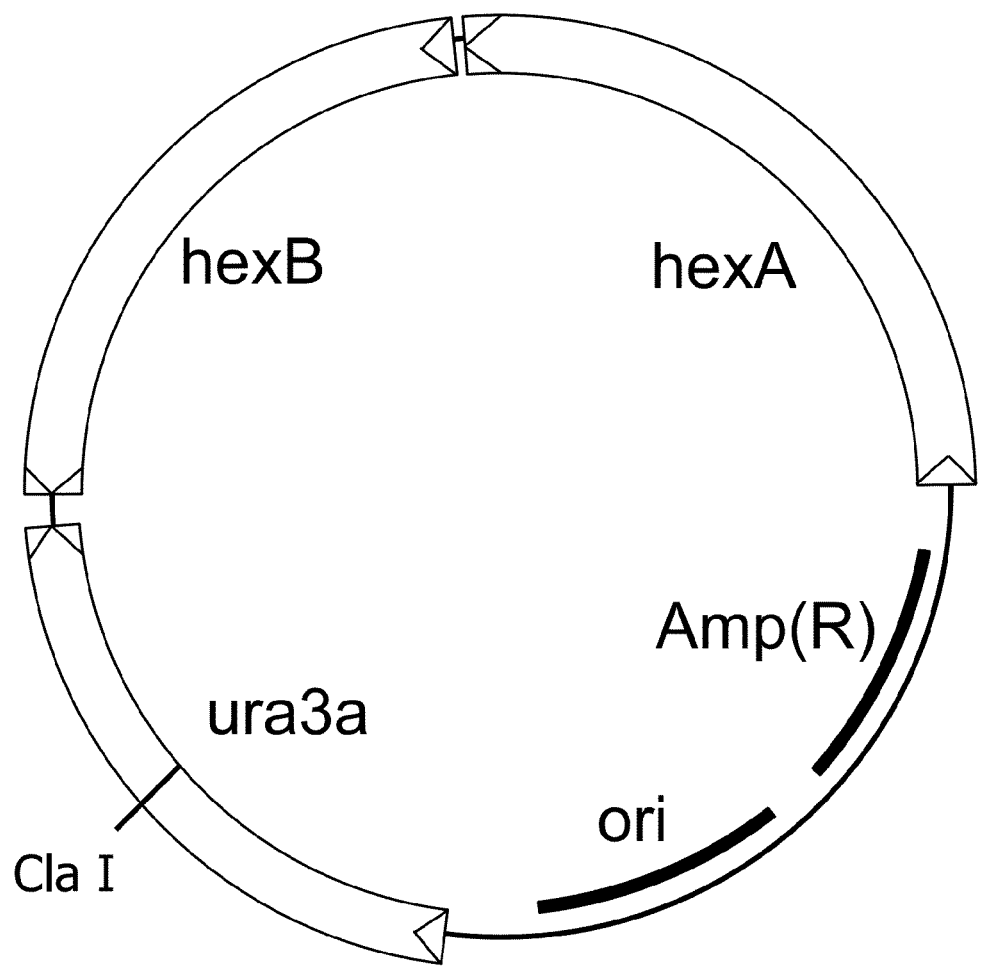
FIG. 5 depicts a plasmid diagram for inserting *Aspergillus* hexanoate synthase genes HEXA and HEXB into *C. tropicalis* or *Y. lipolytica*.
Figure 6:
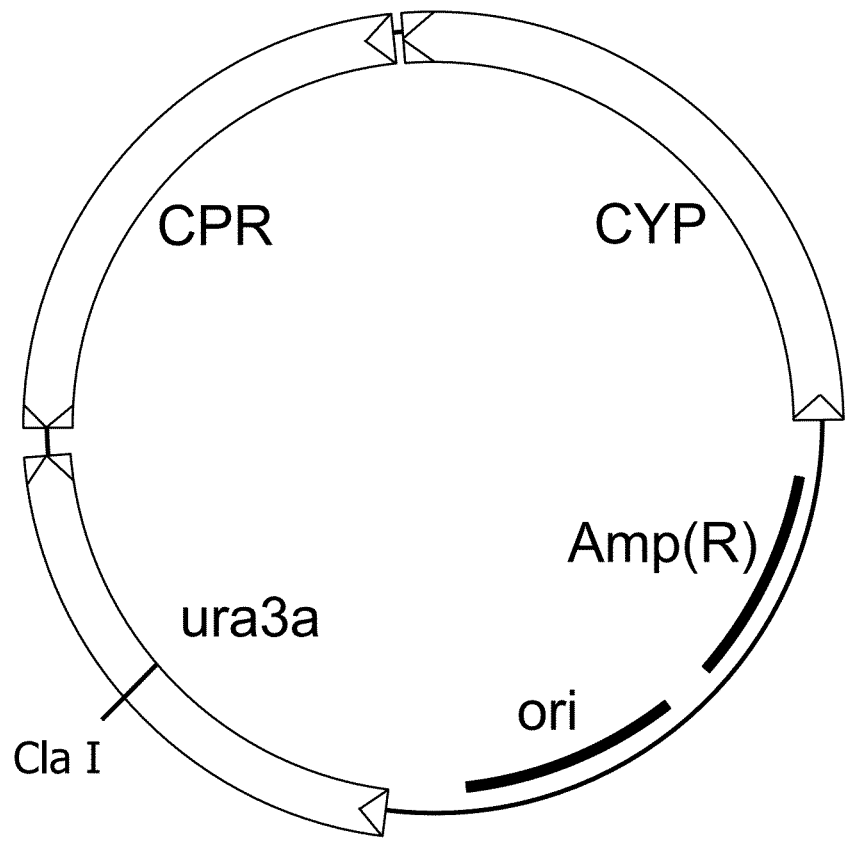
FIG. 6 depicts a plasmid diagram for inserting a heterologous cytochrome P450 monooxygenase gene and cytochrome P450 reductase gene into *C. tropicalis* or *Y. lipolytica*.
Figure 7:
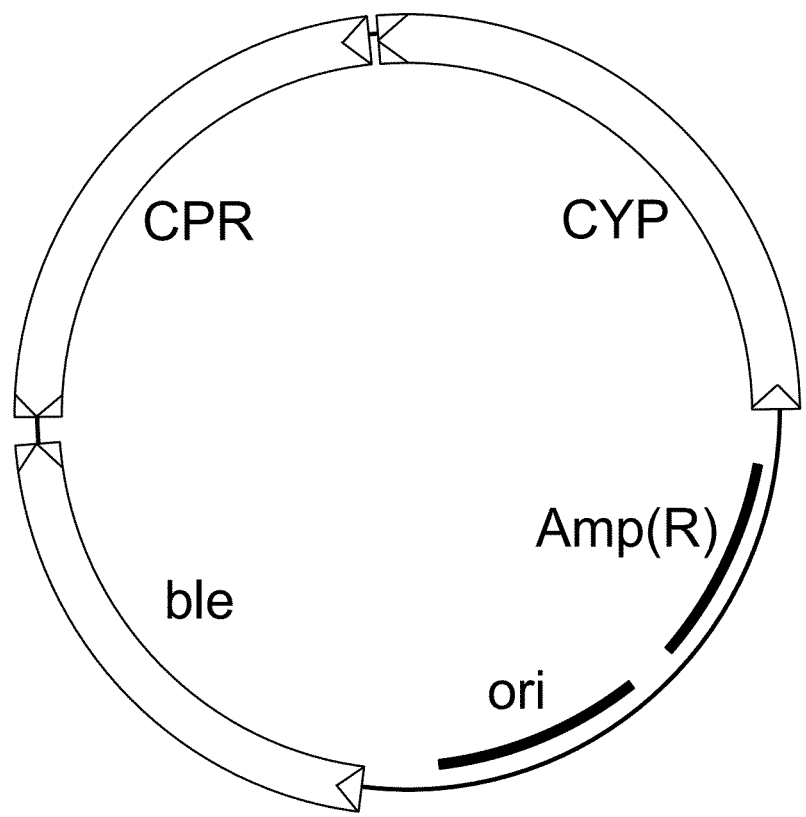
FIG. 7 depicts a plasmid diagram for inserting a heterologous cytochrome P450 monooxygenase gene and cytochrome P450 reductase gene into *A. parasiticus* or *A. nidulans*.
Figure 8:
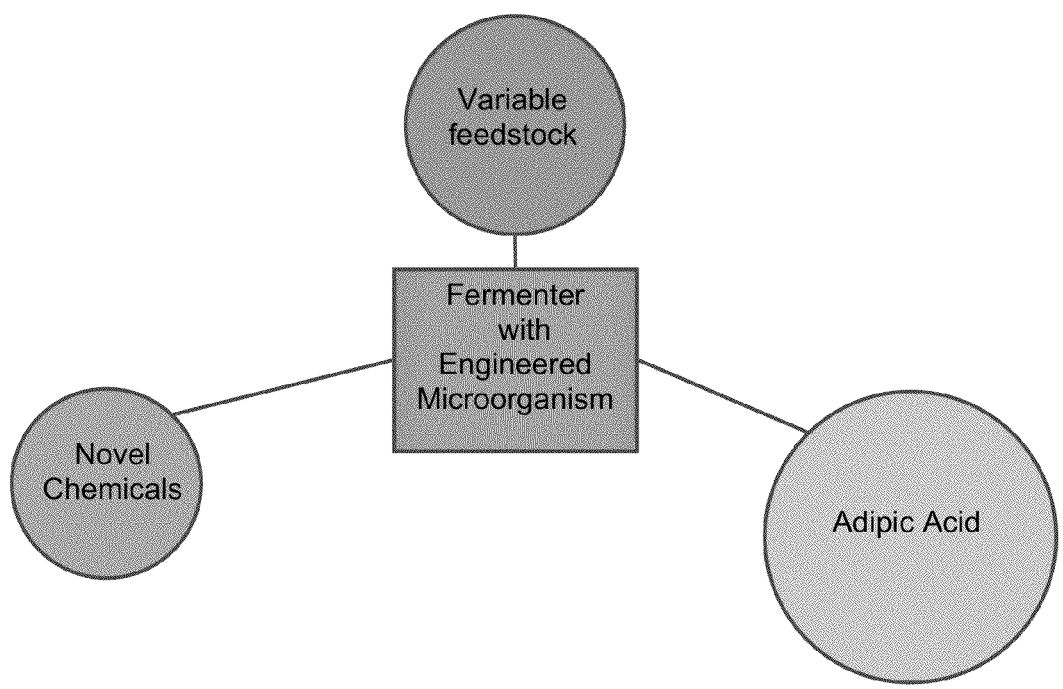
FIG. 8 depicts a system for biological production of a target product. As depicted, a fermenter is populated with microorganisms engineered for target product production. A flexible feedstock supplies the fermenter with an energy and nutrition source for the microorganisms. In some embodiments the feedstock comprises a sugar. In certain embodiments the feedstock comprises fatty acids. The feedstock may also include biomass, industrial waste products and other sources of carbon. Vitamins, minerals, enzymes and other growth or production enhancers may be added to the feedstock. In certain embodiments the fermentation produces adipic acid. The fermentation process may produce other novel chemicals.

| Associated Gene(s) | Description(s) |
|---|---|
| | specific translational activator, and with PET123, encoding a small subunit mitochondrial ribosomal protein |
| MRP17 | Mitochondrial ribosomal protein of the small subunit; MRP17 exhibits genetic interactions with PET122, encoding a COX3-specific translational activator |
| TPI1 | Triose phosphate isomerase, abundant glycolytic enzyme; mRNA half-life is regulated by iron availability; transcription is controlled by activators Reb1p, Gcr1p, and Rap1p through binding sites in the 5' non-coding region |
| PKH3 | Protein kinase with similarity to mammalian phosphoinositide-dependent kinase 1 (PDK1) and yeast Pkh1p and Pkh2p, two redundant upstream activators of Pkc1p; identified as a multicopy suppressor of a pkh1 pkh2 double mutant |
| YGL079W | Putative protein of unknown function; green fluorescent protein (GFP)-fusion protein localizes to the endosome; identified as a transcriptional activator in a high-throughput yeast one-hybrid assay |
| TFB1 | Subunit of TFIIH and nucleotide excision repair factor 3 complexes, required for nucleotide excision repair, target for transcriptional activators |
| PET123 | Mitochondrial ribosomal protein of the small subunit; PET123 exhibits genetic interactions with PET122, which encodes a COX3 mRNA-specific translational activator |
| MHR1 | Protein involved in homologous recombination in mitochondria and in transcription regulation in nucleus; binds to activation domains of acidic activators; required for recombination-dependent mtDNA partitioning |
| MCM1 | Transcription factor involved in cell-type-specific transcription and pheromone response; plays a central role in the formation of both repressor and activator complexes |
| EGD1 | Subunit beta1 of the nascent polypeptide-associated complex (NAC) involved in protein targeting, associated with cytoplasmic ribosomes; enhances DNA binding of the Gal4p activator; homolog of human BTF3b |
| STE5 | Pheromone-response scaffold protein; binds Ste11p, Ste7p, and Fus3p kinases, forming a MAPK cascade complex that interacts with the plasma membrane and Ste4p-Ste18p; allosteric activator of Fus3p that facilitates Ste7p-mediated activation |
| RGT1 | Glucose-responsive transcription factor that regulates expression of several glucose transporter (HXT) genes in response to glucose; binds to promoters and acts both as a transcriptional activator and repressor |
| TYE7 | Serine-rich protein that contains a basic-helix-loop-helix (bHLH) DNA binding motif; binds E-boxes of glycolytic genes and contributes to their activation; may function as a transcriptional activator in Ty1-mediated gene expression |
| VMA13 | Subunit H of the eight-subunit V1 peripheral membrane domain of the vacuolar H+-ATPase (V-ATPase), an electrogenic proton pump found throughout the endomembrane system; serves as an activator or a structural stabilizer of the V-ATPase |
| GAL11 | Subunit of the RNA polymerase II mediator complex; associates with core polymerase subunits to form the RNA polymerase II holoenzyme; affects transcription by acting as target of activators and repressors |
| VAC14 | Protein involved in regulated synthesis of PtdIns(3,5)P(2), in control of trafficking of some proteins to the vacuole lumen via the MVB, and in maintenance of vacuole size and acidity; interacts with Fig4p; activator of Fab1p |

Example 7

Cloning of HEXA and HEXB Genes

*Aspergillus parasiticus* (ATCC 24690) cultures were grown in malt extract broth media (15 g/L malt extract broth, Difco) with shaking at 25° C. for 3 days. *A. parasiticus* pellets were transferred to a 1.5 mL tube to provide a volume of pellets equal to approximately 500 uL. The mycelia were frozen in a dry ice ethanol bath, transferred to a mortar and pestle, and ground into a fine powder. The powder was placed in a 1.5 mL tube with approximately 500 uL 0.7 mm Zirconia beads, and total RNA was prepared using a Ribopure Plant Kit (Ambion), according to manufacturer's recommendations.

First strand synthesis of cDNA was performed with gene-specific primers oAA0031 (for HEXA) and oAA0041 (for HEXB) in a reaction containing 0.2 uL of gene-specific primer (10 uM), 300 ng total RNA, 1.0 uL dNTP (10 mM), and sterile water to bring the volume to 13 uL. The total RNA/primer mixtures were heated at 65° C. for 5 minutes then cooled on ice for 5 minutes before the addition of 4 uL 5× First strand buffer, 1 uL 0.1M DTT, 1 uL H20, and 1 uL Superscript III RT (Invitrogen). First strand synthesis reactions were incubated at 55° C. for 1 hour, followed by inactivation of the enzyme at 70° C. for 15 minutes and cooling of the reactions to 4° C. The primers utilized for isolation of HEXA and HEXB genes were configured to independently amplify the HEXA and HEXB genes in fragments, having fragment lengths in the range of between about 1.0 kilobases (kb) to about 1.6 kb, with approximately 200 bp of overlapping sequence between the fragments. The sequences are shown in the tables below.

HEXA and HEXB gene fragments were PCR amplified using the cDNA generated above by the addition of 5 uL 10×Pfu reaction buffer, 1.0 uL dNTPs (10 mM), 1.0 uL Sense and Antisense Primer Mix (10 uM), 1.0 uL Pfu Ultra Fusion HS (Agilent), 2.0 uL cDNA, 40 uL sterile H20. Thermocycling parameters used to amplify the HEXA and HEXB genes were 94° C. for 5 minutes, 40 cycles of 94° C. 30 seconds, 62° C. 40 seconds, 72° C. 4 minutes, followed by 72° C. 10

| Oligonucleotides for cloning of HEXA DNA fragments | | | |
|---|---|---|---|
| Oligos | Sequence (SEQ ID NOS 247-259, respectively, in order of appearance) | HEXA sequence | PCR product (bp) |
| oAA0022 | ATGGTCATCCAAGGGAAGAGATTGGCCGCCTCCTCTATTCAGC | 1-1149 | 1149 |
| oAA0023 | GTAGGCGTCACAGGAAAGACTGCGTACCA | | |
| oAA0024 | TATCACCAATGCTGGATGTAAAGAAGTCGCG | 941-2270 | 1330 |
| oAA0025 | AATTGGGCTAGGAAACCGGGGATGC | | |
| oAA0026 | CGGTCTAATGACGGCGCATGATATCATAGCCGAAACGGTCGAG | 2067-3016 | 950 |
| oAA0027 | ACTTGGCTGGAGTCCATCCCTTCGGCA | | |
| oAA0028 | CTGCCCGAGTTTGAAGTATCTCAACTTACCGCCGACGCCATG | 2812-4181 | 1370 |
| oAA0029 | TGAGACGCGCTGCGCAGGGC | | |
| oAA0030 | CGAGGTGATCGAGACGCAGATGC | 3975-5016 | 1042 |
| oAA0031 | TTATGAAGCACCAGACATCAGCCCCAGC | | |
| oAA0046 | gtactagtaaaaaaATGGTCATCCAAGGGAAGAGATTGGCCGCCTCCTCTATTCAGC | 1-5016 | 5041 |
| oAA0047 | gtcccgggctaTTATGAAGCACCAGACATCAGCCCCAGC | | |
| oAA0051 | tacccgggctattagtgatggtggtgatggtgTGAAGCACCAGACATCAGCCCCAGC | 1-5016 | 5062 |

| Oligonucleotides for cloning of HEXB DNA fragments | | | |
|---|---|---|---|
| Oligos | Sequence (SEQ ID NOS 260-272, respectively, in order of appearance) | HEXB sequence | PCR product (bp) |
| oAA0032 | ATGGGTTCCGTTAGTAGGGAACATGAGTCAATC | 1-1166 | 1166 |
| oAA0033 | GTTCCTTGTGTGAGCTCCTGAATAAGACTGCATG | | |
| oAA0034 | CCATCAAAATCCCCCTCTATCACACGGGCACTGGGAGCAAC | 962-2042 | 1081 |
| oAA0035 | CCCACGCCTTGCGCATCTATAATCAGG | | |
| oAA0036 | TGTCCGAATATTCTCCTCGTTGTAGGTAGTGGATT | 1837-3527 | 1691 |
| oAA0037 | GCAGTAGTCGATAGGTACACATCCTTGGGGGTTCCATGACTGC | | |
| oAA0038 | AGAGGATCAAGGCATTATACATGAGTCTGTGGAACTTGGGCTTTCC | 3323-4461 | 1139 |
| oAA0039 | TTCCCCGTCCTCCATGGCCTTATGC | | |
| oAA0040 | GGCCTTTGCGCGATACGCTGGTCTCTCGGGTCCCAT | 4256-5667 | 1412 |
| oAA0041 | TCACGCCATTTGTTGAAGCAGGGAATG | | |
| oAA0048 | gtactagtaaaaaaATGGGTTCCGTTAGTAGGGAACATGAGTCAATC | 1-5667 | 5694 |
| oAA0049 | gtgtttaaacctaTCACGCCATTTGTTGAAGCAGGGAATG | | |
| oAA0111 | ggtttaaacctatcagtgatggtggtgatggtgCGCCATTTGTTGAAGCAGGGAATGAA | 1-5667 | 5714 | minutes and a 4° C. hold. PCR products of the correct size were gel purified and ligated into pCR-Blunt II-TOPO (Invitrogen), transformed into competent TOP10 *E. coli* cells (Invitrogen) and clones containing PCR inserts were sequenced to confirm correct DNA sequence.

Figure 11B:
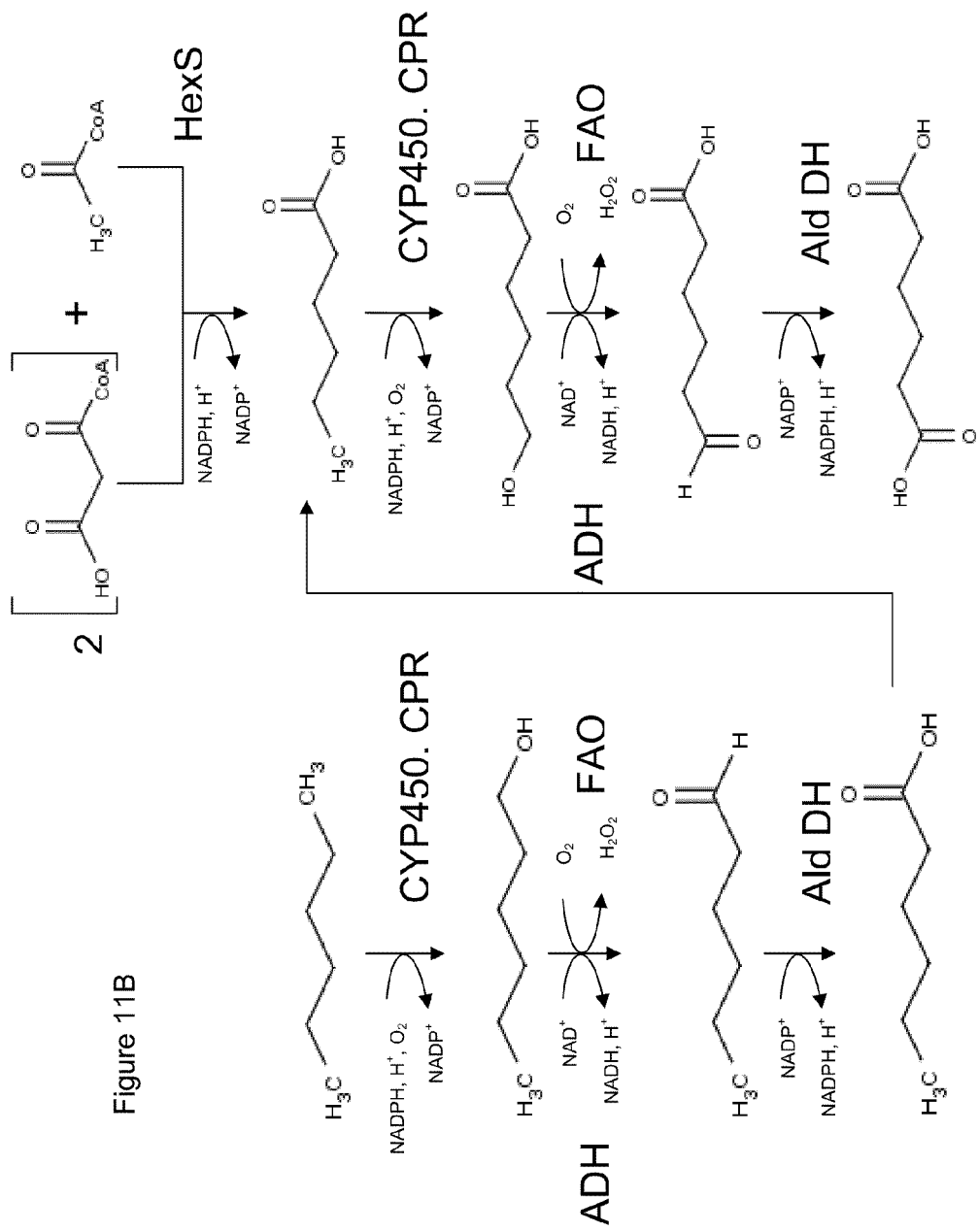
Figure 12:
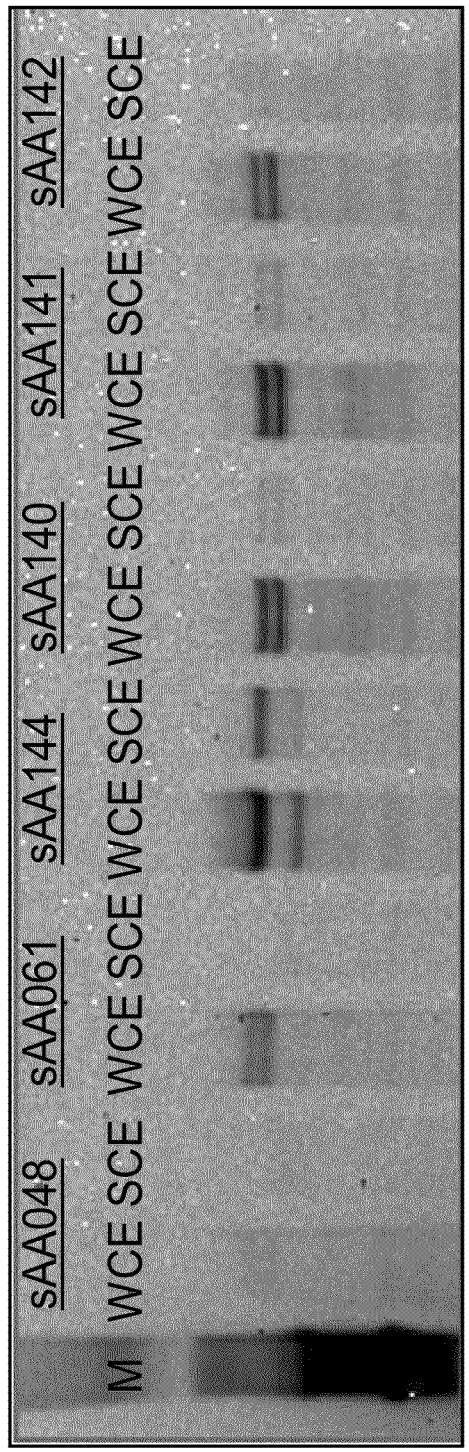
FIG. 12 shows results of immunodetection of 6×His-tagged ("6×His" disclosed as SEQ ID NO: 60) proteins expressed in S. cerevisiae BY4742. Strains sAA061, sAA140, sAA141, sAA142 contain 6×His-tagged ("6×His" disclosed as SEQ ID NO: 60) HEXA and HEXB proteins. Strain sAA144 contains 6×His-tagged ("6×His" disclosed as SEQ ID NO: 60) STCJ and STCK proteins. Strain sAA048 contains only vectors p425GPD and p426GPD.

DNA fragments of HEXA and HEXB were PCR amplified using the sequence-confirmed fragments in pCR-BluntII as template in order to produce overlapping DNA fragments covering the entire sequence of both HEXA and HEXB. The overlapping DNA fragments for each gene were combined in a 50 uL overlap extension PCR reaction containing each DNA fragment at 0.2 nM, sense and antisense primers at 0.2 uM each, 1×Pfu reaction buffer, 1.0 uL Pfu Ultra Fusion HS polymerase, and 0.2 mM dNTPs. Unique restriction sites were incorporated into the sense and antisense primers to allow for cloning the HEXA and HEXB genes into p425GPD and p426GPD respectively. For HEXA the restriction sites were SpeI/SmaI and for HEXB the restriction sites were SpeI/PmeI. Ligation of the HEXA and HEXB genes into p425GPD and p426GPD resulted in plasmids pAA020 and pAA021 respectively. Variants of the HEXA and HEXB genes that incorporated C-terminal 6×His tags ("6×His" disclosed as SEQ ID NO: 60) were constructed by using an antisense primer encoding a 6×His sequence ("6×His" disclosed as SEQ ID NO: 60). Ligation of the HEXA-6×His ("6×His" disclosed as SEQ ID NO: 60) and HEXB-6×His genes ("6×His" disclosed as SEQ ID NO: 60) into p425GPD and p426GPD resulted in plasmids pAA031 and pAA032, respectively. Vectors pAA020, pAA021, pAA031 and pAA032 were used to demonstrate protein expression in *S. cerevisiae*, as shown in FIGS. 11 and 12.

Example 8

Cloning of STCJ and STCK Genes

Total RNA was prepared from *Aspergillus nidulans* (ATCC 38163), as described in Example 1. First strand synthesis of cDNA was performed with gene-specific primers oAA0008 (for STCJ) and oAA0021 (for STCK) in a reaction containing 0.2 uL of gene-specific primer (10 uM), 300 ng total RNA, 1.0 uL dNTP (10 mM), and sterile water to bring the volume to 13 uL. The total RNA/primer mixtures were heated at 65° C. for 5 minutes then cooled on ice for 5 minutes before the addition of 4 uL 5× First strand buffer, 1 uL 0.1M DTT, 1 uL H20, and 1 uL Superscript III RT (Invitrogen). First strand synthesis reactions were incubated at 55° C. for 1 hour, followed by inactivation of the enzyme at 70° C. for 15 minutes and cooling of the reactions to 4° C. Primers design strategies substantially similar to those described herein were used to amplify the STCJ and STCK genes in fragments in the range of between about 1.1 kb to about 1.6 kb, with approximately 200 bp of overlapping sequence between the fragments. The primers used to amplify the STCJ and STCK genes are shown in the tables below.

| Oligonucleotides for cloning of STCJ DNA fragments | | | |
|---|---|---|---|
| Oligos | Sequence (SEQ ID NOS 273-283, respectively, in order of appearance) | STCJ sequence | PCR product (bp) |
| oAA0001 | ATGACCCAAAAGACTATACAGCAGGTCCCAAGA | 1-1290 | 1290 |
| oAA0002 | TATGGTGCATCGAATGTTGTTTGCCTGG | | |
| oAA0009 | AAAATGCGTGAGCACTTTGTCCAGCGC | 1021-2506 | 1486 |
| oAA0004 | CGACGTAATTGACGTTGTCAACATGCCG | | |
| oAA0005 | CATCTCGGGTTCCCATCACTCCCTGAGTATGAC | 2284-3424 | 1141 |
| oAA0006 | GACAAAGAAGCTGGACACCGCAGCCTTGGGATTCCACGAAC | | |
| oAA0007 | GATCTGCCTTGTCGGTGGCTATGACGACCTTCAGCCTGAGGAGTCA | 3234-4680 | 1447 |
| oAA0008 | TTAACGGATGATAGAGGCCAACGGCCAAAGACACCACTTGCGTACAC | | |
| oAA0126 | CacacaactagtaaaaaaATGACCCAAAAGACTATACAGCAGGTCCCAAGA | 1-4680 | 4710 |
| oAA0127 | TgtgtgcccgggTTAACGGATGATAGAGGCCAACGGCCAAAGACACCACTTGCGTACAC | | |
| oAA0154 | TacccgggctattagtgatggtggtgatggtACGGATGATAGAGGCCAAC | 1-4680 | 4730 |

| Oligonucleotides for cloning of STCK DNA fragments | | | |
|---|---|---|---|
| Oligos | Sequence (SEQ ID NOS 284-296, respectively, in order of appearance) | STCK sequence | PCR product (bp) |
| oAA0012 | ATGACTCCATCACCGTTTCTCGATGCTGT | 1-1110 | 1110 |
| oAA0013 | CACATGGGTAGCATCGTTCATTGCCCAACACAAAGCGGGCCAGTTAACTC | | |

-continued

Oligonucleotides for cloning of STCK DNA fragments

| Oligos | Sequence (SEQ ID NOS 284-296, respectively, in order of appearance) | STCK sequence | PCR product (bp) |
|---|---|---|---|
| oAA0014 | GTCGAGCTAAGAGTGACTGATGCCATTGGC | 901-2510 | 1610 |
| oAA0015 | CGTAATTCAGCTTCTGAACCTGAGCCCAGG | | |
| oAA0016 | CTTTGCCCGGCCGTGGTTCGC | 2301-3555 | 1255 |
| oAA0017 | CCCCCAAGCTCGACAACGGGC | | |
| oAA0018 | TTCTCAAAATGCACCGGACTGATTACTTGGA | 3350-4682 | 1333 |
| oAA0019 | CCCATTCCTCTCTCCTGCGTGCCCTGGCCGGTAAAGACGTAT | | |
| oAA0020 | CCCTCCTTCGATGGACTTGTCCGGGCAAACGACCGGTTGCGAATGGAGAT | 4477-5745 | 1268 |
| oAA0021 | CTACCTATTCTCTTCAACCCGCCGTAACAGC | | |
| oAA0128 | CacacaactagtaaaaaaATGACTCCATCACCGTTTCTCGATGCTGT | 1-5745 | 5775 |
| oAA0129 | TgtgtgcccgggCTACCTATTCTCTTCAACCCGCCGTAACAGC | | |
| oAA0170 | TgtgtgcccgggctatcagtgatggtggtgatggtgCCTATTCTCTTCAAC | 1-5745 | 5796 |

STCJ and STCK fragments were amplified using the cDNA prepared above in PCR reactions containing 5 uL 10×Pfu reaction buffer, 1.0 uL dNTPs (10 mM), 1.0 uL Sense and Antisense Primer Mix (10 uM), 1.0 uL Pfu Ultra Fusion HS (Agilent), 2.0 uL cDNA, 40 uL sterile H20. Thermocycling parameters used were 94° C. for 5 minutes, 40 cycles of 94° C. 30 seconds, 62° C. 40 seconds, 72° C. 4 minutes, followed by 72° C. 10 minutes and a 4° C. hold. PCR products of the correct size were gel purified and ligated into pCR-Blunt II-TOPO (Invitrogen), transformed into competent TOP10 E. coli cells (Invitrogen). PCR inserts were sequenced to confirm the correct DNA sequence. DNA fragments of STCJ and STCK were PCR amplified using the sequence-confirmed fragments in pCR-BluntII as template in order to produce overlapping DNA fragments covering the entire sequence of both STCJ and STCK. The overlapping DNA fragments for each gene were combined in a 50 uL overlap extension PCR reaction containing each DNA fragment at 0.2 nM, sense and antisense primers at 0.2 uM each, 1×Pfu reaction buffer, 1.0 uL Pfu Ultra Fusion HS polymerase, and 0.2 mM dNTPs.

Sense and antisense primers were designed to incorporate unique restriction sites for cloning the STCJ and STCK genes into p425GPD and p426GPD respectively. For STCJ the restriction sites were SpeI/XmaI and for STCK the restriction sites were SpeI/SmaI. Ligation of the STCJ and STCK genes into p425GPD and p426GPD resulted in plasmids pAA040 and pAA042 respectively. Variants of the STCJ and STCK genes that incorporated C-terminal 6×His tags ("6×His" disclosed as SEQ ID NO: 60) were constructed by using an antisense primer encoding a 6×His sequence ("6×His" disclosed as SEQ ID NO: 60). Ligation of the STCJ-6×His ("6×His" disclosed as SEQ ID NO: 60) and STCK-6×His genes ("6×His" disclosed as SEQ ID NO: 60) into p425GPD and p426GPD resulted in plasmids pAA041 and pAA043. Vectors pAA040, pAA0421 pAA042 and pAA043 were used to demonstrate protein expression in S. cerevisiae, as shown in FIGS. 11 and 12.

Example 9

Design and Cloning of HEXA and HEXB Genes for C. tropicalis Alternate Genetic Code The HEXA and HEXB genes contain multiple CTG codons, which normally code for leucine. However, certain organisms, Candida tropicalis for example, translate CTG as serine. DNA sequences for HEXA and HEXB were prepared that replaced all CTG codons with TTG codons, which is translated as leucine in C. tropicalis. The TTG codon was chosen due to it being the most frequently used leucine codon in C. tropicalis. The alternate genetic code (AGC) HEXA and HEXB genes were synthesized as equal size fragments with 200 bp overlaps and ligated into pUC57 vector (Integrated DNA Technologies). DNA fragments of AGC-HEXA and AGC-HEXB were PCR amplified using the fragments in pUC57 as template in order to produce overlapping DNA fragments covering the entire sequence of both AGC-HEXA and AGC-HEXB.

The overlapping DNA fragments for each gene were combined in a 50 uL overlap extension PCR reaction containing each DNA fragment at 0.2 nM, sense and antisense primers at 0.2 uM each, 1×Pfu reaction buffer, 1.0 uL Pfu Ultra Fusion HS polymerase, and 0.2 mM dNTPs. Sense and antisense primers incorporated unique SapI restriction sites for cloning the AGC-HEXA and AGC-HEXB genes into pAA105 resulting in plasmids pAA127 and pAA129 respectively. Gene variants of AGC-HEXA and AGC-HEXB that contained C-terminal 6×His tags ("6×His" disclosed as SEQ ID NO: 60) were ligated into pAA105 resulting in plasmids pAA128 and pAA130 respectively. The alternate genetic code primers used to alter leucine codons for C. tropicalis expression of HEXA and HEXB are shown in the tables below.

Oligonucleotides for cloning of AGC-HEXA DNA fragments

| Oligos | Sequence (SEQ (SEQ ID NOS 297-305, respectively, in order of appearance) | AGC-HEXA sequence | PCR product (bp) |
|---|---|---|---|
| oAA0383 | cacacagctcttctagaATGGTCATCCAAGGGAAGAG | 1-1404 | 1421 |
| oAA0055 | AGTATCGACGTCGGCTGACTTGAGACCA | | |
| oAA0056 | CCATCACATCCACAGTGGCGG | 1205-2609 | 1405 |
| oAA0057 | AACCAGGCAAGTTCGACATAACCGGC | | |
| oAA0058 | GTAGGCTATCCCCGTCTCCCCGATTATG | 2410-3814 | 1405 |
| oAA0059 | TGATTGAGGTCAAGGATGATTTGTCCGAGA | | |
| oAA0060 | TCTTCCTATCTATGCGGTCATTGCCAGCT | 3615-5016 | 1419 |
| oAA0384 | cacacagctcttcctttTTATGAAGCACCAGACATCAAC | | |
| oAA0385 | cacacagctcttccttttagtgatggtggtgatggtgTGAAGCACCAGACATCAACCCCAACG | 1-5016 | 5071 |

Oligonucleotides for cloning of AGC-HEXB DNA fragments

| Oligos | (SEQ ID NOS 306-314, respectively, in order of appearance) | AGC-HEXB sequence | PCR product (bp) |
|---|---|---|---|
| oAA0386 | cacacagctcttctagaATGGGTTCCGTTAGTAGGGA | 1-1566 | 1583 |
| oAA0064 | CAAATCCTTGATGACAGAGATCTGCCAGGA | | |
| oAA0065 | GCTGGGACTTTGTCGCTGCCGTTGCTCAAGCTGGAT | 1367-2933 | 1567 |
| oAA0066 | ACTGCTCCTACTTTCTCGAACTTATAGAGCCCTTG | | |
| oAA0067 | ATATCCGACGATGAGTCTGT | 2734-4299 | 1566 |
| oAA0068 | ATGGACAATGGGACCCGAGA | | |
| oAA0069 | GGACTTCTTGCACCGCTACG | 4101-5667 | 1584 |
| oAA0387 | cacacagctcttcctttTCACGCCATTTGTTGAAGCAAAG | | |
| oAA0388 | cacacagctcttccttttcagtgatggtggtgatggtgCGCCATTTGTTGAAGCA | 1-5667 | 5692 |

Example 10

Transformation of S. cerevisiae Procedure

Competent cells of S. cerevisiae strain BY4742 were prepared using the Frozen-EZ Yeast Transformation II Kit (Zymo Research) following manufacturer's instructions. 50 uL aliquots of competent cells were stored at −80° C. until use. Competent cells were transformed by the addition of 0.5-1.0 ug of intact plasmid DNA as instructed by the Frozen-EZ Yeast Transformation II Kit (Zymo Research). Selection for transformants was performed by plating on selective media; SC-URA (for p426-based vectors) or SC-LEU (for p425-based vectors).

Example 11

Transformation of C. tropicalis Procedure 5 mL YPD start cultures were inoculated with a single colony of C. tropicalis and incubated overnight at 30° C., with shaking at about 200 rpm. The following day, fresh 25 mL YPD cultures, containing 0.05% Antifoam B, were inoculated to an initial $OD_{600nm}$ of 0.4 and the culture incubated at 30° C., with shaking at about 200 rpm until an $OD_{600nm}$ of 1.0-2.0 was reached. Cells were pelleted by centrifugation at 1,000×g, 4° C. for 10 minutes. Cells were washed by resuspending in 10 mL sterile water, pelleted, resuspended in 1 mL sterile water and transferred to a 1.5 mL microcentrifuge tube. The cells were then washed in 1 mL sterile TE/LiOAC solution, pH 7.5, pelleted, resuspended in 0.25 mL TE/LiOAC solution and incubated with shaking at 30° C. for 30 minutes.

The cell solution was divided into 50 uL aliquots in 1.5 mL tubes to which was added 5-8 ug of linearized DNA and 5 uL of carrier DNA (boiled and cooled salmon sperm DNA, 10 mg/mL). 300 uL of sterile PEG solution (40% PEG 3500, 1×TE, 1×LiOAC) was added, mixed thoroughly and incubated at 30° C. for 60 minutes with gentle mixing every 15 minutes. 40 uL of DMSO was added, mixed thoroughly and the cell solution was incubated at 42° C. for 15 minutes. Cells were then pelleted by centrifugation at 1,000×g 30 seconds, resuspended in 500 uL of YPD media and incubated at 30° C. with shaking at about 200 rpm for 2 hours. Cells were then pelleted by centrifugation and resuspended in 1 mL 1×TE, cells were pelleted again, resuspended in 0.2 mL 1×TE and plated on selective media. Plates were incubated at 30° C. for growth of transformants.

Example 12

HEXA and HEXB Expression in *S. cerevisiae*

Plasmids pAA031 and pAA032 were transformed into competent BY4742 *S. cerevisiae* cells independently and in combination. Selection for transformants containing pAA031 was performed on SC-LEU plates. Selection for transformants containing pAA032 was performed on SC-URA plates. Selection for transformants containing both pAA031 and pAA032 was performed on SC-URA-LEU plates. Single colonies were used to inoculate 5 mL of SC drop out media and grown overnight at 30° C., with shaking as described herein. Cells from 3 mL of overnight culture were harvested by centrifugation at 12,000 rpm for 2 minutes. Cell pellets were incubated at −80° C. until frozen.

Approximately 500 uL of cold 0.7 mm zirconia beads (Ambion) were added on top of the frozen cell pellets. Yeast lysis buffer (50 mM Tris pH 8.0, 0.1% Triton X100, 0.5 mM EDTA, 1× ProCEASE protease inhibitors [G Biosciences]) was added to fill the tube leaving as little air in the tube as possible, the tubes were placed on ice during manipulations. Cells were broken using three, 2 minute cycles in a Bead Beater (BioSpec) with 1 minute rests on ice between cycles. 200 uL of whole cell extract (WCE) was removed to a new tube and the remainder of the whole cell extract was centrifuged at 16,000×g, 4° C. for 15 minutes to pellet insoluble debris. The supernatant was removed to a new tube as the soluble cell extract (SCE). The protein content in the soluble cell extract was determined by Bradford assay (Pierce). A volume of SCE containing 50 ug of protein (and the same volume WCE) was precipitated by the addition of 4 volumes of cold 100% acetone. After centrifugation at 16,000×g, and 4° C. for 15 minutes, the supernatant was carefully removed and the pellet washed with 200 uL of cold 80% acetone and centrifuged again. The supernatant again was carefully removed and the cell pellets air dried for 5 minutes.

Protein pellets were then resuspended in 1×LDS sample buffer containing 50 mM DTT (Invitrogen) by incubating at 70° C., with shaking at about 1200 rpm. After brief centrifugation and cooling to room temperature, samples (20 ug) were separated by SDS PAGE and transferred to nitrocellulose for immunodetection with mouse anti-6×His antibodies ("6×His" disclosed as SEQ ID NO: 60) (Abcam). Incubation in 1:5,000 primary antibody was performed overnight at room temperature, incubation in 1:5,000 donkey anti-mouse HRP conjugate secondary antibody was performed for 3 hours at room temperature, and detection was performed with SuperSignal West Pico chemiluminescent substrate (Pierce). Multiple clones displayed soluble expression of both HEXA and HEXB subunits of hexanoate synthase. As shown in FIG. 11, a substantial portion of the expressed protein fractionated with the insoluble pellet. Strains sAA061, sAA140, sAA141, sAA142 contained 6×His-tagged ("6×His" disclosed as SEQ ID NO: 60) HEXA and HEXB proteins. Strain sAA048 contained only vectors p425GPD and p426GPD.

Example 13

STCJ and STCK Expression in *S. cerevisiae*

Plasmids pAA041 and pAA043 were cotransformed into competent BY4742 *S. cerevisiae*. Selection for transformants containing both pAA041 and pAA043 was performed on SC-URA-LEU plates. Culture growth, cell extract preparation, SDS PAGE, and immunodetection were performed as described herein. One clone displayed soluble expression of both STCJ and STCK subunits. As shown in FIG. 11, a substantial portion of the expressed protein fractionated with the insoluble pellet. Strain sAA144 contained 6×His-tagged ("6×His" disclosed as SEQ ID NO: 60) STCJ and STCK proteins. Strain sAA048 contained only vectors p425GPD and p426GPD.

Example 14

HEXA and HEXB Expression in *C. tropicalis*

Plasmids pAA128 and pAA130 were linearized using ClaI, and cotransformed into competent sAA103 cells (ura3/ura3, pox4::ura3/pox4::ura3, pox5::ura3/pox5::ura3). The ClaI recognition sites in the HEXA and HEXB ORF's are blocked due to overlapping dam methylation. Selection for transformants containing integrated vector DNA was performed on SC-URA plates. Confirmation of vector integration was performed by PCR using HEXA and HEXB specific primers. Transformants that were PCR positive for both HEXA and HEXB were selected for analysis of target protein expression. Overnight culture growth was performed as described herein. Fresh 5 mL YPD cultures were inoculated from the overnight cultures to an initial $OD_{600nm}$ of 0.4 and incubated until the $OD_{600nm}$ reached ~5-8, at which point the culture was harvested. Cell extract preparation, SDS PAGE, and immunodetection were performed as described herein. Strains sAA269 and sAA270 contained plasmids pAA128 and pAA130 integrated into the genome for expression of 6×His-tagged ("6×His" disclosed as SEQ ID NO: 60) HEXA and HEXB proteins. Both strains displayed soluble expression of 6×His-tagged ("6×His" disclosed as SEQ ID NO: 60) HEXA and HEXB subunits as shown in FIG. 12. 6×His tagged ("6×His" disclosed as SEQ ID NO: 60) HEXA and HEXB expressed in strains sAA269 and sAA270 are indicated with arrows. 6×His tagged ("6×His" disclosed as SEQ ID NO: 60) STCJ and STCK from strain sAA144 were included as a positive control. Strain sAA103 is the parent strain for sAA269 and sAA270 and does not contain integrated vectors for the expression of 6×His-tagged ("6×His" disclosed as SEQ ID NO: 60) HEXA and HEXB.

Example 15

Procedure for Recycling of the URA3 Marker

*C. tropicalis* has a limited number of selectable marker, as compared to *S. cerevisiae*, therefore, the URA3 marker is "recycled" to allow multiple rounds of selection using URA3. To reutilize the URA3 marker for subsequent engineering of *C. tropicalis*, a single colony having the Ura+ phenotype was inoculated into 3 mL YPD and grown overnight at 30° C. with shaking. The overnight culture was then harvested by centrifugation and resuspended in 1 mL YNB+YE (6.7 g/L Yeast Nitrogen Broth, 3 g/L Yeast Extract). The resuspended cells were then serially diluted in YNB+YE and 100 uL aliquots plated on YPD plates (incubation overnight at 30° C.) to determine titer of the original suspension. Additionally, triplicate 100 uL aliquots of the undiluted suspension were plated on SC Dextrose (Bacto Agar 20 g/L, Uracil 0.3 g/L, Dextrose 20 g/L, Yeast Nitrogen Broth 6.7 g/L, Amino Acid Dropout Mix 2.14 g/L) and 5-FOA. at 3 different concentrations (0.5, 0.75, 1 mg/mL).

Plates were incubated for at least 5 days at 30° C. Colonies arising on the SC Dextrose+5-FOA plates were resuspended in 50 uL sterile, distilled water and 5 uL utilized to streak on to YPD and SC-URA (SC Dextrose medium without Uracil)

plates. Colonies growing only on YPD and not on SC-URA plates were then inoculated into 3 mL YPD and grown overnight at 30° C. with shaking. Overnight cultures were harvested by centrifugation and resuspended in 1.5 mL YNB (6.7 g/L Yeast Nitrogen Broth). The resuspended cells were serially diluted in YNB and 100 uL aliquots plated on YPD plates and incubation overnight at 30° C. to determine initial titer. 1 mL of each undiluted cell suspension also was plated on SC-URA and incubated for up to 7 days at 30° C. Colonies on the SC-URA plates are revertants and the isolate with the lowest reversion frequency ($<10^{-7}$) was used for subsequent strain engineering.

Example 16

Omega Oxidation of Hexane and Hexanoic Acid to Adipic Acid

Starter cultures of strain sAA003 were grown in $YPD_{2.0}$ (1% yeast extract, 2% peptone, 2% dextrose) overnight as described. Starter cultures were used to inoculate 100 mL of fresh $YPD_{2.0}$ to an initial $OD_{600nm}$ of 0.4 and incubated overnight at 30° C., with shaking at about 200 rpm. The 100 mL culture was pelleted by centrifugation at 4,000×g, 23° C. for 10 minutes and resuspended in 100 mL fresh $YPD_{0.1}$ media (1% yeast extract, 1% peptone, 0.1% dextrose). The culture was divided into 4×25 mL cultures to which were added either 1% hexane, 0.05% hexanoic acid, 1.0% hexanoic acid, or no other carbon source. Strain sAA003 is completely blocked in -oxidation, therefore fermentation tested the ability of the -oxidation pathway to oxidize C6 substrates. Samples were taken at 24, 48, and 72 hours and analyzed by LC-MS (Scripps Center for Mass Spectrometry) using published methods for the detection of adipic acid (Cheng et al., 2000). The data for the 72 hour time-point, shown in the table below demonstrates that strain sAA003 was able to oxidize both hexanoic acid and hexane to adipic acid. The results also indicate that the 1% hexanoic acid level was toxic to the cells leading to no production of adipic acid over background levels.

| Oxidation of hexane and hexanoic acid to adipic acid | | |
|---|---|---|
| Time (h) | MEDIA | Adipic acid (mg/L) |
| 0 | $YPD_{0.1}$ | 0.000 |
| 72 | $YPD_{0.1}$ | 0.005 |
| 72 | $YPD_{0.1}$ + 0.05% Hexanoic Acid | 0.406 |
| 72 | $YPD_{0.1}$ + 1% Hexanoic Acid | 0.003 |
| 72 | $YPD_{0.1}$ + 1% Hexane | 0.091 |

Example 17

Identification of P450 Alleles Induced by Exposure to Hexane or Hexanoic Acid 350 mL cultures grown overnight in YNB-Salts+2.0% Glucose (6.7 g/L Yeast Nitrogen Broth, 3.0 g/L Yeast Extract, 3.0 g/L ammonium sulfate, 3.0 g/L monopotassium phosphate, 0.5 g/L sodium chloride, and 20 g/L dextrose) were inoculated from a 3 mL overnight culture of YPD (1% Yeast Extract, 2% Peptone, 2% Dextrose), and used for RNA preparation. Cultures were harvested by centrifugation. Each pellet was resuspended in 100 mL of YNB-Salts medium with no glucose. A 1 mL aliquot was taken for RNA isolation as a time=0 control. To each 100 mL suspension, a different inducer was added, 1% glucose, 1% hexane or 0.05% hexanoic acid and aliquoted as two 50 mL portions into 250 mL baffled flasks and incubated for 2 or 4 hours at 30° C. with shaking. At 2 hours and 4 hours, one flask for each inducer was harvested by centrifugation and resuspended in its own spent media in order to collapse culture foam. 1 mL samples were isolated by centrifugation of 1 mL of each culture and RNA prepared using the RiboPure-Yeast Kit, according to the manufacturer's directions, with an additional extraction of the initial RNA preparations with 1 volume of Chloroform: Isoamyl Alcohol (24:1) to the aqueous phase after lysis and extraction with Phenol:Chloroform:Isoamyl Alcohol (25:24:1).

Each RNA preparation was further purified by precipitation with ethanol and treatment with DNase I, again according to manufacturers' recommendations. All RNA preparations were shown to be free of contaminating genomic DNA by electrophoresis and by failure to prime a PCR product of the URA3 gene. First strand synthesis reactions were completed for each RNA preparation using Superscript III Reverse Transcriptase (Invitrogen), as described herein. Reactions for each sample consisted of 1 uL oAA0542 (polyT 10 uM), 1 uL dNTP mix (10 mM each), 1 g RNA in 13 uL sterile, distilled water. The RNA/primer mix was heated to 65° C. for 5 minutes, and on ice for 1 minute. Primers were generated that amplified a substantially unique area of each cytochrome P450 and are shown in the table below.

Figure 13:
FIG. 13 shows results of immunodetection of 6×His-tagged ("6×His" disclosed as SEQ ID NO: 60) proteins expressed in either S. cerevisiae (sAA144) or in C. tropicalis (sAA103, sAA270, sAA269). 6×His tagged ("6×His" disclosed as SEQ ID NO: 60) HEXA and HEXB expressed in strains sAA269 and sAA270 are indicated with arrows. 6×His tagged ("6×His" disclosed as SEQ ID NO: 60) STCJ and STCK from strain sAA144 were included as a positive control. Strain sAA103 is the parent strain for sAA269 and sAA270 and does not contain integrated vectors for the expression of 6×His-tagged ("6×His" disclosed as SEQ ID NO: 60) HEXA and HEXB.
Figure 14:
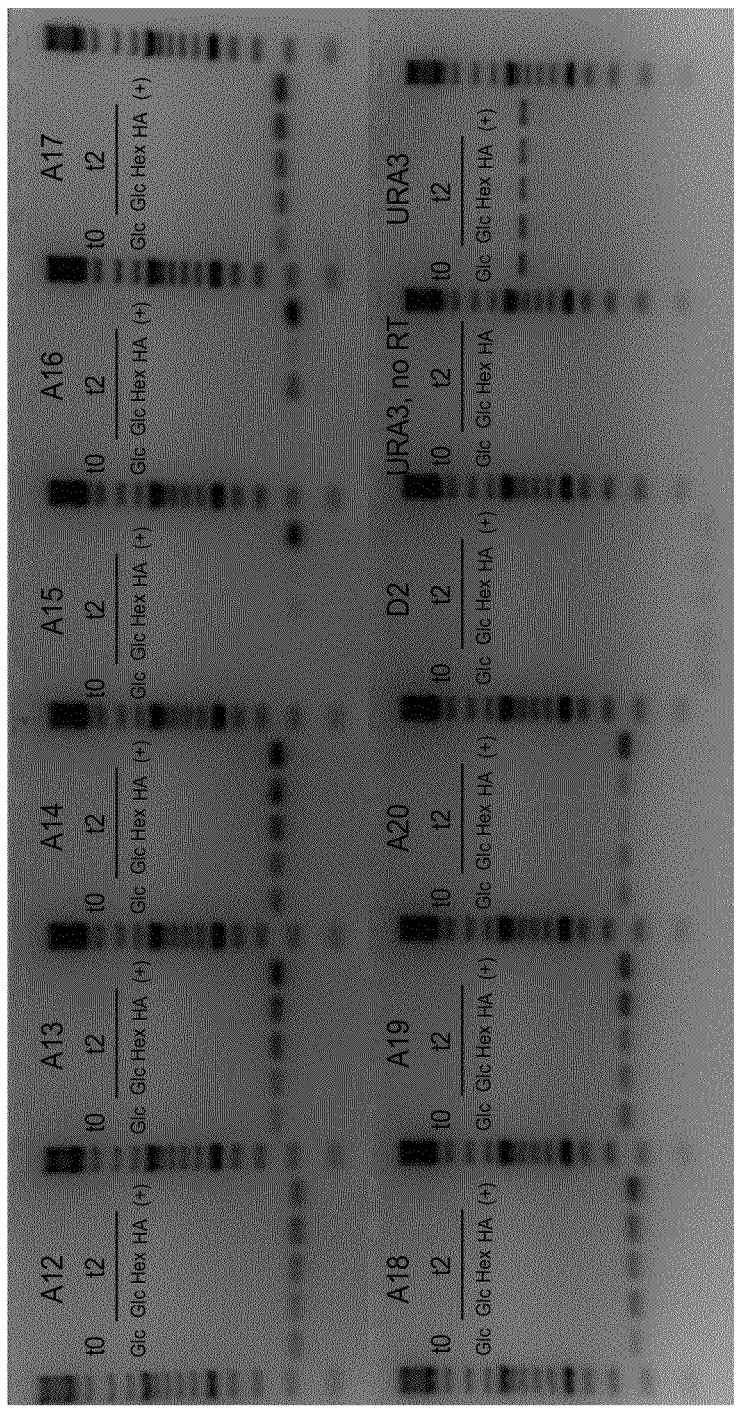
FIG. 14 shows results of RT-PCR from cultures of C. tropicalis strain sAA003 exposed to glucose only (Glc), hexane only (Hex), or hexanoic acid only (HA). PCR products of A15 and A16 alleles show hexane and hexanoic acid specific induction.

PCR reactions were performed on the 2 hour induced cDNA samples and compared to the Time=0 and genomic DNA controls. PCR reactions for each cDNA and primer pair combination consisted of 0.5 uL template, sense and antisense primers at 0.4 uM each, 1× Taq DNA polymerase Buffer (New England Biolabs), 0.1 uL Taq DNA polymerase, and 0.2 mM dNTPs and sterile, distilled water to 25 uL. Cycling parameters used were 95° C. for 5 minutes, 30 cycles of 95° C. 30 seconds, 50° C. 40 seconds, 72° C. 2 minutes, followed by 72° C. 5 minutes and a 4° C. hold. PCR reactions were electrophoresed on 1.2% agarose gels to identify differential expression due to the inducer used. Several P450s displayed increased induction in the presence of hexane or hexanoic acid, however the results were not quantitative. Two Cytochrome P450's, CYP52A15 and CYP52A16, showed induction only in the presence of hexane and hexanoic acid and not in the presence of glucose, as shown in FIG. 13. The primers used for PCR analysis of induced expression are shown in the table below.

| | Oligonucleotides for identification of P450 DNA fragments | | | |
|---|---|---|---|---|
| Oligos | Sequence (SEQ ID NOS 315-334, respectively, in order of appearance) | P450 | P450 sequence | PCR product (bp) |
| oAA0082 | gattactgcagcagtattagtcttc | CYP52A12 | 60-249 | 190 |
| oAA0083 | gtcgaaaacttcatcggcaaag | | | |

Oligonucleotides for identification of P450 DNA fragments

| Oligos | Sequence (SEQ ID NOS 315-334, respectively, in order of appearance) | P450 | P450 sequence | PCR product (bp) |
|---|---|---|---|---|
| oAA0084 | cacgatattatcgccacatacttc | CYP52A13 | 10-256 | 247 |
| oAA0085 | cgggacgatcgagatcgtggatacg | | | |
| oAA0086 | caggatattatcgccacatacatc | CYP52A14 | 10-256 | 247 |
| oAA0087 | ctggacgattgagcgcttggatacg | | | |
| oAA0088 | cgtcttctccatcgtttgcccaagag | CYP52A15 | 5-199 | 195 |
| oAA0089 | ggtccctgacaaagttaccgagtg | | | |
| oAA0090 | cgtcttctccatcgtttgctcaggag | CYP52A16 | 5-199 | 195 |
| oAA0091 | gatccaacacgacgttaccgagcg | | | |
| oAA0092 | ggtatgtcgttgtgccagtgttg | CYP52A17 | 26-248 | 223 |
| oAA0093 | cccacgcttgggttcttggagtggtc | | | |
| oAA0094 | ggtatattgttgtgcctgtgttg | CYP52A18 | 26-248 | 223 |
| oAA0095 | ccgacgcligggliclìggagctgtc | | | |
| oAA0096 | ggaaggatgaggtggtgcagtac | CYP52A19 | 1217-1458 | 242 |
| oAA0097 | gtcttgtgacaagtttggaaactc | | | |
| oAA0098 | gaaagaatgaggtggtgcaatac | CYP52A20 | 1217-1458 | 242 |
| oAA0099 | gtcctgtgacaagctagggaattc | | | |
| oAA0104 | ctatcgtgggatgtgatctgtgtcg | CYP52D2 | 19-231 | 213 |
| oAA0105 | ctcgaatctcttgacactgaactcg | | | |

Example 18

Cloning and Analysis of *C. tropicalis* Fatty Alcohol Oxidase (FAO) Alleles

Isolation of Fatty Alcohol Oxidase Genes from *C. tropicalis*

*C. tropicalis* (ATCC20336) fatty alcohol oxidase genes were isolated by PCR amplification using primers generated to amplify the sequence region covering promoter, fatty alcohol oxidase gene (FAO) and terminator of the FAO1 sequence (GenBank accession number of FAO1 AY538780). The primers used to amplify the fatty alcohol oxidase nucleotide sequences from *C. tropicalis* strain ATCC20336, are showing in the table below.

Oligonucleotides for cloning FAO alleles

| Oligo | Sequence (SEQ ID NOS 335-343, respectively, in order of appearance) |
|---|---|
| oAA0144 | AACGACAAGATTAGATTGGTTGAGA |
| oAA0145 | GTCGAGTTTGAAGTGTGTGTCTAAG |
| oAA0268 | AGATCTCATATGGCTCCATTTTTGCCCGACCAGGTCGACTACAAACACGTC |
| oAA0269 | ATCTGGATCCTCATTACTACAACTTGGCTTTGGTCTTCAAGGAGTCTGCCAAACCTAAC |
| oAA0282 | ACATCTGGATCCTCATTACTACAACTTGGCCTTGGTCT |
| oAA0421 | CACACAGCTCTTCTAGAATGGCTCCATTTTTGCCCGACCAGGTCGAC |
| oAA0422 | CACACAGCTCTTCCTTTCTACAACTTGGCTTTGGTCTTCAAGGAGTCTGC |
| oAA0429 | GTCTACTGATTCCCCTTTGTC |
| oAA0281 | TTCTCGTTGTACCCGTCGCA |

PCR reactions contained 25 uL 2× master mix, 1.5 uL of oAA0144 and oAA0145 (10 uM), 3.0 uL genomic DNA, and 19 uL sterile H$_2$0. Thermocycling parameters used were 98° C. for 2 minutes, 35 cycles of 98° C. 20 seconds, 52° C. 20 seconds, 72° C. 1 minute, followed by 72° C. 5 minutes and a 4° C. hold. PCR products of the correct size were gel purified, ligated into pCR-Blunt II-TOPO (Invitrogen) and transformed into competent TOP10 *E. coli* cells (Invitrogen). Clones containing PCR inserts were sequenced to confirm correct DNA sequence. Four FAO alleles were identified from sequence analysis and designated as FAO-13, FAO-17, FAO-18 and FAO-20. The sequence of the clone designated FAO-18 had a sequence that was substantially identical to the sequence of FAO1 from GenBank. The resulting plasmids of the four alleles were designated pAA083, pAA084, pAA059 and pAA085, respectively. Sequence identity comparisons of FAO genes isolated as described herein are shown in the tables below.

DNA sequence identity

|  | FAO1 | FAO-18 | FAO-17 | FAO-13 | FAO-20 | FAO2a | FAO2b |
|---|---|---|---|---|---|---|---|
| FAO1 | 100 | 100 | 98 | 96 | 95 | 83 | 82 |
| FAO-18 |  | 100 | 98 | 96 | 95 | 83 | 82 |
| FAO-17 |  |  | 100 | 98 | 98 | 83 | 82 |
| FAO-13 |  |  |  | 100 | 99 | 83 | 83 |
| FAO-20 |  |  |  |  | 100 | 83 | 83 |
| FAO2a |  |  |  |  |  | 100 | 96 |
| FAO2b |  |  |  |  |  |  | 100 |

Protein sequence identity

|  | FAO1 | FAO-18 | FAO-17 | FAO-13 | FAO-20 | FAO2a | FAO2b |
|---|---|---|---|---|---|---|---|
| FAO1 | 100 | 100 | 99 | 98 | 98 | 81 | 80 |
| FAO-18 |  | 100 | 99 | 98 | 98 | 81 | 80 |
| FAO-17 |  |  | 100 | 99 | 99 | 82 | 81 |
| FAO-13 |  |  |  | 100 | 99 | 82 | 81 |
| FAO-20 |  |  |  |  | 100 | 82 | 81 |
| FAO2a |  |  |  |  |  | 100 | 97 |
| FAO2b |  |  |  |  |  |  | 100 |

Amino acid differences in FAO alleles

|  | 32 | 75 | 89 | 179 | 185 | 213 | 226 | 352 | 544 | 590 |
|---|---|---|---|---|---|---|---|---|---|---|
| FAO1 | E | M | G | L | Y | T | R | H | S | P |
| FAO-13 | Q | T | A | L | Y | A | K | Q | A | A |
| FAO-20 | Q | T | A | M | D | A | K | Q | A | A |

Expression of FAO Alleles in *E. coli*

To determine the levels of FAO enzyme activity with respect to various carbon sources, the four isolated FAO alleles were further cloned and over-expressed in *E. coli*. The FAOs were amplified using the plasmids mentioned above as DNA template by PCR with primers oAA0268 and oAA0269 for FAO-13 and FAO-20 and oAA0268 and oAA0282 for FAO-17 and FAO-18, using conditions as described herein. PCR products of the correct size were gel purified and ligated into pET11a vector between NdeI and BamHI sites and transformed into BL21 (DE3) *E. coli* cells. The colonies containing corresponding FAOs were confirmed by DNA sequencing. Unmodified pET11a vector also was transformed into BL21 (DE3) cells, as a control. The resulting strains and plasmids were designated sAA153 (pET11a), sAA154 (pAA079 containing FAO-13), sAA155 (pAA080 containing FAO-17), sAA156 (pAA081 containing FAO-18) and sAA157 (pAA082 containing FAO-20), respectively. The strains and plasmids were used for FAO over-expression in *E. coli*. One colony of each strain was transferred into 5 mL of LB medium containing 100 g/mL ampicillin and grown overnight at 37° C., 200 rpm. The overnight culture was used to inoculate a new culture to $OD_{600nm}$ 0.2 in 25 ml LB containing 100 g/ml ampicillin. Cells were induced at $OD_{600nm}$ 0.8 with 0.3 mM IPTG for 3 hours and harvested by centrifugation at 4° C. 1,050×g for 10 minutes. The cell pellet was stored at −20° C.

Expression of FAOs in *C. tropicalis*

Two alleles, FAO-13 and FAO-20, were chosen for amplification in *C. tropicalis* based on their substrate specificity profile, as determined from enzyme assays of soluble cell extracts of *E. coli* with over expressed FAOs. DNA fragments containing FAO-13 and FAO-20 were amplified using plasmids pAA079 and pAA082 as DNA templates, respectively, by PCR with primers oAA0421 and oAA0422. PCR products of the correct sizes were gel purified and ligated into pCR-Blunt II-TOPO (Invitrogen), transformed into competent TOP10 *E. coli* cells (Invitrogen) and clones containing FAO inserts were sequenced to confirm correct DNA sequence. Plasmids containing FAO-13 and FAO-20 were digested with SapI and ligated into vector pAA105, which includes the *C. tropicalis* PGK promoter and terminator. The resulting plasmids were confirmed by restriction digestion and DNA sequencing and designated as pAA115 (FAO-13) and pAA116 (FAO-20), respectively. Plasmids pAA115 and pAA116 were linearized with SpeI, transformed into competent *C. tropicalis* Ura⁻ strains sAA002 (SU-2, ATCC20913) and sAA103. The integration of FAO-13 and FAO-20 was confirmed by colony PCR using primers oAA0429 and oAA0281. The resulting strains were designated as sAA278 (pAA115 integrated in strain sAA002), sAA280 (pAA116 integrated in sAA002), sAA282 (pAA115 integrated in sAA103), and sAA284 (pAA116 integrated in sAA103), and were used for fatty alcohol oxidase over-expression in *C. tropicalis*.

One colony of each strain was inoculated into 5 ml YPD and grown overnight as described herein. The overnight culture was used to inoculate a new 25 mL YPD culture to about $OD_{600nm}$ 0.5. FAO over-expression was regulated by the PGK promoter/terminator, induced with glucose in the medium and expressed constitutively. Strains sAA002 and sAA103 (e.g., untransformed starting strains) were included as negative controls for FAO over-expression. Cells were harvested at early log phase ($OD_{600nm}$=in the range of between about 3 to about 5) by centrifugation at 4° C. for 10 minutes at 1,050× g. Cell pellets were stored at −20° C.

Cell Extract Preparation from *E. coli*

Cell pellets from 25 mL of FAO expressing *E. coli* cultures were resuspended in 10 mL phosphate-glycerol buffer containing 50 mM potassium phosphate buffer (pH7.6), 20% glycerol, 1 mM Phenylmethylsulfonyl fluoride (PMSF), 2 uL Benzonase 25 U/uL, 20 uL 10 mg/mL lysozyme. The cells were then lysed by incubation at room temperature for 50 minutes on a rotating shaker, and the cell suspension centrifuged for 30 minutes at 4° C. using 15,000×g for. The supernatant was aliquoted in 1.5 ml microcentrifuge tubes and stored at −20° C. for FAO enzyme activity assays.

Cell Extract Preparation from *C. tropicalis*

Frozen *C. tropicalis* cell pellets were resuspended in 1.2 ml of phosphate-glycerol buffer containing 50 mM potassium phosphate buffer (pH7.6), 20% glycerol, 1 mM Phenylmethylsulfonyl fluoride (PMSF). Resuspended cells were transferred to 1.5 mL screw-cap tubes containing about 500 uL of zirconia beads on ice. The cells were lysed with a Bead Beater (Biospec) using 2 minute pulses and 1 minute rest intervals on ice. The process was repeated 3 times. The whole cell extract was then transferred to a new 1.5 ml tube and centrifuged at 16,000×g for 15 minutes at 4° C. The supernatant was transferred into a new tube and used for FAO enzyme activity assays.

Protein Concentration Determination

Protein concentration of the cell extracts was determined using the Bradford Reagent following manufacturers' recommendations (Cat#23238, Thermo scientific).

FAO Enzyme Activity Assay

FAO enzyme activity assays were performed using a modification of Eirich et al., 2004). The assay utilizes a two-enzyme coupled reaction (e.g., FAO and horse radish peroxidase (HRP)) and can be monitored by spectrophotometry. 1-Dodecanol was used as a standard substrate for fatty alcohol oxidase enzymatic activity assays. FAO oxidizes the dodecanol to dodecanal while reducing molecular oxygen to hydrogen peroxide simultaneously. HRP reduces (2,2'-azinobis 3-ethylbenzthiazoline-6-sulfonic acid; ABTS) in the two-enzyme coupled reaction, where the electron obtained from oxidizing hydrogen peroxide to ABTS, which can be measured by spectrometry at 405 nm. The assay was modified using aminotriazole (AT) to prevent the destruction of $H_2O_2$ by endogenous catalase, thus eliminating the need for microsomal fractionation. The final reaction mixture (1.0 mL) for FAO enzyme assay consisted of 500 μL of 200 mM HEPES buffer, pH 7.6; 50 μL of a 10 mg/mL ABTS solution in deionized water; 10 μL of 5 mM solution of dodecanol in acetone; 40 μL of 1M AT and 5 μL of a 2 mg/mL horseradish peroxidase solution in 50 mM potassium phosphate buffer, pH 7.6. Reaction activity was measured by measuring light absorbance at 405 nm for 10 minutes at room temperature after adding the extract. The amount of extract added to the reaction mixture was varied so that the activity fell within the range of 0.2 to 1.0 $\Delta A_{405nm}$/min. The actual amounts of extract used were about 1.69 U/mg for E. coli expressed FAO-13, 0.018 U/mg for E. coli expressed FAO-17, 0.35 U/mg for E. coli expressed FAO-18 (e.g., FAO1), 0.47 U/mg E. coli expressed FAO-20, 0.036 U/mg C. tropicalis (strain sAA278) expressed FAO-13, 0.016 U/mg C. tropicalis (strain sAA282) expressed FAO-13, 0.032 U/mg C. tropicalis (strain sAA280) expressed FAO-20 and 0.029 U/mg C. tropicalis (strain sAA284) expressed FAO-20. FAO activity was reported as activity units/mg of total protein (1 unit=1 mole substrate oxidized/min). An extinction coefficient at 405 nm of 18.4 was used for ABTS and was equivalent to 0.5 mM oxidized substrate. The results of the activity assays are shown in the tables below.

| | FAO activity (units/mg total protein) on primary alcohols | | | | | | | |
|---|---|---|---|---|---|---|---|---|
| | 1-Butanol | 1-Pentanol | 1-Hexanol | 1-Octanol | 1-Decanol | 1-Dodecanol | 1-Tetradecanol | Hexadecanol |
| FAO-13 | 0.01 | 0.09 | 1.17 | 82.67 | 70.94 | 100 | 79.35 | 58.88 |
| FAO-17 | 0.72 | 0.26 | 1.06 | 66.23 | 22.00 | 100 | 47.86 | 60.98 |
| FAO-18 | 0.07 | 0.11 | 0.26 | 60.56 | 54.56 | 100 | 114.47 | 50.65 |
| FAO-20 | 0.07 | 0.11 | 0.91 | 55.96 | 74.57 | 100 | 89.52 | 42.59 |

| | FAO activity (units/mg total protein) on omega hydroxy fatty acids | | | | |
|---|---|---|---|---|---|
| | 1-Dodecanol | 6-OH-HA | 10-OH-DA | 12-OH-DDA | 16-OH-HDA |
| FAO-13 | 100 | 4.18 | 4.14 | 6.87 | 8.57 |
| FAO-17 | 100 | 1.18 | 0.00 | 0.59 | 0.94 |
| FAO-18 | 100 | 0.00 | 0.00 | 4.87 | 2.94 |
| FAO-20 | 100 | 0.03 | 0.04 | 2.25 | 7.46 |

Example 19

Construction of C. tropicalis Shuttle Vector pAA061

Figure 30:
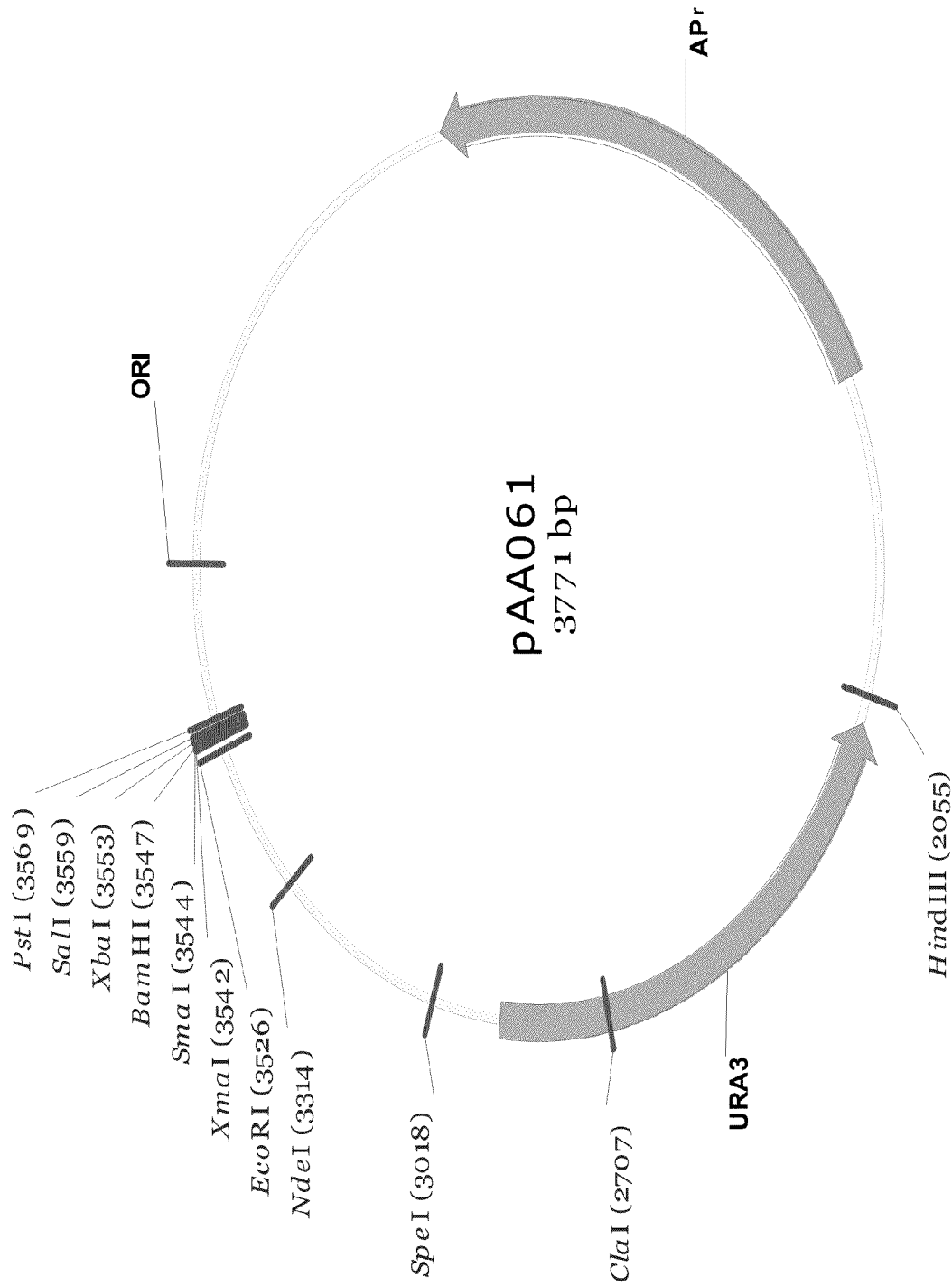
Figure 31:
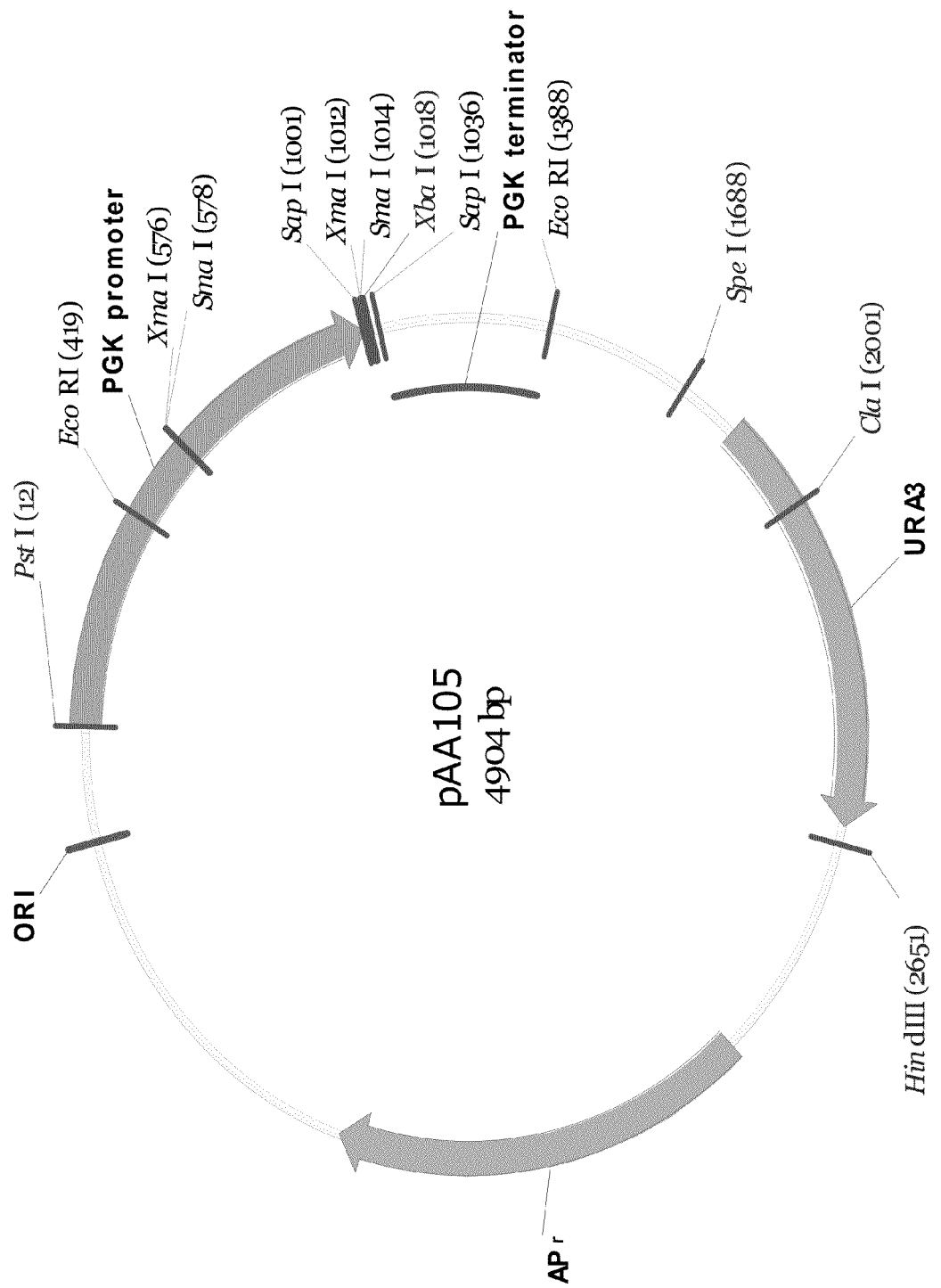

Vector pAA061 was constructed from a pUC19 backbone to harbor the selectable marker URA3 from C. tropicalis strain ATCC20336 as well as modifications to allow insertion of C. tropicalis promoters and terminators. A 1,507 bp DNA fragment containing the promoter, ORF, and terminator of URA3 from C. tropicalis ATCC20336 was amplified using primers oAA0124 and oAA0125, shown in the table below. The URA3 PCR product was digested with NdeI/MluI and ligated into the 2,505 bp fragment of pUC19 digested with NdeI/BsmBI (an MluI compatible overhang was produced by BsmBI). In order to replace the lac promoter with a short 21 bp linker sequence, the resulting plasmid was digested with SphI/SapI and filled in with a linker produced by annealing oligos oAA0173 and oAA0174. The resulting plasmid was named pAA061, and is shown in FIG. 30.

| Oligonucleotides for construction of pAA061 | | |
|---|---|---|
| Oligos | Sequence (SEQ ID NOS 344-347, respectively, in order of appearance) | PCR product (bp) |
| oAA0124<br>oAA0125 | cacacacatatgCGACGGGTACAACGAGAATT<br>cacacaacgcgtAGACGAAGCCGTTCTTCAAG | 1507 |
| oAA0173<br>oAA0174 | ATGATCTGCCATGCCGAACTC<br>AGCGAGTTCGGCATGGCAGATCATCATG | 21 (linker) |

Example 20

Cloning of *C. tropicalis* PGK Promoter and Terminator

Vector pAA105 was constructed from base vector pAA061 to include the phosphoglycerate kinase (PGK) promoter and terminator regions from *C. tropicalis* ATCC20336 with an intervening multiple cloning site (MCS) for insertion of open reading frames (ORF's). The PGK promoter region was amplified by PCR using primers oAA0347 and oAA0348, shown in the table below. The 1,029 bp DNA fragment containing the PGK promoter was digested with restriction enzymes PstI/XmaI. The PGK terminator region was amplified by PCR using primers oAA0351 and oAA0352, also shown in the table below. The 396 bp DNA fragment containing the PGK terminator was digested with restriction enzymes XmaI/EcoRI. The 3,728 bp PstI/EcoRI DNA fragment from pAA061 was used in a three piece ligation reaction with the PGK promoter and terminator regions to produce pAA105. The sequence between the PGK promoter and terminator contains restriction sites for incorporating ORF's to be controlled by the functionally linked constitutive PGK promoter.

| Oligonucleotides for cloning *C. tropicalis* PGK promoter and terminator | | |
|---|---|---|
| Oligos | Sequence (SEQ ID NOS 348-351, respectively, in order of appearance) | PCR product (bp) |
| oAA0347<br>oAA0348 | CACACACTGCAGTTGTCCAATGTAATAATTTT<br>CACACATCTAGACCCGGGCTCTTCTTCTGAATAGGCAATT<br>GATAAACTTACTTATC | 1028 |
| oAA0351<br>oAA0352 | GAGCCCGGGTCTAGATGTGTGCTCTTCCAAAGTACGGTG<br>TTGTTGACA<br>CACACACATATGAATTCTGTACTGGTAGAGCTAAATT | 396 |

Example 21

Cloning of the POX4 Locus

Figure 29:
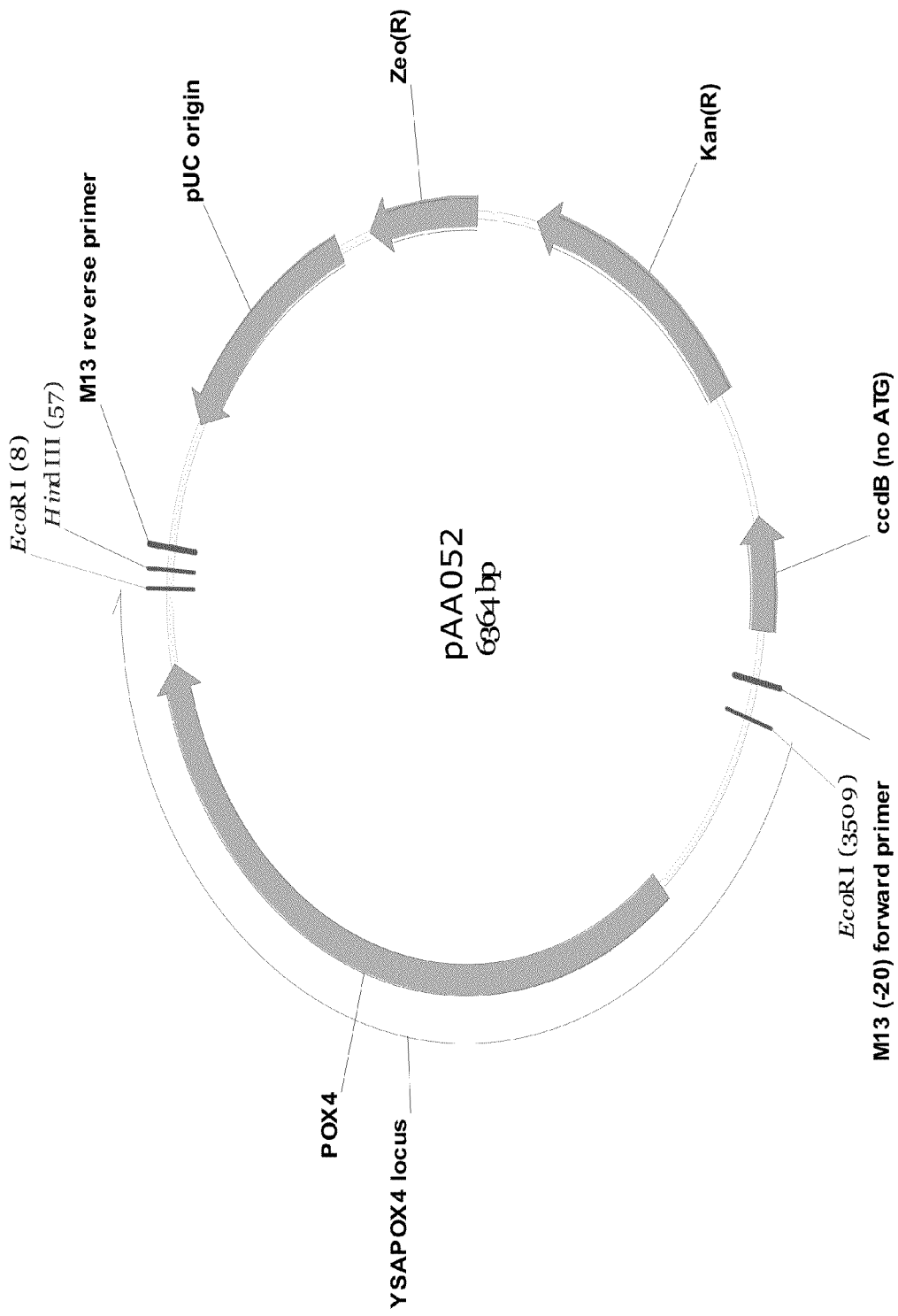

Primers oAA0138 and oAA0141 (shown in the table below) were generated to amplify the entire sequence of NCBI accession number M12160 for the YSAPOX4 locus from genomic DNA prepared from *C. tropicalis* strain ATCC20336. The 2,845 bp PCR product was cloned into the vector, pCR-BluntII-TOPO (Invitrogen), sequenced and designated pAA052, and is shown in FIG. 29.

| Oligonucleotides for cloning of PDX4 | | |
|---|---|---|
| Oligos | Sequence (SEQ ID NOS 352-353, respectively, in order of appearance) | PCR product (bp) |
| oAA0138 | GAGCTCCAATTGTAATATTTCGGG | 2845 |
| oAA0141 | GTCGACCTAAATTCGCAACTATCAA | |

Example 22

Cloning of the POX5 Locus

Figure 28:
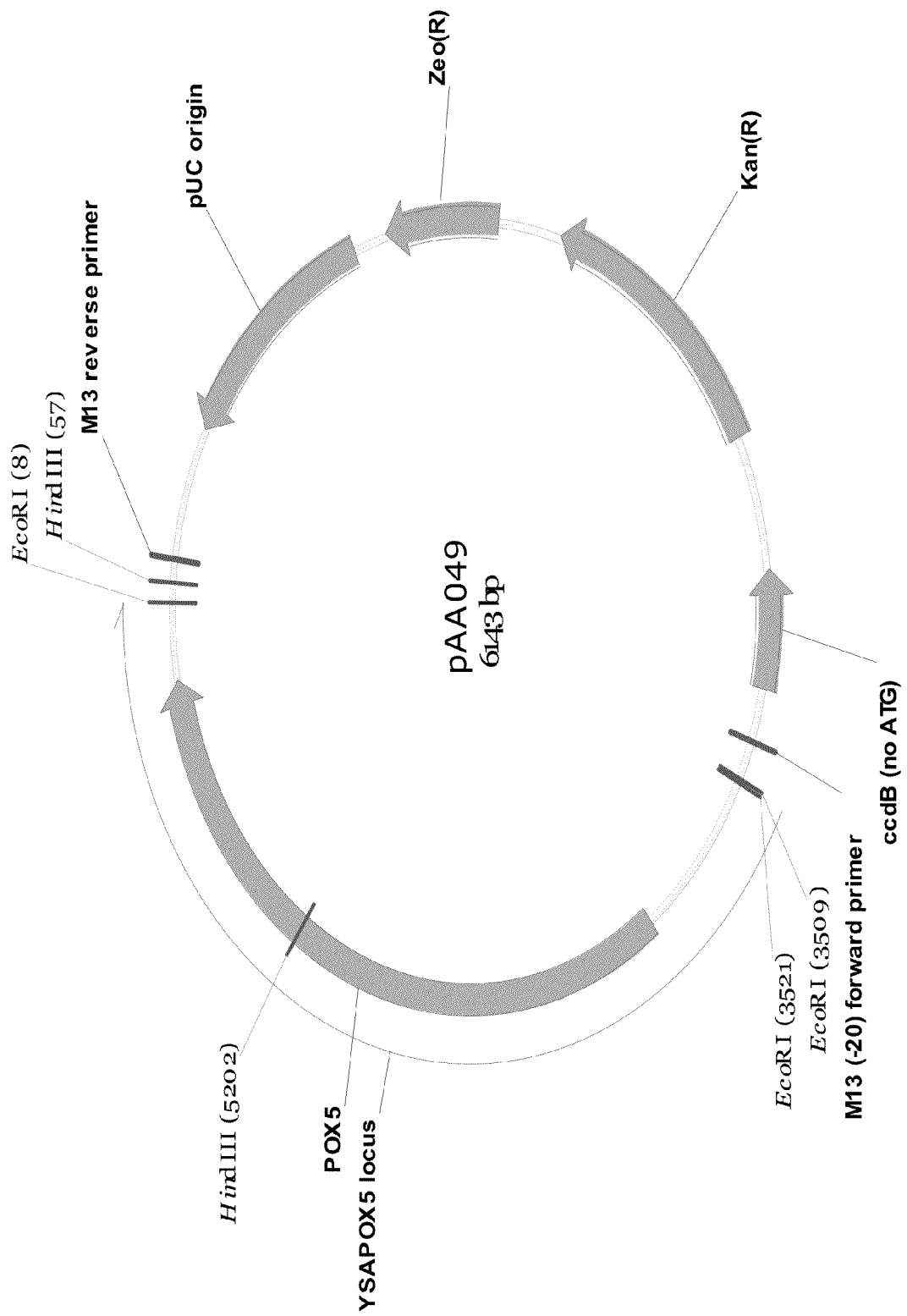

Primers oAA0179 and oAA0182 (shown in the table below) were generated to amplify the entire sequence of NCBI accession number M12161 for the YSAPOX5 locus from genomic DNA prepared from *C. tropicalis* strain ATCC20336. The 2,624 bp PCR product was cloned into the vector, pCR-BluntII-TOPO (Invitrogen), sequenced and designated pAA049, and is shown in FIG. 28.

| Oligonucleotides for cloning of PDX5 | | |
|---|---|---|
| Oligos | Sequence (SEQ ID NOS 354-355, respectively, in order of appearance) | PCR product (bp) |
| oAA0179 | GAATTCACATGGCTAATTTGGCCTC<br>GGTTCCACAACGCACTCAGCATTAA<br>AAA | 2624 |
| oAA0182 | GAGCTCCCCTGCAAACAGGGAAACA<br>CTTGTCATCTGATTT | |

Example 23

Construction of Strain sAA105 and sAA106

Functional POX4 alleles were restored in *C. tropicalis* strain sAA003 (ATCC20962; ura3/ura3, pox4::ura3/pox4::ura3, pox5::ura3/pox5::URA3) by transformation of sAA003 with POX4 linear DNA to replace the ura3-disrupted loci with functional alleles. A 2,845 bp DNA fragment was amplified by PCR using primers oAA0138 and oAA0141 (described in Example 21) that contained the POX4 ORF as well as 531 bp upstream and 184 bp downstream of the ORF, using plasmid pAA052 as template. The purified PCR product was used to transform competent sAA003 cells which were plated on YNB-agar plates supplemented with hexadecane vapor as the carbon source (e.g., by placing a filter paper soaked with hexadecane in the lid of the inverted petri dish) and incubated at 30° C. for 4-5 days. Colonies growing on hexadecane as the sole carbon source were restreaked onto YPD-agar and incubated at 30° C. Single colonies were grown in YPD cultures and used for the preparation of genomic DNA.

PCR analysis of the genomic DNA prepared from the transformants was performed with oligos oAA0138 and oAA0141. An URA3-disrupted POX4 would produce a PCR product of 5,045 bp, while a functional POX4 would produce a PCR product of 2,845 bp. In strain sAA105 only one PCR product was amplified with a size of 2,845 bp indicating that both POX4 alleles had been functionally restored. In strain sAA106 PCR products of both 2,845 bp and 5,045 bp were amplified indicating that one POX4 allele had been functionally restored while the other POX4 allele remained disrupted by URA3. The resultant strain genotypes were: sAA105 (ura3/ura3, POX4/POX4, pox5::ura3/pox5::URA3) and sAA106 (ura3/ura3, POX4/pox4::ura3, pox5::ura3/pox5::URA3).

Example 24

Construction of Strain sAA152

Functional POX5 alleles were restored in *C. tropicalis* strain sAA103 (ura3/ura3, pox4::ura3/pox4::ura3, pox5::ura3/pox5::ura3) by transformation of sAA103 with PmlI-linearized plasmid pAA086 (containing the POX5 promoter, gene, terminator and a URA3 marker). Selection of transformants was performed by plating on SC-URA agar plates. Verification of plasmid integration was performed by PCR with primers oAA179 and oAA182 (described in Example 22). Integration of the plasmid was shown by a PCR product of 2,584 bp indicating the presence of a functional POX5 allele. Other POX5 alleles in sAA152 were disrupted with an ura3 gene increasing the PCR product size for nonfunctional alleles to 4,734 bp. Genotype for strain sAA152 is ura3/ura3, pox4::ura3/pox4::ura3, pox5::ura3/pox5::ura3, ura3::POX5, URA3).

Example 25

Construction of Strain sAA232

Functional POX5 alleles were restored in *C. tropicalis* strain sAA003 by transformation of sAA003 with POX5 linear DNA to replace the URA3-disrupted loci with a functional allele. A 2,584 bp DNA fragment was amplified by PCR using primers oAA0179 and oAA0182 (described in Example 22) that contained the POX5 ORF as well as 456 bp upstream and 179 bp downstream of the ORF using plasmid pAA049 as template. The purified PCR product was used to transform competent sAA003 cells which were plated on SC+URA+5FOA plates and incubated at 30° C. for 3-4 days. Colonies were restreaked onto YPD-agar and incubated at 30° C. Single colonies were grown in YPD cultures and used for the preparation of genomic DNA. PCR analysis of the genomic DNA prepared from the transformants was performed with oligos oAA0179 and oAA0182. An ura3-disrupted POX5 would produce a PCR product of 4,784 bp while a functional POX5 would produce a PCR product of 2,584 bp. In strain sAA232 PCR products of both 2,584 bp and 4,784 bp were amplified indicating that one POX5 allele had been functionally restored while the other POX5 allele remained disrupted by ura3. The resultant genotype of strain sAA232 is ura3/ura3, pox4::ura3/pox4::ura3, pox5::ura3/POX5. 5-FOA selection restored the POX5 allele that had been disrupted with the functional URA3 leaving the sAA232 strain Ura⁻.

Example 26

Construction of Strain sAA235

Functional POX5 alleles were restored in *C. tropicalis* strain sAA003 by transformation of sAA003 with POX5 linear DNA to replace the URA3-disrupted loci with a functional allele. A 2,584 bp DNA fragment was amplified by PCR using primers oAA0179 and oAA0182 (described in Example 22) that contained the POX5 ORF as well as 456 bp upstream and 179 bp downstream of the ORF using plasmid pAA049 as template. The purified PCR product was used to transform competent sAA003 cells which were plated on YNB-agar plates supplemented with dodecane vapor as the carbon source (e.g., by placing a filter paper soaked with dodecane in the lid of the inverted petri dish) and incubated at 30° C. for 4-5 days. Colonies growing on dodecane as the sole carbon source were restreaked onto YPD-agar and incubated at 30° C. Single colonies were grown in YPD cultures and used for the preparation of genomic DNA. PCR analysis of the genomic DNA prepared from the transformants was performed with oligos oAA0179 and oAA0182. An ura3-disrupted POX5 would produce a PCR product of 4,784 bp while a functional POX5 would produce a PCR product of 2,584 bp. In strain sAA235 a PCR product of 2,584 bp was amplified indicating that both POX5 alleles had been functionally restored. An unintended consequence of the selection strategy (YNB-agar with dodecane) was that the cells reverted back to an Ura⁺ phenotype. Without being limited by any theory, it is believed the absence of uracil in the solid media and the replacement of the only functional URA3 forced the cells to mutate one of the other ura3 loci back to a functional allele. Therefore the genotype of the strain sAA235 is believed to be URA3/ura3, pox4::ura3/pox4::ura3, POX5/POX5. Verification of which of the loci is the functional URA3 is underway.

Example 27

Construction of Strains with Amplified CPR and CYP52 Genes

Strains having an increased number of copies of cytochrome P450 reductase (CPR) and/or for cytochrome P450 monooxygenase (CYP52) genes were constructed to determine how over expression of CPR and CYP52 affected diacid production.

Cloning and Integration of the CPR Gene.

Figure 32:
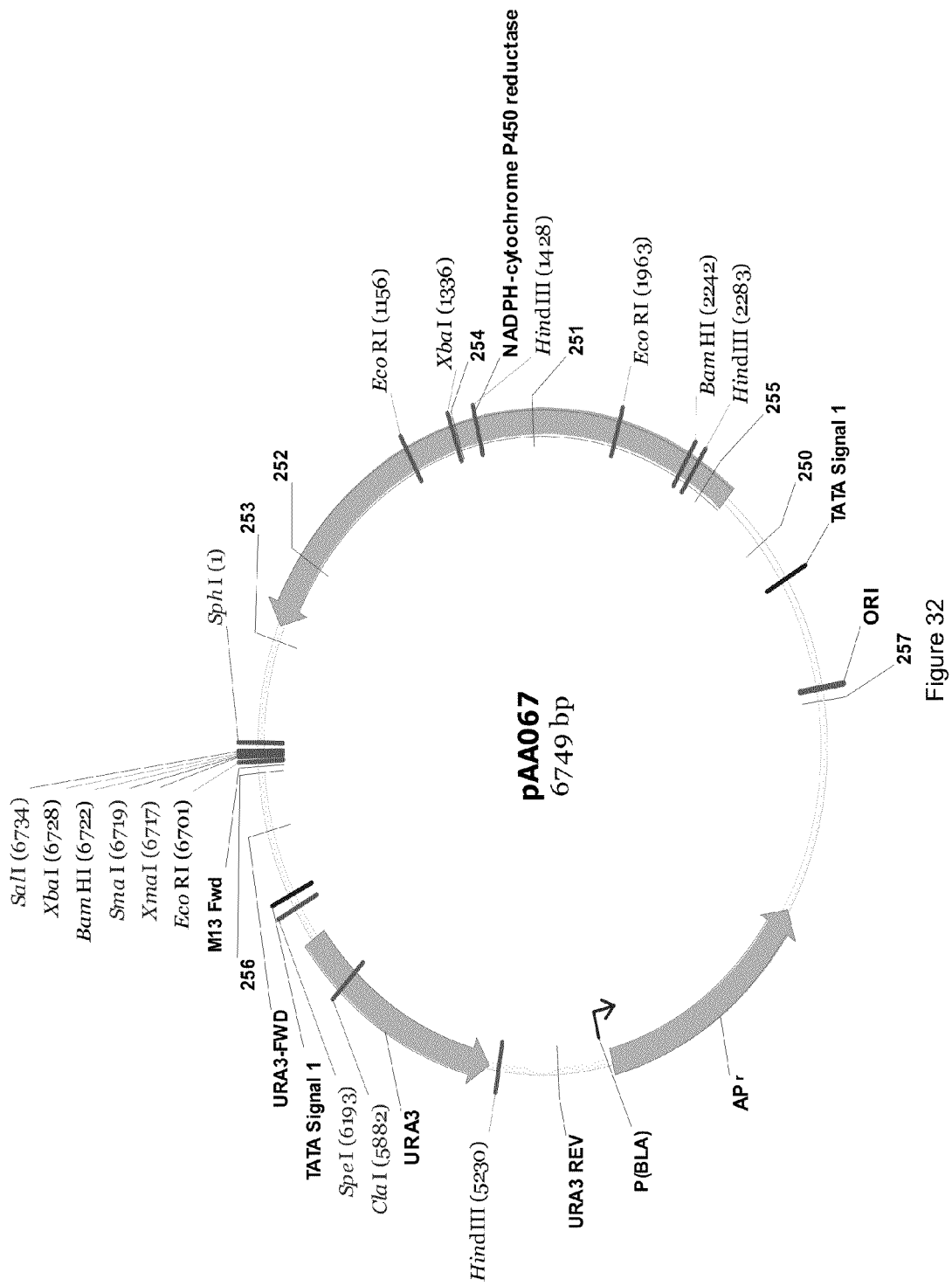

A 3,019 bp DNA fragment encoding the CPR promoter, ORF, and terminator from *C. tropicalis* ATCC750 was amplified by PCR using primers oAA0171 and oAA0172 (see table below) incorporating unique SapI and SphI sites. The amplified DNA fragment was cut with the indicated restriction enzymes and ligated into plasmid pAA061, shown in FIG. 30, to produce plasmid pAA067, shown in FIG. 32. Plasmid pAA067 was linearized with ClaI and transformed into C. tropicalis Ura⁻ strain sAA103 (ura3/ura3, pox4::ura3/pox4::ura3, pox5::ura3/pox5::ura3). Transformations were performed with plasmid pAA067 alone and in combination with plasmids harboring the CYP52A15 or CYP52A16 genes, described below.

Cloning and Integration of CYP52A15 Gene.

Figure 33:
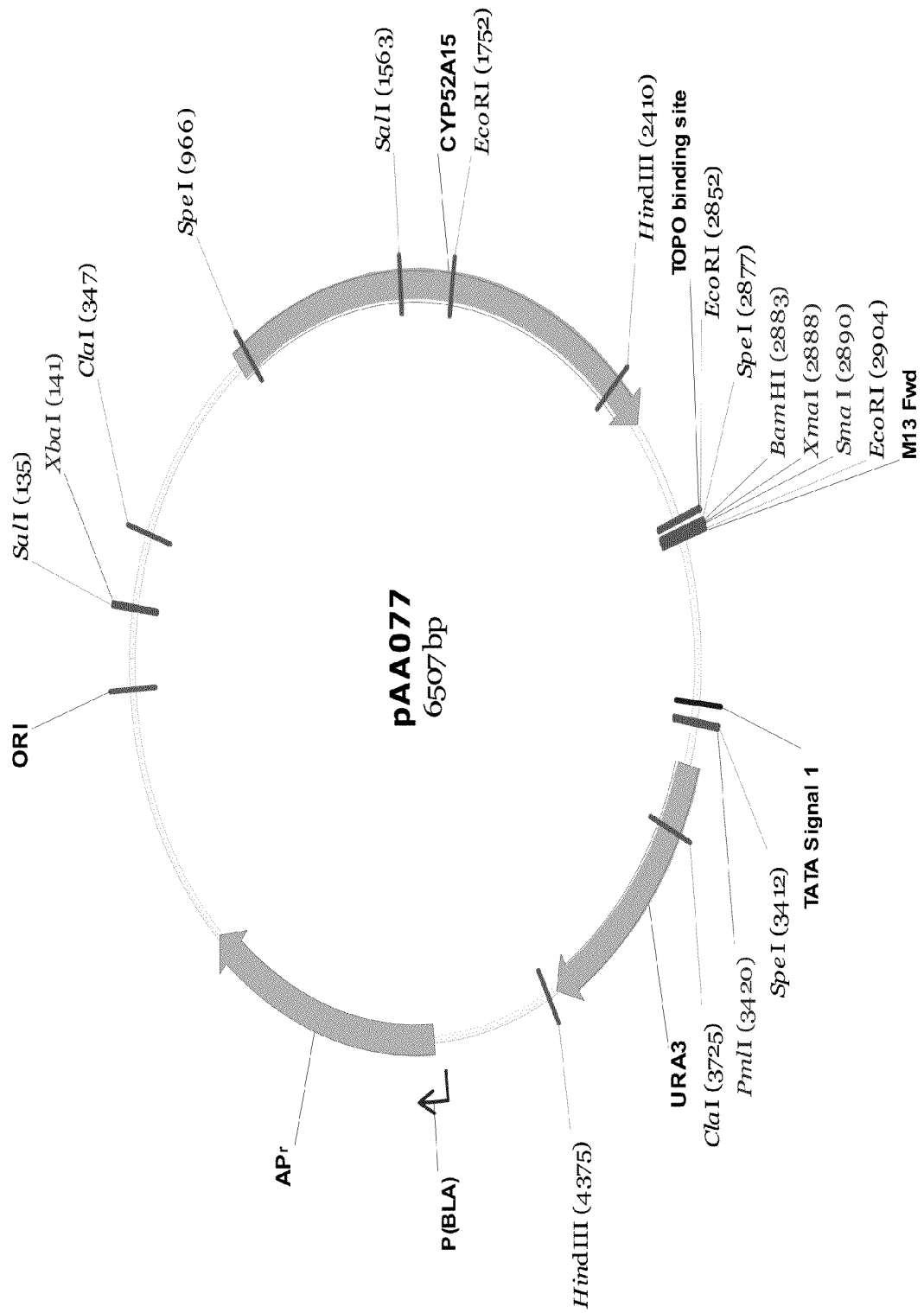

A 2,842 bp DNA fragment encoding the CYP52A15 promoter, ORF, and terminator from C. tropicalis ATCC20336 was amplified by PCR using primers oAA0175 and oAA0178 (see table below) and cloned into pCR-BluntII-TOPO for DNA sequence verification. The cloned CYP52A15 DNA fragment was isolated by restriction digest with XbaI/BamHI (2,742 bp) and ligated into plasmid pAA061, shown in FIG. 30, to produce plasmid pAA077, shown in FIG. 33. Plasmid pAA077 was linearized with PmlI and transformed into C. tropicalis Ura⁻ strain sAA103 (ura3/ura3, pox4::ura3/pox4::ura3, pox5::ura3/pox5::ura3). pAA077 was cotransformed with plasmid pAA067 harboring the CPR gene.

Cloning and Integration of CYP52A16 Gene.

Figure 34:
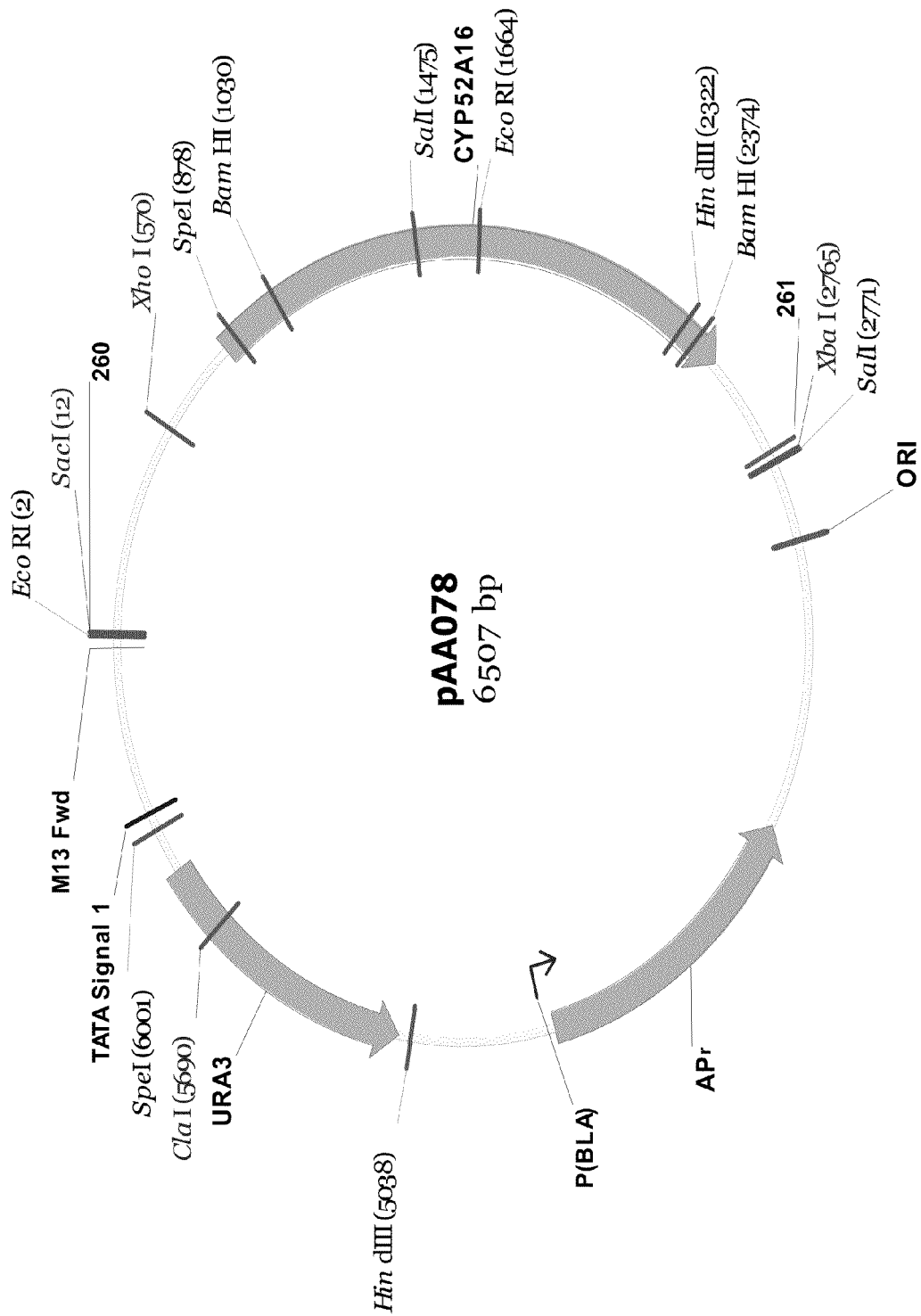

A 2,728 bp DNA fragment encoding the CYP52A16 promoter, ORF, and terminator from C. tropicalis ATCC20336 was amplified by PCR using primers oAA0177 and oAA0178 (see table below) and cloned into pCR-BluntII-TOPO for DNA sequence verification. The cloned CYP52A16 DNA fragment was amplified with primers oAA0260 and oAA0261 (see table below) which incorporated unique SacI/XbaI restriction sites. The amplified DNA fragment was digested with SacI and XbaI restriction enzymes and ligated into plasmid pAA061 to produce plasmid pAA078, shown in FIG. 34. Plasmid pAA078 was linearized with ClaI and transformed into C. tropicalis Ura⁻ strain sAA103 (ura3/ura3, pox4::ura3/pox4::ura3, pox5::ura3/pox5::ura3). pAA078 was cotransformed with plasmid pAA067 harboring the CPR gene.

Preparation of Genomic DNA.

Genomic DNA was prepared from transformants for PCR verification and for Southern blot analysis. Isolated colonies were inoculated into 3 mL YPD and grown overnight at 30° C. with shaking. Cells were pelleted by centrifugation. To each pellet, 200 uL Breaking Buffer (2% Triton X-100, 1% SDS, 100 mM NaCl, 10 mM Tris pH 8 and, 1 mM EDTA) was added, and the pellet resuspended and transferred to a fresh tube containing 200 uL 0.5 mm Zirconia/Silica Beads. 200 uL Phenol:Chloroform:Isoamyl Alcohol (25:24:1) was added to each tube, followed by vortexing for 1 minute. Sterile distilled water was added (200 uL) to each tube and the tubes were centrifuged at 13000 rpm for 10 minutes. The aqueous layer was ethanol precipitated and washed with 70% ethanol. The pellet was resuspended in 100-200 l 10 mM Tris, after drying. Genomic DNA preparation for southern blot analysis was performed using the same procedure on 25 mL cultures for each colony tested.

Characterization of Strains with Amplified CPR and CYP52 Genes.

Verification of integrants was performed by PCR using primers oAA0252 and oAA0256 (CPR), oAA0231 and oAA0281 (CYP52A15), and oAA242 and oAA0257 (CYP52A16). The primers used for verification are shown in the table below.

| Oligonucleotides for PCR verification of CPR, CYP52A15 and CYP52A16 | | |
|---|---|---|
| Oligos | Sequence (SEQ ID NOS 364-369, respectively, in order of appearance) | PCR product (bp) |
| oAA0252 | TTAATGCCTTCTCAAGACAA | 743 |
| oAA0256 | GGTTTTCCCAGTCACGACGT | |
| oAA0231 | CCTTGCTAATTTTCTTCTGTATAGC | 584 |
| oAA0281 | TTCTCGTTGTACCCGTCGCA | |
| oAA0242 | CACACAACTTCAGAGTTGCC | 974 |
| oAA0257 | TCGCCACCTCTGACTTGAGC | |

Southern blot analysis was used to determine the copy number of the CPR, CYP52A15 and CYP52A15 genes.

| Oligonucleotides for cloning of CPR, CYP52A15 and CYP52A16 | | |
|---|---|---|
| Oligos | Sequence (SEQ ID NOS 356-363, respectively, in order of appearance) | PCR product (bp) |
| oAA0171 | cacctcgctcttccAGCTGTCATGTCTATTCAATGCTTCGA | 3019 |
| oAA0172 | cacacagcatgcTAATGTTTATATCGTTGACGGTGAAA | |
| oAA0175 | cacaaagcggaagagcAAATTTTGTATTCTCAGTAGGATTTCATC | 2842 |
| oAA0178 | cacacagcatgCAAACTTAAGGGTGTTGTAGATATCCC | |
| oAA0177 | cacacacccgggATCGACAGTCGATTACGTAATCCATATTATTT | 2772 |
| oAA0178 | cacacagcatgCAAACTTAAGGGTGTTGTAGATATCCC | |
| oAA0260 | cacacagagctcACAGTCGATTACGTAATCCAT | 2772 |
| oAA0261 | cacatctagaGCATGCAAACTTAAGGGTGTTGTA | |

Biotinylated DNA probes were prepared with gene specific oligonucleotides using the NEBlot Phototope Kit from New England BioLabs (Catalog #N7550S) on PCR products generated from each gene target as specified in the table below.

Southern Hybridizations were performed using standard methods (e.g., Sambrook, J. and Russell, D. W. (2001) Molecular Cloning: A Laboratory Manual, (3$^{rd}$ ed.), pp. 6.33-6.64. Cold Spring Harbor Laboratory Press). Detection of hybridized probe was performed using the Phototope-Star Detection Kit from New England BioLabs (Catalog #N7020S). Copy number was determined by densitometry of the resulting bands.

Oligonucleotides for Probe Template PCR of CPR, CYP52A15 and CYP52A16

| Oligos | Sequence (SEQ ID NOS 370-375, respectively, in order of appearance) | Gene | Template | PCR product (bp) |
|---|---|---|---|---|
| oAA0250 | AATTGAACATCAGAAGAGGA | CPR | pAA067 | 1313 |
| oAA0254 | CCTGAAATTTCCAAATGGTGTCTAA | | | |
| oAA0227 | TTTTTTGTGCGCAAGTACAC | CYP52A15 | pAA077 | 905 |
| oAA0235 | CAACTTGACGTGAGAAACCT | | | |
| oAA0239 | AGATGCTCGTTTTACACCCT | CYP52A16 | pAA078 | 672 |
| oAA0247 | ACACAGCTTTGATGTTCTCT | | | |

Example 28

Strain Evaluation of Partially -Oxidation Blocked Strains

Fermentation of Methyl Laurate Feedstock.

5 mL starter cultures, in SP92 media (6.7 g/L Difco yeast nitrogen base, 3.0 g/L Difco yeast extract, 3.0 g/L ammonium sulfate, 1.0 g/L potassium phosphate monobasic, 1.0 g/L potassium phosphate dibasic, 75 g/L dextrose) were incubated overnight at 30° C., with shaking and used to inoculate flasks containing 25 mL of SP92 media to an initial $OD_{600nm}$ of about 0.4. Cultures were incubated approximately 18 hours at 30° C., with shaking at about 200 rpm. Cells were pelleted by centrifugation at 4° C. for 10 minutes at 4,000×g, then resuspended in SP92-D media (6.7 g/L Difco yeast nitrogen base, 3.0 g/L Difco yeast extract, 3.0 g/L ammonium sulfate, 1.0 g/L potassium phosphate monobasic, 1.0 g/L potassium phosphate dibasic) supplemented with 0.1% dextrose and 2% methyl laurate. Incubation of the cultures continued at 30° C., with shaking and samples were taken for analysis of fatty acids and diacids by gas chromatography (GC).

Sample for GC were prepared by adding 0.8 mL of 6.0M HCl to 1 mL of whole culture samples and the samples were stored at 4° C. to await processing. Samples were processed by incubating in a 60° C. water bath for 5 minutes, after which 4.0 mL of MTBE was added to the 1.8 mL acidified whole culture samples and vortexed for 20 seconds. The phases were allowed to separate for 10 min at room temperature. 1 mL of the MTBE phase was drawn and dried with sodium sulfate. Aliquots of the MTBE phase were derivatized with BSTFA reagent (Regis Technologies Inc.) and analyzed by GC equipped with a Flame Ionization Detector. The results of the gas chromatography are shown in the table below.

Fatty acid and Diacid profile (g/L) in Methyl Laurate fermentation

| Strain | Time (h) | C12 Acid | C12 Diacid | C10 Diacid | C8 Diacid | C6 Diacid |
|---|---|---|---|---|---|---|
| sAA105 | 0 | 0.00 | 0.00 | 0.00 | 0.00 | 0.00 |
|  | 24 | 0.05 | 0.00 | 0.00 | 0.07 | 0.42 |
|  | 48 | 0.00 | 0.00 | 0.00 | 0.00 | 0.00 |
| sAA106 | 0 | 0.00 | 0.00 | 0.00 | 0.00 | 0.00 |
|  | 24 | 2.92 | 1.29 | 0.15 | 0.58 | 0.37 |
|  | 48 | 0.04 | 0.02 | 0.00 | 0.00 | 0.01 |
| sAA152 | 0 | 0.02 | 0.00 | 0.00 | 0.00 | 0.00 |
|  | 24 | 0.58 | 0.55 | 0.07 | 0.43 | 0.03 |
|  | 48 | 0.00 | 0.03 | 0.00 | 0.05 | 0.58 |
| sAA003 | 0 | 0.00 | 0.00 | 0.00 | 0.00 | 0.00 |
|  | 24 | 1.96 | 0.41 | 0.00 | 0.00 | 0.00 |
|  | 48 | 1.43 | 0.47 | 0.00 | 0.00 | 0.00 |

Fermentation of Methyl Myristate and Oleic Acid Feedstocks.

Fermentations were performed essentially as described for methyl laurate feedstock except that 2% methyl myristate or 2% oleic acid was substituted for the 2% methyl laurate. The results of the gas chromatography are shown in the tables below.

Fatty acid and Diacid profile (g/L) in Methyl Myristate fermentation

| Strain | Time (h) | C14 Acid | C14 Diacid | C12 Diacid | C10 Diacid | C8 Diacid | C6 Diacid |
|---|---|---|---|---|---|---|---|
| sAA105 | 0 | 0.02 | 0.00 | 0.00 | 0.00 | 0.00 | 0.00 |
|  | 24 | 0.02 | 0.00 | 0.00 | 0.00 | 0.00 | 0.29 |
|  | 48 | 0.01 | 0.00 | 0.00 | 0.00 | 0.00 | 0.03 |
| sAA106 | 0 | 0.01 | 0.00 | 0.00 | 0.00 | 0.00 | 0.00 |
|  | 24 | 0.02 | 0.00 | 0.00 | 0.00 | 0.08 | 1.71 |
|  | 48 | 0.01 | 0.00 | 0.00 | 0.00 | 0.00 | 0.04 |
| sAA232 | 0 | 0.01 | 0.00 | 0.00 | 0.00 | 0.00 | 0.00 |
|  | 24 | 0.01 | 0.00 | 0.00 | 0.00 | 0.59 | 0.26 |
|  | 48 | 0.01 | 0.00 | 0.00 | 0.00 | 0.35 | 0.47 |
| sAA235 | 0 | 0.01 | 0.00 | 0.00 | 0.00 | 0.00 | 0.00 |
|  | 24 | 0.02 | 0.00 | 0.00 | 0.00 | 0.25 | 0.38 |
|  | 48 | 0.01 | 0.00 | 0.00 | 0.00 | 0.04 | 0.66 |
| sAA003 | 0 | 0.02 | 0.01 | 0.01 | 0.00 | 0.00 | 0.00 |
|  | 24 | 0.55 | 0.25 | 0.00 | 0.00 | 0.00 | 0.00 |
|  | 48 | 0.49 | 0.38 | 0.00 | 0.00 | 0.00 | 0.00 |

Diacid profile (g/L) in Oleic acid fermentation

| Strain | Time (h) | C14 Diacid | C12 Diacid | C10 Diacid | C8 Diacid | C6 Diacid |
|---|---|---|---|---|---|---|
| sAA105 | 0 | 0.00 | 0.00 | 0.00 | 0.00 | 0.00 |
|  | 24 | 0.00 | 0.00 | 0.00 | 0.00 | 0.03 |
|  | 48 | 0.00 | 0.00 | 0.00 | 0.00 | 0.01 |
| sAA106 | 0 | 0.00 | 0.00 | 0.00 | 0.00 | 0.00 |
|  | 24 | 0.00 | 0.00 | 0.00 | 0.00 | 1.48 |
|  | 48 | 0.00 | 0.00 | 0.00 | 0.00 | 0.42 |
| sAA232 | 0 | 0.00 | 0.00 | 0.00 | 0.00 | 0.00 |
|  | 24 | 0.00 | 0.00 | 0.00 | 0.00 | 0.09 |
|  | 48 | 0.00 | 0.00 | 0.00 | 0.00 | 0.10 |
| sAA235 | 0 | 0.00 | 0.00 | 0.00 | 0.00 | 0.00 |
|  | 24 | 0.00 | 0.00 | 0.00 | 0.00 | 0.10 |
|  | 48 | 0.00 | 0.00 | 0.00 | 0.00 | 0.11 |

Fermentations also were performed using coconut oil as a feed stock. Coconut oil contains a mixture of fatty acids of different carbon chain lengths. The percent composition of fatty acids, by weight, is about 6% capric acid (C10:0, where 0 refers to the number of double or unsaturated bonds), about 47% lauric acid (C12:0), about 18% myristic acid (C14:0), about 9% palmitic acid (C16:0). About 3% stearic acid (C18:0), about 6% oleic acid (C18:1, where 1 refers to the number of double bonds), and about 2% linoleic acid (omega-6 fatty acid, C18:2). In some embodiments, palm kernel oil can be substituted for coconut oil. Palm kernel oil has a distribution of fatty acids similar to that of coconut oil. Fermentations and GC were carried out essentially as described herein with the exception of feedstock used. The result of fermentations performed using coconut oil as a feedstock are presented below.

Diacid profile (g/L) in Coconut Oil fermentation

| Strain | Time (h) | C14 Diacid | C12 Diacid | C10 Diacid | C8 Diacid | C6 Diacid |
|---|---|---|---|---|---|---|
| sAA105 | 0 | 0.00 | 0.00 | 0.00 | 0.00 | 0.00 |
|  | 24 | 0.00 | 0.00 | 0.00 | 0.00 | 0.00 |
|  | 48 | 0.00 | 0.00 | 0.00 | 0.00 | 0.00 |
| sAA106 | 0 | 0.00 | 0.00 | 0.00 | 0.00 | 0.00 |
|  | 24 | 0.00 | 0.00 | 0.00 | 0.00 | 0.01 |
|  | 48 | 0.00 | 0.00 | 0.00 | 0.00 | 0.00 |
| sAA152 | 0 | 0.00 | 0.00 | 0.00 | 0.00 | 0.00 |
|  | 24 | 0.00 | 0.00 | 0.00 | 0.00 | 0.43 |
|  | 48 | 0.00 | 0.00 | 0.00 | 0.00 | 0.45 |
| sAA232 | 0 | 0.00 | 0.00 | 0.00 | 0.00 | 0.00 |
|  | 24 | 0.00 | 0.00 | 0.00 | 0.00 | 0.41 |
|  | 48 | 0.00 | 0.00 | 0.00 | 0.00 | 0.58 |
| sAA235 | 0 | 0.00 | 0.00 | 0.00 | 0.00 | 0.00 |
|  | 24 | 0.00 | 0.00 | 0.00 | 0.00 | 0.43 |
|  | 48 | 0.00 | 0.00 | 0.00 | 0.00 | 0.76 |

Example 29

Strain Evaluation of Completely -Oxidation Blocked Strains

Fermentations also were performed using methyl myristate as a feed stock. Fermentations and GC were carried out essentially as described herein with the exception of feedstock used. The result of fermentations performed using coconut oil as a feedstock are presented below.

C14 Diacid production in strains with amplified CPR, CYP52A15, and/or CYP52A16

| Strain | C14 diacid, 72 h (g/L) | CPR | A15 | A16 |
|---|---|---|---|---|
| sAA003 | 0.98 | 2 | 1 | 1 |
| sAA318 | 1.19 | 3 | 1 | 1 |
| sAA239 | 2.75 | 3 | 1 | 3 |
| sAA319 | 1.37 | 7 | 1 | 1 |
| sAA238 | 1.93 | 7 | 2 | 1 |

Example 30

Nucleic Acid and Amino Acid Sequences of Novel Fatty Alcohol Oxidase Genes

As noted above, novel fatty alcohol oxidase genes were identified and cloned. The nucleotide and amino acid sequences of the novel sequences are presented herein. Nucleotide and amino acid sequence identity comparison are shown in Example 18.

Nucleotide Sequences

FAO-13

(SEQ ID NO: 1)

```
atggctccattttgcccgaccaggtcgactacaaacacgtcgacacccttatgttattatgtgacgggatcatccacgaaaccaccgtcga
ccaaatcaaagacgttattgctcctgacttccctgctgacaagtacgaagagtacgtcaggacattcaccaaaccctccgaaacccccagg
gttcagggaaaccgtctacaacacagtcaacgcaaacaccacggacgcaatccaccagttcattatcttgaccaatgttttggcatccagg
gtcttggctccagctttgaccaactcgttgacgcctatcaaggacatgagcttggaagaccgtgaaaaattgttggcctcgtggcgcgactc
cccaatcgctgccaaaaggaagttgttcaggttggtttctacgcttaccttggtcacgttcacgagattggccaatgagttgcatttgaaagcc
attcattatccaggaagagaagaccgtgaaaaggcttatgaaacccaggagattgacccttttaagtaccagttttttggaaaaaccgaagt
tttacggcgctgagttgtacttgccagatattgatgtgatcattattggatctggtgccggtgctggtgttgtggcccacactttggccaacgatg
gcttcaagagtttggttttggaaaagggcaaatactttagcaactccgagttgaactttgatgacaaggacggcgttcaagaattataccaa
agtggaggtactttgactacagtcaaccaacagttgtttgttcttgctggttccacttttggttggcggtaccactgtcaattggtcagcctgtctta
agacgccattcaaggtgcgtaaggaatggtatgatgagtttggtgttgactttgctgctgatgaagcatacgataaagcgcaggattatgtttg
```

-continued gcagcaaatgggagcttctaccgaaggcatcaccccactctttggctaacgagattattattgaaggtggtaagaaattaggttacaaggcc aaggtattagaccaaaacagcggtggtcatcctcagcacagatgcggtttctgttatttgggctgtaagcacggtatcaagcagggttctgtt aataactggtttagagacgcagctgcccacggttcccagttcatgcaacaggttagagttttgcaaatacttaacaagaaggggatcgctta cggtatcttgtgtgaggatgttgtaaccggcgccaagttcaccattactggcccaaaaagtttgttgttgctgccggtgctttgaacactccat ctgtgttggtcaactccggcttcaagaacaagaacatcggtaagaacttaactttgcacccagtttctgtcgtgtttggtgattttggcaaagac gttcaagcagaccacttccacaactccatcatgactgccctttgttcagaagccgctgatttagacggcaagggccatggatgcagaattg aaaccatcttgaacgctccattcatccaggcttcattcttaccatggagaggtagtaacgaggctagacgagacttgttgcgttacaacaac atggtggcgatgttgctccttagtcgtgacaccaccagtggttccgtttctgctcatccaaccaaacctgaagctttggttgtcgagtacgacgt gaacaagtttgacagaaactcgatcttgcaggcattgttggtcactgctgacttgttgtatatccaaggtgccaagagaatccttagtccaca ggcatgggtgccaattttgaatccgacaagccaaaggataagagatcaatcaaggacgaggactatgtcgaatggagagccaaggtt gccaagattcctttcgacacctacggctcaccttatggttcggcacatcaaatgtcttcttgccgtatgtcaggtaagggtcctaaatacggtg ctgttgacaccgatggtagattgtttgaatgttcgaatgtttatgttgccgatgcaagtcttttgccaactgcaagcggtgccaaccctatggtca ccaccatgactcttgccagacatgttgcgttaggtttggcagactccttgaagaccaaagccaagttgtag

FAO-17

(SEQ ID NO: 2)

atggctccattttgcccgaccaggtcgactacaaacacgtcgacacccttatgttattatgtgacgggatcatccacgaaaccaccgtgga cgaaatcaaagacgtcattgccctgacttccccgccgacaaatacgaggagtacgtcaggacattcaccaaaccctccgaaacccca gggttcagggaaaccgtctacaacaccgtcaacgcaaacaccatggatgcaatccaccagttcattatcttgaccaatgttttgggatcaa gggtcttggcaccagctttgaccaactcgttgactcctatcaaggacatgagcttggaagaccgtgaaaagttgttagcctcgtggcgtgact cccctattgctgctaaaaggaagttgttcaggttggtttctacgcttaccttggtcacgttcacgagattggccaatgagttgcatttgaaagcc attcattatccaggaagagaagaccgtgaaaaggcttatgaaacccaggagattgaccctttaagtaccagtttttggaaaaaccgaagt tttacggcgctgagttgtacttgccagatattgatgtgatcattattggatctggtgccggtgctggtgttgtgcccacactttggccaacgatg gcttcaagagtttggttttggaaaagggcaaatactttagcaactccgagttgaactttgatgacaaggacggcgttcaagaattataccaa agtggaggtactttgactacagtcaaccaacagttgtttgttcttgctggttccacttttggtggcggtaccactgtcaattggtcagcctgtctta agacgccattcaaggtgcgtaaggaatggtatgatgagtttggtgttgactttgctgctgatgaagcatacgataaagcgcaggattatgtttg gcagcaaatgggagcttctaccgaaggcatcaccccactctttggctaacgagattattattgaaggtggtaagaaattaggttacaaggcc aaggtattagaccaaaacagcggtggtcatcctcagcacagatgcggtttctgttatttgggttgtaagcacggtatcaagcagggctctgtt aataactggtttagagacgcagctgcccacggttctcagttcatgcaacaggttagagttttgcaaatccttaacaagaagggcatcgcttat ggtatcttgtgtgaggatgttgtaaccggtgccaagttcaccattactggccccaaaaagtttgttgttgccgccggcgccttaaacactccat ctgtgttggtcaactccggattcaagaacaagaacatcggtaagaacttaactttgcatccagtttctgtcgtgtttggtgattttggcaaagac gttcaagcagaccacttccacaactccatcatgactgccctttgttcagaagccgctgatttagacggcaagggccatggatgcagaattg aaaccatcttgaacgctccattcatccaggcttcattcttaccatggagaggtagtaacgaggctagacgagacttgttgcgttacaacaac atggtggcgatgttgctccttagtcgtgacaccaccagtggttccgtttctgctcatccaaccaaacctgaagctttggttgtcgagtacgacgt gaacaagtttgacagaaactcgatcttgcaggcattgttggtcactgctgacttgttgtatatccaaggtgccaagagaatccttagtccaca ggcatgggtgccaattttgaatccgacaagccaaaggataagagatcaatcaaggacgaggactatgtcgaatggagagccaaggtt gccaagattcctttcgacacctacggctcaccttatggttcggcacatcaaatgtcttcttgccgtatgtcaggtaagggtcctaaatacggtg ctgttgacaccgatggtagattgtttgaatgttcgaatgtttatgttgccgatgcaagtcttttgccaactgcaagcggtgccaaccctatggtca ccaccatgactcttgcaagacatgttgcgttaggtttggcagactccttgaagaccaaggccaagttgtag

FAO-20

(SEQ ID NO: 3)

atggctccattttgcccgaccaggtcgactacaaacacgtcgacacccttatgttattatgtgacgggatcatccacgaaaccaccgtcga ccaaatcaaagacgttattgctcctgacttccctgctgacaagtacgaagagtacgtcaggacattcaccaaaccctccgaaacccccagg -continued gttcagggaaaccgtctacaacacagtcaacgcaaacaccacggacgcaatccaccagttcattatcttgaccaatgttttggcatccagg gtcttggctccagcttttgaccaactcgttgacgcctatcaaggacatgagcttggaagaccgtgaaaaattgttggcctcgtggcgcgactc cccaatcgctgccaaaaggaaattgttcaggttggtttccacgcttaccttggttactttcacgagattggccaatgagttgcatttgaaagcca ttcactatccaggaagagaagaccgtgaaaaggcttatgaaacccaggagattgacccttttcaagtaccagtttatggaaaagccaaagt ttgacggcgctgagttgtacttgccagatattgatgttatcattattggatctggtgccggtgctggtgttgtggcccacactttggccaacgatg gcttcaagagttttggttttggaaaagggcaaatactttagcaactccgagttgaactttgatgacaaggacggcgttcaagaattataccaa agtggaggtactttgactacagtcaaccaacagttgtttgttcttgctggttccacttttggtggcggtaccactgtcaattggtcagcctgtctta agacgccattcaaggtgcgtaaggaatggtatgatgagtttggtgttgactttgctgctgatgaagcatacgataaagcgcaggattatgtttg gcagcaaatgggagcttctaccgaaggcatcacccactctttggctaacgagattattattgaaggtggtaagaaattaggttacaaggcc aaggtattagaccaaaacagcggtggtcatcctcagcacagatgcgggtttctgttatttgggctgtaagcacggtatcaagcagggttctgtt aataactggtttagagacgcagctgcccacggttcccagttcatgcaacaggttagagttttgcaaatacttaacaagaaggggatcgctta cggtatcttgtgtgaggatgttgtaaccggcgccaagttcaccattactggccccaaaaagtttgttgttgctgccggtgctttgaacactccat ctgtgttggtcaactccggcttcaagaacaagaacatcggtaagaacttaactttgcacccagtttctgtcgtgtttggtgattttggcaaagac gttcaagcagaccacttccacaactccatcatgactgcccttgttcagaagccgctgatttagacggcaagggccatggatgcagaattg aaaccatcttgaacgctccattcatccaggcttcattcttaccatggagaggtagtaacgaggctagacgagacttgttgcgttacaacaac atggtggcgatgttgctccttagtcgtgacaccaccagtggttccgtttctgctcatccaaccaaacctgaagctttggttgtcgagtacgacgt gaacaagtttgacagaaactcgatcttgcaggcattgttggtcactgctgacttgttgtatatccaaggtgccaagagaatccttagtccaca ggcatgggtgccaattttttgaatccgacaagccaaaggataagagatcaatcaaggacgaggactatgtcgaatggagagccaaggtt gccaagattcctttcgacacctacggctcaccttatggttcggcacatcaaatgtcttcttgccgtatgtcaggtaagggtcctaaatacggtg ctgttgacaccgatggtagattgtttgaatgttcgaatgtttatgttgccgatgcaagtcttttgccaactgcaagcggtgccaaccctatggtca ccaccatgactcttgccagacatgttgcgttaggtttggcagactccttgaagaccaaagccaagttgtag FA02a (SEQ ID NO: 4)

atgaataccttcttgccagacgtgctcgaatacaaacacgtcgacaccctttttgttattgtgtgacgggatcatccacgaaaccacagtcgat cagatcaaggacgccattgctcccgacttccctgaggaccagtacgaggagtatctcaagaccttcaccaagccatctgagacccctgg gttcagagaagccgtctacgacacgatcaacgccacccccaaccgatgccgtgcacatgtgtattgtcttgaccaccgcattggactccag aatcttggccccacgttgaccaactcgttgacgcctatcaaggatatgaccttgaaggagcgtgaacaattgttggcctcttggcgtgattc cccgattgcggcaaagagaagattgttcagattgatttcctcgcttaccttgacgacgtttacgagattggccagcgaattgcacttgaaagc catccactaccctggcagagacttgcgtgaaaaggcgtatgaaacccaggtggttgaccctttcaggtacctgtttatggagaaaccaaag tttgacggcgccgaattgtacttgccagatatcgacgtcatcatcattggatcaggcgccggtgctggtgtcatggcccacactctcgccaac gacgggttcaagaccttggttttggaaaagggaaagtatttcagcaactccgagttgaactttaatgacgctgatggcgtgaaagagttgta ccaaggtaaaggtgctttggccaccaccaatcagcagatgtttattcttgccggttccacttgggcggtggtaccactgtcaactggtctgctt gccttaaaacaccatttaaagtgcgtaaggagtggtacgacgagtttggtcttgaatttgctgccgatgaagcctacgacaaagcgcagga ttatgtttggaaacaaatgggtgcttcaacagatggaatcactcactccttggccaacgaagttgtggttgaaggaggtaagaagttgggct acaagagcaaggaaattgagcagaacaacggtggccacccctgaccacccatgtggtttctgttacttgggctgtaagtacggtattaaac agggttctgtgaataactggtttagagacgcagctgcccacgggtccaagttcatgcaacaagtcagagttgtgcaaatcctcaacaaga atggcgtcgcttatggtatcttgtgtgaggatgtcgaaaccggagtcaggttcactattagtggccccaaaaagtttgttgtttctgctggttctttg aacacgccaactgtgttgaccaactccggattcaagaacaagcacattggtaagaacttgacgttgcacccagtttccaccgtgtttggtga ctttggcagagacgtgcaagccgaccatttccacaaatctattatgactcgctttgttacgaggttgctgacttggacggcaagggccacgg atgcagaatcgaaaccatcttgaacgctccattcatccaagcttctttgttgccatggagaggaagtgacgaggtcagaagagacttgttgc gttacaacaacatggtggccatgttgcttatcacgcgtgataccaccagtggttcagtttctgctgacccaaagaagcccgacgctttgattgt cgactatgagattaacaagtttgacaagaatgccatcttgcaagctttcttgatcacttccgacatgttgtacattgaaggtgccaagagaatc

```
ctcagtccacagccatgggtgccaatctttgagtcgaacaagccaaaggagcaaagaacgatcaaggacaaggactatgttgagtgga gagccaaggctgctaagatacctttcgacacctacggttctgcatatgggtccgcacatcaaatgtccacctgtcgtatgtccggaaagggt cctaaatacggtgctgttgatactgatggtagattgtttgaatgttcgaatgtctatgttgctgatgctagtgttttgcctactgccagcggtgccaa cccaatgatatccaccatgacctttgctagacagattgcgttaggtttggctgactccttgaagaccaaacccaagttgtag
```

FAO2b
(SEQ ID NO: 5)
```
atgaataccttcttgccagacgtgctcgaatacaaacacgtcgataccctttgttattatgtgacgggatcatccacgaaaccacagtcgac cagatcagggacgccattgctcccgacttccctgaagaccagtacgaggagtatctcaagaccttcaccaagccatctgagacccctgg gttcagagaagccgtctacgacacgatcaacagcaccccaaccgaggctgtgcacatgtgtattgtattgaccaccgcattggactcgag aatcttggccccacgttgaccaactcgttgacgcctatcaaggatatgaccttgaaagagcgtgaacaattgttggctgcctggcgtgattc cccgatcgcggccaagagaagattgttcagattgatttcctcacttaccttgacgacctttacgagattggccagcgacttgcacttgagagc catccactaccctggcagagacttgcgtgaaaaggcatatgaaacccaggtggttgaccctttcaggtacctgtttatggaaaaaccaaag tttgacggcaccgagttgtacttgccagatatcgacgtcatcatcattggatccggtgccggtgctggtgtcatggcccacactttagccaac gacgggtacaagaccttggttttggaaaagggaaagtatttcagcaactccgagttgaactttaatgatgccgatggtatgaaagagttgta ccaaggtaaatgtgcgttgaccaccacgaaccagcagatgtttattcttgccggttccacttttgggcggtggtaccactgttaactggtctgctt gtcttaaaacaccatttaaagtgcgtaaggagtggtacgacgagtttggtcttgaatttgctgccgacgaagcctacgacaaagcacaaga ctatgtttggaaacaaatgggcgcttctaccgaaggaatcactcactctttggcgaacgcggttgtggttgaaggaggtaagaagttgggtt acaagagcaaggaaatcgagcagaacaatggtggccatcctgaccacccctgtggtttctgttacttgggctgtaagtacggtattaagca gggttctgtgaataactggtttagagacgcagctgcccacgggtccaagttcatgcaacaagtcagagttgtgcaaatcctccacaataaa ggcgtcgcttatggcatcttgtgtgaggatgtcgagaccggagtcaaattcactatcagtggccccaaaaagtttgttgtttctgcaggttctttg aacacgccaacggtgttgaccaactccggattcaagaacaaacatcggtaagaacttgacgttgcacccagtttcgaccgtgtttggtg actttggcagagacgtgcaagccgaccattttccacaaatctattatgacttcgctctgttacgaagtcgctgacttggacggcaagggccac ggatgcagaatcgagaccatcttgaacgctccattcatccaagcttctttgttgccatggagaggaagcgacgaggtcagaagagacttgt tgcgttacaacaacatggtggccatgttgcttatcacccgtgacaccaccagtggttcagtttctgctgacccaaagaagcccgacgctttga ttgtcgactatgacatcaacaagtttgacaagaatgccatcttgcaagctttcttgatcacctccgacatgttgtacatcgaaggtgccaagag aatcctcagtccacaggcatgggtgccaatctttgagtcgaacaagccaaaggagcaaagaacaatcaaggacaaggactatgtcga atggagagccaaggctgccaagatacctttcgacacctacggttctgcctatgggtccgcacatcaaatgtccacctgtcgtatgtccggaa agggtcctaaatacggcgccgttgataccgatggtagattgtttgaatgttcgaatgtctatgttgctgatgctagtgttttgcctactgccagcg gtgccaacccaatgatctccaccatgacgtttgctagacagattgcgttaggtttggctgactcttttgaagaccaaacccaagttgtag
```

In addition to the novel FAO genes isolated, a sequence substantially identical to the sequence used for primer design, described above, also was isolated. The nucleotide sequence of the gene is presented below.

FAO-18
(SEQ ID NO: 6)
```
atggctccattttttgcccgaccaggtcgactacaaacacgtcgacacccttatgttattatgtgacgggatcatccacgaaaccaccgtgga cgaaatcaaagacgtcattgcccctgacttccccgccgacaaatacgaggagtacgtcaggacattcaccaaaccctccgaaacccca gggttcagggaaaccgtctacaacaccgtcaacgcaaacaccatggatgcaatccaccagttcattatcttgaccaatgttttgggatcaa gggtcttggcaccagctttgaccaactcgttgactcctatcaaggacatgagcttggaagaccgtgaaagttgttagcctcgtggcgtgact cccctattgctgctaaaaggaagttgttcaggttggtttctacgcttaccttggtcacgttcacgagattggccaatgagttgcatttgaaagcc attcattatccaggaagagaagaccgtgaaaaggcttatgaaacccaggagattgacccttttaagtaccagtttttggaaaaaccgaagt tttacggcgctgagttgtacttgccagatattgatgtgatcattattggatctggggccggtgctggtgtcgtggcccacactttgaccaacgac ggcttcaagagtttggttttggaaaagggcagatactttagcaactccgagttgaactttgatgacaaggacggggttcaagaattatacca
```

-continued

```
aagtggaggtactttgaccaccgtcaaccagcagttgtttgttcttgctggttccacttttggtggtggtaccactgtcaattggtcggcctgtctta
aaacgccattcaaggtgcgtaaggaatggtatgatgagtttggcgttgactttgctgccgatgaagcctacgacaaagcacaggattatgtt
tggcagcaaatgggagcttctaccgaaggcatcacccactctttggctaacgagattattgaaggtggcaagaaattaggttacaagg
ccaaggtattagaccaaaacagcggtggtcatcctcatcacagatgcggtttctgttatttgggttgtaagcacggtatcaagcagggctctg
ttaataactggtttagagacgcagctgcccacggttctcagttcatgcaacaggttagagttttgcaaatccttaacaagaagggcatcgctt
atggtatcttgtgtgaggatgttgtaaccggtgccaagttcaccattactggccccaaaaagtttgttgttgccgccggcgccttaaacactcc
atctgtgttggtcaactccggattcaagaacaagaacatcggtaagaacttaactttgcatccagtttctgtcgtgtttggtgattttggcaaaga
cgttcaagcagatcacttccacaactccatcatgactgctctttgttcagaagccgctgatttagacggcaagggtcatggatgcagaattga
aaccatcttgaacgctccattcatccaggcttcattcttaccatggagaggtagtaacgaggctagacgagacttgttgcgttacaacaacat
ggtggccatgttacttcttagtcgtgataccaccagtggttccgtttcgtcccatccaactaaacctgaagcattagttgtcgagtacgacgtga
acaagtttgacagaaactccatcttgcaggcattgttggtcactgctgacttgttgtacattcaaggtgccaagagaatccttagtccccaacc
atgggtgccaattttgaatccgacaagccaaaggataagagatcaatcaaggacgaggactatgtcgaatggagagccaaggttgcc
aagattccttttgacacctacggctcgccttatggttcggcgcatcaaatgtcttcttgtcgtatgtcaggtaagggtcctaaatacggtgctgttg
ataccgatggtagattgtttgaatgttcgaatgtttatgttgctgacgctagtcttttgccaactgctagcggtgctaatcctatggtcaccaccat
gactcttgcaagacatgttgcgttaggtttggcagactccttgaagaccaaggccaagttgtag
```

Clustal Nucleotide Sequence Alignments

```
CLUSTAL 2.0.12 multiple sequence alignment
FAO-13   ATGGCTCCATTTTTGCCCGACCAGGTCGACTACAAACACGTCGACACCCTTATGTTATTA    60  (SEQ ID NO: 1)

FAO-20   ATGGCTCCATTTTTGCCCGACCAGGTCGACTACAAACACGTCGACACCCTTATGTTATTA    60  (SEQ ID NO: 3)

FAO-17   ATGGCTCCATTTTTGCCCGACCAGGTCGACTACAAACACGTCGACACCCTTATGTTATTA    60  (SEQ ID NO: 2)

FAO-18   ATGGCTCCATTTTTGCCCGACCAGGTCGACTACAAACACGTCGACACCCTTATGTTATTA    60  (SEQ ID NO: 6)

FAO2a    ATGAATACCTTCTTGCCAGACGTGCTCGAATACAAACACGTCGACACCCTTTTGTTATTG    60  (SEQ ID NO: 4)

FAO2b    ATGAATACCTTCTTGCCAGACGTGCTCGAATACAAACACGTCGATACCCTTTTGTTATTA    60  (SEQ ID NO: 5)
         *** * * ** ***** *** * **** ************** ****** *******

FAO-13   TGTGACGGGATCATCCACGAAACCACCGTCGACCAAATCAAAGACGTTATTGCTCCTGAC   120

FAO-20   TGTGACGGGATCATCCACGAAACCACCGTCGACCAAATCAAAGACGTTATTGCTCCTGAC   120

FAO-17   TGTGACGGGATCATCCACGAAACCACCGTCGACGAAATCAAAGACGTCATTGCCCCTGAC   120

FAO-18   TGTGACGGGATCATCCACGAAACCACCGTGGACGAAATCAAAGACGTCATTGCCCCTGAC   120

FAO2a    TGTGACGGGATCATCCACGAAACCACAGTCGATCAGATCAAGGACGCCATTGCTCCCGAC   120

FAO2b    TGTGACGGGATCATCCACGAAACCACAGTCGACCAGATCAGGGACGCCATTGCTCCCGAC   120
         *************************  ** ** *  **** **** ** ** ** ***

FAO-13   TTCCCTGCTGACAAGTACGAAGAGTACGTCAGGACATTCACCAAACCCTCCGAAACCCCA   180

FAO-20   TTCCCTGCTGACAAGTACGAAGAGTACGTCAGGACATTCACCAAACCCTCCGAAACCCCA   180

FAO-17   TTCCCCGCCGACAAATACGAGGAGTACGTCAGGACATTCACCAAACCCTCCGAAACCCCA   180

FAO-18   TTCCCCGCCGACAAATACGAGGAGTACGTCAGGACATTCACCAAACCCTCCGAAACCCCA   180

FAO2a    TTCCCTGAGGACCAGTACGAGGAGTATCTCAAGACCTTCACCAAGCCATCTGAGACCCCT   180

FAO2b    TTCCCTGAAGACCAGTACGAGGAGTATCTCAAGACCTTCACCAAGCCATCTGAGACCCCT   180
         ***** * *** * ***** ***** *** *** ******** ** ** ** *****

FAO-13   GGGTTCAGGGAAACCGTCTACAACACAGTCAACGCAAACACCACGGACGCAATCCACCAG   240

FAO-20   GGGTTCAGGGAAACCGTCTACAACACAGTCAACGCAAACACCACGGACGCAATCCACCAG   240

FAO-17   GGGTTCAGGGAAACCGTCTACAACACCGTCAACGCAAACACCATGGATGCAATCCACCAG   240

FAO-18   GGGTTCAGGGAAACCGTCTACAACACCGTCAACGCAAACACCATGGATGCAATCCACCAG   240
```

```
FAO2a   GGGTTCAGAGAAGCCGTCTACGACACGATCAACGCCACCCCAACCGATGCCGTGCACATG 240
FAO2b   GGGTTCAGAGAAGCCGTCTACGACACGATCAACAGCACCCCAACCGAGGCTGTGCACATG 240
        ******** *** ******** **** *****  *  *  ** **  * ***  *

FAO-13  TTCATTATCTTGACCAATGTTTTGGCATCCAGGGTCTTGGCTCCAGCTTTGACCAACTCG 300
FAO-20  TTCATTATCTTGACCAATGTTTTGGCATCCAGGGTCTTGGCTCCAGCTTTGACCAACTCG 300
FAO-17  TTCATTATCTTGACCAATGTTTTGGGATCAAGGGTCTTGGCACCAGCTTTGACCAACTCG 300
FAO-18  TTCATTATCTTGACCAATGTTTTGGGATCAAGGGTCTTGGCACCAGCTTTGACCAACTCG 300
FAO2a   TGTATTGTCTTGACCACCGCATTGGACTCCAGAATCTTGGCCCCCACGTTGACCAACTCG 300
FAO2b   TGTATTGTATTGACCACCGCATTGGACTCGAGAATCTTGGCCCCCACGTTGACCAACTCG 300
        * *** * ******* * **** ** ** ******* **  ************

FAO-13  TTGACGCCTATCAAGGACATGAGCTTGGAAGACCGTGAAAAATTGTTGGCCTCGTGGCGC 360
FAO-20  TTGACGCCTATCAAGGACATGAGCTTGGAAGACCGTGAAAAATTGTTGGCCTCGTGGCGC 360
FAO-17  TTGACTCCTATCAAGGACATGAGCTTGGAAGACCGTGAAAAGTTGTTAGCCTCGTGGCGT 360
FAO-18  TTGACTCCTATCAAGGACATGAGCTTGGAAGACCGTGAAAAGTTGTTAGCCTCGTGGCGT 360
FAO2a   TTGACGCCTATCAAGGATATGACCTTGAAGGAGCGTGAACAATTGTTGGCCTCTTGGCGT 360
FAO2b   TTGACGCCTATCAAGGATATGACCTTGAAAGAGCGTGAACAATTGTTGGCTGCCTGGCGT 360
        ***** *********** ****  ****  * ** ****** * ***** ** * *****

FAO-13  GACTCCCCAATCGCTGCCAAAAGGAAGTTGTTCAGGTTGGTTTCTACGCTTACCTTGGTC 420
FAO-20  GACTCCCCAATCGCTGCCAAAAGGAAATTGTTCAGGTTGGTTTCCACGCTTACCTTGGTT 420
FAO-17  GACTCCCCTATTGCTGCTAAAAGGAAGTTGTTCAGGTTGGTTTCTACGCTTACCTTGGTC 420
FAO-18  GACTCCCCTATTGCTGCTAAAAGGAAGTTGTTCAGGTTGGTTTCTACGCTTACCTTGGTC 420
FAO2a   GATTCCCCGATTGCGGCAAAGAGAAGATTGTTCAGATTGATTTCCTCGCTTACCTTGACG 420
FAO2b   GATTCCCCGATCGCGGCCAAGAGAAGATTGTTCAGATTGATTTCCTCACTTACCTTGACG 420
        ** ***** **  ** ** **  *  ********  *** ****  *  *********

FAO-13  ACGTTCACGAGATTGGCCAATGAGTTGCATTTGAAAGCCATTCATTATCCAGGAAGAGAA 480
FAO-20  ACTTTCACGAGATTGGCCAATGAGTTGCATTTGAAAGCCATTCACTATCCAGGAAGAGAA 480
FAO-17  ACGTTCACGAGATTGGCCAATGAGTTGCATTTGAAAGCCATTCATTATCCAGGAAGAGAA 480
FAO-18  ACGTTCACGAGATTGGCCAATGAGTTGCATTTGAAAGCCATTCATTATCCAGGAAGAGAA 480
FAO2a   ACGTTTACGAGATTGGCCAGCGAATTGCACTTGAAAGCCATCCACTACCCTGGCAGAGAC 480
FAO2b   ACCTTTACGAGATTGGCCAGCGACTTGCACTTGAGAGCCATCCACTACCCTGGCAGAGAC 480
        ** **  ************  **  ***** **** **** ** **  ** ** *****

FAO-13  GACCGTGAAAAGGCTTATGAAACCCAGGAGATTGACCCTTTTAAGTACCAGTTTTTGGAA 540
FAO-20  GACCGTGAAAAGGCTTATGAAACCCAGGAGATTGACCCTTTCAAGTACCAGTTTATGGAA 540
FAO-17  GACCGTGAAAAGGCTTATGAAACCCAGGAGATTGACCCTTTTAAGTACCAGTTTTTGGAA 540
FAO-18  GACCGTGAAAAGGCTTATGAAACCCAGGAGATTGACCCTTTTAAGTACCAGTTTTTGGAA 540
FAO2a   TTGCGTGAAAAGGCGTATGAAACCCAGGTGGTTGACCCTTTCAGGTACCTGTTTATGGAG 540
FAO2b   TTGCGTGAAAAGGCATATGAAACCCAGGTGGTTGACCCTTTCAGGTACCTGTTTATGGAA 540
         * ********** ************ * ********* * * *** ***** ****

FAO-13  AAACCGAAGTTTTACGGCGCTGAGTTGTACTTGCCAGATATTGATGTGATCATTATTGGA 600
FAO-20  AAGCCAAAGTTTGACGGCGCTGAGTTGTACTTGCCAGATATTGATGTTATCATTATTGGA 600
FAO-17  AAACCGAAGTTTTACGGCGCTGAGTTGTACTTGCCAGATATTGATGTGATCATTATTGGA 600
FAO-18  AAACCGAAGTTTTACGGCGCTGAGTTGTACTTGCCAGATATTGATGTGATCATTATTGGA 600
FAO2a   AAACCAAAGTTTGACGGCGCCGAATTGTACTTGCCAGATATCGACGTCATCATCATTGGA 600
```

```
FAO2b   AAACCAAAGTTTGACGGCACCGAGTTGTACTTGCCAGATATCGACGTCATCATCATTGGA 600
         ** ** ****** ***** * **  **************** ** ** ***** ******

FAO-13  TCTGGTGCCGGTGCTGGTGTTGTGGCCCACACTTTGGCCAACGATGGCTTCAAGAGTTTG 660

FAO-20  TCTGGTGCCGGTGCTGGTGTTGTGGCCCACACTTTGGCCAACGATGGCTTCAAGAGTTTG 660

FAO-17  TCTGGTGCCGGTGCTGGTGTTGTGGCCCACACTTTGGCCAACGATGGCTTCAAGAGTTTG 660

FAO-18  TCTGGGGCCGGTGCTGGTGTCGTGGCCCACACTTTGACCAACGACGGCTTCAAGAGTTTG 660

FAO2a   TCAGGCGCCGGTGCTGGTGTCATGGCCCACACTCTCGCCAACGACGGGTTCAAGACCTTG 660

FAO2b   TCCGGTGCCGGTGCTGGTGTCATGGCCCACACTTTAGCCAACGACGGGTACAAGACCTTG 660
         ** ** ************** *********** *  ******* ** * ***** ***

FAO-13  GTTTTGGAAAAGGGCAAATACTTTAGCAACTCCGAGTTGAACTTTGATGACAAGGACGGC 720

FAO-20  GTTTTGGAAAAGGGCAAATACTTTAGCAACTCCGAGTTGAACTTTGATGACAAGGACGGC 720

FAO-17  GTTTTGGAAAAGGGCAAATACTTTAGCAACTCCGAGTTGAACTTTGATGACAAGGACGGC 720

FAO-18  GTTTTGGAAAAGGGCAGATACTTTAGCAACTCCGAGTTGAACTTTGATGACAAGGACGGG 720

FAO2a   GTTTTGGAAAAGGGAAAGTATTTCAGCAACTCCGAGTTGAACTTTAATGACGCTGATGGC 720

FAO2b   GTTTTGGAAAAGGGAAAGTATTTCAGCAACTCCGAGTTGAACTTTAATGATGCCGATGGT 720
         **************  ** ** ********************** ****   **  **

FAO-13  GTTCAAGAATTATACCAAAGTGGAGGTACTTTGACTACAGTCAACCAACAGTTGTTTGTT 780

FAO-20  GTTCAAGAATTATACCAAAGTGGAGGTACTTTGACTACAGTCAACCAACAGTTGTTTGTT 780

FAO-17  GTTCAAGAATTATACCAAAGTGGAGGTACTTTGACTACAGTCAACCAACAGTTGTTTGTT 780

FAO-18  GTTCAAGAATTATACCAAAGTGGAGGTACTTTGACCACCGTCAACCAGCAGTTGTTTGTT 780

FAO2a   GTGAAAGAGTTGTACCAAGGTAAAGGTGCTTTGGCCACCACCAATCAGCAGATGTTTATT 780

FAO2b   ATGAAAGAGTTGTACCAAGGTAAATGTGCGTTGACCACCACGAACCAGCAGATGTTTATT 780
         *  **** ** ****** ** * ** *   ** * **  ** *** ***** *****  **

FAO-13  CTTGCTGGTTCCACTTTTGGTGGCGGTACCACTGTCAATTGGTCAGCCTGTCTTAAGACG 840

FAO-20  CTTGCTGGTTCCACTTTTGGTGGCGGTACCACTGTCAATTGGTCAGCCTGTCTTAAGACG 840

FAO-17  CTTGCTGGTTCCACTTTTGGTGGCGGTACCACTGTCAATTGGTCAGCCTGTCTTAAGACG 840

FAO-18  CTTGCTGGTTCCACTTTTGGTGGTGGTACCACTGTCAATTGGTCGGCCTGTCTTAAAACG 840

FAO2a   CTTGCCGGTTCCACTTTGGGCGGTGGTACCACTGTCAACTGGTCTGCTTGCCTTAAAACA 840

FAO2b   CTTGCCGGTTCCACTTTGGGCGGTGGTACCACTGTTAACTGGTCTGCTTGTCTTAAAACA 840
         ***** *********** ** ** *********** ** ***** ** ** ***** **

FAO-13  CCATTCAAGGTGCGTAAGGAATGGTATGATGAGTTTGGTGTTGACTTTGCTGCTGATGAA 900

FAO-20  CCATTCAAGGTGCGTAAGGAATGGTATGATGAGTTTGGTGTTGACTTTGCTGCTGATGAA 900

FAO-17  CCATTCAAGGTGCGTAAGGAATGGTATGATGAGTTTGGTGTTGACTTTGCTGCTGATGAA 900

FAO-18  CCATTCAAGGTGCGTAAGGAATGGTATGATGAGTTTGGCGTTGACTTTGCTGCCGATGAA 900

FAO2a   CCATTTAAAGTGCGTAAGGAGTGGTACGACGAGTTTGGTCTTGAATTTGCTGCCGATGAA 900

FAO2b   CCATTTAAAGTGCGTAAGGAGTGGTACGACGAGTTTGGTCTTGAATTTGCTGCCGACGAA 900
         ***** ** *********** ***** ** ******** **** ******** ** ***

FAO-13  GCATACGATAAAGCGCAGGATTATGTTTGGCAGCAAATGGGAGCTTCTACCGAAGGCATC 960

FAO-20  GCATACGATAAAGCGCAGGATTATGTTTGGCAGCAAATGGGAGCTTCTACCGAAGGCATC 960

FAO-17  GCATACGATAAAGCGCAGGATTATGTTTGGCAGCAAATGGGAGCTTCTACCGAAGGCATC 960

FAO-18  GCCTACGACAAAGCACAGGATTATGTTTGGCAGCAAATGGGAGCTTCTACCGAAGGCATC 960

FAO2a   GCCTACGACAAAGCGCAGGATTATGTTTGGAAACAAATGGGTGCTTCAACAGATGGAATC 960

FAO2b   GCCTACGACAAAGCACAAGACTATGTTTGGAAACAAATGGGCGCTTCTACCGAAGGAATC 960
         ** ***** ***** ** ** ********* * ******** ***** ** **  ** ***
```

```
-continued
FAO-13  ACCCACTCTTTGGCTAACGAGATTATTATTGAAGGTGGTAAGAAATTAGGTTACAAGGCC  1020

FAO-20  ACCCACTCTTTGGCTAACGAGATTATTATTGAAGGTGGTAAGAAATTAGGTTACAAGGCC  1020

FAO-17  ACCCACTCTTTGGCTAACGAGATTATTATTGAAGGTGGTAAGAAATTAGGTTACAAGGCC  1020

FAO-18  ACCCACTCTTTGGCTAACGAGATTATTATTGAAGGTGGCAAGAAATTAGGTTACAAGGCC  1020

FAO2a   ACTCACTCCTTGGCCAACGAAGTTGTGGTTGAAGGAGGTAAGAAGTTGGGCTACAAGAGC  1020

FAO2b   ACTCACTCTTTGGCGAACGCGGTTGTGGTTGAAGGAGGTAAGAAGTTGGGTTACAAGAGC  1020
        ** ***** ***** ****  ** * ******* ** ***** ** ** ****** *

FAO-13  AAGGTATTAGACCAAAACAGCGGTGGTCATCCTCAGCACAGATGCGGTTTCTGTTATTTG  1080

FAO-20  AAGGTATTAGACCAAAACAGCGGTGGTCATCCTCAGCACAGATGCGGTTTCTGTTATTTG  1080

FAO-17  AAGGTATTAGACCAAAACAGCGGTGGTCATCCTCAGCACAGATGCGGTTTCTGTTATTTG  1080

FAO-18  AAGGTATTAGACCAAAACAGCGGTGGTCATCCTCATCACAGATGCGGTTTCTGTTATTTG  1080

FAO2a   AAGGAAATTGAGCAGAACAACGGTGGCCACCCTGACCACCCATGTGGTTTCTGTTACTTG  1080

FAO2b   AAGGAAATCGAGCAGAACAATGGTGGCCATCCTGACCACCCCTGTGGTTTCTGTTACTTG  1080
        ****  *  ** ** ****  *****  ** *** *  ***  ** *********** ***

FAO-13  GGCTGTAAGCACGGTATCAAGCAGGGTTCTGTTAATAACTGGTTTAGAGACGCAGCTGCC  1140

FAO-20  GGCTGTAAGCACGGTATCAAGCAGGGTTCTGTTAATAACTGGTTTAGAGACGCAGCTGCC  1140

FAO-17  GGTTGTAAGCACGGTATCAAGCAGGGCTCTGTTAATAACTGGTTTAGAGACGCAGCTGCC  1140

FAO-18  GGTTGTAAGCACGGTATCAAGCAGGGCTCTGTTAATAACTGGTTTAGAGACGCAGCTGCC  1140

FAO2a   GGCTGTAAGTACGGTATTAAACAGGGTTCTGTGAATAACTGGTTTAGAGACGCAGCTGCC  1140

FAO2b   GGCTGTAAGTACGGTATTAAGCAGGGTTCTGTGAATAACTGGTTTAGAGACGCAGCTGCC  1140
        ** ****** ******* ** ***** ***** ***************************

FAO-13  CACGGTTCCCAGTTCATGCAACAGGTTAGAGTTTTGCAAATACTTAACAAGAAGGGGATC  1200

FAO-20  CACGGTTCCCAGTTCATGCAACAGGTTAGAGTTTTGCAAATACTTAACAAGAAGGGGATC  1200

FAO-17  CACGGTTCTCAGTTCATGCAACAGGTTAGAGTTTTGCAAATCCTTAACAAGAAGGGCATC  1200

FAO-18  CACGGTTCTCAGTTCATGCAACAGGTTAGAGTTTTGCAAATCCTTAACAAGAAGGGCATC  1200

FAO2a   CACGGGTCCAAGTTCATGCAACAAGTCAGAGTTGTGCAAATCCTCAACAAGAATGGCGTC  1200

FAO2b   CACGGGTCCAAGTTCATGCAACAAGTCAGAGTTGTGCAAATCCTCCACAATAAAGGCGTC  1200
        ***** **  *********** ** ****** ** ****  ** ** ** ** **

FAO-13  GCTTACGGTATCTTGTGTGAGGATGTTGTAACCGGCGCCAAGTTCACCATTACTGGCCCC  1260

FAO-20  GCTTACGGTATCTTGTGTGAGGATGTTGTAACCGGCGCCAAGTTCACCATTACTGGCCCC  1260

FAO-17  GCTTATGGTATCTTGTGTGAGGATGTTGTAACCGGTGCCAAGTTCACCATTACTGGCCCC  1260

FAO-18  GCTTATGGTATCTTGTGTGAGGATGTTGTAACCGGTGCCAAGTTCACCATTACTGGCCCC  1260

FAO2a   GCTTATGGTATCTTGTGTGAGGATGTCGAAACCGGAGTCAGGTTCACTATTAGTGGCCCC  1260

FAO2b   GCTTATGGCATCTTGTGTGAGGATGTCGAGACCGGAGTCAAATTCACTATCAGTGGCCCC  1260
        ***** ** ****************  *  ***** * **  ** * * * *******

FAO-13  AAAAGTTTGTTGTTGCTGCCGGTGCTTTGAACACTCCATCTGTGTTGGTCAACTCCGGC  1320

FAO-20  AAAAGTTTGTTGTTGCTGCCGGTGCTTTGAACACTCCATCTGTGTTGGTCAACTCCGGC  1320

FAO-17  AAAAGTTTGTTGTTGCCGCCGGCGCCCTTAAACACTCCATCTGTGTTGGTCAACTCCGGA  1320

FAO-18  AAAAGTTTGTTGTTGCCGCCGGCGCCCTTAAACACTCCATCTGTGTTGGTCAACTCCGGA  1320

FAO2a   AAAAGTTTGTTGTTTCTGCTGGTTCTTTGAACACGCCAACTGTGTTGACCAACTCCGGA  1320

FAO2b   AAAAGTTTGTTGTTTCTGCAGGTTCTTTGAACACGCCAACGGTGTTGACCAACTCCGGA  1320
        **************  * ** ***  ** ***** ****   * ***** ** ********

FAO-13  TTCAAGAACAAGAACATCGGTAAGAACTTAACTTTGCACCCAGTTTCTGTCGTGTTTGGT  1380

FAO-20  TTCAAGAACAAGAACATCGGTAAGAACTTAACTTTGCACCCAGTTTCTGTCGTGTTTGGT  1380
```

```
FAO-17   TTCAAGAACAAGAACATCGGTAAGAACTTAACTTTGCATCCAGTTTCTGTCGTGTTTGGT 1380
FAO-18   TTCAAGAACAAGAACATCGGTAAGAACTTAACTTTGCATCCAGTTTCTGTCGTGTTTGGT 1380
FAO2a    TTCAAGAACAAGCACATTGGTAAGAACTTGACGTTGCACCCAGTTTCCACCGTGTTTGGT 1380
FAO2b    TTCAAGAACAAACACATCGGTAAGAACTTGACGTTGCACCCAGTTTCGACCGTGTTTGGT 1380
         *********** **** *********** ** ***** ********  **********

FAO-13   GATTTTGGCAAAGACGTTCAAGCAGACCACTTCCACAACTCCATCATGACTGCCCTTTGT 1440
FAO-20   GATTTTGGCAAAGACGTTCAAGCAGACCACTTCCACAACTCCATCATGACTGCCCTTTGT 1440
FAO-17   GATTTTGGCAAAGACGTTCAAGCAGACCACTTCCACAACTCCATCATGACTGCCCTTTGT 1440
FAO-18   GATTTTGGCAAAGACGTTCAAGCAGATCACTTCCACAACTCCATCATGACTGCTCTTTGT 1440
FAO2a    GACTTTGGCAGAGACGTGCAAGCCGACCATTTCCACAAATCTATTATGACTTCGCTTTGT 1440
FAO2b    GACTTTGGCAGAGACGTGCAAGCCGACCATTTCCACAAATCTATTATGACTTCGCTCTGT 1440
         ** ******* ****** *****  ** ** ******** ** ** ****** * ** ***

FAO-13   TCAGAAGCCGCTGATTTAGACGGCAAGGGCCATGGATGCAGAATTGAAACCATCTTGAAC 1500
FAO-20   TCAGAAGCCGCTGATTTAGACGGCAAGGGCCATGGATGCAGAATTGAAACCATCTTGAAC 1500
FAO-17   TCAGAAGCCGCTGATTTAGACGGCAAGGGCCATGGATGCAGAATTGAAACCATCTTGAAC 1500
FAO-18   TCAGAAGCCGCTGATTTAGACGGCAAGGGTCATGGATGCAGAATTGAAACCATCTTGAAC 1500
FAO2a    TACGAGGTTGCTGACTTGGACGGCAAGGGCCACGGATGCAGAATCGAAACCATCTTGAAC 1500
FAO2b    TACGAAGTCGCTGACTTGGACGGCAAGGGCCACGGATGCAGAATCGAGACCATCTTGAAC 1500
         * **  ***** ** *********** ** *********** ** ************

FAO-13   GCTCCATTCATCCAGGCTTCATTCTTACCATGGAGAGGTAGTAACGAGGCTAGACGAGAC 1560
FAO-20   GCTCCATTCATCCAGGCTTCATTCTTACCATGGAGAGGTAGTAACGAGGCTAGACGAGAC 1560
FAO-17   GCTCCATTCATCCAGGCTTCATTCTTACCATGGAGAGGTAGTAACGAGGCTAGACGAGAC 1560
FAO-18   GCTCCATTCATCCAGGCTTCATTCTTACCATGGAGAGGTAGTAACGAGGCTAGACGAGAC 1560
FAO2a    GCTCCATTCATCCAAGCTTCTTTGTTGCCATGGAGAGGAAGTGACGAGGTCAGAAGAGAC 1560
FAO2b    GCTCCATTCATCCAAGCTTCTTTGTTGCCATGGAGAGGAAGCGACGAGGTCAGAAGAGAC 1560
         ************** ***** ** ** *********** ** ****** *** *****

FAO-13   TTGTTGCGTTACAACAACATGGTGGCGATGTTGCTCCTTAGTCGTGACACCACCAGTGGT 1620
FAO-20   TTGTTGCGTTACAACAACATGGTGGCGATGTTGCTCCTTAGTCGTGACACCACCAGTGGT 1620
FAO-17   TTGTTGCGTTACAACAACATGGTGGCGATGTTGCTCCTTAGTCGTGACACCACCAGTGGT 1620
FAO-18   TTGTTGCGTTACAACAACATGGTGGCCATGTTACTTCTTAGTCGTGATACCACCAGTGGT 1620
FAO2a    TTGTTGCGTTACAACAACATGGTGGCCATGTTGCTTATCACGCGTGATACCACCAGTGGT 1620
FAO2b    TTGTTGCGTTACAACAACATGGTGGCCATGTTGCTTATCACCCGTGACACCACCAGTGGT 1620
         ************************** ***** ** *  * ***** ************

FAO-13   TCCGTTTCTGCTCATCCAACCAAACCTGAAGCTTTGGTTGTCGAGTACGACGTGAACAAG 1680
FAO-20   TCCGTTTCTGCTCATCCAACCAAACCTGAAGCTTTGGTTGTCGAGTACGACGTGAACAAG 1680
FAO-17   TCCGTTTCTGCTCATCCAACCAAACCTGAAGCTTTGGTTGTCGAGTACGACGTGAACAAG 1680
FAO-18   TCCGTTTCGTCCCATCCAACTAAACCTGAAGCATTAGTTGTCGAGTACGACGTGAACAAG 1680
FAO2a    TCAGTTTCTGCTGACCCAAAGAAGCCCGACGCTTTGATTGTCGACTATGAGATTAACAAG 1680
FAO2b    TCAGTTTCTGCTGACCCAAAGAAGCCCGACGCTTTGATTGTCGACTATGACATCAACAAG 1680
         ** *****   *    ***   **  **  ** **  ****** **  *   * ******

FAO-13   TTTGACAGAAACTCGATCTTGCAGGCATTGTTGGTCACTGCTGACTTGTTGTATATCCAA 1740
FAO-20   TTTGACAGAAACTCGATCTTGCAGGCATTGTTGGTCACTGCTGACTTGTTGTATATCCAA 1740
FAO-17   TTTGACAGAAACTCGATCTTGCAGGCATTGTTGGTCACTGCTGACTTGTTGTATATCCAA 1740
```

```
FAO-18   TTTGACAGAAACTCCATCTTGCAGGCATTGTTGGTCACTGCTGACTTGTTGTACATTCAA 1740

FAO2a    TTTGACAAGAATGCCATCTTGCAAGCTTTCTTGATCACTTCCGACATGTTGTACATTGAA 1740

FAO2b    TTTGACAAGAATGCCATCTTGCAAGCTTTCTTGATCACCTCCGACATGTTGTACATCGAA 1740
         *******  ** * ********  ** ** *** **** * *** ******* ** **

FAO-13   GGTGCCAAGAGAATCCTTAGTCCACAGGCATGGGTGCCAATTTTTGAATCCGACAAGCCA 1800

FAO-20   GGTGCCAAGAGAATCCTTAGTCCACAGGCATGGGTGCCAATTTTTGAATCCGACAAGCCA 1800

FAO-17   GGTGCCAAGAGAATCCTTAGTCCACAGGCATGGGTGCCAATTTTTGAATCCGACAAGCCA 1800

FAO-18   GGTGCCAAGAGAATCCTTAGTCCCCAACCATGGGTGCCAATTTTTGAATCCGACAAGCCA 1800

FAO2a    GGTGCCAAGAGAATCCTCAGTCCACAGCCATGGGTGCCAATCTTTGAGTCGAACAAGCCA 1800

FAO2b    GGTGCCAAGAGAATCCTCAGTCCACAGGCATGGGTGCCAATCTTTGAGTCGAACAAGCCA 1800
         ***************** ***** ** ************* ***** ** ********

FAO-13   AAGGATAAGAGATCAATCAAGGACGAGGACTATGTCGAATGGAGAGCCAAGGTTGCCAAG 1860

FAO-20   AAGGATAAGAGATCAATCAAGGACGAGGACTATGTCGAATGGAGAGCCAAGGTTGCCAAG 1860

FAO-17   AAGGATAAGAGATCAATCAAGGACGAGGACTATGTCGAATGGAGAGCCAAGGTTGCCAAG 1860

FAO-18   AAGGATAAGAGATCAATCAAGGACGAGGACTATGTCGAATGGAGAGCCAAGGTTGCCAAG 1860

FAO2a    AAGGAGCAAAGAACGATCAAGGACAAGGACTATGTTGAGTGGAGAGCCAAGGCTGCTAAG 1860

FAO2b    AAGGAGCAAAGAACAATCAAGGACAAGGACTATGTCGAATGGAGAGCCAAGGCTGCCAAG 1860
         *****  *** * ********** ********** ** ************* *** ***

FAO-13   ATTCCTTTCGACACCTACGGCTCACCTTATGGTTCGGCACATCAAATGTCTTCTTGCCGT 1920

FAO-20   ATTCCTTTCGACACCTACGGCTCACCTTATGGTTCGGCACATCAAATGTCTTCTTGCCGT 1920

FAO-17   ATTCCTTTCGACACCTACGGCTCACCTTATGGTTCGGCACATCAAATGTCTTCTTGCCGT 1920

FAO-18   ATTCCTTTTGACACCTACGGCTCGCCTTATGGTTCGGCGCATCAAATGTCTTCTTGTCGT 1920

FAO2a    ATACCTTTCGACACCTACGGTTCTGCATATGGGTCCGCACATCAAATGTCCACCTGTCGT 1920

FAO2b    ATACCTTTCGACACCTACGGTTCTGCCTATGGGTCCGCACATCAAATGTCCACCTGTCGT 1920
         ** ***** ***********  ** * *****  ** ** ********** *  ** ***

FAO-13   ATGTCAGGTAAGGGTCCTAAATACGGTGCTGTTGACACCGATGGTAGATTGTTTGAATGT 1980

FAO-20   ATGTCAGGTAAGGGTCCTAAATACGGTGCTGTTGACACCGATGGTAGATTGTTTGAATGT 1980

FAO-17   ATGTCAGGTAAGGGTCCTAAATACGGTGCTGTTGACACCGATGGTAGATTGTTTGAATGT 1980

FAO-18   ATGTCAGGTAAGGGTCCTAAATACGGTGCTGTTGATACCGATGGTAGATTGTTTGAATGT 1980

FAO2a    ATGTCCGGAAAGGGTCCTAAATACGGTGCTGTTGATACTGATGGTAGATTGTTTGAATGT 1980

FAO2b    ATGTCCGGAAAGGGTCCTAAATACGGCGCCGTTGATACCGATGGTAGATTGTTTGAATGT 1980
         *****  ** ****************  ** *****  ** *******************

FAO-13   TCGAATGTTTATGTTGCCGATGCAAGTCTTTTGCCAACTGCAAGCGGTGCCAACCCTATG 2040

FAO-20   TCGAATGTTTATGTTGCCGATGCAAGTCTTTTGCCAACTGCAAGCGGTGCCAACCCTATG 2040

FAO-17   TCGAATGTTTATGTTGCCGATGCAAGTCTTTTGCCAACTGCAAGCGGTGCCAACCCTATG 2040

FAO-18   TCGAATGTTTATGTTGCTGACGCTAGTCTTTTGCCAACTGCTAGCGGTGCTAATCCTATG 2040

FAO2a    TCGAATGTCTATGTTGCTGATGCTAGTGTTTTGCCTACTGCCAGCGGTGCCAACCCAATG 2040

FAO2b    TCGAATGTCTATGTTGCTGATGCTAGTGTTTTGCCTACTGCCAGCGGTGCCAACCCAATG 2040
         ******** ******** ** ** *** ******* ***** ******** ** ** ***

FAO-13   GTCACCACCATGACTCTTGCCAGACATGTTGCGTTAGGTTTGGCAGACTCCTTGAAGACC 2100

FAO-20   GTCACCACCATGACTCTTGCCAGACATGTTGCGTTAGGTTTGGCAGACTCCTTGAAGACC 2100

FAO-17   GTCACCACCATGACTCTTGCAAGACATGTTGCGTTAGGTTTGGCAGACTCCTTGAAGACC 2100

FAO-18   GTCACCACCATGACTCTTGCAAGACATGTTGCGTTAGGTTTGGCAGACTCCTTGAAGACC 2100

FAO2a    ATATCCACCATGACCTTTGCTAGACAGATTGCGTTAGGTTTGGCTGACTCCTTGAAGACC 2100
```

-continued

```
FAO2b  ATCTCCACCATGACGTTTGCTAGACAGATTGCGTTAGGTTTGGCTGACTCTTTGAAGACC 2100
       * ********** **** ***** **************** ***** *********

FAO-13 AAAGCCAAGTTGTAG                                              2115

FAO-20 AAAGCCAAGTTGTAG                                              2115

FAO-17 AAGGCCAAGTTGTAG                                              2115

FAO-18 AAGGCCAAGTTGTAG                                              2115

FAO2a  AAACCCAAGTTGTAG                                              2115

FAO2b  AAACCCAAGTTGTAG                                              2115
       ** ***********
```

Amino Acid Sequences

FAO-1 -
SEQ ID NO: 7
MAPFLPDQVDYKHVDTLMLLCDGIIHETTVDEIKDVIAPDFPADKYEEYVRTFTKPSETPGFRETVY

NTVNANTMDAIHQFIILTNVLGSRVLAPALTNSLTPIKDMSLEDREKLLASWRDSPIAAKRKLFRLVS

TLTLVTFTRLANELHLKAIHYPGREDREKAYETQEIDPFKYQFLEKPKFYGAELYLPDIDVIIIGSGAG

AGVVAHTLTNDGFKSLVLEKGRYFSNSELNFDDKDGVQELYQSGGTLTTVNQQLFVLAGSTFGGG

GTTVNWSACLKTPFKVRKEWYDEFGVDFAADEAYDKAQDYVWQQMGASTEGITHSLANEIIIEGG

KKLGYKAKVLDQNSGGHPHHRCGFCYLGCKHGIKQGSVNNWFRDAAAHGSQFMQQVRVLQILN

KKGIAYGILCEDVVTGAKFTITGPKKFVVAAGALNTPSVLVNSGFKNKNIGKNLTLHPVSVVFGDFG

KDVQADHFHNSIMTALCSEAADLDGKGHGCRIETILNAPFIQASFLPWRGSNEARRDLLRYNNMV

AMLLLSRDTTSGSVSSHPTKPEALVVEYDVNKFDRNSILQALLVTADLLYIQGAKRILSPQPWVPIF

ESDKPKDKRSIKDEDYVEWRAKVAKIPFDTYGSPYGSAHQMSSCRMSGKGPKYGAVDTDGRLFE

CSNVYVADASLLPTASGANPMVTTMTLARHVALGLADSLKTKAKL

FAO-13 -
SEQ ID NO: 8
MAPFLPDQVDYKHVDTLMLLCDGIIHETTVDQIKDVIAPDFPADKYEEYVRTFTKPSETPGFRETVY

NTVNANTTDAIHQFIILTNVLASRVLAPALTNSLTPIKDMSLEDREKLLASWRDSPIAAKRKLFRLVST

LTLVTFTRLANELHLKAIHYPGREDREKAYETQEIDPFKYQFLEKPKFYGAELYLPDIDVIIIGSGAGA

GVVAHTLANDGFKSLVLEKGKYFSNSELNFDDKDGVQELYQSGGTLTTVNQQLFVLAGSTFGGG

TTVNWSACLKTPFKVRKEWYDEFGVDFAADEAYDKAQDYVWQQMGASTEGITHSLANEIIIEGGK

KLGYKAKVLDQNSGGHPQHRCGFCYLGCKHGIKQGSVNNWFRDAAAHGSQFMQQVRVLQILNK

KGIAYGILCEDVVTGAKFTITGPKKFVVAAGALNTPSVLVNSGFKNKNIGKNLTLHPVSVVFGDFGK

DVQADHFHNSIMTALCSEAADLDGKGHGCRIETILNAPFIQASFLPWRGSNEARRDLLRYNNMVA

MLLLSRDTTSGSVSAHPTKPEALVVEYDVNKFDRNSILQALLVTADLLYIQGAKRILSPQAWVPIFE

SDKPKDKRSIKDEDYVEWRAKVAKIPFDTYGSPYGSAHQMSSCRMSGKGPKYGAVDTDGRLFEC

SNVYVADASLLPTASGANPMVTTMTLARHVALGLADSLKTKAKL

FAO-20 -
SEQ ID NO: 9
MAPFLPDQVDYKHVDTLMLLCDGIIHETTVDQIKDVIAPDFPADKYEEYVRTFTKPSETPGFRETVY

NTVNANTTDAIHQFIILTNVLASRVLAPALTNSLTPIKDMSLEDREKLLASWRDSPIAAKRKLFRLVST

LTLVTFTRLANELHLKAIHYPGREDREKAYETQEIDPFKYQFMEKPKFDGAELYLPDIDVIIIGSGAG

AGVVAHTLANDGFKSLVLEKGKYFSNSELNFDDKDGVQELYQSGGTLTTVNQQLFVLAGSTFGGG

GTTVNWSACLKTPFKVRKEWYDEFGVDFAADEAYDKAQDYVWQQMGASTEGITHSLANEIIIEGG

-continued

KKLGYKAKVLDQNSGGHPQHRCGFCYLGCKHGIKQGSVNNWFRDAAAHGSQFMQQVRVLQILN

KKGIAYGILCEDVVTGAKFTITGPKKFVVAAGALNTPSVLVNSGFKNKNIGKNLTLHPVSVVFGDFG

KDVQADHFHNSIMTALCSEAADLDGKGHGCRIETILNAPFIQASFLPWRGSNEARRDLLRYNNMV

AMLLLSRDTTSGSVSAHPTKPEALVVEYDVNKFDRNSILQALLVTADLLYIQGAKRILSPQAWVPIF

ESDKPKDKRSIKDEDYVEWRAKVAKIPFDTYGSPYGSAHQMSSCRMSGKGPKYGAVDTDGRLFE

CSNVYVADASLLPTASGANPMVTTMTLARHVALGLADSLKTKAKL

FAO-17 - SEQ ID NO: 10
MAPFLPDQVDYKHVDTLMLLCDGIIHETTVDEIKDVIAPDFPADKYEEYVRTFTKPSETPGFRETVY

NTVNANTMDAIHQFIILTNVLGSRVLAPALTNSLTPIKDMSLEDREKLLASWRDSPIAAKRKLFRLVS

TLTLVTFTRLANELHLKAIHYPGREDREKAYETQEIDPFKYQFLEKPKFYGAELYLPDIDVIIIGSGAG

AGVVAHTLANDGFKSLVLEKGKYFSNSELNFDDKDGVQELYQSGGTLTTVNQQLFVLAGSTFGG

GTTVNWSACLKTPFKVRKEWYDEFGVDFAADEAYDKAQDYVWQQMGASTEGITHSLANEIIIEGG

KKLGYKAKVLDQNSGGHPQHRCGFCYLGCKHGIKQGSVNNWFRDAAAHGSQFMQQVRVLQILN

KKGIAYGILCEDVVTGAKFTITGPKKFVVAAGALNTPSVLVNSGFKNKNIGKNLTLHPVSVVFGDFG

KDVQADHFHNSIMTALCSEAADLDGKGHGCRIETILNAPFIQASFLPWRGSNEARRDLLRYNNMV

AMLLLSRDTTSGSVSAHPTKPEALVVEYDVNKFDRNSILQALLVTADLLYIQGAKRILSPQAWVPIF

ESDKPKDKRSIKDEDYVEWRAKVAKIPFDTYGSPYGSAHQMSSCRMSGKGPKYGAVDTDGRLFE

CSNVYVADASLLPTASGANPMVTTMTLARHVALGLADSLKTKAKL

FAO-2a - SEQ ID NO: 11
MNTFLPDVLEYKHVDTLLLLCDGIIHETTVDQIKDAIAPDFPEDQYEEYLKTFTKPSETPGFREAVYD

TINATPTDAVHMCIVLTTALDSRILAPTLTNSLTPIKDMTLKEREQLLASWRDSPIAAKRRLFRLISSL

TLTTFTRLASELHLKAIHYPGRDLREKAYETQVVDPFRYSFMEKPKFDGAELYLPDIDVIIIGSGAGA

GVVMAHTLANDGFKTLVLEKGKYFSNSELNFNDADGVKELYQGKGALATTNQQMFILAGSTLGGGT

TVNWSACLKTPFKVRKEWYDEFGLEFAADEAYDKAQDYVWKQMGASTDGITHSLANEVVVEGG

KKLGYKSKEIEQNNGGHPDHPCGFCYLGCKYGIKQGSVNNWFRDAAAHGSKFMQQVRVVQILNK

NGVAYGILCEDVETGVRFTISGPKKFVVSAGSLNTPTVLTNSGFKNKHIGKNLTLHPVSTVFGDFG

RDVQADHFHKSIMTSLCYEVADLDGKGHGCRIETILNAPFIQASLLPWRGSDEVRRDLLRYNNMVA

MLLITRDTTSGSVSADPKKPDALIVDYEINKFDKNAILQAFLITSDMLYIEGAKRILSPQPWVPIFESN

KPKEQRTIKDKDYVEWRAKAAKIPFDTYGSAYGSAHQMSTCRMSGKGPKYGAVDTDGRLFECSN

VYVADASVLPTASGANPMISTMTFARQIALGLADSLKTKPKL

FAO-2b - SEQ ID NO: 12
MNTFLPDVLEYKHVDTLLLLCDGIIHETTVDQIRDAIAPDFPEDQYEEYLKTFTKPSETPGFREAVYD

TINSTPTEAVHMCIVLTTALDSRILAPTLTNSLTPIKDMTLKEREQLLAAWRDSPIAAKRRLFRLISSL

TLTTFTRLASDLHLRAIHYPGRDLREKAYETQVVDPFRYSFMEKPKFDGTELYLPDIDVIIIGSGAGA

GVMAHTLANDGYKTLVLEKGKYFSNSELNFNDADGMKELYQGKCALTTTNQQMFILAGSTLGGG

TTVNWSACLKTPFKVRKEWYDEFGLEFAADEAYDKAQDYVWKQMGASTEGITHSLANAVVEGG

KKLGYKSKEIEQNNGGHPDHPCGFCYLGCKYGIKQGSVNNWFRDAAAHGSKFMQQVRVVQILHN

KGVAYGILCEDVETGVKFTISGPKKFVVSAGSLNTPTVLTNSGFKNKHIGKNLTLHPVSTVFGDFGR

DVQADHFHKSIMTSLCYEVADLDGKGHGCRIETILNAPFIQASLLPWRGSDEVRRDLLRYNNMVA

MLLITRDTTSGSVSADPKKPDALIVDYDINKFDKNAILQAFLITSDMLYIEGAKRILSPQAWVPIFESN

KPKEQRTIKDKDYVEWRAKAAKIPFDTYGSAYGSAHQMSTCRMSGKGPKYGAVDTDGRLFECSN

VYVADASVLPTASGANPMISTMTFARQIALGLADSLKTKPKL

Clustal Amino Acid Sequence Alignments

```
FAO-13  MAPFLPDQVDYKHVDTLMLLCDGIIHETTVDQIKDVIAPDFPADKYEEYVRTFTKPSETP    60

FAO-20  MAPFLPDQVDYKHVDTLMLLCDGIIHETTVDQIKDVIAPDFPADKYEEYVRTFTKPSETP    60

FAO-1   MAPFLPDQVDYKHVDTLMLLCDGIIHETTVDEIKDVIAPDFPADKYEEYVRTFTKPSETP    60
        *******************************:****************************

FAO-13  GFRETVYNTVNANTTDAIHQFIILTNVLASRVLAPALTNSLTPIKDMSLEDREKLLASWR   120

FAO-20  GFRETVYNTVNANTTDAIHQFIILTNVLASRVLAPALTNSLTPIKDMSLEDREKLLASWR   120

FAO-1   GFRETVYNTVNANTMDAIHQFIILTNVLGSRVLAPALTNSLTPIKDMSLEDREKLLASWR   120
        **************.************.********************************

FAO-13  DSPIAAKRKLFRLVSTLTLVTFTRLANELHLKAIHYPGREDREKAYETQEIDPFKYQFLE   180

FAO-20  DSPIAAKRKLFRLVSTLTLVTFTRLANELHLKAIHYPGREDREKAYETQEIDPFKYQMLE   180

FAO-1   DSPIAAKRKLFRLVSTLTLVTFTRLANELHLKAIHYPGREDREKAYETQEIDPFKYQFLE   180
        ********************************************************:*

FAO-13  KPKFYGAELYLPDIDVIIIGSGAGAGVVAHTLANDGFKSLVLEKGKYFSNSELNFDDKDG   240

FAO-20  KPKFDGAELYLPDIDVIIIGSGAGAGVVAHTLANDGFKSLVLEKGKYFSNSELNFDDKDG   240

FAO-1   KPKFYGAELYLPDIDVIIIGSGAGAGVVAHTLTNDGFKSLVLEKGRYFSNSELNFDDKDG   240
        **** ***************************:***********:***************

FAO-13  VQELYQSGGTLTTVNQQLFVLAGSTFGGGTTVNWSACLKTPFKVRKEWYDEFGVDFAADE   300

FAO-20  VQELYQSGGTLTTVNQQLFVLAGSTFGGGTTVNWSACLKTPFKVRKEWYDEFGVDFAADE   300

FAO-1   VQELYQSGGTLTTVNQQLFVLAGSTFGGGTTVNWSACLKTPFKVRKEWYDEFGVDFAADE   300
        ************************************************************

FAO-13  AYDKAQDYVWQQMGASTEGITHSLANEIIIEGGKKLGYKAKVLDQNSGGHPQHRCGFCYL   360

FAO-20  AYDKAQDYVWQQMGASTEGITHSLANEIIIEGGKKLGYKAKVLDQNSGGHPQHRCGFCYL   360

FAO-1   AYDKAQDYVWQQMGASTEGITHSLANEIIIEGGKKLGYKAKVLDQNSGGHPHHRCGFCYL   360
        **************************************************:********

FAO-13  GCKHGIKQGSVNNWFRDAAAHGSQFMQQVRVLQILNKKGIAYGILCEDVVTGAKFTITGP   420

FAO-20  GCKHGIKQGSVNNWFRDAAAHGSQFMQQVRVLQILNKKGIAYGILCEDVVTGAKFTITGP   420

FAO-1   GCKHGIKQGSVNNWFRDAAAHGSQFMQQVRVLQILNKKGIAYGILCEDVVTGAKFTITGP   420
        ************************************************************

FAO-13  KKFVVAAGALNTPSVLVNSGFKNKNIGKNLTLHPVSVVFGDFGKDVQADHFHNSIMTALC   480

FAO-20  KKFVVAAGALNTPSVLVNSGFKNKNIGKNLTLHPVSVVFGDFGKDVQADHFHNSIMTALC   480

FAO-1   KKFVVAAGALNTPSVLVNSGFKNKNIGKNLTLHPVSVVFGDFGKDVQADHFHNSIMTALC   480
        ************************************************************

FAO-13  SEAADLDGKGHGCRIETILNAPFIQASFLPWRGSNEARRDLLRYNNMVAMLLLSRDTTSG   540

FAO-20  SEAADLDGKGHGCRIETILNAPFIQASFLPWRGSNEARRDLLRYNNMVAMLLLSRDTTSG   540

FAO-1   SEAADLDGKGHGCRIETILNAPFIQASFLPWRGSNEARRDLLRYNNMVAMLLLSRDTTSG   540
        ************************************************************

FAO-13  SVSAHPTKPEALVVEYDVNKFDRNSILQALLVTADLLYIQGAKRILSPQAWVPIFESDKP   600

FAO-20  SVSAHPTKPEALVVEYDVNKFDRNSILQALLVTADLLYIQGAKRILSPQAWVPIFESDKP   600

FAO-1   SVSSHPTKPEALVVEYDVNKFDRNSILQALLVTADLLYIQGAKRILSPQPWVPIFESDKP   600
        ***:*********************************************.**********

FAO-13  KDKRSIKDEDYVEWRAKVAKIPFDTYGSPYGSAHQMSSCRMSGKGPKYGAVDTDGRLFEC   660
```

```
-continued
FAO-20  KDKRSIKDEDYVEWRAKVAKIPFDTYGSPYGSAHQMSSCRMSGKGPKYGAVDTGRLFEC    660

FAO-1   KDKRSIKDEDYVEWRAKVAKIPFDTYGSPYGSAHQMSSCRMSGKGPKYGAVDTGRLFEC    660
        ************************************************************
```
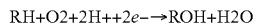
```
                                                                    (SEQ ID NO: 8)
FAO-13  SNVYVADASLLPTASGANPMVTTMTLARHVALGLADSLKTKAKL                      704

(SEQ ID NO: 9)
FAO-20  SNVYVADASLLPTASGANPMVTTMTLARHVALGLADSLKTKAKL                      704

(SEQ ID NO: 7)
FAO-1   SNVYVADASLLPTASGANPMVTTMTLARHVALGLADSLKTKAKL                      704
```

Example 31

Addition and/or Amplification of Monooxygenase and Monooxygenase Reductase Activities Cytochrome P450's often catalyze a monooxygenase reaction, e.g., insertion of one atom of oxygen into an organic substrate (RH) while the other oxygen atom is reduced to water:

$$RH + O_2 + 2H^+ + 2e^- \rightarrow ROH + H_2O$$

The substrates sometimes are of a homogeneous carbon chain length. Enzymes with monooxygenase activity sometimes recognize substrates of specific carbon chain lengths, or a subgroup of carbon chain lengths with respect to organic substrates of homogenous carbon chain length. Addition of novel cytochrome activities (e.g., *B. megaterium* BM3) and/or amplification of certain or all endogenous or heterologous monooxygenase activities (e.g., CYP52A12 polynucleotide, CYP52A13 polynucleotide, CYP52A14 polynucleotide, CYP52A15 polynucleotide, CYP52A16 polynucleotide, CYP52A17 polynucleotide, CYP52A18 polynucleotide, CYP52A19 polynucleotide, CYP52A20 polynucleotide, CYP52D2 polynucleotide, BM3 polynucleotide) can contribute to an overall increase in carbon flux through native and/or engineered metabolic pathways, in some embodiments. In certain embodiments, adding a novel monooxygenase or increasing certain or all endogenous or heterologous monooxygenase activities can increase the flux of substrates of specific carbon chain length or subgroups of substrates with mixtures of specific carbon chain lengths. In some embodiments, the selection of a monooxygenase activity for amplification in an engineered strain is related to the feedstock utilized for growth of the engineered strain, pathways for metabolism of the chosen feedstock and the desire end product (e.g., adipic acid).

Strains engineered to utilize plant-based oils for conversion to adipic acid, would benefit by having one or more monooxygenase activities with substrate specificity that matches the fatty acid chain-length distribution of the oil. For example, the most prevalent fatty acid in coconut oil is lauric acid (12 carbons long), therefore, the monooxygenase activity chosen for a coconut oil-utilizing strain would have a substrate preference for C12 fatty acids. For strains engineered to utilize other plant based oils with different fatty acid chain-length distributions it would be desirable to amplify a monooxygenase activity that has a matching substrate preference. In some embodiments, a genetic modification that alters monooxygenase activity increases the activity of one or more monooxygenase activities with a substrate preference for fatty acids prevalent in coconut oil. In certain embodiments, the genetic modification increases the activity of a monooxygenase activity with a preference for C12 fatty acids.

Strains engineered to utilize glucose for conversion to adipic acid, would benefit by choosing a monooxygenase activity that can utilize the distribution of chain lengths produced by fatty acid synthase (FAS). For strains engineered to utilize the long chain fatty acids produced by FAS, it often is desirable to add and/or amplify one or more monooxygenase activities preferring long chain fatty acids. For strains engineered to utilize a mutant FAS that produces medium- or short-chain fatty acids, or a specialized FAS (e.g., hexanoate synthase), it often is desirable to add and/or amplify one or more monooxygenase activities preferring medium- or short-chain fatty acids. In some embodiments, a genetic modification that alters monooxygenase activity increases the activity of one or more monooxygenase activities with a preference for the long chain fatty acids produced by fatty acid synthase activity (e.g., FAS). In certain embodiments, the genetic modification increases the activity of a monooxygenase activity with a preference for the medium- or short-chain fatty acids produced by a mutant or specialized FAS.

As mentioned previously, the enzymes that carry out the monooxygenase activity are reduced by the activity of monooxygenase reductase, thereby regenerating the enzyme. Selection of a CPR for amplification in an engineered strain depends upon which P450 is amplified, in some embodiments. A particular CPR may interact preferentially with one or more monooxygenase activities, in some embodiments, but not well with other monooxygenases. A monooxygenase reductase from *C. tropicalis* strain ATCC750, two monooxygenase reductase activities from *C. tropicalis* strain ATCC20336 and a monooxygenase reductase activity from *Bacillus megaterium* are being evaluated for activity with the added and/or amplified monooxygenases described herein. Provided in the tables below are nucleotide sequences used to add or amplify monooxygenase and monooxygenase reductase activities.

Monooxygenase Activity Nucleotide Sequences

| SEQ ID NO | Description | Sequence |
|---|---|---|
| SEQ ID NO: 13 | cytochrome P450 A12 (CYP52A12) | atggccacacaagaaatcatcgattctgtacttccgtacttgaccaaatggtacactgtg attactgcagcagtattagtcttccttatctccacaaacatcaagaactacgtcaaggca aagaaattgaaatgtgtcgatccaccatacttgaaggatgccggtctcactggtattctg tctttgatcgccgccatcaaggccaagaacgacggtagattggctaactttgccgatga agtttttcgacgagtacccaaaccacaccttctacttgtctgttgccggtgctttgaagattg |

| SEQ ID NO | Description | Sequence |
|---|---|---|
| | | tcatgactgttgacccagaaaacatcaaggctgtcttggccacccaattcactgacttct<br>ccttgggtaccagacacgcccactttgctcctttgttgggtgacggtatcttcaccttgga<br>cggagaaggttggaagcactccagagctatgttgagaccacagtttgctagagacca<br>gattggacacgttaaagccttggaaccacacatccaaatcatggctaagcagatcaa<br>gttgaaccagggaaagactttcgatatccaagaattgttctttagatttaccgtcgacac<br>cgctactgagttcttgtttggtaatccgttcactccttgtacgatgaaaaattgggcatcc<br>caactccaaacgaaatcccaggaagagaaaacttgccgctgctttcaacgtttccca<br>acactacttggccaccagaagttactcccagacttttttactttttgaccaacccttaagga<br>attcagagactgtaacgccaaggtccaccacttggccaagtactttgtcaacaaggcc<br>ttgaactttactcctgaagaactcgaagagaaatccaagtccggttacgttttcttgtacg<br>aattggttaagcaaaccagagatccaaaggtcttgcaagatcaattgttgaacattatg<br>gttgccggaagagacaccactgccggtttgttgtcctttgctttgtttgaattggctagaca<br>cccagagatgtggtccaagttgagagaagaaatcgaagttaacttggtgttggtgaa<br>gactcccgcgttgaagaaattaccttcgaagccttgaagagatgtgaatacttgaagg<br>ctatccttaacgaaaccttgcgtatgtacccatctgttcctgtcaactttagaaccgccac<br>cagagacaccactttgccaagaggtggtggtgctaacggtaccgacccaatctacatt<br>cctaaaggctccactgttgcttacgttgtctacaagacccaccgtttggaagaatactac<br>ggtaaggacgctaacgacttcagaccagaaagatggtttgaaccatctactaagaag<br>ttgggctgggcttatgttccattcaacggtggtccaagagtctgcttgggtcaacaattcg<br>ccttgactgaagcttcttatgtgatcactagattggcccagatgtttgaaactgtctcatct<br>gatccaggtctcgaatacctccaccaaagtgtattcacttgaccatgagtcacaacg<br>atagtgtctttgtcaagatgtaa |
| SEQ ID NO: 14 | cytochrome<br>P450 A13<br>(CYP52A13) | atgactgtacacgatattatcgccacatacttcaccaaatggtacgtgatagtaccactc<br>gctttgattgcttatagagtcctcgactacttctatggcagatacttgatgtacaagcttggt<br>gctaaaccattttttccagaaacagacagacggctgtttcggattcaaagctccgcttga<br>attgttgaagaagaagcgacggtaccctcatagacttcacactccagcgtatccac<br>gatctcgatcgtcccgatatcccaacttttcacattcccggtctttttccatcaaccttgtcaat<br>acccttgagccggagaacatcaaggccatcttggccactcagttcaacgatttctcctt<br>gggtaccagacactcgcactttgctcctttgttgggtgatggtatctttacgttggatggcg<br>ccggctggaagcacagcagatctatgttgagaccacagtttgccagagaacagattt<br>cccacgtcaagttgttggagcacacgttcaggtgttcttcaaacacgtcagaaaggc<br>acagggcaagacttttgacatccaggaattgttttttcagattgaccgtcgactccgccac<br>cgagttttgtttggtgaatccgttgagtccttgagagatgaatctatcggcatgtccatca<br>atgcgcttgactttgacggcaaggctggctttgctgatgcttttaactattcgcagaattatt<br>tggcttcgagagcggttatgcaacaattgtactgggtgttgaacgggaaaaagtttaag<br>gagtgcaacgctaaagtgcacaagtttgctgactactacgtcaacaaggctttggactt<br>gacgcctgaacaattggaaaagcaggatggttatgtgttttttgtacgaattggtcaagc<br>aaaccagagacaagcaagtgttgagagaccaattgttgaacatcatggttgctggta<br>gagacaccaccgccggtttgttgtcgtttgttttcttgaattggccagaaacccagaagt<br>taccaacaagttgagagaagaaattgaggacaagtttggactcggtgagaatgctag<br>tgttgaagacatttcctttgagtcgttgaagtcctgtgaatacttgaaggctgttctcaacg<br>aaaccttgagattgtacccatccgtgccacagaatttcagagttgccaccaagaacac<br>taccctcccaagaggtggtggtaaggacgggttgtctcctgttttggtgagaaagggtc<br>agaccgttatttacggtgtctacgcagcccacagaaacccagctgtttacggtaagga<br>cgctcttgagtttagaccagagagatggtttgagccagagacaaagaagcttggctgg<br>gccttcctcccattcaacggtggtccaagaatctgtttgggacagcagtttgccttgaca<br>gaagcttcgtatgtcactgtcaggttgctccaggagtttgcacacttgtctatggacccag<br>acaccgaatatccacctaagaaaatgtcgcatttgaccatgtcgcttttcgacggtgcc<br>aatattgagatgtattag |
| SEQ ID NO: 15 | cytochrome<br>P450 A14<br>(CYP52A14) | atgactgcacaggatattatcgccacatacatcaccaaatggtacgtgatagtaccact<br>cgctttgattgcttataggtcctcgactactttacggcagatacttgatgtacaagcttg<br>gtgctaaaccgttttccagaaacaaacagacggttatttcggattcaaagctccacttg<br>aattgttaaaaagaagagtgacggtaccctcatagacttcactctcgagcgtatcca<br>agcgctcaatcgtccagatatcccaactttacattcccaatcttttccatcaaccttatca<br>gcacccttgagccggagaacatcaaggctatcttggccacccagttcaacgatttctcc<br>ttgggcaccagacactcgcactttgctcctttgttgggcgatggtatctttaccttggacgg<br>tgccggctggaagcacagcagatctatgttgagaccacagtttgccagagaacagat<br>ttcccacgtcaagttgttggagccacacatgcaggtgttcttcaagcacgtcagaaagg<br>cacagggcaagacttttgacatccaagaattgttttttcagattgaccgtcgactccgcca<br>ctgagtttttgtttggtgaatccgttgagtccttgagagatgaatctattgggatgtccatca<br>atgcacttgactttgacggcaaggctggctttgctgatgcttttaactactcgcagaacta<br>tttggcttcgagagcggttatgcaacaattgtactgggtgttgaacgggaaaaagtttaa<br>ggagtgcaacgctaaagtgcacaagtttgctgactattacgtcagcaaggctttggact<br>tgacacctgaacaattggaaaagcaggatggttatgtgttcttgtacgagttggtcaag<br>caaaccagagacaggcaagtgttgagagaccagttgttgaacatcatggttgccggt<br>agagacaccaccgccggtttgttgtcgtttgttttcttgaattggccagaaacccagag<br>gtgaccaacaagttgagagaagaaatcgaggacaagtttggtcttggtgagaatgct<br>cgtgttgaagacatttcctttgagtcgttgaagtcatgtgaatacttgaaggctgttctcaa<br>cgaaactttgagattgtacccatccgtgccacagaatttcagagttgccaccaaaaac<br>actaccttccaagggaggtggtaaggacgggttatctcctgttttggtcagaaaggg<br>tcaaaccgttatgtacggtgtctacgctgcccacagaaaccacagctgtctacggtaag<br>gacgcccttgagtttagaccagagaggtggtttgagccagagacaaagaagcttggc<br>tgggccttcctccattcaacggtggtccaagaattgcttgggacagcagtttgccttga<br>cagaagcttcgtatgtcactgtcagattgctccaagagtttggacacttgtctatggaccc<br>caacaccgaatatccacctaggaaaatgtcgcatttgaccatgtcccttttcgacggtg<br>ccaacattgagatgtattag |

| SEQ ID NO | Description | Sequence |
|---|---|---|
| SEQ ID NO: 16 | cytochrome P450 A15 (CYP52A15) | atgtcgtcttctccatcgtttgcccaagaggttctcgctaccactagtccttacatcgagta cttcttgacaactacaccagatggtactacttcataccttttggtgcttctttcgttgaacttta taagtttgctccacacaaggtacttggaacgcaggttccacgccaagccactcggtaa ctttgtcagggaccctacgtttggtatcgctactccgttgcttttgatctacttgaagtcgaa aggtacggtcatgaagtttgcttggggcctctggaacaacaagtacatcgtcagagac ccaaagtacaagacaactgggctcaggattgttggcctcccattgattgaaaccatgg acccagagaacatcaaggctgttttggctactcagttcaatgatttctctttgggaacca gacacgatttcttgtactccttgttgggtgacggtattttcaccttggacggtgctggctgg aaacatagtagaactatgttgagaccacagttttgctagagaacaggtttctcacgtcaa gttgttggagccacacgttcaggtgttcttcaagcacgttagaaagcaccgcggtcaa acgttcgacatccaagaattgttcttcaggttgaccgtcgactccgccaccgagttcttgt ttggtgagtctgctgaatcctgagggacgaatctattggattgaccccaaccaccaag gatttcgatggcagaagagatttcgctgacgctttcaactattcgcagacttaccaggcc tacagatttttgttgcaacaaatgtactggatcttgaatggctcggaattcagaaagtcg attgctgtcgtgcacaagtttgctgaccactatgtgcaaaaggctttggagttgaccgac gatgacttgcagaaacaagacggctatgtgttcttgtacgagttggctaagcaaacca gagacccaaaggtcttgagagaccagttattgaacattttggttgccggtagagacac gaccgccggtttgttgtcatttgttttctacgagttgtcaagaaaccctgaggtgtttgctaa gttgagagaggaggtggaaaacagatttggactcggtgaagaagctcgtgttgaaga gatctcgtttgagtccttgaagtcttgtgagtacttgaaggctgtcatcaatgaaaccttga gattgtacccatcggttccacacaactttagagttgctaccagaaacactaccctccca agaggtggtggtgaagatggatactcgccaattgtcgtcaagaagggtcaagttgtca tgtacactgttattgctacccacagagacccaagtatctacggtgccgacgctgacgtc ttcagaccagaaagatggtttgaaccagaaactagaaagttgggctgggcatacgttc cattcaatggtggtccaagaatctgtttgggtcaacagtttgccttgaccgaagcttcata cgtcactgtcagattgctccaggagtttgcacacttgtctatggacccagacaccgaat atccaccaaaattgcagaacaccttgaccttgtcgctctttgatggtgctgatgttagaat gtactaa |
| SEQ ID NO: 17 | cytochrome P450 A16 (CYP52A16) | atgtcgtcttctccatcgtttgctcaggaggttctcgctaccactagtccttacatcgagta cttcttgacaactacaccagatggtactacttcatccctttggtgcttctttcgttgaacttc atcagcttgctccacacaaagtacttggaacgcaggttccacgccaagccgctcggt aacgtcgtcgttggatcctacgtttggtatcgctactccgttgatcttgatctacttaaagtcg aaaggtacagtcatgaagtttgcctggagcttctggaacaacaagtacattgtcaaag acccaaagtacaagaccactggcttagaatgtcggcctcccattgattgaaaccat agacccagagaacatcaaagctgtgttggctactcagttcaacgatttctccttgggaa ctagacacgatttcttgtactccttgttgggcgatggtattttaccttggacggtgctggct ggaaacacagtagaactatgttgagaccacagttttgctagagaacaggtttcccacgt caagttgttggaaccacacgttcaggtgttcttcaagcacgttagaaaacaccgcggtc agacttttgacatccaagaattgttcttcagattgaccgtcgactccgccaccgagttcct gtttggtgagtctgctgaatcctgagagacgactctgttggtttgaccccaaccaccaa ggatttcgaaggcagaggagatttcgctgacgctttcaactactcgcagacttaccag gcctacagatttttgttgcaacaaatgtactggattttgaatggcgcggaattcagaaag tcgattgccatcgtgcacaagtttgctgaccactatgtgcaaaaggctttggagttgacc gacgatgacttgcagaaacaagacggctatgtgttcttgtacgagttggctaagcaaa ctagagacccaaaggtcttgagagaccagttgttgaacattttggttgccggtagagac acgaccgccggtttgttgtcgtttgtgttctacgagttgtcgagaaaccctgaagtgtttgc caagttgagagaggaggtggaaaacagatttggactcggcgaagaggctcgtgttg aagagatctcttttgagtccttgaagtcctgtgagtacttgaaggctgtcatcaatgaagc cttgagattgtacccatcgttccacacaacttcagagttgccaccagaaacactaccct tccaagaggcggtggtaaagacggatgctcgccaattgttgtcaagaagggtcaagtt gtcatgtacactgtcattggtacccacagagacccaagtatctacggtgccgacgccg acgtcttcagaccagaaagatggttcgagccagaaactagaaagttgggctgggcat atgttccattcaatggtggtccaagaatctgtttgggtcagcagtttgccttgactgaagct tcatacgtcactgtcagattgctccaagagtttggaaacttgtccctggatccaaacgct gagtacccaccaaaattgcagaacaccttgaccttgtcactctttgatggtgctgacgtt agaatgttctaa |
| SEQ ID NO: 18 | cytochrome P450 A17 (CYP52A17) | atgattgaacaactcctagaatattggtatgtcgttgtgccagtgttgtacatcatcaaac aactccttgcataccccaaagactcgcgtctgatgaaaaagttgggtgctgctccagtc acaaacaagttgtacgacaacgctttcggtatcgtcaatggatggaaggctctccagtt caagaaagagggcagggctcaagagtacaacgattacaagtttgaccactccaag aacccaagcgtgggcacctacgtcagtattcttttcggcaccaggatcgtcgtgacca aagatccagagaatatcaaagctatttttgccaacccagtttggtgattttctcttgggcaa gaggcacactcttttaagcctttgttaggtgatgggatcttcacattggacggcgaagg ctggaagcacagcagagccatgttgagaccacagtttgccagagaacaagttgctc atgtgacgtcgttggaaccacacttccagttgttgaagaagcatattcttaagcacaag ggtgaatacttcgatatccaggaattgttcttcagatttaccgttgattcggccacgaagttc ttatttggtgagtccgtgcactccttaaaggacgaatctattggtatcaaccaagacgat atagatttgctggtagaaaggacttgctgagtcgttcaacaaagcccaggaatacttg gctattagaaccttggtgcagacgttctactggtggtcaacaacaaggagtttagaga ctgtaccaagctggtcacaagttcaccaactactatgtgcaaaagctttggatgctct gcccagaagagcttgaaaagcaaagtgggtatgtgttcttgtacgagcttgtcaagca gacaagagaccccaatgtgttgcgtgaccagtctttgaacatcttgttggccggaaga gacaccactgctgggttgttgtcgtttgctgtctttgagttggccagacacccagagatct gggccaagttgagagaggaaattgaacaacagttggtcttggagaagactctcgtgt tgaagagattaccttgagagcttgaagagatgtgagtacttgaaagcgttccttaatga |

| SEQ ID NO | Description | Sequence |
|---|---|---|
| | | aaccttgcgtatttacccaagtgtcccaagaaacttcagaatcgccaccaagaacac<br>gacattgccaaggggcggtggttcagacggtacctcgccaatcttgatccaaaaggg<br>agaagctgtgtcgtatggtatcaactctactcatttggaccctgtctattacggccctgatg<br>ctgctgagttcagaccagagagatggtttgagccatcaaccaaaaagctcggctggg<br>cttacttgccattcaacggtggtccaagaatctgtttgggtcagcagtttgccttgacgga<br>agctggctatgtgttggttagattggtgcaagagttctcccacgttaggctggacccaga<br>cgaggtgtacccgccaaagaggttgaccaacttgaccatgtgtttgcaggatggtgct<br>attgtcaagtttgactag |
| SEQ ID NO: 19 | cytochrome<br>P450 A18<br>(CYP52A18) | atgattgaacaaatcctagaatattggtatattgttgtgcctgtgttgtacatcatcaaaca<br>actcattgcctacagcaagactcgcgtcttgatgaaacagttgggtgctgctccaatca<br>caaaccagttgtacgacaacgttttcggtatcgtcaacggatggaaggctctccagttc<br>aagaaagagggcagagctcaagagtacaacgatcacaagtttgacagctccaaga<br>acccaagcgtcggcacctatgtcagtattcttttggcaccaagattgtcgtgaccaagg<br>atccagagaatatcaaagctattttggcaacccagtttggcgattttttcttgggcaagag<br>acacgctctttttaaacctttgttaggtgatgggatcttcaccttggacggcgaaggctgg<br>aagcatagcagatccatgttaagaccacagtttgccagagaacaagttgctcatgtga<br>cgtcgtggaaccacacttccagttgttgaagaagcatatccttaaacacaagggtga<br>gtactttgatatccaggaattgttctttagatttactgtcgactcggccacggagttcttattt<br>ggtgagtccgtgcactccttaaaggacgaaactatcggtatcaaccaagacgatata<br>gattttgctggtagaaaggactttgctgagtcgttcaacaaagcccaggagtatttgtcta<br>ttagaattttggtgcagaccttctactggttgatcaacaacaaggagtttagagactgtac<br>caagctggtgcacaagtttaccaactactatgttcagaaagctttggatgctaccccag<br>aggaacttgaaaagcaaggcgggtatgtgttcttgtatgagcttgtcaagcagacgag<br>agaccccaaggtgttgcgtgaccagtctttgaacatcttgttggcaggaagagacacc<br>actgctgggttgttgtcctttgctgtgtttgagttggccagaaacccacacatctgggcca<br>agttgagagaggaaattgaacagcagtttggtcttggagaagactctcgtgttgaaga<br>gattaccctttgagagcttgaagagatgtgagtacttgaaagcgttccttaacgaaacctt<br>gcgtgtttacccaagtgtcccaagaaacttcagaatcgccaccaagaatacaacattg<br>ccaaggggtggtggtccagacggtacccagccaatcttgatccaaaagggagaag<br>gtgtgtcgtatggtatcaactctaccccacttagatcctgtctattatgccctgatgctgctg<br>agttcagaccagagagatggttgagccatcaaccagagaaagctcggctgggcttactt<br>gccattcaacggtgggccacgaatctgtttgggtcagcagtttgccttgaccgaagctg<br>gttacgttttggtcagattggtgcaagagttctcccacattaggctggacccagatgaag<br>tgtatccaccaaagaggttgaccaacttgaccatgtgtttgcaggatggtgctattgtca<br>agtttgactag |
| SEQ ID NO: 20 | cytochrome<br>P450 A19<br>(CYP52A19) | atgctcgatcagatcttacattactggtacattgtcttgccattgttggccattatcaaccag<br>atcgtggctcatgtcaggaccaatttatttgatgaagaaattgggtgctaagccattcaca<br>cacgtccaacgtgacgggtggttgggcttcaaattcggccgtgaattcctcaaagcaa<br>aaagtgctgggagactggttgattaatcatctcccgtttccacgataatgaggacactttt<br>ctccagctatgcttttggcaaccatgtggtgttcaccagggaccccgagaatatcaagg<br>cgcttttggcaacccagtttggtgattttcattgggcagcagggtcaagttcttcaaacc<br>attattggggtacggtatcttcacattgacgccgaaggctggaagcacagcagagc<br>catgttgagaccacagtttgccagagaacaagttgctcatgtgacgtcgttggaacca<br>cacttccagttgttgaagaagcatatccttaaacacaagggtgagtactttgatatccag<br>gaattgttctttagatttactgtcgactcggccacggagttcttatttggtgagtccgtgcac<br>tccttaaaggacgaggaaattggctacgacacgaaagacatgtctgaagaaagacg<br>cagatttgccgacgcgttcaacaagtcgcaagtctacgtggccaccagagttgctttac<br>agaacttgtactggttggtcaacaacaaagagttcaaggagtgcaatgacattgtcca<br>caagtttaccaactactatgttcagaaagccttggatgctaccccagaggaacttgaa<br>aagcaaggcgggtatgtgttcttgtatgagcttgtcaagcagacgagagaccccaag<br>gtgttgcgtgaccagtctttgaacatcttgttggcaggaagatacaccactgctgggttg<br>ttgtcctttgctgtgtttgagttggccagaaacccacacatctgggccaagttgagagag<br>gaaattgaacagcagtttggtcttggagaagactctcgtgttgaagagattaccctttgag<br>agcttgaagagatgtgagtacttgaaggccgtgttgaacgaaactttgagattacaccc<br>aagtgtcccaagaaacgcaagatttgcgattaaagcacgacttaccaagaggcg<br>gtggccccaacggcaaggatcctatcttgatcaggaaggatgaggtggtgcagtact<br>ccatctcggcaactcgacaaatcctgcttattatggcgccgatgctgctgattttagac<br>cggaaagatggtttgaaccatcaactagaaacttgggatgggctttcttgccattcaac<br>ggtggtccaagaatctgtttgggacaacagttgctttgactgaagccggttacgttttggt<br>tagacttgttcaggagtttccaaacttgtcacaagaccccgaaaccaagtacccacca<br>cctagattggcacacttgacgatgtgcttgtttgacggtgcacacgtcaagatgtcatag |
| SEQ ID NO: 21 | cytochrome<br>P450 A20<br>(CYP52A20) | atgctcgaccagatcttccattactggtacattgtcttgccattgttggtcattatcaagcag<br>atcgtggctcatgccaggaccaatttatttgatgaagaagttgggcgctaagccattcac<br>acatgtccaactagacgggtggttggcttcaaatttggccgtgaattcctcaaagctaa<br>aagtgctgggaggcaggttgatttaatcatctcccgtttccacgataatgaggacactttt<br>ctccagctatgcttttggcaacccatgtggtgttcaccagggaccccgagaatatcaagg<br>cgcttttggcaacccagtttggtgattttcattgggcagcaggtcaaattcttcaaacc<br>attgttgggtacggtatcttcacccttggacggcgaaggctggaagcacagcagagc<br>catgttgagaccacagtttgccagagagcaagttgctcatgtgacgtcgttggaacca<br>catttccagttgttgaagaagcatattcttaagcacaagggtgagtactttgatatccagg<br>aattgttctttagatttaccgttgattcagcgacggagttcttatttggtgagtccgtgcactc<br>cttaagggacgaggaaattggctacgatacgaaggcatggctgaagaaagacgc<br>aaatttgccgacgcgttcaacaagtcgcaagtctatttgtccaccagagttgctttacag<br>acattgtactggttggtcaacaacaaagagttcaaggagtgcaacgacattgtccaca<br>agttcaccaactactatgttcagaaagccttggatgctaccccagaggaacttgaaaa |

| SEQ ID NO | Description | Sequence |
|---|---|---|
| | | acaaggcgggtatgtgttcttgtacgagcttgccaagcagacgaaagaccccaatgt<br>gttgcgtgaccagtctttgaacatcttgttggctggaagggacaccactgctgggttgttg<br>tcctttgctgtgtttgagttggccaggaacccacacatctgggccaagttgagagagga<br>aattgaatcacacttttgggctgggtgaggactctcgtgttgaagagattacctttgagag<br>cttgaagagatgtgagtacttgaaagccgtgttgaacgaaacgttgagattacaccca<br>agtgtcccaagaaacgcaagatttgcgattaaagacacgactttaccaagaggcggt<br>ggccccaacggcaaggatcctatcttgatcagaaagaatgaggtggtgcaatactcc<br>atctcggcaactcagacaaatcctgcttattatggcgccgatgctgctgattttagaccg<br>gaaagatggtttgagccatcaactagaaacttgggatgggcttacttgccattcaacgg<br>tggtccaagaatctgcttgggacaacagtttgctttgaccgaagccggttacgttttggtt<br>agacttgttcaggaattccctagcttgtcacaggaccccgaaactgagtacccaccac<br>ctagattggcacacttgacgatgtgcttgtttgacggggcatacgtcaagatgcaatag |
| SEQ ID NO: 22 | cytochrome P450 D2 (CYP52D2) | atggctatatctagtttgctatcgtgggatgtgatctgtgtcgtcttcatttgcgtttgtgtttatt<br>tcgggtatgaatattgttatactaaatacttgatgcacaaacatggcgctcgagaaatcg<br>agaatgtgatcaacgatgggttctttgggttccgcttacctttgctactcatgcgagccag<br>caatgagggccgacttatcgagttcagtgtcaagagattcgagtcggcgccacatcca<br>cagaacaagacattggtcaaccgggcattgagcgttcctgtgatactcaccaaggac<br>ccagtgaatatcaaagcgatgctatcgacccagtttgatgactttttcccttgggttgaga<br>ctacaccagtttgcgccgttgttggggaaaggcatctttactttggacggcccagagtg<br>gaagcagagccgatctatgttgcgtccgcaatttgccaaagatcgggtttctcatatcct<br>ggatctagaaccgcattttgtgttgcttcggaagcacattgatggccacaatggagact<br>acttcgacatccaggagctctacttccggttctcgatggatgtggcgacgggggttttgttt<br>ggcgagtctgtggggtcgttgaaagacgaagatgcgaggttcctggaagcattcaat<br>gagtcgcagaagtatttggcaactagggcaacgttgcacgagttgtactttctttgtgac<br>gggtttaggtttcgccagtacaacaaggttgtgcgaaagttctgcagccagtgtgtcca<br>caaggcgttagatgttgcaccggaagacaccagcgagtacgtgtttctccgcgagttg<br>gtcaaacacactcgagatcccgttgttttacaagaccaagcgttgaacgtcttgcttgct<br>ggacgcgacaccaccgcgtcgttattatcgtttgcaacatttgagctagcccggaatga<br>ccacatgtggaggaagctacgagaggaggttatcctgacgatgggaccgtccagtg<br>atgaaataaccgtggccgggttgaagagttgccgttacctcaaagcaatcctaaacg<br>aaactcttcgactataccccaagtgtgcctaggaacgcgagatttgctacgaggaatac<br>gacgcttcctcgtggcggaggtccagatggatcgtttccgattttgataagaaagggcc<br>agccagtggggtatttcatttgtgctacacacttgaatgagaaggtatatgggaatgata<br>gccatgtgtttcgaccggagagatgggctgcgttagagggcaagagtttgggctggtc<br>gtatcttccattcaacggcggcccgagaagctgccttggtcagcagtttgcaatccttga<br>agcttcgtatgttttggctcgattgacacagtgctacacgacgatacagcttagaactac<br>cgagtacccaccaaagaaactcgttcatctcacgatgagtcttctcaacggggtgtac<br>atccgaactagaacttga |

A comparison of the amino acid sequence identities of the monooxygenase activities is presented in the table below. The black colored boxes indicate regions of 100% identity. Many of the monooxygenase activities shown in the table below have a closely related "sibling" sequence.

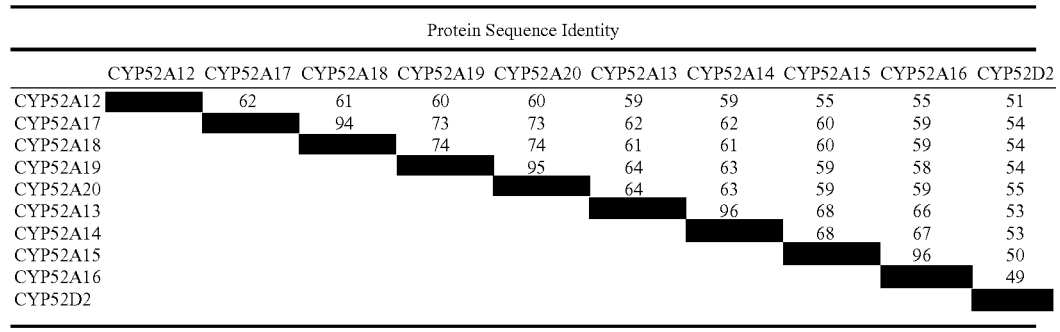

Protein Sequence Identity

| | CYP52A12 | CYP52A17 | CYP52A18 | CYP52A19 | CYP52A20 | CYP52A13 | CYP52A14 | CYP52A15 | CYP52A16 | CYP52D2 |
|---|---|---|---|---|---|---|---|---|---|---|
| CYP52A12 | | 62 | 61 | 60 | 60 | 59 | 59 | 55 | 55 | 51 |
| CYP52A17 | | | 94 | 73 | 73 | 62 | 62 | 60 | 59 | 54 |
| CYP52A18 | | | | 74 | 74 | 61 | 61 | 60 | 59 | 54 |
| CYP52A19 | | | | | 95 | 64 | 63 | 59 | 58 | 54 |
| CYP52A20 | | | | | | 64 | 63 | 59 | 59 | 55 |
| CYP52A13 | | | | | | | 96 | 68 | 66 | 53 |
| CYP52A14 | | | | | | | | 68 | 67 | 53 |
| CYP52A15 | | | | | | | | | 96 | 50 |
| CYP52A16 | | | | | | | | | | 49 |
| CYP52D2 | | | | | | | | | | |

Monooxygenase Reductase Activity Nucleotide Sequences

| SEQ ID NO | Description | Sequence |
|---|---|---|
| SEQ ID NO: 23 | cytochrome P450: NADPH P450 reductase | atgacaattaaagaaatgcctcagccaaaaacgtttggagagcttaaaaatttaccg<br>ttattaaacacagataaaccggttcaagctttgatgaaaattgcggatgaattaggag<br>aaatctttaaattcgaggcgcctggtcgtgtaacgcgctacttatcaagtcagcgtcta<br>attaaagaagcatgcgatgaatcacgctttgataaaaacttaagtcaagcgcttaaat |

| SEQ ID NO | Description | Sequence |
|---|---|---|
| | (*Bacillus megaterium*) nucleotide | ttgtacgtgatttttgcaggagacgggttatttacaagctggacgcatgaaaaaaattg<br>gaaaaaagcgcataatatcttacttccaagcttcagtcagcaggcaatgaaaggct<br>atcatgcgatgatggtcgatatcgccgtgcagcttgttcaaaagtgggagcgtctaaa<br>tgcagatgagcatattgaagtaccggaagacatgacacgtttaacgcttgatacaatt<br>ggtctttgcggctttaactatcgctttaacagcttttaccgagatcagcctcatccatttatt<br>acaagtatggtccgtgcactggatgaagcaatgaacaagctgcagcgagcaaatc<br>cagacgacccagcttatgatgaaaacaagcgccagttcaagaagatatcaaggt<br>gatgaacgacctagtagataaaattattgcagatcgcaaagcaagcggtgaacaa<br>agcgatgatttattaacgcatatgctaaacggaaaagatccagaaacgggtgagcc<br>gcttgatgacgagaacattcgctatcaaattattacattcttaattgcgggacacgaaa<br>caacaagtggtctttatcatttgcgctgtatttcttagtgaaaaatccacatgtattacaa<br>aaagcagcagaagaagcagcacgagttctagtagatcctgttccaagctacaaac<br>aagtcaaacagcttaaatatgtcggcatggtcttaaacgaagcgctgcgcttatggcc<br>aactgctcctgcgttttccctatatgcaaaagaagatacggtgcttggaggagaatat<br>cctttagaaaaaggcgacgaactaatggttctgattcctcagcttcaccgtgataaaa<br>caatttggggagacgatgtggaagagttccgtccagagcgttttgaaaatccaagtg<br>cgattccgcagcatgcgtttaaaccgtttggaaacggtcagcgtgcgtgtatcggtca<br>gcagttcgctcttcatgaagcaacgctggtacttggtatgatgctaaaacactttgactttt<br>gaagatcatacaaactacgagctggatattaaagaaactttaacgttaaaacctgaa<br>ggctttgtggtaaaagcaaaatcgaaaaaaaattccgcttggcggtattccttcaccta<br>gcactgaacagtctgctaaaaaagtacgcaaaaaggcagaaaacgctcataata<br>cgccgctgcttgtgctatacggttcaaatatgggaacagctgaaggaacggcgcgtg<br>atttagcagatattgcaatgagcaaaggatttgcaccgcaggtcgcaacgcttgattc<br>acacgccgaaatcttccgcgcgaaggagctgtattaattgtaacggcgtcttataac<br>ggtcatccgcctgataacgcaaagcaatttgtcgactggttagaccaagcgtctgctg<br>atgaagtaaaaggcgttcgctactccgtatttggatgcggcgataaaaactgggcta<br>ctacgtatcaaaaagtgccttgcttttatcgatgaaacgcttgccgctcaaaggggcaga<br>aaacatcgctgaccgcggtgaagcagatgcaagcgacgactttgaaggcacatat<br>gaagaatggcgtgaacatatgtggagtgacgtagcagcctacttttaacctcgacatt<br>gaaaacagtgaagataataaatctactctttcacttcaatttgtcgacagcgccgcgg<br>atatgccgcttgcgaaaatgcacggtgcgttttcaacgaacgtcgtagcaagcaaag<br>aacttcaacagccaggcagtgcacgaacacgcgacatcttgaaattgaacttcca<br>aaagaagcttcttatcaagaaggagtcatttaggtgttattcctcgcaactatgaagg<br>aatagtaaaccgtgtaacagcaaggttcggcctagatgcatcacagcaaatccgtct<br>ggaagcagaagaagaaaaattagctcatttgccactcgctaaaacagtatccgtag<br>aagagcttctgcaatacgtggagcttcaagatcctgttacgcgcacgacgcttcgcg<br>caatggctgctaaaacggtctgcccgccgcataaagtagagcttgaagccttgcttg<br>aaaagcaagcctacaaagaacaagtgctggcaaaacgtttaacaatgcttgaact<br>gcttgaaaaatacccggcgtgtgaaatgaaattcagcgaatttatcgcccttctgcca<br>agcatacgcccgcgctattactcgatttcttcatcacctcgtgtcgatgaaaaacaagc<br>aagcatcacgttcagcgttgtctcaggagaagcgtggagcggatatggagaatata<br>aaggaattgcgtcgaactatcttgccgagctgcaagaaggagatacgattacgtgct<br>ttatttccacaccgcagtcagaatttacgctgccaaaagaccctgaaacgccgcttat<br>catggtcggaccggaacaggcgtcgcgccgtttagaggcttttgtgcaggcgcgca<br>aacagctaaaagaacaaggacagtcacttggagaagcacatttatacttcggctgc<br>cgttcacctcatgaagactatctgtatcaagaagagcttgaaaacgcccaaagcga<br>aggcatcattacgcttcataccgcttttttctcgcatgccaaatcagccgaaaacatacg<br>ttcagcacgtaatggaacaagacggcaagaaattgattgaacttcttgatcaaggag<br>cgcacttctatatttgcggagacggaagccaaatggcacctgccgttgaagcaacg<br>cttatgaaaagctatgctgacgttcaccaagtgagtgaagcagacgctcgcttatggc<br>tgcagcagctagaagaaaaaggccgatacgcaaaagacgtgtgggcctgggtaa |
| SEQ ID NO: 24 | NADPH cytochrome P450 reductase, CPR (*C. tropicalis* strain ATCC750) | atggcattagataagttagatttatatgttattataacattggtggttgcaattgcagcttat<br>tttgcaaagaatcagtttcttgaccaacaacaagataccggggttccttaatactgatag<br>tggagatggtaattcaagagatatcttacaagctttgaagaagaacaataaaaatac<br>gttattattatttggatcccaaacaggtacagcagaagattatgccaacaaattgtcaa<br>gagaattgcattcaagatttggtttgaaaaccatggttgctgatttcgctgattatgatttc<br>gaaaacttcggagatattactgaagatcttggttttctcttattgttgctacttatggtgaa<br>ggtgaaccaaccgataatgctgacgaatttcacacttggttgactgaagaagctgac<br>accttgagtactttgaaatatactgttttttggtttgggtaattcaacttatgaattcttcaatg<br>ctattggtagaaaatttgacagattgatttgggagaaaaaggtggtgacagatttgctga<br>atacggtgaagtgacgatggtactggtactttagatgaagattcttggcctggaag<br>gataacgtgtttgattccttaaagaatgatttgaattttgaagaaaaagagttgaaatac<br>gaaccaaatgttaaattgactgaaagagatgatttatctggcaatgatccagatgtctc<br>cttgggtgaaccaaatgtcaaatacattaaatctgaaggtgttgacttaactaaaggtc<br>catttgatcatactcatccatttttggctagaattgttaaaactaaagaattgtttacttctg<br>aagacagacattgtgttcatgttgaatttgatatttctgaatcaaacttgaaatataccac<br>cggtgatcatcttgcaatctggccatctaactctgatgaaaacattaagcaatttgcca<br>aatgttttggtttagaagacaaacttgatactgttattgaattgaaagcttggattccact<br>tattccatcccattccctaatccaatcacttatggagctgttattagacaccatttggaaa<br>tttcaggtcctgttttctagacaatttttcttatctattgctggatttgcccctgatgaagaac<br>taaaaagtcatttactagaattggtggtgataagcaagaatttgctagtaaagtcaccc<br>gtgaaaaattcaacattgccgatgctgcttattatttgcttccaacaacagaccacatgg<br>tccgatgttccattcgaattccttattgaaaatgtccaacacttaactcctcgttattactccatttt<br>cttcttcctcattaagtgaaaagcaaaccattaatgttactgctgttgttgaagccgaag<br>aagaagctgatggaagaccagttactggtgttgtcaccaacttgttgaagaatattga<br>aattgaacaaacaaaactggtgaaaccccaatggttcattatgatttgaatggtcca<br>agaggcaaatttagcaagttcagattgccagttcacgttagaagatctaatttcaaatt |

| SEQ ID NO | Description | Sequence |
|---|---|---|
| | | accaaagaatagcactaccccagttattttgattggtccaggtaccggtgttgcaccat<br>tgagaggttttgttagagaaagagttcaacaagttaaaaatggtgttaatgttggtaag<br>actgtattgttttatggatgtagaaaattccgaacaagatttcttgtacaaacaagaatgg<br>agtgaatatgcctcagtattgggagaaaatttcgaaatgtttaatgccttctcaagaca<br>agatccaactaagaaagtttatgttcaagataagattttagaaaatagtgctcttgttga<br>tgagttattatctagtggagcaattatttatgtttgtggtgatgccagtagaatggctaga<br>gatgttcaagctgcaattgccaagattgttgccaaaagtagagatatccacgaagat<br>aaagctgctgaattggttaaatcttggaaagttcaaaatagataccaagaagatgtct<br>gggaa |
| SEQ ID NO: 25 | NADPH cytochrome P450 reductase A, CPRA (C. tropicalis strain ATCC20336) | atggctttagacaagttagatttgtatgtcatcataacattggtggtcgctgtagccgcct<br>attttgctaagaaccagttccttgatcagcccaggacaccgggttcctcaacacgga<br>cagcggaagcaactccagagacgtcttgctgacattgaagaagaataataaaaac<br>acgttgttgttgtttgggcccagacgggtacggcagaagattacgccaacaaattgt<br>ccagagaattgcactccagatttggcttgaaaaccatggttgcagatttcgctgattac<br>gattgggataacttcggagatatcaccgaagacatcttggtgttttcattgttgccacct<br>atggtgagggtgaacctaccgataatgccgacgagttccacacctggttgactgaag<br>aagctgacactttgagtaccttgaaatacaccgtgttcgggttgggtaactccacgtac<br>gagttcttcaatgccattggtagaaagtttgacagattgttgagcgagaaaggtggtg<br>acaggtttgctgaatacgctgaaggtgatgacggtactggcaccttggacgaagattt<br>catggcctggaaggacaatgtctttgacgccttgaagaatgatttgaactttgaagaa<br>aaggaattgaagtacgaaccaaacgtgaaattgactgagagagacgacttgtctgc<br>tgctgactcccaagttccttgggtgagccaaacaagaagtacatcaactccgaggg<br>catcgacttgaccaagggtccattcgaccacaccccatacttggccagaatca<br>ccgagacgagagagttgttcagctccaaggacagacactgtatccacgttgaatttg<br>acatttctgaatcgaacttgaaatacaccaccggtgaccatctagctatctggccatcc<br>aactccgacgaaaacattaagcaatttgccaagtgtttcggattggaagataaactc<br>gacactgttattgaattgaaggcgttggactccacttacaccatcccattcccaacccc<br>aattacctacggtgctgtcattagacaccattagaaatctccggtccagtctcgagac<br>aattcttttgtcaattgctgggtttgctcctgatgaagaaacaaagaaggcttttaccag<br>acttggtggtgacaagcaagaattcgccgccaaggtcacccgcagaaagttcaac<br>atggccgatgccttgttatattcctccaacaacgctccatggtccgatgttccttttgaattc<br>cttattgaaaacgttccacacttgactccacgttactactccatttcgtcttcgtcattgagt<br>gaaaagcaactcatcaacgttactgcagttgttgaagccgaagaagaagctgatgg<br>cagaccagtcactggtgttgtcaccaacttgttgaagaacgttgaaattgtgcaaaac<br>aagactggcgaaaagccacttgtccactacgatttgagcggcccaagaggcaagtt<br>caacaagttcaagttgccagtgcatgtgagaagatccaactttaagttgccaaagaa<br>ctccaccaccccagttatcttgattggtccaggtactggtgttgccccattgagaggttttt<br>gtcagagaaagagttcaacaagtcaagaatggtgtcaatgttggcaagactttgttgt<br>tttatggttgcagaaaactccaacgaggactttttgtacaagcaagaatgggccgagta<br>cgcttctgttttgggtgaaaactttgagatgttcaatgccttctccagacaagacccatc<br>caagaaggtttacgtccaggataagattttagaaaacagccaacttgtgcacgagtt<br>gttgactgaaggtgccattatctacgtctgtggtgatgccagtagaatggctagagac<br>gtgcagaccacaatttccaagattgttgctaaaagcagagaaattagtgaagacaa<br>ggctgctgaattggtcaagtcctggaaggtccaaaatagataccaagaagatgtttg<br>gtag |
| SEQ ID NO: 26 | NADPH cytochrome P450 reductase B, CPRB (C. tropicalis strain ATCC20336) | atggctttagacaagttagatttgtatgtcatcataacattggtggtcgctgtggccgcct<br>attttgctaagaaccagttccttgatcagcccaggacaccgggttcctcaacacgga<br>cagcggaagcaactccagagacgtcttgctgacattgaagaagaataataaaaac<br>acgttgttgttgtttgggcccagacggtacggcagaagattacgccaacaaattgtc<br>aagagaattgcactccagatttggcttgaaaaccatggttgcagatttcgctgattacg<br>attgggataacttcggagatatcaccgaagatatcttggtgttttcatcgttgccaccta<br>cggtgagggtgaacctaccgacaatgccgacgagttccacacctggttgactgaag<br>aagctgacactttgagtactttgagatataccgtgttcgggttgggtaactccacctacg<br>agttcttcaatgctattggtagaaagtttgacagattgttgagtgagaaaggtggtgac<br>agatttgctgaatatgctgaaggtgacggcactggcaccttggacgaagatttc<br>atggcctggaaggataatgtctttgacgccttgaagaatgacttgaactttgaagaaa<br>aggaattgaagtacgaaccaaacgtgaaattgactgagagagatgacttgtctgctg<br>ccgactcccaagttccttgggtgagccaaacaagaagtacatcaactccgagggc<br>atcgacttgaccaagggtccattcgaccacaccccatacttggccaggatcac<br>cgagaccagagagttgttcagctccaaggaaagacactgtattcacgttgaatttga<br>catttctgaatcgaacttgaaatacaccaccggtgaccatctagctatctggccatcc<br>aactccgacgaaaacatcaagcaatttgccaagtgtttcggattggaagataaactc<br>gacactgttattgaattgaaggcgttggactccacttacaccattccattcccaactcca<br>attacttacggtgctgtcattagacaccattagaaatctccggtccagtctcgagaca<br>attcttttgtcgattgctgggtttgctcctgatgaagaaacaaagaagactttcaccag<br>acttggtggtgacaaacaagaattcgccaccaaggttacccgcagaaagttcaaca<br>tggccgatgccttgttatattcctccaacaacactccatggtccgatgttccttttgagttcc<br>ttattgaaaacatccaacacttgactccacgttactactccatttcttcttcgtcgttgagt<br>gaaaaacaactcatcaatgttactgcagtcgttgaggccgaagaagaagccgatg<br>gcagaccagtcactggtgttgttaccaacttgttgaagaacattgaaattgcgcaaaa<br>caagactggcgaaaagccacttgtcactacgatttgagcggccccaagaggcaagt<br>tcaacaagttcaagttgccagtgcacgtgagaagatccaactttaagttgccaaaga<br>actccaccaccccagttatcttgattggtccaggtactggtgttgccccattgagaggtt<br>tcgttagagaaagagttcaacaagtcaagaatggtgtcaatgttggcaagactttgtt<br>gttttatggttgcagaaaactccaacgaggacttttttgtacaagcaagaatgggccgag<br>tacgcttctgttttgggtgaaaactttgagatgttcaatgccttactagacaagacccat |

-continued

| SEQ ID NO | Description | Sequence |
|---|---|---|
| | | ccaagaaggtttacgtccaggataagattttagaaaacagccaacttgtgcacgaat |
| | | tgttgaccgaaggtgccattatctacgtctgtggtgacgccagtagaatggccagag |
| | | acgtccagaccacgatctccaagattgttgccaaaagcagagaaatcagtgaaga |
| | | caaggccgctgaattggtcaagtcctggaaagtccaaaatagataccaagaagat |
| | | gtttggtag |
| SEQ ID NO: 41 | cytochrome P450: NADPH P450 reductase (Bacillus megaterium) amino acid [P450 activity shown in italics, P450 reductase activity shown in normal font] | *mtikempqpktfgelknlpllntdkpvqalmkiadelgeifkfeapgrvtrylssqrlike* *acdesrfdknlsqalkfvrdfagdglftswtheknwkkahnillpsfsqqamkgyha* *mmvdiavqlvqkwerlnadehievpedmtrltldtiglcgfnyrfnsfyrdqphpfits* *mvrasdeamnksqranpddpaydenkrqfqedikvmndlvdkiiadrkasgeqs* *ddllthmlngkdpetgeplddeniryqiitfliaghettsgllsfasyflvknphvlqkaae* *eaarvlvdpvpsykqvkqlkyvgmvlneasrlwptapafslyakedtvlggeyplek* *gdelmvsipqlhrdktiwgddveefrperfenpsaipqhafkpfgngqracigqqfal* *heatsvlgmmlkhfdfedhtnyesdiketltlkpegfvvkakskkiplggipspsteqs* *akkvrkkaenahntpslvlvgsnmgtaegtardladiamskgfapqvatldshagn* *lpregavlivtasynghppdnakqfvdwldqasadevkgvrysvfgcgdknwatty* *qkvpafidetlaakgaeniadrgeadasddfegtyeewrehmwsdvaayfnldie* nsednkstlslqfvdsaadmplakmhgafstnvvaskelqqpgsarstrhleielpk easyqegdhlgviprnyegivnrvtarfgldasqqirseaeeeklahlplaktvsveel sqyvelqdpvtrtqlramaaktvcpphkveleallekqaykeqvsakrltmlesleky pacemkfsefialspsirpryysisssprvdekqasitvsvvsgeawsgygeykgia snylaesqegdtitcfistpqseftspkdpetplimvgpgtgvapfrgfvqarkqlkeq gqslgeahlyfgcrsphedysyqeelenaqsegiitlhtafsrmpnqpktyvqhvm eqdgkklielldqgahfyicgdgsqmapaveatlmksyadvhqvseadarlwsqq leekgryakdvwag* |

Example 32

Amplification of Selected Beta Oxidation Activities

As noted previously, beta oxidation of fatty acids involves two acyl CoA oxidase activities, encoded by POX4 and POX5. FIGS. 15A-15C presented data regarding distribution of fatty acids present in yeast strains that were wild type with respect to acyl CoA oxidase activity (e.g., POX4:POX5, see FIG. 15A), disrupted for POX5 (e.g., POX4:pox5), or disrupted for POX4 (e.g., pox4:POX5). Wild-type *C. tropicalis* has two copies of POX4 and two copies of POX5. The POX4 enzyme has broad substrate specificity (see FIG. 15B), whereas the POX5 enzyme (see FIG. 15C) has a narrow substrate specificity with regard to fatty acid chain length. A partially beta oxidation disrupted strain was generated that contained no POX4 activity (both alleles are disrupted), and two functional copies of POX5, as described herein. The results of experiments conducted with the pox4:pox4/POX5:POX5 strain indicated that since the activity of the POX5 enzyme drops off dramatically with fatty acids shorter than C10, the beta-oxidation products of the POX5 strain are the C8 diacid and C6 diacid (adipic). Additionally, if the strain is starved for carbon (e.g., the only possible source of energy is the C8 diacid), it will convert the C8 diacid to the C6 diacid. Data illustrating that amplification of the number of POX 5 genes in the engineered organism to Increase beta oxidation activity, increases the C6/C8 ratio, is presented below and shown in FIG. 38.

Construction and Shake Flask Evaluation of POX5 Amplified Strains

Plasmid pAA166 ($P_{POX4}$POX5$T_{POX4}$)

A PCR product containing the nucleotide sequence of POX5 was amplified from *C. tropicalis* 20336 genomic DNA using primers oAA540 and oAA541. The PCR product was gel purified and ligated into pCR-Blunt II-TOPO (Invitrogen), transformed into competent TOP10 *E. coli* cells (Invitrogen) and clones containing PCR inserts were sequenced to confirm correct DNA sequence. One such plasmid was designated, pAA165. Plasmid pAA165 was digested with BspQI and a 2-kb fragment was isolated. Plasmid pAA073 which contained a POX4 promoter and POX4 terminator was also digested with BspQI and gel purified. The isolated fragments were ligated together to generate plasmid pAA166. Plasmid pAA166 contains a $P_{POX4}$POX5$T_{POX4}$ fragment.

Plasmid pAA204 (Thiolase Deletion Construct)

A PCR product containing the nucleotide sequence of a short-chain thiolase (e.g., acetyl-coA acetyltransferase) was amplified from *C. tropicalis* 20336 genomic DNA using primers oAA640 and oAA641. The PCR product was gel purified and ligated into pCR-Blunt II-TOPO (Invitrogen), transformed into competent TOP10 *E. coli* cells (Invitrogen) and clones containing PCR inserts were sequenced to confirm correct DNA sequence. One such plasmid was designated, pAA184. A URA3 PCR product was amplified from pAA061 using primers oAA660 and oAA661. The PCR product was gel purified and ligated into pCR-Blunt II-TOPO (Invitrogen), transformed as described and clones containing PCR inserts were sequenced to confirm the correct DNA sequence. One such plasmid was designated pAA192. Plasmid pAA184 was digested with BglII/SalI and gel purified. Plasmid pAA192 was digested with BglII/SalI and a 1.5 kb fragment was gel purified. The isolate fragments were ligated together to create pAA199. An alternative $P_{URA3}$ PCR product was amplified from plasmid pAA061 using primers oAA684 and oAA685. The PCR product was gel purified and ligated into pCR-Blunt II-TOPO (Invitrogen), transformed as described and clones containing PCR inserts were sequenced. One such plasmid was designated, pAA201. Plasmid pAA199 was digested with SalI and gel purified. Plasmid pAA201 was digested with SalI and a 0.43 kb $P_{URA3}$ was gel purified. The isolated fragments were ligated to create plasmid pAA204 that contains a direct repeat of $P_{URA3}$.

Plasmid pAA221 ($P_{POX4}$POX5$T_{POX4}$ in Thiolase Deletion Construct)

A PCR product containing the nucleotide sequence of $P_{POX4}$POX5$T_{POX4}$ was amplified from plasmid pAA166 DNA using primers oAA728 and oAA729. The PCR product was gel purified and ligated into pCR-Blunt II-TOPO, transformed as described and clones containing PCR inserts were sequenced to confirm the sequence of the insert. One such plasmid was designated, pAA220. Plasmid pAA204 was digested with BglII, treated with shrimp alkaline phosphatase (SAP), and a 6.5 kb fragment was gel purified. Plasmid pAA220 was digested with BglII and a 2.7 kb fragment containing $P_{POX4}POX5T_{POX4}$ was gel purified. The isolated fragments were ligated to create plasmid pAA221.

Strain sAA617 ($P_{POX4}POX5T_{POX4}$ in sAA451)

Strain sAA451 is a ura-, partially β-oxidation blocked strain (ura3/ura3 pox4a::ura3/pox4b::ura3 POX5/POX5). Plasmid pAA221 was digested with EcoRI to release a DNA fragment containing $P_{POX4}POX5T_{POX4}$ in a thiolase deletion construct. The DNA was column purified and transformed to strain sAA451 to plate on SCD-ura plate. After two days, colonies were streaked out on YPD plates, single colonies selected and again streaked out on YPD plates. Single colonies were selected from the second YPD plates and characterized by colony PCR. The insertion of $P_{POX4}POX5T_{POX4}$ in strain sAA451, disrupting the short-chain thiolase gene, was confirmed by PCR and one such strain was designated sAA617.

Strain sAA620

Strain sAA617 was grown overnight on YPD medium and plated on SCD+URA+5-FOA, to select for loop-out of URA3. Colonies were streaked out onto YPD plates twice as described for strain sAA617, and single colonies characterized by colony PCR. The loop-out of URA3 by direct repeats of PURA3 was confirmed by PCR. One such strain was designated sAA620. Strain sAA620 has one additional copy of POX5 under control of the POX4 promoter.

Plasmid pAA156

A PCR product containing the nucleotide sequence of CYP52A19 was amplified from C. tropicalis strain 20336 genomic DNA, using primers oAA525 and oAA526. The PCR product was gel purified and ligated into pCR-Blunt II-TOPO, transformed as described, and clones containing PCR inserts were sequenced to confirm correct DNA sequence. One such plasmid was designated, pAA144. Plasmid pAA144 was digested with BspQI and a 1.7-kb fragment was isolated. Plasmid pAA073, which includes a POX4 promoter and POX4 terminator, also was digested with BspQI and gel purified. The isolated fragments were ligated together to generate plasmid, pAA156. Plasmid pAA156 included $P_{POX4}CYP52A19T_{POX4}$ fragment and URA3.

Strain sAA496

Plasmid pAA156 was digested with ClaI and column purified. Strain sAA451 was transformed with this linearized DNA and plated on SCD-ura plate. Colonies were checked for CYP52A19 integration. Colonies positive for plasmid integration were further analyzed by qPCR to determine the number of copies of CYP52A19 integrated. One such strain, designated sAA496 contained about 13 copies of the monooxygenase activity encoded by CYP52A19.

Strains sAA632 and sAA635

Strain sAA620 was transformed with linearized pAA156 DNA and plated on SCD-ura plates. Several colonies were checked for CYP52A19 integration. Colonies positive for plasmid integration were further analyzed by qPCR to determine the number of copies of CYP52A19 integrated. One such strain, designated sAA632 contained about 27 copies of the monooxygenase activity encoded by CYP52A19. Another strain, designated sAA635, contained about 12 copies of the monooxygenase activity encoded by CYP52A19. Shake Flask Characterization of sAA496, sAA632 and sAA635

250 mL glass bottom-baffled flasks containing 50 mL of SP92 media were inoculated with a 5 mL overnight YPD culture (OD=0.4). After 24 h incubation at 30° C., with shaking at 250 rpm (2" throw incubator), sterile antifoam B was added to a final concentration of 0.1% to dissipate foam. The cells were centrifuged and the cell pellet resuspended in 20 mL of TB-lowN media (yeast nitrogen base without amino acids and without ammonium sulfate, 1.7 g/L; yeast extract, 3.0 g/L; potassium phosphate monobasic, 1.0 g/L; potassium phosphate dibasic, 1.0 g/L). 1.6 mL coconut oil containing 20 uL sterile antifoam B was added to start adipic acid production in cultures grown at 30° C., with shaking. Samples were taken every 24 hour for gas chromatographic (GC) analysis.

Figure 38:
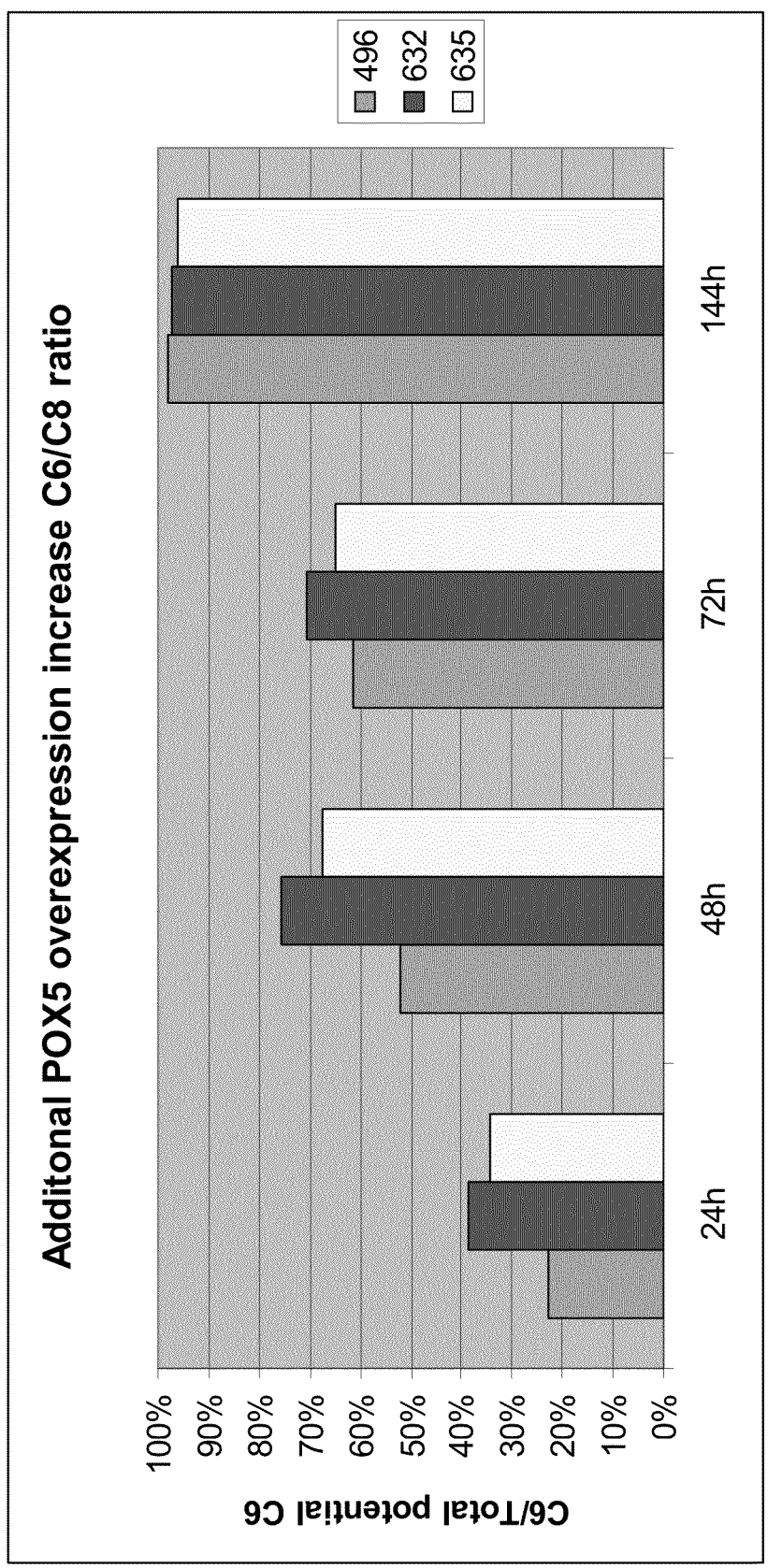
FIG. 38 graphically illustrates the ratio of C6 diacids/(C6+ C8 diacids) produced in yeast cultures grown in shake flasks using coconut oil as the feedstock (e.g., carbon source). Experimental results and conditions are given in Example 32.

Shown in the table below and in FIG. 38, are the diacid profiles for strains described herein, at various time points. Strains with an additional copy of the POX5 gene show an increased proportion of C6 in the C6+C8 diacid pool at early time points of the analysis. An increased proportion of C6 at early time points may indicate that the additional copy of POX5 in these strains increases beta-oxidation activity, allowing chain shortening of the coconut oil feedstock to the C6 diacid rather than to the C8 diacid. At the 144 h time point, the strain without an additional copy of POX5 has the same proportion of C6 in the C6+C8 diacid pool.

| Strain name | time | C6 (g/L) | C6 + C8 (g/L) | C6/(C6 + C8) |
|---|---|---|---|---|
| sAA496 | 24 h | 0.23 | 1.11 | 20% |
| sAA632 | 24 h | 0.39 | 1.14 | 34% |
| sAA635 | 24 h | 0.34 | 0.98 | 35% |
| sAA496 | 48 h | 1.4 | 2.69 | 52% |
| sAA632 | 48 h | 2.34 | 3.09 | 76% |
| sAA635 | 48 h | 1.86 | 2.75 | 68% |
| sAA496 | 72 h | 2.6 | 4.24 | 61% |
| sAA632 | 72 h | 3.6 | 5.1 | 71% |
| sAA635 | 72 h | 2.78 | 4.27 | 65% |
| sAA496 | 144 h | 7.70 | 7.86 | 98% |
| sAA632 | 144 h | 8.55 | 8.79 | 97% |
| sAA635 | 144 h | 7.92 | 8.23 | 96% |

Strains described herein (e.g., partially beta-oxidation blocked, increased monooxygenase activity (e.g., SEQ ID NO: 20 amplified) and increased POX5 activity) have produced greater than 50 g/L of adipic acid under fermentation conditions using coconut oil as the feedstock. In some embodiments, strains described herein have 1 or more, 5 or more, 10 or more, 15 or more, 20 or more, or 25 or more additional copies a nucleotide sequences encoding a monooxygenase activity, a monooxygenase reductase activity, and/or a POX5 activity as compared to a strain native for monooxygenase activity, monooxygenase reductase activity, and/or POX5 activity. In certain embodiments, strains described herein have 2 times or more, 5 times or more, 10 times or more, 15 times or more, 20 times or more, or 25 times or more monooxygenase activity, monooxygenase reductase activity, and/or a POX5 activity, as compared to a strain native for monooxygenase activity, monooxygenase reductase activity, and/or POX5 activity.

The polynucleotide sequences of the POX4 and POX5 genes isolated as described herein are presented below as SEQ ID NOS: 37 and 38, respectively. The amino acid sequences encoded by the polynucleotides of SEQ ID NOS 37 and 38, are presented as SEQ ID NOS: 39 and 40, respectively.

| SEQ ID NO | Description | Sequence |
|---|---|---|
| SEQ ID NO: 37 | acyl CoA oxidase, POX4 (*C. tropicalis* strain ATCC20336) nucleotide | ATGACTTTTACAAAGAAAAACGTTAGTGTATCACAAGG<br>TCCTGACCCTAGATCATCCATCCAAAAGGAAAGAGAC<br>AGCTCCAAATGGAACCCTCAACAAATGAACTACTTCTT<br>GGAAGGCTCCGTCGAAAGAAGTGAGTTGATGAAGGCT<br>TTGGCCCAACAAATGGAAAGAGACCCAATCTTGTTCA<br>CAGACGGCTCCTACTACGACTTGACCAAGGACCAACA<br>AAGAGAATTGACCGCCGTCAAGATCAACAGAATCGCC<br>AGATACAGAGAACAAGAATCCATCGACACTTTCAACAA<br>GAGATTGTCCTTGATTGGTATCTTTGACCCACAGGTCG<br>GTACCAGAATTGGTGTCAACCTCGGTTTGTTCCTTTCT<br>TGTATCAGAGGTAACGGTACCACTTCCCAATTGAACTA<br>CTGGGCTAACGAAAAGGAAACCGCTGACGTTAAAGGT<br>ATCTACGGTTGTTTCGGTATGACCGAATTGGCCCACG<br>GTTCCAACGTTGCTGGTTTGGAAACCACCGCCACATT<br>TGACAAGGAATCTGACGAGTTTGTCATCAACACCCCA<br>CACATTGGTGCCACCAAGTGGTGGATTGGTGGTGCTG<br>CTCACTCCGCCACCCACTGTTCTGTCTACGCCAGATT<br>GATTGTTGACGGTCAAGATTACGGTGTCAAGACTTTTG<br>TTGTCCCATTGAGAGACTCCAACCACGACCTCATGCC<br>AGGTGTCACTGTTGGTGACATTGGTGCCAAGATGGGT<br>AGAGATGGTATCGATAACGGTTGGATCCAATTCTCCAA<br>CGTCAGAATCCCAAGATTCTTTATGTTGCAAAAGTTCT<br>GTAAGGTTTCTGCTGAAGGTGAAGTCACCTTGCCACC<br>TTTGGAACAATTGTCTTACTCCGCCTTGTTGGGTGGTA<br>GAGTCATGATGGTTTTGGACTCCTACAGAATGTTGGCT<br>AGAATGTCCACCATTGCCTTGAGATACGCCATTGGTA<br>GAAGACAATTCAAGGGTGACAATGTCGATCCAAAAGA<br>TCCAAACGCTTTGGAAACCCAATTGATAGATTACCCAT<br>TGCACCAAAAGAGATTGTTCCCATACTTGGCTGCTGC<br>CTACGTCATCTCCGCTGGTGCCCTCAAGGTTGAAGAC<br>ACCATCCATAACACCTTGGCTGAATTGGACGCTGCCG<br>TTGAAAAGAACGACACCAAGGCTATCTTTAAGTCTATT<br>GACGACATGAAGTCATTGTTTGTTGACTCTGGTTCCTT<br>GAAGTCCACTGCCACTTGGTTGGGTGCTGAAGCCATT<br>GACCAATGTAGACAAGCCTGTGGTGGTCACGGTTACT<br>CGTCCTACAACGGCTTCGGTAAAGCCTACAACGATTG<br>GGTTGTCCAATGTACTTGGGAAGGTGACAACAATGTC<br>TTGGCCATGAGTGTTGGTAAGCCAATTGTCAAGCAAG<br>TTATCAGCATTGAAGATGCCGGCAAGACCGTCAGAGG<br>TTCCACCGCTTTCTTGAACCAATTGAAGGACTACACTG<br>GTTCCAACAGCTCCAAGGTTGTTTTGAACACTGTTGCT<br>GACTTGGACGACATCAAGACTGTCATCAAGGCTATTG<br>AAGTTGCCATCATCAGATTGTCCCAAGAAGCTGCTTCT<br>ATTGTCAAGAAGGAATCTTTCGACTATGTCGGCGCTG<br>AATTGGTTCAACTCTCCAAGTTGAAGGCTCACCACTAC<br>TTGTTGACTGAATACATCAGAAGAATTGACACCTTTGA<br>CCAAAAGGACTTGGTTCCATACTTGATCACCCTCGGTA<br>AGTTGTACGCTGCCACTATTGTCTTGGACAGATTTGCC<br>GGTGTCTTCTTGACTTTCAACGTTGCCTCCACCGAAG<br>CCATCACTGCTTTGGCCTCTGTGCAAATTCCAAAGTTG<br>TGTGCTGAAGTCAGACCAAACGTTGTTGCTTACACCG<br>ACTCCTTCCAACAATCCGACATGATTGTCAATTCTGCT<br>ATTGGTAGATACGATGGTGACATCTATGAGAACTACTT<br>TGACTTGGTCAAGTTGCAGAACCCACCATCCAAGACC<br>AAGGCTCCTTACTCTGATGCTTTGGAAGCCATGTTGAA<br>CAGACCAACCTTGGACGAAAGAGAAAGATTTGAAAAG<br>TCTGATGAAACCGCTGCTATCTTGTCCAAGTAA |
| SEQ ID NO: 39 | acyl CoA oxidase, POX4 (*C. tropicalis* strain ATCC20336) amino acid | MTFTKKNVSVSQGPDPRSSIQKERDSSKWNPQQMNYFL<br>EGSVERSELMKALAQQMERDPILFTDGSYYDLTKDQQR<br>ELTAVKINRIARYREQESIDTFNKRLSLIGIFDPQVGTRIGV<br>NLGLFLSCIRGNGTTSQLNYWANEKETADVKGIYGCFGM<br>TELAHGSNVAGLETTATFDKESDEFVINTPHIGATKWWIG<br>GAAHSATHCSVYARLIVDGQDYGVKTFVVPLRDSNHDL<br>MPGVTVGDIGAKMGRDGIDNGWIQFSNVRIPRFFMLQKF<br>CKVSAEGEVTLPPLEQLSYSALLGGRVMMVLDSYRMLA<br>RMSTIALRYAIGRRQFKGDNVDPKDPNALETQLIDYPLH<br>QKRLFPYLAAAYVISAGALKVEDTIHNTLAELDAAVEKND<br>TKAIFKSIDDMKSLFVDSGSLKSTATWLGAEAIDQCRQAC<br>GGHGYSSYNGFGKAYNDWVVQCTWEGDNNVLAMSVG<br>KPIVKQVISIEDAGKTVRGSTAFLNQLKDYTGSNSSKVVL<br>NTVADLDDIKTVIKAIEVAIIRLSQEAASIVKKESFDYVGAE<br>LVQLSKLKAHHYLLTEYIRRIDTFDQKDLVPYLITLGKLYA<br>ATIVLDRFAGVFLTFNVASTEAITALASVQIPKLCAEVRPN<br>VVAYTDSFQQSDMIVNSAIGRYDGDIYENYFDLVKLQNP<br>PSKTKAPYSDALEAMLNRPTLDERERFEKSDETAAILSK* |

| SEQ ID NO | Description | Sequence |
|---|---|---|
| SEQ ID NO: 38 | acyl CoA oxidase, POX5 (*C. tropicalis* strain ATCC20336) nucleotide | ATGCCTACCGAACTTCAAAAGAAAGAGAACTCACCAA<br>GTTCAACCCAAAGGAGTTGAACTACTTCTTGGAAGGTT<br>CCCAAGAAAGATCCGAGATCATCAGCAACATGGTCGA<br>ACAAATGCAAAAAGACCCTATCTTGAAGGTCGACGCTT<br>CATACTACAACTTGACCAAAGACCAACAAAGAGAAGTC<br>ACCGCCAAGAAGATTGCCAGACTCTCCAGATACTTTG<br>AGCACGAGTACCCAGACCAACAGGCCCAGAGATTGTC<br>GATCCTCGGTGTCTTTGACCCACAAGTCTTCACCAGA<br>ATCGGTGTCAACTTGGGTTTGTTTGTTTCCTGTGTCCG<br>TGGTAACGGTACCAACTCCCAGTTCTTCTACTGGACC<br>ATAAATAAGGGTATCGACAAGTTGAGAGGTATCTATGG<br>TTGTTTTGGTATGACTGAGTTGGCCCACGGTTCCAAC<br>GTCCAAGGTATTGAAACCACCGCCACTTTTGACGAAG<br>ACACTGACGAGTTTGTCATCAACACCCCACACATTGGT<br>GCCACCAAGTGGTGGATCGGTGGTGCTGCGCACTCC<br>GCCACCCACTGCTCCGTCTACGCCAGATTGAAGGTCA<br>AAGGAAAGGACTACGGTGTCAAGACCTTTGTTGTCCC<br>ATTGAGAGACTCCAACCACGACCTCGAGCCAGGTGTG<br>ACTGTTGGTGACATTGGTGCCAAGATGGGTAGAGACG<br>GTATCGATAACGGTTGGATCCAGTTCTCCAACGTCAG<br>AATCCCAAGATTCTTTATGTTGCAAAAGTACTGTAAGG<br>TTTCCCGTCTGGGTGAAGTCACCATGCCACCATCTGA<br>ACAATTGTCTTACTCGGCTTTGATTGGTGGTAGAGTCA<br>CCATGATGATGGACTCCTACAGAATGACCAGTAGATT<br>CATCACCATTGCCTTGAGATACGCCATCCACAGAAGA<br>CAATTCAAGAAGAAGGACACCGATACCATTGAAACCA<br>AGTTGATTGACTACCCATTGCATCAAAAGAGATTGTTC<br>CCATTCTTGGCTGCCGCTTACTTGTTCTCCCAAGGTG<br>CCTTGTACTTAGAACAAACCATGAACGCAACCAACGA<br>CAAGTTGGACGAAGCTGTCAGTGCTGGTGAAAAGGAA<br>GCCATTGACGCTGCCATTGTCGAATCCAAGAAATTGTT<br>CGTCGCTTCCGGTTGTTTGAAGTCCACCTGTACCTGG<br>TTGACTGCTGAAGCCATTGACGAAGCTCGTCAAGCTT<br>GTGGTGGTCACGGTTACTCGTCTTACAACGGTTTCGG<br>TAAAGCCTACTCCGACTGGGTTGTCCAATGTACCTGG<br>GAAGGTGACAACAACATCTTGGCCATGAACGTTGCCA<br>AGCCAATGGTTAGAGACTTGTTGAAGGAGCCAGAACA<br>AAAGGGATTGGTTCTCTCCAGCGTTGCCGACTTGGAC<br>GACCCAGCCAAGTTGGTTAAGGCTTTCGACCACGCCC<br>TTTCCGGCTTGGCCAGAGACATTGGTGCTGTTGCTGA<br>AGACAAGGGTTTCGACATTACCGGTCCAAGTTTGGTTT<br>TGGTTTCCAAGTTGAACGCTCACAGATTCTTGATTGAC<br>GGTTTCTTCAAGCGTATCACCCCAGAATGGTCTGAAG<br>TCTTGAGACCTTTGGGTTTCTTGTATGCCGACTGGATC<br>TTGACCAACTTTGGTGCCACCTTCTTGCAGTACGGTAT<br>CATTACCCCAGATGTCAGCAGAAAGATTTCCTCCGAG<br>CACTTCCCAGCCTTGTGTGCCAAGGTTAGACCAAACG<br>TTGTTGGTTTGACTGATGGTTTCAACTTGACTGACATG<br>ATGACCAATGCTGCTATTGGTAGATATGATGGTAACGT<br>CTACGAACACTACTTCGAAACTGTCAAGGCTTTGAACC<br>CACCAGAAAACACCAAGGCTCCATACTCCAAGGCTTT<br>GGAAGACATGTTGAACCGTCCAGACCTTGAAGTCAGA<br>GAAAGAGGTGAAAAGTCCGAAGAAGCTGCTGAAATCT<br>TGTCCAGTTAA |
| SEQ ID NO: 40 | acyl CoA oxidase, POX5 (*C. tropicalis* strain ATCC20336) amino acid | MPTELQKERELTKFNPKELNYFLEGSQERSEIISNMVEQ<br>MQKDPILKVDASYYNLTKDQQREVTAKKIARLSRYFEHE<br>YPDQQAQRLSILGVFDPQVFTRIGVNLGLFVSCVRGNGT<br>NSQFFYWTINKGIDKLRGIYGCFGMTELAHGSNVQGIET<br>TATFDEDTDEFVINTPHIGATKWWIGGAAHSATHCSVYA<br>RLKVKGKDYGVKTFVVPLRDSNHDLEPGVTVGDIGAKM<br>GRDGIDNGWIQFSNVRIPRFFMLQKYCKVSRSGEVTMP<br>PSEQLSYSALIGGRVTMMMDSYRMTSRFITIALRYAIHRR<br>QFKKKDTDTIETKLIDYPLHQKRLFPFLAAAYLFSQGALYL<br>EQTMNATNDKLDEAVSAGEKEAIDAAIVESKKLFVASGC<br>LKSTCTWLTAEAIDEARQACGGHGYSSYNGFGKAYSDW<br>VVQCTWEGDNNILAMNVAKPMVRDLLKEPEQKGLVLSS<br>VADLDDPAKLVKAFDHALSGLARDIGAVAEDKGFDITGP<br>SLVLVSKLNAHRFLIDGFFKRITPEWSEVLRPLGFLYADW<br>ILTNFGATFLQYGIITPDVSRKISSEHFPALCAKVRPNVVG<br>LTDGFNLTDMMTNAAIGRYDGNVYEHYFETVKALNPPEN<br>TKAPYSKALEDMLNRPDLEVRERGEKSEEAAEILSS* |

Example 33

Amplification of Lipase Activity and Analysis of Strains with Increased Lipase Activity The *C. tropicalis* genome contains multiple genes which encode lipase activities. A lipase activity, carried out by a lipase enzyme, liberates fatty acids from a glycerol backbone. This activity is particularly beneficial when using oils (e.g., plant based oils, coconut oil) as the culture feedstock. Amplification of endogenous lipase activity coding sequences in an engineered organism has been shown to improve the level of adipic acid production with respect to a corresponding strain with a native level of lipase activity. Without being limited by any theory, it is believed the increased adipic acid titers seen are the result of improved substrate utilization.

Cloning of *C. tropicalis* Strain Lipase Activity Coding Sequences.

BLAST searches were conducted in the *C. tropicalis* strain ATCC20962 genomic database using the gene sequence of a lipase activity encoded by *Yarrowia lipolytica* (LIP2; GenBank Accession # CAB91111.1). The corresponding *C. tropicalis* sequence was cloned under the control of POX4 or PGK promoters as follows.

Primers were generated to clone the identified *C. tropicalis* lipase homolog into vectors pAA73 (POX4 promoter) and pAA105 (PGK promoter), respectively. For cloning the lipase activity into pAA73 vector, the nucleotide sequence encoding the lipase activity was PCR amplified from *C. tropicalis* strain ATCC20336 using primers oAA734 and oAA735 in a reaction containing 5 uL 10× buffer, 2.0 uL of oAA734 and 2 uL of oAA735 (10 uM), 1.0 uL genomic DNA, 1.0 uL of dNTPs, 1.0 uL of Pfu and 38 uL sterile H2O. The thermocycling parameters used were 95° C. for 2 minutes, 30 cycles of 95° C. 20 seconds, 55° C. 30 seconds, 72° C. 1 minute, followed by 72° C. 5 minutes and a 4° C. hold. PCR product of the correct size was gel purified, ligated into pCR-Blunt II-TOPO and transformed into competent TOP10 *E. coli* cells (Invitrogen). Clones containing PCR inserts were sequenced to confirm correct DNA sequence. The resulting plasmid was designated, pAA234. Plasmid pAA234 was restriction enzyme digested with XmaI and XbaI, according to manufacturer's recommendations. DNA fragments were separated on a 0.8% agarose gel. The DNA fragment containing the nucleotide sequence encoding lipase activity was gel purified and ligated into XmaI/XbaI digested vector pAA073, and transformed into TOP10 *E. coli* cells (Invitrogen). Correct plasmid structure, including the presence of the fragment carrying lipase activity, was confirmed by restriction digestion and designated as pAA235. pAA235 includes the lipase activity coding sequence under control of the POX4 promoter.

For cloning the lipase activity into the pAA105 (PGK promoter) vector, PCR amplification of the lipase activity was performed as above using primers oAA736 and oAA737. PCR product was gel purified, digested with SapI, ligated into pAA105 vector and transformed into TOP10 *E. coli* cells (Invitrogen). Correct plasmid structure, including the presence of the fragment carrying lipase activity, was confirmed by restriction digestion and designated as pAA236. pAA236 includes the lipase activity coding sequence under control of the PGK promoter. The lipase activity cloned into plasmids pAA235 and pAA236 was analyzed to determine the presence or absence of any potential secretion leader sequences. The N-terminal protein secretion leader sequence was predicted by SignalP (SignalP 3.0 Server) and the predicted cleavage site of the lipase activity leader sequence is most likely between pos. 15 and 16: SSA-GK, as shown in the amino acid sequence listing presented in the table below. The nucleotide sequence of the lipase activity cloned into pAA235 and pAA236 also is presented in the table below.

| SEQ ID NO | Description | Sequence |
|---|---|---|
| SEQ ID NO: 27 | C. Tropicalis lipase activity, (identified using Y. lipolytica BLAST search) Nucleotide Seq | ATGATTGTTTTATTCATCCTTGTATTTATTTGTCTATCTT<br>CAGCCGGGAAACCAAACAAACCAGAAGCTCCAGCAAA<br>AGATTACATCAAACTCGTTGAATTCTCCAATTTTGCCGC<br>CGTTGGCTACTGCGTTAATAGAGGTCTAGCAAAGGGC<br>CGTCTAGGAGACGAGGACTCCAACTGTGCCTTGTTGG<br>CATGCAAGAACGACTTCCTTGCGGACGTCGAGATTATT<br>AAGATATTTGACTTCAACCGTCTTAATGAAGTTGGAACA<br>GGTTACTATGCCTTGGACAGGAAGAGAAAGGCAATAAT<br>ATTGGTATTTAGAGGGTCTGTCTCCCGACGTGACTGGG<br>CGACAGACATGGATTTCATCCCCACTTCTTACAAGCCA<br>ATTGTGTATGAGGAAAACTTTGGTTGTGACCCCTACATT<br>CTGACCGAATGCAAGAACTGTCGTGTGCACCGTGGTTT<br>CTACAATTTCTTGAAGGATAACTCTGCAGCAATTATCAC<br>CGAGGGAATTGCGTTGAAAGAAGAGTACCCGGACTAC<br>CAGTTCTTGATCATTGGTCATTCTTTGGGCGCTGCCTT<br>GACAATGTTGAGTGGCATCGAGTTCCAGTTGTTGGGGT<br>ACGATCCTTTGGTGGTGACTTATGGTGGTCCAAAGGTG<br>GGCAACCAAGAGTTTGCTGACTTCACGGACAACTTGTT<br>TGACACGGATGAGGTGGACAATGAAATCGCCACCAAC<br>CGTGATTTTTCAAGAGGATTCATTAGAGTGGTACACAA<br>GTATGATATAATACCATTCTTGCCGCCGTTGTTTAGTCA<br>CGCAGGGTACGAATACTTTATTGACAAGAGAGAGTTGC<br>CCCATGAAGAATGTGATTTGGACAGACGAGGCATGGA<br>GTACTCGGGGATATTTAAGAGATCGCTGACCATAAAAC<br>CGTCCACTTTATGGCCAGATAGGTTGGGGAAGTATGAA<br>CATACACATTATTTTAGAAGAATCACTAGTTGTAGGGAC<br>GACGAT |
| SEQ ID NO: 28 | C. Tropicalis lipase activity, (identified using Y. lipolytica BLAST search) | <u>MIVLFILVFICLSSA</u>GKPNKPEAPAKDYIKLVEFSNPAAVGY<br>CVNRGLAKGRLGDEDSNCALLACKNDPLADVEIIKIFDFN<br>RLNEVGTGYYALDRKRKAIILVFRGSVSRRDWATDMDFIP<br>TSYKPIVYEENFGCDPYILTECKNCRVHRGFYNFLKDNSA<br>AIITEGIALKEEYPDYQFLIIGHSLGAALTMLSGIEFQLLGYD |

| SEQ ID NO | Description | Sequence |
|---|---|---|
| | Amino Acid Seq | PLVVTYGGPKVGNQEFADFTDNLFDTDEVDNEIATNRDF SRGFIRVVHKYDIIPFLPPLFSHAGYEYFIDKRELPHEECDL DRRGMEYSGIFKRSLTIKPSTLWPDRLGKYEHTHYFRRIT SCRDDD |

Figure 39:
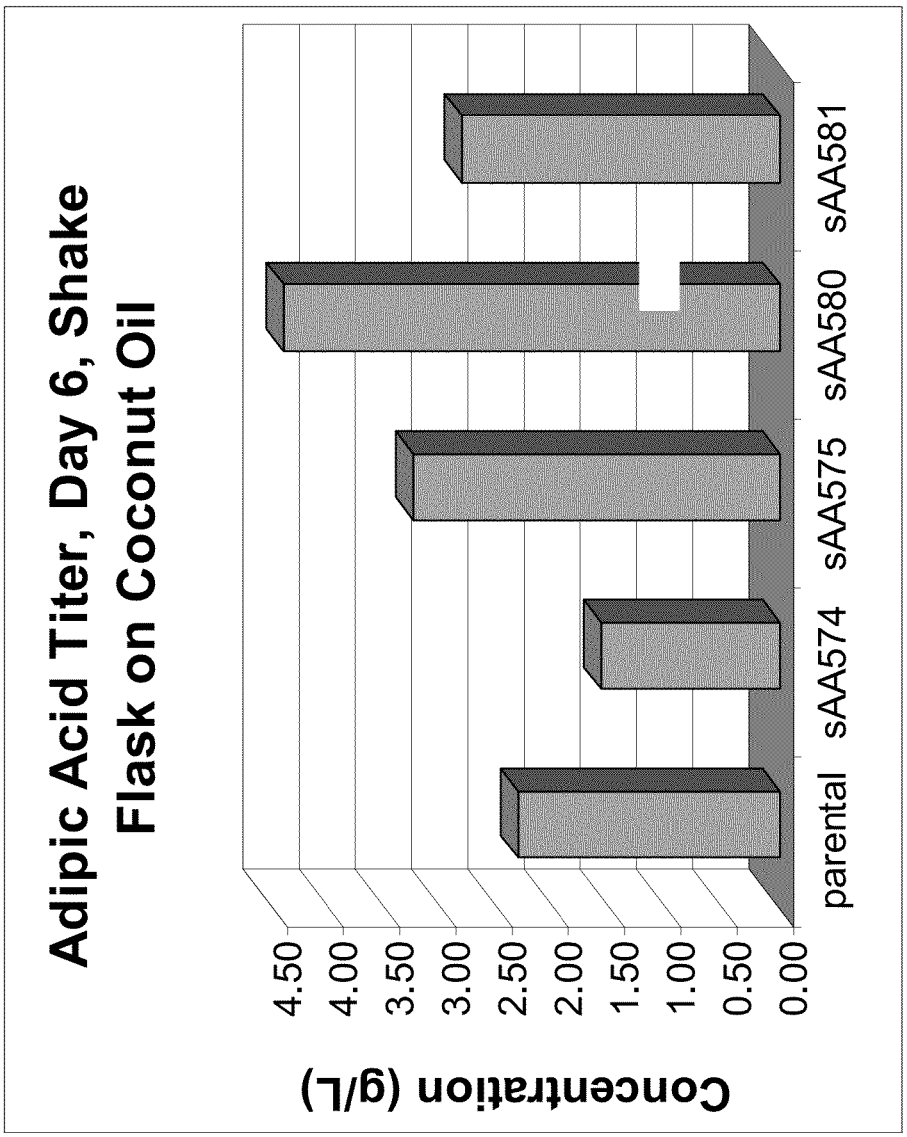
FIG. 39 graphically illustrates the effect of increased lipase activity on the conversion of coconut oil to adipic acid. Experimental results and conditions are given in Example 33.

Plasmids pAA235 and pAA236 were linearized with ClaI and transformed into competent *C. tropicalis* cells of strain sAA329 (URA3 auxotroph). The integration of the linearized plasmids was confirmed by colony PCR using primers oAA734 and oAA281 for the pAA235 integration and oAA736 and oAA281 for the pAA236 integration, respectively. Two transformants from each transformation were selected. Strains from the pAA235 integration were designated as sAA574 and sAA575. Strains from the pAA236 integration were designated as sAA580 and sAA581. The strains were used to evaluate the effects of increased lipase activity on adipic acid production. One colony of each strain was inoculated into 5 mL SP92 and grown overnight at 30° C. with shaking at about 200 rpm. The overnight culture was used to inoculate 50 mL of SP92 medium, in shake flasks (e.g., about $OD_{600nm}$ 0.4), and incubated under the same condition for 24 hours. Cells were harvested and resuspended in 20 mL of TB-lowN medium supplemented with 1.6 mL of coconut oil and 20 uL sterile antifoam B. Samples were taken daily and analyzed for diacid production by gas chromatography. The results are shown graphically in FIG. 39. As shown in FIG. 39, 3 of the 4 strains with increased copy number of the lipase activity nucleotide sequence tested showed increased levels of adipic acid production, when compared to the parental strain. The results shown in FIG. 39 represent the data from six days of fermentation in SP92 medium supplemented with coconut oil as the carbon source.

A second BLAST search utilizing the nucleotide sequence of a lipase activity from *C. dubliniensis* also was performed in the *C. tropicalis* strain ATCC20962 database. The second BLAST search identified another *C. tropicalis* lipase activity homolog (e.g., ORF7657), with an amino acid sequence different from the lipase activity identified using the *Y. lipolytica* lipase activity sequence. The second lipase activity is being cloned and over-expressed in *C. tropicalis* for evaluation in fermentation of adipic acid. The amino acid sequence of the second lipase activity identified in *C. tropicalis* strain ATCC20962 using the *C. dubliniensis* lipase activity sequence in a BLAST search, is presented below as SEQ ID NO: 29.

```
                                         SEQ ID NO: 29
MLRTVRHYSKVINIKDKGEKAARVITSEFAKLKDHYDAPKYPIVLCH

GFSGFDRLGLFPLPNLLEDTTATTKTKEITERSLIELDYWYGIKDALE

NLGSTVFIAKVPAFGDIRSRAISLDKFIEKQCKALRQTESKSSIYNKP

DSSNDDTTTFKDKHQPIKVNLISHSMGGVDSRYLISRIHNDNENYR

VASLTTILTPHHGSECADFIVDLIGDNGVLKKVCPPSIYQLTTLHMKK

FNEVVKDDPSVQYFSFGARFNPRWYNLFGLTWLVMKYQIEKEQAD

RFKHMIDNDGLVSVESSKWGQYIGTLDEVDHLDLINWTNRARSVF

DKVMFAQNPNFNPIALYLEIADQLSKKGL
```

Example 34

Amplification of Acyl-CoA Carboxylase Activity

Acetyl-CoA carboxylase (e.g., ACC) catalyzes the reaction that produces Malonyl-CoA for fatty acid synthesis. The reaction catalyzed by ACC is the committed step in fatty acid synthesis. Strains engineered to convert glucose to adipic acid using a native, mutant, or specialized (e.g., hexanoate synthase) fatty acid synthase would benefit from increased carbon flux through the pathway, as contributed by increased acetyl-CoA carboxylase activity. The nucleotide sequence encoding ACC activity has been cloned and is being over expressed and evaluated for contribution to adipic acid conversion in *C. tropicalis*. The nucleotide sequence encoding the ACC activity from *C. tropicalis* strain ATCC 20336 is presented below as SEQ ID NO: 30.

```
atgagatgccaagtatctcaaccatcacgatttactaacttgcttgtacatagactcccacgaac actacttaattatccagttgtaaatacctatttattcctagacgtcattattcccttaattttcattcaa gaacctactaaagaaaatgacagatctttccccaagtccaacagactcccttaattacacaca gttgcactcatccttgccatcacatttcttaggtgggaactcggtgctcaccgctgagccttctgcc gtgacagatttcgtcaaaacacaccaaggtcacactgttatcaccaaagtcttgattgccaaca acggtattggtgccgtcaaagaaataagatccgtcagaaaatgggcctacgaaacttttggtg acgaaagagctatacagtttgtcgccatggccactcccgaagatatggaggctaacgccgag tacattcgaatggccgaccagtttgtcgaggtcccaggtggtaccaataacaacaactacgcg aatgttgacttgattgtcgaaatcgctgaaagaaccgatgtccacgccgtttgggctggttgggt catgcctccgaaaacccttttgttgccagraaggttggcagcttcccctaagaagatcgtgtttatt ggtcctccagggtctgccatgagatctttgggtgacaagatttcttccaccattgttgcacaacac gccaaagtgccatgtatcccatggtctggtactggtgtcgaagaggtccacgtcgacccagaa
```

-continued

```
accaagttggtgtctgttgacgaccacgtctacgccaaaggttgctgtacctcgccagaagacg gtttggaaaaagccaaacgtatcggattcccagttatggttaaggcatccgaaggtggtggtgg taaaggtatcagaaaagtcgaccacgaaaaggacttcatcagtttgtacaaccaggcggcta acgaaataccagggtcaccaattttcatcatgaagttggccggtgacgccagacacttggaag tgcaattgtttgccgatcagtacggtaccaacatttcgcttttcggtagagattgttctgtgcaaaga agacatcaaaagatcattgaagaagctccagtcacaattgccaacaaagacacttttgttgag atggagaaagctgccgtcagattgggtaagttggttggttacgtgtctgccggtaccgttgaata cctttactcctacgccaagacaagttctacttttggaattgaacccaagattgcaagttgaaca tccaactaccgaaatggtttccggtgtcaacttaccagccgctcagttgcaaattgctatgggtct cccaatgcacagaatcagagacatcagattgttgtacggttgttgatccacactctgccactgag attgatttcgagttcaagtccccaaactcattgatcacgcaaagaaagccagctccaaagggtc actgtaccgcttgtcgtatcacttctgaagatccaggtgaagggttcaagccaagtggtggtact cttcacgagttgaacttccgttcttcgtccaatgtctggggttacttctcggtcgccaaccaatcttct atccactcctttgctgattcccagtttggtcacattttcgcctttggtgaaaatcgtcaagcctctaga aagcacatgattgttgccttgaaggaattgagtatcagaggtgactttagaaccactgttgaata cttgatcaagttgttggagactccagatttcgccgacaacaccatcactaccggttggttggatg agttgatcaccaagaagttgactgccgaaagaccagatcctatcgttgctgttgtctgtggtgcc gtcaccaaagcccacatccaagccgaagaagacaagaaggagtacattgagtctttggaaa agggtcaagttccaaacaagtccttgttgaaaactatcttcccagttgagtttatctacgaaggtg aaagatacaagtttactgccaccaagtcctccgaagacaagtacactttgttcctcaacggttct agatgtgtcattggtgctcgctcattgtctgatggtggcttgttgtgtgctttggacggtaagtcccac tctgtctactggaaggaagaagcagcggccactagattgtctgttgacggtaagacttgcttgttg gaagttgaaaacgacccaacccaattgagaactccgtctccaggtaagttggtcaagtacttg gttgagagtggtgaacacgttgatgccggccaatcttatgccgaagttgaagtcatgaagatgt gtatgcctttgattgcacaagaaaacggtactgttcaattgctcaaacaaccaggttccactctta acgctggtgacatcttggcaatcttggcattggacgatccatctaaagttaaacacgccaagcc atatgaaggcactttgccagagatgggtgatccaactgttaccggttccaaaccagctcacttgt tccaacattacgacaccatcttgaagaacatcttggctggttacgataaccaagtcattttgaact ccactttgaagaacatgatggagatcttgaagaacaaggagttgccttattctgaatggagattg caaatctccgccttgcattcaagaatcccaccaaagttggatgaggctttgacgtccttgattgaa agaaccgaaagcagaggcgccgaattcccagctcgtcagattttgaagctcgtcaacaagac tcttggtgaaccaggcaacgaattgttgggcgatgttgttgctcctcttgtctccattgccaaccgct accagaacggcttggttgaacacgagtacgactactttgcttcattggttaacgagtactgcaat gttgaacacttctttagtggtgaaaacgtgagagaagaagatgttatcttgagattgagagacg agaacaagtctgatttgaagaaggttatcagcatttgcttgtcccactcccgtgtcagtgctaaga acaacttgattttggccatcttggaagcttatgaaccattgttgcaatccaactcttcaactgccgtt gccattagagattcttttgaagaagatagtccagttggattctcgtgcttgtgccaaggttggtttga aagctagagaacttttgattcaatgttctttgccatccatcaaggaaagatctgaccaattggaac acattttgagaagtgcagtcgttgagacttcttatggtgaagttttcgccaagcacagagaaccta aattggaaatcatccaagaagttgtcgaatccaagcacgttgttttcgatgtcttgtcgcaattttg
```

-continued

```
gtccaccaagactgctgggttgccattgctgctgccgaagtctatgttagacgttcctacagagct tatgatttgggtaagatcgattaccacattcatgacagattgccaattgttgaatggaagttcaagt tggctcaaatcgcaggttccagatacaacgccgtccaatctgccagtgttggtgacgactcgac cactatgaagcatgctgcatctgtttctgacttgtcgtttgttgttgattccaagagcgaatccacttc cagaactggtgttttggttccagctagacatttggacgatgttgatgagattctttctgctgcattgg agtacttccaaccatctgatgcactctctttccaagctaagggagaaagaccagagttgttgaat gttttgaacattgtcatcaccgacattgacggttactctgacgaagatgaatgcttgaagagaatt catgaaatcttgaacgagtacgaagacgatttggtctttgctggtgttcgtcgtgttacttttgttttcg cccaccaagttggttcttatccaaagtactacaccttcactggtccagtgtatgaagaaaacaag gttatcagacacatcgaaccagctttggcttttccaattggaattgggaagattagccaactttgac atcaagccaattttcaccaataacagaaacattcatgtttacgaagctattggtaagaatgctcct tcggataagagattcttcactagaggtattattagaggtggtgtcctcaaagatgaaatcagtctt actgagtacttgattgctgaatcgaacagattgatcagtgntatcttggataccttggaagttattg acacttccaactccgatttgaaccacattttcatcaacttctccaacgttttcaacgtccaaccagc tgatgttgaagctgcttttgcttcattcttggaaagatttggtagaagattgtggagattgagagtta ctggtgctgaaatcagaattgtctgtaccgacccacagggcaactcattcccattgcgtgccatt atcaataacgtttcaggttatgttgtcaagtcggaattgtacttggaagtgaagaaccctaagggt gattgggtcttcaaatccattggccaccctggctcaatgcacttgcaaccaatctcgactccatac ccagtcaaggaatccttgcagccaaaacgttacagagctcacaacatgggaaccacttttgttt acgatttcccagagttgttccgtcaagccaccatttcccaatggaagaagcacggcaagaagg ctcctaaagatgtcttcacttctttggagttgatcaccgatgaaaacgatgctttggttgccgttgaa agagatccaggtgccaacaagattggtatggttggtttcaaggtcactgccaagacccctgaat acccacgcggacgttcattcatcattgttgccaatgatatcacccacaagattggttcctttggtcc agatgaagatgaatacttcaacaagtgtaccgacttggccagaaagttgggtgttccaagaatt tacctttctgccaactccggtgccagaattggtgttgctgaagagttgattccattgtaccaagttg cttggaacgaagaaggtaacccagataaaggtttcagatacttgtacttgaacccagacgcca agaagctttggaaaaagacggcaagggtgacactattgttactgaacgtattgtcgaagatg gtcaagaacgtcacgttatcaaggccattattggtgctgagaacggcttgggtgttgaatgtttga aaggttccggtttgattgctggtgccacttcaagagcctacagagacatcttcaccattaccttggt cacttgtagatctgttggtattggtgcctatttggtcagattgggtcaaagagctatccaaattgaa ggtcaaccaatcattttgactggtgcaccagctatcaacaagttgttgggtagagaagtttactcg tcgaacttgcaattgggtggtacccagatcatgtacaacaatggtgtttcccacttaactgccagt gacgatttggctggtgttgagaagatcatggaatggttgtcctacgttccagctaagcgtggtatg ccagtaccaatcttggaaagtgaagatacctgggacagagacattgactactacccaccaaa gcaagaagctttcgacatcagatggatgatcgaaggtaagcaagttgaaggtgaagagtttga atctggtttgtttgacaaaggttcattccaggaaactttatcaggatgggctaaaggtgttgtcgttg gtagagctcgtctcggtggtatcccaattggtgtcattggtgttgagaccagaactattgaaaaca tgatcccagctgacccagccaacccaagttccactgaagccttgatccaagaagccggtcaa gtctggtatccaaactctgcgttcaagaccgcacaagccattaacgacttcaacaacggtgaa caattgccattgatgatcttggccaactggagaggtttctctggtggtcagagagatatgtacaac gaggtcttgaagtacggttccttcattgttgacgctttagttgatttcaagcagccaatcttcacttac
```

-continued

```
atcccaccaaatggtgaattgagaggtggctcttgggtcgttgttgatccaaccatcaactccga catgatggaaatgtatgccgacgttgactccagagctggtgttttggaaccagaaggtatggttg gtatcaaatacagacgggacaagttgttggctaccatgcaaagattggatccaacttatgccca attgaaggagaagttgaacgactcgagcttgtcgccagaagaacatgcccaagtcagcacc aagattgtcaagcgtgaaaaggcattgttgccaatctatgcccaaatttctgtccagtttgccgac ttgcacgacagatccggacgtatgatggctaaaggtgtcattagaaaagaaatcaagtgggtt gacgccagacgtttcttcttctggagattgagaagaagattgaacgaagagtacgttttgaagtt gattggtgaacaggtcaagaatgccaacaagttggaaaaggttgccaggttgaagagttggat gccaactgttgactacgacgatgaccaagctgtcagtacttggattgaagagaaccacgcca aattgcaaaagagagttgaagaattgagacaggagaagaacaagtccgacattgtcaaattg ttgcaagaagacccatcaaacgctgcctctgttatgagggatttcgttgatagattgtccgatgaa gaaaaggaaaagttccttaaatcattgaactag
```

Example 35

Cloning, Amplification and Overexpression of C. tropicalis Fatty Acid Synthase Activity Type I fatty acid synthases contain all of the active domains for fatty acid synthase on one (e.g., alpha) or two (e.g., alpha and beta) polypeptides. Hexanoate synthase, a specialized fatty acid synthase enzyme, is unique in that the fatty acid product is the six carbon long hexanoic acid rather than a fatty acid with a 16 or 18 carbon chain length product produced by native fungal fatty acid synthases. Hexanoate synthase is composed of an A (HexA) and B (HexB) subunit with the same active domain organization as the native fungal fatty acid synthase alpha (Fas2) and beta (Fas1) subunits.

Hexanoate synthase activity was introduced into an engineered strain by placing the nucleotide sequences of HexA and HexB under the control of the C. tropicalis PGK promoter and integrating the heterologous sequence into the C. tropicalis genome, as described herein. To further provide increased carbon flux through engineered pathways and increase the production of adipic acid, additional fatty acid synthase activities were cloned and amplified in engineered strains. Mutant fatty acid synthase activities that produce intermediate chain length products also would beneficial for increasing the conversion of carbon feedstocks to adipic acid. To ensure that the fatty acids produced are not converted to products shorter than 6 carbons (e.g., hexanoic acid), the strains for increased fatty acid synthesis activity also would include a partially blocked beta oxidation pathway (e.g., disrupted for POX4 activity) to reduce or eliminate the degradation of fatty acids to chain lengths below 6 carbons. In some embodiments, FAS mutants can be identified by using serially passaged or mutagenized C. tropicalis strains and determining fatty acid profiles by gas chromatography.

Cloning of C. tropicalis FAS2 and FAS1

The native C. tropicalis FAS2 and FAS1 genes were cloned between the C. tropicalis strain ATCC20336 PGK promoter and terminator, and correct nucleotide sequence was verified by DNA sequencing. The vectors were linearized inside the URA3 selectable marker by restriction enzyme digestion and subsequently co-transformed into a ura-derivative of C. tropicalis strain ATCC20962 by targeted single-crossover integration at the URA3 locus. Correct integration of both the FAS2 and FAS1 constructs was confirmed by PCR. The nucleotide sequences of the C. tropicalis FAS2 and FAS1 activities are presented in the table below as SEQ ID NOS: 31 and 32.

| SEQ ID NO | Description | Sequence |
| --- | --- | --- |
| SEQ ID NO: 31 | FAS2, C. tropicalis ATCC20336 | atgaagccagagattgaacaagaattatcccacaccttgttaacagaattgttagct tatcagttcgcttctccagtcagatggatcgaaacccaagatgtcttcttgaagcaac acaacaccgaaagaatcatcgaaatcggcccttccccaaccttggccggtatggc caacagaaccatcaaggccaaataccaatcctacgacgccgcgttgtccttgcaa agagaagtcttatgctactctaaggacgccaaggagatctactacaagccagatc cagcagatcttgctccaaaggaagaaccaaagaaggaagaagctgccgccgct ccagccgctacaccagctgctgctgctgctgctgctactcctgctgctgccccagtc gccgctgctccagccccatctgctggccctgctgaatccatcccagatgaaccagt caaggcttccttgttgatccacgtcttggttgctcagaaattaaagaaaccattggat gctgttccaatgtccaaggctatcaaagatttagttaacggtaagtccactgtccag aacgaaattcttggtgacttgggtaaagaattcggttccactcctgaaaaaccaga agataccccattggaagaattggccgaacagttccaagactccttcagtggtcaatt gggtaagacttctacttcattgattggtagattgatgtcttctaagatgcctggtggtttct caatcaccgctgccagaaaatacttggaatccagattcggtttgggtgccggtaga caagactctgtcttgttggttgcttttgaccaacgaacctgcaagcagattgggttctg aggccgaagctaagaccttcttggacaccatggctcagaaatatgcctcatctgct ggtatttccttgtcgtcagcttctgccggtgccggtgctggaggtgccgccggtggcg ccgttgttgacagtgctgctttggacgccttgactgctgaaaacaagaaattggcta gacaacaattagaggtcttggctagatacttgcaagtcgacttgaactcaggagct aagtcttttatcaaagaaaagaagcttccgctgttttgcagaaagaattggacttgt |

| SEQ ID NO | Description | Sequence |
|---|---|---|
| | | gggaagccgaacatggtgaattctacgccagaggtatcaaaccaactttctcagct
ttgaaagcaagaacctatgattcctactggaactgggccagacaagatgttttgtcc
atgtactttgatattttgtttggtaagttgacctccgttgacagagaaaccatcgacca
atgtatccaaattatgaacagatccaacccaactttgatcaagttcatgcaatacca
cattgaccactgcccagaatacaaggggtgagacttacaagttggccaagagattg
ggtcaacagttgattgacaactgtaagcaaaccttgaatgaagacccagtgtaca
aggacgtttctagaatcactggtccaaaagaccaccgtctgcgccaagggtaacatt
gaatacgaagaagccgaaaaggattctgttagaaagtttgaacagtacgtctacg
aaatggcccaaggtggtgaaatgaccaagattgcccaaccaactattcaagaag
acttggccagagtttacaaagccatctccaagcaagcttccagagacagcaagtt
ggaattgcagaaagtctacgagcaattgttgaaggttgttgctggttcagacgaaat
tgaaactcagcaattaaccaaggacatcttgcaagctccaactggctccaacacc
caactgatgaagatgaaatttccaccgccgactctgacgatgaaattgcttcattg
ccagacaagacttcaattgcccaaccagtttcttcaactgttccaccccagaccatc
ccattcttgcacattcaaaagaagaccaacgaaggctgggaatacgaccgcaag
ttgtctgccctttacttggacggtttggaatccgctgctgtcaacggtctcaccttcaag
gacaagtacgttttggttaccggtgctggtgctggatccattggtgccgaaatcttgc
aaggtttgatcagtggtggtgccaaggttgttgttaccacctctagattctccaagaa
ggttactgagtactaccaaaacatgtacgccagatacggtgctgccggttctactttg
attgttgttccattcaaccaaggttctaaacaagatgttgacgctttggttcaatacatc
tacgacgatccaaagaagggtggtttaggctgggacttggatgccattatcccattc
gctgctatcccagaaaatggtaacggtatcgacaacattgattctaaatccgaattt
gcccacagaattatgttgaccaaccttttgagatttgttgggtgctgtcaaatccaaga
agactaccgacaccagaccagctcaatgtatcttgccaatgtctcctaaccacggt
actttcggtttcgatgggttgtactctgaatccaagatttccttggaaaaccttgttcaac
agatggtactccgaagattggggctccaagttgaccgtctgtggtgccgttattggtt
ggaccagaggtactggtttgatgagcgccaacaacatcattgccgaaggtatcga
aaagattggtgtcagaaccttctcccaaaaggaaatggctttcaacatcttgggtttg
ttgactccagagattgtcaagttgtgccaagaagaaccagttatggccgacttgaa
cggtggtttgcaattcattgaaaacttgaaggatttcacttccaagttgagatctgactt
gatggaatccgctgaagttagaagagctgtctccattgaatccgccatcgaacaa
aaggttgtcaatggtgacaatgttgatgccaactacaccaaggttaccgttcaacc
aagagccaacatgaaattcgacttcccaaccttgaaatcgtacgatgagatcaag
aaggttgctccagaattggaaggcatgttggacttggaatccgtcgttgttgtcaccg
gttttgccgaagttggtccatgggtaacgccagaaccagatgggaaatggaatc
caagggtgaattctccttggaaggtgccattgaaatggcctggatcatgggtttcatc
aagtaccacaacggtaacttgaagggtaagccttactctggttgggttgatgccaa
gacccaaactccaatcgatgacaaggacatcaaggccaagtacgaagaagag
atcttggaccactctggtattagattgattgagccagaattgttcaatggctacgatcc
aaagaagaagcagatgatccaagaagttgtcatccaacatgacttggaaccattt
gaagcctccaaggaaactgctgaacaatacaaacacgaacacggtgacaagt
gtgagatctttgaaattgaagaatccggtgaatacactgttagaatcttgaaaggtg
ctaccttgtttgttccaaaggctttgagatttgacagattggttgctggtcaaattccaa
ctggttgggatgctcgtacctacggtattccagaagataccattaaccaagttgatcc
tatcactttgtacgtcttggttgctaccgttgaagctttgttgtctgctggtatcaccgacc
catatgaattctacaagtacgtccacgtttccgaagttggtaactgttctggttccggt
atgggtggtgtctctgccttgagaggaatgttcaaggacagatacgccgacagac
cagtgcaaaacgatatcttgcaagaatctttcatcaacaccatgtccgcctgggtta
acatgttgttgttgtcttcttcgggtccaatcaagaccccagttggtgcctgtgctaccg
ctgttgaatccgttgacattggtattgaaactattttgtctggtaaggctaaggttgttat
ggttggtggttacgatgacttccaggaagaaggttcttatgaattcgccaacatgaat
gccacttccaactcccttgacgagtttgctcacggcagaacttccaaaggagatgtc
cagaccaactaccaccaccagacacggtttcatggaggcccaaggttctggtatc
caagttattatgactgctgacttggccatcaagatgggtgttccaattcacgctgtgtt
ggccatgtctgctactgctaccgacaagattggtagatctgttccagctccaggtaa
gggtattttgaccactgccagggaacaccacgtaacttgaagtacccatctccag
ctttgaacatcaagtacagaaagagacaattgaaggctagattagaccaaatcaa
ggcttgggaagaagctgaaattgcttacttgcaagacgaagctgagttggccaag
gaagaaatgggcgatgagttctccatgcacgaattcttgaaggaaagaactgaa
gaagtgtaccgtgaatccaagagacaagtttctgacgctaagaagcaatgggta
accaattctacaagtctgacccaagaattgctccattgagagggtgccttggctgcttt
caacttgaccattgacgatcttggtgttgcttccttccacggtacttctaccgtcgccaa
cgataagaacgaatccgccactattaacagcatgatgcaacacttgggcagatct
gaaggtaacccagtgtttggtgttttccagaagtacttgactggtcatccaaagggtg
ctgctggtgcttggatgttgaacggtgccatccagatctggtgtctggtattgttcca
ggtaacagaaatgccgataacgttgacaaggtcttggaagaatacgagtacgtctt
gtacccatccagatccatccaaactgacggtatcaaggccgtttccgtgacctctttc
ggtttcggtcaaaaaggtgctcaagctgttgtcgtccacccagactacttgtttgctgtt
ttggatagatctacttatgaggactacgccaccagagtttctgccagaaacaagaa
gacttaccgttacatgcacaatgctattactagaaacactatgtttgttgctaaggata
aggctccatatgccgatgaattggaacaaccagtttacttggacccattagccccgtg
ttgaaaacgctaaggaaaagcttgccttcagcaacaagagtatccaatccaacca
agctatgctggtgaaaatgccagaaccactgccaaggctttgagctgccttgaaca
agtcatccaaggggtgttggtgtcgacgttgaattattgtctgagctcaacttggagaat
gaaactttgttgcaagaaacttcactcctggtgaaatccaatactgctccaagagt
gccaacccacaagcttcatacaccggcacttggtctgctaaagaagctgtcttcaa
ggcattaggtgttgaatctaaaggtgctggtgccagcttggttgacattgagatcact
cgtgacgtcaacggcgctccacaagttgtcttgcacggtgatgcggcaaaatcag |

| SEQ ID NO | Description | Sequence |
|---|---|---|
| | | ccgccaaagctggtgtcaagaacgtcaagatttccatctcccatgacgacttccaa gccactgctgttgccttgagtgaattctag |
| SEQ ID NO: 32 | FAS1, C. tropicalis ATCC20336 | atgtctactcatagacctttccaattgacccacggttccatcgaacacaccttgttggt gccaaacgagttgttcttcaactattcacagttaaaagacgaattcataaagacctt gcctgaaccaaccgaaggtttcgctggcgacgatgaaccttccagtcctgctgaat tgtacggcaaattcctcggctacatcagtgacaacaccgttcaattccccccagatctt acaattgtccttgcaagacttccagcagcgattcttggacaaccacgacaacatcc actcctttgccgtcagattattagaagatgaagcttatccaacaacaatcaccaaag tcaaggaaaatatcatcaagaactactacaaagccatcaagtccatcgacaagg tcgagtcaaacttgttgtaccactgcaaacatgacgccaagttggccgctatattcg gtggtcaaggtaacaccgacgactactttgaagaattgcgtgaattgtacaccttat accagggcttgattgaggacctccttatctccattgccgacaagttggacgagttata ccctttcttttgacaagatctacacccagggtttgaacatcttgggctggttgaagcac ccagaaaccacccctgaccaagattacttgttgtccgtaccagtgagttgtcctgtta tctgtatcatccaattgtgtcactacaccatcacctgcaaagttcttggttgacccctg gtgaatttagagactcgttgaagtggtccaccggtcactcccaaggtttggttactgc taccgctatttccagttccgactcctgggactccttcaaacaaaactccattgctgcc gtctccttgatgcttttcattggtgccagatgtgtttggcttaccaagaactaccttgc caccaaccatgttgcaagacttccttggaacacggtgaaggtagaccatctccaat gttgtcagttagagacttgaccatcacccaagttgagaagtttattgaacagaccaa ctctcacttgccaaaggaaaagcacattgccgtcagtttggtcaatggtgccagaa atttggttctttctggtcccccggagtccctttacggtttcaacttgaacttgagaaacc aaaaggctccaatgggattggaccaatcacgtgttccattcagtgaacgtaagttg aagtgttccaacagattcttgccaattttttgcaccattccactctcacttgttggctgatg ccactgagtacatttttggatgatgtcaaagaacaccgtttgtctttccagaaattgaa gattgcagtctacgatacctacgacggctccaacttccaagagagcaaggaacc aattattgacagactcgtcaagtcatccgagttgccagttcactgggaaaccgc caccaaccacaggccaccccacattttggatttcggcccaggtggtgtctccggttt gggtgtttttgacccacagaaacaaggaaggtactggtgctagaataattgttgctg gtgctcttgactccaacccaattgacgatgagtatggtttcaagcacgaaatcttcca gacttctgccgacaagtccatcaagtgggctagcgattggttggaagaattcaaac caactttggtcaagacttcccagggaaagatctacgtcaacaccaagttctcgcaa ttgttgggcagagctcccttgatggtcccaggtatgacaccaaccactgttaaccca gacatcattgccgcctctttgaatgctggctatcacattgaattagccggtggtggtta tttcgccggcaggatcatgaccaaagccattgaccaaattgttgccgacatcaagc caggttacgtttgggtatcaacttgatttacgtcaaaccattcatgttgcaatggggt attccattgattaaggagttgagagaaaagggttatccaatccaatctttgaccattg gtgctggtgttccatctttggaagttgccactgaatacattgaagagtgggtctcacg cacttgggcttgaaaccaggttcgattgacgccatcagccaagtcatcaccattgc caaggctcatccaaagttcccaattgtcttgcaatggactggtggtagaggtggtgg ccaccactcttttgaagatttccaccaaccaatcctccagatgtactccaagatcag aagatgcccaaacattgtcttggttgctggttccgggtttggttctgacgaagacacc tacccatacttgactggttcttggtccaagagattcaactacccaccaatgccatac gatggtgtcttgtttggttccagagtcatgaccgccaaggaggcccacacttcgttgg aagctaagaaattgattgcctcgtgccaggtgtcccagatgagaagtgggagca aacctacaagaagccaaccggtggtatcatcactgttagatctgaaatgggtgag ccaatcccacaagattgccaccagaggtgtcatgttctggaaggaattggacgaca ctatcttcaaccttccaaagccaaaagccttggaagccatcaagaagaagagag actacatcatcaagaagttgaacagcgacttccaaaagccatggtttggtaagaat gcttctggtgtttgtgacttgcaagaaatgacctacgaggaaatcgccaacgattg gttgagttgatgtacgtcaagaagtctcaaaagatggattgacgtttccttaagaaact tgtacggtgacttttttgagaagagttgaagaaagattcacttctgctgccggcgtggtt tccttgttgcaaaacttcatccagttgaacgacccagaaacattcagtgccgagttct tcaacaagttcccacaagccaaggaacaattgatttccgaagaagacgctgacc acttttttgttgttggctgccagaccagggcaaaagccggttccattcgtgccagtcttg gacgaaagatttgaattcttcttcaagaaagattctctttggcaatctgaagacttgga aagtgttgtcgacgaagacgttcaaagaacttgtatcttgcacggtccagttgcctcc caattcaccaagaaggttgatgaaccaattggcgaaatcttggactctatccacga gggccatattgccaagttgatcaaggatgaatacgctggtgatgcatccaagatcc cagttgttgagtacttcggtggtttcaagaccgacaaggttaatgctaacaatgttca agtcaatgctaccagaaaggaaaccgtctacgaaattggttccaagttgccagcc aggcaagactggttgacttgttggccggtactgaattgaactggttgcacgctttca tctccaccaacagaattgtccaaggctccaagcacgtcgccaacccattgacga cattttggctcccgttgccagatccagtgtttccattgacaaggtaccaagaaattg actgcttatgaaaaggtcaagggtgagttggttccagttgttgaaattgaattggtca agccaaacaccattcaattgtctttgattgaacacagaactgctgatggcaaacca gttgctttgccattcttgtacaagtacgacccaactgatgggtttgcaccagtcttgga gatcatggaaaacagaaacaaggaatcaaggaattctactgaagttgtggttc ggtgcttccgtcccttacgacaatgacatcgatgtcgaagagcaaatcttgggtgac gaaatcaccatttcttctcaagacattggtgaattcacacacgctattggtaacaagt gtgaagcctttgtcaacagaccaggtaaggtcactttggctccaatggatttcgccat tgttgttggtggaaagctatcatcaagtccatcttcccaaagccacggtgacggtgac ttgttgaagttggtccacttgtccaacggttacaagatgatccctggtgcagctccatt gcaaagggcgatgttgtttccactagatctgacatcaaggctgttttgaaccaacc aagtggtaagttggttgaagttgttggtaccatcttccgtgaaggcaagccagttatg gaagtcacttcacaattcttgtaccgtggtgaatacgacgactactgcaacaccttc caaaaggtcactgaaactccagttcaagtctcattcaagtctcctaaggatttggctg |

| SEQ ID NO | Description | Sequence |
|---|---|---|
| | | ttttgagatccaaggaatggttccatttggaaaaggatgtcgagtttgatgctttgactt
tcagatgtgaatccacttacaagttcaagtctgccaacgtctactcgtccatcagaa
cgaccggtcaagttttcttggagttgtccaccaaagaagttatccaagttggttctgtt
gactatgaagctggtacctcttatggtaacccagtcactgactacttgaacagaaac
ggtaagaccattgaagaggctgttacttttgagaatgccatcccttgtcgtctggtg
aagagttgaccaccaaggctccgggtaccaacgagccatatgctattgtttctggtg
actacaacccaatccacgttccagagtcttttctgcttacgccaagttgccaggtact
atcacccacggtatgtactcttctgccgccatcagagccttggttgaagagtgggct
gccaacaacgttgcccaagagtcagagccttcaagtgtgaatttgttggtatggttt
tgccaaacgacactttgcaaaccactatggaacacgttggtatgatcaatggccgt
aagatcatcaaggtcaagactgtcaatgccgagaccgagactccagtcttgcttgc
tgaagccgaaattgaacaaccaaccaccacctatgttttcactggtcaaggttccc
aagaacaaggcatgggtatggatttgtacaactcttctgaagttgcccgtaacgtttg
ggataccgccgacaagcatttcatcaaccactatggcttctccatcttggacattgtg
caaaacaaccctaaggaattgactatccactttggaggtgctaaaggtagagctat
cagagacaactacattggtatgatgtttgaaacaattggtgaagacggttctttgaa
gtccgaaaagatcttcaaggacattgacgaaaacaccacttcctacacctttgtttct
gacactgggttgttgtctgctactcaattcacccaacccgctttgactttgatggagaa
ggctgcctacgacgatatcaagtctaaaggattgattccaagtgacatcatgtttgct
ggtcactctcttggtgaatactctgctttgacttccttggccaacgttatgcctattgaat
ccttggttgatgttgtcttctacagaggtatgaccatgcaagttgctgttccaagagac
gagtttggtagatccaactacggtatggttgctgtcaacccaaccagagtcagccc
aacatttgacgatgccgccatgagatttgttgttgacgagactgccaagagaacca
cctggttgttggaaattgtcaactacaatgttgaaaaccaacagtacgttgctgctgg
tgacttgagagccttggataccttgaccaacgtgttgaatgttttgaagatcaacaag
attgatattgtcagattgcaagaacaattatccctcgacaaggtcaaggagcacttg
tacgagattgttgatgaagttgctgccaagtccattgctaagccacaaccaattgaa
ttagaaagaggttttgctgttatcccattgaagggtatttctgtcccattccactcttccta
cttgatgtctggtgtcaagccattccagagattcttgtgcaagaagattccaaaggct
tccatcaaaccacaagatttgattggcaagtacattcctaacttgactgctaagccat
ttgaacttactaaggaatacttccaggatgtctacgacttgactaaatctgaaaagat
caaggctatcttggacaactgggaaaaatacgaatag |

Cultures of positive transformants were grown overnight in YPD medium at 30° C. and 200 rpm shaking until stationary phase. Cells from 4 mL of the culture were harvested by centrifugation and the cell pellet was frozen at −20° C. until used. Cell pellets were treated for lysis by resuspension in cold yeast lysis buffer (50 mM Tris pH 8.0, 0.1% Triton X-100, 0.5 mM EDTA, 1× ProCEASE protease inhibitors), working on ice during the entire lysis procedure. The resuspended cell pellet solutions were added to prechilled screw-cap tubes containing zirconia beads and cycled on a Bead Beater (BioSpec Products) once for 2 minutes. A volume of the whole cell extract (200 uL) was removed for later analysis and stored at 4° C. The remainder of the whole cell extract was removed to a new tube and centrifuged for 15 minutes at 16,000×g 4° C. to pellet insoluble debris. The supernatant soluble cell extract was removed to a new tube and stored at 4° C. Protein concentration was determined by Bradford assay (Pierce). For SDS PAGE analysis, a volume of whole cell extract and soluble cell extract from each sample equivalent to 50 ug total protein was acetone precipitated at −20° C. for 2 hours and centrifuged for 15 minutes at 16,000×g 4° C.

The protein pellet was washed with cold 80% acetone and recentrifuged. The protein pellet was allowed to air dry for 10 minutes before adding 50 uL of 1XLDS sample buffer (Invitrogen) containing 50 mM DTT and incubated overnight at 4° C. The samples were heated at 70° C. for 10 minutes before SDS PAGE on 4-12% NuPAGE gels (Invitrogen) and transfer to nitrocellulose. Immunodetection was performed using overnight incubation in 1:5,000 mouse anti-6×HIS ("6×HIS" disclosed as SEQ ID NO: 60) (Abcam) primary antibody and four hour incubation in 1:5,000 donkey anti-mouse HRP (Abcam) secondary antibody. Signal development was performed with Supersignal Pico West reagent (Pierce). For NativePAGE analysis, samples of soluble cell extract were prepared at a final concentration of 0.35 ug/uL in yeast lysis buffer and 1× NativePAGE sample buffer (Invitrogen) containing 0.025% G250. Samples (3.5 ug) were resolved on 3-12% NativePAGE gels (Invitrogen) and transferred to PVDF according to manufacturer's instructions. Immunodetection of 6×HIS tagged ("6×HIS" disclosed as SEQ ID NO: 60) oligomeric complexes was performed as described herein.

Figures 40, 41:
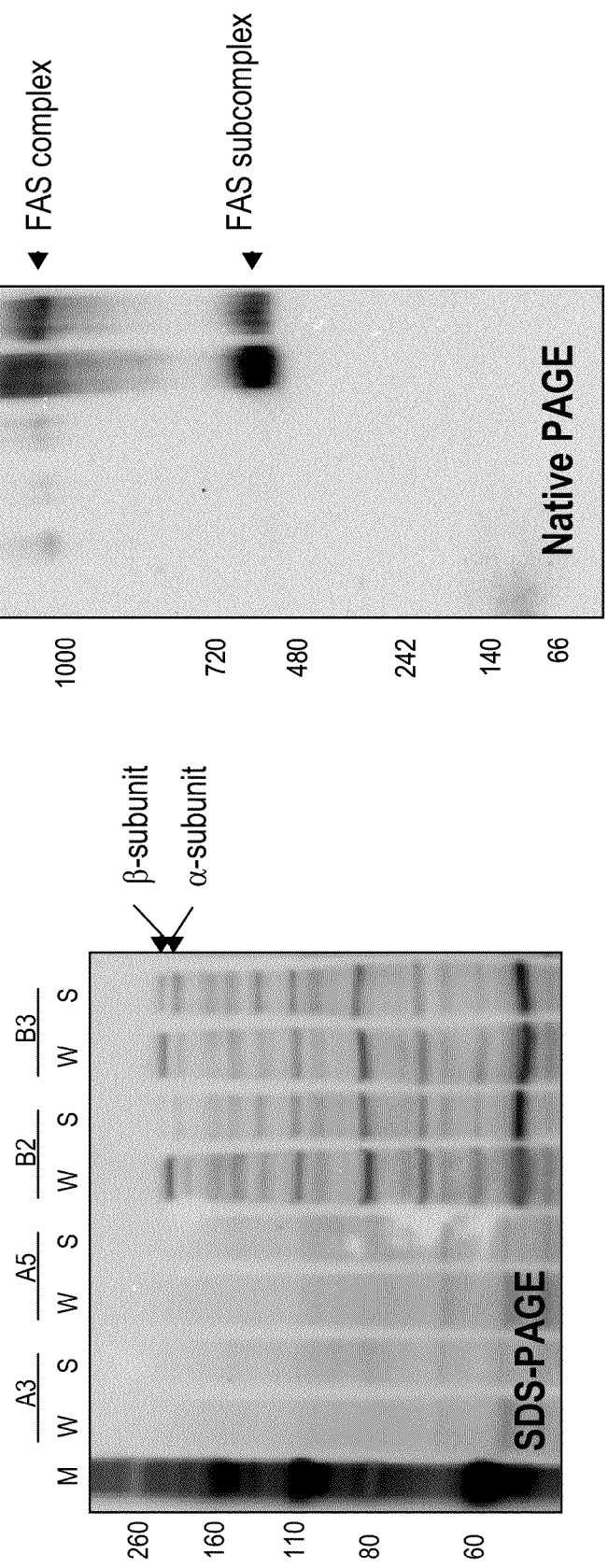
FIG. 40 shows the results of immunodetection of over expressed polypeptides coding FAS2 and FAS1 activities after denaturing polyacrylamide gel electrophoresis (SDS-PAGE).
FIG. 41 shows the results of immunodetection of over expressed polypeptides coding FAS2 and FAS1 activities after native polyacrylamide gel electrophoresis (Native-PAGE). Experimental results and conditions are given in Example 35.

Immunodetection of the expressed proteins is shown in FIGS. 40 and 41. Denaturing SDS PAGE (see FIG. 40) shows immunoreactive bands at sizes expected for the Fas2 (206 kDa) and Fas1 (229 kDa) subunits indicating successful overexpression of both FAS subunits. Native electrophoresis allowed detection of oligomeric complexes formed by the 6×HIS-tagged ("6×HIS" disclosed as SEQ ID NO: 60) subunits. Immunodetection of the native PAGE (see FIG. 41) shows no detectable signal at the size for the individual subunits indicating that all subunits are in oligomeric complexes. Two sizes of oligomeric complexes are detected, one at an estimated size of about 600 kDa and another with an estimated size of about 1.1 MDa. The detected large complex is smaller than the predicted size for the native alpha$_6$beta$_6$ FAS (2.6 MDa), however migration of large oligomeric complexes in native PAGE is known to frequently be subject to large migration error, thereby hampering accurate size estimation. qPCR analysis of strains engineered for amplified FAS activity indicated that in some strains about 2 additional copies of FAS2 and FAS1 subunits were present (data not shown).

In some embodiments, strains engineered for conversion of glucose to adipic acid include two or more additional copies of each of the nucleotide sequences identical to SEQ ID NOS: 31 and 32. In certain embodiments, strains engineered for conversion of glucose to adipic acid produce two or more times the fatty acid synthase activity encoded by nucleotide sequences identical to SEQ ID NOS: 31 and 32, as compared to a strain with native fatty acid synthase activity.

In some embodiments, strains engineered for conversion of paraffins (e.g., oils, petroleum distillates, plant based oils, coconut oil) to adipic acid include two or more additional copies of each of the nucleotide sequences identical to SEQ ID NOS: 31 and 32. In certain embodiments, strains engineered for conversion of paraffins to adipic acid produce two or more times the fatty acid synthase activity encoded by nucleotide sequences identical to SEQ ID NOS: 31 and 32, as compared to a strain with native fatty acid synthase activity.

Example 36

Cloning of the *C. tropicalis* ATCC20336 ZWF Gene

Plasmid pAA246

A PCR product containing the ZWF (glucose 6 phosphate dehydrogenase) nucleotide sequence was amplified from *C. tropicalis* 20336 genomic DNA using primers oAA831 and oAA832. The PCR product was gel purified and ligated into pCR-Blunt II-TOPO (Invitrogen), transformed into competent TOP10 *E. coli* cells (Invitrogen) and clones containing PCR inserts were sequenced to confirm correct DNA sequence. One such plasmid was designated pAA246. Plasmid pAA246 was digested with BspQI and a 1.5-kb fragment was isolated. Plasmid pAA073 which contained a POX4 promoter and POX4 terminator also was digested with BspQI and gel purified. The isolated fragments were ligated together to generate plasmid pAA253. Plasmid pAA253 contains PPOX4ZWFTPOX4 fragment and URA3.

Strains sAA650 and sAA651

Plasmids pAA253 and pAA156 were digested with ClaI and column purified. Strain sAA329 was transformed with this linearized DNA and plated on SCD-ura plate. Several colonies were checked for ZWF and CYP52A19 integration. From those colonies, qPCR was performed to check the copy number of ZWF and CYP52A19 integration. Strain sAA650 contains 5 copies of ZWF and 9 copies of CYP52A19. Strain sAA651 contains 5 copies of ZWF and 12 copies of CYP52A19.

The nucleotide and amino acid sequence encoded by the *C. tropicalis* strain ATC20336 ZWF gene are presented below as SEQ ID NOS: 33 and 34

ZWF nucleotide sequence
SEQ ID NO: 33
ATGTCTTATGATTCATTCGGTGACTACGTCACTATCGTCGTTTTC

GGTGCTTCCGGTGACTTGGCCAGCAAAAAAACCTTCCCTGCCTT

GTTTGGCTTGTTTAGAGAAAAGCAATTGCCCCCAACCGTCCAGA

TCATTGGCTATGCCAGATCCCATTTGTCCGACAAGGACTTCAAA

ACCAAGATCTCCTCCCACTTCAAGGGCGGCGACGAAAAAACCA

AGCAAGACTTCTTGAACTTGTGTACTTATATCAGCGACCCATAC

GACACTGACGATGGTTACAAGAGATTGGAAGCCGCCGCTCAAG

AATACGAATCCAAGCACAACGTCAAGGTCCCTGAAAGATTGTTT

TACTTGGCCTTGCCTCCTTCTGTCTTCCACACCGTCTGTGAGCA

AGTCAAGAAGATCGTCTACCCTAAGGACGGTAAGCTCAGAATCA

TCATTGAAAAGCCGTTCGGACGTGATTTGGCCACCTACCGTGAA

TTGCAAAAGCAAATCTCCCCATTGTTCACCGAAGACGAACTCTA

CAGAATTGACCACTACTTGGGTAAAGAAATGGTCAAGAACTTGT

TGGTTTTGAGATTCGGTAACGAATTGTTCAGTGGGATCTGGAAC

AACAAGCACATCACCTCGGTGCAAATCTCCTTCAAGGAACCCTT

CGGTACCGAAGGTAGAGGTGGCTACTTTGACAACATTGGTATCA

TCAGAGATGTCATGCAAAACCACTTGTTGCAAGTCTTGACCTTG

TTGACCATGGAAAGACCAGTCTCTTTTGACCCAGAAGCTGTCAG

AGACGAAAAGGTCAAGGTTTTGAAAGCTTTTGACAAGATTGACG

TCAACGACGTTCTTTTGGGACAATACGCCAAGTCTGAGGATGGC

TCCAAGCCAGGTTACTTGGATGACTCCACCGTCAAGCCAAACTC

CAAGGCTGTCACCTACGCCGCTTTCAGAGTCAACATCCACAACG

AAAGATGGGACGGTGTTCCAATTGTTTTGAGAGCCGGTAAGGCT

TTAGACGAAGGTAAAGTTGAAATTAGAATCCAATTCAAGCCAGTT

GCCAAAGGTATGTTTAAGGAGATCCAAAGAAACGAATTGGTTAT

TAGAATCCAACCAGACGAAGCCATCTACTTGAAGATCAACTCCA

AGATCCCAGGTATCTCCACCGAAACTTCCTTGACCGACTTGGAC

TTGACTTACTCCAAGCGTTACTCCAAGGACTTCTGGATCCCAGA

AGCATACGAAGCCTTGATCAGAGACTGTTACTTGGGCAACCACT

CCAACTTTGTCAGAGACGATGAATTGGAAGTTGCTTGGAAGCTC

TTCACCCCATTGTTGGAAGCCGTTGAAAAAGAAGACGAAGTCAG

CTTGGGAACCTACCCATACGGATCCAAGGGTCCTAAAGAATTGA

GAAAGTACTTGGTCGACCACGGTTACGTCTTCAACGACCCAGGT

ACTTACCAATGGCCATTGACCAACACCGATGTCAAAGGTAAGAT

CTAAGAATAG

ZWF amino acid sequence
SEQ ID NO: 34
msydsfgdyvtivvfgasgdlaskktfpalfglfrekqlpptvqiigyar shlsdkdfktkisshfkggdektkqdflnlctyisdpydtddgykrleaa aqeyeskhnvkvperlfylalppsvfhtvceqvkkivypkdgklriiiek pfgrdlatyrelqkqisplftedelyridhylgkemvknllvlrfgnelf sgiwnnkhitsvgisfkepfgtegrggyfdnigiirdvmqnhllqvltll tmerpvsfdpeavrdekvkvlkafdkidyndvllgqyaksedgskpgyld dstvkpnskavtyaafrvnihnerwdgvpivlragkaldegkveiriqfk pvakgmfkeiqrnelviriqpdeaiylkinskipgistetsltdldltys kryskdfwipeayealirdcylgnhsnfvrddelevawklftplleavek edevslgtypygskgpkelrkylvdhgyvfndpgtyqwpltntdvkgki Example 37

Cloning of *C. tropicalis* ACH Genes

ACH PCR product was amplified from *C. tropicalis* 20336 genomic DNA using primers oAA1095 and oAA1096, shown in the table below. The PCR product was gel purified and ligated into pCR-Blunt II-TOPO (Invitrogen), transformed into competent TOP10 *E. coli* cells (Invitrogen) and clones containing PCR inserts were sequenced to confirm correct DNA sequence.

Figure 51:
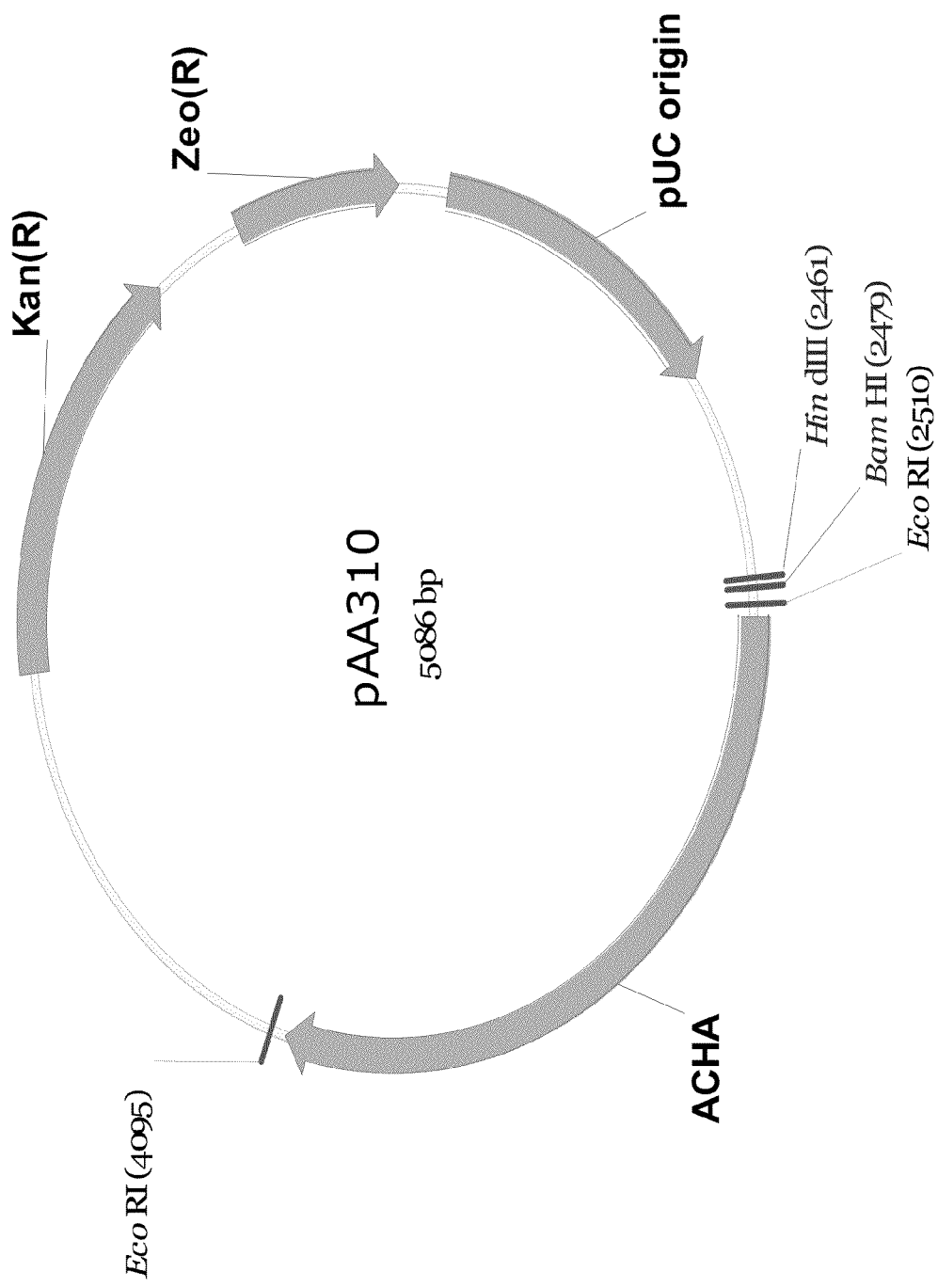
FIG. 51 illustrates a plasmid used for cloning the ACHA allele from *C. tropicalis*.
Figure 52:
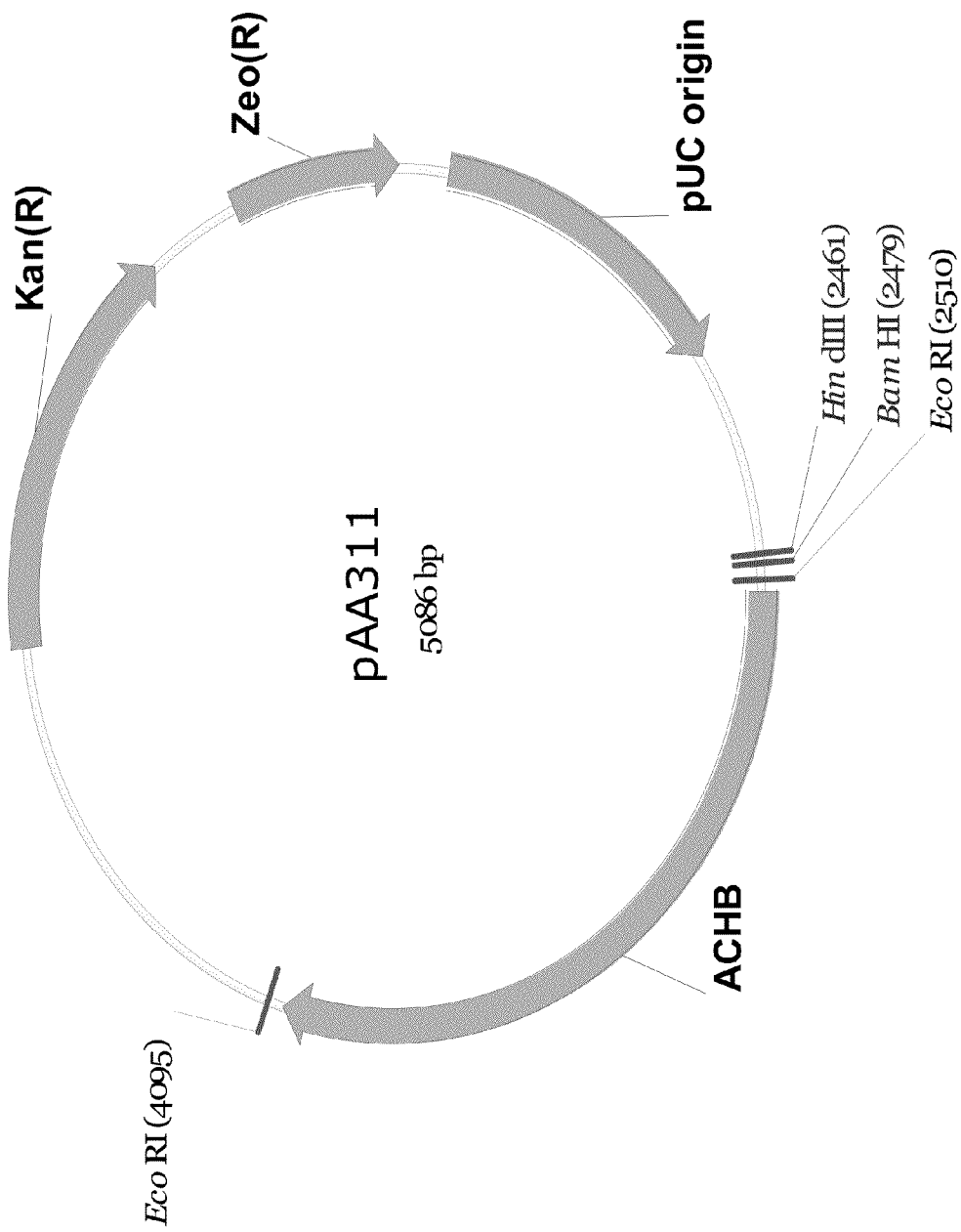
FIG. 52 illustrates a plasmid used for cloning ACHB from *C. tropicalis*. See Example 37 for experimental details.

Sequence analysis of multiple transformants revealed the presence of allelic sequences for the ACH gene, which were designated ACHA and ACHB. A vector containing the DNA sequence for the ACHA allele was generated and designated pAA310 (see FIG. 51). A vector containing the DNA sequence for the ACHB allele was generated and designated pAA311 (see FIG. 52).

| Primer | sequence (SEQ ID NOS 245-246, respectively, in order of appearance) |
|---|---|
| oAA1095 | CACACACCCGGGATGATCAGAACCGTCCGTTATCAAT |
| oAA1096 | CACACATCTAGACTCTCTTCTATTCTTAATTGCCGCT TCCACTAAACGGCAAAGTCTCCACG |

Example 38

Cloning of C. tropicalis FAT1 Gene

Figure 53:
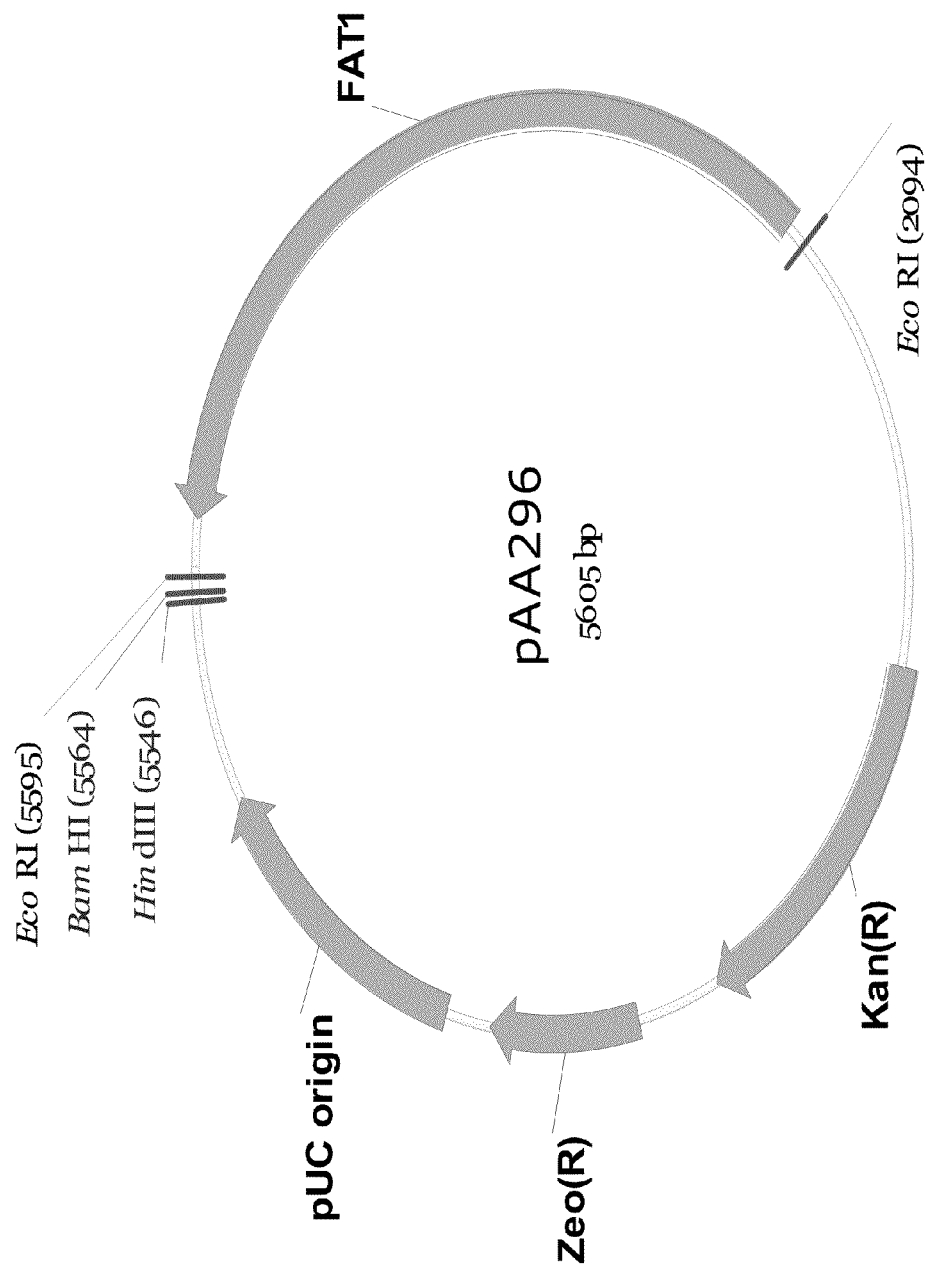
FIG. 53. illustrates a plasmid used for cloning the FAT1 gene from *C. tropicalis*. See Example 38 for experimental details. The cloned FAT1 DNA sequence are used to construct FAT1 "knock out" constructs.

FAT1 PCR product was amplified from C. tropicalis 20336 genomic DNA using primers oAA1023 and oAA1024, shown in the table below. The PCR product was gel purified and ligated into pCR-Blunt II-TOPO (Invitrogen), transformed into competent TOP10 E. coli cells (Invitrogen) and clones containing PCR inserts were sequenced to confirm correct DNA sequence. A vector containing the DNA sequence for the FAT1 gene was designated pAA296 (see FIG. 53).

| Primer | sequence (SEQ ID NOS 376-377, respectively, in order of appearance) |
|---|---|
| oAA1023 | GATATTATTCCACCTTCCCTTCATT |
| oAA1024 | CCGTTAAACAAAAATCAGTCTGTAAA |

Example 39

Cloning of C. tropicalis ARE1 and ARE2 Genes

Figure 54:
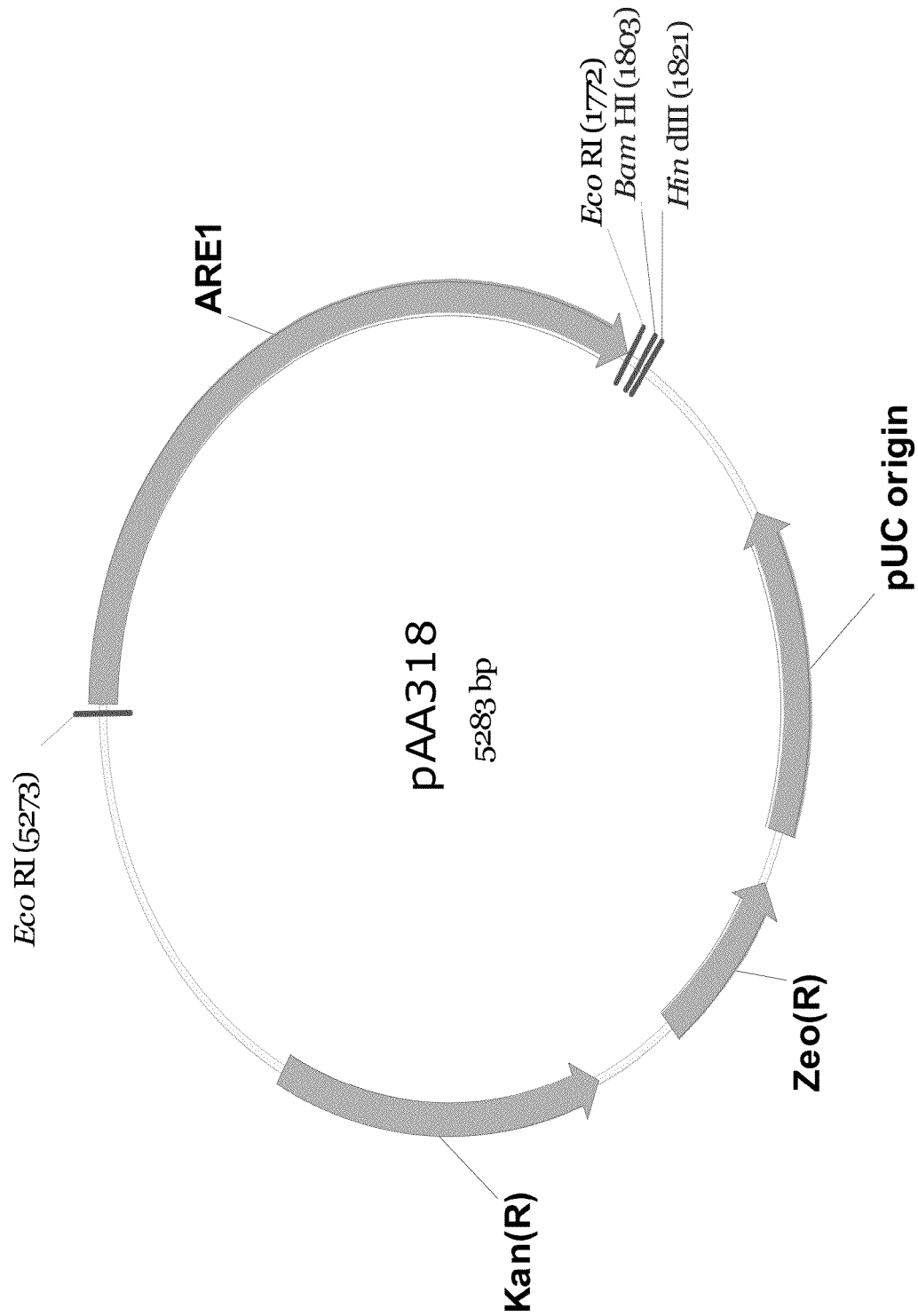
FIG. 54 illustrates a plasmid used for cloning the ARE1 gene from *C. tropicalis*.
Figure 55:
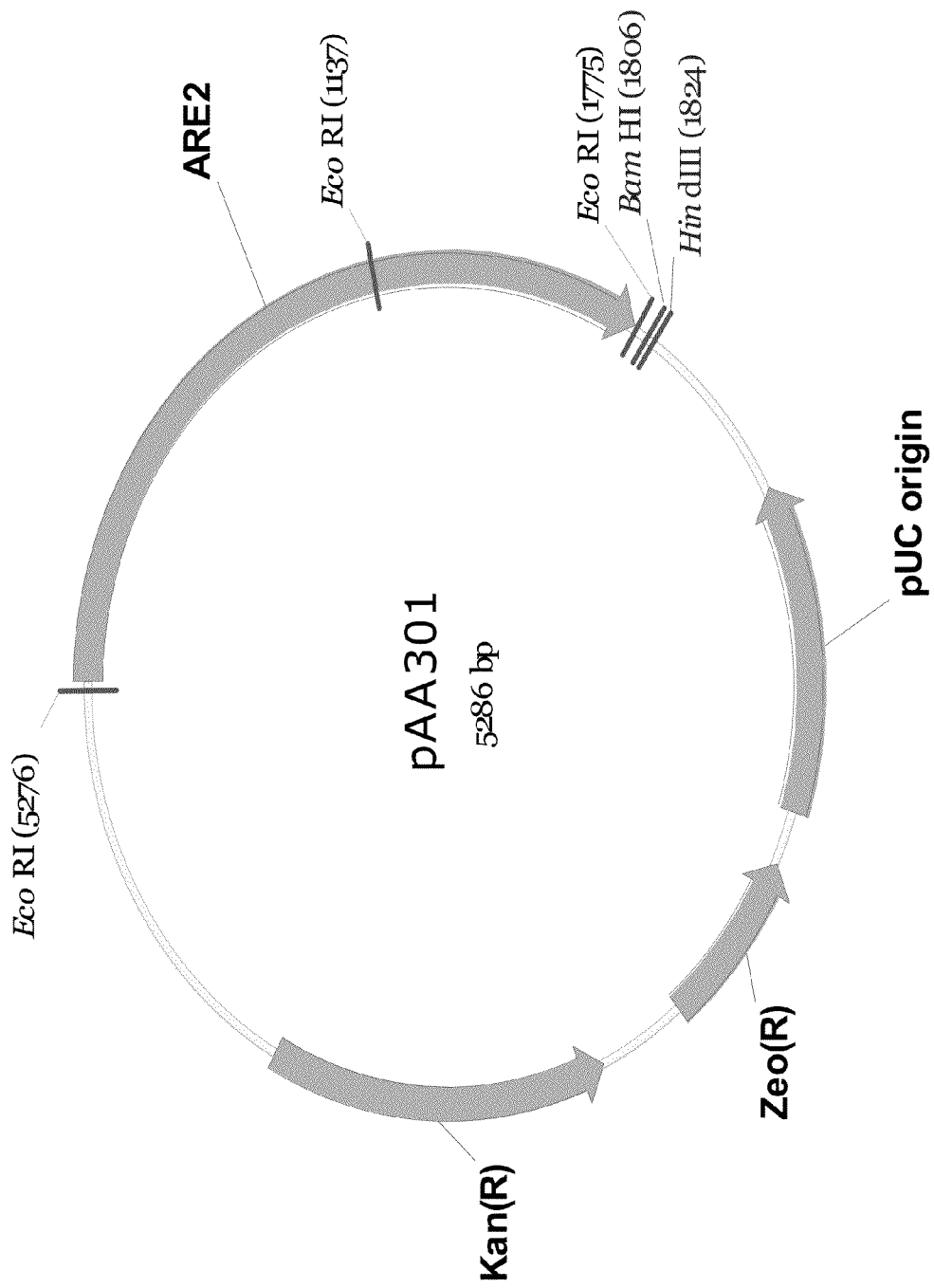
FIG. 55 illustrates a plasmid used for cloning the ARE2 gene from *C. tropicalis*. See Example 39 for experimental details. The cloned ARE1 and ARE2 DNA sequence are used to construct ARE1 and ARE2 "knock out" constructs.

ARE1 and ARE2 PCR products were amplified from C. tropicalis 20336 genomic DNA using primers oAA2006/oAA2007 and oAA1012/oAA1018, respectively, shown in the table below. The PCR products were gel purified and ligated into pCR-Blunt II-TOPO (Invitrogen), transformed into competent TOP10 E. coli cells (Invitrogen) and clones containing PCR inserts were sequenced to confirm correct DNA sequence. A vector containing the DNA sequence for the ARE1 gene was designated pAA318 (see FIG. 54). A vector containing the DNA sequence for the ARE2 gene was designated pAA301 (see FIG. 55).

| Primer | sequence (SEQ ID NOS 378-381, respectively, in order of appearance) |
|---|---|
| oAA1012 | ATGTCCGACGACGAGATAGCAGGAATAGTCAT |
| oAA1018 | TCAGAAGAGTAAATACAACGCACTAACCAAGCT |
| oAA2006 | ATGCTGAAGAGAAAGAGACAACTCGACAAG |
| oAA2007 | GTGGTTATCGGACTCTACATAATGTCAACG |

Example 40

Construction of an Optimized TESA Gene for Expression in C. tropicalis

Figure 43:
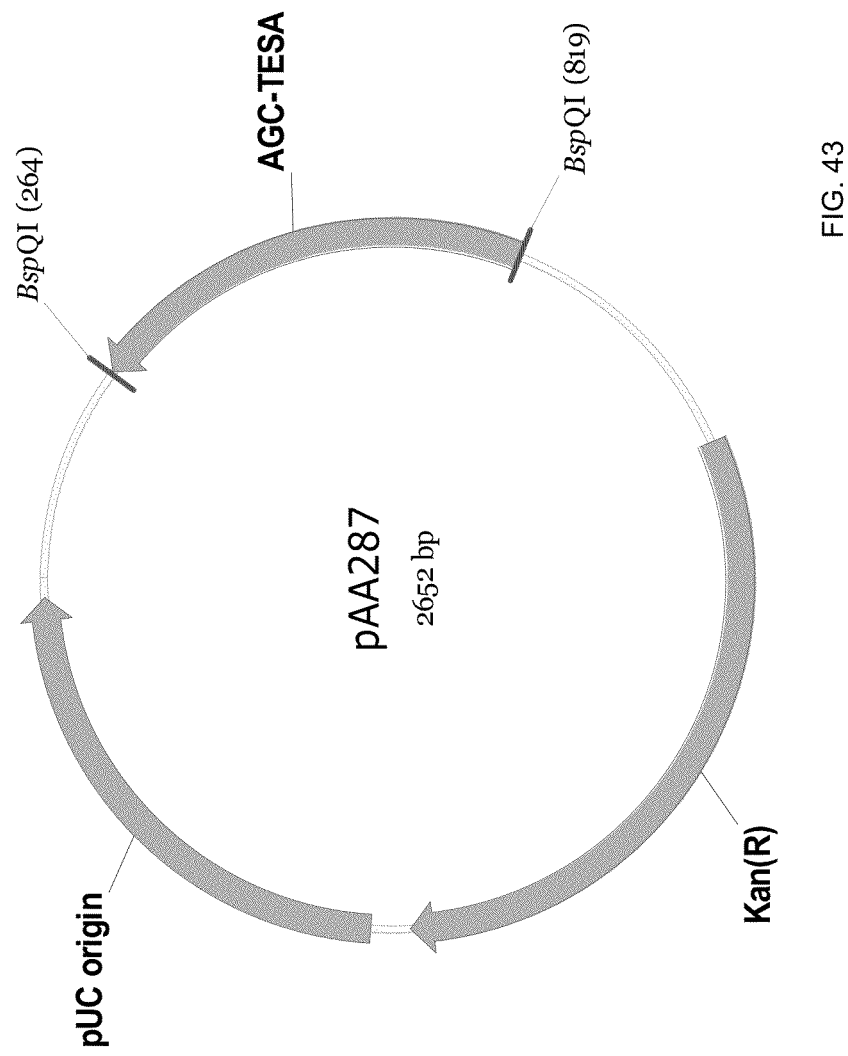
FIG. 43 illustrates a plasmid used for cloning the TESA gene from *E. coli*, which also was codon optimized for proper functionality in *C. tropicalis*. The codon optimization included altering CTG codons which are translated differently in *C. tropicalis* with respect to *E. coli*, as noted herein.
Figure 44:
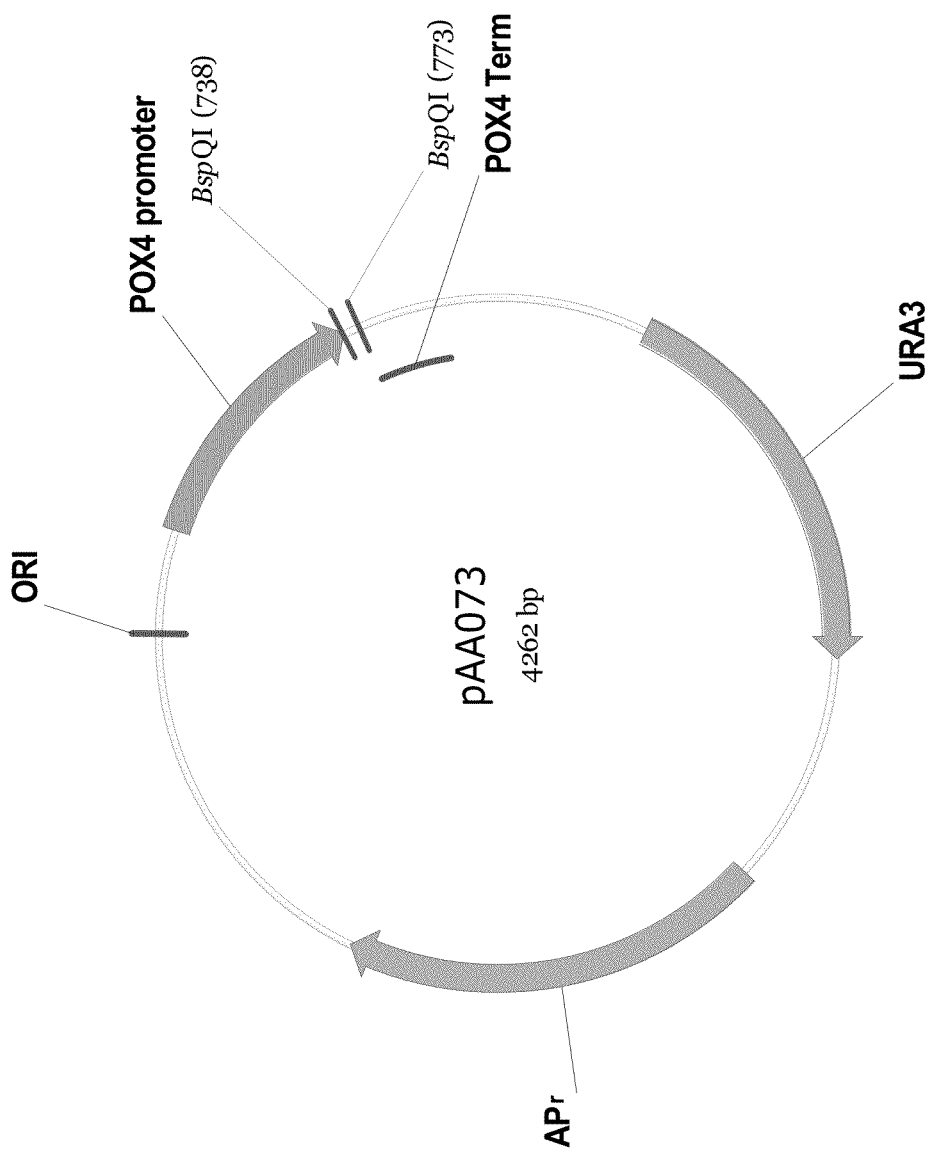
FIG. 44 depicts a plasmid used to donate the POX4 promoter which is used to drive transcription of various genes described herein. For example, the POX4 promoter is the promoter that drives transcription of the TESA gene included in the plasmid shown in FIG. 43.
Figure 45:
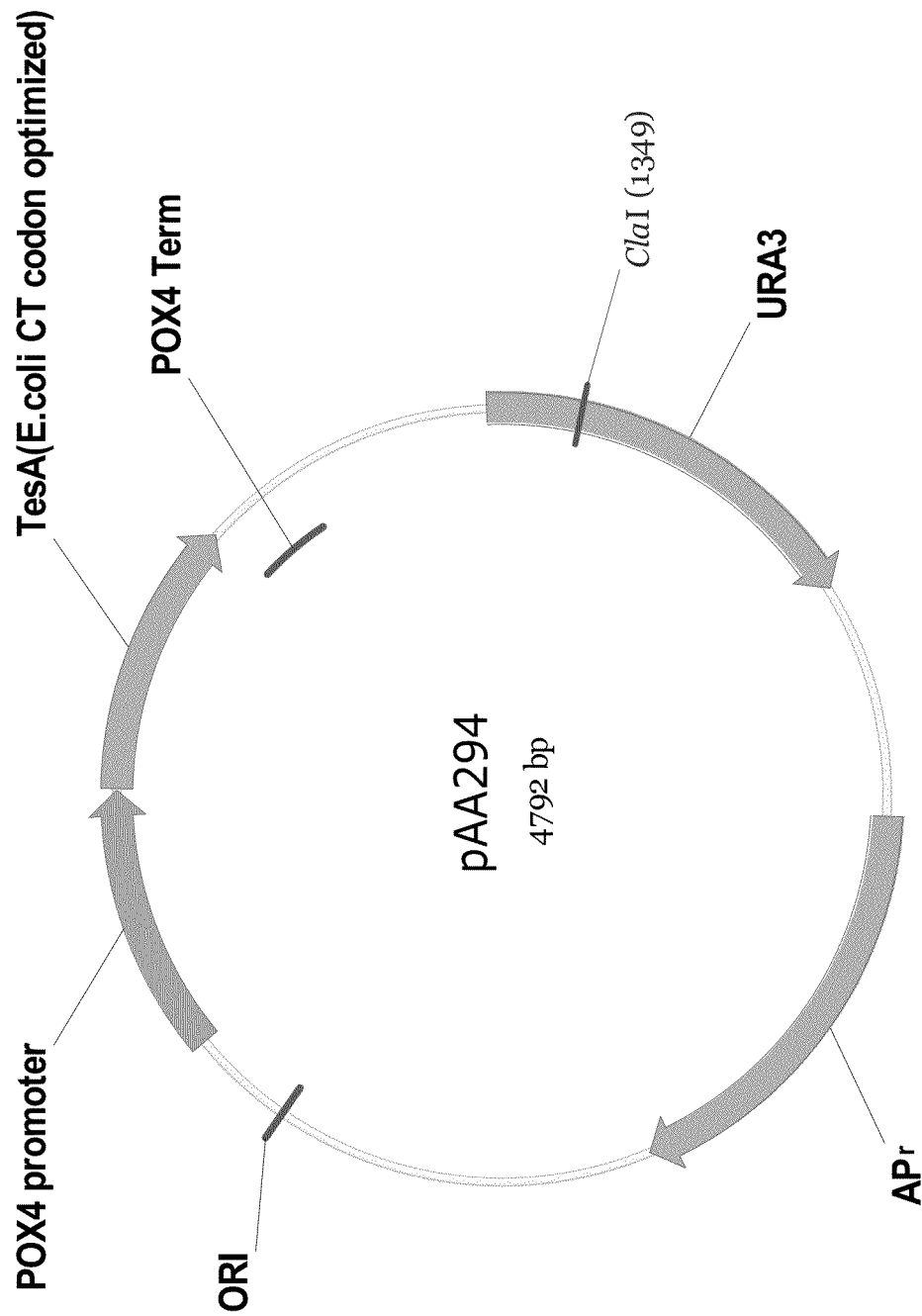
FIG. 45 depicts a plasmid used for integration of the codon optimized TESA gene into *C. tropicalis*. The plasmid depicted in FIG. 45 is assembled from pieces of the plasmids depicted in FIGS. 43 and 44. See Example 40 for experimental details and results.

The gene sequence for the E. coli TESA gene was optimized for expression in C. tropicalis by codon replacement. A new TESA gene sequence was constructed using codons from C. tropicalis with similar usage frequency for each of the codons in the native E. coli TESA gene (avoiding the use of the CTG codon due to the alternative yeast nuclear genetic code utilized by C. tropicalis). The optimized TESA gene was synthesized with flanking BspQI restriction sites and provided in vector pIDTSMART-Kan (Integrated DNA Technologies). The vector was designated as pAA287 (see FIG. 43). Plasmid pAA287 was cut with BspQI and the 555 bp DNA fragment was gel purified. Plasmid pAA073 (see FIG. 44) also was cut with BspQI and the linear DNA fragment was gel purified. The two DNA fragments were ligated together to place the optimized TESA gene under the control of the C. tropicalis POX4 promoter. The resulting plasmid was designated pAA294 (see FIG. 45).

Example 41

Cloning of C. tropicalis DGA1 Gene

Figure 56:
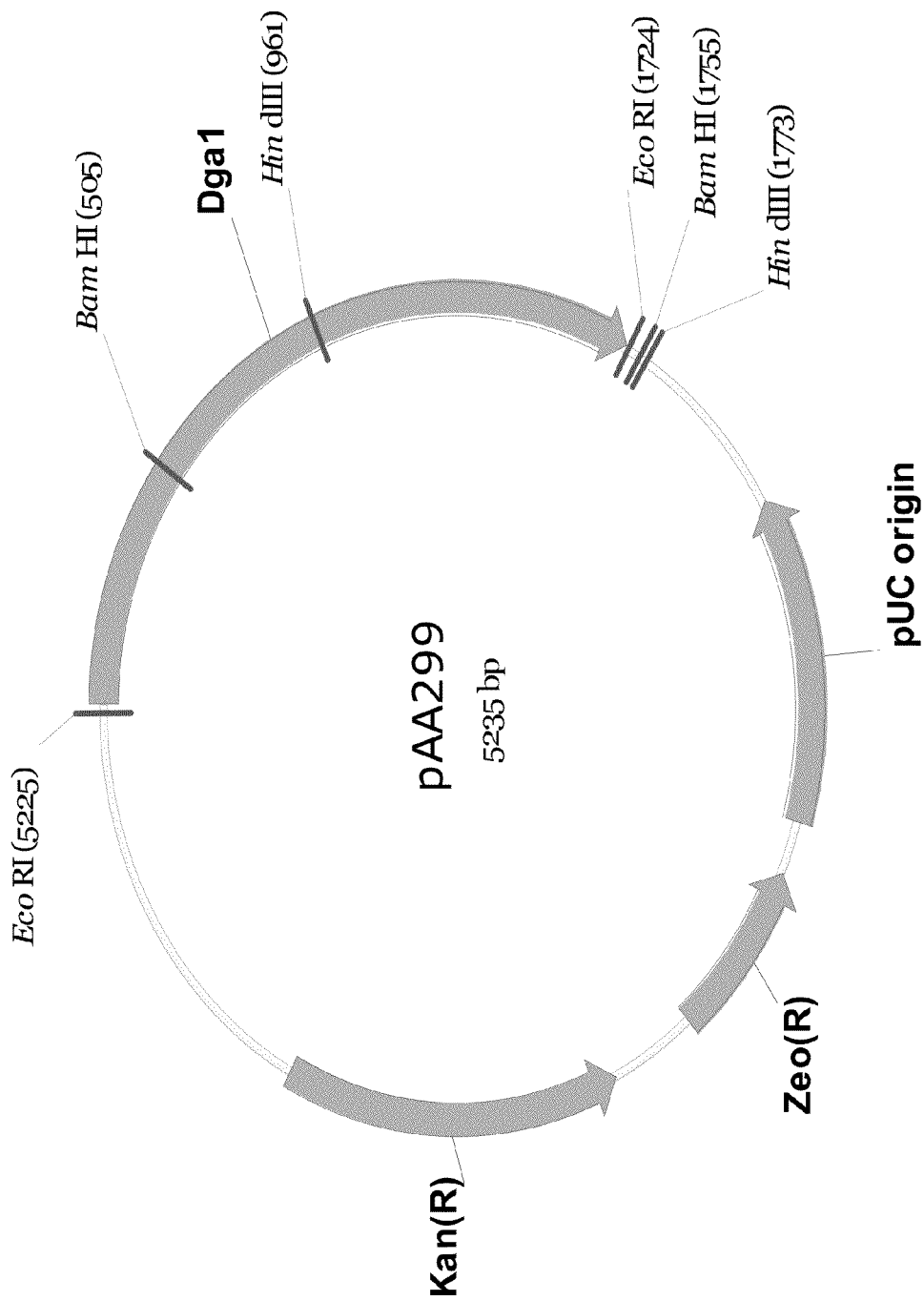
FIG. 56 illustrates a plasmid used for cloning the DGA1 gene from *C. tropicalis*. See Example 41 for experimental details. The cloned DGA1 DNA sequence are used to construct DGA1 "knock out" constructs.

DGA1 PCR product was amplified from C. tropicalis 20336 genomic DNA using primers oAA996 and oAA997, shown in the table below. The PCR product was gel purified and ligated into pCR-Blunt II-TOPO (Invitrogen), transformed into competent TOP10 E. coli cells (Invitrogen) and clones containing PCR inserts were sequenced to confirm correct DNA sequence. A vector containing the DNA sequence of the DGA1 gene was designated pAA299 (see FIG. 56).

| Primer | Sequence (SEQ ID NOS 382-383, respectively, in order of appearance) |
|---|---|
| oAA996 | ATGACTCAGGACTATAAAGACGATAGTCCTACGTCCACTGAGTTG |
| oAA997 | CTATTCTACAATGTTTAATTCAACATCACCGTAGCCAAACCT |

Example 42

Cloning of C. tropicalis LRO1 Gene

Figure 57:
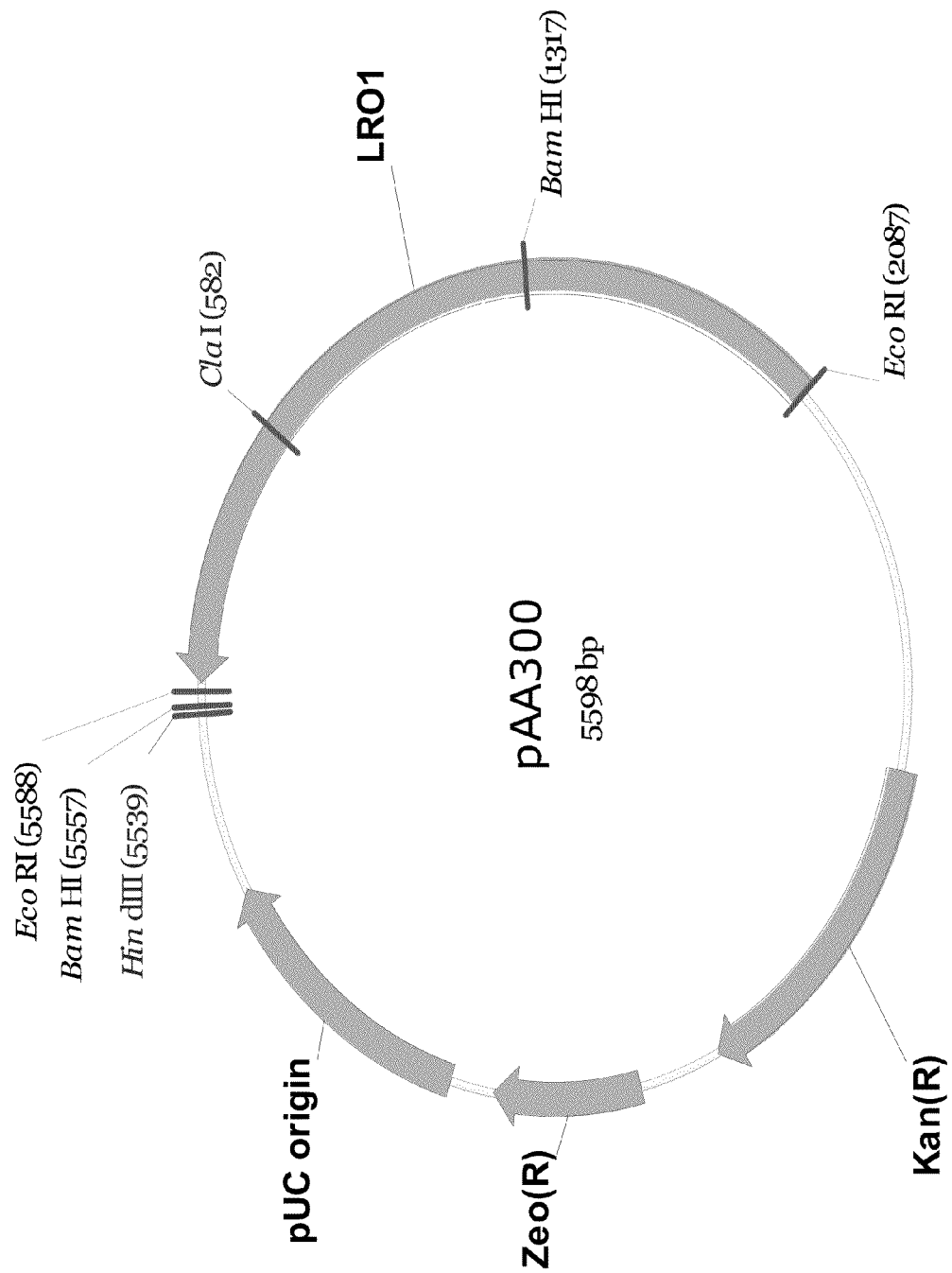
FIG. 57 illustrates a plasmid used for cloning the LRO1 gene from *C. tropicalis*. See Example 42 for experimental details. The cloned LRO1 DNA sequence are used to construct LRO1 "knock out" constructs.

LRO1 PCR product was amplified from C. tropicalis 20336 genomic DNA using primers oAA998 and oAA999, shown in the table below. The PCR product was gel purified and ligated into pCR-Blunt II-TOPO (Invitrogen), transformed into competent TOP10 E. coli cells (Invitrogen) and clones containing PCR inserts were sequenced to confirm correct DNA sequence. A vector containing the DNA sequence of the LRO1 gene was designated pAA300 (see FIG. 57).

| Primer | sequence (SEQ ID NOS 384-385, respectively, in order of appearance) |
|---|---|
| oAA998 | ATGTCGTCTTTAAAGAACAGAAAATC |
| oAA999 | TTATAAATTTATGGCCTCTACTATTTCT |

Example 43

Cloning of C. tropicalis ACS1 Gene and Construction of Deletion Cassette

Figure 46:
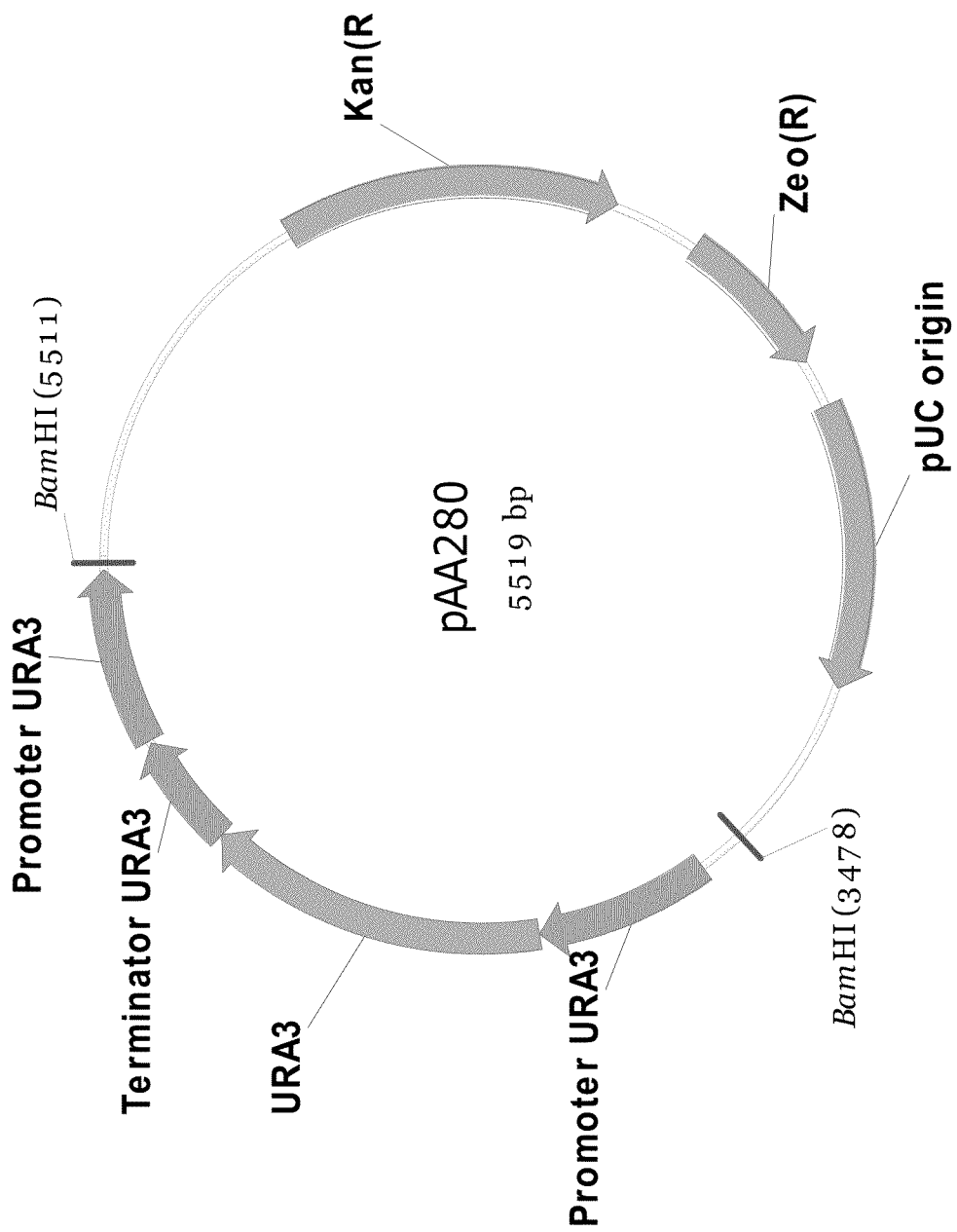
FIG. 46 depicts a plasmid used to donate a "knockout cassette", for disrupting various genes described herein.
Figure 47:
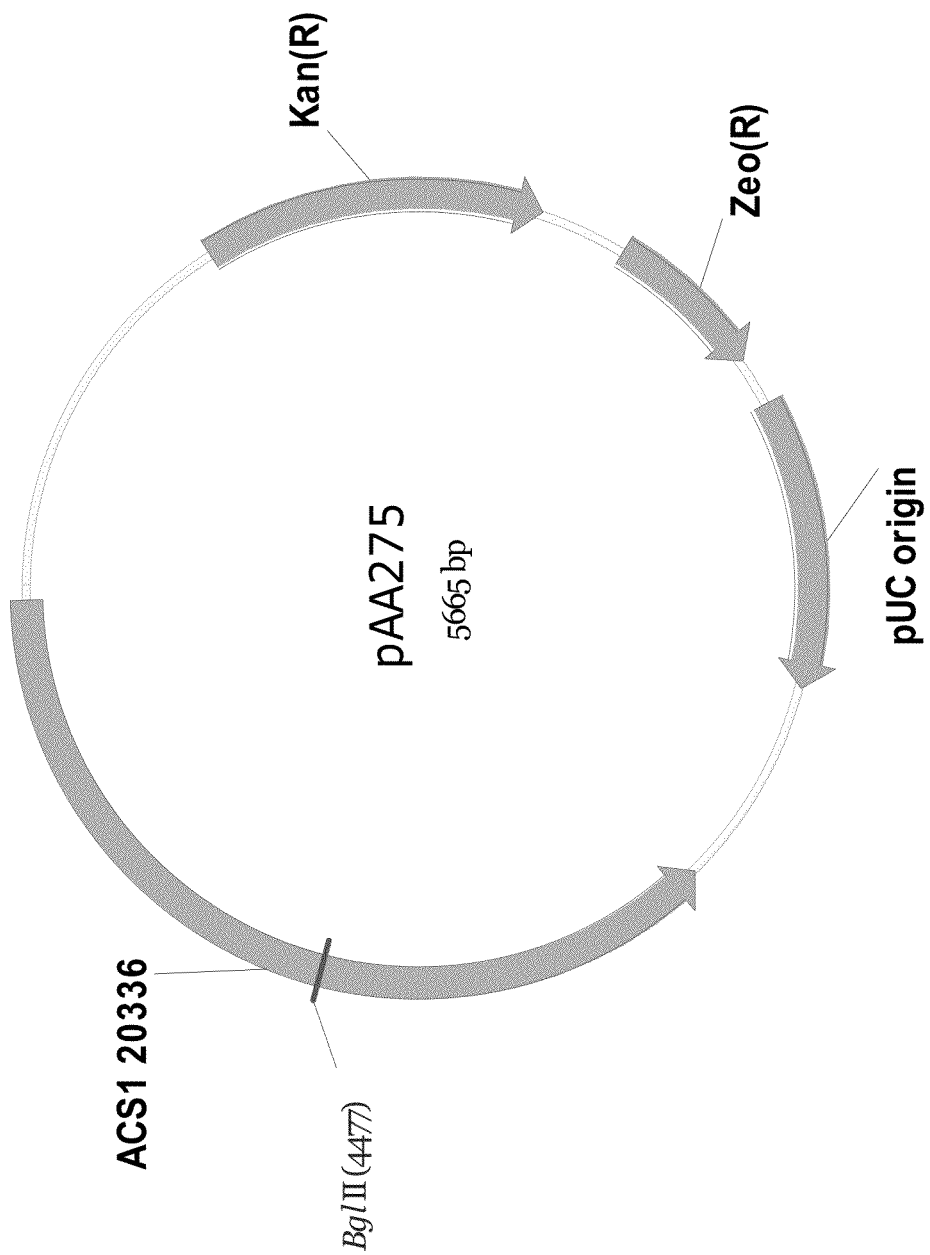
FIG. 47 depicts a plasmid used for cloning the ACS1 gene from *C. tropicalis*, for use in generating an ACS1 knockout construct.
Figure 48:
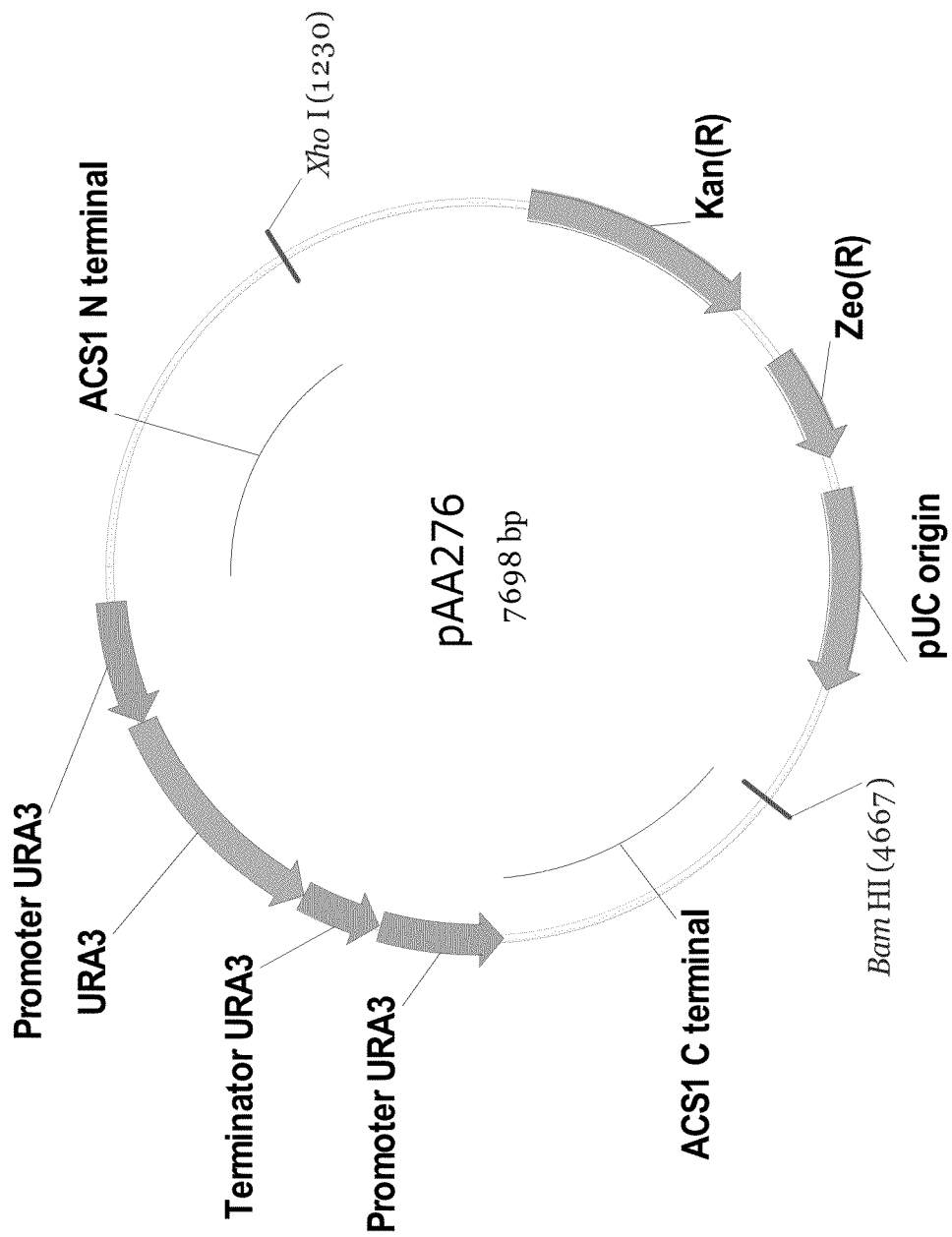
FIGS. 48 and 49 depict the ACS1 knockout constructs generated from pieces of the plasmids depicted in FIGS. 46 and 47. The difference between the constructs illustrated in FIGS. 48 and 49 is the orientation of the URA3 cassette (e.g., Promoter URA3-URA3-Terminator URA3-Promoter URA3). See Example 43 for experimental details and results.
Figure 49:
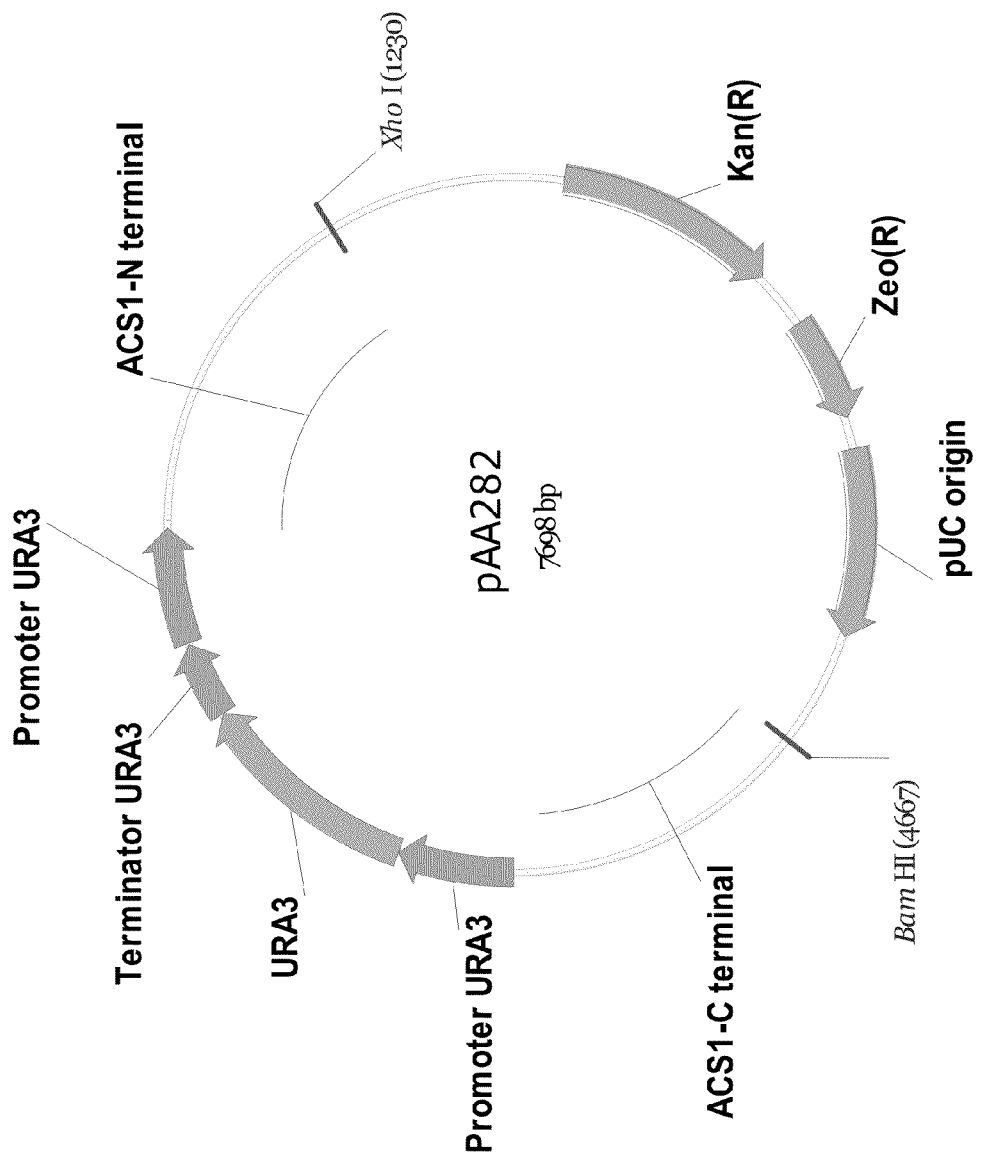

ACS1 PCR product was amplified from C. tropicalis 20336 genomic DNA using primers oAA951 and oAA952, shown in the table below. The PCR product was gel purified and ligated into pCR-Blunt II-TOPO (Invitrogen), transformed into competent TOP10 E. coli cells (Invitrogen) and clones containing PCR inserts were sequenced to confirm the DNA sequence. One such plasmid was designated pAA275 (see FIG. 47). Plasmid pAA280 (see FIG. 46) was digested with BamHI to release a 2.0 kb $P_{URA3}URA3T_{URA3}P_{URA3}$ cassette. Plasmid pAA275 was digested with BglII and gel purified. The two pieces were ligated together to generate plasmid pAA276 (see FIG. 48) and pAA282 (see FIG. 49). Plasmid pAA276 and pAA282 have the $P_{URA3}URA3T_{URA3}P_{URA3}$ cassette inserted into the ACS gene in opposite orientations.

| Primer | Sequence (SEQ ID NOS 386-387, respectively, in order of appearance) |
|---|---|
| oAA951 | CCTACTTCCACAGCTTTAATCTACTATCAT |
| oAA952 | TTTAAGAAAACAACTAAGAGAAGCCAC |

Example 44

Construction of Strain sAA722 (pox4a::ura3/pox4b::ura3 POX5/POX5 ACS1/acs1::$P_{URA3}URA3T_{URA3}P_{URA3}$)

Plasmid pAA276 was digested with BamHI/XhoI and column purified. Strain sAA329 (ura3/ura3 pox4a::ura3/pox4b::ura3 POX5/POX5) was transformed with the linearized DNA and plated on SCD-ura plate. Several colonies were checked for ACS1 disruption. One such strain was designated sAA722.

Example 45

Construction of Strain sAA741 (pox4a::ura3/pox4b::ura3 POX5/POX5 ACS1/acs1::$P_{URA3}$)

Strain sAA722 was grown in YPD media overnight and plated on 5-FOA plate. Colonies that grew in the presence of 5-FOA were PCR screened for the looping out of the URA3 gene leaving behind only the URA3 promoter ($P_{URA3}$) in the ACS1 site. Out of 30 colonies analyzed, only one strain showed the correct genetic modification. The strain was designated sAA741.

Example 46

Construction of Strain sAA776 (pox4a::ura3/pox4b::ura3 POX5/POX5 acs1:$P_{URA3}URA3T_{URA3}P_{URA3}$/acs1::$P_{URA3}$)

Plasmid pAA282 was digested with BamHI/XhoI and column purified. Strain sAA741 (see Example 45) was transformed with the linearized DNA and plated on SCD-ura plate. Several colonies were checked for double ACS1 knockout by insertional inactivation. One such strain was designated sAA776.

Example 47

Construction of Strain sAA779 (pox4a::ura3/pox4b::ura3 POX5/POX5 acs1::$P_{URA3}$/acs1::$P_{URA3}$)

Strain sAA776 (see Example 46) was grown in YPD media overnight and plated on 5-FOA plates. Colonies that grew in the presence of 5-FOA were PCR screened for the looping out of the URA3 gene leaving behind only the URA3 promoter ($P_{URA3}$) in both ACS1 copies. One such strain was designated sAA779.

Example 48

Construction of Strain sAA811 (pox4a::ura3/pox4b::ura3 POX5/POX5 acs1::$P_{URA3}$/acs1::$P_{URA3}$ ura3::3x$P_{POX4}$P450A19)

Figure 50:
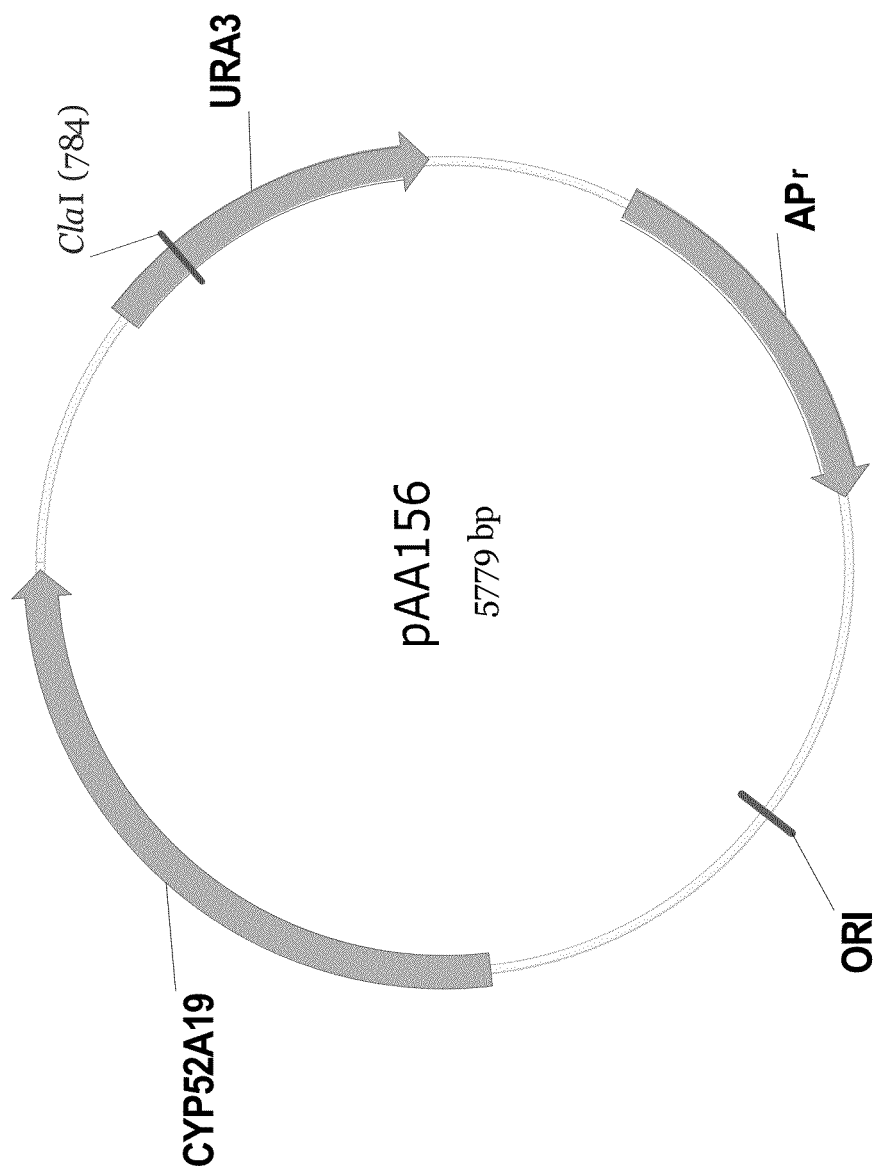
FIG. 50 illustrates the plasmid used to amplify the number of copies of cytochrome P450 A19 (e.g., CYP52A19). See Examples 48 and 49 for experimental details and results.

Plasmid pAA156 (see FIG. 50) containing a P450A19 integration cassette was digested with ClaI and column purified. Strain sAA779 (see Example 47) was transformed with the linearized DNA and plated on SCD-ura plate. Several colonies were checked for P450A19 integration. From those colonies, qPCR was performed to check the copy number of P450A19 integration. One strain, designated sAA811, contained 3 copies of P450A19.

Example 49

Construction of Strain sAA810 (pox4a::ura3/pox4b::ura3 POX5/POX5 acs1::$P_{URA3}$/acs1::$P_{URA3}$ ura3::5x$P_{POX4}$P450A19 ura3::8x$P_{POX4}$TESA)

Plasmid pAA156 containing a P450-A19 integration cassette was digested with ClaI and column purified. Plasmid pAA294 containing a TESA integration cassette also was digested with ClaI and column purified. Strain sAA779 was cotransformed with both linearized DNAs and plated on SCD-ura plate. Several colonies were checked for both P450A19 integration and TESA integration. Colonies that were positive for both TESA and P450A19 were further analyzed by qPCR. qPCR was performed to check the copy number of the P450A19 and TESA integration events. One strain, designated sAA810, contained 5 copies of P450A19 and 8 copies of TESA.

Example 50

Shake Flask Characterization of sAA235, sAA776, sAA810 and sAA811

Starter cultures (5 mL) in SP92-glycerol media (6.7 g/L Difco yeast nitrogen base, 3.0 g/L Difco yeast extract, 3.0 g/L ammonium sulfate, 1.0 g/L potassium phosphate monobasic, 1.0 g/L potassium phosphate dibasic, 75 g/L glycerol) were incubated overnight at 30° C., with shaking at approximately 250 rpm. The overnight cultures were used to inoculate 25 mL fresh SP92-glycerol media to an initial $OD_{600nm}$ of 0.4 and incubated approximately 18 hours at 30° C., and 300 rpm shaking. Cells were pelleted by centrifugation for 10 minutes at 4,000×g, at 4° C., then resuspended in TB-lowN media (1.7 g/L Difco yeast nitrogen base without amino acids and ammonium sulfate, 3.0 g/L Difco yeast extract, 1.0 g/L potassium phosphate monobasic, 1.0 g/L potassium phosphate dibasic). 1 mL coconut oil was added to start the adipic acid production at 30° C., and shaking at approximately 300 rpm, in 250 mL shake flasks. Incubation of the cultures continued for 96 hours and samples were taken for analysis of fatty acids and diacids by GC. The experiment was performed with shake flasks in triplicate.

Yields of product per consumed substrate ($Y_{p/s}$) were determined with the equation [adipic acid (g/L)*final volume of culture in flask (L)]/[coconut oil added to the flask (g)]. The calculation assumes all of the coconut oil added to the flask was consumed. GC analysis revealed that there were diacids of chain length C6 to C14 in all flasks with the majority represented as C8 and C6. All of the diacids except for the C6 (adipic) were ignored for yield calculations. The maximum theoretical yield ($Y_{max}$) for the conversion of coconut oil to adipic acid was calculated to be 0.6 g adipic acid/g coconut oil. The percent of $Y_{max}$ (% $Y_{max}$) was calculated as $Y_{p/s}/Y_{max}*100$.

Figure 58:
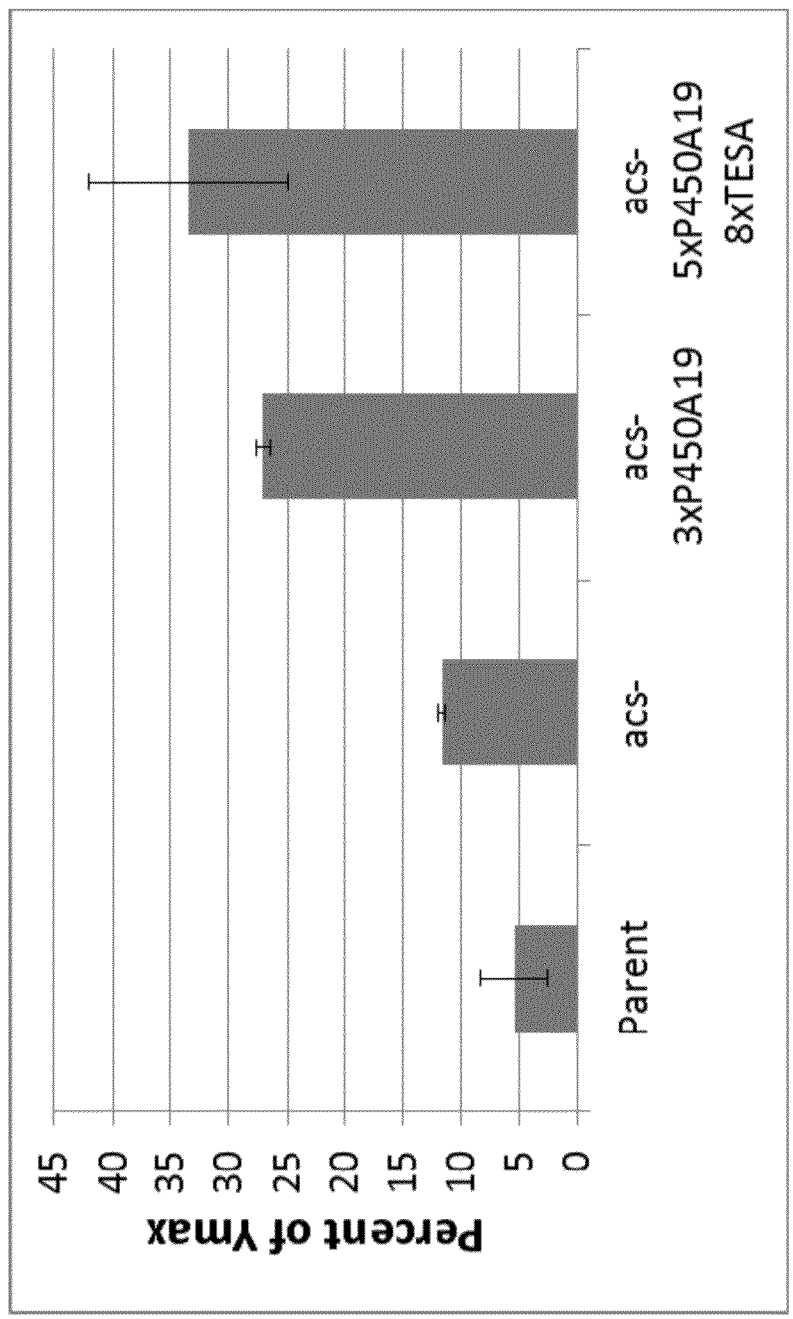
FIG. 58 graphically illustrates the percent of theoretical maximum yield for production of adipic acid from various parental and engineered strains of *C. tropicalis*. See Example 50 for experimental details and results.

The results of the shake flask experiments are shown in FIG. 58. Based on calculations for $Y_{p/s}$ shown in the previous paragraph, the results indicate that the yield of adipic acid on coconut oil was higher in the strain with disrupted ACS1 genes (11.6% Ymax) than the parental strain (5.4% Ymax). The yield of adipic acid on coconut oil was further improved by the gene amplification of P450A19 (27.1% Ymax) and by the coordinate gene amplification of P450A19 and TESA (33.5% Ymax), as shown graphically in FIG. 58.

Example 51

Nucleotide and Amino Acid Sequences Used for Manipulations Described in Examples 37-50

| SEQ ID NO: | Sequence description | Sequence |
|---|---|---|
| SEQ ID NO: 42 | Acyl-CoA Hydrolase (ACHA) Nucleotide Seq | atgatcagaaccgtccgttatcaatccctcaagaggttcagacctctggctttgtctcctgttttcgtccacgctacaact cccagaaggccaatttccaccgtccagaccaccctgggtccgacgagccagctgaagccgccgacgccgccgccacgatcct cgccgagttgcgagacaagcagacgaacccgaacaaggccacctggctcgatgcgttaacggagcgggagaagttgcgtgcc gagggcaagacgattgacagtttcagctacgttgaccccaagacgaccgtcgtggggagaagacacgcagtgactcgttct cgttcttgttgttgccgttcaaggacgacaagtggttgtgtgacgcgtacatcaatgcgtttggccggttgcgtgtagcgca gttgttccaggacttggacgccttggcggggcgcatcgcgtacaggcactgttccccagcggagcccgtgaatgtcacggcg agcgtggatagggtgtacatggtgaagaaagtggacgagattaacaattacaatttcgtgttggcggggtccgtgacgtgga ccgggagatcgtcgatggagatcacggtgaaagggtatgcttttgaagacgccgtgccggatataacgaacgaggagtcctt gccggcagagaatgtgttttggctgctaatttcaccttcgtggcacggaacccacttacacacaagtcctttgctattaac agattgttgcccgtgactgagaaggactgggtcgactatcgccgtgctgagtcccacaacgccaagaagaagttgatggcaa agaacaagaagatcttggagcctaccgcggaagagtccaagttgatctacgacatgtggagatcgtccaagtccttacagaa catcgagagggccaacgatgggatcgcgttcatgaaggacacgaccatgaagtccaccttgttcatgcagcccccagtaccgt aacagacactcatacatgatttcggagggtacttgttaagacaaactttcgaattggcctactgtaccgcggcaacgtttt ccctggccgggcccgtttcgtcagcttggactccaccacgttcaagaacccgtgcccgtggggtcggtgctcaccatgga ctcgtcgatctcgtacacggagcacgtgcacgagggagtggaggagattgacgcggactcaccgttcaacttcagcttgcct gccacgaacaagatctcgaagaaccccgaggcgttcttgtcggaacccggcacgttgattcaagtcaaggtcgacacataca tccaggagttagagcagagtgtgaagaagcccgcgggtacgttcatctactcgttctatgttgataaagaaagcgttactgt tgatggaaaggcgtcgttttgttcagttatcccgcagacgtactccgagatgatgacttatgtgggcgggagaagaagagcc caggatactgctaactacgtggagactttgccgtttagtggaagcggcaattaa |
| SEQ ID NO: 43 | Acyl-CoA Hydrolase (ACHA) Amino Acid Seq | MIRTVRYQSLKRFRPSALSPVFRPRYNSQKANFHRPDHPGSDEPAEAADAAATILAELRDKQT NPNKATWLDALTEREKLRAEGKTIDSFSYVDPKTTVVGEKTRSDSFSFLLLPFKDDKWLCDAYI NAFGRLRVAGLFQDLDALAGRIAYRHCSPAEPVNVTASVDRVYMVKKVDEINNYNFVLAGSVT WTGRSSMEITVKGYAFEDAVPDITNEESLPAENVFLAANFTFVARNPLTHKSFAINRLLPVTEK DWVDYRRAESHNAKKKLMAKNKKILEPTAEESKLIYDMWRSSKSLQNIERANDGIAFMKDTTM KSTLFMQPQYRNRHSYMIFGGYLLRQTFELAYCTAATFSSAGPRFVSLDSTTFKNPVPVGSVL TMDSSISYTEHVHEGVEEIDADSPFNFSLPATNKISKNPEAFLSEPGTLIQVKVDTYIQELEQSV KKPAGTFIYSFYVDKESVTVDGKASFCSVIPQTYSEMMTYVGGRRRAQDTANYVETLPFSGS GN |
| SEQ ID NO: 44 | Acyl-CoA Hydrolase (ACHB) Nucleotide Seq | atgatcagaaccgtccgttatcaatccttcaagaggttcaaacctctgactttatccccgttttccgtccacgctacaact cccagaaggccaatttccaccgtccagaccacgctgggtccgacgagccagccgaagccgccgacgccgctgccacgatcct cgccgagttgcgagacaagcagacgaacccgaacaaggccacctggctcgatgcgttaacggagcgggagaagttgcgtgcc gagggcaagacaatcgacagcttcagctacgttgaccccaagacaaccgtcgtggggagaagacacgcagcgactcgttct cgttcttgttgttgccgttcaaggacgacaagtggttgtgtgacgcgtacatcaatgcgtttggccggttgcgtgtagcgca gttgttccaggacttggacgccttggcggggccgcatcgcgtacaggcactgttccccgctgagcccgtgaatgtcacggcg agcgtggatagagtgtatatggtgaagaaagtggacgagattaataattacaatttcgtgttggcgggtccgtgacgtgga ccgggagatcgtcgatggagatcacggtcaaagggtatgcttttgaagacgccgtgccggagataactaacgaggagtcctt gccggcagagaatgtgttcttggctgttaatttcaccttcgtggcacgtaacccactcacacacaagtccttcgctattaac agattgttgcccgtgactgagaaggactgggtcgattatcgccgtgctgagtcccacaacgccaagaagaagtgatggcaat agaacaagaagatcttggagcctacccccgaagagtccaagttgatctacgacatgtggagatcgtccaagtccttacagaa catcgagaaggccaacgacgggatcgcgttcatgaaggacacgataatgaagtccaccttgttcatgcagcccccagtaccgt aacagacactcatacatgatttcggtgggtatttgttaagacaaactttcgaattggcctattgtaccgcagcaacgtttt ccctggcgggacccgtttcgtcagcttggactccaccacgttcaagaacccgtgcccgtggggtcggtgctcaccatgga ctcgtcgatctcgtacacggagcacgtccacgatggcgttgaggagattgacgccgactcccgttcaacttcagcttgcct gccacgaacaagatctcgaagaaccccgaggcgttcttgtcggagcccggcacgttgatccaagtcaaggtcgacacgtaca tccaggagttagagcaaagtgtgaagaagcctgcgggaacgttcatctactcgttctatgttgataaagagagcgttactgt |

-continued

| SEQ ID NO: | Sequence description | Sequence |
|---|---|---|
| | | ggatggaaaggcgtcgttttgttcagttatcccgcagacgtactccgagatgatgacttatgtgggcgggagaagaagagcc<br>caggatactgctaattacgtggagactttgccgtttagtggaagcggcaattaa |
| SEQ ID NO: 45 | Acyl-CoA Hydrolase (ACHB) | MIRTVRYQSFKRFKPLTLSPVFRPRYNSQKANFHRPDHAGSDEPAEAADAAATILAELRDKQT<br>NPNKATWLDALTEREKLRAEGKTIDSFSYVDPKTTVVGEKTRSDSFSFLLLPFKDDKWLCDAYI<br>NAFGRLRVAQLFQDLDALAGRIAYRHCSPAEPVNVTASVDRVYMVKKVDEINNYNFVLAGSVT<br>WTGRSSMEITVKGYAFEDAVPEITNEESLPAENVFLAVNFTFVARNPLTHKSFAINRLLPVTEK<br>DWVDYRRAESHNAKKKLMAKNKKILEPTPEEESKLIYDMWRSSKSLQNIEKANDGIAFMKDTIM<br>KSTLFMQPQYRNRHSYMIFGGYLLRQTFELAYCTAATFSLAGPRFVSLDSTTFKNPVPVGSVL<br>TMDSSISYTEHVHDGVEEIDADSPFNFSLPATNKISKNPEAFLSEPGTLIQVKVDTYIQELEQSV<br>KKPAGTFIYSFYVDKESVTVDGKASFCSVIPQTYSEMMTYVGGRRRAQDTANYVETLPFSGS<br>GN |
| SEQ ID NO: 46 | E. coli Acyl-CoA Thioesterase (TESA) gene without signal peptide sequence optimized for C. tropicalis Nucleotide Seq | atggccgatacattgctcatcttgggtgactcttgtctgcagggtatcggatgtccgcatctgccgcatggcctgcactcc<br>tcaatgacaaatggcaaagcaagacatcggtcgtgaatgcatctatctctggcgataccgcagcaggggttgggcccgtct<br>cccagccttgttgaagcaacatcaaccacgttgggtcttggtcgaattgggcggcaatgatggtctcagaggttttcaacct<br>caacagaccgagcagacattgcgtcaaatcctccaagacgtgaaggcagcaaacgccgaacctctcttgatgcagataagat<br>tgcctgccaactatgtcgtagatacaatgaagccttttctgcaatctacccgaagcttgcaaaggagtttgacgtcccatt<br>gttgccgttttttgatggaagaggtgtaccttaagcctcagtggatgcaagacgatggtatccatccgaaccgtgatgcacaa<br>ccattcatcgcagattggatggccaaacaactccaacctttggtcaatcatgatagctaa |
| SEQ ID NO: 47 | E. coli Acyl-CoA (TESA) without signal peptide Amino Acid Seq | MADTLLILGDSLSAGYRMSASAAWPALLNDKWQSKTSVVNASISGDTSQQGLARLPALLKQH<br>QPRWVLVELGGNDGLRGFQPQQTEQTLRQILQDVKAANAEPLLMQIRLPANYGRRYNEAFSA<br>IYPKLAKEFDVPLLPFLMEEVYLKPQWMQDDGIHPNRDAQPFIADWMAKQLQPLVNHDS |
| SEQ ID NO: 48 | Acyl-CoA Synthetase (ACS1) Nuc. Seq | atgggtgccccttaacagtcgccgttggcgaagcaaaaccaggcgaaaccgctccaagaagaaaagccgctcaaaaatgg<br>cctctgtcgaacgcccaacagactcaaaggcaaccacttttgccagacttcattgaagagtgttttgcagaaacggcaccag<br>agatgccatggcctggagagacttggtcgaaatccacgtcgaaaccaaacaggttaccaaaatcattgacggcgaacagaca<br>aaggtcgataaggactggatctactacgaaatgggtccttacaactacatatcctaccccaagttgttgacgttgtcaaga<br>actactccaagggtttgttggagttgggcttggccccagatcaagaatccaagttgatgatctttgccagtacctcccacaa<br>gtggatgcagacctttcttagcctccagttttccaaggtatcccgttgtcacgccctacgacctctgggtcggcgggttg<br>acccactcctggtgcaaaccgaatccgatgccgtgttcaccgacaaccaattgttgtcctccttgattcgtccttggaga<br>aggccacctccgtcaagtatgtcatccacggggaaaagattgaccctaacgacaagagacagggcggcaaaatctaccagga<br>tgcggaaaaggccaaggagaagattttacaaattagaccagatattaaatttatttctttcgacgaggttgttgcattggtt<br>gaacaatcgtcgaagaatttgcatttcccaaaaccagaagaccaatctgtatcatgtacacctcgggttccaccggtgctc<br>caaagggtgtggttatcaccaatgccaacattgttgccgccgtgggtgtatctccaccaatgctactagagacttggttag<br>aactgtcgacagagtgattgcattttttgccattggccacatttttcgagttggcctttgagttggttaccttctggtggggg<br>gctccattgggtacgccaatgtcaagactttgaccgaagcctcctgcagaaactgtcagccagacttgattgaattcaaac<br>caaccatcatggttggtgttgctgccgtttgggaatcggtcagaaagggttgcttctgctcaaattgaaacaggcttctccaat<br>ccaacaaaagatcttctgggctgcattcaatgccaagtctactttgaaccgttatgcgttgccaggccggtgggttgtttgac<br>gctgtcttcaagaaggttaaagccgccactggtggccaattgcgttatgtgttgaatggtgggtcccccaatctctgttgatg<br>cccaagtgtttatctccaccttgcttgcgccaatgttgttgggttacggtttgactgaaacctgtgccaataccaccattgt<br>cgaacacacgcgcttccagattggtacttttgggtcacttggttggatcgtcactgccaagttggttgatgttgctgatgct<br>ggatactacgccaagaacaaccagggtgaaatctggttgaacggcggtccagttgtcaaggaatactacaagaactgaagaag<br>aaaccaaggctgcattcaccgaagatggctggttcaagactggtgatattggtgaatggaccgccgacggtggtttgaacat<br>cattgaccgtaagaagaacttggtcaagactttgaatggtgaatacattgctttggagaaattggaaagtatttacagatcc<br>aaccacttgattttgaacttgtgtgtttacgctgaccaaaccaaggtcaagccaattgctattgtcttgccaattgaagcca<br>acttgaagtctatgttgaaggacgaaaagatttatcccagatgctgattcacaagaattgagcagcttggttcacaacaagaa<br>ggttgcccaagctgtcttgagacacttgcttccaaaccggtaaacaacaaggtttgaaaggtattgaattgttgcagaatgtt<br>gtcttgttggatgacgagtggaccccacagaatggttttgttacttctgcccaaaagttgcagaaaagaagatttagaaa<br>gttgtaaaaagaagttgaagaggcatacaagtcgtcttag |
| SEQ ID NO: 49 | Acyl-Coa Synthetase (ACS1) A. A. Seq | MGAPLTVAVGEAKPGETAPRRKAAQKMASVERPTDSKATTLPDFIEECFARNGTRDAMAWR<br>DLVEIHVETKQVTKIIDGEQKKVDKDWIYYEMGPYNYISYPKLLTLVKNYSKGLLELGLAPDQES<br>KLMIFASTSHKWMQTFLASSFQGIPVVTAYDTLGESGLTHSLVQTESDAVFTDNGLLSSLIRPL<br>EKATSVKYVIHGEKIDPNDKRQGGKIYQDAEKAKEKILQIRPDIKFISFDEVVALGEQSSKELHF<br>PKPEDPICIMYTSGSTGAPKGVVITNANIVAAVGGISTNATRDLVRTVDRVIAFLPLAHIFELAFE<br>LVTFWWGAPLGYANVKTLTEASCRNCQPDLIEFKPTIMVGVAAVWESVRKGVLSKLKQASPIQ<br>QKIFWAAFNAKSTLNRYGLPGGGLFDAVFKKVKAATGGQLRYVLNGGSPISVDAQVFISTLLA<br>PMLLGYGLTETCANTTIVEHTRFQIGTLGTLVGSVTAKLVDADAGYYAKNNQGEIWLKGGPV<br>VKEYYKNEEETKAAFTEDGWFKTGDIGEWTADGGLNIIDRKKNLVKTLNGEYIALEKLESIYRS<br>NHLILNLCVYADQTKVKPIAIVLPIEANLKSMLKDEKIIPDADSQELSSLVHNKKVAQAVLRHLLQ<br>TGKQQGLKGIELLQNVVLLDDEWTPQNGFVTSAQKLQRKKILESCKKEVEEAYKSS |
| SEQ ID NO: 50 | Long-chain Acyl-Coa Synthetase (FAT1) Nuc. Seq | atgtcaggattagaaatagccgctgctgccatccttggtagtcagttattggaagccaaatatttaattgccgacgacgtgc<br>tgttagccaagacagtcgctgtcaatgcctcccatacttgtggaaagccagcagaggtaaggcatacatactggtactttt<br>tcgagcagtccgtgttcaagaacccaaacaacaaagcgttggcgttcccaagaccaagaaagaatgccccacccccaagac<br>cgacgccgagggattccagatctacgacgatcagtttgacctagaagaatacacctacaaggaattgtacgacatggttttg<br>aagtactcatacatcttgaagaacgagtacggcgtcactgccaacgacaccatcggtgttcttgtatgaacaagccgctt |

| SEQ ID NO: | Sequence description | Sequence |
|---|---|---|
| | | tcattgtcttgtggttggcattgtggaacattggtgccttgcctgcgttcttgaacttcaacaccaaggacaagccattgat<br>ccactgtcttaagattgtcaacgcttcgcaagttttcgttgaccggactgtgattccccaatcagagataccgaggctcag<br>atcagagaggaattgccacatgtgcaaataaactacattgacgagtttgccttgtttgacagattgagactcaagtcgactc<br>caaaacacagagccgaggacaagaccagaagaccaaccgatactgactcctccgcttgtgcattgatttacacctcgggtac<br>caccggtttgccaaaaagccggtatcatgtcctggagaaaagccttcatggcctcggttttcttggccacatcatgaagatt<br>gactcgaaatcgaacgtcttgaccgccatgcccttgtaccactccaccgcggccatgttggggttgtgtcctactttgattg<br>tcggtggctgtgtctccgtgtcccagaaattctccgctacttcgttctggacccaggccagattatgtggtgccacccacgt<br>gcaatacgtcggtgaggtctgtcgttacttgttgaactccaagcctcatccagaccaagacagacacaatgtcagaattgcc<br>tacggtaacggggttgcgtccagatatatggtctgagttcaagcgcagattccacattggacgtatcggtgagttctacgccg<br>ccaccgagtcccctatcgccaccaccaacttgcagtacggtgagtacggtgtcggcgcctgtcgtaagtacgggtccctcat<br>cagctgtcttgtattgtctacccagcagaaattggccaagatggacccagaagacgagagtgaaatctacaaggaccccaagacc<br>gggttctgtaccgaggccgcttacaacgagccaggtgagttgttgatgagaatcttgaaccctaacgacgtcagaaatcct<br>tccaggggttattatggtaacaagtccgccaccaacagcaaaatcctcaccaatgttttcaaaaaaggtgacgctggtacag<br>atccggtgacttgttgaagatggacgaggacaaattgttgtactttgtcgacagattaggtgacacttccgttggaagtcc<br>gaaaacgtctccgccaccgaggtcgagaacgaattgatgggctccaaggccttgaagcagtccgtcgtgttgtcggtgtcaagg<br>tgccaaaccacgaaggtagagcctgttttgccgtctgtgaagccaaggacgagttgagccatgaagaaatcttgaaattgat<br>tcactctcacgtgaccaagtcttgcctgtgtatgctgcaccctgcgttcataagattggcaccattgaggcttcgcacaac<br>cacaaggttcctaagaaccaattcaagaaccaaaagttgccaaagggtgaagacggcaaggatttgatctactggttgaatg<br>gcgacaagtaccaggagtgactgaagacgattggtcttgatttgtaccggtaaagccaaattg |
| SEQ ID NO: 51 | Long-chain Acyl-CoA Synthetase (FAT1) A. A. Seq | MSGLEIAAAAILGSQLLEAKYLIADDVSLAKTVAVNALPYLWKASRGKASYWYFFEQSVFKNPN<br>NKALAFPRPRKNAPTPKTDAEGFQIYDDQFDLEEYTYKELYDMVLKYSYILKNEYGVTANDTIG<br>VSCMNKPLFIVLWLALWNIGALPAFLNFNTKDKPLIHCLKIVNASQVFVDPDCDSPIRDTEAQIR<br>EELPHVQINYIDEFALFDRLRLKSTPKHRAEDKTRRPTDTDSSACALIYTSGTTGLPKAGIMSW<br>RKAFMASVFFGHIMKIDSKSNVLTAMPLYHSTAAMLGLCPTLIVGGCVSVSQKFSATSFWTQA<br>RLCGATHVGYVGEVCRYLLNSKPHPDQDRHNVRIAYGNGLRPDIWSEFKRRFHIEGIGEFYAA<br>TESPIATTNLQYGEYGVGACRKYGSLISLLLSTQQKLAKMDPEDESEIYKDPKTGFCTEAAYNE<br>PGELLMRILNPNDVQKSFQGYYGNKSATNSKILTNVFKKGDAWYRSGDLLKMDEDKLLYFVD<br>RLGDTFRWKSENVSATEVENELMGSKALKGSVVVGVKVPNHEGRACFAVCEAKDELSHEEIL<br>KLIHSHVTKSLPVYAQPAFIKIGTIEASHNHKVPKNQFKNQKLPKGEDGKDLIYWLNGDKYQEL<br>TEDDWSLICTGKAKL |
| SEQ ID NO: 52 | Acyl-CoA Sterol acyl transferase (ARE1) Nuc. Seq | atgtccgacgacgagatagcaggaatagtcattgaaatcgacgatgacgtgaaatccacgtcttcgttccaggaagaactag<br>tcgaggttgaaatgtccaactcgtccattaacgaatcccagacgatgagtcgtaccgtcctgaagaaacctcattgcatta<br>caggaggaagtcccacaggaccccgtcagaggagtcgtcctagagatcaccaagaacgtgaatgatccggatctagtttcc<br>aagattgagaacctaaggggcaaagtaagccaacggaagacaggttgaggaagcactaccttcacacctcccaggacgtca<br>agtcttgtcccggttcaacgacatcaagttcaagctgaactccgcgacgattctagattcggatgcgttttacaagagtga<br>atactttggagtcttgaccatcttctgggtggttatcgcactctacatattgtcaacgttgtcagatgtttacttggcatg<br>gccaagccttactggactggatcatcataggaatgttcaagcaggacttggtgaaagttgcactcgttgatcttgccatgt<br>acctatcctcgtattttccttattctttcaggttgcatgcaaacgggtgatgtatcttggcatgtgccatggatcttcc<br>cttggatgggcaatacaggggggtttacagcttggtgttttttgacgttctggacggtagttccgcaggagttgttggattgca<br>cgaattttcttgatcttgcattgcttggtgttttattatgaagatgcaatcatacaatggatacctttgggatg<br>tgtatcaggaaggattggcctctgaggctgatctcagggacccttctgagtatgatgaagatttcccctggatcacgtgga<br>ggttctagaacagagcttgtggtttgccaaacacgagttggagtttcaatcgaatggaactgctgagaggaaggaccaccat<br>caccatgtatttcgacgaaaaggatgtcaacaaaccaatacgtgtcttgcaagaagagggaattatcaagtttccggcaaaca<br>tcaacttcaaggatttttcgagtacatgatctcccaacgctagtcacacgttgagcttccccgaactgcagattag<br>atggacgtatgtgttgcagaagttttgggaacatttgccttagtgtttgccatgattatctcgccgaagagagtttctgc<br>cccttgatgcaagaagttgatcagtacacaaaatttgccaaccaaccaaaggttcccaaaatacttcgtcgttctttcccact<br>tgatattaccgctcggcaagcagtacttgctctcattcatcctcatctggaatgaaattctcaacggcatagcggagttaag<br>caggtttggcgaccggcatttctacggcgcttggtggtcgagcgtcgattacatcgagtgactattcaagaaaatggaaccaccatc<br>gtgcaccgattcctccgtcggcacgtttacaattcgagcattcacatcctcggtattccaggacgcaagccgcgatagtta<br>cactttttgctttctgccacaatccacgaactcgttatgtacgtcctatttggcaaattacgagggtacctattccttacgat<br>gcttgtccagatccccatgaccgtcacctccaagttcaacaaccgtgtttggggcaacatcatgttctggttgacgtattta<br>tctgggccccagcttggttagtgcgttgtatttactcttctag |
| SEQ ID NO: 53 | Acyl-CoA Sterol acyl transferase (ARE1) A. A. Seq | MSDDEIAGIVIEIDDDVKSTSSFQEELVEVEMSNSSINESOTDESYRPEETSLHYRRKSHRTPS<br>EESFLEITKNVNDPDLVSKIENLRGKVSQREDRLRKHYLHTSQDVKFLSRFNDIKFKLNSATILD<br>SDAFYKSEYFGVLTIFWVVIALYILSTLSDVYFGMAKPLLDWIIIGMFKQDLVKVALVDLAMYLSS<br>YFPYFLQVACKRGDVSWHGLGWAIQGVYSLFLTFWTVVFPELAMDLPWIARIFLILHCLVFIM<br>KMQSYGHYNGYLWDVYQEGLASEADLRDLSEYDEDFPLDHVEVLEQSLWFAKHELEFQSNG<br>TAERKDHHHHVFDEKDVNKPIRVLQEEGIIKFPANINFKDYFEYSMPPTLVYTLSFPRTRQIRW<br>TYVLQKVLGTFALVSFAMIIVAEESFCPLMQEVDOYTKLPTNQRFPKYFVVLSHLILPLGKQYLLS<br>FILIWNEILNGIAELSRFGDRHFYGAWWSSVDYMDYSRKWNTIVHRFLRRHVYNSSIHILGISRT<br>QAAIVTLLLSATIHELVMYVLFGKLRGYLFLTMLVQIPMTVTSKFNNRVWGNIMFWLTYLSGPS<br>LVSALYLLF |
| SEQ ID NO: 54 | Acyl-CoA Sterol acyl transferase (ARE2) Nuc. Seq | atgtccgacgacgagatagcaggaatagtcattgaaatcgacgatgacgtgaaatctacgtcttcgttccaggaagacctag<br>tcgaggttgagatgtccaactcgtccattaacgaatcccagacggatgagttgtcgtaccgtcctgaagaaatctcattgca<br>ttcgagaaggaagtcccacaagacccgtcagatgagtcgttcctagagatcaccaagaacgtgaatgatccggatctagtc<br>tccaagattgagaacttaaggggcaaagtaagccaacgggaagacaggttgaggaaacactacctccacacatcccaggacg<br>tcaagtcttctcggttcaacgacatcaagttcaagctgaactccgcgacgattctagattcggatgcgttttacaagag<br>cgagcacttcggagtcttgactatcttctgggttgttatcgcactctacatattgtcaacgttgtcagatgtattttgac<br>atggccaagcccttactggactggataatcataggaatgttcaagagagatttgatgcaagttgcactcgttgatcttgtca<br>tgtacttatcctcgtattttccttattcctacaggttgcatgcaagaccggagctatatcttggcatggtcttggatgggc<br>catacaggggggtttacagcttggtgttttttaactttctgggcggtacttccgctggagctggccatggatcttccttggatt<br>gcacgagttcttgatcttgcattgcttggtgttattatgaagatgcaatcatatggacattacaatggatacctttggg |

| SEQ ID NO: | Sequence description | Sequence |
|---|---|---|
| | | atgtatatcaggaaggattggtctcggaagctgatctcacggctgtttctgagtatgatgatgatttcccctggatcacgg ggaggttctagaacagagcttgtggttcgccaaacacgagttggagtttcaatctaatggaactacggagaggaaggatcac catcatcatgtattcgacgaaaaggatgtcaacaaaccaatgcgtgtcttgcaagaagagggaattatcaaatttccggcaa acatcaatttcaaggattatttcgagtacagtatgttccccacgctagtctacacattgaactteccagaattcgacatat tagatgggcgtatgtgttgcagaaagttttgggaacattttgccttagtgtttgccatgattatcgtcgccgaagagagtttc tgtcccttgatgcaagaagttgaacagtacacaagattgccaaccaaccaaaggttctcaaagtacttcgtcgttctttccc acttgatattgcccctcggcaaacagtacttgctctcgtttatcctcatttggaacgaaattctcaacgggatagcggagtt aagcaggtttggggatcgccatttctacggcgcctggtggtcaagcgtcgactacatggactattcaagaaaatggaacacg atcgtgcaccgattcctccgccggcacgtttacaattcgaccattcgcatcctcggtatttccaggacccaagccgcgacga gataattacacttttgctttcagccacaatccacgaactgttatgtacatcctatttggaaaattggtacctattccttac gatgcttgtccagatcccatgacagtcaccgccaagttcaacaaccgtttgtggggcaacatcatgttctggttgacgtat ttatctggccccagcttggttagtgcgttgtattactcttctga |
| SEQ ID NO: 55 | Acyl-CoA Sterol acyl transferase (ARE2) A. A. Seq | MSDDEIAGIVIEIDDDVKSTSSFOEDLVEVEMSNSSINESQTDELSYRPEEISLHSRRKSHKTPS DESFLEITKNVNDPDLVSKIENLRGKVSQREDRLRKHYLHTSQDVKFLSRFNDIKFKSNSATILD SDAFYKSEHFGVLTIFWVVIGLYIMSTLSDMYFGMAKPLSDWIIIGMFKKDLMQVALVDLVMYL SSYFPYFLQVACKTGAISWHGLGWAIQGVFLTFWAVLPSESAMDLPWIARVFLILHCLVF IMKMQSYGHYNGYLWDVYQEGLVSEADLTAVSEYDDDFPSDHGEVLEQSLWFAKHELEFQS NGTTERKDHHHHVFDEKDVNKPMRVLQEEGIIKFPANINFKDYFEYSMFPTLVYTLNFPRIRHI RWAYVLQKVLGTFALVFAMIIVAEESFCPLMQEVEQYTRLPTNQRFSKYFVVLSHLILPLGKQY LLSFILIWNEILNGIAELSRFGDRHFYGAWWSSVDYMDYSRKWNTIVHRFLRRHVYNSTIRILGI SRTQAAMTLLLSATIHELVMYILFGKLRGYLFLTMLVQIPMTVTAKFNNRLWGNIMFWLTYLSGP SLVSALYLLF |
| SEQ ID NO: 56 | Diacylglycerol acyltransferase (DGA1) Nuc. Seq | atgactcaggactataaagacgatagtcctacgtccactgagttggacactaacatagaagaggtggaaagcactgcaaccc tagagtcggaactcagacagagaaaacagaccacggaaactccagcatcaaccccaccaccacctgcacaacaacagcaggc gcataagaaagccctgaagaatggcaagaggaagagaccatttataaacgtggcgccgctcaacaccccgttggctcacagg ctcgagactttggctgttgtttggcactgtgtcagtatcccgttcttatgttttgttcttgcttacggtctccatggggt tgcttgggtggttctttatcattttgccatatttcatttggtggtacggtttcgacttgcacactccatcgaatggtaaagt tgtctatcgtgtgcgcaactcgttcaagaatttcatcatttgggactgttgttgtcaagtatttccgattgaagtgccaag acggtcgagttggatcctacttttagcgaattgcctgtggaagagagcggcgacagttcggacgacgacgaacaagacttgg tgtctgagcacagcagaactttggttgatcaaatcttcaagttttteggtgaagaaacgcttgaatgacacctccctggg caaaccagagacattcaagaatgtgcctacggtccaagtatattttgggtaccacccacacggagtgatttctatggg gcagtggggttgttgccaacaacgcctgaggaacgaaccatacgccaatttccaaatggttaaaaccattcttccacg acagttccaaggcgagagattgttccctggtattggcaatatcttcccattgacgcttaccacagtttgcgctcccatt ttaccgtgactacttgatggcttggggatcactagtgcatcggctaaaaacattagaagcttgatcaacaatggagacaac tctgtgtgtctcgtcgttggcggtgcacaagaatcgttgttgaacaatatgattgccaagcacgccagagtcgggtacggtt acaaagagagcctagatattcatggcgacagtccgaagaagaagaagaagagcagctagagaaccc aagtcctaaacgtgaagtgcaattggtcttgaacaaacgtaaagttttgtgaagttggctatcgaactaggaaatgtttcc tttggtgccatttttgcattcggagaagctgatgtttacagattggcccagccagcaccaggctcgttcttgtacaagttcc agcaatggatgaaggcaactttteaattcaccatcccattgttttagtgctcgaggcgtgttcatctatgatttcggattgtt gccattcagaaacccaataaacatttcggaagtcgctctacattccgcacaacgtcttgcaagaatacaagcaaaag caccccagaggagtttgccgaagaggaacctgccagtaccccgatgaagaagtctggatctttcaccgatatgttcaagctg gtgaaaagaagcccaagacttcaagtatcaagactaaaatcccacctgcattactagacaagtaccacaagctatacgtcga cgagttgaagaaggtctatgaagagaacaaggaaaggtttggctacggtgatgttgaattaaacattgtagaatag |
| SEQ ID NO: 57 | Diacylglycerol acyltransferase (DGA1) A. A. Seq | MTQDYKDDSPTSTELDTNIEEVESTATLESELRQRKQTTETPASTPPPPPQQQQAHKKASKN GKRKRPFINVAPLNTPLAHRLETLAVVWHCVSIPFFMFLFLLTVSMGLLGWFFIILPYFIWWYGF DLHTPSNGKVVYRVRNSFKNFIIWDWFVKYFPIEVHKTVELDPTFSELPVEESGDSSDDDEQD LVSEHSRTLVDQIFKFFGLKKRLNDTSSGKPETFKNVPTGPRYIFGYHPHGVFGAVPLFAN NALRNEPYTPISKWLKPFFHDSSKGERLFPGIGNIFPLTLTTQFALPFYRDYLMALGITSASAKN IRSLINNGDNSVCLVVGGAQESLLNNMIAKHARVGYGYKESLDIHGDQSEEEEEEDDTKQLE NPSPKREVQLVLNKRKGFVKLAIELGNVSLVPIFAFGEADVYRLAQPAPGSFLYKFQQWMKAT FQFTIPLFSARGVFIYDFGLLPFRNPINICVGRPVYIPHNVLQEYKQKHPEEFAEEEPASTPMKK SGSFTDMFKAGEKKPKTSSIKTKIPPALLDKYHKLYVDELKKVYEENKERFGYGDVELNIVE |
| SEQ ID NO: 58 | Diacylglycerol acyltransferase (LRO1) Nuc. Seq | atgtcgtctttaaagaacagaaaatccgcaagcgtcgccacaagcgatacagaagactcagaaacagaggcagtatcctcct caattgatcccaacggcaccatattgcgaccagtcctacatgacgaaccccaccacagccatcaccaccacaacataactag accagtattggaggacgatggcagcatcctggtgtcagggatcgtcgatctccaaatccgacgacctgcaggcaaagcaa aagaagaagaaacccaagaagaagatctggagtctcgtcgggtcatgtttatctttggtacctcattgggtaatctttg cgtgggcgtttaccacagacacgcatcctttcaatggcgacttggagaagtttatcaactttgaccagctcaacgggatctt tgacgactggaagaactggaaggatatcttgcccaacagcatccagacgtacttgcaggaatcgggcaagggcgaagataac gacggggttgcatggtctggccgattcttctccgtcgggtccgttgaaagcccagaaagaacttcactgacaacacaatg tcgtgttggttcctggtggtgagcacggggttggaatcgtgggaacaaccaccaccggtgattgtccatctatcggata cttcaggaagagattgtgggatcattttatatgttaaggacaatgattttggagaaaacgtgctggttgaagcatatccag ttggacgagaagacggggttggatcctcccaatattaaggtccgtgcggcgcagggtttcgaagcggcagatttcttatgg ctgggtactggataccggaacaagatcttgcagaacttggcggttatggtacgacccaaataacatggtgagtgctagtta tgactggagattggcttacattgacttggagagaagagatggataattttttgaaacttaaagcgcagattgagttgaataac aagttgaacaacaagaagactgtgttgattggccactcgatgggaccccagattatttttctactttttgaaatgggtcgaag ccaccggaaaccatactatgcaatggcggaccaaactgggtaatgatcatattgagtcgattattgacatcagtgggtc gacttttgggtaccccaagagtcttcctgttgttgatctctgggaaatgaaacaccgttcaattgaacgcgttggccggtt acgggttggagcaattttcagcaggcgtgaaagagtcgatatgttgcgtacatttggtggcgttgccagtatgttacccva ggggggagacaagatatgggcaacttgacgcatgcgccagatgatccaatttccacattcagtgatgacgaagttacggac aagccacgacctaaagatcgttcttttggtacgtttatccaattcaagaaccaaactagcgacgctaagccatacagggaga tcaccatggctgaaggtatcgatgaattgttggacaaatcaccagactggtattccaagagagtccgtgagaactactctta cggcattacagacagcaaggcgcaattagagaagaacaacaatgaccacctgaagtggtcgaaccccattagaagctgccttg |

| SEQ ID NO: | Sequence description | Sequence |
|---|---|---|
| | | cctaaagcacccgacatgaagatctattgtttctacggagttggaaatcctaccgaaagggcatacaagtatgtgactgccg
ataaaaaagccacgaaattggactacataatagacgccgacgatgccaatggagtcatattaggagacggagacggcactgt
ttcgttattaacccactcgatgtgccatgagtgggccaagggagacaagtcgagatacaacccagccaactcgaaggttacc
attgttgaaatcaagcacgagccagacagatttgatttacgaggcggcgccaagactgcggaacatgttgatattttgggga
gtgccgagttgaacgagttgattttgactgtggttagcgggaacggggacgagattgagaatagatatgtcagcaacttaaa
agaaatagtagaggccataaatttataa |
| SEQ ID NO: 59 | Diacylglycerol acyltransferase (LRO1) A. A. Seq | MSSLKNRKSASVATSDTEDSETEAVSSSIDPNGTILRPVLHDEPHHSHHHHNITRPVLEDDGSI
SVSRRSSISKSDDSQAKQKKKKPKKKILESRRVMFIFGTLIGLIFAWAFTTDTHPFNGDLEKFIN
FDQLNGIFDDWKNWKDILPNSIQTYLQESGKGEDNDGLHGSADSFSVGLRLKAQKNFTDNHN
VVLVPGVVSTGLESWGTTTTGDCPSIGYFRKRLWGSFYMLRTMILEKTCWLKHIQLDEKTGLD
PPNIKVRAAQGFEAADFFMAGYWIWNKILQNLAVIGYGPNNMVSASYDWRLAYIDLERRDGYF
SKLKAQIELNNKLNNKKTVLIGHSMGTQIIFYFLKWVEATGKPYYGNGGPNWVNDHIESIIDISG
STLGTPKSIPVLISGEMKDTVQLNALAVYGLEQFFSRRERVDMLRTFGGVASMLPKGGDKIWG
NLTHAPDDPISTFSDDEVTDSHEPKDRSFGTFIQFKNQTSDAKPYREITMAEGIDELLDKSPDW
YSKRVRENYSYGITDSKAQLEKNNNDHSKWSNPLEAALPKAPDMKIYCFYGVGNPTERAYKY
VTADKKATKLDYIIDADDANGVILGDGDGTVSLLTHSMCHEWAKGDKSRYNPANSKVTIVEIKH
EPDRFDLRGGAKTAEHVDILGSAELNELILTVVSGNGDEIENRYVSNLKEIVEAINL |

Example 52

Production of Genetically Modified *Candida tropicalis* Strains

Strain sAA779 (pox4a::ura3/pox4b::ura3 POX5/POX5 acs1::PURA3/acs1::PURA3)

Strain sAA776 was grown in YPD media overnight and plated on 5-FOA plate. Colonies that grew in the presence of 5-FOA were PCR screened for the looping out of the URA3 gene leaving behind only the URA3 promoter (PURA3) in both ACS1 copies. One such strain was named sAA779. As such both alleles of the ACS1 gene were disrupted.

Strain sAA865 (pox4a::ura3/pox4b::ura3 POX5/POX5 acs1::PURA3/acs1::PURA3 fat1-Δ1::URA3/FAT1)

The full-length coding sequence of the Fat1 gene was amplified from *C. tropicalis* (ATCC20336) genomic DNA using primers oAA1023 and oAA1024. The 2,086 bp PCR product was gel purified and ligated into pCR-Blunt II-TOPO (Invitrogen), transformed into competent TOP10 *E. coli* cells (Invitrogen) and clones containing PCR inserts were sequenced to confirm correct DNA sequence. One such plasmid was named pAA296.

Figure 59:
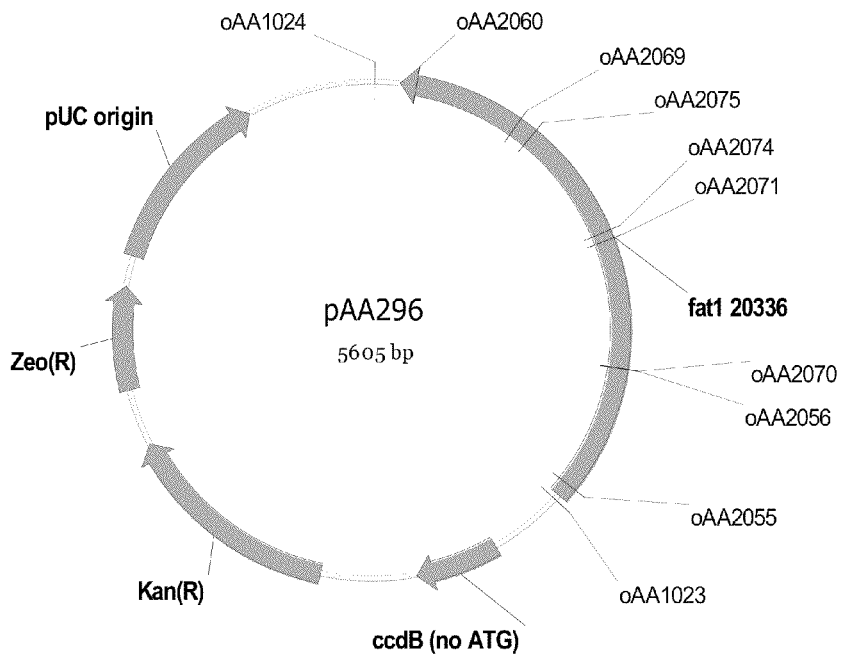
FIG. 59 and FIG. 60 graphically illustrate nucleic acid design features for certain *C. tropicalis* strains addressed in Examples 52 and 53.
Figure 60:
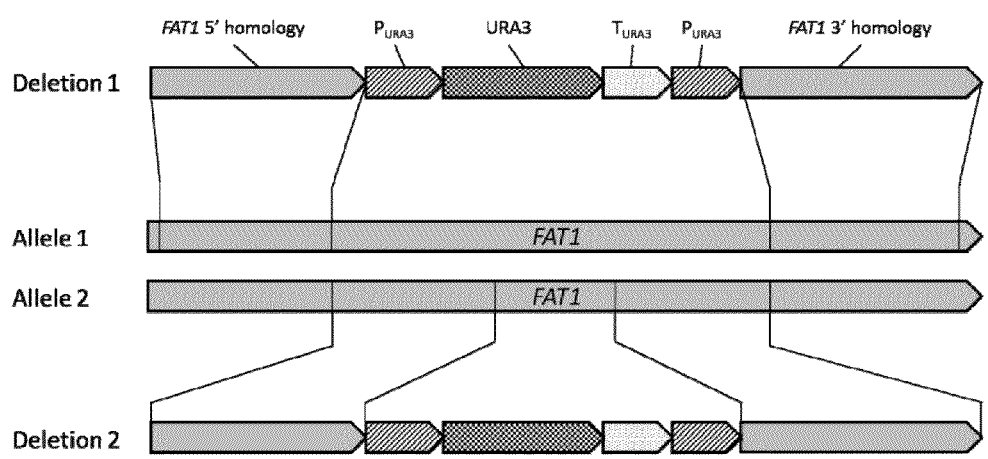

Deletion of each FAT1 allele was achieved by transforming cells with linear DNA cassettes constructed by overlap extension PCR (OE-PCR). The deletion cassette for the first FAT1 allele in sAA779 was created from three DNA fragments. The first DNA fragment (FAT1 5' homology) was amplified from plasmid pAA296 using primers oAA2055 and oAA2056. The second DNA fragment (PURA3URA3TURA3PURA3) was amplified from plasmid pAA298 using primers oAA2057 and oAA2068. The third DNA fragment (FAT1 3' homology) was amplified from plasmid pAA296 using primers oAA2069 and oAA2060. The location of primer annealing sites in pAA296 that amplify FAT1 DNA fragments are shown in FIG. 59. All three DNA fragments were combined in the same reaction to generate the full-length deletion cassette (FIG. 60) by OE-PCR using primers oAA2055 and oAA2060.

Strain sAA779 was transformed with the full-length deletion cassette and plated on SCD-Ura plate. Several colonies were screened by PCR for integration of the deletion cassette at the first FAT1 allele. One such strain was named sAA865.

Strain sAA869 (pox4a::ura3/pox4b::ura3 POX5/POX5 acs1::PURA3/acs1::PURA3 fat1-Δ1::PURA3/FAT1)

Strain sAA865 was grown in YPD media overnight and plated on 5-FOA plate. Colonies that grew in the presence of 5-FOA were PCR screened for the looping out of the URA3 gene leaving behind only the URA3 promoter (PURA3) in the first FAT1 allele. One such strain was named sAA869.

Strain sAA875 (pox4a::ura3/pox4b::ura3 POX5/POX5 acs1::PURA3/acs1::PURA3 fat1-Δ1::PURA3/fat1-Δ2::URA3)

The deletion of the second FAT1 allele in sAA869 was performed by transformation with a deletion cassette created by OE-PCR. The deletion cassette for the second FAT1 allele was constructed from three DNA fragments. The first DNA fragment (FAT1 5' homology) was amplified from plasmid pAA296 using primers oAA2070 and oAA2071. The second DNA fragment (PURA3URA3TURA3PURA3) was amplified from plasmid pAA298 using primers oAA2072 and oAA2073. The third DNA fragment (FAT1 3' homology) was amplified from plasmid pAA296 using primers oAA2074 and oAA2075. The location of primer annealing sites in pAA296 that amplify FAT1 DNA fragments are shown in FIG. 59. All three DNA fragments were combined in the same reaction to create the full-length deletion (FIG. 60) cassette by OE-PCR using primers oAA2070 and oAA2071.

Strain sAA869 was transformed with the full-length deletion cassette and plated on SCD-Ura plate. Several colonies were screened by PCR for integration of the deletion cassette at the second FAT1 allele. One such strain was named sAA875.

| Primer | sequence (SEQ ID NOS 388-401, respectively, in order of appearance) |
|---|---|
| oAA1023 | GATATTATTCCACCTTCCCTTCATT |
| oAA1024 | CCGTTAAACAAAAATCAGTCTGTAAA |
| oAA2055 | TGCCATCCTTGGTAGTCAGTTATT |

-continued

| Primer | sequence (SEQ ID NOS 388-401, respectively, in order of appearance) |
|---|---|
| oAA2056 | CCGAAACAACCGTAGATACCTTTAATGGCTTGTCCTTGGTGTTGA |
| oAA2057 | TCAACACCAAGGACAAGCCATTAAAGGTATCTACGGTTGTTTCGG |
| oAA2068 | TCCTCGTCCATCTTCAACAAGTCGGTACCGAGCTCTGCGAATT |
| oAA2069 | AATTCGCAGAGCTCGGTACCGACTTGTTGAAGATGGACGAGGA |
| oAA2060 | TGTCGCCATTCAACCAGTAGAT |
| oAA2070 | TTGATCCACTGTCTTAAGATTGTCAA |
| oAA2071 | CCGAAACAACCGTAGATACCTTTAACCAGAACGAAGTAGCGGAGAAT |
| oAA2072 | ATTCTCCGCTACTTCGTTCTGGTTAAAGGTATCTACGGTTGTTTCGG |
| oAA2073 | CGACAGACCTCACCGACGTATGGTACCGAGCTCTGCGAATT |
| oAA2074 | AATTCGCAGAGCTCGGTACCATACGTCGGTGAGGTCTGTCG |
| oAA2075 | AGGATTTTGCTGTTGGTGGC |

Example 53

Shake Flask Characterization of *Candida tropicalis* Strains sAA776, sAA865 and sAA875

Starter cultures (5 mL) in SP92glycerol media (6.7 g/L Difco yeast nitrogen base, 3.0 g/L Difco yeast extract, 3.0 g/L ammonium sulfate, 1.0 g/L potassium phosphate monobasic, 1.0 g/L potassium phosphate dibasic, 75 g/L glycerol) were incubated overnight at 30° C., 250 rpm and used to inoculate 25 mL fresh SP92glycerol media to an initial OD600 nm of 0.4 and incubated ~18 hours at 30° C., 300 rpm. Cells were then pelleted by centrifugation for 10 minutes at 4,000×g, 4° C. then resuspended in 12.5 mL of TB-lowN media (1.7 g/L Difco yeast nitrogen base without amino acids and ammonium sulfate, 3.0 g/L Difco yeast extract, 1.0 g/L potassium phosphate monobasic, 1.0 g/L potassium phosphate dibasic). Oleic acid, 0.821 mL, was added to start the adipic acid production at 30° C., 300 rpm in 250 mL shake flasks. Incubation of the cultures continued for 48 hours and samples were taken for analysis of fatty acids and diacids by GC. The experiment was performed with shake flasks in triplicate.

GC analysis revealed that there were diacids of chain length C8 and C6 in most flasks. Both C8 diacid and adipic acid were considered for yield calculations. A correction factor of 0.84 was applied to the concentration of C8 diacid (MW adipic acid/MW C8 diacid=0.84). Yield of product per consumed substrate (Yp/s) was determined with the equation [(adipic acid (g/L)+(C8 diacid (g/L)*0.84))*final volume of culture in flask (L)]/[oleic acid consumed (g)]. The maximum theoretical yield (Ymax) for the conversion of oleic acid to adipic acid was calculated to be 0.52 g adipic acid/g oleic acid. The percent of Ymax (% Ymax) was calculated as Yp/s/Ymax*100.

Figure 61:
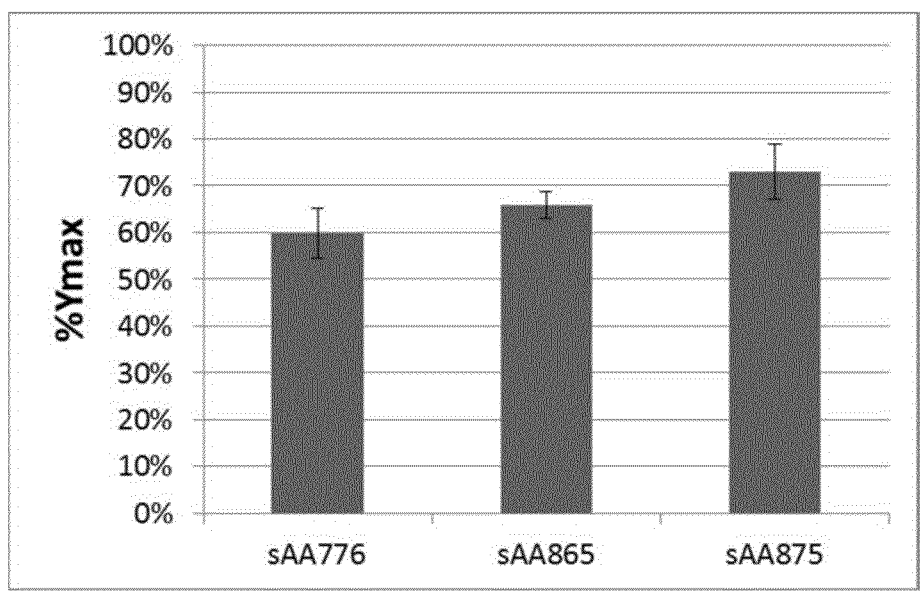
FIG. 61 shows the yield of adipic acid produced by these strains.

The shake flask results (FIG. 61) showed that strain sAA875 produced about 6.0 grams of adipic acid per liter of fermentation broth. Further the yield of adipic acid improved with each FAT1 allele deletion from 60% of Ymax in sAA776 (FAT1/FAT1), to 66% of Ymax in sAA865 (FAT1/fat1) and finally 73% of Ymax in sAA875 (fat1/fat1).

Example 54

Shake Flask Conversion of Mixed Chain-Length Fatty Acid Oils to Adipic Acid

Starter cultures (5 mL) of strain sAA776 in SP92glycerol media (6.7 g/L Difco yeast nitrogen base, 3.0 g/L Difco yeast extract, 3.0 g/L ammonium sulfate, 1.0 g/L potassium phosphate monobasic, 1.0 g/L potassium phosphate dibasic, 75 g/L glycerol) were incubated overnight at 30° C., 250 rpm and used to inoculate 25 mL fresh SP92glycerol media to an initial OD600 nm of 0.4 and incubated ~18 hours at 30° C., 300 rpm. Cells were then pelleted by centrifugation for 10 minutes at 4,000×g, 4° C. then resuspended in 12.5 mL of TB-lowN media (1.7 g/L Difco yeast nitrogen base without amino acids and ammonium sulfate, 3.0 g/L Difco yeast extract, 1.0 g/L potassium phosphate monobasic, 1.0 g/L potassium phosphate dibasic). One milliliter of either palm oil, soybean oil, or coconut oil was added to start the adipic acid production at 30° C., 300 rpm in 250 mL shake flasks. Incubation of the cultures continued for 96 hours and samples were taken for analysis of fatty acids and diacids by GC. The experiment was performed with shake flasks in duplicate. The fatty acid composition of each feedstock oil is shown in Table 1 and the resulting diacid profile from each oil feedstock is shown in Table 2.

TABLE 1

Fatty acid composition of plant-based oil feedstocks

| Chain length | Fatty acid | MW (g/mol) | Weight percent, Palm Oil | Weight percent, Soybean Oil | Weight percent, Coconut Oil |
|---|---|---|---|---|---|
| C6:0 | Caproic | 116.16 | 0.0 | 0.0 | 0.5 |
| C8:0 | Caprylic | 144.21 | 0.0 | 0.0 | 7.8 |
| C10:0 | Capric | 172.26 | 0.0 | 0.0 | 6.7 |
| C12:0 | Lauric | 200.32 | 0.2 | 0.0 | 47.5 |
| C14:0 | Myrstic | 228.37 | 1.1 | 0.0 | 18.1 |
| C16:0 | Palmitic | 256.42 | 44.0 | 11.0 | 8.8 |
| C18:0 | Stearic | 284.48 | 4.5 | 4.0 | 2.6 |
| C20:0 | Arachidic | 312.53 | 0.0 | 0.0 | 0.1 |
| C18:1 | Oleic | 282.46 | 39.2 | 24.0 | 6.2 |
| C18:2 | Linoleic | 280.45 | 11.0 | 54.0 | 1.6 |
| C18:3 | Linolenic | 278.43 | 0.0 | 7.0 | 0.0 |

TABLE 2

Shake flask conversion of oil feedstocks to Adipic Acid

|  | C14 Diacid (g/L) | C12 Diacid (g/L) | C10 Diacid (g/L) | C8 Diacid (g/L) | Adipic Acid (g/L) |
|---|---|---|---|---|---|
| Cocount Oil | 0.23 | 0.07 | 0.22 | 6.92 | 3.73 |
| Palm Oil | 0.01 | 0.00 | 0.00 | 0.19 | 2.53 |
| Soybean Oil | 0.00 | 0.00 | 0.00 | 0.09 | 2.20 |

Example 55

Fermentation Procedure for Conversion of Oleic Acid to Adipic Acid

Fermentation medium of composition 14.0 g/L ammonium sulfate, 10.2 g/L potassium phosphate monobasic, 1.0 g/L magnesium sulfate, 0.2 g/L calcium chloride, 120 mg/L citric acid, 46 mg/L ferric chloride, 0.4 mg/L biotin, 54 g/L glucose and 2× trace metals mix was filter sterilized and transferred to a sterile fermentation vessel. Growth of *Candida tropicalis* strain sAA875 was initiated with a 5% inoculum (initial OD600 nm=1.0) and growth conditions of 35° C., 1000 rpm, 1 vvm, pH 5.8 and initial volume of 1.0 L. Growth continued for approximately 15 hours before exhaustion of the initial carbon source. The temperature control was changed to 30° C. and the conversion phase was initiated by the addition of oleic acid to 5 g/L. At the same time as the oleic acid bolus, a continuous feed of oleic acid was initiated at a rate of 1.5 g/L-h. Fermentation conditions were maintained at 30° C., 1000 rpm, 1 vvm, and pH 5.8 for 24 hours at which point the pH set-point was changed to 3.5. At 72 hours after initiating the conversion phase, the oleic acid feed was turned off and a glucose feed was initiated at a rate of 1.5 g/L-h. The fermentation was carried out for a total of 135 hours. Samples were collected for GC analysis every 24 hours after initiating the conversion phase. At the end of the fermentation run, the diacid composition was 0.43 g/L cis-9-octadecenedioic acid, 13.93 g/L octanedioic acid, and 29.45 g/L adipic acid.

Example 56

Examples of Embodiments

Provided hereafter are non-limiting examples of certain embodiments.

A1. An engineered microorganism capable of producing adipic acid, which microorganism comprises one or more altered activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, acyl-CoA hydrolase, acyl-CoA thioesterase enoyl-CoA hydratase activity, 3-L-hydroxyacyl-CoA dehydrogenase activity and acetyl-CoA C-acyltransferase activity.

A1.1. The engineered microorganism of embodiment A1, which comprises a genetic modification that adds or increases the 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, acyl-CoA hydrolase, acyl-CoA thioesterase enoyl-CoA hydratase activity, 3-L-hydroxyacyl-CoA dehydrogenase activity and/or acetyl-CoA C-acyltransferase activity.

A1.2. The engineered microorganism of embodiment A1, which comprises a genetic modification that reduces the acyl-CoA oxidase activity.

A1.3. The engineered microorganism of embodiment A1.1, wherein the genetic modification comprises increased copies of a polynucleotide that encodes a polypeptide having 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, acyl-CoA hydrolase, acyl-CoA thioesterase enoyl-CoA hydratase activity, 3-L-hydroxyacyl-CoA dehydrogenase activity or acetyl-CoA C-acyltransferase activity.

A1.4. The engineered microorganism of embodiment A1.1, wherein the genetic modification comprises insertion of a heterologous promoter and/or 5' UTR, into genomic DNA of the microorganism in functional connection with a polynucleotide that encodes a polypeptide having 6-oxohexanoic acid dehydrogenase activity, 6-hydroxyhexanoic acid dehydrogenase activity, glucose-6-phosphate dehydrogenase, hexanoate synthase activity, lipase activity, fatty acid synthase activity, acetyl CoA carboxylase activity, monooxygenase activity, monooxygenase reductase activity, fatty alcohol oxidase activity, acyl-CoA ligase activity, acyl-CoA oxidase activity, acyl-CoA hydrolase, acyl-CoA thioesterase enoyl-CoA hydratase activity, 3-L-hydroxyacyl-CoA dehydrogenase activity or acetyl-CoA C-acyltransferase activity.

A2. The engineered microorganism of any one of embodiments A1 to A1.4, which comprises an altered thioesterase activity.

A2.1. The engineered microorganism of embodiment A2, which comprises a genetic alteration that adds or increases a thioesterase activity.

A2.2. The engineered microorganism of embodiment A2.1, which comprises a heterologous polynucleotide encoding a polypeptide having thioesterase activity.

A3. The engineered microorganism of any one of embodiments A1 to A2.2, which comprises a heterologous polynucleotide encoding a polypeptide having 6-oxohexanoic acid dehydrogenase activity.

A3.1 The engineered microorganism of any one of embodiments A1 to A3, which comprises a heterologous polynucleotide encoding a polypeptide having omega oxo fatty acid dehydrogenase activity.

A4. The engineered microorganism of embodiment A3 and A3.1, wherein the heterologous polynucleotide is from a bacterium.

A5. The engineered microorganism of embodiment A4, wherein the bacterium is an *Acinetobacter, Nocardia, Pseudomonas* or *Xanthobacter* bacterium.

A6. The engineered microorganism of embodiment A1 or A2, which comprises a heterologous polynucleotide encoding a polypeptide having 6-hydroxyhexanoic acid dehydrogenase activity.

A6.1 The engineered microorganism of embodiment A1 or A2, which comprises a heterologous polynucleotide encoding a polypeptide having omega hydroxyl fatty acid dehydrogenase activity A7. The engineered microorganism of embodiment A6 or A6.1, wherein the heterologous polynucleotide is from a bacterium.

A8. The engineered microorganism of embodiment A7, wherein the bacterium is an *Acinetobacter, Nocardia, Pseudomonas* or *Xanthobacter* bacterium.

A9. The engineered microorganism of embodiment A1 or A2, which comprises a heterologous polynucleotide encoding a polypeptide having hexanoate synthase subunit A activity.

A10. The engineered microorganism of embodiment A1 or A2, which comprises a heterologous polynucleotide encoding a polypeptide having hexanoate synthase subunit B activity.

A11. The engineered microorganism of embodiment A9 or A10, wherein the heterologous polynucleotide independently is selected from a bacterium.

A12. The engineered microorganism of embodiment A11, wherein the bacterium is a *Bacillus* bacterium.

A13. The engineered microorganism of embodiment A12, wherein the *Bacillus* bacterium is *B. megaterium*.

A14. The engineered microorganism of embodiment A1 or A2, which comprises a heterologous polynucleotide encoding a polypeptide having monooxygenase activity.

A15. The engineered microorganism of embodiment A14, wherein the heterologous polynucleotide is from a fungus.

A16. The engineered microorganism of embodiment A15, wherein the fungus is an *Aspergillus* fungus.

A17. The engineered microorganism of embodiment A16, wherein the *Aspergillus* fungus is *A. parasiticus*.

A18. The engineered microorganism of embodiment A1 or A2, which comprises a genetic modification that results in primary hexanoate usage by monooxygenase activity.

A19. The engineered microorganism of embodiment A18, wherein the genetic modification reduces a polyketide synthase activity.

A20. The engineered microorganism of any one of embodiments A1-A19, which is a eukaryote.

A21. The engineered microorganism of embodiment A20, which is a yeast.

A22. The engineered microorganism of embodiment A21, wherein the yeast is a *Candida* yeast.

A23. The engineered microorganism of embodiment A22, wherein the *Candida* yeast is a *C. tropicalis* strain.

A24. The engineered microorganism of embodiment A20, which is a fungus.

A25. The engineered microorganism of embodiment A24, wherein the fungus is a *Yarrowia* fungus.

A26. The engineered microorganism of embodiment A25, wherein the *Yarrowia* fungus is *Y. lipolytica*.

A27. The engineered microorganism of embodiment A24, wherein the fungus is an *Aspergillus* fungus.

A28. The engineered microorganism of embodiment A27, wherein the *Aspergillus* fungus is a *A. parasiticus* strain or a *A. nidulans* strain.

A29. The engineered microorganism of any one of embodiments A1-A28, which comprises a genetic modification that reduces 6-hydroxyhexanoic acid conversion.

A30. The engineered microorganism of embodiment A29, wherein the genetic modification reduces 6-hydroxyhexanoic acid dehydrogenase activity.

A31. The engineered microorganism of any one of embodiments A1-A30, which comprises a genetic modification that reduces beta-oxidation activity.

A32. The engineered microorganism of embodiment A31, wherein the genetic modification renders beta-oxidation activity undetectable.

A33. The engineered microorganism of embodiment A31, wherein the genetic modification partially reduces beta-oxidation activity.

A34. The engineered microorganism of any one of embodiments A31 to A33, wherein the genetic modification comprises disrupting a polynucleotide that encodes a polypeptide having an acyl-CoA oxidase activity.

A35. The engineered microorganism of any one of embodiments A31 to A33, wherein the genetic modification comprises disrupting a promoter in functional connection with a polynucleotide that encodes a polypeptide having the acyl-CoA oxidase activity.

A36. The engineered microorganism of embodiment A34 or A35, wherein the polypeptide having the acyl-CoA oxidase activity is a POX polypeptide.

A37. The engineered microorganism of embodiment A36, wherein the POX polypeptide is a POX4 polypeptide, POX5 polypeptide or POX4 polypeptide and POX5 polypeptide.

A38. The engineered microorganism of any one of embodiments A1 to A37, which is in contact with a feedstock.

A39. The engineered microorganism of embodiment A38, wherein the feedstock comprises a saccharide.

A40. The engineered microorganism of embodiment A39, wherein the saccharide is a monosaccharide, polysaccharide or a mixture or a monosaccharide and polysaccharide.

A41. The engineered microorganism of embodiment A38, wherein the feedstock comprises a paraffin.

A42. The engineered microorganism of embodiment A41, wherein the paraffin is a saturated paraffin, unsaturated paraffin, substituted paraffin, branched paraffin, linear paraffin or combination thereof.

A43. The engineered microorganism of embodiment A41 or A42, wherein the paraffin includes about 1 to about 60 carbon atoms.

A44. The engineered microorganism of embodiments A41 to A43, wherein the paraffin is in a mixture of paraffins.

A45. The engineered microorganism of embodiment A44, wherein the paraffins in the mixture of paraffins have a mean number of carbon atoms of about 8 to about 18 carbon atoms.

A46. The engineered microorganism of embodiment A45, wherein the mean number of carbon atoms is about 10 to about 16 carbon atoms.

A46.1. The engineered microorganism of embodiment A46, wherein the mean number of carbon atoms is about 12 atoms.

A47. The engineered microorganism of any one of embodiments A41 to A46.1, wherein the paraffin is in a wax.

A48. The engineered microorganism of any one of embodiments A41 to A46.1, wherein the paraffin is in an oil.

A49. The engineered microorganism of any one of embodiments A41 to A48, wherein the paraffin is from a petroleum product.

A50. The engineered microorganism of embodiment A49, wherein the petroleum product is a petroleum distillate.

A51. The engineered microorganism of any one of embodiments A41 to A48, wherein the paraffin is from a plant or plant product.

B1. An engineered microorganism that produces adipic acid, which microorganism comprises an altered monooxygenase activity.

B1.1. The engineered microorganism of embodiment B1, which comprises a genetic modification that alters the monooxygenase activity.

B1.2. The engineered microorganism of embodiment B1 or B1.1, which comprises a genetic modification that alters a monooxygenase activity selected from the group consisting of.

B2. The engineered microorganism of embodiment B1.1, which comprises a heterologous polynucleotide encoding a polypeptide having monooxygenase activity.

B3. The engineered microorganism of embodiment B2, wherein the heterologous polynucleotide is from a fungus.

B4. The engineered microorganism of embodiment B3, wherein the fungus is an *Aspergillus* fungus.

B5. The engineered microorganism of embodiment B4, wherein the *Aspergillus* fungus is *A. parasiticus*.

B6. The engineered microorganism of any one of embodiments B1-B5, which comprises a genetic modification that results in substantial hexanoate usage by the monooxygenase activity.

B7. The engineered microorganism of embodiment B6, wherein the genetic modification reduces a polyketide synthase activity.

B8. The engineered microorganism of any one of embodiments B1-B5, which comprises an altered hexanoate synthase activity.

B9. The engineered microorganism of embodiment B8, wherein the altered hexanoate synthase activity is an altered hexanoate synthase subunit A activity, altered hexanoate synthase subunit B activity, or altered hexanoate synthase subunit A activity and altered hexanoate synthase subunit B activity.

B9.1. The engineered microorganism of embodiment B9, which comprises a genetic alteration that adds or increases hexanoate synthase activity.

B10. The engineered microorganism of any one of embodiments B8, B9 or B9.1, which comprises a heterologous polynucleotide encoding a polypeptide having hexanoate synthase activity.

B11. The engineered microorganism of embodiment B10, wherein the heterologous polynucleotide is from a fungus.

B12. The engineered microorganism of embodiment B11, wherein the fungus is an *Aspergillus* fungus.

B13. The engineered microorganism of embodiment B11, wherein the *Aspergillus* fungus is *A. parasiticus*.

B14. The engineered microorganism of any one of embodiments B1-B13, which comprises an altered thioesterase activity.

B14.1. The engineered microorganism of embodiment B14, which comprises a genetic modification that adds or increases the thioesterase activity.

B14.2. The engineered microorganism of embodiment B14 or B14.1, which comprises a heterologous polynucleotide encoding a polypeptide having thioesterase activity.

B15. The engineered microorganism of any one of embodiments B1-B14.2, which comprises an altered 6-oxohexanoic acid dehydrogenase activity.

B15.1. The engineered microorganism of embodiment B15, which comprises a genetic modification that adds or increases the 6-oxohexanoic acid dehydrogenase activity.

B15.2 The engineered microorganism of any one of embodiments B1 to B15.1, which comprises an altered omega oxo fatty acid dehydrogenase activity.

B15.3 The engineered microorganism of embodiment B15.2, which comprises a genetic modification that adds or increases the omega oxo fatty acid dehydrogenase activity B16. The engineered microorganism of any one of embodiments B15 to B15.3, which comprises a heterologous polynucleotide encoding a polypeptide having 6-oxohexanoic acid dehydrogenase activity.

B16.1 The engineered microorganism of any one of embodiments B15 to B16, which comprises a heterologous polynucleotide encoding a polypeptide having omega oxo fatty acid dehydrogenase activity.

B17. The engineered microorganism of embodiment B16 or B16.1, wherein the heterologous polynucleotide is from a bacterium.

B18. The engineered microorganism of embodiment B17, wherein the bacterium is a *Acinetobacter*, *Nocardia*, *Pseudomonas* or *Xanthobacter* bacterium.

B19. The engineered microorganism of any one of embodiments B1-B18, which comprises an altered 6-hydroxyhexanoic acid dehydrogenase activity.

B19.1. The engineered microorganism of embodiment B19, which comprises a genetic modification that adds or increases the 6-hydroxyhexanoic acid dehydrogenase activity.

B19.2 The engineered microorganism of any one of embodiments B1-B19.1, which comprises an altered omega hydroxyl fatty acid dehydrogenase activity.

B19.3 The engineered microorganism of embodiment B19.2, which comprises a genetic modification that adds or increases the omega hydroxyl fatty acid dehydrogenase activity.

B20. The engineered microorganism of any one of embodiments B19 to B19.3, which comprises a heterologous polynucleotide encoding a polypeptide having 6-hydroxyhexanoic acid dehydrogenase activity.

B20.1 The engineered microorganism of any one of embodiments B19 to B20, which comprises a heterologous polynucleotide encoding a polypeptide having omega hydroxyl fatty acid dehydrogenase activity.

B21. The engineered microorganism of embodiment B20 or B20.1, wherein the heterologous polynucleotide is from a bacterium.

B22. The engineered microorganism of embodiment B21, wherein the bacterium is a *Acinetobacter*, *Nocardia*, *Pseudomonas* or *Xanthobacter* bacterium.

B23. The engineered microorganism of any one of embodiments B1-B22, which is a eukaryote.

B24. The engineered microorganism of embodiment B23, which is a yeast.

B25. The engineered microorganism of embodiment B24, wherein the yeast is a *Candida* yeast.

B26. The engineered microorganism of embodiment B25, wherein the *Candida* yeast is *C. tropicalis*.

B27. The engineered microorganism of embodiment B23, which is a fungus.

B28. The engineered microorganism of embodiment B27, wherein the fungus is a *Yarrowia* fungus.

B29. The engineered microorganism of embodiment B28, wherein the *Yarrowia* fungus is *Y. lipolytica*.

B30. The engineered microorganism of embodiment B27, wherein the fungus is *Aspergillus*.

B31. The engineered microorganism of embodiment B30, wherein the *Aspergillus* fungus is *A. parasiticus* or *A. nidulans*.

B32. The engineered microorganism of any one of embodiments B1-B31, which comprises a genetic modification that reduces 6-hydroxyhexanoic acid conversion.

B33. The engineered microorganism of embodiment B32, wherein the genetic modification reduces 6-hydroxyhexanoic acid dehydrogenase activity.

B34. The engineered microorganism of any one of embodiments B1-B33, which comprises a genetic modification that reduces beta-oxidation activity.

B35. The engineered microorganism of embodiment B34, wherein the genetic modification renders beta-oxidation activity undetectable.

C1. A method for manufacturing adipic acid, which comprises culturing an engineered microorganism of any one of embodiments A1-B35 under culture conditions in which the cultured microorganism produces adipic acid.

C1.1. The method of embodiment C1, wherein the host microorganism from which the engineered microorganism is produced does not produce a detectable amount of adipic acid.

C2. The method of embodiment C1 of C1.1, wherein the culture conditions comprise fermentation conditions.

C3. The method of any one of embodiments C1-C2, wherein the culture conditions comprise introduction of biomass.

C4. The method of C1 or C2, wherein the culture conditions comprise introduction of glucose.

C5. The method of C1 or C2, wherein the culture conditions comprise introduction of hexane.

C6. The method of any one of embodiments C1-C5, wherein the adipic acid is produced with a yield of greater than about 0.3 grams per gram of glucose added.

C7. The method of any one of embodiments C1-C6, which comprises purifying the adipic acid from the cultured microorganisms.

C8. The method of embodiment C7, which comprises modifying the adipic acid, thereby producing modified adipic acid.

C9. The method of any one of embodiments C1-C8, which comprises placing the cultured microorganisms, the adipic acid or the modified adipic acid in a container.

C10. The method of embodiment C9, which comprises shipping the container.

D1. A method for manufacturing 6-hydroxyhexanoic acid, which comprises culturing an engineered microorganism of any one of embodiments A29, A30, B32 or B33 under culture conditions in which the cultured microorganism produces 6-hydroxyhexanoic acid.

D1.1. The method of embodiment D1, wherein the host microorganism from which the engineered microorganism is produced does not produce a detectable amount of 6-hydroxyhexanoic acid.

D2. The method of embodiment D1 or D1.1, wherein the culture conditions comprise fermentation conditions.

D3. The method of any one of embodiments D1-D2, wherein the culture conditions comprise introduction of biomass.

D4. The method of D1 or D2, wherein the culture conditions comprise introduction of glucose.

D5. The method of D1 or D2, wherein the culture conditions comprise introduction of hexane.

D6. The method of any one of embodiments D1-D5, wherein the 6-hydroxyhexanoic acid is produced with a yield of greater than about 0.3 grams per gram of glucose added.

D7. The method of any one of embodiments D1-D6, which comprises purifying the 6-hydroxyhexanoic acid from the cultured microorganisms.

D8. The method of embodiment D7, which comprises modifying the 6-hydroxyhexanoic acid, thereby producing modified 6-hydroxyhexanoic acid.

D9. The method of any one of embodiments D1-D8, which comprises placing the cultured microorganisms, the 6-hydroxyhexanoic acid or the modified 6-hydroxyhexanoic acid in a container.

D10. The method of embodiment D9, which comprises shipping the container.

E1. A method for preparing an engineered microorganism that produces adipic acid, which comprises:
(a) introducing a genetic modification to a host organism that adds or increases monooxygenase activity, thereby producing engineered microorganisms having detectable and/or increased monooxygenase activity; and
(b) selecting for engineered microorganisms that produce adipic acid.

E1.1. The method of embodiment E1, wherein the monooxygenase activity is incorporation of a hydroxyl moiety into a six-carbon molecule.

E1.2. The method of embodiment E1 or E1.1, wherein the six-carbon molecule is hexanoate.

E2. A method for preparing an engineered microorganism that produces adipic acid, which comprises:
(a) culturing a host organism with hexane as a nutrient source, thereby producing engineered microorganisms having detectable monooxygenase activity; and
(b) selecting for engineered microorganisms that produce adipic acid.

E2.1. The method of embodiment E2, wherein the monooxygenase activity is incorporation of a hydroxyl moiety into a six-carbon molecule.

E2.2. The method of embodiment E2 or E2.1, wherein the six-carbon molecule is hexanoate.

E3. The method of any one of embodiments E1-E2.2, which comprises selecting the engineered microorganisms that have a detectable amount of the monooxygenase activity.

E4. The method of any one of embodiments E1-E3, which comprises introducing a genetic modification that adds or increases a hexanoate synthase activity, thereby producing engineered microorganisms, and selecting for engineered microorganisms having detectable and/or increased hexanoate synthase activity.

E5. The method of embodiment E4, wherein the genetic modification encodes a polypeptide having a hexanoate synthase subunit A activity, a hexanoate synthase subunit B activity, or a hexanoate synthase subunit A activity and a hexanoate synthase subunit B activity.

E6. The method of any one of embodiments E1-E5, which comprises introducing a genetic modification that adds or increases 6-oxohexanoic acid dehydrogenase activity, thereby producing engineered microorganisms, and selecting for engineered microorganisms having detectable and/or increased 6-oxohexanoic acid dehydrogenase activity relative to the host microorganism.

E7. The method of any one of embodiments E1-E6, which comprises introducing a genetic modification that adds or increases a 6-hydroxyhexanoic acid dehydrogenase activity, thereby producing engineered microorganisms, and selecting for engineered microorganisms having a detectable and/or increased 6-hydroxyhexanoic acid dehydrogenase activity relative to the host microorganism.

E7.1 The method of any one of embodiments E1-E7, which comprises introducing a genetic modification that adds or increases a 6-hydroxyhexanoic acid dehydrogenase activity, thereby producing engineered microorganisms, and selecting for engineered microorganisms having a detectable and/or increased omega hydroxyl fatty acid dehydrogenase activity relative to the host microorganism.

E8. The method of any one of embodiments E1-E7.1, which comprises introducing a genetic modification that adds or increases a thioesterase activity, thereby producing engineered microorganisms, and selecting for engineered microorganisms having a detectable and/or increased thioesterase activity relative to the host microorganism.

E9. The method of any one of embodiments E1-E8, which comprises introducing a genetic modification that reduces 6-hydroxyhexanoic acid conversion, thereby producing engineered microorganisms, and selecting for engineered microorganisms having reduced 6-hydroxyhexanoic acid conversion relative to the host microorganism.

E10. The method of any one of embodiments E1-E9, which comprises introducing a genetic modification that reduces beta-oxidation activity, thereby producing engineered microorganisms, and selecting for engineered microorganisms having reduced beta-oxidation activity relative to the host microorganism.

E11. The method of any one of embodiments E1-E11, which comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism.

F1. A method for preparing a microorganism that produces adipic acid, which comprises: (a) introducing one or more genetic modifications to a host organism that add or increase one or more activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, monooxygenase activity, and monooxygenase reductase activity, thereby producing engineered microorganisms, and (b) selecting for engineered microorganisms that produce adipic acid.

F2. The method of embodiment F1, which comprises selecting for engineered microorganisms having one or more detectable and/or increased activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, monooxygenase activity, and monooxygenase reductase activity, relative to the host microorganism.

F3. The method of embodiment F1 or F2, which comprises introducing a genetic modification that reduces 6-hydroxyhexanoic acid conversion, thereby producing engineered microorganisms, and selecting for engineered microorganisms having reduced 6-hydroxyhexanoic acid conversion relative to the host microorganism.

F4. The method of any one of embodiments F1-F3, which comprises introducing a genetic modification that reduces beta-oxidation activity, thereby producing engineered microorganisms, and selecting for engineered microorganisms having reduced beta-oxidation activity relative to the host microorganism.

F5. The method of any one of embodiments F1-F4, which comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism.

G1. A method for preparing a microorganism that produces 6-hydroxyhexanoic acid, which comprises: (a) introducing one or more genetic modifications to a host organism that add or increase one or more activities selected from the group consisting of 6-oxohexanoic acid dehydrogenase activity, glucose-6-phosphate dehydrogenase, hexanoate synthase activity, lipase activity, fatty acid synthase activity, acetyl CoA carboxylase activity, monooxygenase activity, and monooxygenase reductase activity, thereby producing engineered microorganisms, (b) introducing a genetic modification to the host organism that reduces 6-hydroxyhexanoic acid conversion, and (c) selecting for engineered microorganisms that produce 6-hydroxyhexanoic acid.

G2. The method of embodiment G1, which comprises selecting for engineered microorganisms having reduced 6-hydroxyhexanoic acid conversion relative to the host microorganism.

G3. The method of embodiment G1 or G2, which comprises selecting for engineered microorganisms having one or more detectable and/or increased activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, monooxygenase activity, and monooxygenase reductase activity, relative to the host microorganism.

G4. The method of any one of embodiments G1-G3, which comprises introducing a genetic modification that reduces beta-oxidation activity, thereby producing engineered microorganisms, and selecting for engineered microorganisms having reduced beta-oxidation activity relative to the host microorganism.

G5. The method of any one of embodiments G1-G4, which comprises introducing a genetic modification that results in substantial hexanoate usage by the monooxygenase activity, thereby producing engineered microorganisms, and selecting for engineered microorganisms in which substantial hexanoate usage is by the monooxygenase activity relative to the host microorganism.

H1. A method, comprising:
contacting an engineered microorganism with an feedstock comprising one or more polysaccharides, wherein the engineered microorganism comprises:
a. a genetic alteration that blocks beta oxidation activity, and
b. a genetic alteration that adds or increases a monooxygenase activity or a genetic alteration that adds or increases hexanoate synthetase activity; and
culturing the engineered microorganism under conditions in which adipic acid is produced.

H1.1. The method of embodiment H1, wherein the engineered microorganism comprises a genetic alteration that adds or increases hexanoate synthetase activity.

H1.2. The method of embodiment H1.1, wherein the engineered microorganism comprises a heterologous polynucleotide encoding a polypeptide having hexanoate synthase subunit A activity.

H1.3. The method of embodiment H1.1, wherein the engineered microorganism comprises a heterologous polynucleotide encoding a polypeptide having hexanoate synthase subunit B activity.

H1.4. The method of embodiment H1.2 or H1.3, wherein the heterologous polynucleotide independently is selected from a bacterium.

H1.5. The method of embodiment H1.4, wherein the bacterium is a *Bacillus* bacterium.

H1.6. The method of embodiment H1.5, wherein the *Bacillus* bacterium is *B. megaterium*.

H2. The method of any one of embodiment H1 or H1.6, wherein the microorganism is a *Candida* yeast.

H3. The method of embodiment H2, wherein the microorganism is a *C. tropicalis* strain.

H4. The method of any one of embodiments H1 to H3, wherein the genetic alteration that increases monooxygenase activity comprises a genetic alteration that increases cytochrome P450 reductase activity.

H5. The method of embodiment H4, wherein the genetic alteration increases the number of copies of a polynucleotide that encodes a polypeptide having the cytochrome P450 reductase activity.

H6. The method of embodiment H4, wherein the genetic alteration places a promoter in functional connection with a polynucleotide that encodes a polypeptide having the cytochrome P450 reductase activity.

H7. The method of any one of embodiments H1 to H6, wherein the monooxygenase activity is a CYP52A15 activity, CYP52A16 activity, or a CYP52A15 activity and CYP52A16 activity.

H8. The method of any one of embodiments H1 to H7, wherein the genetic alteration increases the number of copies of a polynucleotide that encodes a polypeptide having the monooxygenase activity.

H9. The method of any one of embodiments H1 to H7, wherein the genetic alteration places a promoter in functional connection with a polynucleotide that encodes a polypeptide having the monooxygenase activity.

H10. The method of any one of embodiments H1 to H7, wherein the genetic alteration that blocks beta oxidation activity disrupts acyl-CoA oxidase activity.

H11. The method of embodiment H10, wherein the genetic alteration disrupts POX4 and POX5 activity.

H12. The method of embodiment H10 or H11, wherein the genetic alteration disrupts a polynucleotide that encodes a polypeptide having the acyl-CoA oxidase activity.

H13. The method of embodiment H10 or H11, wherein the genetic alteration disrupts a promoter in functional connection with a polynucleotide that encodes a polypeptide having the acyl-CoA oxidase activity.

H14. The method of any one of embodiments H1 to H13, wherein the feedstock comprises a 6-carbon sugar.

H15. The method of any one of embodiments H1 to H13, wherein the feedstock comprises a 5-carbon sugar.

H16. The method of any one of embodiments H1 to H15, wherein the adipic acid is produced at a level of about 80% or more of theoretical yield.

H17. The method of any one of embodiments H1 to H16, comprising detecting the amount of adipic acid produced.

H18. The method of any one of embodiments H1 to H17, comprising isolating the adipic acid produced.

H19. The method of any one of embodiments H1 to H18, wherein the culture conditions comprise fermenting the engineered microorganism.

I1. A method, comprising:
contacting an engineered microorganism with a feedstock comprising one or more paraffins, wherein the engineered microorganism comprises a genetic alteration that partially blocks beta oxidation activity; and
culturing the engineered microorganism under conditions in which adipic acid is produced.

I1.1. The method of embodiment I1, wherein the microorganism comprises a genetic alteration that increases a monooxygenase activity.

I2. The method of embodiment I1 or I1.1, wherein the microorganism is a *Candida* yeast.

I3. The method of embodiment I2, wherein the microorganism is a *C. tropicalis* strain.

I4. The method of any one of embodiments I1 to I3, wherein the genetic alteration that increases monooxygenase activity comprises a genetic alteration that increases cytochrome P450 reductase activity.

I5. The method of embodiment I4, wherein the genetic alteration increases the number of copies of a polynucleotide that encodes a polypeptide having the cytochrome P450 reductase activity.

I6. The method of embodiment I4, wherein the genetic alteration places a promoter in functional connection with a polynucleotide that encodes a polypeptide having the cytochrome P450 reductase activity.

I7. The method of any one of embodiments I1 to I6, wherein the monooxygenase activity is a CYP52A15 activity, CYP52A16 activity, or a CYP52A15 activity and CYP52A16 activity.

I8. The method of any one of embodiments I1 to I7, wherein the genetic alteration increases the number of copies of a polynucleotide that encodes a polypeptide having the monooxygenase activity.

I9. The method of any one of embodiments I1 to I7, wherein the genetic alteration places a promoter in functional connection with a polynucleotide that encodes a polypeptide having the monooxygenase activity.

I10. The method of any one of embodiments I1 to I7, wherein the genetic alteration that blocks beta oxidation activity disrupts acyl-CoA oxidase activity.

I11. The method of embodiment I10, wherein the genetic alteration disrupts POX4 or POX5 activity.

I12. The method of embodiment I10 or I11, wherein the genetic alteration disrupts a polynucleotide that encodes a polypeptide having the acyl-CoA oxidase activity.

I13. The method of embodiment I10 or I11, wherein the genetic alteration disrupts a promoter in functional connection with a polynucleotide that encodes a polypeptide having the acyl-CoA oxidase activity.

I14. The method of any one of embodiments I1 to I13, wherein the adipic acid is produced at a level of about 80% or more of theoretical yield.

I15. The method of any one of embodiments I1 to I14, comprising detecting the amount of adipic acid produced.

I16. The method of any one of embodiments I1 to I15, comprising isolating the adipic acid produced.

I17. The method of any one of embodiments I1 to I16, wherein the culture conditions comprise fermenting the engineered microorganism.

I18. The method of any one of embodiments I1 to I17, wherein the paraffin is a saturated paraffin, unsaturated paraffin, substituted paraffin, branched paraffin, linear paraffin or combination thereof.

I19. The method of any one of embodiments I1 to I18, wherein the paraffin includes about 1 to about 60 carbon atoms.

I20. The method of any one of embodiments I1 to I19, wherein the paraffin is in a mixture of paraffins.

I21. The method of embodiment I20, wherein the paraffins in the mixture of paraffins have a mean number of carbon atoms of about 8 to about 18 carbon atoms.

I22. The method of embodiment I21, wherein the mean number of carbon atoms is about 10 to about 16 carbon atoms.

I23. The method of embodiment I22, wherein the mean number of carbon atoms is about 12 atoms.

I24. The method of any one of embodiments I1 to I23, wherein the paraffin is in a wax.

I25. The method of any one of embodiments I1 to I23, wherein the paraffin is in an oil.

I26. The method of any one of embodiments I1 to I25, wherein the paraffin is from a petroleum product.

I27. The method of embodiment I26, wherein the petroleum product is a petroleum distillate.

I28. The method of any one of embodiments I1 to I27, wherein the paraffin is from a plant or plant product.

J1. An isolated polynucleotide selected from the group consisting of:
a polynucleotide having a nucleotide sequence 96% or more identical to the nucleotide sequence of SEQ ID NO: 1;
a polynucleotide having a nucleotide sequence that encodes a polypeptide of SEQ ID NO: 8; and
a polynucleotide having a portion of a nucleotide sequence 96% or more identical to the nucleotide sequence of SEQ ID NO: 1 and encodes a polypeptide having fatty alcohol oxidase activity.

J2. An isolated polynucleotide selected from the group consisting of:
a polynucleotide having a nucleotide sequence 98% or more identical to the nucleotide sequence of SEQ ID NO: 2;
a polynucleotide having a nucleotide sequence that encodes a polypeptide of SEQ ID NO: 10; and
a polynucleotide having a portion of a nucleotide sequence 98% or more identical to the nucleotide sequence of SEQ ID NO: 2 and encodes a polypeptide having fatty alcohol oxidase activity.

J3. An isolated polynucleotide selected from the group consisting of:
a polynucleotide having a nucleotide sequence 95% or more identical to the nucleotide sequence of SEQ ID NO: 3;
a polynucleotide having a nucleotide sequence that encodes a polypeptide of SEQ ID NO: 9; and
a polynucleotide having a portion of a nucleotide sequence 95% or more identical to the nucleotide sequence of SEQ ID NO: 3 and encodes a polypeptide having fatty alcohol oxidase activity.

J3.1. An isolated polynucleotide selected from the group consisting of:
a polynucleotide having a nucleotide sequence 83% or more identical to the nucleotide sequence of SEQ ID NO: 4;
a polynucleotide having a nucleotide sequence that encodes a polypeptide of SEQ ID NO: 11; and
a polynucleotide having a portion of a nucleotide sequence 83% or more identical to the nucleotide sequence of SEQ ID NO: 4 and encodes a polypeptide having fatty alcohol oxidase activity.

J3.2. An isolated polynucleotide selected from the group consisting of:
a polynucleotide having a nucleotide sequence 82% or more identical to the nucleotide sequence of SEQ ID NO: 5;
a polynucleotide having a nucleotide sequence that encodes a polypeptide of SEQ ID NO: 12; and
a polynucleotide having a portion of a nucleotide sequence 82% or more identical to the nucleotide sequence of SEQ ID NO: 5 and encodes a polypeptide having fatty alcohol oxidase activity.

J4. An expression vector comprising a polynucleotide of any one of embodiments J1 to J3.2.

J5. An integration vector comprising a polynucleotide of any one of embodiments J1 to J3.2.

J6. A microorganism comprising an expression vector of embodiment J4 or an integration vector of embodiment J5.

J7. A culture comprising a microorganism of embodiment J6.

J8. A fermentation device comprising a microorganism of embodiment J7.

J10. A polypeptide encoded by a polynucleotide of any one of embodiments J1 to J3 or produced by an expression vector of embodiment J4 or microorganism of embodiment J6.

J11. An antibody that specifically binds to a polypeptide of embodiment J10.

K1. An engineered microorganism capable of producing adipic acid, which microorganism comprises genetic alterations resulting in commitment of molecular pathways in directions for production of adipic acid, which pathways and directions include: (i) fatty acid synthesis pathway in the direction of acetyl CoA to long-chain fatty acids, (ii) omega oxidation pathway in the direction of long-chain fatty acids to diacids and (iii) beta oxidation pathway in the direction of diacids to adipic acid.

K2. The engineered microorganism of embodiment K1, which comprises an increased activity, relative to the microorganism not containing the genetic alterations, independently in each pathway.

K3. The engineered microorganism of embodiment K2, comprising an increased acetyl CoA carboxylase activity in the fatty acid synthesis pathway.

K4. The engineered microorganism of embodiment K2 or K3, comprising an increased fatty acid synthase activity in the fatty acid synthesis pathway.

K5. The engineered microorganism of any one of embodiments K2 to K4, comprising an increased monooxygenase activity.

K6. The engineered microorganism of any one of embodiments K2 to K5, comprising an increased monooxygenase reductase activity.

K7. The engineered microorganism of any one of embodiments K2 to K6, comprising an increased acyl-CoA oxidase activity.

K8. An engineered microorganism capable of producing adipic acid, which microorganism comprises genetic alterations resulting in increased activities, relative to the microorganism not containing the genetic alterations, selected from the group consisting of acetyl CoA carboxylase activity, fatty acid synthase activity, monooxygenase activity, monooxygenase reductase activity and acyl-CoA oxidase activity.

K9. The engineered microorganism of any one of embodiments K2 to K8, wherein each of the increased activities independently is provided by an enzyme encoded by a gene endogenous to the microorganism.

K10. The engineered microorganism of embodiment K9, wherein each of the increased activities independently is provided by an enzyme encoded by a gene exogenous to the microorganism.

K11. The engineered microorganism of any one of embodiments K2 to K10, wherein each of the increased activities independently is provided by an increased amount of an enzyme from a yeast.

K12. The engineered microorganism of embodiment K11, wherein the yeast is a *Candida* yeast.

K13. The engineered microorganism of embodiment K12, wherein the yeast is a *Candida tropicalis* yeast.

K14. The engineered microorganism of any one of embodiments K2 to K13, wherein each one of the increased activities independently results from increasing the copy number of a gene that encodes an enzyme that provides the activity.

K15. The engineered microorganism of any one of embodiments K1 to K14, wherein each one of the increased activities independently results from inserting a promoter in functional proximity to a gene that encodes an enzyme that provides the activity.

K16. The engineered microorganism of embodiment K14 or K15, wherein the gene is in plasmid nucleic acid.

K17. The engineered microorganism of embodiment K14 or K15, wherein the gene is in genomic nucleic acid of the microorganism.

K18. The engineered microorganism of any one of embodiments K1 to K17, wherein the acetyl CoA carboxylase activity is provided by an increased amount of an enzyme comprising (i) the amino acid sequence encoded by SEQ ID NO: 30, (ii) an amino acid sequence 90% or more identical to (i), or (iii) an amino acid sequence that includes 1 to 10 amino acid substitutions, insertions or deletions with respect to (i).

K19. The engineered microorganism of any one of embodiments K1 to K18, wherein the fatty acid synthase activity is provided by an increased amount of a FAS1-encoded enzyme, a FAS2-encoded enzyme, or FAS1-encoded enzyme and FAS2-encoded enzyme.

K20. The engineered microorganism of embodiment K19, wherein the FAS1-encoded enzyme comprises (i) the amino acid sequence encoded by SEQ ID NO: 32, (ii) an amino acid sequence 90% or more identical to (i), or (iii) an amino acid sequence that includes 1 to 10 amino acid substitutions, insertions or deletions with respect to (i).

K21. The engineered microorganism of embodiment K19, wherein the FAS2-encoded enzyme comprises (i) the amino acid sequence encoded by SEQ ID NO: 31, (ii) an amino acid sequence 90% or more identical to (i), or (iii) an amino acid sequence that includes 1 to 10 amino acid substitutions, insertions or deletions with respect to (i).

K22. The engineered microorganism of any one of embodiments K1 to K21, wherein the monooxygenase activity is provided by an increased amount of a cytochrome P450 enzyme.

K23. The engineered microorganism of embodiment K22, wherein the monooxygenase activity is provided by an exogenous cytochrome P450 enzyme.

K24. The engineered microorganism of embodiment K23, wherein the exogenous cytochrome P450 enzyme is from *Bacillus megaterium*.

K25. The engineered microorganism of embodiment K24, wherein the exogenous cytochrome P450 enzyme comprises (i) the amino acid sequence of SEQ ID NO: 41, (ii) an amino acid sequence 90% or more identical to (i), or (iii) an amino acid sequence that includes 1 to 10 amino acid substitutions, insertions or deletions with respect to (i).

K26. The engineered microorganism of embodiment K22, wherein two or more endogenous cytochrome P450 enzymes are expressed in increased amounts.

K27. The engineered microorganism of embodiment K22, wherein all endogenous cytochrome P450 enzymes are expressed in increased amounts.

K28. The engineered microorganism of embodiment K26 or K27, wherein the endogenous cytochrome P450 enzymes comprise (i) an amino acid sequence encoded by a polynucleotide selected from the group consisting of SEQ ID NO: 13, 14, 15, 16, 17, 18, 19, 20, 21, and 22, (ii) an amino acid sequence 90% or more identical to (i), or (iii) an amino acid sequence that includes 1 to 10 amino acid substitutions, insertions or deletions with respect to (i).

K29. The engineered microorganism of any one of embodiments K1 to K21, wherein the monooxygenase reductase activity is provided by an increased amount of an enzyme comprising (i) the amino acid sequence encoded by any one of SEQ ID NOS: 23 to 26, (ii) an amino acid sequence 90% or more identical to (i), or (iii) an amino acid sequence that includes 1 to 10 amino acid substitutions, insertions or deletions with respect to (i).

K30. The engineered microorganism of any one of embodiments K1 to K29, wherein the acyl-CoA oxidase activity is provided by an increased amount of a POX4-encoded enzyme, a POX5-encoded enzyme, or a POX4-encoded enzyme and a POX5-encoded enzyme an enzyme.

K31. The engineered microorganism of embodiment K30, wherein the POX4-encoded enzyme comprises (i) the amino acid sequence of SEQ ID NO: 39, (ii) an amino acid sequence 90% or more identical to (i), or (iii) an amino acid sequence that includes 1 to 10 amino acid substitutions, insertions or deletions with respect to (i).

K32. The engineered microorganism of embodiment K30, wherein the POX5-encoded enzyme comprises (i) the amino acid sequence of SEQ ID NO: 40, (ii) an amino acid sequence 90% or more identical to (i), or (iii) an amino acid sequence that includes 1 to 10 amino acid substitutions, insertions or deletions with respect to (i).

K33. The engineered microorganism of any one of embodiments K1 to K32, wherein the microorganism lacks an enzyme providing an acyl-CoA oxidase activity.

K34. The engineered microorganism of embodiment K33, wherein the enzyme is a POX4-encoded enzyme or a POX5-encoded enzyme.

K35. The engineered microorganism of any one of embodiments K1 to K34, wherein the microorganism is a yeast.

K36. The engineered microorganism of embodiment K35, wherein the yeast is a *Candida* yeast.

K37. The engineered microorganism of embodiment K36, wherein the yeast is a *Candida tropicalis* yeast.

K38. The engineered microorganism of any one of embodiments K1 to K37, wherein the microorganism is haploid.

K39. The engineered microorganism of any one of embodiments K1 to K37, wherein the microorganism is diploid.

L1. A method for producing adipic acid, comprising culturing an engineered microorganism of any one of embodiments K1 to K39 under conditions in which adipic acid is produced.

L2. The method of embodiment L1, wherein the culture conditions comprise fermentation conditions.

L3. The method of embodiment L1 or L2, wherein the culture conditions comprise introduction of biomass.

L4. The method of any one of embodiments L1 to L3, wherein the culture conditions comprise introduction of a feedstock comprising glucose.

L5. The method of any one of embodiments L1 to L4, wherein the culture conditions comprise introduction of a feedstock comprising hexane.

L6. The method of any one of embodiments L1 to L5, wherein the culture conditions comprise introduction of a feedstock comprising an oil.

L7. The method of any one of embodiments L4 to L6, wherein the adipic acid is produced with a yield of greater than about 0.15 grams per gram of the glucose, hexane or oil.

L7.1. The method of any one of embodiments L4 to L7, wherein the adipic acid is produced at between about 25% and about 100% of maximum theoretical yield of any introduced feedstock.

L7.2. The method of any one of embodiments L4 to L7.1, wherein the adipic acid is produced in a concentration range of between about 50 g/L to about 1000 g/L of culture media.

L7.3. The method of any one of embodiments, L4 to L7.2, wherein the adipic acid is produced at a rate of between about 0.5 g/L/hour to about 5 g/L/hour.

L7.4. The method of any one of embodiments, L1 to L7.3, wherein the engineered organism comprises between about a 5-fold to about a 300-fold increase in adipic acid production when compared to wild-type or partially engineered organisms of the same strain, under identical fermentation conditions.

L8. The method of any one of embodiments L1 to L7.4, which comprises purifying the adipic acid from the cultured microorganisms.

L9. The method of embodiment L8, which comprises modifying the adipic acid, thereby producing modified adipic acid.

L10. The method of any one of embodiments L1 to L9, which comprises placing the cultured microorganisms, the adipic acid or the modified adipic acid in a container.

L11. The method of embodiment L10, which comprises shipping the container.

M1. An engineered microorganism capable of producing adipic acid, which microorganism comprises genetic alterations resulting in commitment of molecular pathways in directions for production of adipic acid, which pathways and directions include: (i) hexanoic acid synthesis pathway in the direction of acetyl CoA to hexanoic acid, and (ii) omega oxidation pathway in the direction of hexanoic acid to adipic acid.

M2. The engineered microorganism of embodiment M1, which comprises an increased activity, relative to the microorganism not containing the genetic alterations, independently in each pathway.

M3. The engineered microorganism of embodiment M1 and M2, comprising an increased acetyl CoA carboxylase activity in the hexanoic acid synthesis pathway.

M4. The engineered microorganism of any one of embodiments M1 to M3, comprising increased hexanoate synthase activity in the hexanoic acid synthesis pathway.

M5. The engineered microorganism of any one of embodiments M1 to M4, comprising increased monooxygenase activity in the omega oxidation pathway.

M6. The engineered microorganism of any one of embodiments M1 to M5, comprising increased monooxygenase reductase activity in the omega oxidation pathway.

M7. An engineered microorganism capable of producing adipic acid, which microorganism comprises genetic alterations resulting in increased activities, relative to the microorganism not containing the genetic alterations, selected from the group consisting of acetyl CoA carboxylase activity, hexanoate synthase activity, monooxygenase activity and monooxygenase reductase activity.

M8. The engineered microorganism of any one of embodiments M2 to M7, wherein each of the increased activities independently is provided by an enzyme encoded by a gene endogenous to the microorganism.

M9. The engineered microorganism of embodiment M8, wherein each of the increased activities independently is provided by an enzyme encoded by a gene exogenous to the microorganism.

M10. The engineered microorganism of any one of embodiments M2 to M9, wherein each of the increased activities independently is provided by an increased amount of an enzyme from a yeast.

M11. The engineered microorganism of embodiment M10, wherein the yeast is a *Candida* yeast.

M12. The engineered microorganism of embodiment M11, wherein the yeast is a *Candida tropicalis* yeast.

M13. The engineered microorganism of any one of embodiments M2 to M12, wherein each one of the increased activities independently results from increasing the copy number of a gene that encodes an enzyme that provides the activity.

M14. The engineered microorganism of any one of embodiments M1 to M13, wherein each one of the increased activities independently results from inserting a promoter in functional proximity to a gene that encodes an enzyme that provides the activity.

M15. The engineered microorganism of embodiment M13 or M14, wherein the gene is in plasmid nucleic acid.

M16. The engineered microorganism of embodiment M13 or M14, wherein the gene is in genomic nucleic acid of the microorganism.

M17. The engineered microorganism of any one of embodiments M1 to M16, wherein the acetyl CoA carboxylase activity is provided by an increased amount of an enzyme comprising (i) the amino acid sequence encoded by SEQ ID NO: 30, (ii) an amino acid sequence 90% or more identical to (i), or (iii) an amino acid sequence that includes 1 to 10 amino acid substitutions, insertions or deletions with respect to (i).

M18. The engineered microorganism of any one of embodiments M1 to M17, wherein the hexanoate synthase activity is provided by an increased amount of a HEXA-encoded enzyme, a HEXB-encoded enzyme, or HEXA-encoded enzyme and HEXB-encoded enzyme.

M19. The engineered microorganism of embodiment M18, wherein the HEXA-encoded enzyme comprises (i) the amino acid sequence encoded by SEQ ID NO: 35, (ii) an amino acid sequence 90% or more identical to (i), or (iii) an amino acid sequence that includes 1 to 10 amino acid substitutions, insertions or deletions with respect to (i).

M20. The engineered microorganism of embodiment M18, wherein the HEXB-encoded enzyme comprises (i) the amino acid sequence encoded by SEQ ID NO: 36, (ii) an amino acid sequence 90% or more identical to (i), or (iii) an amino acid sequence that includes 1 to 10 amino acid substitutions, insertions or deletions with respect to (i).

M21. The engineered microorganism of any one of embodiments M1 to M20, wherein the monooxygenase activity is provided by an increased amount of a cytochrome P450 enzyme.

M22. The engineered microorganism of embodiment M21, wherein the monooxygenase activity is provided by an exogenous cytochrome P450 enzyme.

M23. The engineered microorganism of embodiment M22, wherein the exogenous cytochrome P450 enzyme is from *Bacillus megaterium*.

M24. The engineered microorganism of embodiment M23, wherein the exogenous cytochrome P450 enzyme comprises (i) the amino acid sequence of SEQ ID NO: 41, (ii) an amino acid sequence 90% or more identical to (i), or (iii) an amino acid sequence that includes 1 to 10 amino acid substitutions, insertions or deletions with respect to (i).

M25. The engineered microorganism of embodiment M21, wherein two or more endogenous cytochrome P450 enzymes are expressed in increased amounts.

M26. The engineered microorganism of embodiment M21, wherein all endogenous cytochrome P450 enzymes are expressed in increased amounts.

M27. The engineered microorganism of embodiment M25 or M26, wherein the endogenous cytochrome P450 enzymes comprise (i) an amino acid sequence selected from the group consisting of amino acid sequences encoded by any one of SEQ ID NO: 13, 14, 15, 16, 17, 18, 19, 20, 21, and 22, (ii) an amino acid sequence 90% or more identical to (i), or (iii) an amino acid sequence that includes 1 to 10 amino acid substitutions, insertions or deletions with respect to (i).

M28. The engineered microorganism of any one of embodiments M1 to M27, wherein the monooxygenase reductase activity is provided by an increased amount of an enzyme comprising (i) an amino acid sequence encoded by any one of SEQ ID NO: 23 to 26, (ii) an amino acid sequence 90% or more identical to (i), or (iii) an amino acid sequence that includes 1 to 10 amino acid substitutions, insertions or deletions with respect to (i).

M29. The engineered microorganism of any one of embodiments M1 to M28, wherein the monooxygenase reductase activity is provided by an increased amount of a cytochrome P450:NADPH P450 reductase-encoded enzyme, a CPR-encoded enzyme, a CPRA-encoded enzyme, a CPRB-encoded enzyme, or a cytochrome P450:NADPH P450 reductase-encoded enzyme, a CPR-encoded enzyme, a CPRA-encoded enzyme, and/or a CPRB-encoded enzyme.

M30. The engineered microorganism of embodiment M29, wherein the cytochrome P450:NADPH P450 reductase-encoded enzyme comprises (i) the amino acid sequence of SEQ ID NO: 41 (ii) an amino acid sequence 90% or more identical to (i), or (iii) an amino acid sequence that includes 1 to 10 amino acid substitutions, insertions or deletions with respect to (i).

M31. The engineered microorganism of embodiment K30, wherein the CPR-, CPRA and/or CPRB encoded enzymes comprise (i) an amino acid sequence encoded by any one of SEQ ID NOS: 24 to 26, (ii) an amino acid sequence 90% or more identical to (i), or (iii) an amino acid sequence that includes 1 to 10 amino acid substitutions, insertions or deletions with respect to (i).

M32. The engineered microorganism of any one of embodiments M1 to M31, wherein the microorganism is a yeast.

M33. The engineered microorganism of embodiment M32, wherein the yeast is a *Candida* yeast.

M34. The engineered microorganism of embodiment M33, wherein the yeast is a *Candida tropicalis* yeast.

M35. The engineered microorganism of any one of embodiments M1 to M34, wherein the mircroorganism is haploid.

M36. The engineered microorganism of any one of embodiments M1 to M34, wherein the mircroorganism is diploid.

N1. A method for producing adipic acid, comprising culturing an engineered microorganism of any one of embodiments M1 to M36 under conditions in which adipic acid is produced.

N2. The method of embodiment N1, wherein the culture conditions comprise fermentation conditions.

N3. The method of embodiment N1 or N2, wherein the culture conditions comprise introduction of biomass.

N4. The method of any one of embodiments N1 to N3, wherein the culture conditions comprise introduction of a feedstock comprising glucose.

N5. The method of any one of embodiments N1 to N4, wherein the culture conditions comprise introduction of a feedstock comprising hexane.

N6. The method of any one of embodiments N1 to N5, wherein the culture conditions comprise introduction of a feedstock comprising an oil.

N7. The method of any one of embodiments N4 to N6, wherein the adipic acid is produced with a yield of greater than about 0.15 grams per gram of the glucose, hexane or oil.

N7.1. The method of any one of embodiments N4 to N7, wherein the adipic acid is produced at between about 25% and about 100% of maximum theoretical yield of any introduced feedstock.

N7.2. The method of any one of embodiments N4 to N7.1, wherein the adipic acid is produced in a concentration range of between about 50 g/L to about 1000 g/L of culture media.

N7.3. The method of any one of embodiments, N4 to N7.2, wherein the adipic acid is produced at a rate of between about 0.5 g/L/hour to about 5 g/L/hour.

N7.4. The method of any one of embodiments, N1 to N7.3, wherein the engineered organism comprises between about a 5-fold to about a 300-fold increase in adipic acid production when compared to wild-type or partially engineered organisms of the same strain, under identical fermentation conditions.

N8. The method of any one of embodiments N1 to N7.4, which comprises purifying the adipic acid from the cultured microorganisms.

N9. The method of embodiment N8, which comprises modifying the adipic acid, thereby producing modified adipic acid.

N10. The method of any one of embodiments N1 to N9, which comprises placing the cultured microorganisms, the adipic acid or the modified adipic acid in a container.

N11. The method of embodiment N10, which comprises shipping the container.

O1. An engineered microorganism capable of producing adipic acid, which microorganism comprises genetic alterations resulting in commitment of molecular pathways in directions for production of adipic acid, which pathways and directions include: (i) gluconeogenesis pathway in the direction of triacyl glycerides to 6-phosphoglucono-lactone and nicotinamide adenine dinucleotide phosphate (NADPH), (ii) omega oxidation pathway in the direction of fatty acids to diacids, (iii) beta oxidation pathway in the direction of diacids to adipic acid and (iv) fatty acid synthesis pathway in the direction of acetyl CoA to fatty acids.

O2. The engineered microorganism of embodiment O1, which comprises an increased activity, relative to the microorganism not containing the genetic alterations, independently in each pathway.

O3. The engineered microorganism of embodiment O2, comprising an increased lipase activity in the gluconeogenesis pathway.

O4. The engineered microorganism of O1 or O2, comprising an increased glucose-6-phosphate dehydrogenase activity in the gluconeogenesis pathway.

O5. The engineered microorganism of any one of embodiments O2 to O4, comprising an increased fatty acid synthase activity in the fatty acid synthesis pathway.

O6. The engineered microorganism of any one of embodiments O2 to O5, comprising an increased monooxygenase activity in the omega oxidation pathway.

O7. The engineered microorganism of any one of embodiments O2 to O6, comprising an increased monooxygenase reductase activity in the omega oxidation pathway.

O8. The engineered microorganism of any one of embodiments O2 to O7, comprising an increased acyl-CoA oxidase activity in the beta oxidation pathway.

O9. An engineered microorganism capable of producing adipic acid, which microorganism comprises genetic alterations resulting in increased activities, relative to the microorganism not containing the genetic alterations, selected from the group consisting of lipase activity, glucose-6-phosphate dehydrogenase activity, fatty acid synthase activity, monooxygenase activity, monooxygenase reductase activity, acyl-CoA hydrolase, acyl-CoA thioesterase and acyl-CoA oxidase activity.

O10. The engineered microorganism of any one of embodiments O2 to O9, wherein each of the increased activities independently is provided by an enzyme encoded by a gene endogenous to the microorganism.

O11. The engineered microorganism of embodiment O10, wherein each of the increased activities independently is provided by an enzyme encoded by a gene exogenous to the microorganism.

O12. The engineered microorganism of any one of embodiments O2 to O10, wherein each of the increased activities independently is provided by an increased amount of an enzyme from a yeast.

O13. The engineered microorganism of embodiment O12, wherein the yeast is a *Candida* yeast.

O14. The engineered microorganism of embodiment O13, wherein the yeast is a *Candida tropicalis* yeast.

O15. The engineered microorganism of any one of embodiments O2 to O14, wherein each one of the increased activities independently results from increasing the copy number of a gene that encodes an enzyme that provides the activity.

O16. The engineered microorganism of any one of embodiments O1 to O15, wherein each one of the increased activities independently results from inserting a promoter in functional proximity to a gene that encodes an enzyme that provides the activity.

O17. The engineered microorganism of embodiment O15 or O16, wherein the gene is in plasmid nucleic acid.

O18. The engineered microorganism of embodiment O15 or O16, wherein the gene is in genomic nucleic acid of the microorganism.

O19. The engineered microorganism of any one of embodiments O1 to O18, wherein the lipase activity is provided by an increased amount of an enzyme comprising (i) any one of the amino acid sequences of SEQ ID NO: 28 and 29, (ii) an amino acid sequence 90% or more identical to (i), or (iii) an amino acid sequence that includes 1 to 10 amino acid substitutions, insertions or deletions with respect to (i).

O20. The engineered microorganism of any one of embodiments O1 to O19, wherein the fatty acid synthase activity is provided by an increased amount of a FAS1-encoded enzyme, a FAS2-encoded enzyme, or FAS1-encoded enzyme and FAS2-encoded enzyme.

O21. The engineered microorganism of embodiment O20, wherein the FAS1-encoded enzyme comprises (i) the amino acid sequence of SEQ ID NO: 32, (ii) an amino acid sequence 90% or more identical to (i), or (iii) an amino acid sequence that includes 1 to 10 amino acid substitutions, insertions or deletions with respect to (i).

O22. The engineered microorganism of embodiment O20, wherein the FAS2-encoded enzyme comprises (i) the amino acid sequence of SEQ ID NO: 31, (ii) an amino acid sequence 90% or more identical to (i), or (iii) an amino acid sequence that includes 1 to 10 amino acid substitutions, insertions or deletions with respect to (i).

O23. The engineered microorganism of any one of embodiments O1 to O22, wherein the glucose-6-phosphate dehydrogenase activity is provided by an increased amount of an enzyme comprising (i) the amino acid sequence of SEQ ID NO: 34, (ii) an amino acid sequence 90% or more identical to (i), or (iii) an amino acid sequence that includes 1 to 10 amino acid substitutions, insertions or deletions with respect to (i).

O24. The engineered microorganism of any one of embodiments O1 to O23, wherein the monooxygenase activity is provided by an increased amount of a cytochrome P450 enzyme.

O25. The engineered microorganism of embodiment O24, wherein the monooxygenase activity is provided by an exogenous cytochrome P450 enzyme.

O26. The engineered microorganism of embodiment O25, wherein the exogenous cytochrome P450 enzyme is from *Bacillus megaterium*.

O27. The engineered microorganism of embodiment O26, wherein the exogenous cytochrome P450 enzyme comprises (i) the amino acid sequence of SEQ ID NO: 41, (ii) an amino acid sequence 90% or more identical to (i), or (iii) an amino acid sequence that includes 1 to 10 amino acid substitutions, insertions or deletions with respect to (i).

O28. The engineered microorganism of embodiment O24, wherein two or more endogenous cytochrome P450 enzymes are expressed in increased amounts.

O29. The engineered microorganism of embodiment O24, wherein all endogenous cytochrome P450 enzymes are expressed in increased amounts.

O30. The engineered microorganism of embodiment O28 or O29, wherein the endogenous cytochrome P450 enzymes comprise (i) an amino acid sequence encoded by a polynucleotide selected from the group consisting of SEQ ID NOS: 13, 14, 15, 16, 17, 18, 19, 20, 21, and 22, (ii) an amino acid sequence 90% or more identical to (i), or (iii) an amino acid sequence that includes 1 to 10 amino acid substitutions, insertions or deletions with respect to (i).

O31. The engineered microorganism of any one of embodiments O1 to O30, wherein the monooxygenase reductase activity is provided by an increased amount of an enzyme comprising (i) an amino acid sequence encoded by any one of SEQ ID NOS: 23 to 26, (ii) an amino acid sequence 90% or more identical to (i), or (iii) an amino acid sequence that includes 1 to 10 amino acid substitutions, insertions or deletions with respect to (i).

O32. The engineered microorganism of any one of embodiments O1 to O31, wherein the acyl-CoA oxidase activity is provided by an increased amount of a POX4-encoded enzyme, a POX5-encoded enzyme, or a POX4-encoded enzyme and a POX5-encoded enzyme an enzyme.

O33. The engineered microorganism of embodiment O32, wherein the POX4-encoded enzyme comprises (i) the amino acid sequence of SEQ ID NO: 39, (ii) an amino acid sequence 90% or more identical to (i), or (iii) an amino acid sequence that includes 1 to 10 amino acid substitutions, insertions or deletions with respect to (i).

O34. The engineered microorganism of embodiment O32, wherein the POX5-encoded enzyme comprises (i) the amino acid sequence of SEQ ID NO: 40, (ii) an amino acid sequence 90% or more identical to (i), or (iii) an amino acid sequence that includes 1 to 10 amino acid substitutions, insertions or deletions with respect to (i).

O35. The engineered microorganism of any one of embodiments O1 to O34, wherein the microorganism lacks an enzyme providing an acyl-CoA oxidase activity.

O36. The engineered microorganism of embodiment O35, wherein the enzyme is a POX4-encoded enzyme or a POX5-encoded enzyme.

O37. The engineered microorganism of any one of embodiments O1 to O36, wherein the acyl-CoA hydrolase activity is provided by an increased amount of an enzyme comprising (i) an amino acid sequence encoded by any one of SEQ ID NOS: 43 or 45, (ii) an amino acid sequence 98% or more identical to (i), or (iii) an amino acid sequence that includes 1 to 10 amino acid substitutions, insertions or deletions with respect to (i).

O38. The engineered microorganism of any one of embodiments O1 to O37, wherein the acyl-CoA thioesterase activity is provided by an increased amount of an enzyme comprising (i) an amino acid sequence encoded by SEQ ID NO: 47, or (ii) an amino acid sequence that includes 1 to 10 amino acid substitutions, insertions or deletions with respect to (i).

O39. The engineered microorganism of any one of embodiments O1 to O38, wherein the microorganism is a yeast.

O40. The engineered microorganism of embodiment O39, wherein the yeast is a *Candida* yeast.

O41. The engineered microorganism of embodiment O40, wherein the yeast is a *Candida tropicalis* yeast.

O42. The engineered microorganism of any one of embodiments O1 to O41, wherein the mircroorganism is haploid.

O43. The engineered microorganism of any one of embodiments O1 to O41, wherein the mircroorganism is diploid.

P1. A method for producing adipic acid, comprising culturing an engineered microorganism of any one of embodiments O1 to O41 under conditions in which adipic acid is produced.

P2. The method of embodiment P1, wherein the culture conditions comprise fermentation conditions.

P3. The method of embodiment P1 or P2, wherein the culture conditions comprise introduction of biomass.

P4. The method of any one of embodiments P1 to P3, wherein the culture conditions comprise introduction of a feedstock comprising glucose.

P5. The method of any one of embodiments P1 to P4, wherein the culture conditions comprise introduction of a feedstock comprising hexane.

P6. The method of any one of embodiments P1 to P5, wherein the culture conditions comprise introduction of a feedstock comprising an oil.

P7. The method of any one of embodiments P4 to P6, wherein the adipic acid is produced with a yield of greater than about 0.15 grams per gram of the glucose, hexane or oil.

P7.1. The method of any one of embodiments P4 to P7, wherein the adipic acid is produced at between about 25% and about 100% of maximum theoretical yield of any introduced feedstock.

P7.2. The method of any one of embodiments P4 to P7.1, wherein the adipic acid is produced in a concentration range of between about 50 g/L to about 1000 g/L of culture media.

P7.3. The method of any one of embodiments, P4 to P7.2, wherein the adipic acid is produced at a rate of between about 0.5 g/L/hour to about 5 g/L/hour.

P7.4. The method of any one of embodiments, P1 to P7.3, wherein the engineered organism comprises between about a 5-fold to about a 300-fold increase in adipic acid production when compared to wild-type or partially engineered organisms of the same strain, under identical fermentation conditions.

P8. The method of any one of embodiments P1 to P7.4, which comprises purifying the adipic acid from the cultured microorganisms.

P9. The method of embodiment P8, which comprises modifying the adipic acid, thereby producing modified adipic acid.

P10. The method of any one of embodiments P1 to P9, which comprises placing the cultured microorganisms, the adipic acid or the modified adipic acid in a container.

P11. The method of embodiment P10, which comprises shipping the container.

Q1. A genetically modified microorganism comprising one or more increased activities, with respect to the activity level in an unmodified or parental strain, which increased activities are chosen from: a monooxygenase activity, a monooxygenase reductase activity, an acyl-CoA oxidase activity, an acyl-CoA hydrolase activity, an acyl-CoA thioesterase activity and combinations of the forgoing.

Q1.1. The genetically modified microorganism of embodiment Q1, wherein the monooxygenase activity comprises a cytochrome P450 A19 (e.g., CYP52A19) activity.

Q1.2. The genetically modified microorganism of embodiment Q1, wherein the monooxygenase activity consists of a cytochrome P450 A19 (e.g., CYP52A19) activity.

Q1.3. The genetically modified microorganism of embodiment Q1, wherein the monooxygenase reductase activity comprises one or more activities selected from CPR, CPRA, CPRB, and combinations of the foregoing.

Q1.4. The genetically modified microorganism of embodiment Q1, wherein the acyl-CoA oxidase activity comprises a POX5 activity.

Q1.5. The genetically modified microorganism of embodiment Q1, wherein the acyl-CoA oxidase activity consists of POX5 activity.

Q1.6. The genetically modified microorganism of embodiment Q1, wherein the acyl-CoA hydrolase activity comprises one or more activities selected from ACHA activity, ACHB activity, and ACHA activity and ACHB activity.

Q1.7. The genetically modified microorganism of embodiment Q1, wherein the acyl-CoA thioesterase activity comprises a TESA activity.

Q2. The genetically modified microorganism of embodiment Q1, wherein the one or more increased activities are three or more increased activities.

Q3. The genetically modified microorganism of embodiment Q2, wherein the three or more increased activities are four or more increased activities.

Q4. The genetically modified microorganism of embodiment Q2, wherein the three or more increased activities are five or more increased activities.

Q5. The genetically modified microorganism of embodiment Q2, wherein the three or more increased activities comprise an increased monooxygenase activity, an increased monooxygenase reductase activity, and an increased acyl-CoA hydrolase activity.

Q6. The genetically modified microorganism of embodiment Q2, wherein the three or more increased activities comprise an increased monooxygenase activity, an increased monooxygenase reductase activity, and an increased acyl-CoA thioesterase activity.

Q7. The genetically modified microorganism of embodiment Q3, wherein the four or more increased activities comprise an increased monooxygenase activity, an increased monooxygenase reductase activity, an increased acyl-CoA oxidase activity and an increased acyl-CoA hydrolase activity.

Q8. The genetically modified microorganism of embodiment Q3, wherein the four or more increased activities comprise an increased monooxygenase activity, an increased monooxygenase reductase activity, an increased acyl-CoA hydrolase activity and an increased acyl-CoA thioesterase activity.

Q9. The genetically modified microorganism of embodiment Q4, wherein the five or more increased activities comprise an increased monooxygenase activity, an increased monooxygenase reductase activity, an increased acyl-CoA oxidase activity, and increased acyl-CoA thioesterase activity and an increased acyl-CoA hydrolase activity.

Q10. The genetically modified microorganism of any one of embodiments Q1 to Q9, further comprising one or more reduced activities, with respect to the activity level in an unmodified or parental strain, which reduced activities are chosen from: acyl-CoA synthetase activity, long chain acyl-CoA synthetase activity, acyl-CoA sterol acyl transferase activity, acyltransferase activity, and combinations of the foregoing.

Q10.1. The genetically modified microorganism of embodiment Q10, wherein the acyl-CoA synthetase activity comprises an ACS1 activity.

Q10.2. The genetically modified microorganism of embodiment Q10, wherein the long chain acyl-CoA synthetase activity comprises a FAT1 activity.

Q10.3. The genetically modified microorganism of embodiment Q10, wherein the acyl-CoA sterol acyl transferase activity comprises one or more activities selected from an ARE1 activity, an ARE2 activity, and an ARE1 activity and an ARE2 activity.

Q10.4. The genetically modified microorganism of embodiment Q10, wherein the acyltransferase activity is a diacylglycerol acyltransferase activity.

Q10.5. The genetically modified microorganism of embodiment Q10.4, wherein the diacylglycerol acyltransferase activity comprises one or more activities selected from a DGA1 activity, a LRO1 activity and a DGA1 activity and a LRO1 activity.

Q11. The genetically modified microorganism of any one of embodiments Q10 to Q10.5, wherein the one or more reduced activities is three or more reduced activities.

Q12. The genetically modified microorganism of embodiment Q11, wherein the three or more reduced activities are four or more reduced activities.

Q13. The genetically modified microorganism of embodiment Q12, wherein the three or more reduced activities are five or more reduced activities.

Q14. The genetically modified microorganism of any one of embodiments Q10 to Q13, comprising a reduced ACS1 activity, a reduced FAT1 activity, a reduced ARE1 activity, a reduced ARE2 activity, a reduced DGA1 activity and a reduced LRO1 activity.

R1. A method for preparing a microorganism that produces adipic acid, which comprises: (a) introducing one or more genetic modifications to a host organism that add or increase one or more activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, acyl-CoA hydrolase activity, acyl-CoA thioesterase activity, monooxygenase activity, and monooxygenase reductase activity, thereby producing engineered microorganisms, and (b) selecting for engineered microorganisms that produce adipic acid.

R2. The method of embodiment R1, which comprises selecting for engineered microorganisms having one or more detectable and/or increased activities selected from the group consisting of 6-oxohexanoic acid dehydrogenase activity, omega oxo fatty acid dehydrogenase activity, 6-hydroxyhexanoic acid dehydrogenase activity, omega hydroxyl fatty acid dehydrogenase activity, glucose-6-phosphate dehydrogenase, hexanoate synthase activity, lipase activity, fatty acid synthase activity, acetyl CoA carboxylase activity, acyl-CoA hydrolase activity, acyl-CoA thioesterase activity, monooxygenase activity, and monooxygenase reductase activity, relative to the host microorganism.

R3. The method of embodiment R1 or R2, which comprises introducing a genetic modification that reduces one or more activities selected from acyl-CoA oxidase, acyl-CoA synthetase activity, long chain acyl-CoA synthetase activity, acyl-CoA sterol acyl transferase activity, acyltransferase activity, and 6-hydroxyhexanoic acid conversion activity, thereby producing engineered microorganisms, and selecting for engineered microorganisms having one or more reduced activities selected from acyl-CoA oxidase, acyl-CoA synthetase activity, long chain acyl-CoA synthetase activity, acyl-CoA sterol acyl transferase activity, acyltransferase activity, and 6-hydroxyhexanoic acid conversion activity relative to the host microorganism.

S1. A method for producing adipic acid, comprising:
contacting an engineered microorganism with a feedstock comprising one or more sugars, cellulose, fatty acids, triacylglycerides or combinations of the forgoing, wherein the engineered microorganism comprises:
a. a genetic alteration that partially blocks beta oxidation activity,
b. a genetic alteration that adds or increases a monooxygenase activity,
c. a genetic alteration that adds or increases a monooxygenase reductase activity, and
d. a genetic alteration that adds or increases an acyl-CoA hydrolase and/or an acyl-CoA thioesterase activity,
culturing the engineered microorganism under conditions in which adipic acid is produced.

S2. The method of embodiment S1, wherein the engineered microorganism further comprises one or more genetic alterations that reduce an activity selected from an acyl-CoA oxidase activity, an acyl-CoA synthetase activity, a long chain acyl-CoA synthetase activity, an acyl-CoA sterol acyl transferase activity, and an acyltransferase activity.

S3. The method of embodiment S2, wherein the acyltransferase activity is a diacyl-glycerol acyltransferase activity.

S4. The method of any one of embodiments S1-S3, wherein the engineered microorganism comprises a heterologous polynucleotide encoding a polypeptide having acyl-CoA thioesterase activity.

S5. The method of embodiment S4, wherein the heterologous polynucleotide independently is selected from a bacterium S6. The method of embodiment S5, wherein the bacterium is an *Enteric* bacterium.

S7. The method of embodiment S6, wherein the *Enteric* bacterium is *E. coli*.

S8. The method of any one of embodiments S1 to S7, wherein the microorganism is a *Candida* yeast.

S9. The method of embodiment S8, wherein the *Candida* yeast is *C. tropicalis*

S10. The method of any one of embodiments S1 to S9, wherein the engineered microorganism comprises a heterologous polynucleotide encoding a polypeptide having acyl-CoA thioesterase activity, and further wherein the polynucleotide sequence has been codon optimized for expression in *C. tropicalis*.

S11. The method of any one of embodiments S1 to S10, wherein the genetic alteration that partially blocks beta oxidation activity reduces or eliminates POX4 activity.

S12. The method of any one of embodiments S1 to S11, wherein the genetic alteration that adds or increases monooxygenase activity, increases CYP52A19 activity.

S13. The method of any one of embodiments S1 to S12, wherein the genetic alteration that adds or increases monooxygenase reductase activity increases a CPR activity, a CPRA activity, a CPRB activity, or combinations thereof.

S14. The method of any one of embodiments S1 to S13, wherein the genetic alteration that adds or increases acyl-CoA hydrolase activity increases an ACHA activity, an ACHB activity or an ACHA activity and an ACHB activity.

S15. The method of any one of embodiments S1 to S14, wherein the genetic alteration that adds or increases acyl-CoA thioesterase activity adds an *E. coli* derived TESA activity.

S16. The method of any one of embodiments S2 to S15, wherein the genetic alteration that reduces an acyl-CoA synthetase activity, reduces or eliminates an ACS1 activity.

S17. The method of any one of embodiments S2 to S16, wherein the genetic alteration that reduces a long chain acyl-CoA synthetase activity, reduces or eliminates an FAT1 activity.

S18. The method of any one of embodiments S2 to S17, wherein the genetic alteration that reduces an acyl-CoA sterol acyl transferase activity, reduces or eliminates an ARE1 activity, an ARE2 activity, or an ARE1 activity and an ARE2 activity.

S19. The method of any one of embodiments S2 to S18, wherein the genetic alteration that reduces an acyltransferase activity, reduces or eliminates a DGA1 activity, a LRO1 activity or a DGA1 activity and a LRO1 activity.

S20. The method of any one of embodiments S2 to S19, wherein the adipic acid is produced at a level of about 80% or more of the theoretical yield S21. The method of any one of embodiments S2 to S19, the maximum theoretical yield ($Y_{max}$) is about 0.6 grams of adipic acid produced per gram of coconut oil added, the percentage of $Y_{max}$ for the engineered microorganism under conditions in which adipic acid is produced is calculated as (% $Y_{max}$)=$Y_{p/s}/Y_{max}$*100, where ($Y_{p/s}$)=[adipic acid (g/L]*final volume of culture in flask (L)]/[feedstock added to flask (g)].

S22. The method of any one of embodiments S2 to S24, wherein the engineered microorganism produces adipic acid at about 10% to about 100% of maximum theoretical yield.

T1. An isolated polynucleotide selected from the group consisting of:
a polynucleotide having a nucleotide sequence 96% or more identical to the nucleotide sequence of SEQ ID NO: 42 or 44:
a polynucleotide having a nucleotide sequence that encodes a polypeptide of SEQ ID NO: 43 or 45; and
a polynucleotide having a portion of a nucleotide sequences 96% or more identical to the nucleotide sequence of SEQ ID NO: 42 or 44 and encodes a polypeptide having acyl-coA hydrolase activity.

T2. An isolated polynucleotide selected from the group consisting of:
a polynucleotide having a nucleotide sequences identical to the nucleotide sequence of SEQ ID NO: 46:
a polynucleotide having a nucleotide sequence that encodes a polypeptide of SEQ ID NO: 47; and
a polynucleotide having a portion of a nucleotide sequence identical to the nucleotide sequences of SEQ ID NO: 46 and encodes a polypeptide having acyl-CoA thioesterase activity.

T3. An expression vector comprising a polynucleotide of embodiments T1 or T2.

T4. An integration vector comprising a polynucleotide of embodiments T1 or T2.

T5. A microorganism comprising an expression vector of embodiment T3, or an integration vector of embodiment T4.

T6. A culture comprising a microorganism of embodiment T5.

T7. A fermentation device comprising a microorganism of embodiment T6.

T8. A polypeptide encoded by a polynucleotide of embodiment T1 or T2 or produced by an expression vector of embodiment T3 or microorganism of embodiment T5.

T9. An antibody that specifically binds to a polypeptide of embodiment T8.

U1. An engineered microorganism capable of producing adipic acid, which microorganism comprises genetic alterations resulting in one or more increased activities and further resulting in commitment of molecular pathways in directions for production of adipic acid, which pathways and directions include: (i) fatty acid synthesis pathway in the direction of acetyl CoA to long-chain fatty acids and away from synthesis or generation of biomass and/or carbon storage molecules, (ii) omega oxidation pathway in the direction of long-chain fatty acids to diacids and (iii) beta oxidation pathway in the direction of diacids to adipic acid.

U2. The engineered microorganism of embodiment U1, wherein carbon storage molecules comprise storage starches, storage lipids and combinations thereof.

U3. The engineered microorganism of embodiment U1 or U2, which comprises an increased activity, relative to the microorganism not containing the genetic alterations, independently in each pathway.

U4. The engineered microorganism of any one of embodiments U1 to U3, comprising an increased monooxygenase activity.

U5. The engineered microorganism of any one of embodiments U1 to U4, comprising an increased monooxygenase reductase activity.

U6. The engineered microorganism of any one of embodiments U1 to U5, comprising an increased acyl-CoA oxidase activity.

U7. The engineered microorganism of any one of embodiments U1 to U6, comprising an increased acetyl CoA carboxylase activity in the fatty acid synthesis pathway.

U8. The engineered microorganism of any one of embodiments U1 to U7, comprising an increased fatty acid synthase activity in the fatty acid synthesis pathway.

U9. The engineered microorganism of any one of embodiments U1 to U8, comprising an increased acyl-CoA hydrolase activity in the fatty acid synthesis pathway.

U10. The engineered microorganism of any one of embodiments U1 to U9, wherein each of the increased activities independently is provided by an enzyme encoded by a gene endogenous to the microorganism.

U11. The engineered microorganism of any one of embodiments U1 to U10, wherein each of the increased activities independently is provided by an increased amount of an enzyme from a yeast.

U12. The engineered microorganism of embodiment U11, wherein the yeast is a *Candida* yeast.

U13. The engineered microorganism of embodiment U12, wherein the yeast is a *Candida tropicalis* yeast.

U14. The engineered microorganism of any one of embodiments U1 to U13, comprising an added acyl-CoA thioesterase activity in the fatty acid synthesis pathway.

U15. The engineered microorganism of embodiment U14, wherein the added activity independently is provided by an enzyme encoded by a gene exogenous to the microorganism.

U16. The engineered microorganism of any one of embodiments U1 to U15, further comprising one or more reduced activities selected from an acyl-CoA oxidase activity, an acyl-CoA synthetase activity, a long chain acyl-CoA synthetase activity, an acyl-CoA sterol acyl transferase activity, and an acyltransferase activity.

U17. The method of embodiment U16, wherein the acyltransferase activity is a diacyl-glycerol acyltransferase activity.

V1. A *Candida* yeast comprising:
(i) a genetic alteration that partially blocks beta oxidation activity;
(ii) a genetic alteration that reduces or eliminates long chain acyl-CoA synthetase activity; and
(iii) a genetic alteration that reduces or eliminates acyl-CoA synthetase activity.

V2. The *Candida* yeast of embodiment V1, wherein the genetic alteration of (ii) eliminates the long chain acyl-CoA synthetase activity.

V3. The *Candida* yeast of embodiment V2, wherein the genetic alteration of (ii) comprises disrupting a polynucleotide that encodes a FAT1 polypeptide.

V4. The *Candida* yeast of embodiment V3, wherein the FAT1 polypeptide comprises the amino acid sequence of SEQ ID NO: 51.

V5. The *Candida* yeast of embodiment V1, wherein the genetic alteration of (iii) eliminates the acyl-CoA synthetase activity.

V6. The *Candida* yeast of embodiment V5, wherein the genetic alteration of (iii) comprises disrupting a polynucleotide that encodes a ACS1 polypeptide.

V7. The *Candida* yeast of embodiment V6, wherein the ACS1 polypeptide comprises the amino acid sequence of SEQ ID NO: 49.

V8. The *Candida* yeast of embodiment V1, wherein the *Candida* yeast comprises a genetic alteration that increases a CYP52A15 activity.

V9. The *Candida* yeast of embodiment V8, wherein the genetic alteration that increases the CYP52A15 activity is (i) a copy number increase of a homologous or heterologous polynucleotide that encodes a polypeptide having the CYP52A15 activity, or (ii) a CYP52A15 promoter modification.

V10. The *Candida* yeast of embodiment V9, wherein the polynucleotide comprises the polynucleotide of SEQ ID NO: 16.

V11. The *Candida* yeast of embodiment V1, wherein the *Candida* yeast comprises a genetic alteration that increases a CYP52A16 activity.

V12. The *Candida* yeast of embodiment V11, wherein the genetic alteration that increases the CYP52A16 activity is (i) a copy number increase of a homologous or heterologous polynucleotide that encodes a polypeptide having the CYP52A16 activity, or (ii) a CYP52A16 promoter modification.

V13. The *Candida* yeast of embodiment V12, wherein the polynucleotide comprises the nucleotide sequence of SEQ ID NO: 17.

V14. The *Candida* yeast of embodiment V1, wherein the *Candida* yeast comprises a genetic alteration that increases a CYP52A19 activity.

V15. The *Candida* yeast of embodiment V14, wherein the genetic alteration that increases the CYP52A19 activity is (i) a copy number increase of a homologous or heterologous polynucleotide that encodes a polypeptide having the CYP52A19 activity, or (ii) a CYP52A19 promoter modification.

V16. The *Candida* yeast of embodiment V15, wherein the polynucleotide comprises the nucleotide sequence of SEQ ID NO: 20.

V17. The *Candida* yeast of embodiment V1, wherein the genetic alteration of (i) reduces the amount of a polypeptide having an acyl-CoA oxidase activity.

V18. The *Candida* yeast of embodiment V17, wherein the polypeptide is a POX4 polypeptide.

V19. The *Candida* yeast of embodiment V18, comprising an increased POX5 activity.

V20. The *Candida* yeast of embodiment V1, wherein the *Candida* yeast is a *Candida tropicalis* yeast.

W1. A method for producing adipic acid, comprising:
(a) contacting a *Candida* yeast with a feedstock comprising a vegetable oil, wherein the *Candida* yeast comprises:
(i) a genetic alteration that partially blocks beta oxidation activity,
(ii) a genetic alteration that reduces or eliminates long chain acyl-CoA synthetase activity, and
(iii) a genetic alteration that reduces or eliminates acyl-CoA synthetase activity; and
(b) culturing the *Candida* yeast under conditions in which adipic acid is produced.

W2. The method of embodiment W1, wherein the adipic acid is produced at a level of at least 2 grams per liter.

W3. The method of embodiment W1, wherein the adipic acid is produced at a level of at least 20% of maximum theoretical yield for the feedstock.

W4. The method of embodiment W1, wherein the vegetable oil is a palm oil or a soybean oil.

W5. The method of embodiment W1, wherein the vegetable oil is oleic acid.

W6. The method of embodiment W1, wherein the vegetable oil is a fatty acid soap stock.

W7. The method of embodiment W1, wherein the genetic alteration of (i) reduces the amount of a polypeptide having an acyl-CoA oxidase activity.

W8. The method of embodiment W7, wherein the polypeptide is a POX4 polypeptide or a POX5 polypeptide.

W9. The method of embodiment W8, wherein the polypeptide is a POX4 polypeptide.

W10. The method of embodiment W9, wherein the *Candida* yeast comprises a genetic alteration that increases POX5 activity.

W11. The method of embodiment W1, wherein the *Candida* yeast is a *Candida tropicalis* yeast.

W12. The method of embodiment W1, wherein the genetic alteration of (ii) eliminates the long chain acyl-CoA synthetase activity.

W13. The method of embodiment W12, wherein the genetic alteration of (ii) comprises disrupting a polynucleotide that encodes a FAT1 polypeptide.

W14. The method of embodiment W13, wherein the FAT1 polypeptide comprises the amino acid sequence of SEQ ID NO: 51.

W15. The method of embodiment W1, wherein the genetic alteration of (iii) eliminates the acyl-CoA synthetase activity.

W16. The method of embodiment W15, wherein the genetic alteration of (iii) comprises disrupting a polynucleotide that encodes a ACS1 polypeptide.

W17. The method of embodiment W16, wherein the ACS1 polypeptide comprises the amino acid sequence of SEQ ID NO: 49.

W18. The method of embodiment W1, wherein the *Candida* yeast comprises a genetic alteration that increases a CYP52A15 activity.

W19. The method of embodiment W1, wherein the *Candida* yeast comprises a genetic alteration that increases a CYP52A16 activity.

W20. The method of embodiment W1, wherein the *Candida* yeast comprises a genetic alteration that increases a CYP52A19 activity.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the claimed technology. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for producing adipic acid, comprising:
   (a) contacting a *Candida* yeast with a feedstock comprising a vegetable oil, wherein the *Candida* yeast comprises:
      (i) a disruption, deletion or knockout of (1) a polynucleotide that encodes a POX4 polypeptide or (2) a promoter operably linked to a polynucleotide that encodes a POX4 polypeptide, whereby POX4 activity is reduced or removed and POX5 activity is not reduced or removed,
      (ii) a disruption, deletion or knockout of (1) a polynucleotide that encodes a long chain acyl-CoA synthetase polypeptide or (2) a promoter operably linked to a polynucleotide that encodes a long chain acyl-CoA synthetase polypeptide, whereby a long chain acyl-CoA synthetase activity is reduced or removed, and (iii) a disruption, deletion or knockout of (1) a polynucleotide that encodes a long chain acyl-CoA synthetase polypeptide or (2) a promoter operably linked to a polynucleotide that encodes a long chain acyl-CoA synthetase polypeptide, whereby an acyl-CoA synthetase activity is reduced or removed; and (b) culturing the *Candida* yeast under conditions in which adipic acid is produced.

2. The method of claim 1, wherein the adipic acid is produced at a level of at least 2 grams per liter of culture medium.

3. The method of claim 1, wherein the adipic acid is produced at a level of at least 20% of maximum theoretical yield for the feedstock.

4. The method of claim 1, wherein the vegetable oil is a palm oil or a soybean oil.

5. The method of claim 1, wherein the vegetable oil is oleic acid.

6. The method of claim 1, wherein the vegetable oil is a fatty acid soap stock.

7. The method of claim 1, wherein the *Candida* yeast comprises a genetic alteration that increases POX5 activity.

8. The method of claim 1, wherein the *Candida* yeast is a genetically modified *Candida* strain ATCC20692.

9. The method of claim 1, wherein the long chain acyl-CoA synthetase activity is removed.

10. The method of claim 9, wherein the long chain acyl-CoA synthetase polypeptide is a FAT1 polypeptide.

11. The method of claim 10, wherein the FAT1 polypeptide comprises the amino acid sequence of SEQ ID NO: 51.

12. The method of claim 1, wherein the acyl-CoA synthetase activity is removed.

13. The method of claim 12, wherein the acyl-CoA synthetase polypeptide is an ACS1 polypeptide.

14. The method of claim 13, wherein the ACS1 polypeptide comprises the amino acid sequence of SEQ ID NO: 49.

15. The method of claim 1, wherein the *Candida* yeast comprises a genetic alteration that increases the number of copies of a polynucleotide that encodes a CYP52A15, CYP52A16 or CYP52A19 polypeptide.

16. The method of claim 1, wherein the *Candida* yeast comprises a genetic alteration that inserts a promoter in functional connection with a polynucleotide that encodes a CYP52A15, CYP52A16 or CYP52A19 polypeptide.

17. The method of claim 15, wherein the *Candida* yeast comprises a genetic alteration that increases the number of copies of a polynucleotide that encodes a CYP52A19 polypeptide.

18. The method of claim 17, wherein the CYP52A19 polypeptide is a *Candida* yeast polypeptide.

19. The method of claim 16, wherein the *Candida* yeast comprises a genetic alteration that inserts a promoter in functional connection with a polynucleotide that encodes a CYP52A19 polypeptide.

20. The method of claim 19, wherein the CYP52A19 polypeptide is a *Candida* yeast polypeptide.

* * * * *

```
                              SEQUENCE LISTING

<160> NUMBER OF SEQ ID NOS: 401

<210> SEQ ID NO 1
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggctccat ttttgcccga ccaggtcgac tacaaacacg tcgacaccct tatgttatta      60
tgtgacggga tcatccacga aaccaccgtc gaccaaatca aagacgttat tgctcctgac     120
ttccctgctg acaagtacga agagtacgtc aggacattca ccaaaccctc cgaaacccca     180
gggttcaggg aaaccgtcta caacacagtc aacgcaaaca ccacggacgc aatccaccag     240
ttcattatct tgaccaatgt tttggcatcc agggtcttgg ctccagcttt gaccaactcg     300
ttgacgccta tcaaggacat gagcttggaa gaccgtgaaa aattgttggc ctcgtggcgc     360
gactccccaa tcgctgccaa aaggaagttg ttcaggttgg tttctacgct taccttggtc     420
acgttcacga gattggccaa tgagttgcat ttgaaagcca ttcattatcc aggaagagaa     480
gaccgtgaaa aggcttatga aacccaggag attgaccctt ttaagtacca gtttttggaa     540
aaaccgaagt tttacggcgc tgagttgtac ttgccagata ttgatgtgat cattattgga     600
tctggtgccg gtgctggtgt tgtggcccac actttggcca acgatggctt caagagtttg     660
gttttggaaa agggcaaata ctttagcaac tccgagttga actttgatga caaggacggc     720
gttcaagaat tataccaaag tggaggtact ttgactacag tcaaccaaca gttgtttgtt     780
cttgctggtt ccacttttgg tggcggtacc actgtcaatt ggtcagcctg tcttaagacg     840
```

```
ccattcaagg tgcgtaagga atggtatgat gagtttggtg ttgactttgc tgctgatgaa      900
gcatacgata aagcgcagga ttatgtttgg cagcaaatgg gagcttctac cgaaggcatc      960
acccactctt tggctaacga gattattatt gaaggtggta agaaattagg ttacaaggcc     1020
aaggtattag accaaaacag cggtggtcat cctcagcaca gatgcggttt ctgttatttg     1080
ggctgtaagc acggtatcaa gcagggttct gttaataact ggtttagaga cgcagctgcc     1140
cacggttccc agttcatgca acaggttaga gttttgcaaa tacttaacaa gaagggatc      1200
gcttacggta tcttgtgtga ggatgttgta accggcgcca agttcaccat tactggcccc     1260
aaaaagtttg ttgttgctgc cggtgctttg aacactccat ctgtgttggt caactccggc     1320
ttcaagaaca agaacatcgg taagaactta actttgcacc cagtttctgt cgtgtttggt     1380
gattttggca aagacgttca agcagaccac ttccacaact ccatcatgac tgcccttgt      1440
tcagaagccg ctgatttaga cggcaagggc catggatgca gaattgaaac catcttgaac     1500
gctccattca tccaggcttc attcttacca tggagaggta gtaacgaggc tagacgagac     1560
ttgttgcgtt acaacaacat ggtggcgatg ttgctcctta gtcgtgacac caccagtggt     1620
tccgtttctg ctcatccaac caaacctgaa gctttggttg tcgagtacga cgtgaacaag     1680
tttgacagaa actcgatctt gcaggcattg ttggtcactg ctgacttgtt gtatatccaa     1740
ggtgccaaga gaatccttag tccacaggca tgggtgccaa ttttttgaatc cgacaagcca     1800
aaggataaga gatcaatcaa ggacgaggac tatgtcgaat ggagagccaa ggttgccaag     1860
attcctttcg acacctacgg ctcacccttat ggttcggcac atcaaaatgtc ttcttgccgt     1920
atgtcaggta agggtcctaa atacggtgct gttgacaccg atggtagatt gtttgaatgt     1980
tcgaatgttt atgttgccga tgcaagtctt ttgccaactg caagcggtgc caaccctatg     2040
gtcaccacca tgactcttgc cagacatgtt gcgttaggtt tggcagactc cttgaagacc     2100
aaagccaagt tgtag                                                      2115
```

<210> SEQ ID NO 2
<211> LENGTH: 2115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
atggctccat ttttgcccga ccaggtcgac tacaaacacg tcgacaccct tatgttatta       60
tgtgacggga tcatccacga aaccaccgtg gacgaaatca aagacgtcat tgcccctgac      120
ttccccgccg acaaatacga ggagtacgtc aggacattcc caaacccctc cgaaaccccca     180
gggttcaggg aaaccgtcta acaccgtc aacgcaaaca ccatggatgc aatccaccag        240
ttcattatct tgaccaatgt tttgggatca agggtcttgg caccagcttt gaccaactcg      300
ttgactccta tcaaggacat gagcttggaa gaccgtgaaa agttgttagc ctcgtggcgt      360
gactccccta ttgctgctaa aaggaagttg ttcaggttgg tttctacgct taccttggtc      420
acgttcacga gattggccaa tgagttgcat ttgaaagcca ttcattatcc aggaagagaa      480
gaccgtgaaa aggcttatga aacccaggag attgacccct ttaagtacca gttttttggaa    540
aaaccgaagt tttacggcgc tgagttgtac ttgccagata ttgatgtgat cattattgga      600
tctggtgccg gtgctggtgt tgtggcccac actttggcca acgatggctt caagagtttg     660
gttttggaaa agggcaaata ctttagcaac tccgagttga acttttgatga caaggacggc     720
```

```
gttcaagaat tataccaaag tggaggtact ttgactacag tcaaccaaca gttgtttgtt    780
cttgctggtt ccacttttgg tggcggtacc actgtcaatt ggtcagcctg tcttaagacg    840
ccattcaagg tgcgtaagga atggtatgat gagtttggtg ttgactttgc tgctgatgaa    900
gcatacgata aagcgcagga ttatgtttgg cagcaaatgg gagcttctac cgaaggcatc    960
acccactctt tggctaacga gattattatt gaaggtggta agaaattagg ttacaaggcc   1020
aaggtattag accaaaacag cggtggtcat cctcagcaca gatgcggttt ctgttatttg   1080
ggttgtaagc acggtatcaa gcagggctct gttaataact ggtttagaga cgcagctgcc   1140
cacggttctc agttcatgca acaggttaga gttttgcaaa tccttaacaa gaagggcatc   1200
gcttatggta tcttgtgtga ggatgttgta accggtgcca agttcaccat tactggcccc   1260
aaaaagtttg ttgttgccgc cggcgcctta aacactccat ctgtgttggt caactccgga   1320
ttcaagaaca agaacatcgg taagaactta actttgcatc cagtttctgt cgtgtttggt   1380
gattttggca aagacgttca agcagaccac ttccacaact ccatcatgac tgcccttttgt  1440
tcagaagccg ctgatttaga cggcaagggc catggatgca gaattgaaac catcttgaac   1500
gctccattca tccaggcttc attcttacca tggagaggta gtaacgaggc tagacgagac   1560
ttgttgcgtt acaacaacat ggtggcgatg ttgctcctta gtcgtgacac caccagtggt   1620
tccgtttctg ctcatccaac caaacctgaa gctttggttg tcgagtacga cgtgaacaag   1680
tttgacagaa actcgatctt gcaggcattg ttggtcactg ctgacttgtt gtatatccaa   1740
ggtgccaaga gaatccttag tccacaggca tgggtgccaa tttttgaatc cgacaagcca   1800
aaggataaga gatcaatcaa ggacgaggac tatgtcgaat ggagagccaa ggttgccaag   1860
attcctttcg acacctacgg ctcacccttat ggttcggcac atcaaatgtc ttcttgccgt   1920
atgtcaggta agggtcctaa atacggtgct gttgacaccg atggtagatt gttttgaatgt  1980
tcgaatgttt atgttgccga tgcaagtctt ttgccaactg caagcggtgc caaccctatg   2040
gtcaccacca tgactcttgc aagacatgtt gcgttaggtt tggcagactc cttgaagacc   2100
aaggccaagt tgtag                                                   2115
```

<210> SEQ ID NO 3
<211> LENGTH: 2115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atggctccat ttttgcccga ccaggtcgac tacaaacacg tcgacaccct tatgttatta     60
tgtgacggga tcatccacga aaccaccgtc gaccaaatca aagacgttat tgctcctgac    120
ttccctgctg acaagtacga agagtacgtc aggacattca ccaaaccctc cgaaacccca    180
gggttcaggg aaaccgtcta caacacagtc aacgcaaaca ccacggacgc aatccaccag    240
ttcattatct tgaccaatgt tttggcatcc agggtcttgg ctccagcttt gaccaactcg    300
ttgacgccta tcaaggacat gagcttggaa gaccgtgaaa aattgttggc ctcgtggcgc    360
gactccccaa tcgctgccaa aaggaaattg ttcaggttgg tttccacgct taccttggtt    420
actttcacga gattggccaa tgagttgcat ttgaaagcca ttcactatcc aggaagagaa    480
gaccgtgaaa aggcttatga aacccaggag attgaccctt tcaagtacca gtttatggaa    540
aagccaaagt tgacggcgc tgagttgtac ttgccagata ttgatgttat cattattgga    600
tctggtgccg gtgctggtgt tgtggcccac actttggcca acgatggctt caagagtttg    660
```

```
gttttggaaa agggcaaata ctttagcaac tccgagttga actttgatga caaggacggc    720
gttcaagaat tataccaaag tggaggtact ttgactacag tcaaccaaca gttgtttgtt    780
cttgctggtt ccacttttgg tggcggtacc actgtcaatt ggtcagcctg tcttaagacg    840
ccattcaagg tgcgtaagga atggtatgat gagtttggtg ttgactttgc tgctgatgaa    900
gcatacgata aagcgcagga ttatgtttgg cagcaaatgg gagcttctac cgaaggcatc    960
acccactctt tggctaacga gattattatt gaaggtggta agaaattagg ttacaaggcc   1020
aaggtattag accaaaacag cggtggtcat cctcagcaca gatgcggttt ctgttatttg   1080
ggctgtaagc acggtatcaa gcagggttct gttaataact ggtttagaga cgcagctgcc   1140
cacggttccc agttcatgca acaggttaga gttttgcaaa tacttaacaa gaagggatc    1200 gcttacggta tcttgtgtga ggatgttgta accggcgcca agttcaccat tactggcccc   1260
aaaaagtttg ttgttgctgc cggtgctttg aacactccat ctgtgttggt caactccggc   1320
ttcaagaaca agaacatcgg taagaactta actttgcacc cagtttctgt cgtgtttggt   1380
gattttggca agacgttca agcagaccac ttccacaact ccatcatgac tgccctttgt   1440
tcagaagccg ctgatttaga cggcaagggc catggatgca gaattgaaac catcttgaac   1500
gctccattca tccaggcttc attcttacca tggagaggta gtaacgaggc tagacgagac   1560
ttgttgcgtt acaacaacat ggtggcgatg ttgctcctta gtcgtgacac caccagtggt   1620
tccgtttctg ctcatccaac caaacctgaa gctttggttg tcgagtacga cgtgaacaag   1680
tttgacagaa actcgatctt gcaggcattg ttggtcactg ctgacttgtt gtatatccaa   1740
ggtgccaaga gaatccttag tccacaggca tgggtgccaa ttttttgaatc cgacaagcca   1800 aaggataaga gatcaatcaa ggacgaggac tatgtcgaat ggagagccaa ggttgccaag   1860
attcctttcg acacctacgg ctcaccttat ggttcggcac atcaaatgtc ttcttgccgt   1920
atgtcaggta agggtcctaa atacggtgct gttgacaccg atggtagatt gttttgaatgt   1980 tcgaatgttt atgttgccga tgcaagtctt ttgccaactg caagcggtgc caaccctatg   2040
gtcaccacca tgactcttgc cagacatgtt gcgttaggtt tggcagactc cttgaagacc   2100
aaagccaagt tgtag                                                    2115

<210> SEQ ID NO 4
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4 atgaataccct tcttgccaga cgtgctcgaa tacaaacacg tcgacaccct tttgttattg     60
tgtgacggga tcatccacga aaccacagtc gatcagatca aggacgccat tgctcccgac    120
ttccctgagg accagtacga ggagtatctc aagaccttca ccaagccatc tgagacccct    180
gggttcagag aagccgtcta cgacacgatc aacgccaccc caaccgatgc cgtgcacatg    240
tgtattgtct tgaccaccgc attggactcc agaatcttgg cccccacgtt gaccaactcg    300
ttgacgccta tcaaggatat gaccttgaag gagcgtgaac aattgttggc ctcttggcgt    360
gattccccga ttgcggcaaa agaagattg ttcagattga tttcctcgct taccttgacg    420
acgtttacga gattggccag cgaattgcac ttgaaagcca tccactaccc tggcagagac    480
ttgcgtgaaa aggcgtatga aacccaggtg gttgacccctt tcaggtacct gtttatggag    540
```

```
aaaccaaagt tgacggcgc cgaattgtac ttgccagata tcgacgtcat catcattgga    600
tcaggcgccg gtgctggtgt catggcccac actctcgcca acgacgggtt caagaccttg    660
gttttggaaa agggaaagta tttcagcaac tccgagttga actttaatga cgctgatggc    720
gtgaaagagt tgtaccaagg taaaggtgct ttggccacca ccaatcagca gatgtttatt    780
cttgccggtt ccactttggg cggtggtacc actgtcaact ggtctgcttg ccttaaaaca    840
ccatttaaag tgcgtaagga gtggtacgac gagtttggtc ttgaatttgc tgccgatgaa    900
gcctacgaca agcgcagga ttatgtttgg aaacaaatgg gtgcttcaac agatggaatc    960
actcactcct tggccaacga agttgtggtt gaaggaggta agaagttggg ctacaagagc   1020
aaggaaattg agcagaacaa cggtggccac cctgaccacc catgtggttt ctgttacttg   1080
ggctgtaagt acggtattaa acagggttct gtgaataact ggtttagaga cgcagctgcc   1140
cacgggtcca agttcatgca acaagtcaga gttgtgcaaa tcctcaacaa gaatggcgtc   1200
gcttatggta tcttgtgtga ggatgtcgaa accggagtca ggttcactat tagtggcccc   1260
aaaaagtttg ttgtttctgc tggttctttg aacacgccaa ctgtgttgac caactccgga   1320
ttcaagaaca agcacattgg taagaacttg acgttgcacc cagtttccac cgtgtttggt   1380
gactttggca gagacgtgca agccgaccat ttccacaaat ctattatgac ttcgctttgt   1440
tacgaggttg ctgacttgga cggcaagggc cacggatgca gaatcgaaac catcttgaac   1500
gctccattca tccaagcttc tttgttgcca tggagaggaa gtgacgaggt cagaagagac   1560
ttgttgcgtt acaacaacat ggtggccatg ttgcttatca cgcgtgatac caccagtggt   1620
tcagtttctg ctgacccaaa gaagcccgac gctttgattg tcgactatga gattaacaag   1680
tttgacaaga atgccatctt gcaagctttc ttgatcactt ccgacatgtt gtacattgaa   1740
ggtgccaaga gaatcctcag tccacagcca tgggtgccaa tctttgagtc gaacaagcca   1800
aaggagcaaa gaacgatcaa ggacaaggac tatgttgagt ggagagccaa ggctgctaag   1860 ataccttttcg acacctacgg ttctgcatat gggtccgcac atcaaatgtc cacctgtcgt   1920
atgtccggaa agggtcctaa atacggtgct gttgatactg atggtagatt gtttgaatgt   1980
tcgaatgtct atgttgctga tgctagtgtt ttgcctactg ccagcggtgc caacccaatg   2040
atatccacca tgacctttgc tagacagatt gcgttaggtt tggctgactc cttgaagacc   2100
aaacccaagt tgtag                                                    2115

<210> SEQ ID NO 5
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgaatacct tcttgccaga cgtgctcgaa tacaaacacg tcgataccct tttgttatta     60
tgtgacggga tcatccacga aaccacagtc gaccagatca gggacgccat tgctcccgac    120
ttccctgaag accagtacga ggagtatctc aagaccttca ccaagccatc tgagacccct    180
gggttcagag aagccgtcta cgacacgatc aacagcaccc caaccgaggc tgtgcacatg    240
tgtattgtat tgaccaccgc attggactcg agaatcttgg ccccacgtt gaccaactcg    300 ttgacgccta tcaaggatat gaccttgaaa gagcgtgaac aattgttggc tgcctggcgt    360
gattccccga tcgcggccaa gagaagattg ttcagattga tttcctcact taccttgacg    420
acctttacga gattggccag cgacttgcac ttgagagcca tccactaccc tggcagagac    480
```

```
ttgcgtgaaa aggcatatga aacccaggtg gttgacccct tcaggtacct gtttatggaa      540
aaaccaaagt ttgacggcac cgagttgtac ttgccagata tcgacgtcat catcattgga      600
tccggtgccg gtgctggtgt catggcccac actttagcca acgacgggta caagaccttg      660
gttttggaaa agggaaagta tttcagcaac tccgagttga actttaatga tgccgatggt      720
atgaaagagt tgtaccaagg taaatgtgcg ttgaccacca cgaaccagca gatgtttatt      780
cttgccggtt ccactttggg cggtggtacc actgttaact ggtctgcttg tcttaaaaca      840
ccatttaaag tgcgtaagga gtggtacgac gagtttggtc ttgaatttgc tgccgacgaa      900
gcctacgaca aagcacaaga ctatgtttgg aaacaaatgg gcgcttctac cgaaggaatc      960
actcactctt tggcgaacgc ggttgtggtt gaaggaggta agaagttggg ttacaagagc     1020
aaggaaatcg agcagaacaa tggtggccat cctgaccacc cctgtggttt ctgttacttg     1080
ggctgtaagt acggtattaa gcagggttct gtgaataact ggtttagaga cgcagctgcc     1140
cacgggtcca agttcatgca acaagtcaga gttgtgcaaa tcctccacaa taaaggcgtc     1200
gcttatggca tcttgtgtga ggatgtcgag accggagtca aattcactat cagtggcccc     1260
aaaaagtttg ttgtttctgc aggttctttg aacacgccaa cggtgttgac caactccgga     1320
ttcaagaaca aacacatcgg taagaacttg acgttgcacc cagtttcgac cgtgtttggt     1380
gactttggca gagacgtgca agccgaccat ttccacaaat ctattatgac ttcgctctgt     1440
tacgaagtcg ctgacttgga cggcaagggc cacggatgca gaatcgagac catcttgaac     1500
gctccattca tccaagcttc tttgttgcca tggagaggaa gcgacgaggt cagaagagac     1560
ttgttgcgtt acaacaacat ggtggccatg ttgcttatca cccgtgacac caccagtggt     1620
tcagtttctg ctgacccaaa gaagcccgac gctttgattg tcgactatga catcaacaag     1680
tttgacaaga atgccatctt gcaagctttc ttgatcacct ccgacatgtt gtacatcgaa     1740
ggtgccaaga gaatcctcag tccacaggca tgggtgccaa tctttgagtc gaacaagcca     1800
aaggagcaaa gaacaatcaa ggacaaggac tatgtcgaat ggagagccaa ggctgccaag     1860 ataccttttcg acacctacgg ttctgcctat gggtccgcac atcaaatgtc cacctgtcgt     1920
atgtccggaa agggtcctaa atacggcgcc gttgataccg atggtagatt gtttgaatgt     1980
tcgaatgtct atgttgctga tgctagtgtt ttgcctactg ccagcggtgc caacccaatg     2040
atctccacca tgacgtttgc tagacagatt gcgttaggtt tggctgactc tttgaagacc     2100
aaacccaagt tgtag                                                      2115
```

<210> SEQ ID NO 6
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atggctccat ttttgcccga ccaggtcgac tacaaacacg tcgacaccct tatgttatta       60
tgtgacggga tcatccacga aaccaccgtg gacgaaatca aagacgtcat tgcccctgac      120
ttccccgccg acaaatacga ggagtacgtc aggacattca ccaaacccct cgaaaccccca      180 gggttcaggg aaaccgtcta caacaccgtc aacgcaaaca ccatggatgc aatccaccag      240
ttcattatct tgaccaatgt tttgggatca agggtcttgg caccagcttt gaccaactcg      300
ttgactccta tcaaggacat gagcttggaa gaccgtgaaa agttgttagc ctcgtggcgt      360
```

```
gactccccta ttgctgctaa aaggaagttg ttcaggttgg tttctacgct taccttggtc    420
acgttcacga gattggccaa tgagttgcat ttgaaagcca ttcattatcc aggaagagaa    480
gaccgtgaaa aggcttatga aacccaggag attgacccctt ttaagtacca gtttttggaa   540
aaaccgaagt tttacggcgc tgagttgtac ttgccagata ttgatgtgat cattattgga    600
tctggggccg gtgctggtgt cgtggcccac actttgacca cgacggctt caagagtttg     660 gttttggaaa agggcagata ctttagcaac tccgagttga actttgatga caaggacggg    720
gttcaagaat tataccaaag tggaggtact ttgaccaccg tcaaccagca gttgtttgtt    780
cttgctggtt ccacttttgg tggtggtacc actgtcaatt ggtcggcctg tcttaaaacg    840
ccattcaagg tgcgtaagga atggtatgat gagtttggcg ttgactttgc tgccgatgaa    900
gcctacgaca agcacagga ttatgtttgg cagcaaatgg gagcttctac cgaaggcatc     960
acccactctt tggctaacga gattattatt gaaggtggca agaaattagg ttacaaggcc    1020
aaggtattag accaaaacag cggtggtcat cctcatcaca gatgcggttt ctgttatttg    1080
ggttgtaagc acggtatcaa gcagggctct gttaataact ggtttagaga cgcagctgcc    1140
cacggttctc agttcatgca acaggttaga gttttgcaaa tccttaacaa gaagggcatc    1200
gcttatggta tcttgtgtga ggatgttgta accggtgcca agttcaccat tactggcccc    1260
aaaaagtttg ttgttgccgc cggcgcctta aacactccat ctgtgttggt caactccgga   1320
ttcaagaaca agaacatcgg taagaactta actttgcatc cagtttctgt cgtgtttggt    1380
gattttggca aagacgttca gcagatcac ttccacaact ccatcatgac tgctcttttgt    1440 tcagaagccg ctgatttaga cggcaagggt catggatgca gaattgaaac catcttgaac    1500
gctccattca tccaggcttc attcttacca tggagaggta gtaacgaggc tagacgagac    1560
ttgttgcgtt acaacaacat ggtggccatg ttacttctta gtcgtgatac caccagtggt    1620
tccgtttcgt cccatccaac taaacctgaa gcattagttg tcgagtacga cgtgaacaag    1680
tttgacagaa actccatctt gcaggcattg ttggtcactg ctgacttgtt gtacattcaa    1740
ggtgccaaga gaatccttag tccccaacca tgggtgccaa tttttgaatc cgacaagcca    1800
aaggataaga gatcaatcaa ggacgaggac tatgtcgaat ggagagccaa ggttgccaag    1860
attccttttg acacctacgg ctcgccttat ggttcggcgc atcaaatgtc ttcttgtcgt    1920
atgtcaggta agggtcctaa atacggtgct gttgataccg atggtagatt gtttgaatgt    1980
tcgaatgttt atgttgctga cgctagtctt ttgccaactg ctagcggtgc taatcctatg    2040
gtcaccacca tgactcttgc aagacatgtt gcgttaggtt tggcagactc cttgaagacc    2100
aaggccaagt tgtag                                                     2115
```

<210> SEQ ID NO 7
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Glu
                20                  25                  30

Ile Lys Asp Val Ile Ala Pro Asp Phe Pro Ala Asp Lys Tyr Glu Glu
            35                  40                  45

```
Tyr Val Arg Thr Phe Thr Lys Pro Ser Glu Thr Pro Gly Phe Arg Glu
50                  55                  60

Thr Val Tyr Asn Thr Val Asn Ala Asn Thr Met Asp Ala Ile His Gln
65                  70                  75                  80

Phe Ile Ile Leu Thr Asn Val Leu Gly Ser Arg Val Leu Ala Pro Ala
            85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Gly Ser Gly Ala Gly Ala Gly Val Val
        195                 200                 205

Ala His Thr Leu Thr Asn Asp Gly Phe Lys Ser Leu Val Leu Glu Lys
210                 215                 220

Gly Arg Tyr Phe Ser Asn Ser Glu Leu Asn Phe Asp Asp Lys Asp Gly
225                 230                 235                 240

Val Gln Glu Leu Tyr Gln Ser Gly Gly Thr Leu Thr Thr Val Asn Gln
            245                 250                 255

Gln Leu Phe Val Leu Ala Gly Ser Thr Phe Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Val Asp Phe Ala Ala Asp Glu Ala Tyr Asp Lys
        290                 295                 300

Ala Gln Asp Tyr Val Trp Gln Gln Met Gly Ala Ser Thr Glu Gly Ile
305                 310                 315                 320

Thr His Ser Leu Ala Asn Glu Ile Ile Ile Glu Gly Gly Lys Lys Leu
            325                 330                 335

Gly Tyr Lys Ala Lys Val Leu Asp Gln Asn Ser Gly Gly His Pro His
            340                 345                 350

His Arg Cys Gly Phe Cys Tyr Leu Gly Cys Lys His Gly Ile Lys Gln
        355                 360                 365

Gly Ser Val Asn Asn Trp Phe Arg Asp Ala Ala Ala His Gly Ser Gln
370                 375                 380

Phe Met Gln Gln Val Arg Val Leu Gln Ile Leu Asn Lys Lys Gly Ile
385                 390                 395                 400

Ala Tyr Gly Ile Leu Cys Glu Asp Val Val Thr Gly Ala Lys Phe Thr
            405                 410                 415

Ile Thr Gly Pro Lys Lys Phe Val Val Ala Ala Gly Ala Leu Asn Thr
            420                 425                 430

Pro Ser Val Leu Val Asn Ser Gly Phe Lys Asn Lys Asn Ile Gly Lys
        435                 440                 445

Asn Leu Thr Leu His Pro Val Ser Val Val Phe Gly Asp Phe Gly Lys
        450                 455                 460

Asp Val Gln Ala Asp His Phe His Asn Ser Ile Met Thr Ala Leu Cys
465                 470                 475                 480
```

```
Ser Glu Ala Ala Asp Leu Asp Gly Lys Gly His Gly Cys Arg Ile Glu
            485                 490                 495

Thr Ile Leu Asn Ala Pro Phe Ile Gln Ala Ser Phe Leu Pro Trp Arg
        500                 505                 510

Gly Ser Asn Glu Ala Arg Arg Asp Leu Leu Arg Tyr Asn Asn Met Val
        515                 520                 525

Ala Met Leu Leu Leu Ser Arg Asp Thr Thr Ser Gly Ser Val Ser Ser
530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
                565                 570                 575

Leu Tyr Ile Gln Gly Ala Lys Arg Ile Leu Ser Pro Gln Pro Trp Val
            580                 585                 590

Pro Ile Phe Glu Ser Asp Lys Pro Lys Asp Lys Arg Ser Ile Lys Asp
        595                 600                 605

Glu Asp Tyr Val Glu Trp Arg Ala Lys Val Ala Lys Ile Pro Phe Asp
        610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Leu Leu Pro
            660                 665                 670

Thr Ala Ser Gly Ala Asn Pro Met Val Thr Thr Met Thr Leu Ala Arg
        675                 680                 685

His Val Ala Leu Gly Leu Ala Asp Ser Leu Lys Thr Lys Ala Lys Leu
        690                 695                 700

<210> SEQ ID NO 8
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Gln
            20                  25                  30

Ile Lys Asp Val Ile Ala Pro Asp Phe Pro Ala Asp Lys Tyr Glu Glu
        35                  40                  45

Tyr Val Arg Thr Phe Thr Lys Pro Ser Glu Thr Pro Gly Phe Arg Glu
    50                  55                  60

Thr Val Tyr Asn Thr Val Asn Ala Asn Thr Thr Asp Ala Ile His Gln
65                  70                  75                  80

Phe Ile Ile Leu Thr Asn Val Leu Ala Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140
```

```
Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Ile Gly Ser Gly Ala Gly Ala Gly Val Val
            195                 200                 205

Ala His Thr Leu Ala Asn Asp Gly Phe Lys Ser Leu Val Leu Glu Lys
    210                 215                 220

Gly Lys Tyr Phe Ser Asn Ser Glu Leu Asn Phe Asp Asp Lys Asp Gly
225                 230                 235                 240

Val Gln Glu Leu Tyr Gln Ser Gly Gly Thr Leu Thr Thr Val Asn Gln
                245                 250                 255

Gln Leu Phe Val Leu Ala Gly Ser Thr Phe Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Val Asp Phe Ala Ala Asp Glu Ala Tyr Asp Lys
290                 295                 300

Ala Gln Asp Tyr Val Trp Gln Gln Met Gly Ala Ser Thr Glu Gly Ile
305                 310                 315                 320

Thr His Ser Leu Ala Asn Glu Ile Ile Ile Glu Gly Gly Lys Lys Leu
                325                 330                 335

Gly Tyr Lys Ala Lys Val Leu Asp Gln Asn Ser Gly Gly His Pro Gln
                340                 345                 350

His Arg Cys Gly Phe Cys Tyr Leu Gly Cys Lys His Gly Ile Lys Gln
        355                 360                 365

Gly Ser Val Asn Asn Trp Phe Arg Asp Ala Ala Ala His Gly Ser Gln
370                 375                 380

Phe Met Gln Gln Val Arg Val Leu Gln Ile Leu Asn Lys Lys Gly Ile
385                 390                 395                 400

Ala Tyr Gly Ile Leu Cys Glu Asp Val Val Thr Gly Ala Lys Phe Thr
                405                 410                 415

Ile Thr Gly Pro Lys Lys Phe Val Val Ala Ala Gly Ala Leu Asn Thr
            420                 425                 430

Pro Ser Val Leu Val Asn Ser Gly Phe Lys Asn Lys Asn Ile Gly Lys
        435                 440                 445

Asn Leu Thr Leu His Pro Val Ser Val Val Phe Gly Asp Phe Gly Lys
    450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
                485                 490                 495

Thr Ile Leu Asn Ala Pro Phe Ile Gln Ala Ser Phe Leu Pro Trp Arg
            500                 505                 510

Gly Ser Asn Glu Ala Arg Arg Asp Leu Leu Arg Tyr Asn Asn Met Val
        515                 520                 525

Ala Met Leu Leu Leu Ser Arg Asp Thr Thr Ser Gly Ser Val Ser Ala
    530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
```

```
                       565                 570                 575
Leu Tyr Ile Gln Gly Ala Lys Arg Ile Leu Ser Pro Gln Ala Trp Val
                580                 585                 590

Pro Ile Phe Glu Ser Asp Lys Pro Lys Asp Lys Arg Ser Ile Lys Asp
            595                 600                 605

Glu Asp Tyr Val Glu Trp Arg Ala Lys Val Ala Lys Ile Pro Phe Asp
        610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Leu Leu Pro
            660                 665                 670

Thr Ala Ser Gly Ala Asn Pro Met Val Thr Thr Met Thr Leu Ala Arg
        675                 680                 685

His Val Ala Leu Gly Leu Ala Asp Ser Leu Lys Thr Lys Ala Lys Leu
    690                 695                 700

<210> SEQ ID NO 9
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Gln
            20                  25                  30

Ile Lys Asp Val Ile Ala Pro Asp Phe Pro Ala Asp Lys Tyr Glu Glu
        35                  40                  45

Tyr Val Arg Thr Phe Thr Lys Pro Ser Glu Thr Pro Gly Phe Arg Glu
    50                  55                  60

Thr Val Tyr Asn Thr Val Asn Ala Asn Thr Thr Asp Ala Ile His Gln
65                  70                  75                  80

Phe Ile Ile Leu Thr Asn Val Leu Ala Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Met Glu Lys Pro Lys Phe Asp Gly Ala Glu Leu Tyr Leu Pro
            180                 185                 190

Asp Ile Asp Val Ile Ile Gly Ser Gly Ala Gly Ala Gly Val Val
        195                 200                 205

Ala His Thr Leu Ala Asn Asp Gly Phe Lys Ser Leu Val Leu Glu Lys
    210                 215                 220

Gly Lys Tyr Phe Ser Asn Ser Glu Leu Asn Phe Asp Asp Lys Asp Gly
```

-continued

```
               225                 230                 235                 240
Val Gln Glu Leu Tyr Gln Ser Gly Gly Thr Leu Thr Thr Val Asn Gln
                245                 250                 255

Gln Leu Phe Val Leu Ala Gly Ser Thr Phe Gly Gly Thr Thr Val
            260                 265                 270

Asn Trp Ser Ala Cys Leu Lys Thr Pro Phe Lys Val Arg Lys Glu Trp
            275                 280                 285

Tyr Asp Glu Phe Gly Val Asp Phe Ala Ala Asp Glu Tyr Asp Lys
            290                 295                 300

Ala Gln Asp Tyr Val Trp Gln Gln Met Gly Ala Ser Thr Glu Gly Ile
305                 310                 315                 320

Thr His Ser Leu Ala Asn Glu Ile Ile Ile Glu Gly Lys Lys Leu
                325                 330                 335

Gly Tyr Lys Ala Lys Val Leu Asp Gln Asn Ser Gly Gly His Pro Gln
                340                 345                 350

His Arg Cys Gly Phe Cys Tyr Leu Gly Cys Lys His Gly Ile Lys Gln
                355                 360                 365

Gly Ser Val Asn Asn Trp Phe Arg Asp Ala Ala His Gly Ser Gln
            370                 375                 380

Phe Met Gln Gln Val Arg Val Leu Gln Ile Leu Asn Lys Lys Gly Ile
385                 390                 395                 400

Ala Tyr Gly Ile Leu Cys Glu Asp Val Val Thr Gly Ala Lys Phe Thr
                405                 410                 415

Ile Thr Gly Pro Lys Lys Phe Val Val Ala Ala Gly Ala Leu Asn Thr
                420                 425                 430

Pro Ser Val Leu Val Asn Ser Gly Phe Lys Asn Lys Asn Ile Gly Lys
            435                 440                 445

Asn Leu Thr Leu His Pro Val Ser Val Val Phe Gly Asp Phe Gly Lys
450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
                485                 490                 495

Thr Ile Leu Asn Ala Pro Phe Ile Gln Ala Ser Phe Leu Pro Trp Arg
                500                 505                 510

Gly Ser Asn Glu Ala Arg Arg Asp Leu Leu Arg Tyr Asn Asn Met Val
            515                 520                 525

Ala Met Leu Leu Leu Ser Arg Asp Thr Thr Ser Gly Ser Val Ser Ala
530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
                565                 570                 575

Leu Tyr Ile Gln Gly Ala Lys Arg Ile Leu Ser Pro Gln Ala Trp Val
                580                 585                 590

Pro Ile Phe Glu Ser Asp Lys Pro Lys Asp Lys Arg Ser Ile Lys Asp
            595                 600                 605

Glu Asp Tyr Val Glu Trp Arg Ala Lys Val Ala Lys Ile Pro Phe Asp
            610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
                645                 650                 655
```

```
Leu Phe Glu Cys Ser Asn Val Tyr Val Ala Asp Ala Ser Leu Leu Pro
            660                 665                 670

Thr Ala Ser Gly Ala Asn Pro Met Val Thr Met Thr Leu Ala Arg
            675                 680                 685

His Val Ala Leu Gly Leu Ala Asp Ser Leu Lys Thr Lys Ala Lys Leu
    690                 695                 700

<210> SEQ ID NO 10
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Pro Phe Leu Pro Asp Gln Val Asp Tyr Lys His Val Asp Thr
1               5                   10                  15

Leu Met Leu Leu Cys Asp Gly Ile Ile His Glu Thr Val Asp Glu
            20                  25                  30

Ile Lys Asp Val Ile Ala Pro Asp Phe Pro Ala Asp Lys Tyr Glu Glu
        35                  40                  45

Tyr Val Arg Thr Phe Thr Lys Pro Ser Glu Thr Pro Gly Phe Arg Glu
    50                  55                  60

Thr Val Tyr Asn Thr Val Asn Ala Asn Thr Met Asp Ala Ile His Gln
65                  70                  75                  80

Phe Ile Ile Leu Thr Asn Val Leu Gly Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
    130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Gly Ser Gly Ala Gly Ala Gly Val Val
        195                 200                 205

Ala His Thr Leu Ala Asn Asp Gly Phe Lys Ser Leu Val Leu Glu Lys
    210                 215                 220

Gly Lys Tyr Phe Ser Asn Ser Glu Leu Asn Phe Asp Asp Lys Asp Gly
225                 230                 235                 240

Val Gln Glu Leu Tyr Gln Ser Gly Gly Thr Leu Thr Thr Val Asn Gln
                245                 250                 255

Gln Leu Phe Val Leu Ala Gly Ser Thr Phe Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Val Asp Phe Ala Ala Asp Glu Ala Tyr Asp Lys
    290                 295                 300

Ala Gln Asp Tyr Val Trp Gln Gln Met Gly Ala Ser Thr Glu Gly Ile
305                 310                 315                 320
```

Thr His Ser Leu Ala Asn Glu Ile Ile Ile Glu Gly Lys Lys Leu
            325                 330                 335

Gly Tyr Lys Ala Lys Val Leu Asp Gln Asn Ser Gly Gly His Pro Gln
            340                 345                 350

His Arg Cys Gly Phe Cys Tyr Leu Gly Cys Lys His Gly Ile Lys Gln
            355                 360                 365

Gly Ser Val Asn Asn Trp Phe Arg Asp Ala Ala His Gly Ser Gln
370                 375                 380

Phe Met Gln Gln Val Arg Val Leu Gln Ile Leu Asn Lys Lys Gly Ile
385                 390                 395                 400

Ala Tyr Gly Ile Leu Cys Glu Asp Val Val Thr Gly Ala Lys Phe Thr
            405                 410                 415

Ile Thr Gly Pro Lys Lys Phe Val Val Ala Gly Ala Leu Asn Thr
            420                 425                 430

Pro Ser Val Leu Val Asn Ser Gly Phe Lys Asn Lys Asn Ile Gly Lys
            435                 440                 445

Asn Leu Thr Leu His Pro Val Ser Val Phe Gly Asp Phe Gly Lys
450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
            485                 490                 495

Thr Ile Leu Asn Ala Pro Phe Ile Gln Ala Ser Phe Leu Pro Trp Arg
            500                 505                 510

Gly Ser Asn Glu Ala Arg Arg Asp Leu Leu Arg Tyr Asn Asn Met Val
            515                 520                 525

Ala Met Leu Leu Leu Ser Arg Asp Thr Thr Ser Gly Ser Val Ser Ala
530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
            565                 570                 575

Leu Tyr Ile Gln Gly Ala Lys Arg Ile Leu Ser Pro Gln Ala Trp Val
            580                 585                 590

Pro Ile Phe Glu Ser Asp Lys Pro Lys Asp Lys Arg Ser Ile Lys Asp
            595                 600                 605

Glu Asp Tyr Val Glu Trp Arg Ala Lys Val Ala Lys Ile Pro Phe Asp
610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
            645                 650                 655

Leu Phe Glu Cys Ser Asn Val Tyr Val Ala Asp Ala Ser Leu Leu Pro
            660                 665                 670

Thr Ala Ser Gly Ala Asn Pro Met Val Thr Met Thr Leu Ala Arg
            675                 680                 685

His Val Ala Leu Gly Leu Ala Asp Ser Leu Lys Thr Lys Ala Lys Leu
            690                 695                 700

<210> SEQ ID NO 11
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Asn Thr Phe Leu Pro Asp Val Leu Glu Tyr Lys His Val Asp Thr
1               5                   10                  15
Leu Leu Leu Leu Cys Asp Gly Ile Ile His Glu Thr Thr Val Asp Gln
            20                  25                  30
Ile Lys Asp Ala Ile Ala Pro Asp Phe Pro Glu Asp Gln Tyr Glu Glu
        35                  40                  45
Tyr Leu Lys Thr Phe Thr Lys Pro Ser Glu Thr Pro Gly Phe Arg Glu
    50                  55                  60
Ala Val Tyr Asp Thr Ile Asn Ala Thr Pro Thr Asp Ala Val His Met
65                  70                  75                  80
Cys Ile Val Leu Thr Thr Ala Leu Asp Ser Arg Ile Leu Ala Pro Thr
                85                  90                  95
Leu Thr Asn Ser Leu Thr Pro Ile Lys Asp Met Thr Leu Lys Glu Arg
            100                 105                 110
Glu Gln Leu Leu Ala Ser Trp Arg Asp Ser Pro Ile Ala Ala Lys Arg
        115                 120                 125
Arg Leu Phe Arg Leu Ile Ser Ser Leu Thr Leu Thr Thr Phe Thr Arg
    130                 135                 140
Leu Ala Ser Glu Leu His Leu Lys Ala Ile His Tyr Pro Gly Arg Asp
145                 150                 155                 160
Leu Arg Glu Lys Ala Tyr Glu Thr Gln Val Val Asp Pro Phe Arg Tyr
                165                 170                 175
Ser Phe Met Glu Lys Pro Lys Phe Asp Gly Ala Glu Leu Tyr Leu Pro
            180                 185                 190
Asp Ile Asp Val Ile Ile Gly Ser Gly Ala Gly Ala Gly Val Met
        195                 200                 205
Ala His Thr Leu Ala Asn Asp Gly Phe Lys Thr Leu Val Leu Glu Lys
210                 215                 220
Gly Lys Tyr Phe Ser Asn Ser Glu Leu Asn Phe Asn Asp Ala Asp Gly
225                 230                 235                 240
Val Lys Glu Leu Tyr Gln Gly Lys Gly Ala Leu Ala Thr Thr Asn Gln
                245                 250                 255
Gln Met Phe Ile Leu Ala Gly Ser Thr Leu Gly Gly Thr Thr Val
            260                 265                 270
Asn Trp Ser Ala Cys Leu Lys Thr Pro Phe Lys Val Arg Lys Glu Trp
        275                 280                 285
Tyr Asp Glu Phe Gly Leu Glu Phe Ala Ala Asp Glu Ala Tyr Asp Lys
    290                 295                 300
Ala Gln Asp Tyr Val Trp Lys Gln Met Gly Ala Ser Thr Asp Gly Ile
305                 310                 315                 320
Thr His Ser Leu Ala Asn Glu Val Val Val Glu Gly Lys Lys Leu
                325                 330                 335
Gly Tyr Lys Ser Lys Glu Ile Glu Gln Asn Asn Gly His Pro Asp
            340                 345                 350
His Pro Cys Gly Phe Cys Tyr Leu Gly Cys Lys Tyr Gly Ile Lys Gln
        355                 360                 365
Gly Ser Val Asn Asn Trp Phe Arg Asp Ala Ala His Gly Ser Lys
    370                 375                 380
Phe Met Gln Gln Val Arg Val Val Gln Ile Leu Asn Lys Asn Gly Val
385                 390                 395                 400
Ala Tyr Gly Ile Leu Cys Glu Asp Val Glu Thr Gly Val Arg Phe Thr
                405                 410                 415
```

Ile Ser Gly Pro Lys Lys Phe Val Ser Ala Gly Ser Leu Asn Thr
            420                 425                 430

Pro Thr Val Leu Thr Asn Ser Gly Phe Lys Asn Lys His Ile Gly Lys
        435                 440                 445

Asn Leu Thr Leu His Pro Val Ser Thr Val Phe Gly Asp Phe Gly Arg
    450                 455                 460

Asp Val Gln Ala Asp His Phe His Lys Ser Ile Met Thr Ser Leu Cys
465                 470                 475                 480

Tyr Glu Val Ala Asp Leu Asp Gly Lys Gly His Gly Cys Arg Ile Glu
                485                 490                 495

Thr Ile Leu Asn Ala Pro Phe Ile Gln Ala Ser Leu Leu Pro Trp Arg
            500                 505                 510

Gly Ser Asp Glu Val Arg Arg Asp Leu Leu Arg Tyr Asn Asn Met Val
        515                 520                 525

Ala Met Leu Leu Ile Thr Arg Asp Thr Thr Ser Gly Ser Val Ser Ala
    530                 535                 540

Asp Pro Lys Lys Pro Asp Ala Leu Ile Val Asp Tyr Glu Ile Asn Lys
545                 550                 555                 560

Phe Asp Lys Asn Ala Ile Leu Gln Ala Phe Leu Ile Thr Ser Asp Met
                565                 570                 575

Leu Tyr Ile Glu Gly Ala Lys Arg Ile Leu Ser Pro Gln Pro Trp Val
            580                 585                 590

Pro Ile Phe Glu Ser Asn Lys Pro Lys Glu Gln Arg Thr Ile Lys Asp
        595                 600                 605

Lys Asp Tyr Val Glu Trp Arg Ala Lys Ala Ala Lys Ile Pro Phe Asp
610                 615                 620

Thr Tyr Gly Ser Ala Tyr Gly Ser Ala His Gln Met Ser Thr Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Val Leu Pro
            660                 665                 670

Thr Ala Ser Gly Ala Asn Pro Met Ile Ser Thr Met Thr Phe Ala Arg
        675                 680                 685

Gln Ile Ala Leu Gly Leu Ala Asp Ser Leu Lys Thr Lys Pro Lys Leu
    690                 695                 700

<210> SEQ ID NO 12
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asn Thr Phe Leu Pro Asp Val Leu Glu Tyr Lys His Val Asp Thr
1               5                   10                  15

Leu Leu Leu Leu Cys Asp Gly Ile Ile His Glu Thr Val Asp Gln
                20                  25                  30

Ile Arg Asp Ala Ile Ala Pro Asp Phe Pro Glu Asp Gln Tyr Glu Glu
            35                  40                  45

Tyr Leu Lys Thr Phe Thr Lys Pro Ser Glu Thr Pro Gly Phe Arg Glu
        50                  55                  60

Ala Val Tyr Asp Thr Ile Asn Ser Thr Pro Thr Glu Ala Val His Met
65                  70                  75                  80

```
Cys Ile Val Leu Thr Thr Ala Leu Asp Ser Arg Ile Leu Ala Pro Thr
                85                  90                  95

Leu Thr Asn Ser Leu Thr Pro Ile Lys Asp Met Thr Leu Lys Glu Arg
            100                 105                 110

Glu Gln Leu Leu Ala Ala Trp Arg Asp Ser Pro Ile Ala Ala Lys Arg
            115                 120                 125

Arg Leu Phe Arg Leu Ile Ser Ser Leu Thr Leu Thr Thr Phe Thr Arg
        130                 135                 140

Leu Ala Ser Asp Leu His Leu Arg Ala Ile His Tyr Pro Gly Arg Asp
145                 150                 155                 160

Leu Arg Glu Lys Ala Tyr Glu Thr Gln Val Val Asp Pro Phe Arg Tyr
                165                 170                 175

Ser Phe Met Glu Lys Pro Lys Phe Asp Gly Thr Glu Leu Tyr Leu Pro
            180                 185                 190

Asp Ile Asp Val Ile Ile Gly Ser Gly Ala Gly Ala Gly Val Met
            195                 200                 205

Ala His Thr Leu Ala Asn Asp Gly Tyr Lys Thr Leu Val Leu Glu Lys
        210                 215                 220

Gly Lys Tyr Phe Ser Asn Ser Glu Leu Asn Phe Asn Asp Ala Asp Gly
225                 230                 235                 240

Met Lys Glu Leu Tyr Gln Gly Lys Cys Ala Leu Thr Thr Thr Asn Gln
                245                 250                 255

Gln Met Phe Ile Leu Ala Gly Ser Thr Leu Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Leu Glu Phe Ala Ala Asp Glu Ala Tyr Asp Lys
290                 295                 300

Ala Gln Asp Tyr Val Trp Lys Gln Met Gly Ala Ser Thr Glu Gly Ile
305                 310                 315                 320

Thr His Ser Leu Ala Asn Ala Val Val Glu Gly Lys Lys Leu
            325                 330                 335

Gly Tyr Lys Ser Lys Glu Ile Glu Gln Asn Asn Gly Gly His Pro Asp
                340                 345                 350

His Pro Cys Gly Phe Cys Tyr Leu Gly Cys Lys Tyr Gly Ile Lys Gln
            355                 360                 365

Gly Ser Val Asn Asn Trp Phe Arg Asp Ala Ala His Gly Ser Lys
370                 375                 380

Phe Met Gln Gln Val Arg Val Val Gln Ile Leu His Asn Lys Gly Val
385                 390                 395                 400

Ala Tyr Gly Ile Leu Cys Glu Asp Val Glu Thr Gly Val Lys Phe Thr
                405                 410                 415

Ile Ser Gly Pro Lys Lys Phe Val Val Ser Ala Gly Ser Leu Asn Thr
            420                 425                 430

Pro Thr Val Leu Thr Asn Ser Gly Phe Lys Asn Lys His Ile Gly Lys
        435                 440                 445

Asn Leu Thr Leu His Pro Val Ser Thr Val Phe Gly Asp Phe Gly Arg
450                 455                 460

Asp Val Gln Ala Asp His Phe His Lys Ser Ile Met Thr Ser Leu Cys
465                 470                 475                 480

Tyr Glu Val Ala Asp Leu Asp Gly Lys Gly His Gly Cys Arg Ile Glu
                485                 490                 495

Thr Ile Leu Asn Ala Pro Phe Ile Gln Ala Ser Leu Leu Pro Trp Arg
```

|   |   |   |   |   | 500 |   |   |   |   | 505 |   |   |   |   | 510 |   |   |
|---|---|---|---|---|---|---|---|---|---|---|---|---|---|---|---|---|---|
| Gly | Ser | Asp | Glu | Val | Arg | Arg | Asp | Leu | Leu | Arg | Tyr | Asn | Asn | Met | Val | | |
| | | | | | 515 | | | | | 520 | | | | | 525 | | |

Ala Met Leu Leu Ile Thr Arg Asp Thr Thr Ser Gly Ser Val Ser Ala
    530                 535                 540

Asp Pro Lys Lys Pro Asp Ala Leu Ile Val Asp Tyr Asp Ile Asn Lys
545                 550                 555                 560

Phe Asp Lys Asn Ala Ile Leu Gln Ala Phe Leu Ile Thr Ser Asp Met
                565                 570                 575

Leu Tyr Ile Glu Gly Ala Lys Arg Ile Leu Ser Pro Gln Ala Trp Val
                580                 585                 590

Pro Ile Phe Glu Ser Asn Lys Pro Lys Glu Gln Arg Thr Ile Lys Asp
                595                 600                 605

Lys Asp Tyr Val Glu Trp Arg Ala Lys Ala Ala Lys Ile Pro Phe Asp
610                 615                 620

Thr Tyr Gly Ser Ala Tyr Gly Ser Ala His Gln Met Ser Thr Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Val Leu Pro
                660                 665                 670

Thr Ala Ser Gly Ala Asn Pro Met Ile Ser Thr Met Thr Phe Ala Arg
                675                 680                 685

Gln Ile Ala Leu Gly Leu Ala Asp Ser Leu Lys Thr Lys Pro Lys Leu
                690                 695                 700

<210> SEQ ID NO 13
<211> LENGTH: 1572
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atggccacac aagaaatcat cgattctgta cttccgtact tgaccaaatg gtacactgtg      60
attactgcag cagtattagt cttccttatc tccacaaaca tcaagaacta cgtcaaggca     120
aagaaattga atgtgtcga tccaccatac ttgaaggatg ccggtctcac tggtattctg     180
tctttgatcg ccgccatcaa ggccaagaac gacggtagat ggctaacttt gccgatgaa      240
gttttcgacg agtacccaaa ccacaccttc tacttgtctg ttgccggtgc tttgaagatt     300
gtcatgactg ttgacccaga aaacatcaag gctgtcttgg ccacccaatt cactgacttc     360
tccttgggta ccagacacgc ccactttgct cctttgttgg gtgacggtat cttccacttg     420
gacggagaag gttggaagca ctccagagct atgttgagac acagtttgc tagagaccag      480
attggacacg ttaaagcctt ggaaccacac atccaaatca tggctaagca gatcaagttg     540
aaccagggaa agactttcga tatccaagaa ttgttcttta gatttaccgt cgacaccgct     600
actgagttct gtttggtga atccgttcac tccttgtacg atgaaaaatt gggcatccca     660
actccaaacg aaatcccagg aagagaaaac tttgccgctg ctttcaacgt tcccaacac      720
tacttggcca ccagaagtta ctcccagact ttttactttt tgaccaaccc taaggaattc     780
agagactgta acgccaaggt ccaccacttg gccaagtact tgtcaacaa ggccttgaac      840
tttactcctg aagaactcga agagaaatcc aagtccggtt acgttttctt gtacgaattg     900
gttaagcaaa ccagagatcc aaaggtcttg caagatcaat tgttgaacat tatggttgcc     960
```

```
ggaagagaca ccactgccgg tttgttgtcc tttgctttgt ttgaattggc tagacaccca   1020
gagatgtggt ccaagttgag agaagaaatc gaagttaact ttggtgttgg tgaagactcc   1080
cgcgttgaag aaattacctt cgaagccttg aagagatgtg aatacttgaa ggctatcctt   1140
aacgaaacct tgcgtatgta cccatctgtt cctgtcaact ttagaaccgc caccagagac   1200
accactttgc caagaggtgg tggtgctaac ggtaccgacc caatctacat tcctaaaggc   1260
tccactgttg cttacgttgt ctacaagacc caccgtttgg aagaatacta cggtaaggac   1320
gctaacgact tcagaccaga agatggtttt gaaccatcta ctaagaagtt gggctgggct   1380
tatgttccat tcaacggtgg tccaagagtc tgcttgggtc aacaattcgc cttgactgaa   1440
gcttcttatg tgatcactag attggcccag atgtttgaaa ctgtctcatc tgatccaggt   1500
ctcgaatacc ctccaccaaa gtgtattcac ttgaccatga gtcacaacga tggtgtcttt   1560
gtcaagatgt aa                                                       1572
```

<210> SEQ ID NO 14
<211> LENGTH: 1569
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atgactgtac acgatattat cgccacatac ttcaccaaat ggtacgtgat agtaccactc     60
gctttgattg cttatagagt cctcgactac ttctatggca gatacttgat gtacaagctt    120
ggtgctaaac catttttcca gaaacagaca gacggctgtt tcggattcaa agctccgctt    180
gaattgttga agaagaagag cgacggtacc ctcatagact tcacactcca gcgtatccac    240
gatctcgatc gtcccgatat cccaactttc acattcccgg tcttttccat caaccttgtc    300 aataccottg agccggagaa catcaaggcc atcttggcca ctcagttcaa cgatttctcc    360
ttgggtacca gacactcgca cttttgctcct tgttgggtg atggtatctt tacgttggat    420
ggcgccggct ggaagcacag cagatctatg ttgagaccac agtttgccag agaacagatt    480
tcccacgtca agttgttgga gccacacgtt caggtgttct tcaaacacgt cagaaaggca    540
cagggcaaga cttttgacat ccaggaattg tttttcagat tgaccgtcga ctccgccacc    600 gagttttttgt ttggtgaatc cgttgagtcc ttgagagatg aatctatcgg catgtccatc    660
aatgcgcttg actttgacgg caaggctggc tttgctgatg cttttaacta ttcgcagaat    720
tatttggctt cgagagcggt tatgcaacaa ttgtactggg tgttgaacgg gaaaaagttt    780
aaggagtgca acgctaaagt gcacaagttt gctgactact acgtcaacaa ggcttttggac   840 ttgacgcctg aacaattgga aaagcaggat ggttatgtgt ttttgtacga attggtcaag    900
caaaccagag acaagcaagt gttgagagac caattgttga acatcatggt tgctggtaga    960
gacaccaccg ccggtttgtt gtcgtttgtt ttctttgaat tggccagaaa cccagaagtt   1020
accaacaagt tgagagaaga aattgaggac aagtttggac tcggtgagaa tgctagtgtt   1080
gaagacattt cctttgagtc gttgaagtcc tgtgaatact tgaaggctgt tctcaacgaa   1140
accttgagat tgtacccatc cgtgccacag aatttcagag ttgccaccaa gaacactacc   1200
ctcccaagag gtggtggtaa ggacgggttg tctcctgttt tggtgagaaa gggtcagacc   1260
gttatttacg tgtctacgc agcccacaga aacccagctg tttacggtaa ggacgctctt   1320
gagtttagac cagagagatg gtttgagcca gagacaaaga agcttggctg ggccttcctc   1380
```

| | |
|---|---|
| ccattcaacg gtggtccaag aatctgtttg ggacagcagt ttgccttgac agaagcttcg | 1440 |
| tatgtcactg tcaggttgct ccaggagttt gcacacttgt ctatggaccc agacaccgaa | 1500 |
| tatccaccta agaaaatgtc gcatttgacc atgtcgcttt tcgacggtgc caatattgag | 1560 |
| atgtattag | 1569 |

<210> SEQ ID NO 15
<211> LENGTH: 1569
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

| | |
|---|---|
| atgactgcac aggatattat cgccacatac atcaccaaat ggtacgtgat agtaccactc | 60 |
| gctttgattg cttatagggt cctcgactac ttttacggca gatacttgat gtacaagctt | 120 |
| ggtgctaaac cgttttttcca gaaacaaaca gacggttatt tcggattcaa agctccactt | 180 |
| gaattgttaa aaagaagag tgacggtacc ctcatagact tcactctcga gcgtatccaa | 240 |
| gcgctcaatc gtccagatat cccaactttt acattcccaa tcttttccat caaccttatc | 300 |
| agcacccttg agccggagaa catcaaggct atcttggcca cccagttcaa cgatttctcc | 360 |
| ttgggcacca gacactcgca ctttgctcct tgttgggcg atggtatctt taccttggac | 420 |
| ggtgccggct ggaagcacag cagatctatg ttgagaccac agtttgccag agaacagatt | 480 |
| tcccacgtca agtgttgga gccacacatg caggtgttct tcaagcacgt cagaaaggca | 540 |
| cagggcaaga cttttgacat ccaagaattg tttttcagat tgaccgtcga ctccgccact | 600 |
| gagttttgt ttggtgaatc cgttgagtcc ttgagagatg aatctattgg gatgtccatc | 660 |
| aatgcacttg actttgacgg caaggctggc tttgctgatg cttttaacta ctcgcagaac | 720 |
| tatttggctt cgagagcggt tatgcaacaa ttgtactggg tgttaacgg aaaaagttt | 780 |
| aaggagtgca acgctaaagt gcacaagttt gctgactatt acgtcagcaa ggctttggac | 840 |
| ttgacacctg aacaattgga aaagcaggat ggttatgtgt tcttgtacga gttggtcaag | 900 |
| caaaccagag acaggcaagt gttgagagac cagttgttga acatcatggt tgccggtaga | 960 |
| gacaccaccg ccggtttgtt gtcgtttgtt ttctttgaat tggccagaaa cccagaggtg | 1020 |
| accaacaagt tgagagaaga aatcgaggac aagtttggtc ttggtgagaa tgctcgtgtt | 1080 |
| gaagacattt cctttgagtc gttgaagtca tgtgaatact tgaaggctgt tctcaacgaa | 1140 |
| actttgagat tgtacccatc cgtgccacag aatttcagag ttgccaccaa aaacactacc | 1200 |
| cttccaaggg gaggtggtaa ggacgggtta tctcctgttt tggtcagaaa gggtcaaacc | 1260 |
| gttatgtacg gtgtctacgc tgcccacaga aacccagctg tctacggtaa ggacgccctt | 1320 |
| gagtttagac cagagaggtg gtttgagcca gagacaaaga agcttggctg ggccttcctt | 1380 |
| ccattcaacg gtggtccaag aatttgcttg ggacagcagt ttgccttgac agaagcttcg | 1440 |
| tatgtcactg tcagattgct ccaagagttt ggacacttgt ctatggaccc caacaccgaa | 1500 |
| tatccaccta ggaaaatgtc gcatttgacc atgtcccttt tcgacggtgc caacattgag | 1560 |
| atgtattag | 1569 |

<210> SEQ ID NO 16
<211> LENGTH: 1623
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 16

```
atgtcgtctt ctccatcgtt tgcccaagag gttctcgcta ccactagtcc ttacatcgag    60
tactttcttg acaactacac cagatggtac tacttcatac ctttggtgct tctttcgttg   120
aactttataa gtttgctcca cacaaggtac ttggaacgca ggttccacgc caagccactc   180
ggtaactttg tcagggaccc tacgtttggt atcgctactc cgttgctttt gatctacttg   240
aagtcgaaag gtacggtcat gaagtttgct tggggcctct ggaacaacaa gtacatcgtc   300
agagacccaa agtacaagac aactgggctc aggattgttg ccctcccatt gattgaaacc   360
atggacccag agaacatcaa ggctgttttg gctactcagt tcaatgattt ctctttggga   420
accagacacg atttcttgta ctccttgttg ggtgacggta ttttcacctt ggacggtgct   480
ggctggaaac atagtagaac tatgttgaga ccacagtttg ctagagaaca ggtttctcac   540
gtcaagttgt tggagccaca cgttcaggtg ttcttcaagc acgttagaaa gcaccgcggt   600
caaacgttcg acatccaaga attgttcttc aggttgaccg tcgactccgc caccgagttc   660
ttgtttggtg agtctgctga atccttgagg gacgaatcta ttggattgac cccaaccacc   720
aaggatttcg atggcagaag agatttcgct gacgctttca actattcgca gacttaccag   780
gcctacagat ttttgttgca acaaatgtac tggatcttga atggctcgga attcagaaag   840
tcgattgctg tcgtgcacaa gtttgctgac cactatgtgc aaaaggcttt ggagttgacc   900
gacgatgact tgcagaaaca agacggctat gtgttcttgt acgagttggc taagcaaacc   960
agagacccaa aggtcttgag agaccagtta ttgaacattt tggttgccgg tagagacacg  1020
accgccggtt tgttgtcatt tgttttctac gagttgtcaa gaaaccctga ggtgtttgct  1080
aagttgagag aggaggtgga aaacagattt ggactcggtg aagaagctcg tgttgaagag  1140
atctcgtttg agtccttgaa gtcttgtgag tacttgaagg ctgtcatcaa tgaaaccttg  1200
agattgtacc catcggttcc acacaacttt agagttgcta ccagaaacac taccctccca  1260
agaggtggtg gtgaagatgg atactcgcca attgtcgtca agaagggtca agttgtcatg  1320
tacactgtta ttgctaccca cagagaccca agtatctacg gtgccgacgc tgacgtcttc  1380
agaccagaaa gatggtttga accagaaact agaaagttgg gctgggcata cgttccattc  1440
aatggtggtc aagaatctgt ttgggtcaa cagtttgcct tgaccgaagc ttcatacgtc  1500
actgtcagat tgctccagga gtttgcacac ttgtctatgg acccagacac cgaatatcca  1560
ccaaaattgc agaacacctt gaccttgtcg ctctttgatg gtgctgatgt tagaatgtac  1620
taa                                                                1623
```

<210> SEQ ID NO 17
<211> LENGTH: 1623
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
atgtcgtctt ctccatcgtt tgctcaggag gttctcgcta ccactagtcc ttacatcgag    60
tactttcttg acaactacac cagatggtac tacttcatcc ctttggtgct tctttcgttg   120
aacttcatca gcttgctcca cacaaagtac ttggaacgca ggttccacgc caagccgctc   180
ggtaacgtcg tgttggatcc tacgtttggt atcgctactc cgttgatctt gatctactta   240
aagtcgaaag gtacagtcat gaagtttgcc tggagcttct ggaacaacaa gtacattgtc   300
```

| | |
|---|---|
| aaagacccaa agtacaagac cactggcctt agaattgtcg gcctcccatt gattgaaacc | 360 |
| atagacccag agaacatcaa agctgtgttg gctactcagt tcaacgattt ctccttggga | 420 |
| actagacacg atttcttgta ctccttgttg ggcgatggta tttttacctt ggacggtgct | 480 |
| ggctggaaac acagtagaac tatgttgaga ccacagtttg ctagagaaca ggtttcccac | 540 |
| gtcaagttgt tggaaccaca cgttcaggtg ttcttcaagc acgttagaaa acaccgcggt | 600 |
| cagactttg acatccaaga attgttcttc agattgaccg tcgactccgc caccgagttc | 660 |
| ttgtttggtg agtctgctga atccttgaga gacgactctg ttggtttgac cccaaccacc | 720 |
| aaggatttcg aaggcagagg agatttcgct gacgctttca actactcgca gacttaccag | 780 |
| gcctacagat ttttgttgca acaaatgtac tggattttga atggcgcgga attcagaaag | 840 |
| tcgattgcca tcgtgcacaa gtttgctgac cactatgtgc aaaaggcttt ggagttgacc | 900 |
| gacgatgact tgcagaaaca agacggctat gtgttcttgt acgagttggc taagcaaact | 960 |
| agagacccaa aggtcttgag agaccagttg ttgaacattt tggttgccgg tagagacacg | 1020 |
| accgccggtt tgttgtcgtt tgtgttctac gagttgtcga gaaaccctga agtgtttgcc | 1080 |
| aagttgagag aggaggtgga aaacagattt ggactcggcg aagaggctcg tgttgaagag | 1140 |
| atctctttg agtccttgaa gtcctgtgag tacttgaagg ctgtcatcaa tgaagccttg | 1200 |
| agattgtacc catctgttcc acacaacttc agagttgcca ccagaaacac tacccttcca | 1260 |
| agaggcggtg gtaaagacgg atgctcgcca attgttgtca agaagggtca agttgtcatg | 1320 |
| tacactgtca ttggtaccca cagagaccca agtatctacg gtgccgacgc cgacgtcttc | 1380 |
| agaccagaaa gatggttcga gccagaaact agaaagttgg gctgggcata tgttccattc | 1440 |
| aatggtggtc caagaatctg tttgggtcag cagtttgcct tgactgaagc ttcatacgtc | 1500 |
| actgtcagat tgctccaaga gtttggaaac ttgtccctgg atccaaacgc tgagtaccca | 1560 |
| ccaaaattgc agaacacctt gaccttgtca ctctttgatg gtgctgacgt tagaatgttc | 1620 |
| taa | 1623 |

<210> SEQ ID NO 18
<211> LENGTH: 1554
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

| | |
|---|---|
| atgattgaac aactcctaga atattggtat gtcgttgtgc cagtgttgta catcatcaaa | 60 |
| caactccttg catacacaaa gactcgcgtc ttgatgaaaa agttgggtgc tgctccagtc | 120 |
| acaaacaagt tgtacgacaa cgctttcggt atcgtcaatg gatggaaggc tctccagttc | 180 |
| aagaaagagg gcagggctca agagtacaac gattacaagt tgaccactc caagaaccca | 240 |
| agcgtgggca cctacgtcag tattctttc ggcaccagga tcgtcgtgac caaagatcca | 300 |
| gagaatatca agctattttt ggcaacccag tttggtgatt tttctttggg caagaggcac | 360 |
| actcttttta agcctttgtt aggtgatggg atcttcacat tggacggcga aggctggaag | 420 |
| cacagcagag ccatgttgag accacagttt gccagagaac aagttgctca tgtgacgtcg | 480 |
| ttggaaccac acttccagtt gttgaagaag catattctta agcacaaggg tgaatacttt | 540 |
| gatatccagg aattgttctt tagatttacc gttgattcgg ccacggagtt cttatttggt | 600 |
| gagtccgtgc actccttaaa ggacgaatct attggtatca accaagacga tatagatttt | 660 |

```
gctggtagaa aggactttgc tgagtcgttc aacaaagccc aggaatactt ggctattaga    720
accttggtgc agacgttcta ctggttggtc aacaacaagg agtttagaga ctgtaccaag    780
ctggtgcaca agttcaccaa ctactatgtt cagaaagctt tggatgctag cccagaagag    840
cttgaaaagc aaagtgggta tgtgttcttg tacgagcttg tcaagcagac aagagacccc    900
aatgtgttgc gtgaccagtc tttgaacatc ttgttggccg aagagacac cactgctggg    960 ttgttgtcgt ttgctgtctt tgagttggcc agacacccag agatctgggc caagttgaga   1020
gaggaaattg aacaacagtt tggtcttgga aagactctc gtgttgaaga gattaccttt   1080
gagagcttga agagatgtga gtacttgaaa gcgttcctta atgaaacctt gcgtatttac   1140
ccaagtgtcc aagaaacttt cagaatcgcc accaagaaca cgacattgcc aagggggggt   1200
ggttcagacg gtacctcgcc aatcttgatc caaaagggag aagctgtgtc gtatggtatc   1260
aactctactc atttggaccc tgtctattac ggccctgatg ctgctgagtt cagaccagag   1320
agatggtttg agccatcaac caaaaagctc ggctgggctt acttgccatt caacggtggt   1380
ccaagaatct gtttgggtca gcagtttgcc ttgacggaag ctggctatgt gttggttaga   1440
ttggtgcaag agttctccca cgttaggctg gacccagacg aggtgtaccc gccaaagagg   1500
ttgaccaact tgaccatgtg tttgcaggat ggtgctattg tcaagtttga ctag          1554

<210> SEQ ID NO 19
<211> LENGTH: 1554
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgattgaac aaatcctaga atattggtat attgttgtgc ctgtgttgta catcatcaaa     60
caactcattg cctacagcaa gactcgcgtc ttgatgaaac agttgggtgc tgctccaatc    120
acaaaccagt tgtacgacaa cgttttcggt atcgtcaacg gatggaaggc tctccagttc    180
aagaaagagg gcagagctca agagtacaac gatcacaagt tgacagctc caagaaccca    240 agcgtcggca cctatgtcag tattcttttt ggcaccaaga ttgtcgtgac caaggatcca    300
gagaatatca aagctatttt ggcaacccag tttggcgatt tttcttggg caagagacac    360 gctcttttta aacctttgtt aggtgatggg atcttcacct tggacggcga aggctggaag    420
catagcagat ccatgttaag accacagttt gccagagaac aagttgctca tgtgacgtcg    480
ttggaaccac acttccagtt gttgaagaag catatcctta acacaagggt gagtactttt    540
gatatccagg aattgttctt tagatttact gtcgactcgg ccacggagtt cttatttggt    600
gagtccgtgc actccttaaa ggacgaaact atcggtatca accaagacga tatagatttt    660
gctggtagaa aggactttgc tgagtcgttc aacaaagccc aggagtattt gtctattaga    720
attttggtgc agaccttcta ctggttgatc aacaacaagg agtttagaga ctgtaccaag    780
ctggtgcaca agtttaccaa ctactatgtt cagaaagctt tggatgctac cccagaggaa    840
cttgaaaagc aaggcgggta tgtgttcttg tatgagcttg tcaagcagac gagagacccc    900
aaggtgttgc gtgaccagtc tttgaacatc ttgttggcag aagagacac cactgctggg    960 ttgttgtcct ttgctgtgtt tgagttggcc agaacccac acatctgggc caagttgaga   1020
gaggaaattg aacagcagtt tggtcttgga aagactctc gtgttgaaga gattaccttt   1080
gagagcttga agagatgtga gtacttgaaa gcgttcctta acgaaacctt gcgtgtttac   1140
ccaagtgtcc aagaaacttt cagaatcgcc accaagaata caacattgcc aagggtggt   1200
```

```
ggtccagacg gtacccagcc aatcttgatc caaaagggag aaggtgtgtc gtatggtatc    1260
aactctaccc acttagatcc tgtctattat ggccctgatg ctgctgagtt cagaccagag    1320
agatggtttg agccatcaac cagaaagctc ggctgggctt acttgccatt caacggtggg    1380
ccacgaatct gtttgggtca gcagtttgcc ttgaccgaag ctggttacgt tttggtcaga    1440
ttggtgcaag agttctccca cattaggctg gacccagatg aagtgtatcc accaaagagg    1500
ttgaccaact tgaccatgtg tttgcaggat ggtgctattg tcaagtttga ctag          1554

<210> SEQ ID NO 20
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atgctcgatc agatcttaca ttactggtac attgtcttgc cattgttggc cattatcaac      60
cagatcgtgg ctcatgtcag gaccaattat ttgatgaaga aattgggtgc taagccattc     120
acacacgtcc aacgtgacgg gtggttgggc ttcaaattcg gccgtgaatt cctcaaagca     180
aaaagtgctg ggagactggt tgatttaatc atctcccgtt ccacgataaa tgaggacact     240
ttctccagct atgcttttgg caaccatgtg gtgttcacca gggaccccga gaatatcaag     300
gcgcttttgg caacccagtt tggtgatttt tcattgggca gcagggtcaa gttcttcaaa     360
ccattattgg ggtacggtat cttcacattg gacgccgaag gctggaagca cagcagagcc     420
atgttgagac acagtttgc cagagaacaa gttgctcatg tgacgtcgtt ggaaccacac      480
ttccagttgt tgaagaagca tatccttaaa cacaaggggtg agtactttga tatccaggaa    540 ttgttctttta gatttactgt cgactcggcc acggagttct tatttggtga gtccgtgcac    600
tccttaaagg acgaggaaat tggctacgac acgaaagaca tgtctgaaga agacgcaga     660 tttgccgacg cgttcaacaa gtcgcaagtc tacgtggcca ccagagttgc tttacagaac    720
ttgtactggt tggtcaacaa caaagagttc aaggagtgca tgacattgt ccacaagttt     780 accaactact atgttcagaa agccttggat gctaccccag aggaacttga aaagcaaggc    840
gggtatgtgt tcttgtatga gcttgtcaag cagacgagag accccaaggt gttgcgtgac    900
cagtctttga acatcttgtt ggcaggaaga gacaccactg ctgggttgtt gtcctttgct    960
gtgtttgagt tggccagaaa cccacacatc tgggccaagt tgagagagga aattgaacag   1020
cagtttggtc ttggagaaga ctctcgtgtt gaagagatta cctttgagag cttgaagaga   1080
tgtgagtact tgaaggccgt gttgaacgaa actttgagat acacccaag tgtcccaaga    1140 aacgcaagat ttgcgattaa agacacgact ttaccaagag gcggtggccc caacggcaag   1200
gatcctatct tgatcaggaa ggatgaggtg gtgcagtact ccatctcggc aactcagaca   1260
aatcctgctt attatggcgc cgatgctgct gattttagac cggaaagatg gtttgaacca   1320
tcaactagaa acttgggatg ggctttcttg ccattcaacg tggtccaag aatctgtttg    1380 ggacaacagt ttgctttgac tgaagccggt tacgttttgg ttagacttgt tcaggagttt   1440
ccaaacttgt cacaagaccc cgaaaccaag tacccaccac ctagattggc acacttgacg   1500
atgtgcttgt ttgacggtgc acacgtcaag atgtcatag                         1539

<210> SEQ ID NO 21
<211> LENGTH: 1539
<212> TYPE: DNA
```

```
<213> ORGANISM: Artificial Sequence
<220> FEATURE:
<223> OTHER INFORMATION: Description of Artificial Sequence: Synthetic
      polynucleotide

<400> SEQUENCE: 21
atgctcgacc agatcttcca ttactggtac attgtcttgc cattgttggt cattatcaag      60
cagatcgtgg ctcatgccag gaccaattat tgatgaaga agttgggcgc taagccattc     120
acacatgtcc aactagacgg gtggtttggc ttcaaatttg ccgtgaatt cctcaaagct     180 aaaagtgctg ggaggcaggt tgatttaatc atctcccgtt tccacgataa tgaggacact     240
ttctccagct atgcttttgg caaccatgtg gtgttcacca gggaccccga gaatatcaag     300
gcgcttttgg caacccagtt tggtgatttt tcattgggaa gcagggtcaa attcttcaaa     360
ccattgttgg ggtacggtat cttcaccttg gacggcgaag gctggaagca cagcagagcc     420
atgttgagac acagtttgc cagagagcaa gttgctcatg tgacgtcgtt ggaaccacat     480
ttccagttgt tgaagaagca tattcttaag cacaaggggtg aatactttga tatccaggaa     540 ttgttctttta gatttaccgt tgattcagcg acggagttct tatttggtga gtccgtgcac     600
tccttaaggg acgaggaaat tggctacgat acgaaggaca tggctgaaga agacgcaaa     660 tttgccgacg cgttcaacaa gtcgcaagtc tatttgtcca ccagagttgc tttacagaca     720
ttgtactggt tggtcaacaa caaagagttc aaggagtgca cgacattgt ccacaagttc     780 accaactact atgttcagaa agccttggat gctaccccag aggaacttga aaaacaaggc     840
gggtatgtgt tcttgtacga gcttgccaag cagacgaaag accccaatgt gttgcgtgac     900
cagtctttga acatcttgtt ggctggaagg gacaccactg ctgggttgtt gtcctttgct     960
gtgtttgagt tggccaggaa cccacacatc tgggccaagt tgagagagga aattgaatca    1020
cactttgggc tgggtgagga ctctcgtgtt gaagagatta cctttgagag cttgaagaga    1080
tgtgagtact tgaaagccgt gttgaacgaa acgttgagat tacacccaag tgtcccaaga    1140
aacgcaagat tgcgattaa agacacgact ttaccaagag gcggtggccc caacggcaag    1200
gatcctatct tgatcagaaa gaatgaggtg gtgcaatact ccatctcggc aactcagaca    1260
aatcctgctt attatggcgc cgatgctgct gattttagac cggaaagatg gtttgagcca    1320
tcaactagaa acttgggatg gcttacttg ccattcaacg gtggtccaag aatctgcttg    1380
ggacaacagt ttgctttgac cgaagccggt tacgttttgg ttagacttgt tcaggaattc    1440
cctagcttgt cacaggaccc cgaaactgag tacccaccac ctagattggc acacttgacg    1500
atgtgcttgt ttgacggggc atacgtcaag atgcaatag                           1539

<210> SEQ ID NO 22
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atggctatat ctagtttgct atcgtgggat gtgatctgtg tcgtcttcat ttgcgtttgt      60
gtttatttcg ggtatgaata ttgttatact aaatacttga tgcacaaaca tggcgctcga     120
gaaatcgaga atgtgatcaa cgatgggttc tttgggttcc gcttaccttt gctactcatg     180
cgagccagca atgagggccg acttatcgag ttcagtgtca agagattcga gtcggcgcca     240
catccacaga acaagacatt ggtcaaccgg gcattgagcg ttcctgtgat actcaccaag     300
```

-continued

```
gacccagtga atatcaaagc gatgctatcg acccagtttg atgactttc ccttgggttg    360 agactacacc agtttgcgcc gttgttgggg aaaggcatct ttactttgga cggcccagag    420
tggaagcaga gccgatctat gttgcgtccg caatttgcca agatcgggt ttctcatatc    480 ctggatctag aaccgcattt tgtgttgctt cggaagcaca ttgatggcca caatggagac    540
tacttcgaca tccaggagct ctacttccgg ttctcgatgg atgtggcgac ggggttttg    600 tttggcgagt ctgtggggtc gttgaaagac gaagatgcga ggttcctgga agcattcaat    660
gagtcgcaga agtatttggc aactagggca acgttgcacg agttgtactt tctttgtgac    720
gggtttaggt ttcgccagta caacaaggtt gtgcgaaagt tctgcagcca gtgtgtccac    780
aaggcgttag atgttgcacc ggaagacacc agcgagtacg tgtttctccg cgagttggtc    840
aaacacactc gagatcccgt tgttttacaa gaccaagcgt tgaacgtctt gcttgctgga    900
cgcgacacca ccgcgtcgtt attatcgttt gcaacatttg agctagcccg gaatgaccac    960
atgtggagga agctacgaga ggaggttatc ctgacgatgg gaccgtccag tgatgaaata   1020
accgtggccg ggttgaagag ttgccgttac ctcaaagcaa tcctaaacga aactcttcga   1080
ctatacccaa gtgtgcctag gaacgcgaga tttgctacga ggaatacgac gcttcctcgt   1140
ggcggaggtc cagatggatc gtttccgatt ttgataagaa agggccagcc agtggggtat   1200
ttcatttgtg ctacacactt gaatgagaag gtatatggga atgatagcca tgtgtttcga   1260
ccggagagat gggctgcgtt agagggcaag agtttgggct ggtcgtatct tccattcaac   1320
ggcggcccga gaagctgcct tggtcagcag tttgcaatcc ttgaagcttc gtatgttttg   1380
gctcgattga cacagtgcta cacgacgata cagcttagaa ctaccgagta cccaccaaag   1440
aaactcgttc atctcacgat gagtcttctc aacggggtgt acatccgaac tagaacttga   1500
```

<210> SEQ ID NO 23
<211> LENGTH: 3150
<212> TYPE: DNA
<213> ORGANISM: Bacillus megaterium

<400> SEQUENCE: 23

```
atgacaatta aagaaatgcc tcagccaaaa acgtttggag agcttaaaaa tttaccgtta     60
ttaaacacag ataaaccggt tcaagctttg atgaaaattg cggatgaatt aggagaaatc    120
tttaaattcg aggcgcctgg tcgtgtaacg cgctacttat caagtcagcg tctaattaaa    180
gaagcatgcg atgaatcacg ctttgataaa aacttaagtc aagcgcttaa atttgtacgt    240
gattttgcag agacggggtt atttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga cgacctagt agataaaatt    660 attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
```

```
gaagcgctgc gcttatggcc aactgctcct gcgttttccc tatatgcaaa agaagatacg    1020
gtgcttggag gagaatatcc tttagaaaaa ggcgacgaac taatggttct gattcctcag    1080
cttcaccgtg ataaaacaat ttggggagac gatgtggaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctggata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg ctttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc cgcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                    3150

<210> SEQ ID NO 24
<211> LENGTH: 2043
<212> TYPE: DNA
<213> ORGANISM: Candida tropicalis
```

<400> SEQUENCE: 24

```
atggcattag ataagttaga tttatatgtt attataacat tggtggttgc aattgcagct    60
tattttgcaa agaatcagtt tcttgaccaa caacaagata ccgggttcct taatactgat   120
agtggagatg gtaattcaag agatatctta caagctttga agaagaacaa taaaaatacg   180
ttattattat ttggatccca aacaggtaca gcagaagatt atgccaacaa attgtcaaga   240
gaattgcatt caagatttgg tttgaaaacc atggttgctg atttcgctga ttatgatttc   300
gaaaacttcg gagatattac tgaagatatc ttggttttct ttattgttgc tacttatggt   360
gaaggtgaac caaccgataa tgctgacgaa tttcacactt ggttgactga agaagctgac   420
accttgagta ctttgaaata tactgttttt ggtttgggta attcaactta tgaattcttc   480
aatgctattg gtagaaaatt tgacagattg ttgggagaaa aggtggtgga cagatttgct   540
gaatacggtg aaggtgacga tggtactggt actttagatg aagatttctt ggcctggaag   600
gataacgtgt ttgattcctt aaagaatgat ttgaattttg aagaaaaga gttgaaatac   660
gaaccaaatg ttaaattgac tgaaagagat gatttatctg gcaatgatcc agatgtctcc   720
ttgggtgaac aaatgtcaa atacattaaa tctgaaggtg ttgacttaac taaaggtcca   780
tttgatcata ctcatccatt tttggctaga attgttaaaa ctaaagaatt gtttacttct   840
gaagacagac attgtgttca tgttgaattt gatatttctg aatcaaactt gaaatatacc   900
accggtgatc atcttgcaat ctggccatct aactctgatg aaaacattaa gcaatttgcc   960
aaatgttttg gttagaaga caaacttgat actgttattg aattgaaagc tttggattcc  1020
acttattcca tcccattccc taatccaatc acttatggag ctgttattag acaccatttg  1080
gaaatttcag gtcctgtttc tagacaattt ttcttatcta ttgctggatt tgcccctgat  1140
gaagaaacta aaagtcatt tactagaatt ggtggtgata agcaagaatt tgctagtaaa  1200
gtcacccgta gaaaattcaa cattgccgat gctttattat ttgcttccaa caacagacca  1260
tggtccgatg ttccattcga attccttatt gaaaatgtcc aacacttaac tcctcgttat  1320
tactccattt cttcttcctc attaagtgaa aagcaaacca ttaatgttac tgctgttgtt  1380
gaagccgaag aagaagctga tggaagacca gttactggtg ttgtcaccaa cttgttgaag  1440
aatattgaaa ttgaacaaaa caaaactggt gaaaccccaa tggttcatta tgatttgaat  1500
ggtccaagag gcaaatttag caagttcaga ttgccagttc acgttagaag atctaatttc  1560
aaattaccaa agaatagcac taccccagtt attttgattg gtccaggtac cggtgttgca  1620
ccattgagag gttttgttag agaaagagtt caacaagtta aaaatggtgt taatgttggt  1680
aagactgtat tgttttatgg atgtagaaat tccgaacaag atttcttgta caaacaagaa  1740
tggagtgaat atgcctcagt attgggagaa aatttcgaaa tgtttaatgc cttctcaaga  1800
caagatccaa ctaagaaagt ttatgttcaa gataagattt tagaaaatag tgctcttgtt  1860
gatgagttat tatctagtgg agcaattatt tatgtttgtg gtgatgccag tagaatggct  1920
agagatgttc aagctgcaat tgccaagatt gttgccaaaa gtagagatat ccacgaagat  1980
aaagctgctg aattggttaa atcttggaaa gttcaaaata gataccaaga agatgtctgg  2040
taa                                                                2043
```

<210> SEQ ID NO 25
<211> LENGTH: 2040
<212> TYPE: DNA
<213> ORGANISM: Candida tropicalis

<400> SEQUENCE: 25

```
atggctttag acaagttaga tttgtatgtc atcataacat tggtggtcgc tgtagccgcc    60
tattttgcta agaaccagtt ccttgatcag ccccaggaca ccgggttcct caacacggac   120
agcggaagca actccagaga cgtcttgctg acattgaaga gaataataa aaacacgttg    180
ttgttgtttg ggtcccagac gggtacggca gaagattacg ccaacaaatt gtccagagaa   240
ttgcactcca gatttggctt gaaaacgatg gttgcagatt cgctgatta cgattgggat    300
aacttcggag atatcaccga agacatcttg gtgttttca ttgttgccac ctatggtgag    360
ggtgaaccta ccgataatgc cgacgagttc cacacctggt tgactgaaga agctgacact   420
ttgagtacct tgaaatacac cgtgttcggg ttgggtaact ccacgtacga gttcttcaat   480
gccattggta gaaagtttga cagattgttg agcgagaaag gtggtgacag gtttgctgaa   540
tacgctgaag gtgatgacgg tactggcacc ttggacgaag atttcatggc ctggaaggac   600
aatgtctttg acgccttgaa gaatgatttg aactttgaag aaaaggaatt gaagtacgaa    660
ccaaacgtga aattgactga gagagacgac ttgtctgctg ctgactccca gtttccttg    720
ggtgagccaa caagaagta catcaactcc gagggcatcg acttgaccaa gggtccattc    780
gaccacaccc acccatactt ggccagaatc ccgagacga gagagttgtt cagctccaag    840
gacagacact gtatccacgt tgaatttgac atttctgaat cgaacttgaa atacaccacc    900
ggtgaccatc tagctatctg gccatccaac tccgacgaaa acattaagca atttgccaag    960
tgtttcggat tggaagataa actcgacact gttattgaat tgaaggcgtt ggactccact   1020
tacaccatcc cattcccaac cccaattacc tacggtgctg tcattagaca ccatttagaa   1080
atctccggtc cagtctcgag acaattcttt ttgtcaattg ctgggtttgc tcctgatgaa   1140
gaaacaaaga aggcttttac cagacttggt ggtgacaagc aagaattcgc cgccaaggtc   1200
acccgcagaa agttcaacat tgccgatgcc ttgttatatt cctccaacaa cgctccatgg   1260
tccgatgttc cttttgaatt ccttattgaa aacgttccac acttgactcc acgttactac   1320
tccatttcgt cttcgtcatt gagtgaaaag caactcatca acgttactgc agttgttgaa   1380
gccgaagaag aagctgatgg cagaccagtc actggtgttg tcaccaactt gttgaagaac   1440
gttgaaattg tgcaaaacaa gactggcgaa aagccacttg tccactacga tttgagcggc   1500
ccaagaggca agttcaacaa gttcaagttg ccagtgcatg tgagaagatc caactttaag   1560
ttgccaaaga actccaccac cccagttatc ttgattggtc caggtactgg tgttgcccca   1620
ttgagaggtt ttgtcagaga aagagttcaa caagtcaaga tggtgtcaa tgttggcaag   1680
actttgttgt tttatggttg cagaaactcc aacgaggact ttttgtacaa gcaagaatgg   1740
gccgagtacg cttctgtttt gggtgaaaac tttgagatgt tcaatgcctt ctccagacaa   1800
gacccatcca gaaggttta cgtccaggat aagattttag aaaacagcca acttgtgcac   1860
gagttgttga ctgaaggtgc cattatctac gtctgtggtg atgccagtag aatggctaga   1920
gacgtgcaga ccacaatttc caagattgtt gctaaaagca gagaaattag tgaagacaag   1980
gctgctgaat tggtcaagtc ctggaaggtc caaaatagat accaagaaga tgtttggtag   2040
```

<210> SEQ ID NO 26
<211> LENGTH: 2040
<212> TYPE: DNA
<213> ORGANISM: Candida tropicalis

<400> SEQUENCE: 26

```
atggctttag acaagttaga tttgtatgtc atcataacat tggtggtcgc tgtggccgcc    60
tattttgcta agaaccagtt ccttgatcag ccccaggaca ccgggttcct caacacggac   120
```

```
agcggaagca actccagaga cgtcttgctg acattgaaga agaataataa aaacacgttg    180
ttgttgtttg ggtcccagac cggtacggca gaagattacg ccaacaaatt gtcaagagaa    240
ttgcactcca gatttggctt gaaaaccatg gttgcagatt cgctgattac gattgggat     300 aacttcggag atatcaccga agatatcttg gtgtttttca tcgttgccac ctacggtgag    360
ggtgaaccta ccgacaatgc cgacgagttc cacacctggt tgactgaaga agctgacact    420
ttgagtactt tgagatatac cgtgttcggg ttgggtaact ccacctacga gttcttcaat    480
gctattggta gaaagtttga cagattgttg agtgagaaag gtggtgacag atttgctgaa    540
tatgctgaag gtgacgacgg cactggcacc ttggacgaag atttcatggc ctggaaggat    600
aatgtctttg acgccttgaa gaatgacttg aactttgaag aaaaggaatt gaagtacgaa    660
ccaaacgtga aattgactga gagagatgac ttgtctgctg ccgactccca gtttccttg     720 ggtgagccaa caagaagta catcaactcc gagggcatcg acttgaccaa gggtccattc     780
gaccacaccc acccatactt ggccaggatc accgagacca gagagttgtt cagctccaag    840
gaaagacact gtattcacgt tgaatttgac atttctgaat cgaacttgaa atacaccacc    900
ggtgaccatc tagccatctg gccatccaac tccgacgaaa acatcaagca atttgccaag    960
tgtttcggat tggaagataa actcgacact gttattgaat tgaaggcatt ggactccact   1020
tacaccattc cattcccaac tccaattact tacggtgctg tcattagaca ccatttagaa   1080
atctccggtc cagtctcgag acaattcttt ttgtcgattg ctgggtttgc tcctgatgaa   1140
gaaacaaaga agactttcac cagacttggt ggtgacaaac aagaattcgc caccaaggtt   1200
acccgcagaa agttcaacat tgccgatgcc ttgttatatt cctccaacaa cactccatgg   1260
tccgatgttc cttttgagtt ccttattgaa aacatccaac acttgactcc acgttactac   1320
tccatttctt cttcgtcgtt gagtgaaaaa caactcatca atgttactgc agtcgttgag   1380
gccgaagaag aagccgatgg cagaccagtc actggtgttg ttaccaactt gttgaagaac   1440
attgaaattg cgcaaaacaa gactggcgaa aagccacttg ttcactacga tttgagcggc   1500
ccaagaggca gttcaacaa gttcaagttg ccagtgcacg tgagaagatc caactttaag   1560
ttgccaaaga actccaccac cccagttatc ttgattggtc caggtactgg tgttgcccca   1620
ttgagaggtt tcgttagaga aagagttcaa caagtcaaga atggtgtcaa tgttggcaag   1680
actttgttgt tttatggttg cagaaactcc aacgaggact ttttgtacaa gcaagaatgg   1740
gccgagtacg cttctgtttt gggtgaaaac tttgagatgt tcaatgcctt ctctagacaa   1800
gacccatcca gaaggtttta cgtccaggat aagattttag aaaacagcca acttgtgcac   1860
gaattgttga ccgaaggtgc cattatctac gtctgtggtg acgccagtag aatggccaga   1920
gacgtccaga ccacgatctc caagattgtt gccaaaagca gagaaatcag tgaagacaag   1980
gccgctgaat tggtcaagtc ctggaaagtc caaaatagat accaagaaga tgtttggtag   2040
```

<210> SEQ ID NO 27
<211> LENGTH: 996
<212> TYPE: DNA
<213> ORGANISM: Candida tropicalis

<400> SEQUENCE: 27

```
atgattgttt tattcatcct tgtatttatt tgtctatctt cagccgggaa accaaacaaa     60
ccagaagctc cagcaaaaga ttacatcaaa ctcgttgaat tctccaattt tgccgccgtt    120
ggctactgcg ttaatagagg tctagcaaag ggccgtctag agacgaggca ctccaactgt    180
gccttgttgg catgcaagaa cgacttcctt gcggacgtcg agattattaa gatatttgac    240
```

```
ttcaaccgtc ttaatgaagt tggaacaggt tactatgcct tggacaggaa gagaaaggca    300
ataatattgg tatttagagg gtctgtctcc cgacgtgact gggcgacaga catggatttc    360
atccccactt cttacaagcc aattgtgtat gaggaaaact ttggttgtga cccctacatt    420
ctgaccgaat gcaagaactg tcgtgtgcac cgtggtttct acaatttctt gaaggataac    480
tctgcagcaa ttatcaccga gggaattgcg ttgaaagaag agtacccgga ctaccagttc    540
ttgatcattg gtcattcttt gggcgctgcc ttgacaatgt tgagtggcat cgagttccag    600 ttgttgggt acgatccttt ggtggtgact tatggtggtc aaaggtggg caaccaagag      660 tttgctgact tcacggacaa cttgtttgac acggatgagg tggacaatga aatcgccacc    720
aaccgtgatt tttcaagagg attcattaga gtggtacaca agtatgatat aataccattc    780
ttgccgccgt tgtttagtca cgcagggtac gaatacttta ttgacaagag agagttgccc    840
catgaagaat gtgatttgga cagacgaggc atggagtact cggggatatt taagagatcg    900
ctgaccataa aaccgtccac tttatggcca gataggttgg ggaagtatga acatacacat    960
tattttagaa gaatcactag ttgtagggac gacgat                              996

<210> SEQ ID NO 28
<211> LENGTH: 332
<212> TYPE: PRT
<213> ORGANISM: Candida tropicalis

<400> SEQUENCE: 28

Met Ile Val Leu Phe Ile Leu Val Phe Ile Cys Leu Ser Ser Ala Gly
1               5                   10                  15

Lys Pro Asn Lys Pro Glu Ala Pro Ala Lys Asp Tyr Ile Lys Leu Val
                20                  25                  30

Glu Phe Ser Asn Phe Ala Ala Val Gly Tyr Cys Val Asn Arg Gly Leu
            35                  40                  45

Ala Lys Gly Arg Leu Gly Asp Glu Asp Ser Asn Cys Ala Leu Leu Ala
        50                  55                  60

Cys Lys Asn Asp Phe Leu Ala Asp Val Glu Ile Ile Lys Ile Phe Asp
65                  70                  75                  80

Phe Asn Arg Leu Asn Glu Val Gly Thr Gly Tyr Tyr Ala Leu Asp Arg
                85                  90                  95

Lys Arg Lys Ala Ile Ile Leu Val Phe Arg Gly Ser Val Ser Arg Arg
            100                 105                 110

Asp Trp Ala Thr Asp Met Asp Phe Ile Pro Thr Ser Tyr Lys Pro Ile
        115                 120                 125

Val Tyr Glu Glu Asn Phe Gly Cys Asp Pro Tyr Ile Leu Thr Glu Cys
    130                 135                 140

Lys Asn Cys Arg Val His Arg Gly Phe Tyr Asn Phe Leu Lys Asp Asn
145                 150                 155                 160

Ser Ala Ala Ile Ile Thr Glu Gly Ile Ala Leu Lys Glu Glu Tyr Pro
                165                 170                 175

Asp Tyr Gln Phe Leu Ile Ile Gly His Ser Leu Gly Ala Ala Leu Thr
            180                 185                 190

Met Leu Ser Gly Ile Glu Phe Gln Leu Leu Gly Tyr Asp Pro Leu Val
        195                 200                 205

Val Thr Tyr Gly Gly Pro Lys Val Gly Asn Gln Glu Phe Ala Asp Phe
    210                 215                 220

Thr Asp Asn Leu Phe Asp Thr Asp Glu Val Asp Asn Glu Ile Ala Thr
225                 230                 235                 240

Asn Arg Asp Phe Ser Arg Gly Phe Ile Arg Val Val His Lys Tyr Asp
```

-continued

```
                245                 250                 255
Ile Ile Pro Phe Leu Pro Pro Leu Phe Ser His Ala Gly Tyr Glu Tyr
            260                 265                 270

Phe Ile Asp Lys Arg Glu Leu Pro His Glu Glu Cys Asp Leu Asp Arg
            275                 280             285

Arg Gly Met Glu Tyr Ser Gly Ile Phe Lys Arg Ser Leu Thr Ile Lys
            290                 295             300

Pro Ser Thr Leu Trp Pro Asp Arg Leu Gly Lys Tyr Glu His Thr His
305                 310                 315                 320

Tyr Phe Arg Arg Ile Thr Ser Cys Arg Asp Asp Asp
            325                 330

<210> SEQ ID NO 29
<211> LENGTH: 356
<212> TYPE: PRT
<213> ORGANISM: Candida tropicalis

<400> SEQUENCE: 29

Met Leu Arg Thr Val Arg His Tyr Ser Lys Val Ile Asn Ile Lys Asp
1               5                   10                  15

Lys Gly Glu Lys Ala Ala Arg Val Ile Thr Ser Glu Phe Ala Lys Leu
            20                  25                  30

Lys Asp His Tyr Asp Ala Pro Lys Tyr Pro Ile Val Leu Cys His Gly
        35                  40                  45

Phe Ser Gly Phe Asp Arg Leu Gly Leu Phe Pro Leu Pro Asn Leu Leu
    50                  55                  60

Glu Asp Thr Thr Ala Thr Thr Lys Thr Lys Glu Ile Thr Glu Arg Ser
65                  70                  75                  80

Leu Ile Glu Leu Asp Tyr Trp Tyr Gly Ile Lys Asp Ala Leu Glu Asn
                85                  90                  95

Leu Gly Ser Thr Val Phe Ile Ala Lys Val Pro Ala Phe Gly Asp Ile
            100                 105                 110

Arg Ser Arg Ala Ile Ser Leu Asp Lys Phe Ile Glu Lys Gln Cys Lys
        115                 120                 125

Ala Leu Arg Gln Thr Glu Ser Lys Ser Ser Ile Tyr Asn Lys Pro Asp
    130                 135                 140

Ser Ser Asn Asp Asp Thr Thr Thr Phe Lys Asp Lys His Gln Pro Ile
145                 150                 155                 160

Lys Val Asn Leu Ile Ser His Ser Met Gly Gly Val Asp Ser Arg Tyr
                165                 170                 175

Leu Ile Ser Arg Ile His Asn Asp Asn Glu Asn Tyr Arg Val Ala Ser
            180                 185                 190

Leu Thr Thr Ile Leu Thr Pro His His Gly Ser Glu Cys Ala Asp Phe
        195                 200                 205

Ile Val Asp Leu Ile Gly Asp Asn Gly Val Leu Lys Lys Val Cys Pro
    210                 215                 220

Pro Ser Ile Tyr Gln Leu Thr Thr Leu His Met Lys Lys Phe Asn Glu
225                 230                 235                 240

Val Val Lys Asp Asp Pro Ser Val Gln Tyr Phe Ser Phe Gly Ala Arg
                245                 250                 255

Phe Asn Pro Arg Trp Tyr Asn Leu Phe Gly Leu Thr Trp Leu Val Met
            260                 265                 270

Lys Tyr Gln Ile Glu Lys Glu Gln Ala Asp Arg Phe Lys His Met Ile
        275                 280                 285

Asp Asn Asp Gly Leu Val Ser Val Glu Ser Ser Lys Trp Gly Gln Tyr
```

```
            290                 295                 300
Ile Gly Thr Leu Asp Glu Val Asp His Leu Asp Leu Ile Asn Trp Thr
305                 310                 315                 320

Asn Arg Ala Arg Ser Val Phe Asp Lys Val Met Phe Ala Gln Asn Pro
                325                 330                 335

Asn Phe Asn Pro Ile Ala Leu Tyr Leu Glu Ile Ala Asp Gln Leu Ser
            340                 345                 350

Lys Lys Gly Leu
        355

<210> SEQ ID NO 30
<211> LENGTH: 6825
<212> TYPE: DNA
<213> ORGANISM: Candida tropicalis
<220> FEATURE:
<221> NAME/KEY: modified_base
<222> LOCATION: (4232)..(4232)
<223> OTHER INFORMATION: a, c, t, g, unknown or other

<400> SEQUENCE: 30
atgagatgcc aagtatctca accatcacga tttactaact tgcttgtaca tagactccca      60
cgaacactac ttaattatcc agttgtaaat accctatta ttcctagacg tcattattcc     120 cttaatttt cattcaagaa cctactaaag aaaatgacag atctttcccc aagtccaaca      180 gactcccta attacacaca gttgcactca tccttgccat cacatttctt aggtgggaac      240
tcggtgctca ccgctgagcc ttctgccgtg acagatttcg tcaaaacaca ccaaggtcac      300
actgttatca ccaaagtctt gattgccaac aacggtattg gtgccgtcaa agaaataaga     360
tccgtcagaa atgggccta cgaaactttt ggtgacgaaa gagctataca gtttgtcgcc     420
atggccactc ccgaagatat ggaggctaac gccgagtaca ttcgaatggc cgaccagttt     480
gtcgaggtcc caggtggtac caataacaac aactacgcga atgttgactt gattgtcgaa     540
atcgctgaaa gaaccgatgt ccacgccgtt tgggctggtt ggggtcatgc ctccgaaaac     600
cctttgttgc cagraaggtt ggcagcttcc cctaagaaga tcgtgtttat tggtcctcca     660
gggtctgcca tgagatcttt gggtgacaag atttcttcca ccattgttgc acaacacgcc     720
aaagtgccat gtatcccatg gtctggtact ggtgtcgaag aggtccacgt cgacccagaa     780
accaagttgg tgtctgttga cgaccacgtc tacgccaaag gttgctgtac ctcgccagaa     840
gacggttggg aaaaagccaa acgtatcgga ttcccagtta tggttaaggc atccgaaggt     900
ggtggtggta aggtatcag aaaagtcgac cacgaaaagg acttcatcag tttgtacaac     960
caggcggcta acgaaatacc agggtcacca ttttcatca tgaagttggc cggtgacgcc    1020
agacacttgg aagtgcaatt gtttgccgat cagtacggta ccaacatttc gcttttcggt    1080
agagattgtt ctgtgcaaag aagacatcaa aagatcattg aagaagctcc agtcacaatt    1140
gccaacaaag acacttttgt tgagatggag aaagctgccg tcagattggg taagttggtt    1200
ggttacgtgt ctgccggtac cgttgaatac ctttactcct acgccgaaga caagttctac    1260
tttttggaat tgaacccaag attgcaagtt gaacatccaa ctaccgaaat ggtttccggt    1320
gtcaacttac cagccgctca gttgcaaatt gctatgggtc tcccaatgca cagaatcaga    1380 gacatcgat tgttgtacgg tgttgatcca cactctgcca ctgagattga tttcgagttc    1440 aagtcccaa actcattgat cacgcaaaga aagccagctc caaagggtca ctgtaccgct    1500
tgtcgtatca cttctgaaga tccaggtgaa gggttcaagc caagtggtgg tactcttcac    1560
gagttgaact tccgttcttc gtccaatgtc tggggttact tctcggtcgc caaccaatct    1620
```

```
tctatccact cctttgctga ttcccagttt ggtcacattt tcgcctttgg tgaaaatcgt    1680
caagcctcta gaaagcacat gattgttgcc ttgaaggaat tgagtatcag aggtgacttt    1740
agaaccactg ttgaatactt gatcaagttg ttggagactc cagatttcgc cgacaacacc    1800
atcactaccg gttggttgga tgagttgatc accaagaagt tgactgccga aagaccagat    1860
cctatcgttg ctgttgtctg tggtgccgtc accaaagccc acatccaagc cgaagaagac    1920
aagaaggagt acattgagtc tttggaaaag gtcaagttc  caaacaagtc cttgttgaaa    1980
actatcttcc cagttgagtt tatctacgaa ggtgaaagat acaagtttac tgccaccaag    2040
tcctccgaag acaagtacac tttgttcctc aacggttcta gatgtgtcat ggtgctcgc    2100 tcattgtctg atggtggctt gttgtgtgct ttggacggta agtcccactc tgtctactgg    2160
aaggaagaag cagcggccac tagattgtct gttgacggta agacttgctt gttggaagtt    2220
gaaaacgacc caacccaatt gagaactccg tctccaggta agttggtcaa gtacttggtt    2280
gagagtggtg aacacgttga tgccggccaa tcttatgccg aagttgaagt catgaagatg    2340
tgtatgcctt tgattgcaca agaaaacggt actgttcaat tgctcaaaca accaggttcc    2400
actcttaacg ctggtgacat cttggcaatc ttggcattgg acgatccatc taaagttaaa    2460
cacgccaagc catatgaagg cactttgcca gagatgggtg atccaactgt taccggttcc    2520
aaaccagctc acttgttcca acattacgac accatcttga gaacatctt  ggctggttac    2580 gataaccaag tcattttgaa ctccactttg aagaacatga tggagatctt gaagaacaag    2640
gagttgcctt attctgaatg gagattgcaa atctccgcct tgcattcaag aatcccacca    2700
aagttggatg aggctttgac gtccttgatt gaaagaaccg aaagcagagg cgccgaattc    2760
ccagctcgtc agattttgaa gctcgtcaac aagactcttg gtgaaccagg caacgaattg    2820
ttgggcgatg ttgttgctcc tcttgtctcc attgccaacc gctaccagaa cggcttggtt    2880
gaacacgagt acgactactt tgcttcattg gttaacgagt actgcaatgt tgaacacttc    2940
tttagtggtg aaaacgtgag agaagaagat gttatcttga gattgagaga cgagaacaag    3000
tctgatttga gaaggttat  cagcattgc  ttgtcccact cccgtgtcag tgctaagaac    3060
aacttgattt tggccatctt ggaagcttat gaaccattgt tgcaatccaa ctcttcaact    3120
gccgttgcca ttagagattc tttgaagaag atagtccagt tggattctcg tgcttgtgcc    3180
aaggttggtt tgaaagctag agaacttttg attcaatgtt cttttgccatc catcaaggaa    3240 agatctgacc aattggaaca cattttgaga agtgcagtcg ttgagacttc ttatggtgaa    3300
gttttcgcca agcacagaga acctaaattg gaaatcatcc aagaagttgt cgaatccaag    3360
cacgttgttt tcgatgtctt gtcgcaattt ttggtccacc aagactgctg ggttgccatt    3420
gctgctgccg aagtctatgt tagacgttcc tacagagctt atgatttggg taagatcgat    3480
taccacattc atgacagatt gccaattgtt gaatggaagt tcaagttggc tcaaatcgca    3540
ggttccagat acaacgccgt ccaatctgcc agtgttggtg acgactcgac cactatgaag    3600
catgctgcat ctgtttctga cttgtcgttt gttgttgatt ccaagagcga atccacttcc    3660
agaactggtg ttttggttcc agctagacat ttggacgatg ttgatgagat tctttctgct    3720
gcattggagt acttccaacc atctgatgca ctctcttttcc aagctaaggg agaaagacca    3780
gagttgttga atgttttgaa cattgtcatc accgacattg acggttactc tgacgaagat    3840
gaatgcttga agagaattca tgaaatcttg aacgagtacg aagacgattt ggtctttgct    3900
ggtgttcgtc gtgttacttt tgttttcgcc caccaagttg gttcttatcc aaagtactac    3960
accttcactg gtccagtgta tgaagaaaac aaggttatca gacacatcga accagctttg    4020
```

```
gctttccaat tggaattggg aagattagcc aactttgaca tcaagccaat tttcaccaat    4080
aacagaaaca ttcatgttta cgaagctatt ggtaagaatg ctccttcgga taagagattc    4140
ttcactagag gtattattag aggtggtgtc ctcaaagatg aaatcagtct tactgagtac    4200
ttgattgctg aatcgaacag attgatcagt gntatcttgg ataccttgga agttattgac    4260
acttccaact ccgatttgaa ccacattttc atcaacttct ccaacgtttt caacgtccaa    4320
ccagctgatg ttgaagctgc ttttgcttca ttcttggaaa gatttggtag aagattgtgg    4380
agattgagag ttactggtgc tgaaatcaga attgtctgta ccgacccaca gggcaactca    4440
ttcccattgc gtgccattat caataacgtt tcaggttatg ttgtcaagtc ggaattgtac    4500
ttggaagtga agaaccctaa gggtgattgg gtcttcaaat ccattggcca ccctggctca    4560
atgcacttgc aaccaatctc gactccatac ccagtcaagg aatccttgca gccaaaacgt    4620
tacagagctc acaacatggg aaccactttt gtttacgatt tcccagagtt gttccgtcaa    4680
gccaccattt cccaatggaa gaagcacggc aagaaggctc ctaaagatgt cttcacttct    4740
ttggagttga tcaccgatga aaacgatgct ttggttgccg ttgaaagaga tccaggtgcc    4800
aacaagattg gtatggttgg tttcaaggtc actgccaaga cccctgaata cccacgcgga    4860
cgttcattca tcattgttgc caatgatatc acccacaaga ttggttcctt tggtccagat    4920
gaagatgaat acttcaacaa gtgtaccgac ttggccagaa agttgggtgt tccaagaatt    4980
tacctttctg ccaactccgg tgccagaatt ggtgttgctg aagagttgat tccattgtac    5040
caagttgctt ggaacgaaga aggtaaccca gataaaggtt tcagatactt gtacttgaac    5100
ccagacgcca aagaagcttt ggaaaaagac ggcaagggtg acactattgt tactgaacgt    5160
attgtcgaag atggtcaaga acgtcacgtt atcaaggcca ttattggtgc tgagaacggc    5220
ttgggtgttg aatgtttgaa aggttccggt ttgattgctg gtgccacttc aagagcctac    5280
agagacatct tcaccattac cttggtcact tgtagatctg ttggtattgg tgcctatttg    5340
gtcagattgg gtcaaagagc tatccaaatt gaaggtcaac caatcatttt gactggtgca    5400
ccagctatca acaagttgtt gggtagagaa gtttactcgt cgaacttgca attgggtggt    5460
acccagatca tgtacaacaa tggtgtttcc cacttaactg ccagtgacga tttggctggt    5520
gttgagaaga tcatggaatg gttgtcctac gttccagcta agcgtggtat gccagtacca    5580
atcttggaaa gtgaagatac ctgggacaga gacattgact actacccacc aaagcaagaa    5640
gctttcgaca tcagatggat gatcgaaggt aagcaagttg aaggtgaaga gtttgaatct    5700
ggtttgtttg acaaaggttc attccaggaa actttatcag gatgggctaa aggtgttgtc    5760
gttggtagag ctcgtctcgg tggtatccca attggtgtca ttggtgttga gaccagaact    5820
attgaaaaca tgatcccagc tgacccagcc aacccaagtt ccactgaagc cttgatccaa    5880
gaagccggtc aagtctggta tccaaactct gcgttcaaga ccgcacaagc cattaacgac    5940
ttcaacaacg gtgaacaatt gccattgatg atccttggcca actggagagg tttctctggt    6000
ggtcagagag atatgtacaa cgaggtcttg aagtacggtt ccttcattgt tgacgcttta    6060
gttgatttca gcagccaat cttcacttac atcccaccaa atggtgaatt gagaggtggc    6120
tcttgggtcg ttgttgatcc aaccatcaac tccgacatga tggaaatgta tgccgacgtt    6180
gactccagag ctggtgtttt ggaaccagaa ggtatggttg gtatcaaata cagacgggac    6240
aagttgttgg ctaccatgca aagattggat ccaacttatg cccaattgaa ggagaagttg    6300
aacgactcga gcttgtcgcc agaagaacat gcccaagtca gcaccaagat tgtcaagcgt    6360
gaaaaggcat tgttgccaat ctatgcccaa atttctgtcc agtttgccga cttgcacgac    6420
```

```
agatccggac gtatgatggc taaaggtgtc attagaaaag aaatcaagtg ggttgacgcc    6480
agacgtttct tcttctggag attgagaaga agattgaacg aagagtacgt tttgaagttg    6540
attggtgaac aggtcaagaa tgccaacaag ttggaaaagg ttgccaggtt gaagagttgg    6600
atgccaactg ttgactacga cgatgaccaa gctgtcagta cttggattga agagaaccac    6660
gccaaattgc aaaagagagt tgaagaattg agacaggaga gaacaagtc cgacattgtc     6720 aaattgttgc aagaagaccc atcaaacgct gcctctgtta tgagggattt cgttgataga    6780
ttgtccgatg aagaaaagga aaagttcctt aaatcattga actag                   6825

<210> SEQ ID NO 31
<211> LENGTH: 5661
<212> TYPE: DNA
<213> ORGANISM: Candida tropicalis

<400> SEQUENCE: 31
atgaagccag agattgaaca agaattatcc cacaccttgt taacagaatt gttagcttat     60
cagttcgctt ctccagtcag atggatcgaa acccaagatg tcttcttgaa gcaacacaac    120
accgaaagaa tcatcgaaat cggcccttcc ccaaccttgg ccggtatggc caacagaacc    180
atcaaggcca ataccaatc ctacgacgcc gcgttgtcct tgcaaagaga agtcttatgc     240
tactctaagg acgccaagga gatctactac aagccagatc cagcagatct tgctccaaag    300
gaagaaccaa agaaggaaga agctgccgcc gctccagccg ctacaccagc tgctgctgct    360
gctgctgcta ctcctgctgc tgccccagtc gccgctgctc cagccccatc tgctggccct    420
gctgaatcca tcccagatga accagtcaag gcttccttgt tgatccacgt cttggttgct    480
cagaaattaa agaaaccatt ggatgctgtt ccaatgtcca aggctatcaa agatttagtt    540
aacggtaagt ccactgtcca gaacgaaatt cttggtgact gggtaaaga attcggttcc    600 actcctgaaa aaccagaaga taccccattg aagaattgg ccgaacagtt ccaagactcc    660
ttcagtggtc aattgggtaa gacttctact tcattgattg gtagattgat gtcttctaag    720
atgcctggtg gtttctcaat caccgctgcc agaaaatact ggaatccag attcggtttg     780 ggtgccggta gacaagactc tgtcttgttg gttgctttga ccaacgaacc tgcaagcaga    840
ttgggttctg aggccgaagc taagaccttc ttggacacca tggctcagaa atatgcctca    900
tctgctggta tttccttgtc gtcagcttct gccggtgccg tgctggagg tgccgccggt    960 ggcgccgttg ttgacagtgc tgctttggac gccttgactg ctgaaaacaa gaaattggct   1020
agacaacaat tagaggtctt ggctagatac ttgcaagtcg acttgaactc aggagctaag   1080
tcttttatca agaaaaaga agcttccgct gttttgcaga agaattgga cttgtgggaa     1140 gccgaacatg tgaattcta cgccagaggt atcaaaccaa ctttctcagc tttgaaagca    1200
agaacctatg attcctactg gaactgggcc agacaagatg ttttgtccat gtactttgat    1260 atttttgtttg gtaagttgac ctccgttgac agagaaacca tcgaccaatg tatccaaatt   1320
atgaacagat ccaacccaac tttgatcaag ttcatgcaat accacattga ccactgccca   1380
gaatacaagg tgagactta caagttggcc aagagattgg gtcaacagtt gattgacaac    1440
tgtaagcaaa ccttgaatga agacccagtg tacaaggacg tttctagaat cactggtcca    1500
aagaccaccg tctgcgccaa gggtaacatt gaatacgaag aagccgaaaa ggattctgtt    1560
agaaagtttg aacagtacgt ctacgaaatg gcccaaggtg gtgaaatgac caagattgcc    1620
caaccaacta ttcaagaaga cttggccaga gttacaaag ccatctccaa gcaagcttcc     1680
agagacagca agttggaatt gcagaaagtc tacgagcaat tgttgaaggt tgttgctggt    1740
```

-continued

```
tcagacgaaa ttgaaactca gcaattaacc aaggacatct tgcaagctcc aactggctcc    1800
aacaccccaa ctgatgaaga tgaaatttcc accgccgact ctgacgatga aattgcttca    1860
ttgccagaca agacttcaat tgcccaacca gtttcttcaa ctgttccacc ccagaccatc    1920
ccattcttgc acattcaaaa gaagaccaac gaaggctggg aatacgaccg caagttgtct    1980 gcccttttact tggacggttt ggaatccgct gctgtcaacg gtctcacctt caaggacaag    2040
tacgttttgg ttaccggtgc tggtgctgga tccattggtg ccgaaatctt gcaaggtttg    2100
atcagtggtg gtgccaaggt tgttgttacc acctctagat tctccaagaa ggttactgag    2160
tactaccaaa acatgtacgc cagatacggt gctgccggtt ctactttgat tgttgttcca    2220
ttcaaccaag ttctaaaca agatgttgac gctttggttc aatacatcta cgacgatcca    2280
aagaagggtg gtttaggctg ggacttggat gccattatcc cattcgctgc tatcccagaa    2340
aatggtaacg gtatcgacaa cattgattct aaatccgaat tgcccacag aattatgttg    2400 accaaccttt tgagattgtt gggtgctgtc aaatccaaga agactaccga caccagacca    2460
gctcaatgta tcttgccaat gtctcctaac cacggtactt tcggtttcga tgggttgtac    2520
tctgaatcca agatttcctt ggaaaccttg ttcaacagat ggtactccga agattggggc    2580
tccaagttga ccgtctgtgg tgccgttatt ggttggacca gaggtactgg tttgatgagc    2640
gccaacaaca tcattgccga aggtatcgaa aagattggtg tcagaacctt ctcccaaaag    2700
gaaatggctt tcaacatctt gggtttgttg actccagaga ttgtcaagtt gtgccaagaa    2760
gaaccagtta tggccgactt gaacggtggt ttgcaattca ttgaaaactt gaaggatttc    2820
acttccaagt tgagatctga cttgatggaa tccgctgaag ttagaagagc tgtctccatt    2880
gaatccgcca tcgaacaaaa ggttgtcaat ggtgacaatg ttgatgccaa ctacaccaag    2940
gttaccgttc aaccaagagc caacatgaaa ttcgacttcc aaccttgaa atcgtacgat    3000 gagatcaaga aggttgctcc agaattggaa ggcatgttgg acttggaatc cgtcgttgtt    3060
gtcaccggtt ttgccgaagt tggtccatgg ggtaacgcca gaaccagatg ggaaatggaa    3120
tccaagggtg aattctcctt ggaaggtgcc attgaaatgg cctggatcat gggtttcatc    3180
aagtaccaca acgtaacctt gaagggtaag ccttactctg gttgggttga tgccaagacc    3240
caaactccaa tcgatgacaa ggacatcaag gccaagtacg aagaagagat cttggaccac    3300
tctggtatta gattgattga gccagaattg ttcaatggct acgatccaaa gaagaagcag    3360
atgatccaag aagttgtcat ccaacatgac ttggaaccat tgaagcctc caaggaaact    3420 gctgaacaat acaaacacga acacggtgac aagtgtgaga tctttgaaat tgaagaatcc    3480
ggtgaataca ctgttagaat cttgaaaggt gctaccttgt tgttccaaa ggctttgaga    3540 tttgacagat tggttgctgg tcaaattcca actggttggg atgctcgtac ctacggtatt    3600
ccagaagata ccattaacca agttgatcct atcactttgt acgtcttggt tgctaccgtt    3660
gaagctttgt tgtctgctgg tatcaccgac ccatatgaat tctacaagta cgtccacgtt    3720
tccgaagttg gtaactgttc tggttccggt atgggtggtg tctctgcctt gagaggaatg    3780
ttcaaggaca gatacgccga cagaccagtg caaaacgata tcttgcaaga atctttcatc    3840
aacaccatgt ccgcctgggt taacatgttg ttgttgtctt cttcgggtcc aatcaagacc    3900
ccagttggtg cctgtgctac cgctgttgaa tccgttgaca ttggtattga aactattttg    3960
tctggtaagg ctaaggttgt tatggttggt ggttacgatg acttccagga agaaggttct    4020
tatgaattcg ccaacatgaa tgccacttcc aactcccttg acgagtttgc tcacggcaga    4080
actccaaagg agatgtccag accaactacc accaccagac acggtttcat ggaggcccaa    4140
```

```
ggttctggta tccaagttat tatgactgct gacttggcca tcaagatggg tgttccaatt      4200
cacgctgtgt tggccatgtc tgctactgct accgacaaga ttggtagatc tgttccagct      4260
ccaggtaagg gtattttgac cactgccagg gaacaccacg gtaacttgaa gtacccatct      4320
ccagctttga acatcaagta cagaaagaga caattgaagg ctagattaga ccaaatcaag      4380
gcttgggaag aagctgaaat tgcttacttg caagacgaag ctgagttggc caaggaagaa      4440
atgggcgatg agttctccat gcacgaattc ttgaaggaaa gaactgaaga agtgtaccgt      4500
gaatccaaga gacaagtttc tgacgctaag aagcaatggg gtaaccaatt ctacaagtct      4560
gacccaagaa ttgctccatt gagaggtgcc ttggctgctt tcaacttgac cattgacgat      4620
cttggtgttg cttccttcca cggtacttct accgtcgcca acgataagaa cgaatccgcc      4680
actattaaca gcatgatgca cacttgggc agatctgaag gtaacccagt gtttggtgtt      4740
ttccagaagt acttgactgg tcatccaaag ggtgctgctg gtgcttggat gttgaacggt      4800
gccatccaga tcttggagtc tggtattgtt ccaggtaaca gaaatgccga taacgttgac      4860
aaggtcttgg aagaatacga gtacgtcttg tacccatcca gatccatcca aactgacggt      4920
atcaaggccg tttccgtgac ctcttcggt tccggtcaaa aggtgctca gctgttgtc      4980 gtccacccag actacttgtt tgctgttttg gatagatcta cttatgagga ctacgccacc      5040
agagtttctg ccagaaacaa gaagacttac cgttacatgc acaatgctat tactagaaac      5100
actatgtttg ttgctaagga taaggctcca tatgccgatg aattggaaca accagtttac      5160
ttggacccat tagcccgtgt tgaaaacgct aaggaaaagc ttgccttcag caacaagagt      5220
atccaatcca ccaagcttta tgctggtgaa atgccagaac ccactgccaa ggctttggct      5280
gccttgaaca agtcatccaa gggtgttggt gtcgacgttg aattattgtc tgagctcaac      5340
ttggagaatg aaacttttgt tgcaagaaac ttcactcctg gtgaaatcca atactgctcc      5400
aagagtgcca acccacaagc ttcatacacc ggcacttggt ctgctaaaga agctgtcttc      5460
aaggcattag gtgttgaatc taaaggtgct ggtgccagct tggttgacat tgagatcact      5520
cgtgacgtca acggcgctcc acaagttgtc ttgcacggtg atgcggcaaa atcagccgcc      5580
aaagctggtg tcaagaacgt caagatttcc atctcccatg acgacttca agccactgct      5640 gttgccttga gtgaattcta g                                                5661

<210> SEQ ID NO 32
<211> LENGTH: 6120
<212> TYPE: DNA
<213> ORGANISM: Candida tropicalis

<400> SEQUENCE: 32
atgtctactc atagaccttt ccaattgacc cacggttcca tcgaacacac cttgttggtg        60
ccaaacgagt tgttcttcaa ctattcacag ttaaaagacg aattcataaa gaccttgcct       120
gaaccaaccg aaggtttcgc tggcgacgat gaaccttcca gtcctgctga attgtacggc       180
aaattcctcg gctacatcag tgacaacacc gttcaattcc cccagatctt acaattgtcc       240
ttgcaagact ccagcagcg attcttggac aaccacgaca catccactc ctttgccgtc       300 agattattag aagatgaagc ttatccaaca acaatcacca agtcaagga aaatatcatc       360 aagaactact acaaagccat caagtccatc gacaaggtcg agtcaaactt gttgtaccac       420
tgcaaacatg acgccaagtt ggccgctata ttcggtggtc aaggtaacac cgacgactac       480
tttgaagaat tgcgtgaatt gtacaccta taccagggct tgattgagga cctccttatc       540
tccattgccg acaagttgga cgagttatac ccttctttg acaagatcta cacccagggt       600
```

-continued

```
ttgaacatct tgggctggtt gaagcaccca gaaaccaccc ctgaccaaga ttacttgttg    660
tccgtaccag tgagttgtcc tgttatctgt atcatccaat tgtgtcacta caccatcacc    720
tgcaaagttc ttggtttgac ccctggtgaa tttagagact cgttgaagtg gtccaccggt    780
cactcccaag gtttggttac tgctaccgct atttccagtt ccgactcctg ggactccttc    840
aaacaaaact ccattgctgc cgtctccttg atgcttttca ttggtgccag atgtttgatg    900
gcttacccaa gaactacctt gccaccaacc atgttgcaag actccttgga acacggtgaa    960
ggtagaccat ctccaatgtt gtcagttaga gacttgacca tcacccaagt tgagaagttt   1020
attgaacaga ccaactctca cttgccaaag gaaaagcaca ttgccgtcag tttggtcaat   1080
ggtgccagaa atttggttct ttctggtccc ccggagtccc tttacggttt caacttgaac   1140
ttgagaaacc aaaaggctcc aatgggattg accaatcac gtgttccatt cagtgaacgt    1200
aagttgaagt gttccaacag attcttgcca attttttgcac cattccactc tcacttgttg   1260
gctgatgcca ctgagtacat tttggatgat gtcaaagaac accgtttgtc tttccagaaa   1320
ttgaagattg cagtctacga tacctacgac ggctccaact tccaagagag caaggaacca   1380
attattgaca gactcgtcaa gttgatcacc gagttgccag ttcactggga aaccgccacc   1440
aaccacaggg ccacccacat tttggatttc ggcccaggtg gtgtctccgg tttgggtgtt   1500
ttgacccaca gaaacaagga aggtactggt gctagaataa ttgttgctgg tgctcttgac   1560
tccaacccaa ttgacgatga gtatggtttc aagcacgaaa tcttccagac ttctgccgac   1620
aagtccatca gtgggctagc gattggttg gaagaattca aaccaacttt ggtcaagact    1680
tcccagggaa agatctacgt caacaccaag ttctcgcaat tgttgggcag agctcccttg   1740
atggtcccag gtatgacacc aaccactgtt aacccagaca tcattgccgc ctctttgaat   1800
gctggctatc acattgaatt agccggtggt ggttatttcg ccggcaggat catgaccaaa   1860
gccattgacc aaattgttgc cgacatcaag ccaggttacg gtttgggtat caacttgatt   1920
tacgtcaacc cattcatgtt gcaatggggt attccattga ttaaggagtt gagagaaaag   1980
ggttatccaa tccaatcttt gaccattggt gctggtgttc catctttgga agttgccact   2040
gaatacattg aagagttggg tctcacgcac ttgggcttga aaccaggttc gattgacgcc   2100
atcagccaag tcatcaccat tgccaaggct catccaaagt tcccaattgt cttgcaatgg   2160
actggtggta gaggtggtgg ccaccactct tttgaagatt tccaccaacc aatcctccag   2220
atgtactcca agatcagaag atgcccaaac attgtcttgg ttgctggttc cgggtttggt   2280
tctgacgaag acacctaccc atacttgact ggttcttggt ccaagagatt caactaccca   2340
ccaatgccat acgatggtgt cttgtttggt tccagagtca tgaccgccaa ggaggcccac   2400
acttcgttgg aagctaagaa attgattgcc tcgtgcccag tgtcccaga tgagaagtgg    2460
gagcaaacct acaagaagcc aaccggtggt atcatcactg ttagatctga aatgggtgag   2520
ccaatccaca gattgccac cagaggtgtc atgttctgga aggaattgga cgacactatc    2580
ttcaaccttc caaagccaaa agccttggaa gccatcaaga agaagagaga ctacatcatc   2640
aagaagttga acgcgacttt ccaaaagcca tggtttggta agaatgcttc tggtgtttgt   2700
gacttgcaag aaatgaccta cgaggaaatc gccaacagat tggttgagtt gatgtacgtc   2760
aagaagtctc aaagatggat tgacgtttcc ttaagaaact tgtacggtga cttttttgaga   2820
agagttgaag aaagattcac ttctgctgcc ggcgtggttt ccttgttgca aaacttcatc   2880
cagttgaacg acccagaaac attcagtgcc gagttcttca acaagttccc acaagccaag   2940
gaacaattga tttccgaaga agacgctgac cacttttttgt tgttggctgc cagaccaggg   3000
```

-continued

```
caaaagccgg ttccattcgt gccagtcttg gacgaaagat ttgaattctt cttcaagaaa    3060
gattctcttt ggcaatctga agacttggaa agtgttgtcg acgaagacgt tcaaagaact    3120
tgtatcttgc acggtccagt tgcctcccaa ttcaccaaga aggttgatga accaattggc    3180
gaaatcttgg actctatcca cgagggccat attgccaagt tgatcaagga tgaatacgct    3240
ggtgatgcat ccaagatccc agttgttgag tacttcggtg gtttcaagac cgacaaggtt    3300
aatgctaaca atgttcaagt caatgctacc agaaaggaaa ccgtctacga aattggttcc    3360
aagttgccag ccaggcaaga ctggttggac ttgttggccg gtactgaatt gaactggttg    3420
cacgctttca tctccaccaa cagaattgtc caaggctcca agcacgtcgc caacccattg    3480
cacgacattt tggctcccgt tgccagatcc agtgtttcca ttgacaaggc taccaagaaa    3540
ttgactgctt atgaaaaggt caagggtgag ttggttccag ttgttgaaat tgaattggtc    3600
aagccaaaca ccattcaatt gtctttgatt gaacacagaa ctgctgatgg caaaccagtt    3660
gctttgccat tcttgtacaa gtacgaccca actgatgggt ttgcaccagt cttggagatc    3720
atggaaaaca gaaacgacag aatcaaggaa ttctactgga agttgtggtt cggtgcttcc    3780
gtcccttacg acaatgacat cgatgtcgaa gagcaaatct tgggtgacga aatcaccatt    3840
tcttctcaag acattggtga attcacacac gctattggta acaagtgtga agcctttgtc    3900
aacagaccag gtaaggtcac tttggctcca atggatttcg ccattgttgt tggttggaaa    3960
gctatcatca agtccatctt cccaaagacc gttgacggtg acttgttgaa gttggtccac    4020
ttgtccaacg gttacaagat gatccctggt gcagctccat gcaaagggg cgatgttgtt    4080
tccactagat ctgacatcaa ggctgttttg aaccaaccaa gtggtaagtt ggttgaagtt    4140
gttggtacca tcttccgtga aggcaagcca gttatggaag tcacttcaca attcttgtac    4200
cgtggtgaat acgacgacta ctgcaacacc ttccaaaagg tcactgaaac tccagttcaa    4260
gtctcattca gtctcctaa ggatttggct gttttgagat ccaaggaatg gttccatttg    4320
gaaaaggatg tcgagtttga tgctttgact ttcagatgtg aatccactta caagttcaag    4380
tctgccaacg tctactcgtc catcagaacg accggtcaag ttttcttgga gttgtccacc    4440
aaagaagtta tccaagttgg ttctgttgac tatgaagctg gtacctctta tggtaaccca    4500
gtcactgact acttgaacag aaacggtaag accattgaag aggctgttac ttttgagaat    4560
gccatcccct tgtcgtctgg tgaagagttg accaccaagg ctccgggtac caacgagcca    4620
tatgctattg tttctggtga ctacaaccca atccacgttt ccagagtctt ttctgcttac    4680
gccaagttgc aggtactat cacccacggt atgtactctt ctgccgccat cagagccttg    4740
gttgaagagt gggctgccaa caacgttgcc ccaagagtca gagccttcaa gtgtgaattt    4800
gttggtatgg ttttgccaaa cgacactttg caaaccacta tggaacacgt tggtatgatc    4860
aatggccgta agatcatcaa ggtcaagact gtcaatgccg agaccgagac tccagtcttg    4920
cttgctgaag ccgaaattga acaaccaacc accaccatg ttttcactgg tcaaggttcc    4980
caagaacaag gcatgggtat ggatttgtac aactcttctg aagttgcccg taacgtttgg    5040
gataccgccg acaagcattt catcaaccac tatggcttct ccatcttgga cattgtgcaa    5100
aacaacccta aggaattgac tatccacttt ggaggtgcta aggtagagc tatcagagac    5160
aactacattg gtatgatgtt tgaaacaatt ggtgaagacg gttctttgaa gtccgaaaag    5220
atcttcaagg acattgacga aaacaccact tcctacacct ttgtttctga cactgggttg    5280
ttgtctgcta ctcaattcac ccaacccgct ttgactttga tggagaaggc tgcctacgac    5340
gatatcaagt ctaaaggatt gattccaagt gacatcatgt ttgctggtca ctctcttggt    5400
```

-continued

| | | |
|---|---|---|
| gaatactctg ctttgacttc cttggccaac gttatgccta ttgaatcctt ggttgatgtt | 5460 |
| gtcttctaca gaggtatgac catgcaagtt gctgttccaa gagacgagtt tggtagatcc | 5520 |
| aactacggta tggttgctgt caacccaacc agagtcagcc caacatttga cgatgccgcc | 5580 |
| atgagatttg ttgttgacga gactgccaag agaaccacct ggttgttgga aattgtcaac | 5640 |
| tacaatgttg aaaaccaaca gtacgttgct gctggtgact tgagagcctt ggataccttg | 5700 |
| accaacgtgt tgaatgtttt gaagatcaac aagattgata ttgtcagatt gcaagaacaa | 5760 |
| ttatccctcg acaaggtcaa ggagcacttg tacgagattg ttgatgaagt tgctgccaag | 5820 |
| tccattgcta agccacaacc aattgaatta gaaagaggtt ttgctgttat cccattgaag | 5880 |
| ggtatttctg tcccattcca ctcttcctac ttgatgtctg gtgtcaagcc attccagaga | 5940 |
| ttcttgtgca agaagattcc aaaggcttcc atcaaaccac aagatttgat tggcaagtac | 6000 |
| attcctaact tgactgctaa gccatttgaa cttactaagg aatacttcca ggatgtctac | 6060 |
| gacttgacta atctgaaaaa gatcaaggct atcttggaca actgggaaaa atacgaatag | 6120 |

<210> SEQ ID NO 33
<211> LENGTH: 1506
<212> TYPE: DNA
<213> ORGANISM: Candida tropicalis

<400> SEQUENCE: 33

| | | |
|---|---|---|
| atgtcttatg attcattcgg tgactacgtc actatcgtcg ttttcggtgc ttccggtgac | 60 |
| ttggccagca aaaaaacctt ccctgccttg tttggcttgt ttagagaaaa gcaattgccc | 120 |
| ccaaccgtcc agatcattgg ctatgccaga tcccatttgt ccgacaagga cttcaaaacc | 180 |
| aagatctcct cccacttcaa gggcggcgac gaaaaaacca agcaagactt cttgaacttg | 240 |
| tgtacttata tcagcgaccc atacgacact gacgatggtt acaagagatt ggaagccgcc | 300 |
| gctcaagaat acgaatccaa gcacaacgtc aaggtccctg aaagattgtt tacttggcc | 360 |
| ttgcctcctt ctgtcttcca caccgtctgt gagcaagtca gaagatcgt ctaccctaag | 420 |
| gacggtaagc tcagaatcat cattgaaaag ccgttcggac gtgatttggc cacctaccgt | 480 |
| gaattgcaaa agcaaatctc cccattgttc accgaagacg aactctacag aattgaccac | 540 |
| tacttgggta agaaatggt caagaacttg ttggttttga gattcggtaa cgaattgttc | 600 |
| agtgggatct ggaacaacaa gcacatcacc tcggtgcaaa tctccttcaa ggaacccttc | 660 |
| ggtaccgaag gtagaggtgg ctactttgac aacattggta tcatcagaga tgtcatgcaa | 720 |
| aaccacttgt tgcaagtctt gaccttgttg accatgaaa gaccagtctc ttttgaccca | 780 |
| gaagctgtca gagacgaaaa ggtcaaggtt ttgaaagctt ttgacaagat tgacgtcaac | 840 |
| gacgttcttt tgggacaata cgccaagtct gaggatggcc caagccagg ttacttggat | 900 |
| gactccaccg tcaagccaaa ctccaaggct gtcacctacg ccgctttcag agtcaacatc | 960 |
| cacaacgaaa gatgggacgg tgttccaatt gtttgagag ccggtaaggc tttagacgaa | 1020 |
| ggtaaagttg aaattagaat ccaattcaag ccagttgcca aaggtatgtt taaggagatc | 1080 |
| caaagaaacg aattggttat tagaatccaa ccagacgaag ccatctactt gaagatcaac | 1140 |
| tccaagatcc caggtatctc caccgaaact tccttgaccg acttggactt gacttactcc | 1200 |
| aagcgttact ccaaggactt ctggatccca gaagcatacg aagccttgat cagagactgt | 1260 |
| tactgggca accactccaa ctttgtcaga gacgatgaat ggaagttgc ttggaagctc | 1320 |
| ttcacccat tgttggaagc cgttgaaaaa gaagacgaag tcagcttggg aacctaccca | 1380 |
| tacggatcca agggtcctaa agaattgaga aagtacttgg tcgaccacgg ttacgtcttc | 1440 |

```
aacgacccag gtacttacca atggccattg accaacaccg atgtcaaagg taagatctaa   1500
gaatag                                                              1506
```

<210> SEQ ID NO 34
<211> LENGTH: 499
<212> TYPE: PRT
<213> ORGANISM: Candida tropicalis

<400> SEQUENCE: 34

```
Met Ser Tyr Asp Ser Phe Gly Asp Tyr Val Thr Ile Val Val Phe Gly
1               5                   10                  15

Ala Ser Gly Asp Leu Ala Ser Lys Lys Thr Phe Pro Ala Leu Phe Gly
            20                  25                  30

Leu Phe Arg Glu Lys Gln Leu Pro Pro Thr Val Gln Ile Ile Gly Tyr
        35                  40                  45

Ala Arg Ser His Leu Ser Asp Lys Asp Phe Lys Thr Lys Ile Ser Ser
    50                  55                  60

His Phe Lys Gly Gly Asp Glu Lys Thr Lys Gln Asp Phe Leu Asn Leu
65                  70                  75                  80

Cys Thr Tyr Ile Ser Asp Pro Tyr Asp Thr Asp Gly Tyr Lys Arg
                85                  90                  95

Leu Glu Ala Ala Gln Glu Tyr Glu Ser Lys His Asn Val Lys Val
                100                 105                 110

Pro Glu Arg Leu Phe Tyr Leu Ala Leu Pro Pro Ser Val Phe His Thr
            115                 120                 125

Val Cys Glu Gln Val Lys Lys Ile Val Tyr Pro Lys Asp Gly Lys Leu
130                 135                 140

Arg Ile Ile Ile Glu Lys Pro Phe Gly Arg Asp Leu Ala Thr Tyr Arg
145                 150                 155                 160

Glu Leu Gln Lys Gln Ile Ser Pro Leu Phe Thr Glu Asp Glu Leu Tyr
                165                 170                 175

Arg Ile Asp His Tyr Leu Gly Lys Glu Met Val Lys Asn Leu Leu Val
            180                 185                 190

Leu Arg Phe Gly Asn Glu Leu Phe Ser Gly Ile Trp Asn Asn Lys His
        195                 200                 205

Ile Thr Ser Val Gln Ile Ser Phe Lys Glu Pro Phe Gly Thr Glu Gly
    210                 215                 220

Arg Gly Gly Tyr Phe Asp Asn Ile Gly Ile Ile Arg Asp Val Met Gln
225                 230                 235                 240

Asn His Leu Leu Gln Val Leu Thr Leu Thr Met Glu Arg Pro Val
                245                 250                 255

Ser Phe Asp Pro Glu Ala Val Arg Asp Glu Lys Val Lys Val Leu Lys
            260                 265                 270

Ala Phe Asp Lys Ile Asp Val Asn Asp Val Leu Leu Gly Gln Tyr Ala
        275                 280                 285

Lys Ser Glu Asp Gly Ser Lys Pro Gly Tyr Leu Asp Asp Ser Thr Val
    290                 295                 300

Lys Pro Asn Ser Lys Ala Val Thr Tyr Ala Ala Phe Arg Val Asn Ile
305                 310                 315                 320

His Asn Glu Arg Trp Asp Gly Val Pro Ile Val Leu Arg Ala Gly Lys
                325                 330                 335

Ala Leu Asp Glu Gly Lys Val Glu Ile Arg Ile Gln Phe Lys Pro Val
            340                 345                 350

Ala Lys Gly Met Phe Lys Glu Ile Gln Arg Asn Glu Leu Val Ile Arg
        355                 360                 365
```

```
Ile Gln Pro Asp Glu Ala Ile Tyr Leu Lys Ile Asn Ser Lys Ile Pro
        370                 375                 380
Gly Ile Ser Thr Glu Thr Ser Leu Thr Asp Leu Asp Leu Thr Tyr Ser
385                 390                 395                 400
Lys Arg Tyr Ser Lys Asp Phe Trp Ile Pro Glu Ala Tyr Glu Ala Leu
                405                 410                 415
Ile Arg Asp Cys Tyr Leu Gly Asn His Ser Asn Phe Val Arg Asp Asp
                420                 425                 430
Glu Leu Glu Val Ala Trp Lys Leu Phe Thr Pro Leu Leu Glu Ala Val
        435                 440                 445
Glu Lys Glu Asp Glu Val Ser Leu Gly Thr Tyr Pro Tyr Gly Ser Lys
        450                 455                 460
Gly Pro Lys Glu Leu Arg Lys Tyr Leu Val Asp His Gly Tyr Val Phe
465                 470                 475                 480
Asn Asp Pro Gly Thr Tyr Gln Trp Pro Leu Thr Asn Thr Asp Val Lys
                485                 490                 495
Gly Lys Ile

<210> SEQ ID NO 35
<211> LENGTH: 5016
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atggtcatcc aagggaagag attggccgcc tcctctattc agcttctcgc aagctcgtta      60
gacgcgaaga agctttgtta tgagtatgac gagaggcaag ccccaggtgt aacccaaatc     120
accgaggagg cgcctacaga gcaaccgcct ctctctaccc ctccctcgct accccaaacg     180
cccaatattt cgcctataag tgcttcaaag atcgtgatcg acgatgtggc gctatctcga     240
gtgcaaattg ttcaggctct tgttgccaga aagttgaaga cggcaattgc tcagcttcct     300
acatcaaagt caatcaaaga gttgtcgggt ggtcggtctt ctttgcagaa cgagctcgtg     360
ggggatatac acaacgagtt cagctccatc ccggatgcac cagagcagat cttgttgcgg     420
gactttggcg acgccaaccc aacagtgcaa ttggggaaaa cgtcctccgc ggcagttgcc     480
aaactaatct cgtccaagat gcctagtgac ttcaacgcca acgctattcg agcccaccta     540
gcaaacaagt ggggtctagg acccttgcga caaacagcgg tgttgctcta cgccattgcg     600
tcagaacccc catcgcgttt agcttcatcg agcgcagcgg aagagtactg ggacaacgtg     660
tcatccatgt acgccgaatc gtgtggcatc accctccgcc cgagacaaga cactatgaat     720
gaagatgcta tggcatcgtc ggcgattgat ccggctgtgg tagccgagtt ttccaagggg     780
caccgtaggc tcggagttca acagttccaa gcgctagcag aatacttaca aattgatttg     840
tcggggtctc aagcctctca gtcggatgct ttggtggcgg aacttcagca gaaagtcgat     900
ctctggacgg ccgaaatgac ccccgagttt ctcgccggga tatcaccaat gttggatgta     960
aagaagtcgc gacgctatgg ctcgtggtgg aacatggcac ggcaggatgt cttggccttc    1020
tatcgccgtc cttcctacag tgaattcgtg gacgacgcct tggccttcaa agtttttctc    1080
aatcgtctct gtaaccgagc tgatgaggcc ctcctcaaca tggtacgcag tctttcctgt    1140
gacgcctact tcaagcaagg ttcttttgcc ggatatcatg ccgcctcgcg actccttgag    1200
caggccatca catccacagt ggcggattgc ccgaaggcac gcctcattct cccggcggtg    1260
```

```
ggcccccaca ccaccattac aaaggacggc acgattgaat acgcggaggc accgcgccag   1320
ggagtgagtg gtcccactgc gtacatccag tctctccgcc aaggcgcatc tttcattggt   1380
ctcaagtcag ccgacgtcga tactcagagc aacttgaccg acgctttgct tgacgccatg   1440
tgcttagcac tccataatgg aatctcgttt gttggtaaaa cctttttggt gacgggagcg   1500
ggtcaggggt caataggagc gggagtggtg cgtctattgt tagagggagg agcccgagta   1560
ttggtgacga cgagcaggga gccggcgacg acatccagat acttccagca gatgtacgat   1620
aatcacggtg cgaagttctc cgagttgcgg gtagttcctt gcaatctagc cagcgcccaa   1680
gattgcgaag ggttgatccg gcacgtctac gatccccgtg ggctaaattg ggatttggat   1740
gccatccttc ccttcgctgc cgcgtccgac tacagcaccg agatgcatga cattcgggga   1800
cagagcgagt tgggccaccg gctaatgttg gtcaatgtct tccgcgtgtt ggggcatatc   1860
gtccactgta aacgagatgc cggggttgac tgccatccga cgcaggtgtt gttgccattg   1920
tcgccaaatc acggcatctt cggtggcgat gggatgtatc cggagtcaaa gctagccctt   1980
gagagcttgt tccatcgcat ccgatcagag tcttggtcag accagttatc tatatgcggc   2040
gttcgtatcg gttggacccg gtcgaccggt ctaatgacgg cgcatgatat catagccgaa   2100
acggtcgagg aacacggaat acgcacattt tccgtggccg agatggcact caacatagcc   2160
atgttgttaa cccccgactt tgtggcccat tgtgaagatg gacctttgga tgccgatttc   2220
accggcagct tgggaacatt gggtagcatc cccggtttcc tagcccaatt gcaccagaaa   2280
gtccagttgg cagccgaggt gatccgtgcc gtgcaggccg aggatgagca tgagagattc   2340
ttgtctccgg gaacaaaacc taccttgcaa gcacccgtgg ccccaatgca cccccgcagt   2400
agccttcgtg taggctatcc ccgtctcccc gattatgagc aagagattcg cccgttgtcc   2460
ccacggttgg aaaggttgca agatccggcc aatgctgtgg tggtggtcgg gtactcggag   2520
ttggggccat ggggtagcgc gcgattacgg tgggaaatag agagccaggg ccagtggact   2580
tcagccggtt atgtcgaact tgcctggttg atgaacctca tccgccacgt caacgatgaa   2640
tcctacgtcg gctgggtgga tactcagacc ggaaagccag tgcgggatgg cgagatccag   2700
gcattgtacg gggaccacat tgacaaccac accggtatcc gtcctatcca gtccacctcg   2760
tacaacccag agcgcatgga ggtcttgcag gaggtcgctg tcgaggagga tttgcccgag   2820
tttgaagtat ctcaacttac cgccgacgcc atgcgtctcc gccatggagc taacgtttcc   2880
atccgcccca gtggaaatcc cgacgcatgc cacgtgaagc ttaaacgagg cgctgttatc   2940
cttgttccca agacagttcc ctttgtttgg ggatcgtgtg ccggtgagtt gccgaaggga   3000
tggactccag ccaagtacgg catccctgag aacctaattc atcaggtcga ccccgtcacg   3060
ctctatacaa tttgctgcgt ggcggaggca ttttacagtg ccggtataac tcaccctctt   3120
gaggtctttc gacacattca cctctcggaa ctaggcaact ttatcggatc ctccatgggt   3180
gggccgacga agactcgtca gctctaccga gatgtctact tcgaccatga gattccgtcg   3240
gatgttttgc aagacactta tctcaacaca cctgctgcct gggttaatat gctactcctt   3300
ggctgcacgg ggccgatcaa aactcccgtc ggcgcatgtg ccaccggggt cgagtcgatc   3360
gattccggct acgagtcaat catggcgggc aagacaaaga tgtgtcttgt gggtggctac   3420
gacgatttgc aggaggaggc atcgtatgga ttcgcacaac ttaaggccac ggtcaacgtt   3480
gaagaggaga tcgcctgcgg tcgacagccc tcggagatgt cgcgccccat ggctgagagt   3540
cgtgctggct tgtcgaggc gcatggctgc ggtgtacagt tgttgtgtcg aggtgacatc   3600
gccttgcaaa tgggtcttcc tatctatgcg gtcattgcca gctcagccat ggccgccgac   3660
```

```
aagatcggtt cctcggtgcc agcacgggc cagggcattc taagcttctc ccgtgagcgc    3720
gctcgatcca gtatgatatc cgtcacgtcg cgcccgagta gccgtagcag cacatcatct    3780
gaagtctcgg acaaatcatc cttgacctca atccctcaa tcagcaatcc cgctcctcgt    3840
gcacaacgcg cccgatccac cactgatatg gctccgttgc gagcagcgct tgcgacttgg    3900
gggttgacta tcgacgactt ggatgtggcc tcattgcacg gcacctcgac gcgcggtaac    3960
gatctcaatg agcccgaggt gatcgagacg cagatgcgcc atttaggtcg cactcctggc    4020
cgccccttgt gggccatctg ccaaaagtca gtgacgggac accctaaagc cccagcggcc    4080
gcatggatgc tcaatggatg cttgcaagta ttggactcgg ggttggtgcc gggcaaccgc    4140
aatcttgaca cgttggacga ggccttgcgc agcgcgtctc atctctgctt ccctacgcgc    4200
accgtgcagc tacgtgaggt caaggcattc ttgttgacct catttggctt cggacagaag    4260
gggggccaag tcgtcggcgt tgcccccaag tacttctttg ctacgctccc ccgccccgag    4320
gttgagggct actatcgcaa ggtgagggtt cgaaccgagg cgggtgatcg cgcctacgcc    4380
gcggcggtca tgtcgcaggc ggtggtgaag atccagacgc aaaacccgta cgacgagccg    4440 gatgccccc gcattttct cgatcccttg gcacgtatct cccaggatcc gtcgacgggc    4500
cagtatcggt ttcgttccga tgccactccc gccctcgatg atgatgcttt gccacctccc    4560
ggcgaaccca ccgagctagt gaagggcatc tcctccgcct ggatcgagga aaggtgcga    4620 ccgcatatgt ctcccggcgg cacggtgggc gtggacttgg ttcctctcgc ctccttcgac    4680
gcatacaaga atgccatctt tgttgagcgc aattatacgg taaggagcg cgattgggct    4740 gaaaagagtg cggatgtgcg cgcggcctat gccagtcggt ggtgtgcaaa agaggcggtg    4800
ttcaaatgtc tccagacaca ttcacagggc gcggggcag ccatgaaaga gattgagatc    4860
gagcatggag gtaacggcgc accgaaagtc aagctccggg gtgctgcgca aacagcggcg    4920
cggcaacgag gattggaagg agtgcaattg agcatcagct atggcgacga tgcggtgata    4980
gcggtggcgt tggggttgat gtctggtgct tcataa                            5016
```

<210> SEQ ID NO 36
<211> LENGTH: 5667
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
atgggttccg ttagtaggga acatgagtca atccccatcc aggccgccca gagaggcgct     60
gcccggatct gcgctgcttt tggaggtcaa gggtctaaca atttggacgt gttaaaaggt    120
ctattggagt tatacaagcg gtatggccca gatttggatg agctactaga cgtggcatcc    180
aacacgcttt cgcagttggc atcttcccct gctgcaatag acgtccacga accctggggt    240
ttcgacctcc gacaatggtt gaccacaccg gaggttgctc ctagcaaaga aattcttgcc    300
ttgccaccac gaagctttcc cttaaatacg ttacttagct tggcgctcta ttgtgcaact    360
tgtcgagagc ttgaacttga tcctgggcaa tttcgatccc tccttcatag ttccacgggg    420
cattcccaag gcatattggc ggcggtggcc atcacccaag ccgagagctg gccaaccttt    480
tatgacgcct gcaggacggt gctccagatc tcttctctgga ttggactcga ggcttacctc    540
ttcactccat cctccgccgc ctcggatgcc atgatccaag attgcatcga acatggcgag    600
ggccttcttt cctcaatgct aagtgtctcc gggtctcccc gctcccaagt tgagcgagta    660
attgagcacg tcaataaagg gctcggagaa tgcaaccgat gggttcactt ggccttggtt    720
```

-continued

```
aactcccacg aaaagttcgt cttagcggga ccacctcaat ccttatgggc cgtttgtctt    780
catgtccgac ggatcagagc agacaatgac ctcgaccagt cgcgtatctt gttccgcaac    840
cgaaagccta tagtggatat attatttctt cccatatccg caccatttca cacaccgtac    900
ttggacggtg ttcaagatcg cgttatcgag gctttgagct ctgcttcgtt ggctctccat    960
tccatcaaaa tccccctcta tcacacgggc actgggagca acctacaaga actacaacca   1020
catcagctaa tcccgactct tatccgcgcc attaccgtgg accaattgga ctggccgttg   1080
gtttgccggg gcttgaacgc aacgcacgtg ttggactttg gacctggaca acatgcagt    1140 cttattcagg agctcacaca aggaacaggt gtatcagtga tccagttgac tactcaatcg   1200
ggaccaaaac ccgttggagg ccatttggcg gcagtgaact gggaggccga gtttggctta   1260
cgacttcatg ccaatgtcca cggtgcagct aaattgcaca accgtatgac aacattgctt   1320
gggaagcctc ctgtgatggt agccggaatg acacctacta cggtgcgctg ggactttgtc   1380
gctgccgttg ctcaagctgg ataccacgtc gaattggctg gtggtggcta ccacgcagag   1440
cgccagttcg aggccgagat tcggcgcttg gcaactgcca tcccagcaga tcatggcatc   1500
acctgcaatc tcctctacgc caagcctacg acttttttcct ggcagatctc tgtcatcaag   1560
gatttggtgc gccagggagt tcccgtggaa ggaatcacca tcggcgccgg catcccttct   1620
ccggaggtcg tccaagaatg tgtacagtcc atcggactca agcacatctc attcaagcct   1680
gggtctttcg aagccattca ccaagtcata cagatcgcgc gtacccatcc taacttttttg   1740 atcgggttgc aatggaccgc aggacgaggg ggaggacatc attcctggga agacttccat   1800
ggacctattt tggcaaccta cgctcaaatc cgatcatgtc cgaatattct cctcgttgta   1860
ggtagtggat tcggtggagg cccggacacg tttcccctacc tcacgggcca atgggcccag   1920
gcctttggct atccatgcat gcccttcgac ggagtgttgc tcggcagtcg catgatggtg   1980
gctcgggaag cccatacgtc agcccaggca aaacgcttga ttatagatgc gcaaggcgtg   2040
ggagatgcag attggcacaa gtctttcgat gagcctaccg gcggcgtagt gacggtcaac   2100
tcggaattcg gtcaacctat ccacgttcta gctactcgcg gagtgatgtt gtggaaagaa   2160
ctcgacaacc gggtcttttc aatcaaagac acttctaagc gcttagaata tttgcgcaac   2220
caccggcaag aaattgtgag ccgtcttaac gcagactttg cccgtccctg gtttgccgtt   2280
gacggacacg gacagaatgt ggagttggag gacatgacct acctcgaggt tctccgccgt   2340
ttgtgcgatc tcacgtatgt ttcccaccag aagcgatggg tagatccatc atatcgaata   2400
ttattgttgg acttcgttca tttgcttcga gaacgattcc aatgcgctat tgacaaccccc   2460 ggcgaatatc cactcgacat catcgtccgg gtggaagaga gcttgaagga taaagcatac   2520
cgcacgcttt atccagaaga tgtctctctt ctaatgcatt tgttcagccg acgtgacatc   2580
aagcccgtac cattcatccc caggttggat gagcgttttg agacctggtt taaaaaagac   2640
tcattgtggc aatccgaaga tgtggaggcg gtaattggac aggacgtcca gcgaatcttc   2700
atcattcaag ggcctatggc cgttcagtac tcaatatccg acgatgagtc tgttaaagac   2760
attttacaca atatttgtaa tcattacgtg gaggctctac aggctgattc aagagaaact   2820
tctatcggcg atgtacactc gatcacgcaa aaacctctca gcgcgtttcc tgggctcaaa   2880
gtgacgacaa ataggtccca agggctctat aagttcgaga agtaggagc agtccccgaa   2940 atggacgttc ttttttgagca tattgtcgga ttgtcgaagt catgggctcg gacatgtttg   3000
atgagtaaat cggtctttag ggacggttct cgtttgcata accccattcg cgccgcactc   3060
cagctccagc gcggcgacac catcgaggtg ctttttaacag cagactcgga aattcgcaag   3120
```

```
attcgactta tttcacccac gggggatggt ggatccactt ctaaggtcgt attagagata    3180
gtctctaacg acggacaaag agttttcgcc accttggccc ctaacatccc actcagcccc    3240
gagcccagcg tcgtcttttg cttcaaggtc gaccagaagc cgaatgagtg gacccttgag    3300
gaggatgcgt ctggccgggc agagaggatc aaggcattat acatgagttt gtggaacttg    3360
ggctttccga acaaggcctc tgttttgggt cttaattcgc aattcacggg agaagaattg    3420
atgatcacaa cggacaagat tcgtgatttc gaaagggtat tgcggcaaac cagtcctctt    3480
cagttgcagt catggaaccc ccaaggatgt gtacctatcg actactgcgt ggtcatcgcc    3540
tggtctgctc ttaccaagcc tttgatggtc tcctctttga aatgcgacct cttggatttg    3600
ctccacagcg ctataagctt ccactatgct ccatctgtca aaccattgcg ggtgggcgat    3660
attgtcaaaa cctcatcccg tatcctagcg gtctcggtga gacctagggg aactatgttg    3720
acggtgtcgg cggacattca gcgccaggga caacatgtag tcactgtcaa atcagatttc    3780
tttctcggag gccccgtttt ggcatgtgaa acccctttcg aactcactga ggagcctgaa    3840
atggttgtcc atgtcgactc tgaagtgcgc cgtgctattt tacacagccg caagtggctc    3900
atgcgagaag atcgcgcgct agatttgcta gggaggcagc tcctcttcag attaaagagc    3960
gaaaaattgt tcaggccaga cggccagcta gcattgttac aggtaacagg ttccgtgttc    4020
agctacagcc ccgatgggtc aacgacagca ttcggtcgcg tatacttcga aagcgagtct    4080
tgtacaggga acgtggtgat ggacttcttg caccgctacg gtgcacctcg ggcgcagttg    4140
ttggagttgc aacatcccgg gtggacgggc acctctactg tggcagtaag aggtcctcga    4200
cgcagccaat cctacgcacg cgtctccctc gatcataatc ccatccatgt tgtccggcc     4260
tttgcgcgat acgctggtct ctcgggtccc attgtccatg ggatggaaac ctctgccatg    4320
atgcgcagaa ttgccgaatg ggccatcgga gatgcagacc ggtctcggtt ccggagctgg    4380
catatcacct tgcaagcacc cgtccacccc aacgacccct tgcgggtgga gttgcagcat    4440
aaggccatgg aggacgggga aatggttttg aaagtacaag catttaacga aaggacggaa    4500
gaacgcgtag cggaggcaga tgcccatgtt gagcaggaaa ctacggctta cgtcttctgt    4560
ggccagggca gtcaacgaca ggggatggga atggacttgt acgtcaactg tccggaggct    4620
aaagcgttgt gggctcgcgc cgacaagcat ttgtgggaga atatgggtt ctccatcttg     4680
cacattgtgc aaaacaaccc tccagccctc actgttcact ttggcagcca gcgagggcgc    4740
cgtattcgtg ccaactattt gcgcatgatg ggacagccac cgatagatgg tagacatccg    4800
cccatattga agggattgac gcggaattcg acctcgtaca ccttctccta ttcccagggg    4860
ttgttgatgt ccacccagtt cgcccagccc gcattggcgt tgatgaaat ggctcagttc     4920
gaatggctca aagcccaggg agtcgttcag aagggtgcgc ggttcgcggg acattcgttg    4980
ggagaatatg ccgcccttgg agcttgtgct tccttcctct catttgaaga tctcatatct    5040
ctcatctttt atcggggctt gaagatgcag aatgcgttgc cgcgcgatgc caacggccac    5100
accgactatg gaatgttggc tgccgatcca tcgcggatag gaaaaggttt cgaggaagcg    5160
agtttgaaat gtcttgtcca tatcattcaa caggagaccg gctggttcgt ggaagtcgtc    5220
aactacaaca tcaactcgca gcaatacgtc tgtgcaggcc atttccgagc cctttggatg    5280
ttgggtaaga tatgcgatga cctttcatgc caccctcaac cggagactgt tgaaggccaa    5340
gagctacggg ccatggtctg gaagcatgtc ccgacggtgg agcaggtgcc ccgcgaggat    5400
cgcatggaac gaggtcgagc gaccattccg ttgccgggga tcgatatccc ataccattcg    5460
accatgttac gagggagat tgagccttat cgtgaatatt tgtctgaacg tatcaaggtg     5520
```

```
gggatgtga agccgtgcga attggtggga cgctggatcc ctaatgttgt tggccagcct    5580
ttctccgtcg ataagtctta cgttcagttg gtgcacggca tcacaggtag tcctcggctt    5640
cattccttgc ttcaacaaat ggcgtga                                        5667
```

<210> SEQ ID NO 37
<211> LENGTH: 2130
<212> TYPE: DNA
<213> ORGANISM: Candida tropicalis

<400> SEQUENCE: 37

```
atgactttta caaagaaaaa cgttagtgta tcacaaggtc ctgaccctag atcatccatc      60
caaaaggaaa gagacagctc caaatggaac cctcaacaaa tgaactactt cttggaaggc     120
tccgtcgaaa gaagtgagtt gatgaaggct ttggcccaac aaatggaaag agacccaatc     180
ttgttcacag acggctccta ctacgacttg accaaggacc aacaaagaga attgaccgcc     240
gtcaagatca cagaatcgc cagatacaga gaacaagaat ccatcgacac tttcaacaag     300
agattgtcct tgattggtat ctttgaccca caggtcggta ccagaattgg tgtcaacctc     360
ggtttgttcc tttcttgtat cagaggtaac ggtaccactt cccaattgaa ctactgggct     420
aacgaaaagg aaaccgctga cgttaaaggt atctacggtt gtttcggtat gaccgaattg     480
gcccacggtt ccaacgttgc tggtttggaa accaccgcca catttgacaa ggaatctgac     540
gagtttgtca tcaacacccc acacattggt gccaccaagt ggtggattgg tggtgctgct     600
cactccgcca cccactgttc tgtctacgcc agattgattg ttgacggtca agattacggt     660
gtcaagactt tgttgtccc attgagagac tccaaccacg acctcatgcc aggtgtcact     720
gttggtgaca ttggtgccaa gatgggtaga gatggtatcg ataacggttg gatccaattc     780
tccaacgtca gaatcccaag attctttatg ttgcaaaagt tctgtaaggt ttctgctgaa     840
ggtgaagtca ccttgccacc tttggaacaa ttgtcttact ccgccttgtt gggtggtaga     900
gtcatgatgg ttttggactc ctacagaatg ttggctagaa tgtccaccat gccttgaga     960 tacgccattg gtagaagaca attcaagggt gacaatgtcg atccaaaaga tccaaacgct    1020
ttggaaaccc aattgataga ttacccattg caccaaaaga gattgttccc atacttggct    1080
gctgcctacg tcatctccgc tggtgccctc aaggttgaag acaccatcca taacaccttg    1140
gctgaattgg acgctgccgt tgaaaagaac gacaccaagg ctatctttaa gtctattgac    1200
gacatgaagt cattgtttgt tgactctggt tccttgaagt ccactgccac ttggttgggt    1260
gctgaagcca ttgaccaatg tagacaagcc tgtggtggtc acggttactc gtcctacaac    1320
ggcttcggta agcctacaa cgattgggtt gtccaatgta cttgggaagg tgacaacaat    1380
gtcttggcca tgagtgttgg taagccaatt gtcaagcaag ttatcagcat gaagatgcc    1440 ggcaagaccg tcagaggttc caccgctttc ttgaaccaat tgaaggacta cactggttcc    1500
aacagctcca aggttgtttt gaacactgtt gctgacttgg acgacatcaa gactgtcatc    1560
aaggctattg aagttgccat catcagattg tcccaagaag ctgcttctat tgtcaagaag    1620
gaatctttcg actatgtcgg cgctgaattg gttcaactct ccaagttgaa ggctcaccac    1680
tacttgttga ctgaatacat cagaagaatt gacaccttg accaaaagga cttggttcca    1740
tacttgatca ccctcggtaa gttgtacgct gccactattg tcttggacag atttgccggt    1800
gtcttcttga ctttcaacgt tgcctccacc gaagccatca ctgctttggc ctctgtgcaa    1860
attccaaagt tgtgtgctga agtcagacca aacgttgttg cttacaccga ctccttccaa    1920
caatccgaca tgattgtcaa ttctgctatt ggtagatacg atggtgacat ctatgagaac    1980
```

```
tactttgact tggtcaagtt gcagaaccca ccatccaaga ccaaggctcc ttactctgat    2040
gctttggaag ccatgttgaa cagaccaacc ttggacgaaa gagaaagatt tgaaaagtct    2100
gatgaaaccg ctgctatctt gtccaagtaa                                    2130
```

<210> SEQ ID NO 38
<211> LENGTH: 1989
<212> TYPE: DNA
<213> ORGANISM: Candida tropicalis

<400> SEQUENCE: 38

```
atgcctaccg aacttcaaaa agaaagagaa ctcaccaagt tcaacccaaa ggagttgaac      60
tacttcttgg aaggttccca agaaagatcc gagatcatca gcaacatggt cgaacaaatg     120
caaaaagacc ctatcttgaa ggtcgacgct tcatactaca acttgaccaa agaccaacaa     180
agagaagtca ccgccaagaa gattgccaga ctctccagat actttgagca cgagtaccca     240
gaccaacagg cccagagatt gtcgatcctc ggtgtctttg acccacaagt cttcaccaga     300
atcggtgtca acttgggttt gtttgttttcc tgtgtccgtg gtaacggtac caactcccag     360
ttcttctact ggaccataaa taagggtatc gacaagttga gaggtatcta tggttgtttt     420
ggtatgactg agttggccca cggttccaac gtccaaggta ttgaaaccac cgccactttt     480
gacgaagaca ctgacgagtt tgtcatcaac accccacaca ttggtgccac caagtggtgg     540
atcggtggtg ctgcgcactc cgccacccac tgctccgtct acgccagatt gaaggtcaaa     600
ggaaaggact acggtgtcaa gacctttgtt gtcccattga gagactccaa ccacgacctc     660
gagccaggtg tgactgttgg tgacattggt gccaagatgg gtagagacgg tatcgataac     720
ggttggatcc agttctccaa cgtcagaatc ccaagattct ttatgttgca aaagtactgt     780
aaggtttccc gtctgggtga agtcaccatg ccaccatctg aacaattgtc ttactcggct     840
ttgattggtg gtagagtcac catgatgatg gactcctaca atgaccagt agattcatc     900 accattgcct tgagatacgc catccacaga agacaattca gaagaagga caccgatacc     960 attgaaacca agttgattga ctacccattg catcaaaaga gattgttccc attcttggct    1020
gccgcttact tgttctccca aggtgccttg tacttagaac aaaccatgaa cgcaaccaac    1080
gacaagttgg acgaagctgt cagtgctggt gaaaaggaag ccattgacgc tgccattgtc    1140
gaatccaaga aattgttcgt cgcttccggt tgtttgaagt ccacctgtac ctggttgact    1200
gctgaagcca ttgacgaagc tcgtcaagct tgtggtggtc acggttactc gtcttacaac    1260
ggtttcggta agcctactc cgactgggtt gtccaatgta cctgggaagg tgacaacaac    1320
atcttggcca tgaacgttgc caagccaatg gttagagact tgttgaagga gccgaacaa    1380 aagggattgg ttctctccag cgttgccgac ttggacgacc cagccaagtt ggttaaggct    1440
ttcgaccacg ccctttccgg cttggccaga gacattggtg ctgttgctga agacaagggt    1500
ttcgacatta ccggtccaag tttggttttg gtttccaagt gaacgctca cagattcttg    1560 attgacggtt tcttcaagcg tatcacccca gaatggtctg aagtcttgag acctttgggt    1620
ttcttgtatg ccgactggat cttgaccaac tttggtgcca ccttcttgca gtacggtatc    1680
attaccccag atgtcagcag aaagatttcc tccgagcact tcccagccct gtgtgccaag    1740
gttagaccaa acgttgttgg tttgactgat ggtttcaact tgactgacat gatgaccaat    1800
gctgctattg gtagatatga tggtaacgtc tacgaacact acttcgaaac tgtcaaggct    1860
ttgaacccac cagaaacacc caaggctcca tactccaagg ctttggaaga catgttgaac    1920
cgtccagacc ttgaagtcag agaaagaggt gaaaagtccg aagaagctgc tgaaatcttg    1980
``` tccagttaa                                                                 1989

<210> SEQ ID NO 39
<211> LENGTH: 709
<212> TYPE: PRT
<213> ORGANISM: Candida tropicalis

<400> SEQUENCE: 39

```
Met Thr Phe Thr Lys Lys Asn Val Ser Val Ser Gln Gly Pro Asp Pro
1               5                   10                  15

Arg Ser Ser Ile Gln Lys Glu Arg Asp Ser Ser Lys Trp Asn Pro Gln
            20                  25                  30

Gln Met Asn Tyr Phe Leu Glu Gly Ser Val Glu Arg Ser Glu Leu Met
        35                  40                  45

Lys Ala Leu Ala Gln Gln Met Glu Arg Asp Pro Ile Leu Phe Thr Asp
    50                  55                  60

Gly Ser Tyr Tyr Asp Leu Thr Lys Asp Gln Gln Arg Glu Leu Thr Ala
65                  70                  75                  80

Val Lys Ile Asn Arg Ile Ala Arg Tyr Arg Glu Gln Glu Ser Ile Asp
                85                  90                  95

Thr Phe Asn Lys Arg Leu Ser Leu Ile Gly Ile Phe Asp Pro Gln Val
            100                 105                 110

Gly Thr Arg Ile Gly Val Asn Leu Gly Leu Phe Leu Ser Cys Ile Arg
        115                 120                 125

Gly Asn Gly Thr Thr Ser Gln Leu Asn Tyr Trp Ala Asn Glu Lys Glu
    130                 135                 140

Thr Ala Asp Val Lys Gly Ile Tyr Gly Cys Phe Gly Met Thr Glu Leu
145                 150                 155                 160

Ala His Gly Ser Asn Val Ala Gly Leu Glu Thr Thr Ala Thr Phe Asp
                165                 170                 175

Lys Glu Ser Asp Glu Phe Val Ile Asn Thr Pro His Ile Gly Ala Thr
            180                 185                 190

Lys Trp Trp Ile Gly Gly Ala Ala His Ser Ala Thr His Cys Ser Val
        195                 200                 205

Tyr Ala Arg Leu Ile Val Asp Gly Gln Asp Tyr Gly Val Lys Thr Phe
    210                 215                 220

Val Val Pro Leu Arg Asp Ser Asn His Asp Leu Met Pro Gly Val Thr
225                 230                 235                 240

Val Gly Asp Ile Gly Ala Lys Met Gly Arg Asp Gly Ile Asp Asn Gly
                245                 250                 255

Trp Ile Gln Phe Ser Asn Val Arg Ile Pro Arg Phe Phe Met Leu Gln
            260                 265                 270

Lys Phe Cys Lys Val Ser Ala Glu Gly Glu Val Thr Leu Pro Pro Leu
        275                 280                 285

Glu Gln Leu Ser Tyr Ser Ala Leu Leu Gly Gly Arg Val Met Met Val
    290                 295                 300

Leu Asp Ser Tyr Arg Met Leu Ala Arg Met Ser Thr Ile Ala Leu Arg
305                 310                 315                 320

Tyr Ala Ile Gly Arg Arg Gln Phe Lys Gly Asp Asn Val Asp Pro Lys
                325                 330                 335

Asp Pro Asn Ala Leu Glu Thr Gln Leu Ile Asp Tyr Pro Leu His Gln
            340                 345                 350

Lys Arg Leu Phe Pro Tyr Leu Ala Ala Ala Tyr Val Ile Ser Ala Gly
        355                 360                 365
```

Ala Leu Lys Val Glu Asp Thr Ile His Asn Thr Leu Ala Glu Leu Asp
    370                 375                 380

Ala Ala Val Glu Lys Asn Asp Thr Lys Ala Ile Phe Lys Ser Ile Asp
385                 390                 395                 400

Asp Met Lys Ser Leu Phe Val Asp Ser Gly Ser Leu Lys Ser Thr Ala
                405                 410                 415

Thr Trp Leu Gly Ala Glu Ala Ile Asp Gln Cys Arg Gln Ala Cys Gly
            420                 425                 430

Gly His Gly Tyr Ser Ser Tyr Asn Gly Phe Gly Lys Ala Tyr Asn Asp
        435                 440                 445

Trp Val Val Gln Cys Thr Trp Glu Gly Asp Asn Asn Val Leu Ala Met
    450                 455                 460

Ser Val Gly Lys Pro Ile Val Lys Gln Val Ile Ser Ile Glu Asp Ala
465                 470                 475                 480

Gly Lys Thr Val Arg Gly Ser Thr Ala Phe Leu Asn Gln Leu Lys Asp
                485                 490                 495

Tyr Thr Gly Ser Asn Ser Ser Lys Val Val Leu Asn Thr Val Ala Asp
            500                 505                 510

Leu Asp Asp Ile Lys Thr Val Ile Lys Ala Ile Glu Val Ala Ile Ile
        515                 520                 525

Arg Leu Ser Gln Glu Ala Ala Ser Ile Val Lys Lys Glu Ser Phe Asp
    530                 535                 540

Tyr Val Gly Ala Glu Leu Val Gln Leu Ser Lys Leu Lys Ala His His
545                 550                 555                 560

Tyr Leu Leu Thr Glu Tyr Ile Arg Arg Ile Asp Thr Phe Asp Gln Lys
                565                 570                 575

Asp Leu Val Pro Tyr Leu Ile Thr Leu Gly Lys Leu Tyr Ala Ala Thr
            580                 585                 590

Ile Val Leu Asp Arg Phe Ala Gly Val Phe Leu Thr Phe Asn Val Ala
        595                 600                 605

Ser Thr Glu Ala Ile Thr Ala Leu Ala Ser Val Gln Ile Pro Lys Leu
    610                 615                 620

Cys Ala Glu Val Arg Pro Asn Val Val Ala Tyr Thr Asp Ser Phe Gln
625                 630                 635                 640

Gln Ser Asp Met Ile Val Asn Ser Ala Ile Gly Arg Tyr Asp Gly Asp
                645                 650                 655

Ile Tyr Glu Asn Tyr Phe Asp Leu Val Lys Leu Gln Asn Pro Pro Ser
            660                 665                 670

Lys Thr Lys Ala Pro Tyr Ser Asp Ala Leu Glu Ala Met Leu Asn Arg
        675                 680                 685

Pro Thr Leu Asp Glu Arg Glu Arg Phe Glu Lys Ser Asp Glu Thr Ala
    690                 695                 700

Ala Ile Leu Ser Lys
705

<210> SEQ ID NO 40
<211> LENGTH: 662
<212> TYPE: PRT
<213> ORGANISM: Candida tropicalis

<400> SEQUENCE: 40

Met Pro Thr Glu Leu Gln Lys Glu Arg Glu Leu Thr Lys Phe Asn Pro
1               5                   10                  15

Lys Glu Leu Asn Tyr Phe Leu Glu Gly Ser Gln Glu Arg Ser Glu Ile
            20                  25                  30

```
Ile Ser Asn Met Val Glu Gln Met Gln Lys Asp Pro Ile Leu Lys Val
         35                  40                  45

Asp Ala Ser Tyr Tyr Asn Leu Thr Lys Asp Gln Gln Arg Glu Val Thr
 50                  55                  60

Ala Lys Lys Ile Ala Arg Leu Ser Arg Tyr Phe Glu His Glu Tyr Pro
 65                  70                  75                  80

Asp Gln Gln Ala Gln Arg Leu Ser Ile Leu Gly Val Phe Asp Pro Gln
                 85                  90                  95

Val Phe Thr Arg Ile Gly Val Asn Leu Gly Leu Phe Val Ser Cys Val
             100                 105                 110

Arg Gly Asn Gly Thr Asn Ser Gln Phe Phe Tyr Trp Thr Ile Asn Lys
             115                 120                 125

Gly Ile Asp Lys Leu Arg Gly Ile Tyr Gly Cys Phe Gly Met Thr Glu
 130                 135                 140

Leu Ala His Gly Ser Asn Val Gln Gly Ile Glu Thr Thr Ala Thr Phe
 145                 150                 155                 160

Asp Glu Asp Thr Asp Glu Phe Val Ile Asn Thr Pro His Ile Gly Ala
                 165                 170                 175

Thr Lys Trp Trp Ile Gly Gly Ala Ala His Ser Ala Thr His Cys Ser
             180                 185                 190

Val Tyr Ala Arg Leu Lys Val Lys Gly Lys Asp Tyr Gly Val Lys Thr
             195                 200                 205

Phe Val Val Pro Leu Arg Asp Ser Asn His Asp Leu Glu Pro Gly Val
 210                 215                 220

Thr Val Gly Asp Ile Gly Ala Lys Met Gly Arg Asp Gly Ile Asp Asn
225                 230                 235                 240

Gly Trp Ile Gln Phe Ser Asn Val Arg Ile Pro Arg Phe Phe Met Leu
                 245                 250                 255

Gln Lys Tyr Cys Lys Val Ser Arg Ser Gly Glu Val Thr Met Pro Pro
             260                 265                 270

Ser Glu Gln Leu Ser Tyr Ser Ala Leu Ile Gly Gly Arg Val Thr Met
             275                 280                 285

Met Met Asp Ser Tyr Arg Met Thr Ser Arg Phe Ile Thr Ile Ala Leu
 290                 295                 300

Arg Tyr Ala Ile His Arg Arg Gln Phe Lys Lys Lys Asp Thr Asp Thr
305                 310                 315                 320

Ile Glu Thr Lys Leu Ile Asp Tyr Pro Leu His Gln Lys Arg Leu Phe
                 325                 330                 335

Pro Phe Leu Ala Ala Tyr Leu Phe Ser Gln Gly Ala Leu Tyr Leu
             340                 345                 350

Glu Gln Thr Met Asn Ala Thr Asn Asp Lys Leu Asp Glu Ala Val Ser
             355                 360                 365

Ala Gly Glu Lys Glu Ala Ile Asp Ala Ala Ile Val Glu Ser Lys Lys
 370                 375                 380

Leu Phe Val Ala Ser Gly Cys Leu Lys Ser Thr Cys Thr Trp Leu Thr
385                 390                 395                 400

Ala Glu Ala Ile Asp Glu Ala Arg Gln Ala Cys Gly Gly His Gly Tyr
                 405                 410                 415

Ser Ser Tyr Asn Gly Phe Gly Lys Ala Tyr Ser Asp Trp Val Val Gln
             420                 425                 430

Cys Thr Trp Glu Gly Asp Asn Asn Ile Leu Ala Met Asn Val Ala Lys
             435                 440                 445

Pro Met Val Arg Asp Leu Leu Lys Glu Pro Glu Gln Lys Gly Leu Val
 450                 455                 460
```

```
Leu Ser Ser Val Ala Asp Leu Asp Pro Ala Lys Leu Val Lys Ala
465                 470                 475                 480

Phe Asp His Ala Leu Ser Gly Leu Ala Arg Asp Ile Gly Ala Val Ala
            485                 490                 495

Glu Asp Lys Gly Phe Asp Ile Thr Gly Pro Ser Leu Val Leu Val Ser
            500                 505                 510

Lys Leu Asn Ala His Arg Phe Leu Ile Asp Gly Phe Lys Arg Ile
            515                 520                 525

Thr Pro Glu Trp Ser Glu Val Leu Arg Pro Leu Gly Phe Leu Tyr Ala
            530                 535                 540

Asp Trp Ile Leu Thr Asn Phe Gly Ala Thr Phe Leu Gln Tyr Gly Ile
545                 550                 555                 560

Ile Thr Pro Asp Val Ser Arg Lys Ile Ser Ser Glu His Phe Pro Ala
                565                 570                 575

Leu Cys Ala Lys Val Arg Pro Asn Val Val Gly Leu Thr Asp Gly Phe
            580                 585                 590

Asn Leu Thr Asp Met Met Thr Asn Ala Ala Ile Gly Arg Tyr Asp Gly
            595                 600                 605

Asn Val Tyr Glu His Tyr Phe Glu Thr Val Lys Ala Leu Asn Pro Pro
            610                 615                 620

Glu Asn Thr Lys Ala Pro Tyr Ser Lys Ala Leu Glu Asp Met Leu Asn
625                 630                 635                 640

Arg Pro Asp Leu Glu Val Arg Glu Arg Gly Glu Lys Ser Glu Ala
                645                 650                 655

Ala Glu Ile Leu Ser Ser
            660

<210> SEQ ID NO 41
<211> LENGTH: 1049
<212> TYPE: PRT
<213> ORGANISM: Bacillus megaterium

<400> SEQUENCE: 41

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
            85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Pro Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
            165                 170                 175
```

```
Ser Met Val Arg Ala Ser Asp Glu Ala Met Asn Lys Ser Gln Arg Ala
            180                 185                 190

Asn Pro Asp Asp Pro Ala Tyr Asp Glu Asn Lys Arg Gln Phe Gln Glu
            195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
            245                 250                 255

Tyr Gln Ile Ile Thr Phe Leu Ile Ala Gly His Glu Thr Thr Ser Gly
            260                 265                 270

Leu Leu Ser Phe Ala Ser Tyr Phe Leu Val Lys Asn Pro His Val Leu
            275                 280                 285

Gln Lys Ala Ala Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Ser Arg Leu Trp Pro Thr Ala Pro Ala Phe Ser Leu Tyr Ala
            325                 330                 335

Lys Glu Asp Thr Val Leu Gly Gly Glu Tyr Pro Leu Glu Lys Gly Asp
            340                 345                 350

Glu Leu Met Val Ser Ile Pro Gln Leu His Arg Asp Lys Thr Ile Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Ser Val Leu Gly
            405                 410                 415

Met Met Leu Lys His Phe Asp Phe Glu Asp His Thr Asn Tyr Glu Ser
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Ser Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
```

-continued

```
                595                 600                 605
Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
                675                 680                 685

Leu Pro Lys Glu Ala Ser Tyr Gln Glu Gly Asp His Leu Gly Val Ile
                690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Ser Glu Ala Glu Glu Lys Leu
                725                 730                 735

Ala His Leu Pro Leu Ala Lys Thr Val Ser Val Glu Glu Leu Ser Gln
                740                 745                 750

Tyr Val Glu Leu Gln Asp Pro Val Thr Arg Thr Gln Leu Arg Ala Met
                755                 760                 765

Ala Ala Lys Thr Val Cys Pro Pro His Lys Val Leu Glu Ala Leu
                770                 775                 780

Leu Glu Lys Gln Ala Tyr Lys Glu Gln Val Ser Ala Lys Arg Leu Thr
785                 790                 795                 800

Met Leu Glu Ser Leu Glu Lys Tyr Pro Ala Cys Glu Met Lys Phe Ser
                805                 810                 815

Glu Phe Ile Ala Leu Ser Pro Ser Ile Arg Pro Arg Tyr Tyr Ser Ile
                820                 825                 830

Ser Ser Ser Pro Arg Val Asp Glu Lys Gln Ala Ser Ile Thr Val Ser
                835                 840                 845

Val Val Ser Gly Glu Ala Trp Ser Gly Tyr Gly Glu Tyr Lys Gly Ile
850                 855                 860

Ala Ser Asn Tyr Leu Ala Glu Ser Gln Glu Gly Asp Thr Ile Thr Cys
865                 870                 875                 880

Phe Ile Ser Thr Pro Gln Ser Glu Phe Thr Ser Pro Lys Asp Pro Glu
                885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
                915                 920                 925

Gly Glu Ala His Leu Tyr Phe Gly Cys Arg Ser Pro His Glu Asp Tyr
                930                 935                 940

Ser Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
                980                 985                 990

Gln Gly Ala His Phe Tyr Ile Cys Gly Asp Gly Ser Gln Met Ala Pro
                995                 1000                1005

Ala Val Glu Ala Thr Leu Met Lys Ser Tyr Ala Asp Val His Gln
   1010                1015                 1020
```

Val Ser Glu Ala Asp Ala Arg Leu Trp Ser Gln Gln Leu Glu Glu
1025                1030                1035

Lys Gly Arg Tyr Ala Lys Asp Val Trp Ala Gly
    1040                1045

<210> SEQ ID NO 42
<211> LENGTH: 1530
<212> TYPE: DNA
<213> ORGANISM: Candida tropicalis

<400> SEQUENCE: 42

```
atgatcagaa ccgtccgtta tcaatccctc aagaggttca gacctctggc tttgtctcct        60
gtttttcgtc cacgctacaa ctcccagaag gccaatttcc accgtccaga ccaccctggg       120
tccgacgagc cagctgaagc cgccgacgcc gccgccacga tcctcgccga gttgcgagac       180
aagcagacga acccgaacaa ggccacctgg ctcgatgcgt taacggagcg ggagaagttg       240
cgtgccgagg gcaagacgat tgacagtttc agctacgttg accccaagac gaccgtcgtg       300
ggggagaaga cacgcagtga ctcgttctcg ttcttgttgt tgccgttcaa ggacgacaag       360
tggttgtgtg acgcgtacat caatgcgttt ggccggttgc gtgtagcgca gttgttccag       420
gacttggacg ccttggcggg gcgcatcgcg tacaggcact gttccccagc ggagcccgtg       480
aatgtcacgg cgagcgtgga tagggtgtac atggtgaaga agtggacga gattaacaat       540
tacaatttcg tgttggcggg gtccgtgacg tggaccggga gatcgtcgat ggagatcacg       600
gtgaaagggt atgcttttga agacgccgtg ccggatataa cgaacgagga gtccttgccg       660
gcagagaatg tgttttttggc tgctaatttc accttcgtgg cacggaaccc acttacacac       720
aagtcctttg ctattaacag attgttgccc gtgactgaga aggactgggt cgactatcgc       780
cgtgctgagt cccacaacgc caagaagaag ttgatggcaa agaacaagaa gatcttggag       840
cctaccgcgg aagagtccaa gttgatctac gacatgtgga gatcgtccaa gtccttacag       900
aacatcgaga gggccaacga tgggatcgcg ttcatgaagg acacgaccat gaagtccacc       960
ttgttcatgc agccccagta ccgtaacaga cactcataca tgatttttcgg agggtacttg      1020
ttaagacaaa ctttcgaatt ggcctactgt accgcggcaa cgtttttccct ggccgggccc      1080
cgtttcgtca gcttggactc caccacgttc aagaaccccg tgcccgtggg gtcggtgctc      1140
accatggact cgtcgatctc gtacacggag cacgtgcacg agggagtgga ggagattgac      1200
gcggactcac cgttcaactt cagcttgcct gccacgaaca agatctcgaa gaaccccgag      1260
gcgttcttgt cggaacccgg cacgttgatt caagtcaagg tcgacacata catccaggag      1320
ttagagcaga gtgtgaagaa gcccgcgggt acgttcatct actcgttcta tgttgataaa      1380
gaaagcgtta ctgttgatgg aaaggcgtcg ttttgttcag ttatcccgca gacgtactcc      1440
gagatgatga cttatgtggg cgggagaaga agagcccagg atactgctaa ctacgtggag      1500
actttgccgt ttagtggaag cggcaattaa                                       1530
```

<210> SEQ ID NO 43
<211> LENGTH: 509
<212> TYPE: PRT
<213> ORGANISM: Candida tropicalis

<400> SEQUENCE: 43

Met Ile Arg Thr Val Arg Tyr Gln Ser Leu Lys Arg Phe Arg Pro Ser
1               5                   10                  15

Ala Leu Ser Pro Val Phe Arg Pro Arg Tyr Asn Ser Gln Lys Ala Asn
            20                  25                  30

```
Phe His Arg Pro Asp His Pro Gly Ser Asp Glu Pro Ala Glu Ala Ala
         35                  40                  45

Asp Ala Ala Thr Ile Leu Ala Glu Leu Arg Asp Lys Gln Thr Asn
 50                  55                  60

Pro Asn Lys Ala Thr Trp Leu Asp Ala Leu Thr Glu Arg Glu Lys Leu
 65                  70                  75                  80

Arg Ala Glu Gly Lys Thr Ile Asp Ser Phe Ser Tyr Val Asp Pro Lys
                 85                  90                  95

Thr Thr Val Val Gly Glu Lys Thr Arg Ser Asp Ser Phe Ser Phe Leu
            100                 105                 110

Leu Leu Pro Phe Lys Asp Lys Trp Leu Cys Asp Ala Tyr Ile Asn
        115                 120                 125

Ala Phe Gly Arg Leu Arg Val Ala Gln Leu Phe Gln Asp Leu Asp Ala
130                 135                 140

Leu Ala Gly Arg Ile Ala Tyr Arg His Cys Ser Pro Ala Glu Pro Val
145                 150                 155                 160

Asn Val Thr Ala Ser Val Asp Arg Val Tyr Met Val Lys Lys Val Asp
                165                 170                 175

Glu Ile Asn Asn Tyr Asn Phe Val Leu Ala Gly Ser Val Thr Trp Thr
            180                 185                 190

Gly Arg Ser Ser Met Glu Ile Thr Val Lys Gly Tyr Ala Phe Glu Asp
        195                 200                 205

Ala Val Pro Asp Ile Thr Asn Glu Glu Ser Leu Pro Ala Glu Asn Val
210                 215                 220

Phe Leu Ala Ala Asn Phe Thr Phe Val Ala Arg Asn Pro Leu Thr His
225                 230                 235                 240

Lys Ser Phe Ala Ile Asn Arg Leu Leu Pro Val Thr Glu Lys Asp Trp
                245                 250                 255

Val Asp Tyr Arg Arg Ala Glu Ser His Asn Ala Lys Lys Leu Met
            260                 265                 270

Ala Lys Asn Lys Lys Ile Leu Glu Pro Thr Ala Glu Glu Ser Lys Leu
        275                 280                 285

Ile Tyr Asp Met Trp Arg Ser Ser Lys Ser Leu Gln Asn Ile Glu Arg
290                 295                 300

Ala Asn Asp Gly Ile Ala Phe Met Lys Asp Thr Thr Met Lys Ser Thr
305                 310                 315                 320

Leu Phe Met Gln Pro Gln Tyr Arg Asn Arg His Ser Tyr Met Ile Phe
                325                 330                 335

Gly Gly Tyr Leu Leu Arg Gln Thr Phe Glu Leu Ala Tyr Cys Thr Ala
            340                 345                 350

Ala Thr Phe Ser Ser Ala Gly Pro Arg Phe Val Ser Leu Asp Ser Thr
        355                 360                 365

Thr Phe Lys Asn Pro Val Pro Val Gly Ser Val Leu Thr Met Asp Ser
370                 375                 380

Ser Ile Ser Tyr Thr Glu His Val His Glu Gly Val Glu Glu Ile Asp
385                 390                 395                 400

Ala Asp Ser Pro Phe Asn Phe Ser Leu Pro Ala Thr Asn Lys Ile Ser
                405                 410                 415

Lys Asn Pro Glu Ala Phe Leu Ser Glu Pro Gly Thr Leu Ile Gln Val
            420                 425                 430

Lys Val Asp Thr Tyr Ile Gln Glu Leu Glu Gln Ser Val Lys Lys Pro
        435                 440                 445

Ala Gly Thr Phe Ile Tyr Ser Phe Tyr Val Asp Lys Glu Ser Val Thr
450                 455                 460
```

Val Asp Gly Lys Ala Ser Phe Cys Ser Val Ile Pro Gln Thr Tyr Ser
465                 470                 475                 480

Glu Met Met Thr Tyr Val Gly Gly Arg Arg Arg Ala Gln Asp Thr Ala
            485                 490                 495

Asn Tyr Val Glu Thr Leu Pro Phe Ser Gly Ser Gly Asn
        500                 505

<210> SEQ ID NO 44
<211> LENGTH: 1530
<212> TYPE: DNA
<213> ORGANISM: Candida tropicalis

<400> SEQUENCE: 44

```
atgatcagaa ccgtccgtta tcaatccttc aagaggttca aacctctgac tttatccccc      60
gttttccgtc cacgctacaa ctcccagaag gccaatttcc accgtccaga ccacgctggg     120
tccgacgagc cagccgaagc cgccgacgcc gctgccacga tcctcgccga gttgcgagac     180
aagcagacga acccgaacaa ggccacctgg ctcgatgcgt taacggagcg ggagaagttg     240
cgtgccgagg gcaagacaat cgacagcttc agctacgttg accccaagac aaccgtcgtg     300
ggggagaaga cacgcagcga ctcgttctcg ttcttgttgt tgccgttcaa ggacgacaag     360
tggttgtgtg acgcgtacat caatgcgttt ggccggttgc gtgtagcgca gttgttccag     420
gacttggacg ccttggcggg ccgcatcgcg tacaggcact gttccccgc tgagccgtg      480
aatgtcacgg cgagcgtgga tagagtgtat atggtgaaga agtggacga gattaataat      540
tacaatttcg tgttggcggg gtccgtgacg tggaccggga gatcgtcgat ggagatcacg     600
gtcaaagggt atgcttttga agacgccgtg ccggagataa ctaacgagga gtccttgccg     660
gcagagaatg tgttcttggc tgttaatttc accttcgtgg cacgtaaccc actcacacac     720
aagtccttcg ctattaacag attgttgccc gtgactgaga aggactgggt cgattatcgc     780
cgtgctgagt cccacaacgc caagaagaag ttgatggcaa agaacaagaa gatcttggag     840
cctaccccgg aagagtccaa gttgatctac gacatgtgga gatcgtccaa gtccttacag     900
aacatcgaga aggccaacga cgggatcgcg ttcatgaagg cacgataat gaagtccacc      960
ttgttcatgc agccccagta ccgtaacaga cactcataca tgattttcgg tgggtatttg    1020
ttaagacaaa ctttcgaatt ggcctattgt accgcagcaa cgttttccct ggcgggaccc    1080
cgtttcgtca gcttggactc caccacgttc aagaaccccg tgcccgtggg gtcggtgctc    1140
accatggact cgtcgatctc gtacacggag cacgtccacg atggcgttga ggagattgac    1200
gccgactccc cgttcaactt cagcttgcct gccacgaaca agatctcgaa gaaccccgag    1260
gcgttcttgt cggagcccgg cacgttgatc caagtcaagg tcgacacgta catccaggag    1320
ttagagcaaa gtgtgaagaa gcctgcggga acgttcatct actcgttcta tgttgataaa    1380
gagagcgtta ctgtggatgg aaaggcgtcg ttttgttcag ttatcccgca gacgtactcc    1440
gagatgatga cttatgtggg cgggagaaga agagcccagg atactgctaa ttacgtggag    1500
actttgccgt ttagtggaag cggcaattaa                                     1530
```

<210> SEQ ID NO 45
<211> LENGTH: 509
<212> TYPE: PRT
<213> ORGANISM: Candida tropicalis

<400> SEQUENCE: 45

Met Ile Arg Thr Val Arg Tyr Gln Ser Phe Lys Arg Phe Lys Pro Leu
1               5                   10                  15

Thr Leu Ser Pro Val Phe Arg Pro Arg Tyr Asn Ser Gln Lys Ala Asn
              20                  25                  30

Phe His Arg Pro Asp His Ala Gly Ser Asp Glu Pro Ala Glu Ala Ala
            35                  40                  45

Asp Ala Ala Thr Ile Leu Ala Glu Leu Arg Asp Lys Gln Thr Asn
50                  55                  60

Pro Asn Lys Ala Thr Trp Leu Asp Ala Leu Thr Glu Arg Glu Lys Leu
65                  70                  75                  80

Arg Ala Glu Gly Lys Thr Ile Asp Ser Phe Ser Tyr Val Asp Pro Lys
                85                  90                  95

Thr Thr Val Val Gly Glu Lys Thr Arg Ser Asp Ser Phe Ser Phe Leu
              100                 105                 110

Leu Leu Pro Phe Lys Asp Asp Lys Trp Leu Cys Asp Ala Tyr Ile Asn
              115                 120                 125

Ala Phe Gly Arg Leu Arg Val Ala Gln Leu Phe Gln Asp Leu Asp Ala
              130                 135                 140

Leu Ala Gly Arg Ile Ala Tyr Arg His Cys Ser Pro Ala Glu Pro Val
145                 150                 155                 160

Asn Val Thr Ala Ser Val Asp Arg Val Tyr Met Val Lys Lys Val Asp
              165                 170                 175

Glu Ile Asn Asn Tyr Asn Phe Val Leu Ala Gly Ser Val Thr Trp Thr
              180                 185                 190

Gly Arg Ser Ser Met Glu Ile Thr Val Lys Gly Tyr Ala Phe Glu Asp
              195                 200                 205

Ala Val Pro Glu Ile Thr Asn Glu Glu Ser Leu Pro Ala Glu Asn Val
              210                 215                 220

Phe Leu Ala Val Asn Phe Thr Phe Val Ala Arg Asn Pro Leu Thr His
225                 230                 235                 240

Lys Ser Phe Ala Ile Asn Arg Leu Leu Pro Val Thr Glu Lys Asp Trp
              245                 250                 255

Val Asp Tyr Arg Arg Ala Glu Ser His Asn Ala Lys Lys Lys Leu Met
              260                 265                 270

Ala Lys Asn Lys Lys Ile Leu Glu Pro Thr Pro Glu Glu Ser Lys Leu
              275                 280                 285

Ile Tyr Asp Met Trp Arg Ser Ser Lys Ser Leu Gln Asn Ile Glu Lys
              290                 295                 300

Ala Asn Asp Gly Ile Ala Phe Met Lys Asp Thr Ile Met Lys Ser Thr
305                 310                 315                 320

Leu Phe Met Gln Pro Gln Tyr Arg Asn Arg His Ser Tyr Met Ile Phe
              325                 330                 335

Gly Gly Tyr Leu Leu Arg Gln Thr Phe Glu Leu Ala Tyr Cys Thr Ala
              340                 345                 350

Ala Thr Phe Ser Leu Ala Gly Pro Arg Phe Val Ser Leu Asp Ser Thr
              355                 360                 365

Thr Phe Lys Asn Pro Val Pro Val Gly Ser Val Leu Thr Met Asp Ser
              370                 375                 380

Ser Ile Ser Tyr Thr Glu His Val His Asp Gly Val Glu Glu Ile Asp
385                 390                 395                 400

Ala Asp Ser Pro Phe Asn Phe Ser Leu Pro Ala Thr Asn Lys Ile Ser
              405                 410                 415

Lys Asn Pro Glu Ala Phe Leu Ser Glu Pro Gly Thr Leu Ile Gln Val
              420                 425                 430

Lys Val Asp Thr Tyr Ile Gln Glu Leu Glu Gln Ser Val Lys Lys Pro

```
                435                 440                 445
Ala Gly Thr Phe Ile Tyr Ser Phe Tyr Val Asp Lys Glu Ser Val Thr
    450                 455                 460
Val Asp Gly Lys Ala Ser Phe Cys Ser Val Ile Pro Gln Thr Tyr Ser
465                 470                 475                 480
Glu Met Met Thr Tyr Val Gly Arg Arg Ala Gln Asp Thr Ala
            485                 490                 495
Asn Tyr Val Glu Thr Leu Pro Phe Ser Gly Ser Gly Asn
        500                 505
```

<210> SEQ ID NO 46
<211> LENGTH: 552
<212> TYPE: DNA
<213> ORGANISM: Escherichia coli

<400> SEQUENCE: 46

```
atggccgata cattgctcat cttgggtgac tctttgtctg cagggtatcg gatgtccgca      60
tctgccgcat ggcctgcact cctcaatgac aaatggcaaa gcaagacatc ggtcgtgaat     120
gcatctatct ctggcgatac ctcgcagcag gggttggccc gtctcccagc cttgttgaag     180
caacatcaac cacgttgggt cttggtcgaa ttgggcggca atgatggtct cagaggtttt     240
caacctcaac agaccgagca gacattgcgt caaatcctcc aagacgtgaa ggcagcaaac     300
gccgaacctc tcttgatgca gataagattg cctgccaact atggtcgtag atacaatgaa     360
gcctttctg caatctaccc gaagcttgca aaggagtttg acgtcccatt gttgccgttt      420
ttgatggaag aggtgtacct taagcctcag tggatgcaag acgatggtat ccatccgaac     480
cgtgatgcac aaccattcat cgcagattgg atggccaaac aactccaacc tttggtcaat     540
catgatagct aa                                                         552
```

<210> SEQ ID NO 47
<211> LENGTH: 183
<212> TYPE: PRT
<213> ORGANISM: Escherichia coli

<400> SEQUENCE: 47

```
Met Ala Asp Thr Leu Leu Ile Leu Gly Asp Ser Leu Ser Ala Gly Tyr
1               5                   10                  15
Arg Met Ser Ala Ser Ala Ala Trp Pro Ala Leu Leu Asn Asp Lys Trp
            20                  25                  30
Gln Ser Lys Thr Ser Val Val Asn Ala Ser Ile Ser Gly Asp Thr Ser
        35                  40                  45
Gln Gln Gly Leu Ala Arg Leu Pro Ala Leu Leu Lys Gln His Gln Pro
    50                  55                  60
Arg Trp Val Leu Val Glu Leu Gly Gly Asn Asp Gly Leu Arg Gly Phe
65                  70                  75                  80
Gln Pro Gln Gln Thr Glu Gln Thr Leu Arg Gln Ile Leu Gln Asp Val
                85                  90                  95
Lys Ala Ala Asn Ala Glu Pro Leu Leu Met Gln Ile Arg Leu Pro Ala
            100                 105                 110
Asn Tyr Gly Arg Arg Tyr Asn Glu Ala Phe Ser Ala Ile Tyr Pro Lys
        115                 120                 125
Leu Ala Lys Glu Phe Asp Val Pro Leu Leu Pro Phe Leu Met Glu Glu
    130                 135                 140
Val Tyr Leu Lys Pro Gln Trp Met Gln Asp Asp Gly Ile His Pro Asn
145                 150                 155                 160
```

Arg Asp Ala Gln Pro Phe Ile Ala Asp Trp Met Ala Lys Gln Leu Gln
             165                 170                 175

Pro Leu Val Asn His Asp Ser
        180

<210> SEQ ID NO 48
<211> LENGTH: 2091
<212> TYPE: DNA
<213> ORGANISM: Candida tropicalis

<400> SEQUENCE: 48

| | | | | | |
|---|---|---|---|---|---|
| atgggtgccc | ctttaacagt | cgccgttggc | gaagcaaaac | caggcgaaac | cgctccaaga | 60 |
| agaaaagccg | ctcaaaaaat | ggcctctgtc | gaacgcccaa | cagactcaaa | ggcaaccact | 120 |
| ttgccagact | tcattgaaga | gtgttttgcc | agaaacggca | ccagagatgc | catggcctgg | 180 |
| agagacttgg | tcgaaatcca | cgtcgaaacc | aaacaggtta | ccaaaatcat | tgacggcgaa | 240 |
| cagaaaaagg | tcgataagga | ctggatctac | tacgaaatgg | gtccttacaa | ctacatatcc | 300 |
| taccccaagt | tgttgacgtt | ggtcaagaac | tactccaagg | gtttgttgga | gttgggcttg | 360 |
| gccccagatc | aagaatccaa | gttgatgatc | tttgccagta | cctcccacaa | gtggatgcag | 420 |
| accttcttag | cctccagttt | ccaaggtatc | ccgttgtca | ccgcctacga | caccttgggt | 480 |
| gagtcgggct | tgacccactc | cttggtgcaa | accgaatccg | atgccgtgtt | caccgacaac | 540 |
| caattgttgt | cctccttgat | tcgtcctttg | agaaggcca | cctccgtcaa | gtatgtcatc | 600 |
| cacggggaaa | agattgaccc | taacgacaag | agacagggcg | gcaaaatcta | ccaggatgcg | 660 |
| gaaaaggcca | aggagaagat | tttacaaatt | agaccagata | ttaaatttat | ttctttcgac | 720 |
| gaggttgttg | cattgggtga | acaatcgtcc | aaagaattgc | atttcccaaa | accagaagac | 780 |
| ccaatctgta | tcatgtacac | ctcgggttcc | accggtgctc | caagggtgt | ggttatcacc | 840 |
| aatgccaaca | ttgttgccgc | cgtgggtggt | atctccacca | atgctactag | agacttggtt | 900 |
| agaactgtcg | acagagtgat | tgcatttttg | ccattggccc | acattttcga | gttggccttt | 960 |
| gagttggtta | cttctggtg | ggggctcca | ttgggttacg | ccaatgtcaa | gactttgacc | 1020 |
| gaagcctcct | gcagaaactg | tcagccagac | ttgattgaat | tcaaaccaac | catcatggtt | 1080 |
| ggtgttgctg | ccgtttggga | atcggtcaga | aagggtgtct | tgtctaaatt | gaaacaggct | 1140 |
| tctccaatcc | aacaaaagat | cttctgggct | gcattcaatg | ccagtctac | tttgaaccgt | 1200 |
| tatggcttgc | aggcggtgg | gttgtttgac | gctgtcttca | gaaggttaa | agccgccact | 1260 |
| ggtggccaat | gcgttatgt | gttgaatggt | gggtccccaa | tctctgttga | tgcccaagtg | 1320 |
| tttatctcca | ccttgcttgc | gccaatgttg | ttgggttacg | gtttgactga | aacctgtgcc | 1380 |
| aataccacca | ttgtcgaaca | cacgcgcttc | cagattggta | ctttgggtac | cttggttgga | 1440 |
| tctgtcactg | ccaagttggt | tgatgttgct | gatgctggat | actacgccaa | gaacaaccag | 1500 |
| ggtgaaatct | ggttgaaagg | cggtccagtt | gtcaaggaat | actacaagaa | cgaagaagaa | 1560 |
| accaaggctg | cattcaccga | gatggctgg | ttcaagactg | gtgatattgg | tgaatggacc | 1620 |
| gccgacggtg | gtttgaacat | cattgaccgt | aagaagaact | ggtcaagac | tttgaatggt | 1680 |
| gaatacattg | ctttggagaa | attggaaagt | atttacagat | ccaaccactt | gattttgaac | 1740 |
| ttgtgtgttt | acgctgacca | aaccaaggtc | aagccaattg | ctattgtctt | gccaattgaa | 1800 |
| gccaacttga | agtctatgtt | gaaggacgaa | aagattatcc | cagatgctga | ttcacaagaa | 1860 |
| ttgagcagct | ggttcacaa | caagaaggtt | gcccaagctg | tcttgagaca | cttgctccaa | 1920 |
| accggtaaac | aacaaggttt | gaaaggtatt | gaattgttgc | agaatgttgt | cttgttggat | 1980 |

```
gacgagtgga cccccacagaa tggttttgtt acttctgccc aaaagttgca gagaaagaag   2040
attttagaaa gttgtaaaaa agaagttgaa gaggcataca agtcgtctta g             2091
```

<210> SEQ ID NO 49
<211> LENGTH: 696
<212> TYPE: PRT
<213> ORGANISM: Candida tropicalis

<400> SEQUENCE: 49

```
Met Gly Ala Pro Leu Thr Val Ala Val Gly Glu Ala Lys Pro Gly Glu
1               5                   10                  15

Thr Ala Pro Arg Arg Lys Ala Ala Gln Lys Met Ala Ser Val Glu Arg
            20                  25                  30

Pro Thr Asp Ser Lys Ala Thr Thr Leu Pro Asp Phe Ile Glu Glu Cys
        35                  40                  45

Phe Ala Arg Asn Gly Thr Arg Asp Ala Met Ala Trp Arg Asp Leu Val
    50                  55                  60

Glu Ile His Val Glu Thr Lys Gln Val Thr Lys Ile Ile Asp Gly Glu
65                  70                  75                  80

Gln Lys Lys Val Asp Lys Asp Trp Ile Tyr Tyr Glu Met Gly Pro Tyr
                85                  90                  95

Asn Tyr Ile Ser Tyr Pro Lys Leu Leu Thr Leu Val Lys Asn Tyr Ser
            100                 105                 110

Lys Gly Leu Leu Glu Leu Gly Leu Ala Pro Asp Gln Glu Ser Lys Leu
        115                 120                 125

Met Ile Phe Ala Ser Thr Ser His Lys Trp Met Gln Thr Phe Leu Ala
    130                 135                 140

Ser Ser Phe Gln Gly Ile Pro Val Val Thr Ala Tyr Asp Thr Leu Gly
145                 150                 155                 160

Glu Ser Gly Leu Thr His Ser Leu Val Gln Thr Glu Ser Asp Ala Val
                165                 170                 175

Phe Thr Asp Asn Gln Leu Leu Ser Ser Leu Ile Arg Pro Leu Glu Lys
            180                 185                 190

Ala Thr Ser Val Lys Tyr Val Ile His Gly Glu Lys Ile Asp Pro Asn
        195                 200                 205

Asp Lys Arg Gln Gly Gly Lys Ile Tyr Gln Asp Ala Glu Lys Ala Lys
    210                 215                 220

Glu Lys Ile Leu Gln Ile Arg Pro Asp Ile Lys Phe Ile Ser Phe Asp
225                 230                 235                 240

Glu Val Val Ala Leu Gly Glu Gln Ser Ser Lys Glu Leu His Phe Pro
                245                 250                 255

Lys Pro Glu Asp Pro Ile Cys Ile Met Tyr Thr Ser Gly Ser Thr Gly
            260                 265                 270

Ala Pro Lys Gly Val Val Ile Thr Asn Ala Asn Ile Val Ala Ala Val
        275                 280                 285

Gly Gly Ile Ser Thr Asn Ala Thr Arg Asp Leu Val Arg Thr Val Asp
    290                 295                 300

Arg Val Ile Ala Phe Leu Pro Leu Ala His Ile Phe Glu Leu Ala Phe
305                 310                 315                 320

Glu Leu Val Thr Phe Trp Trp Gly Ala Pro Leu Gly Tyr Ala Asn Val
                325                 330                 335

Lys Thr Leu Thr Glu Ala Ser Cys Arg Asn Cys Gln Pro Asp Leu Ile
            340                 345                 350

Glu Phe Lys Pro Thr Ile Met Val Gly Val Ala Ala Val Trp Glu Ser
        355                 360                 365
```

Val Arg Lys Gly Val Leu Ser Lys Leu Lys Gln Ala Ser Pro Ile Gln
            370                 375                 380

Gln Lys Ile Phe Trp Ala Ala Phe Asn Ala Lys Ser Thr Leu Asn Arg
385                 390                 395                 400

Tyr Gly Leu Pro Gly Gly Leu Phe Asp Ala Val Phe Lys Lys Val
            405                 410                 415

Lys Ala Ala Thr Gly Gly Gln Leu Arg Tyr Val Leu Asn Gly Gly Ser
            420                 425                 430

Pro Ile Ser Val Asp Ala Gln Val Phe Ile Ser Thr Leu Leu Ala Pro
            435                 440                 445

Met Leu Leu Gly Tyr Gly Leu Thr Glu Thr Cys Ala Asn Thr Thr Ile
    450                 455                 460

Val Glu His Thr Arg Phe Gln Ile Gly Thr Leu Gly Thr Leu Val Gly
465                 470                 475                 480

Ser Val Thr Ala Lys Leu Val Asp Val Ala Asp Ala Gly Tyr Tyr Ala
            485                 490                 495

Lys Asn Asn Gln Gly Glu Ile Trp Leu Lys Gly Gly Pro Val Val Lys
            500                 505                 510

Glu Tyr Tyr Lys Asn Glu Glu Thr Lys Ala Ala Phe Thr Glu Asp
            515                 520                 525

Gly Trp Phe Lys Thr Gly Asp Ile Gly Glu Trp Thr Ala Asp Gly Gly
    530                 535                 540

Leu Asn Ile Ile Asp Arg Lys Lys Asn Leu Val Lys Thr Leu Asn Gly
545                 550                 555                 560

Glu Tyr Ile Ala Leu Glu Lys Leu Glu Ser Ile Tyr Arg Ser Asn His
            565                 570                 575

Leu Ile Leu Asn Leu Cys Val Tyr Ala Asp Gln Thr Lys Val Lys Pro
            580                 585                 590

Ile Ala Ile Val Leu Pro Ile Glu Ala Asn Leu Lys Ser Met Leu Lys
            595                 600                 605

Asp Glu Lys Ile Ile Pro Asp Ala Asp Ser Gln Glu Leu Ser Ser Leu
    610                 615                 620

Val His Asn Lys Lys Val Ala Gln Ala Val Leu Arg His Leu Leu Gln
625                 630                 635                 640

Thr Gly Lys Gln Gln Gly Leu Lys Gly Ile Glu Leu Leu Gln Asn Val
            645                 650                 655

Val Leu Leu Asp Asp Glu Trp Thr Pro Gln Asn Gly Phe Val Thr Ser
            660                 665                 670

Ala Gln Lys Leu Gln Arg Lys Lys Ile Leu Glu Ser Cys Lys Lys Glu
            675                 680                 685

Val Glu Glu Ala Tyr Lys Ser Ser
    690                 695

<210> SEQ ID NO 50
<211> LENGTH: 1950
<212> TYPE: DNA
<213> ORGANISM: Candida tropicalis

<400> SEQUENCE: 50
atgtcaggat tagaaatagc cgctgctgcc atccttggta gtcagttatt ggaagccaaa     60
tatttaattg ccgacgacgt gctgttagcc aagacagtcg ctgtcaatgc cctcccatac    120
ttgtggaaag ccagcagagg taaggcatca tactggtact ttttcgagca gtccgtgttc    180
aagaacccaa acaacaaagc gttggcgttc ccaagaccaa gaagaatgc ccccacccc     240

```
aagaccgacg ccgagggatt ccagatctac gacgatcagt ttgacctaga agaatacacc    300
tacaaggaat tgtacgacat ggttttgaag tactcataca tcttgaagaa cgagtacggc    360
gtcactgcca acgacaccat cggtgtttct tgtatgaaca agccgctttt cattgtcttg    420
tggttggcat tgtggaacat tggtgccttg cctgcgttct tgaacttcaa caccaaggac    480
aagccattga tccactgtct taagattgtc aacgcttcgc aagttttcgt tgacccggac    540
tgtgattccc caatcagaga taccgaggct cagatcagag aggaattgcc acatgtgcaa    600
ataaactaca ttgacgagtt tgccttgttt gacagattga gactcaagtc gactccaaaa    660
cacagagccg aggacaagac cagaagacca accgatactg actcctccgc ttgtgcattg    720
atttacacct cgggtaccac cggtttgcca aaagccggta tcatgtcctg gagaaaagcc    780
ttcatggcct cggttttctt tggccacatc atgaagattg actcgaaatc gaacgtcttg    840
accgccatgc ccttgtacca ctccaccgcg gccatgttgg ggttgtgtcc tactttgatt    900
gtcggtggct gtgtctccgt gtcccagaaa ttctccgcta cttcgttctg gacccaggcc    960
agattatgtg gtgccaccca cgtgcaatac gtcggtgagg tctgtcgtta cttgttgaac   1020
tccaagcctc atccagacca agacagacac aatgtcagaa ttgcctacgg taacgggttg   1080
cgtccagata tatggtctga gttcaagcgc agattccaca ttgaaggtat cggtgagttc   1140
tacgccgcca ccgagtcccc tatcgccacc accaacttgc agtacggtga gtacggtgtc   1200
ggcgcctgtc gtaagtacgg gtccctcatc agcttgttat tgtctaccca gcagaaattg   1260
gccaagatgg acccgaaaga cgagagtgaa atctacaagg accccaagac cgggttctgt   1320
accgaggccg cttacaacga gccaggtgag ttgttgatga gaatcttgaa ccctaacgac   1380
gtgcagaaat ccttccaggg ttattatggt aacaagtccg ccaccaacag caaaatcctc   1440
accaatgttt tcaaaaaagg tgacgcgtgg tacagatccg gtgacttgtt gaagatggac   1500
gaggacaaat tgttgtactt tgtcgacaga ttaggtgaca ctttccgttg aagtccgaa   1560 aacgtctccg ccaccgaggt cgagaacgaa ttgatgggct ccaaggcctt gaagcagtcc   1620
gtcgttgtcg gtgtcaaggt gccaaaccac gaaggtagag cctgttttgc cgtctgtgaa   1680
gccaaggacg agttgagcca tgaagaaatc ttgaaattga ttcactctca cgtgaccaag   1740
tctttgcctg tgtatgctca acctgcgttc atcaagattg caccattga ggcttcgcac    1800 aaccacaagg ttcctaagaa ccaattcaag aaccaaaagt tgccaaaggg tgaagacggc   1860
aaggatttga tctactggtt gaatggcgac aagtaccagg agttgactga agacgattgg   1920
tctttgattt gtaccggtaa agccaaattg                                    1950
```

<210> SEQ ID NO 51
<211> LENGTH: 650
<212> TYPE: PRT
<213> ORGANISM: Candida tropicalis

<400> SEQUENCE: 51

Met Ser Gly Leu Glu Ile Ala Ala Ala Ile Leu Gly Ser Gln Leu
1               5                   10                  15

Leu Glu Ala Lys Tyr Leu Ile Ala Asp Asp Val Ser Leu Ala Lys Thr
            20                  25                  30

Val Ala Val Asn Ala Leu Pro Tyr Leu Trp Lys Ala Ser Arg Gly Lys
        35                  40                  45

Ala Ser Tyr Trp Tyr Phe Phe Glu Gln Ser Val Phe Lys Asn Pro Asn
    50                  55                  60

Asn Lys Ala Leu Ala Phe Pro Arg Pro Arg Lys Asn Ala Pro Thr Pro
65                  70                  75                  80

```
Lys Thr Asp Ala Glu Gly Phe Gln Ile Tyr Asp Asp Gln Phe Asp Leu
                85                  90                  95

Glu Glu Tyr Thr Tyr Lys Glu Leu Tyr Asp Met Val Leu Lys Tyr Ser
            100                 105                 110

Tyr Ile Leu Lys Asn Glu Tyr Gly Val Thr Ala Asn Asp Thr Ile Gly
        115                 120                 125

Val Ser Cys Met Asn Lys Pro Leu Phe Ile Val Leu Trp Leu Ala Leu
    130                 135                 140

Trp Asn Ile Gly Ala Leu Pro Ala Phe Leu Asn Phe Asn Thr Lys Asp
145                 150                 155                 160

Lys Pro Leu Ile His Cys Leu Lys Ile Val Asn Ala Ser Gln Val Phe
                165                 170                 175

Val Asp Pro Asp Cys Asp Ser Pro Ile Arg Asp Thr Glu Ala Gln Ile
            180                 185                 190

Arg Glu Glu Leu Pro His Val Gln Ile Asn Tyr Ile Asp Glu Phe Ala
        195                 200                 205

Leu Phe Asp Arg Leu Arg Leu Lys Ser Thr Pro Lys His Arg Ala Glu
    210                 215                 220

Asp Lys Thr Arg Arg Pro Thr Asp Thr Asp Ser Ser Ala Cys Ala Leu
225                 230                 235                 240

Ile Tyr Thr Ser Gly Thr Thr Gly Leu Pro Lys Ala Gly Ile Met Ser
                245                 250                 255

Trp Arg Lys Ala Phe Met Ala Ser Val Phe Phe Gly His Ile Met Lys
            260                 265                 270

Ile Asp Ser Lys Ser Asn Val Leu Thr Ala Met Pro Leu Tyr His Ser
        275                 280                 285

Thr Ala Ala Met Leu Gly Leu Cys Pro Thr Leu Ile Val Gly Gly Cys
    290                 295                 300

Val Ser Val Ser Gln Lys Phe Ser Ala Thr Ser Phe Trp Thr Gln Ala
305                 310                 315                 320

Arg Leu Cys Gly Ala Thr His Val Gln Tyr Val Gly Glu Val Cys Arg
                325                 330                 335

Tyr Leu Leu Asn Ser Lys Pro His Pro Asp Gln Asp Arg His Asn Val
            340                 345                 350

Arg Ile Ala Tyr Gly Asn Gly Leu Arg Pro Asp Ile Trp Ser Glu Phe
        355                 360                 365

Lys Arg Arg Phe His Ile Glu Gly Ile Gly Glu Phe Tyr Ala Ala Thr
    370                 375                 380

Glu Ser Pro Ile Ala Thr Thr Asn Leu Gln Tyr Gly Glu Tyr Gly Val
385                 390                 395                 400

Gly Ala Cys Arg Lys Tyr Gly Ser Leu Ile Ser Leu Leu Leu Ser Thr
                405                 410                 415

Gln Gln Lys Leu Ala Lys Met Asp Pro Glu Asp Glu Ser Glu Ile Tyr
            420                 425                 430

Lys Asp Pro Lys Thr Gly Phe Cys Thr Glu Ala Ala Tyr Asn Glu Pro
        435                 440                 445

Gly Glu Leu Leu Met Arg Ile Leu Asn Pro Asn Asp Val Gln Lys Ser
    450                 455                 460

Phe Gln Gly Tyr Tyr Gly Asn Lys Ser Ala Thr Asn Ser Lys Ile Leu
465                 470                 475                 480

Thr Asn Val Phe Lys Lys Gly Asp Ala Trp Tyr Arg Ser Gly Asp Leu
                485                 490                 495

Leu Lys Met Asp Glu Asp Lys Leu Leu Tyr Phe Val Asp Arg Leu Gly
```

```
                500             505             510
Asp Thr Phe Arg Trp Lys Ser Glu Asn Val Ser Ala Thr Glu Val Glu
            515                 520                 525

Asn Glu Leu Met Gly Ser Lys Ala Leu Lys Gln Ser Val Val Val Gly
            530                 535                 540

Val Lys Val Pro Asn His Glu Gly Arg Ala Cys Phe Ala Val Cys Glu
545                 550                 555                 560

Ala Lys Asp Glu Leu Ser His Glu Glu Ile Leu Lys Leu Ile His Ser
                565                 570                 575

His Val Thr Lys Ser Leu Pro Val Tyr Ala Gln Pro Ala Phe Ile Lys
            580                 585                 590

Ile Gly Thr Ile Glu Ala Ser His Asn His Lys Val Pro Lys Asn Gln
            595                 600                 605

Phe Lys Asn Gln Lys Leu Pro Lys Gly Glu Asp Gly Lys Asp Leu Ile
            610                 615                 620

Tyr Trp Leu Asn Gly Asp Lys Tyr Gln Glu Leu Thr Glu Asp Asp Trp
625                 630                 635                 640

Ser Leu Ile Cys Thr Gly Lys Ala Lys Leu
                645                 650

<210> SEQ ID NO 52
<211> LENGTH: 1764
<212> TYPE: DNA
<213> ORGANISM: Candida tropicalis

<400> SEQUENCE: 52
atgtccgacg acgagatagc aggaatagtc attgaaatcg acgatgacgt gaaatccacg      60
tcttcgttcc aggaagaact agtcgaggtt gaaatgtcca actcgtccat taacgaatcc     120
cagaccgatg agtcgtaccg tcctgaagaa acctcattgc attacaggag gaagtcccac     180
aggaccccgt cagaggagtc gttcctagag atcaccaaga acgtaatga tccggatcta     240
gtttccaaga ttgagaacct aaggggcaaa gtaagccaac gggaagacag gttgaggaag     300
cactaccttc acacctccca ggacgtcaag ttcttgtccc ggttcaacga catcaagttc     360
aagctgaact ccgcgacgat tctagattcg gatgcgtttt acaagagtga atactttgga     420
gtcttgacca tcttctgggt ggttatcgca ctctacatat tgtcaacgtt gtcagatgtt     480
tactttggca tggccaagcc cttactggac tggatcatca taggaatgtt caagcaggac     540
ttggtgaaag ttgcactcgt tgatcttgcc atgtacctat cctcgtattt tccttatttc     600
ttgcaggttg catgcaaacg gggtgatgta tcttggcatg tcttggatgg gcaatacag      660
ggggtttaca gcttggtgtt tttgacgttc tggacggtag ttccgcagga gttggccatg     720
gatcttcctt ggattgcacg aattttcttg atcttgcatt gcttggtgtt tattatgaag     780
atgcagtcgt atgggcatta caatggatac ctttgggatg tgtatcagga aggattggcc     840
tctgaggctg atctcaggga ccttttctgag tatgatgaag atttcccccct ggatcacgtg     900
gaggttctag aacagagctt gtggtttgcc aaacacgagt tggagtttca atcgaatgga     960
actgctgaga ggaaggacca ccatcaccat gtattcgacg aaaaggatgt caacaaacca    1020
atacgtgtct tgcaagaaga gggaattatc aagtttccgg caaacatcaa cttcaaggat    1080
tatttcgagt acagtatgtt cccaacgcta gtctacacgt tgagcttccc ccgaactcga    1140
cagattagat ggacgtatgt gttgcagaag gttttgggaa catttgcctt agtgtttgcc    1200
atgattatcg tcgccgaaga gagtttctgc cccttgatgc aagaagttga tcagtacaca    1260
aaattgccaa ccaaccaaag gttcccaaaa tacttcgtcg ttctttccca cttgatatta    1320
```

-continued

```
ccgctcggca agcagtactt gctctcattc atcctcatct ggaatgaaat tctcaacggc   1380
atagcggagt taagcaggtt tggcgaccgg catttctacg gcgcttggtg gtcgagcgtc   1440
gattacatgg actattcaag aaaatggaac accatcgtgc accgattcct ccgtcggcac   1500
gtttacaatt cgagcattca catcctcggt atttccagga cgcaagccgc gatagttaca   1560
cttttgcttt ctgccacaat ccacgaactc gttatgtacg tcctatttgg caaattacga   1620
gggtacctat tccttacgat gcttgtccag atccccatga ccgtcacctc caagttcaac   1680
aaccgtgttt ggggcaacat catgttctgg ttgacgtatt tatctggccc cagcttggtt   1740
agtgcgttgt atttactctt ctag                                          1764
```

<210> SEQ ID NO 53
<211> LENGTH: 587
<212> TYPE: PRT
<213> ORGANISM: Candida tropicalis

<400> SEQUENCE: 53

```
Met Ser Asp Asp Glu Ile Ala Gly Ile Val Ile Glu Ile Asp Asp
1               5                   10                  15

Val Lys Ser Thr Ser Ser Phe Gln Glu Leu Val Glu Val Met
            20                  25                  30

Ser Asn Ser Ser Ile Asn Glu Ser Gln Thr Asp Glu Ser Tyr Arg Pro
            35                  40                  45

Glu Glu Thr Ser Leu His Tyr Arg Arg Lys Ser His Arg Thr Pro Ser
        50                  55                  60

Glu Glu Ser Phe Leu Glu Ile Thr Lys Asn Val Asn Asp Pro Asp Leu
65                  70                  75                  80

Val Ser Lys Ile Glu Asn Leu Arg Gly Lys Val Ser Gln Arg Glu Asp
                85                  90                  95

Arg Leu Arg Lys His Tyr Leu His Thr Ser Gln Asp Val Lys Phe Leu
            100                 105                 110

Ser Arg Phe Asn Asp Ile Lys Phe Lys Leu Asn Ser Ala Thr Ile Leu
            115                 120                 125

Asp Ser Asp Ala Phe Tyr Lys Ser Glu Tyr Phe Gly Val Leu Thr Ile
        130                 135                 140

Phe Trp Val Val Ile Ala Leu Tyr Ile Leu Ser Thr Leu Ser Asp Val
145                 150                 155                 160

Tyr Phe Gly Met Ala Lys Pro Leu Leu Asp Trp Ile Ile Gly Met
                165                 170                 175

Phe Lys Gln Asp Leu Val Lys Val Ala Leu Val Asp Leu Ala Met Tyr
            180                 185                 190

Leu Ser Ser Tyr Phe Pro Tyr Phe Leu Gln Val Ala Cys Lys Arg Gly
            195                 200                 205

Asp Val Ser Trp His Gly Leu Gly Trp Ala Ile Gln Gly Val Tyr Ser
        210                 215                 220

Leu Val Phe Leu Thr Phe Trp Thr Val Val Pro Gln Glu Leu Ala Met
225                 230                 235                 240

Asp Leu Pro Trp Ile Ala Arg Ile Phe Leu Ile Leu His Cys Leu Val
                245                 250                 255

Phe Ile Met Lys Met Gln Ser Tyr Gly His Tyr Asn Gly Tyr Leu Trp
            260                 265                 270

Asp Val Tyr Gln Glu Gly Leu Ala Ser Glu Ala Asp Leu Arg Asp Leu
            275                 280                 285

Ser Glu Tyr Asp Glu Asp Phe Pro Leu Asp His Val Glu Val Leu Glu
```

```
                290                 295                 300
Gln Ser Leu Trp Phe Ala Lys His Glu Leu Glu Phe Gln Ser Asn Gly
305                 310                 315                 320

Thr Ala Glu Arg Lys Asp His His His Val Phe Asp Glu Lys Asp
                325                 330                 335

Val Asn Lys Pro Ile Arg Val Leu Gln Glu Glu Gly Ile Ile Lys Phe
                340                 345                 350

Pro Ala Asn Ile Asn Phe Lys Asp Tyr Phe Glu Tyr Ser Met Phe Pro
                355                 360                 365

Thr Leu Val Tyr Thr Leu Ser Phe Pro Arg Thr Arg Gln Ile Arg Trp
370                 375                 380

Thr Tyr Val Leu Gln Lys Val Leu Gly Thr Phe Ala Leu Val Phe Ala
385                 390                 395                 400

Met Ile Ile Val Ala Glu Glu Ser Phe Cys Pro Leu Met Gln Glu Val
                405                 410                 415

Asp Gln Tyr Thr Lys Leu Pro Thr Asn Gln Arg Phe Pro Lys Tyr Phe
                420                 425                 430

Val Val Leu Ser His Leu Ile Leu Pro Leu Gly Lys Gln Tyr Leu Leu
                435                 440                 445

Ser Phe Ile Leu Ile Trp Asn Glu Ile Leu Asn Gly Ile Ala Glu Leu
450                 455                 460

Ser Arg Phe Gly Asp Arg His Phe Tyr Gly Ala Trp Trp Ser Ser Val
465                 470                 475                 480

Asp Tyr Met Asp Tyr Ser Arg Lys Trp Asn Thr Ile Val His Arg Phe
                485                 490                 495

Leu Arg Arg His Val Tyr Asn Ser Ser Ile His Ile Leu Gly Ile Ser
                500                 505                 510

Arg Thr Gln Ala Ala Ile Val Thr Leu Leu Ser Ala Thr Ile His
                515                 520                 525

Glu Leu Val Met Tyr Val Leu Phe Gly Lys Leu Arg Gly Tyr Leu Phe
530                 535                 540

Leu Thr Met Leu Val Gln Ile Pro Met Thr Val Thr Ser Lys Phe Asn
545                 550                 555                 560

Asn Arg Val Trp Gly Asn Ile Met Phe Trp Leu Thr Tyr Leu Ser Gly
                565                 570                 575

Pro Ser Leu Val Ser Ala Leu Tyr Leu Leu Phe
                580                 585

<210> SEQ ID NO 54
<211> LENGTH: 1767
<212> TYPE: DNA
<213> ORGANISM: Candida tropicalis

<400> SEQUENCE: 54
atgtccgacg acgagatagc aggaatagtc attgaaatcg acgatgacgt gaaatctacg      60
tcttcgttcc aggaagacct agtcgaggtt gagatgtcca actcgtccat taacgaatcc     120
cagacggatg agttgtcgta ccgtcctgaa gaaatctcat tgcattcgag aaggaagtcc     180
cacaagaccc cgtcagatga gtcgttccta gagatcacca gaacgtgaa tgatccggat      240 ctagtctcca agattgagaa cttaaggggc aaagtaagcc aacgggaaga caggttgagg     300
aaacactacc tccacacatc ccaggacgtc aagttcttgt ctcggttcaa cgacatcaag     360
ttcaagctga actccgcgac gattctagat tcggatgcgt tttacaagag cgagcacttt     420
ggagtcttga ctatcttctg gtggttatc ggactctaca taatgtcaac gttgtcagac     480
```

-continued

```
atgtattttg gcatggccaa gcccttactg gactggataa tcataggaat gttcaagaag     540
gatttgatgc aagttgcact cgttgatctt gtcatgtact tatcctcgta ttttccttat     600
ttcctacagg ttgcatgcaa gaccggagct atatcttggc atggtcttgg atgggccata     660
caggggtttt acagcttggt gttttaact ttctgggcgg tacttccgct ggagctggcc      720
atggatcttc cttggattgc acgagttttc ttgatcttgc attgcttggt gtttattatg     780
aagatgcaat catatggaca ttacaatgga tacctttggg atgtatatca ggaaggattg     840
gtctcggaag ctgatctcac ggctgtttct gagtatgatg atgatttccc cctggatcac     900
ggggaggttc tagaacagag cttgtggttc gccaaacacg agttggagtt tcaatctaat     960
ggaactacgg agaggaagga tcaccatcat catgtattcg acgaaaagga tgtcaacaaa    1020
ccaatgcgtg tcttgcaaga gagggaatt atcaaatttc cggcaaacat caatttcaag     1080
gattatttcg agtacagtat gttccccacg ctagtctaca cattgaactt ccccagaatt    1140
cgacatatta gatgggcgta tgtgttgcag aaagttttgg gaacatttgc cttagtgttt    1200
gccatgatta tcgtcgccga agagagtttc tgtcccttga tgcaagaagt tgaacagtac    1260
acaagattgc caaccaacca aaggttctca aagtacttcg tcgttctttc ccacttgata    1320
ttgcccctcg gcaaacagta cttgctctcg tttatcctca tttggaacga aattctcaac    1380
gggatagcgg agttaagcag gtttggggat cgccatttct acggcgcctg gtggtcaagc    1440
gtcgactaca tggactattc aagaaaatgg aacacgatcg tgcaccgatt cctccgccgg    1500
cacgtttaca attcgaccat tcgcatcctc ggtatttcca ggacccaagc cgcgataatt    1560
acacttttgc tttcagccac aatccacgaa ctcgttatgt acatcctatt tggaaaatta    1620
cgagggtacc tattccttac gatgcttgtc cagatcccca tgacagtcac cgccaagttc    1680
aacaaccgtt tgtggggcaa catcatgttc tggttgacgt atttatctgg ccccagcttg    1740
gttagtgcgt tgtatttact cttctga                                        1767
```

<210> SEQ ID NO 55
<211> LENGTH: 588
<212> TYPE: PRT
<213> ORGANISM: Candida tropicalis

<400> SEQUENCE: 55

```
Met Ser Asp Asp Glu Ile Ala Gly Ile Val Ile Glu Ile Asp Asp
1               5                   10                  15

Val Lys Ser Thr Ser Ser Phe Gln Glu Asp Leu Val Glu Val Glu Met
            20                  25                  30

Ser Asn Ser Ser Ile Asn Glu Ser Gln Thr Asp Glu Leu Ser Tyr Arg
        35                  40                  45

Pro Glu Glu Ile Ser Leu His Ser Arg Arg Lys Ser His Lys Thr Pro
    50                  55                  60

Ser Asp Glu Ser Phe Leu Glu Ile Thr Lys Asn Val Asn Asp Pro Asp
65                  70                  75                  80

Leu Val Ser Lys Ile Glu Asn Leu Arg Gly Lys Val Ser Gln Arg Glu
                85                  90                  95

Asp Arg Leu Arg Lys His Tyr Leu His Thr Ser Gln Asp Val Lys Phe
            100                 105                 110

Leu Ser Arg Phe Asn Asp Ile Lys Phe Lys Ser Asn Ser Ala Thr Ile
        115                 120                 125

Leu Asp Ser Asp Ala Phe Tyr Lys Ser Glu His Phe Gly Val Leu Thr
    130                 135                 140

Ile Phe Trp Val Val Ile Gly Leu Tyr Ile Met Ser Thr Leu Ser Asp
```

```
                145                 150                 155                 160
Met Tyr Phe Gly Met Ala Lys Pro Leu Ser Asp Trp Ile Ile Ile Gly
                    165                 170                 175

Met Phe Lys Lys Asp Leu Met Gln Val Ala Leu Val Asp Leu Val Met
                180                 185                 190

Tyr Leu Ser Ser Tyr Phe Pro Tyr Phe Leu Gln Val Ala Cys Lys Thr
            195                 200                 205

Gly Ala Ile Ser Trp His Gly Leu Gly Trp Ala Ile Gln Gly Val Tyr
        210                 215                 220

Ser Leu Val Phe Leu Thr Phe Trp Ala Val Leu Pro Ser Glu Ser Ala
225                 230                 235                 240

Met Asp Leu Pro Trp Ile Ala Arg Val Phe Leu Ile Leu His Cys Leu
                245                 250                 255

Val Phe Ile Met Lys Met Gln Ser Tyr Gly His Tyr Asn Gly Tyr Leu
            260                 265                 270

Trp Asp Val Tyr Gln Glu Gly Leu Val Ser Glu Ala Asp Leu Thr Ala
        275                 280                 285

Val Ser Glu Tyr Asp Asp Phe Pro Ser Asp His Gly Glu Val Leu
290                 295                 300

Glu Gln Ser Leu Trp Phe Ala Lys His Glu Leu Glu Phe Gln Ser Asn
305                 310                 315                 320

Gly Thr Thr Glu Arg Lys Asp His His His Val Phe Asp Glu Lys
                325                 330                 335

Asp Val Asn Lys Pro Met Arg Val Leu Gln Glu Glu Gly Ile Ile Lys
                340                 345                 350

Phe Pro Ala Asn Ile Asn Phe Lys Asp Tyr Phe Glu Tyr Ser Met Phe
                355                 360                 365

Pro Thr Leu Val Tyr Thr Leu Asn Phe Pro Arg Ile Arg His Ile Arg
        370                 375                 380

Trp Ala Tyr Val Leu Gln Lys Val Leu Gly Thr Phe Ala Leu Val Phe
385                 390                 395                 400

Ala Met Ile Ile Val Ala Glu Glu Ser Phe Cys Pro Leu Met Gln Glu
                405                 410                 415

Val Glu Gln Tyr Thr Arg Leu Pro Thr Asn Gln Arg Phe Ser Lys Tyr
                420                 425                 430

Phe Val Val Leu Ser His Leu Ile Leu Pro Leu Gly Lys Gln Tyr Leu
            435                 440                 445

Leu Ser Phe Ile Leu Ile Trp Asn Glu Ile Leu Asn Gly Ile Ala Glu
        450                 455                 460

Leu Ser Arg Phe Gly Asp Arg His Phe Tyr Gly Ala Trp Trp Ser Ser
465                 470                 475                 480

Val Asp Tyr Met Asp Tyr Ser Arg Lys Trp Asn Thr Ile Val His Arg
                485                 490                 495

Phe Leu Arg Arg His Val Tyr Asn Ser Thr Ile Arg Ile Leu Gly Ile
                500                 505                 510

Ser Arg Thr Gln Ala Ala Ile Ile Thr Leu Leu Ser Ala Thr Ile
            515                 520                 525

His Glu Leu Val Met Tyr Ile Leu Phe Gly Lys Leu Arg Gly Tyr Leu
        530                 535                 540

Phe Leu Thr Met Leu Val Gln Ile Pro Met Thr Val Thr Ala Lys Phe
545                 550                 555                 560

Asn Asn Arg Leu Trp Gly Asn Ile Met Phe Trp Leu Thr Tyr Leu Ser
                565                 570                 575
```

Gly Pro Ser Leu Val Ser Ala Leu Tyr Leu Leu Phe
        580                 585

<210> SEQ ID NO 56
<211> LENGTH: 1716
<212> TYPE: DNA
<213> ORGANISM: Candida tropicalis

<400> SEQUENCE: 56

| | | | | | |
|---|---|---|---|---|---|
| atgactcagg | actataaaga | cgatagtcct | acgtccactg | agttggacac | taacatagaa | 60 |
| gaggtggaaa | gcactgcaac | cctagagtcg | gaactcagac | agagaaaaca | gaccacggaa | 120 |
| actccagcat | caaccccacc | accacctcca | caacaacagc | aggcgcataa | gaaagccctg | 180 |
| aagaatggca | agaggaagag | accatttata | aacgtggcgc | cgctcaacac | cccgttggct | 240 |
| cacaggctcg | agactttggc | tgttgtttgg | cactgtgtca | gtatcccgtt | ctttatgttt | 300 |
| ttgttcttgc | ttacggtctc | catggggttg | cttgggtggt | tctttatcat | tttgccatat | 360 |
| ttcatttggt | ggtacggttt | cgacttgcac | actccatcga | atggtaaagt | tgtctatcgt | 420 |
| gtgcgcaact | cgttcaagaa | tttcatcatt | tgggactggt | ttgtcaagta | tttcccgatt | 480 |
| gaagtgcaca | gacggtcga | gttggatcct | acttttagcg | aattgcctgt | ggaagagagc | 540 |
| ggcgacagtt | cggacgacga | cgaacaagac | ttggtgtctg | agcacagcag | aactttggtt | 600 |
| gatcaaatct | tcaagttttt | cgggttgaag | aaacgcttga | atgacacctc | cctgggcaaa | 660 |
| ccagagacat | tcaagaatgt | gcctacgggt | ccaaggtata | ttttgggta | ccacccacac | 720 |
| ggagtgattt | ctatggggc | agtggggttg | tttgccaaca | acgccttgag | gaacgaacca | 780 |
| tatacgccaa | tttccaaatg | gttaaaacca | ttcttccacg | acagctccaa | gggcgagaga | 840 |
| tgttccctg | gtattggcaa | tatcttccca | ttgacgctta | ccacacagtt | tgcgctccca | 900 |
| ttttaccgtg | actacttgat | ggctttgggg | atcactagtg | catcggctaa | aaacattaga | 960 |
| agcttgatca | caatggaga | caactctgtg | tgtctcgtcg | ttggcggtgc | acaagaatcg | 1020 |
| ttgttgaaca | atatgattgc | caagcacgcc | agagtcgggt | acggttacaa | agagagccta | 1080 |
| gatattcatg | cgaccagtc | cgaagaagaa | gaagaagaag | aggatgatac | caagcagcta | 1140 |
| gagaacccaa | gtcctaaacg | tgaagtgcaa | ttggtcttga | caaacgtaa | aggttttgtg | 1200 |
| aagttggcta | tcgaactagg | aaatgttttcc | ttggtgccta | ttttgcatt | cggagaagct | 1260 |
| gatgtttaca | gattggccca | gccagcacca | ggctcgttct | tgtacaagtt | ccagcaatgg | 1320 |
| atgaaggcaa | cttttcaatt | caccatccca | ttgtttagtg | ctcgaggcgt | gttcatctat | 1380 |
| gatttcggat | tgttgccatt | cagaaaccca | ataaacattt | gcgtcggtag | accgtctac | 1440 |
| attccgcaca | acgtcttgca | agaatacaag | caaaagcacc | cagaggagtt | tgccgaagag | 1500 |
| gaacctgcca | gtacccgat | gaagaagtct | ggatctttca | ccgatatgtt | caaagctggt | 1560 |
| gaaaagaagc | ccaagacttc | aagtatcaag | actaaaatcc | cacctgcatt | actagacaag | 1620 |
| taccacaagc | tatacgtcga | cgagttgaag | aaggtctatg | aagagaacaa | ggaaaggttt | 1680 |
| ggctacggtg | atgttgaatt | aaacattgta | gaatag | | | 1716 |

<210> SEQ ID NO 57
<211> LENGTH: 571
<212> TYPE: PRT
<213> ORGANISM: Candida tropicalis

<400> SEQUENCE: 57

Met Thr Gln Asp Tyr Lys Asp Asp Ser Pro Thr Ser Thr Glu Leu Asp
1               5                   10                  15

-continued

```
Thr Asn Ile Glu Glu Val Glu Ser Thr Ala Thr Leu Glu Ser Glu Leu
         20                  25                  30

Arg Gln Arg Lys Gln Thr Thr Glu Thr Pro Ala Ser Thr Pro Pro Pro
     35                  40                  45

Pro Pro Gln Gln Gln Gln Ala His Lys Lys Ala Ser Lys Asn Gly Lys
 50                  55                  60

Arg Lys Arg Pro Phe Ile Asn Val Ala Pro Leu Asn Thr Pro Leu Ala
 65                  70                  75                  80

His Arg Leu Glu Thr Leu Ala Val Val Trp His Cys Val Ser Ile Pro
                 85                  90                  95

Phe Phe Met Phe Leu Phe Leu Leu Thr Val Ser Met Gly Leu Leu Gly
             100                 105                 110

Trp Phe Ile Ile Leu Pro Tyr Phe Ile Trp Trp Tyr Gly Phe Asp
         115                 120                 125

Leu His Thr Pro Ser Asn Gly Lys Val Val Tyr Arg Val Arg Asn Ser
     130                 135                 140

Phe Lys Asn Phe Ile Ile Trp Asp Trp Phe Val Lys Tyr Phe Pro Ile
145                 150                 155                 160

Glu Val His Lys Thr Val Glu Leu Asp Pro Thr Phe Ser Glu Leu Pro
                 165                 170                 175

Val Glu Glu Ser Gly Asp Ser Ser Asp Asp Glu Gln Asp Leu Val
             180                 185                 190

Ser Glu His Ser Arg Thr Leu Val Asp Gln Ile Phe Lys Phe Phe Gly
         195                 200                 205

Leu Lys Lys Arg Leu Asn Asp Thr Ser Ser Gly Lys Pro Glu Thr Phe
210                 215                 220

Lys Asn Val Pro Thr Gly Pro Arg Tyr Ile Phe Gly Tyr His Pro His
225                 230                 235                 240

Gly Val Ile Ser Met Gly Ala Val Gly Leu Phe Ala Asn Asn Ala Leu
                 245                 250                 255

Arg Asn Glu Pro Tyr Thr Pro Ile Ser Lys Trp Leu Lys Pro Phe Phe
             260                 265                 270

His Asp Ser Ser Lys Gly Glu Arg Leu Phe Pro Gly Ile Gly Asn Ile
         275                 280                 285

Phe Pro Leu Thr Leu Thr Thr Gln Phe Ala Leu Pro Phe Tyr Arg Asp
     290                 295                 300

Tyr Leu Met Ala Leu Gly Ile Thr Ser Ala Ser Ala Lys Asn Ile Arg
305                 310                 315                 320

Ser Leu Ile Asn Asn Gly Asp Asn Ser Val Cys Leu Val Val Gly Gly
                 325                 330                 335

Ala Gln Glu Ser Leu Leu Asn Asn Met Ile Ala Lys His Ala Arg Val
             340                 345                 350

Gly Tyr Gly Tyr Lys Glu Ser Leu Asp Ile His Gly Asp Gln Ser Glu
         355                 360                 365

Glu Glu Glu Glu Glu Glu Asp Asp Thr Lys Gln Leu Glu Asn Pro Ser
     370                 375                 380

Pro Lys Arg Glu Val Gln Leu Val Leu Asn Lys Arg Lys Gly Phe Val
385                 390                 395                 400

Lys Leu Ala Ile Glu Leu Gly Asn Val Ser Leu Val Pro Ile Phe Ala
                 405                 410                 415

Phe Gly Glu Ala Asp Val Tyr Arg Leu Ala Gln Pro Ala Pro Gly Ser
             420                 425                 430

Phe Leu Tyr Lys Phe Gln Gln Trp Met Lys Ala Thr Phe Gln Phe Thr
         435                 440                 445
```

```
Ile Pro Leu Phe Ser Ala Arg Gly Val Phe Ile Tyr Asp Phe Gly Leu
            450                 455                 460

Leu Pro Phe Arg Asn Pro Ile Asn Ile Cys Val Gly Arg Pro Val Tyr
465                 470                 475                 480

Ile Pro His Asn Val Leu Gln Glu Tyr Lys Gln Lys His Pro Glu Glu
                485                 490                 495

Phe Ala Glu Glu Pro Ala Ser Thr Pro Met Lys Lys Ser Gly Ser
            500                 505                 510

Phe Thr Asp Met Phe Lys Ala Gly Lys Lys Pro Lys Thr Ser Ser
            515                 520                 525

Ile Lys Thr Lys Ile Pro Pro Ala Leu Leu Asp Lys Tyr His Lys Leu
530                 535                 540

Tyr Val Asp Glu Leu Lys Lys Val Tyr Glu Asn Lys Glu Arg Phe
545                 550                 555                 560

Gly Tyr Gly Asp Val Glu Leu Asn Ile Val Glu
            565                 570

<210> SEQ ID NO 58
<211> LENGTH: 2079
<212> TYPE: DNA
<213> ORGANISM: Candida tropicalis

<400> SEQUENCE: 58
atgtcgtctt taaagaacag aaaatccgca agcgtcgcca caagcgatac agaagactca      60
gaaacagagg cagtatcctc ctcaattgat cccaacggca ccatattgcg accagtccta     120
catgacgaac cccaccacag ccatcaccac acaacataa ctagaccagt attggaggac      180
gatggcagca tcctggtgtc cagaagatcg tcgatctcca aatccgacga cctgcaggca     240
aagcaaaaga gaagaaaacc caagaagaag atcttggagt ctcgtcgggt catgtttatc     300
tttggtaccc tcattgggtt aatctttgcg tgggcgttta ccacagacac gcatcctttc     360
aatggcgact tggagaagtt tatcaacttt gaccagctca acgggatctt tgacgactgg     420
aagaactgga aggatatctt gcccaacagc atccagacgt acttgcagga atcgggcaag     480
ggcgaagata cgacgggtt gcatggtctg gccgattcct tctccgtcgg gctccgcttg     540
aaagcccaga gaacttcac tgacaaccac aatgtcgtgt tggttcctgg tgtggtgagc     600
acggggttgg aatcgtgggg aacaaccacc accggtgatt gtccatctat cggatacttc     660
aggaagagat tgtggggatc atttatatg ttaaggacaa tgattttga gaaaacgtgc       720 tggttgaagc atatccagtt ggacgagaag acggggttgg atcctcccaa tattaaggtc     780
cgtgcggcgc agggtttcga agcggcagat ttctttatgg ctgggtactg gatctggaac     840
aagatcttgc agaacttggc ggttattggg tacggaccaa ataacatggt gagtgctagt     900
tatgactgga gattggctta cattgacttg gagagaagag atggatattt ttcgaaactt    960
aaagcgcaga ttgagttgaa taacaagttg aacaacaaga gactgtgtt gattggccac    1020 tcgatgggga cccagattat tttctacttt ttgaaatggg tcgaagccac cgggaaacca    1080
tactatggca atggcggacc aaactgggtg aatgatcata ttgagtcgat tattgacatc    1140
agtgggtcga cttttgggtac ccccaagagt attcctgtgt tgatctctgg ggaaatgaaa   1200
gacaccgttc aattgaacgc gttggcggtt acgggttgg agcaatttt cagcaggcgt     1260 gaaagagtcg atatgttgcg tacatttggt ggcgttgcca gtatgttacc caagggggga    1320
gacaagatat ggggcaactt gacgcatgcg ccagatgatc caatttccac attcagtgat    1380
gacgaagtta cggacagcca cgaacctaaa gatcgttctt ttggtacgtt tatccaattc    1440
```

-continued

```
aagaaccaaa ctagcgacgc taagccatac agggagatca ccatggctga aggtatcgat    1500
gaattgttgg acaaatcacc agactggtat tccaagagag tccgtgagaa ctactcttac    1560
ggcattacag acagcaaggc gcaattagag aagaacaaca atgaccacct gaagtggtcg    1620
aacccattag aagctgcctt gcctaaagca cccgacatga agatctattg tttctacgga    1680
gttggaaatc ctaccgaaag ggcatacaag tatgtgactg ccgataaaaa agccacgaaa    1740
ttggactaca taatagacgc cgacgatgcc aatggagtca tattaggaga cggagacggc    1800
actgtttcgt tattaaccca ctcgatgtgc catgagtggg ccaagggaga caagtcgaga    1860
tacaacccag ccaactcgaa ggttaccatt gttgaaatca agcacgagcc agacagattt    1920
gatttacgag gcggcgccaa gactgcggaa catgttgata ttttggggag tgccgagttg    1980
aacgagttga ttttgactgt ggttagcggg aacgggacg agattgagaa tagatatgtc    2040
agcaacttaa agaaatagt agaggccata aatttataa                             2079
```

<210> SEQ ID NO 59
<211> LENGTH: 692
<212> TYPE: PRT
<213> ORGANISM: Candida tropicalis

<400> SEQUENCE: 59

```
Met Ser Ser Leu Lys Asn Arg Lys Ser Ala Ser Val Ala Thr Ser Asp
1               5                   10                  15

Thr Glu Asp Ser Glu Thr Glu Ala Val Ser Ser Ile Asp Pro Asn
            20                  25                  30

Gly Thr Ile Leu Arg Pro Val Leu His Asp Glu Pro His Ser His
        35                  40                  45

His His His Asn Ile Thr Arg Pro Val Leu Glu Asp Asp Gly Ser Ile
    50                  55                  60

Ser Val Ser Arg Arg Ser Ser Ile Ser Lys Ser Asp Asp Ser Gln Ala
65                  70                  75                  80

Lys Gln Lys Lys Lys Lys Pro Lys Lys Lys Ile Leu Glu Ser Arg Arg
                85                  90                  95

Val Met Phe Ile Phe Gly Thr Leu Ile Gly Leu Ile Phe Ala Trp Ala
            100                 105                 110

Phe Thr Thr Asp Thr His Pro Phe Asn Gly Asp Leu Glu Lys Phe Ile
        115                 120                 125

Asn Phe Asp Gln Leu Asn Gly Ile Phe Asp Asp Trp Lys Asn Trp Lys
    130                 135                 140

Asp Ile Leu Pro Asn Ser Ile Gln Thr Tyr Leu Gln Glu Ser Gly Lys
145                 150                 155                 160

Gly Glu Asp Asn Asp Gly Leu His Gly Ser Ala Asp Ser Phe Ser Val
                165                 170                 175

Gly Leu Arg Leu Lys Ala Gln Lys Asn Phe Thr Asp Asn His Asn Val
            180                 185                 190

Val Leu Val Pro Gly Val Val Ser Thr Gly Leu Glu Ser Trp Gly Thr
        195                 200                 205

Thr Thr Thr Gly Asp Cys Pro Ser Ile Gly Tyr Phe Arg Lys Arg Leu
    210                 215                 220

Trp Gly Ser Phe Tyr Met Leu Arg Thr Met Ile Leu Glu Lys Thr Cys
225                 230                 235                 240

Trp Leu Lys His Ile Gln Leu Asp Glu Lys Thr Gly Leu Asp Pro Pro
                245                 250                 255

Asn Ile Lys Val Arg Ala Ala Gln Gly Phe Glu Ala Ala Asp Phe Phe
```

-continued

```
                260                 265                 270
Met Ala Gly Tyr Trp Ile Trp Asn Lys Ile Leu Gln Asn Leu Ala Val
            275                 280                 285
Ile Gly Tyr Gly Pro Asn Asn Met Val Ser Ala Ser Tyr Asp Trp Arg
            290                 295                 300
Leu Ala Tyr Ile Asp Leu Glu Arg Arg Asp Gly Tyr Phe Ser Lys Leu
305                 310                 315                 320
Lys Ala Gln Ile Glu Leu Asn Asn Lys Leu Asn Asn Lys Lys Thr Val
            325                 330                 335
Leu Ile Gly His Ser Met Gly Thr Gln Ile Ile Phe Tyr Phe Leu Lys
            340                 345                 350
Trp Val Glu Ala Thr Gly Lys Pro Tyr Tyr Gly Asn Gly Gly Pro Asn
            355                 360                 365
Trp Val Asn Asp His Ile Glu Ser Ile Ile Asp Ile Ser Gly Ser Thr
            370                 375                 380
Leu Gly Thr Pro Lys Ser Ile Pro Val Leu Ile Ser Gly Glu Met Lys
385                 390                 395                 400
Asp Thr Val Gln Leu Asn Ala Leu Ala Val Tyr Gly Leu Glu Gln Phe
            405                 410                 415
Phe Ser Arg Arg Glu Arg Val Asp Met Leu Arg Thr Phe Gly Gly Val
            420                 425                 430
Ala Ser Met Leu Pro Lys Gly Gly Asp Lys Ile Trp Gly Asn Leu Thr
            435                 440                 445
His Ala Pro Asp Asp Pro Ile Ser Thr Phe Ser Asp Asp Glu Val Thr
            450                 455                 460
Asp Ser His Glu Pro Lys Asp Arg Ser Phe Gly Thr Phe Ile Gln Phe
465                 470                 475                 480
Lys Asn Gln Thr Ser Asp Ala Lys Pro Tyr Arg Glu Ile Thr Met Ala
            485                 490                 495
Glu Gly Ile Asp Glu Leu Leu Asp Lys Ser Pro Asp Trp Tyr Ser Lys
            500                 505                 510
Arg Val Arg Glu Asn Tyr Ser Tyr Gly Ile Thr Asp Ser Lys Ala Gln
            515                 520                 525
Leu Glu Lys Asn Asn Asn Asp His Ser Lys Trp Ser Asn Pro Leu Glu
            530                 535                 540
Ala Ala Leu Pro Lys Ala Pro Asp Met Lys Ile Tyr Cys Phe Tyr Gly
545                 550                 555                 560
Val Gly Asn Pro Thr Glu Arg Ala Tyr Lys Tyr Val Thr Ala Asp Lys
            565                 570                 575
Lys Ala Thr Lys Leu Asp Tyr Ile Ile Asp Ala Asp Ala Asn Gly
            580                 585                 590
Val Ile Leu Gly Asp Gly Asp Gly Thr Val Ser Leu Leu Thr His Ser
            595                 600                 605
Met Cys His Glu Trp Ala Lys Gly Asp Lys Ser Arg Tyr Asn Pro Ala
            610                 615                 620
Asn Ser Lys Val Thr Ile Val Glu Ile Lys His Glu Pro Asp Arg Phe
625                 630                 635                 640
Asp Leu Arg Gly Gly Ala Lys Thr Ala Glu His Val Asp Ile Leu Gly
            645                 650                 655
Ser Ala Glu Leu Asn Glu Leu Ile Leu Thr Val Val Ser Gly Asn Gly
            660                 665                 670
Asp Glu Ile Glu Asn Arg Tyr Val Ser Asn Leu Lys Glu Ile Val Glu
            675                 680                 685
```

Ala Ile Asn Leu
        690

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 60

His His His His His His
1               5

<210> SEQ ID NO 61
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln

```
                      275                 280                 285
Lys Leu His Lys Phe Asp Val Lys Thr Gly Asp Ser Ile Arg Lys Gly
            290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
                355                 360                 365

Asn Gly Gly Arg Ser Gln Tyr Lys His Leu Leu Arg Leu Glu Asp Gly
            370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Ala Ser

<210> SEQ ID NO 62
<211> LENGTH: 2109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Ala Gln Ser Arg Gln Leu Phe Leu Phe Gly Asp Gln Thr Ala Asp
1               5                   10                  15

Phe Val Pro Lys Leu Arg Ser Leu Leu Ser Val Gln Asp Ser Pro Ile
                20                  25                  30

Leu Ala Ala Phe Leu Asp Gln Ser His Tyr Val Val Arg Ala Gln Met
            35                  40                  45

Leu Gln Ser Met Asn Thr Val Asp His Lys Leu Ala Arg Thr Ala Asp
        50                  55                  60

Leu Arg Gln Met Val Gln Lys Tyr Val Asp Gly Lys Leu Thr Pro Ala
65                  70                  75                  80

Phe Arg Thr Ala Leu Val Cys Leu Cys Gln Leu Gly Cys Phe Ile Arg
                85                  90                  95

Glu Tyr Glu Glu Ser Gly Asn Met Tyr Pro Gln Pro Ser Asp Ser Tyr
                100                 105                 110

Val Leu Gly Phe Cys Met Gly Ser Leu Ala Ala Val Ala Val Ser Cys
            115                 120                 125

Ser Arg Ser Leu Ser Glu Leu Leu Pro Ile Ala Val Gln Thr Val Leu
        130                 135                 140

Ile Ala Phe Arg Leu Gly Leu Cys Ala Leu Glu Met Arg Asp Arg Val
145                 150                 155                 160

Asp Gly Cys Ser Asp Arg Gly Asp Pro Trp Ser Thr Ile Val Trp
                165                 170                 175

Gly Leu Asp Pro Gln Gln Ala Arg Asp Gln Ile Glu Val Phe Cys Arg
            180                 185                 190

Thr Thr Asn Val Pro Gln Thr Arg Arg Pro Trp Ile Ser Cys Ile Ser
        195                 200                 205

Lys Asn Ala Ile Thr Leu Ser Gly Ser Pro Ser Thr Leu Arg Ala Phe
    210                 215                 220
```

-continued

```
Cys Ala Met Pro Gln Met Ala Gln His Arg Thr Ala Pro Ile Pro Ile
225                 230                 235                 240

Cys Leu Pro Ala His Asn Gly Ala Leu Phe Thr Gln Ala Asp Ile Thr
            245                 250                 255

Thr Ile Leu Asp Thr Thr Pro Thr Thr Pro Trp Glu Gln Leu Pro Gly
        260                 265                 270

Gln Ile Pro Tyr Ile Ser His Val Thr Gly Asn Val Val Gln Thr Ser
    275                 280                 285

Asn Tyr Arg Asp Leu Ile Glu Val Ala Leu Ser Glu Thr Leu Leu Glu
290                 295                 300

Gln Val Arg Leu Asp Leu Val Glu Thr Gly Leu Pro Arg Leu Leu Gln
305                 310                 315                 320

Ser Arg Gln Val Lys Ser Val Thr Ile Val Pro Phe Leu Thr Arg Met
                325                 330                 335

Asn Glu Thr Met Ser Asn Ile Leu Pro Asp Ser Phe Ile Ser Thr Glu
            340                 345                 350

Thr Arg Thr Asp Thr Gly Arg Ala Ile Pro Ala Ser Gly Arg Pro Gly
        355                 360                 365

Ala Gly Lys Cys Lys Leu Ala Ile Val Ser Met Ser Gly Arg Phe Pro
    370                 375                 380

Glu Ser Pro Thr Thr Glu Ser Phe Trp Asp Leu Leu Tyr Lys Gly Leu
385                 390                 395                 400

Asp Val Cys Lys Glu Val Pro Arg Arg Trp Asp Ile Asn Thr His
                405                 410                 415

Val Asp Pro Ser Gly Lys Ala Arg Asn Lys Gly Ala Thr Lys Trp Gly
            420                 425                 430

Cys Trp Leu Asp Phe Ser Gly Asp Phe Asp Pro Arg Phe Phe Gly Ile
        435                 440                 445

Ser Pro Lys Glu Ala Pro Gln Met Asp Pro Ala Gln Arg Met Ala Leu
    450                 455                 460

Met Ser Thr Tyr Glu Ala Met Glu Arg Ala Gly Leu Val Pro Asp Thr
465                 470                 475                 480

Thr Pro Ser Thr Gln Arg Asp Arg Ile Gly Val Phe His Gly Val Thr
                485                 490                 495

Ser Asn Asp Trp Met Glu Thr Asn Thr Ala Gln Asn Ile Asp Thr Tyr
            500                 505                 510

Phe Ile Thr Gly Gly Asn Arg Gly Phe Ile Pro Gly Arg Ile Asn Phe
        515                 520                 525

Cys Phe Glu Phe Ala Gly Pro Ser Tyr Thr Asn Asp Thr Ala Cys Ser
    530                 535                 540

Ser Ser Leu Ala Ala Ile His Leu Ala Cys Asn Ser Leu Trp Arg Gly
545                 550                 555                 560

Asp Cys Asp Thr Ala Val Ala Gly Gly Thr Asn Met Ile Tyr Thr Pro
                565                 570                 575

Asp Gly His Thr Gly Leu Asp Lys Gly Phe Phe Leu Ser Arg Thr Gly
            580                 585                 590

Asn Cys Lys Pro Tyr Asp Asp Lys Ala Asp Gly Tyr Cys Arg Ala Glu
        595                 600                 605

Gly Val Gly Thr Val Phe Ile Lys Arg Leu Glu Asp Ala Leu Ala Asp
    610                 615                 620

Asn Asp Pro Ile Leu Gly Val Ile Leu Asp Ala Lys Thr Asn His Ser
625                 630                 635                 640

Ala Met Ser Glu Ser Met Thr Arg Pro His Val Gly Ala Gln Ile Asp
```

```
                    645                 650                 655
Asn Met Thr Ala Ala Leu Asn Thr Thr Gly Leu His Pro Asn Asp Phe
        660                 665                 670
Ser Tyr Ile Glu Met His Gly Thr Gly Thr Gln Val Gly Asp Ala Val
        675                 680                 685
Glu Met Glu Ser Val Leu Ser Val Phe Ala Pro Ser Glu Thr Ala Arg
        690                 695                 700
Lys Ala Asp Gln Pro Leu Phe Val Gly Ser Ala Lys Ala Asn Val Gly
705                 710                 715                 720
His Gly Glu Gly Val Ser Gly Val Thr Ser Leu Ile Lys Val Leu Met
                725                 730                 735
Met Met Gln His Asp Thr Ile Pro Pro His Cys Gly Ile Lys Pro Gly
                740                 745                 750
Ser Lys Ile Asn Arg Asn Phe Pro Asp Leu Gly Ala Arg Asn Val His
                755                 760                 765
Ile Ala Phe Glu Pro Lys Pro Trp Pro Arg Thr His Thr Pro Arg Arg
        770                 775                 780
Val Leu Ile Asn Asn Phe Ser Ala Ala Gly Gly Asn Thr Ala Leu Ile
785                 790                 795                 800
Val Glu Asp Ala Pro Glu Arg His Trp Pro Thr Glu Lys Asp Pro Arg
                805                 810                 815
Ser Ser His Ile Val Ala Leu Ser Ala His Val Gly Ala Ser Met Lys
                820                 825                 830
Thr Asn Leu Glu Arg Leu His Gln Tyr Leu Leu Lys Asn Pro His Thr
        835                 840                 845
Asp Leu Ala Gln Leu Ser Tyr Thr Thr Thr Ala Arg Arg Trp His Tyr
        850                 855                 860
Leu His Arg Val Ser Val Thr Gly Ala Ser Val Glu Glu Val Thr Arg
865                 870                 875                 880
Lys Leu Glu Met Ala Ile Gln Asn Gly Asp Gly Val Ser Arg Pro Lys
                885                 890                 895
Ser Lys Pro Lys Ile Leu Phe Ala Phe Thr Gly Gln Gly Ser Gln Tyr
                900                 905                 910
Ala Thr Met Gly Lys Gln Val Tyr Asp Ala Tyr Pro Ser Phe Arg Glu
        915                 920                 925
Asp Leu Glu Lys Phe Asp Arg Leu Ala Gln Ser His Gly Phe Pro Ser
        930                 935                 940
Phe Leu His Val Cys Thr Ser Pro Lys Gly Asp Val Glu Glu Met Ala
945                 950                 955                 960
Pro Val Val Val Gln Leu Ala Ile Thr Cys Leu Gln Met Ala Leu Thr
                965                 970                 975
Asn Leu Met Thr Ser Phe Gly Ile Arg Pro Asp Val Thr Val Gly His
                980                 985                 990
Ser Leu Gly Glu Phe Ala Ala Leu  Tyr Ala Ala Gly Val  Leu Ser Ala
        995                 1000                1005
Ser Asp Val Val Tyr Leu Val  Gly Gln Arg Ala Glu  Leu Leu Gln
        1010                1015                1020
Glu Arg Cys Gln Arg Gly Thr  His Ala Met Leu Ala  Val Lys Ala
        1025                1030                1035
Thr Pro Glu Ala Leu Ser Gln  Trp Ile Gln Asp His  Asp Cys Glu
        1040                1045                1050
Val Ala Cys Ile Asn Gly Pro  Glu Asp Thr Val Leu  Ser Gly Thr
        1055                1060                1065
```

```
Thr Lys Asn Val Ala Glu Val Gln Arg Ala Met Thr Asp Asn Gly
1070            1075                1080

Ile Lys Cys Thr Leu Leu Lys Leu Pro Phe Ala Phe His Ser Ala
1085            1090                1095

Gln Val Gln Pro Ile Leu Asp Asp Phe Glu Ala Leu Ala Gln Gly
1100            1105                1110

Ala Thr Phe Ala Lys Pro Gln Leu Leu Ile Leu Ser Pro Leu Leu
1115            1120                1125

Arg Thr Glu Ile His Glu Gln Gly Val Val Thr Pro Ser Tyr Val
1130            1135                1140

Ala Gln His Cys Arg His Thr Val Asp Met Ala Gln Ala Leu Arg
1145            1150                1155

Ser Ala Arg Glu Lys Gly Leu Ile Asp Asp Lys Thr Leu Val Ile
1160            1165                1170

Glu Leu Gly Pro Lys Pro Leu Ile Ser Gly Met Val Lys Met Thr
1175            1180                1185

Leu Gly Asp Lys Ile Ser Thr Leu Pro Thr Leu Ala Pro Asn Lys
1190            1195                1200

Ala Ile Trp Pro Ser Leu Gln Lys Ile Leu Thr Ser Val Tyr Thr
1205            1210                1215

Gly Gly Trp Asp Ile Asn Trp Lys Lys Tyr His Ala Pro Phe Ala
1220            1225                1230

Ser Ser Gln Lys Val Val Asp Leu Pro Ser Tyr Gly Trp Asp Leu
1235            1240                1245

Lys Asp Tyr Tyr Ile Pro Tyr Gln Gly Asp Trp Cys Leu His Arg
1250            1255                1260

His Gln Gln Asp Cys Lys Cys Ala Ala Pro Gly His Glu Ile Lys
1265            1270                1275

Thr Ala Asp Tyr Gln Val Pro Pro Glu Ser Thr Pro His Arg Pro
1280            1285                1290

Ser Lys Leu Asp Pro Ser Lys Glu Ala Phe Pro Glu Ile Lys Thr
1295            1300                1305

Thr Thr Thr Leu His Arg Val Val Glu Glu Thr Thr Lys Pro Leu
1310            1315                1320

Gly Ala Thr Leu Val Val Glu Thr Asp Ile Ser Arg Lys Asp Val
1325            1330                1335

Asn Gly Leu Ala Arg Gly His Leu Val Asp Gly Ile Pro Leu Cys
1340            1345                1350

Thr Pro Ser Phe Tyr Ala Asp Ile Ala Met Gln Val Gly Gln Tyr
1355            1360                1365

Ser Met Gln Arg Leu Arg Ala Gly His Pro Gly Ala Gly Ala Ile
1370            1375                1380

Asp Gly Leu Val Asp Val Ser Asp Met Val Val Asp Lys Ala Leu
1385            1390                1395

Val Pro His Gly Lys Gly Pro Gln Leu Leu Arg Thr Thr Leu Thr
1400            1405                1410

Met Glu Trp Pro Pro Lys Ala Ala Ala Thr Thr Arg Ser Ala Lys
1415            1420                1425

Val Lys Phe Ala Thr Tyr Phe Ala Asp Gly Lys Leu Asp Thr Glu
1430            1435                1440

His Ala Ser Cys Thr Val Arg Phe Thr Ser Asp Ala Gln Leu Lys
1445            1450                1455

Ser Leu Arg Arg Ser Val Ser Glu Tyr Lys Thr His Ile Arg Gln
1460            1465                1470
```

-continued

```
Leu His Asp Gly His Ala Lys Gly Gln Phe Met Arg Tyr Asn Arg
    1475            1480                1485
Lys Thr Gly Tyr Lys Leu Met Ser Ser Met Ala Arg Phe Asn Pro
    1490            1495                1500
Asp Tyr Met Leu Leu Asp Tyr Leu Val Leu Asn Glu Ala Glu Asn
    1505            1510                1515
Glu Ala Ala Ser Gly Val Asp Phe Ser Leu Gly Ser Ser Glu Gly
    1520            1525                1530
Thr Phe Ala Ala His Pro Ala His Val Asp Ala Ile Thr Gln Val
    1535            1540                1545
Ala Gly Phe Ala Met Asn Ala Asn Asp Asn Val Asp Ile Glu Lys
    1550            1555                1560
Gln Val Tyr Val Asn His Gly Trp Asp Ser Phe Gln Ile Tyr Gln
    1565            1570                1575
Pro Leu Asp Asn Ser Lys Ser Tyr Gln Val Tyr Thr Lys Met Gly
    1580            1585                1590
Gln Ala Lys Glu Asn Asp Leu Val His Gly Asp Val Val Val Leu
    1595            1600                1605
Asp Gly Glu Gln Ile Val Ala Phe Phe Arg Gly Leu Thr Leu Arg
    1610            1615                1620
Ser Val Pro Arg Gly Ala Leu Arg Val Val Leu Gln Thr Thr Val
    1625            1630                1635
Lys Lys Ala Asp Arg Gln Leu Gly Phe Lys Thr Met Pro Ser Pro
    1640            1645                1650
Pro Pro Pro Thr Thr Thr Met Pro Ile Ser Pro Tyr Lys Pro Ala
    1655            1660                1665
Asn Thr Gln Val Ser Ser Gln Ala Ile Pro Ala Glu Ala Thr His
    1670            1675                1680
Ser His Thr Pro Pro Gln Pro Lys His Ser Pro Val Pro Glu Thr
    1685            1690                1695
Ala Gly Ser Ala Pro Ala Ala Lys Gly Val Gly Val Ser Asn Glu
    1700            1705                1710
Lys Leu Asp Ala Val Met Arg Val Val Ser Glu Glu Ser Gly Ile
    1715            1720                1725
Ala Leu Glu Glu Leu Thr Asp Asp Ser Asn Phe Ala Asp Met Gly
    1730            1735                1740
Ile Asp Ser Leu Ser Ser Met Val Ile Gly Ser Arg Phe Arg Glu
    1745            1750                1755
Asp Leu Gly Leu Asp Leu Gly Pro Glu Phe Ser Leu Phe Ile Asp
    1760            1765                1770
Cys Thr Thr Val Arg Ala Leu Lys Asp Phe Met Leu Gly Ser Gly
    1775            1780                1785
Asp Ala Gly Ser Gly Ser Asn Val Glu Asp Pro Pro Ser Ala
    1790            1795                1800
Thr Pro Gly Ile Asn Pro Glu Thr Asp Trp Ser Ser Ser Ala Ser
    1805            1810                1815
Asp Ser Ile Phe Ala Ser Glu Asp His Gly His Ser Ser Glu Ser
    1820            1825                1830
Gly Ala Asp Thr Gly Ser Pro Pro Ala Leu Asp Leu Lys Pro Tyr
    1835            1840                1845
Cys Arg Pro Ser Thr Ser Val Val Leu Gln Gly Leu Pro Met Val
    1850            1855                1860
Ala Arg Lys Thr Leu Phe Met Leu Pro Asp Gly Gly Gly Ser Ala
```

```
                 1865                1870                1875

Phe Ser Tyr Ala Ser Leu Pro Arg Leu Lys Ser Asp Thr Ala Val
             1880                1885                1890

Val Gly Leu Asn Cys Pro Tyr Ala Arg Asp Pro Glu Asn Met Asn
             1895                1900                1905

Cys Thr His Gly Ala Met Ile Glu Ser Phe Cys Asn Glu Ile Arg
             1910                1915                1920

Arg Arg Gln Pro Arg Gly Pro Tyr His Leu Gly Gly Trp Ser Ser
             1925                1930                1935

Gly Gly Ala Phe Ala Tyr Val Val Ala Glu Ala Leu Val Asn Gln
             1940                1945                1950

Gly Glu Glu Val His Ser Leu Ile Ile Ile Asp Ala Pro Ile Pro
             1955                1960                1965

Gln Ala Met Glu Gln Leu Pro Arg Ala Phe Tyr Glu His Cys Asn
             1970                1975                1980

Ser Ile Gly Leu Phe Ala Thr Gln Pro Gly Ala Ser Pro Asp Gly
             1985                1990                1995

Ser Thr Glu Pro Pro Ser Tyr Leu Ile Pro His Phe Thr Ala Val
             2000                2005                2010

Val Asp Val Met Leu Asp Tyr Lys Leu Ala Pro Leu His Ala Arg
             2015                2020                2025

Arg Met Pro Lys Val Gly Ile Val Trp Ala Ala Asp Thr Val Met
             2030                2035                2040

Asp Glu Arg Asp Ala Pro Lys Met Lys Gly Met His Phe Met Ile
             2045                2050                2055

Gln Lys Arg Thr Glu Phe Gly Pro Asp Gly Trp Asp Thr Ile Met
             2060                2065                2070

Pro Gly Ala Ser Phe Asp Ile Val Arg Ala Asp Gly Ala Asn His
             2075                2080                2085

Phe Thr Leu Met Gln Lys Glu His Val Ser Ile Ile Ser Asp Leu
             2090                2095                2100

Ile Asp Arg Val Met Ala
             2105

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Tyr Lys Asp Asp Asp Asp Lys Gly
1               5

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Lys Pro Ile Pro Asn Pro Leu Leu Gly Leu Asp Ser Thr
1               5                   10

<210> SEQ ID NO 65
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Gln Lys Leu Ile Ser Glu Glu Asp Leu
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Pro Glu Leu Ala Pro Glu Asp Pro Glu Asp
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Pro Tyr Asp Val Pro Asp Tyr Ala
1               5

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Tyr Thr Asp Ile Glu Met Asn Arg Leu Gly Lys
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid and this region may encompass
      1-3 residues

<400> SEQUENCE: 69

Cys Cys Xaa Xaa Xaa Cys Cys
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 70

Cys Cys Pro Gly Cys Cys
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Val Pro Arg Gly Ser
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Asp Asp Asp Lys
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Glu Asn Leu Tyr Phe Gln Gly
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Glu Val Leu Phe Gln Gly Pro
1               5

<210> SEQ ID NO 75
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
atggtcatcc aagggaagag attggccgcc tcctctattc agc        43

<210> SEQ ID NO 76
<211> LENGTH: 29
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 76
gtaggcgtca caggaaagac tgcgtacca                                          29

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tatcaccaat gctggatgta aagaagtcgc g                                       31

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
aattgggcta ggaaaccggg gatgc                                              25

<210> SEQ ID NO 79
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cggtctaatg acggcgcatg atatcatagc cgaaacggtc gag                          43

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
acttggctgg agtccatccc ttcggca                                            27

<210> SEQ ID NO 81
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctgcccgagt ttgaagtatc tcaacttacc gccgacgcca tg                           42

<210> SEQ ID NO 82
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 82
tgagacgcgc tgcgcagggc                                               20

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cgaggtgatc gagacgcaga tgc                                           23

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ttatgaagca ccagacatca gccccagc                                      28

<210> SEQ ID NO 85
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
atgggttccg ttagtaggga acatgagtca atc                                33

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gttccttgtg tgagctcctg aataagactg catg                               34

<210> SEQ ID NO 87
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ccatcaaaat cccctctat cacacgggca ctgggagcaa c                        41

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 88
cccacgcctt gcgcatctat aatcagg        27

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tgtccgaata ttctcctcgt tgtaggtagt ggatt        35

<210> SEQ ID NO 90
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gcagtagtcg ataggtacac atccttgggg gttccatgac tgc        43

<210> SEQ ID NO 91
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agaggatcaa ggcattatac atgagtctgt ggaacttggg ctttcc        46

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ttccccgtcc tccatggcct tatgc        25

<210> SEQ ID NO 93
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggcctttgcg cgatacgctg gtctctcggg tccat        36

<210> SEQ ID NO 94
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94

```
tcacgccatt tgttgaagca gggaatg                                              27
```

<210> SEQ ID NO 95
<211> LENGTH: 12
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 95

```
tcrnnnnnna cg                                                              12
```

<210> SEQ ID NO 96
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(14)
<223> OTHER INFORMATION: a, c, t, g, unknown or other

<400> SEQUENCE: 96

```
cggnnnnnnn nnnnccg                                                         17
```

<210> SEQ ID NO 97
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 97

```
gaannttcnn gaa                                                             13
```

<210> SEQ ID NO 98
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(9)
<223> OTHER INFORMATION: a, c, t, g, unknown or other

<400> SEQUENCE: 98

```
tgatgtannt                                                                 10
```

<210> SEQ ID NO 99
<211> LENGTH: 10
<212> TYPE: DNA
<213> ORGANISM: Artificial Sequence

```
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(5)
<223> OTHER INFORMATION: a, c, t, g, unknown or other

<400> SEQUENCE: 99 ccnnnwwrgg                                                              10

<210> SEQ ID NO 100
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 100 wwwwsyggggg                                                             10

<210> SEQ ID NO 101
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(9)
<223> OTHER INFORMATION: a, c, t, g, unknown or other

<400> SEQUENCE: 101
rmacccannc ayy                                                          13

<210> SEQ ID NO 102
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 102
tycgtnnrna rtgaya                                                       16

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
```

```
<400> SEQUENCE: 103
rrraararaa nanraraa                                              18

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 104
anagngagag agnggcag                                              18

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 105
tnnccwnttt ktttc                                                 15

<210> SEQ ID NO 106
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 106
aaaaararaa aarma                                                 15

<210> SEQ ID NO 107
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(14)
<223> OTHER INFORMATION: a, c, t, g, unknown or other

<400> SEQUENCE: 107
ykytyttytt nnnnky                                                16
```

```
<210> SEQ ID NO 108
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 108
cgtccggcgc                                                          10

<210> SEQ ID NO 109
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 109
gaaaaagmaa aaaaa                                                    15

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 110
ttttyyttyt tkyntynt                                                 18

<210> SEQ ID NO 111
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 111
catkyttttt tkyty                                                    15

<210> SEQ ID NO 112
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 112 cacgtgacya                                                          10

<210> SEQ ID NO 113
<211> LENGTH: 14
<212> TYPE: DNA
<213> ORGANISM: Artificial Sequence
<220> FEATURE:
<223> OTHER INFORMATION: Description of Artificial Sequence: Synthetic
``` binding motif oligonucleotide
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 113
cannnacaca sana                                                            14

<210> SEQ ID NO 114
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 114
ggnanannar narggcn                                                         17

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 115
tttkytktty nytttkty                                                        18

<210> SEQ ID NO 116
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 116 wttktttty ttttnt                                                           17

<210> SEQ ID NO 117
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 117
ttkttttytt c                                                           11

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 118
aaannraang arraanar                                                    18

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 119
gtgmaknmgr angng                                                       15

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

```
<400> SEQUENCE: 120
nttwacaycc rtacayny                                                18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 121
tttnctttky ttnytttt                                                18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 122
aaaranraaa naaarnaa                                                18

<210> SEQ ID NO 123
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 123
cacacacaca cacacac                                                 17

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 124
ttgcttgaac gsatgcca                                                18

<210> SEQ ID NO 125
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 125
yctttttttt yttyykg                                                    17

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 126
rrsccgmcgm grcgcgcs                                                   18

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 127
aaanararnr aaaarrar                                                   18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 128
ggaagctgaa acgymwrr                                                   18

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 129
ggagaggcat gatggggg                                                   18

<210> SEQ ID NO 130
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
```

```
<222> LOCATION: (3)..(3)
<223> OTHER INFORMATION: a, c, t, g, unknown or other

<400> SEQUENCE: 130 ctnccttct                                                           10

<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 131
gaaarraaaa aamrmara                                                 18

<210> SEQ ID NO 132
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (8)..(9)
<223> OTHER INFORMATION: a, c, t, g, unknown or other

<400> SEQUENCE: 132
gngccrsnnt m                                                        11

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 133 tttttyttt tynktttt                                                  18

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
```

```
<222> LOCATION: (18)..(18)
<223> OTHER INFORMATION: a, c, t, g, unknown or other

<400> SEQUENCE: 134
yttcttttyt nyncnktn                                                 18

<210> SEQ ID NO 135
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other

<400> SEQUENCE: 135
tnsykctttt cytty                                                    15

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 136
sttnytttyn ttytyyyy                                                 18

<210> SEQ ID NO 137
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 137
ykntttwyyt c                                                        11

<210> SEQ ID NO 138
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
```

```
<222> LOCATION: (13)..(13)
<223> OTHER INFORMATION: a, c, t, g, unknown or other

<400> SEQUENCE: 138
aaaananaar arnag                                                        15

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 139
waaaaaagaa aanaaaar                                                     18

<210> SEQ ID NO 140
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 140
aaanggnara m                                                            11

<210> SEQ ID NO 141
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(12)
<223> OTHER INFORMATION: a, c, t, g, unknown or other

<400> SEQUENCE: 141
tyttcyagaa nnttcy                                                       16

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 142
cacacacaca cacacaca                                                     18

<210> SEQ ID NO 143
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      binding motif oligonucleotide

<400> SEQUENCE: 143
tttycacatg c                                                              11

<210> SEQ ID NO 144
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 144
gnngcatgtg aaaa                                                           14

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 145
gaaaanaaaa aaaarana                                                       18

<210> SEQ ID NO 146
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 146
gaaaaaraar aanaa                                                          15

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other

<400> SEQUENCE: 147
yttktnnttt ttytyttt                                                       18
```

<210> SEQ ID NO 148
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other

<400> SEQUENCE: 148 gcagngcagg                                                              10

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 149
tttytykttt nyyttttt                                                     18

<210> SEQ ID NO 150
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 150
tttccnaawn rggaaa                                                       16

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 151
yttyyttytt ttytyttc                                                     18

<210> SEQ ID NO 152
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 152 mttttttytyt yttc                                                        14

<210> SEQ ID NO 153
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other

<400> SEQUENCE: 153
tatacanagm krtatatg                                                18

<210> SEQ ID NO 154
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 154
tmtttntync ttntttwk                                                18

<210> SEQ ID NO 155
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(4)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 155
ktnnttwtta ttccnc                                                  16

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other

```
<220> FEATURE:
<221> NAME/KEY: modified_base
<222> LOCATION: (11)..(11)
<223> OTHER INFORMATION: a, c, t, g, unknown or other

<400> SEQUENCE: 156
rnnaaaanra naaraaat                                                   18

<210> SEQ ID NO 157
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 157 tttttttttcw ctttkyc                                                   17

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 158
tttynytktt tynyttyt                                                   18

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 159
ttynnttytt nytttyyy                                                   18

<210> SEQ ID NO 160
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
```

<400> SEQUENCE: 160
tnygtgkryg tnyg                                                       14

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 161
ttyyyttttt yttttytt                                                   18

<210> SEQ ID NO 162
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 162
gamaaaaaar aaaar                                                      15

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 163
cycgggaagc sammnccg                                                   18

<210> SEQ ID NO 164
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 164
grtgyayggr tgy                                                        13

<210> SEQ ID NO 165
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 165
kmaaraaaaa raar                                                       14

<210> SEQ ID NO 166
<211> LENGTH: 18
<212> TYPE: DNA
<213> ORGANISM: Artificial Sequence
<220> FEATURE:

```
<223> OTHER INFORMATION: Description of Artificial Sequence: Synthetic
      binding motif oligonucleotide

<400> SEQUENCE: 166
aygraaaara raaaaraa                                                         18

<210> SEQ ID NO 167
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 167
ggaksccntt tyngmrta                                                         18

<210> SEQ ID NO 168
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other

<400> SEQUENCE: 168
ttttcnkttt yttttc                                                           17

<210> SEQ ID NO 169
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 169
araagmagaa arraa                                                            15

<210> SEQ ID NO 170
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 170
yttttctttt yntttt                                                           17

<210> SEQ ID NO 171
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 171
arraraaagg n                                                            11

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 172
ystnykntyt tnctcccm                                                     18

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 173
garanaaaar nraaraaa                                                     18

<210> SEQ ID NO 174
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 174
cynnggssan c                                                            11
```

```
<210> SEQ ID NO 175
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 175
cacacacaca cacaya                                                       16

<210> SEQ ID NO 176
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 176
cttytwttkt tktsa                                                        15

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 177
yttyyytytt tytyyttt                                                     18

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 178
amaaaaaraa rwaranaa                                                     18

<210> SEQ ID NO 179
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 179
araaaarraa aaagnraa                                                     18

<210> SEQ ID NO 180
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
```

-continued

```
<400> SEQUENCE: 180
raaraaaaar cmrsraaa                                               18

<210> SEQ ID NO 181
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 181
ttytktytyn tyykttty                                               18

<210> SEQ ID NO 182
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 182
gaaaamaana aaanaaa                                                18

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 183
yaanaraara aaanaam                                                18

<210> SEQ ID NO 184
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other
```

<400> SEQUENCE: 184 tynttttty ttttntk                                                18

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 185
raaraaraaa naanrnaa                                              18

<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 186
cacacacaca cacacaca                                              18

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 187
raarrraaaa anaaamaa                                              18

<210> SEQ ID NO 188
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 188
gccagaccta c                                                     11

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic

```
        binding motif oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 189
ttyttyttyt ttynytyt                                                 18

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: Synthetic
        binding motif oligonucleotide

<400> SEQUENCE: 190
yksgcgcgyc kcgkcggs                                                 18

<210> SEQ ID NO 191
<211> LENGTH: 17
<212> TYPE: DNA
<213> ORGANISM: Artificial Sequence
<220> FEATURE:
<223> OTHER INFORMATION: Description of Artificial Sequence: Synthetic
        binding motif oligonucleotide

<400> SEQUENCE: 191
ttttyytttt yyyyktt                                                  17

<210> SEQ ID NO 192
<211> LENGTH: 13
<212> TYPE: DNA
<213> ORGANISM: Artificial Sequence
<220> FEATURE:
<223> OTHER INFORMATION: Description of Artificial Sequence: Synthetic
        binding motif oligonucleotide

<400> SEQUENCE: 192
ttcttktyyt ttt                                                      13

<210> SEQ ID NO 193
<211> LENGTH: 18
<212> TYPE: DNA
<213> ORGANISM: Artificial Sequence
<220> FEATURE:
<223> OTHER INFORMATION: Description of Artificial Sequence: Synthetic
        binding motif oligonucleotide

<400> SEQUENCE: 193
ttyttttyty ytttyttt                                                 18

<210> SEQ ID NO 194
<211> LENGTH: 18
<212> TYPE: DNA
<213> ORGANISM: Artificial Sequence
<220> FEATURE:
<223> OTHER INFORMATION: Description of Artificial Sequence: Synthetic
        binding motif oligonucleotide

<400> SEQUENCE: 194
ttgcttgaac ggatgcca                                                 18

<210> SEQ ID NO 195
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 195
mgnmcaaaaa taaaas                                                          16

<210> SEQ ID NO 196
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 196
tycgtnnrna rtgaya                                                          16

<210> SEQ ID NO 197
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 197
gtgtgtgtgt gtgtg                                                           15

<210> SEQ ID NO 198
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(9)
<223> OTHER INFORMATION: a, c, t, g, unknown or other

<400> SEQUENCE: 198
ytstysttnt tgytwtt                                                         17

<210> SEQ ID NO 199
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 199
gcatgaccat ccacg                                                           15

<210> SEQ ID NO 200
<211> LENGTH: 17
<212> TYPE: DNA
```

-continued

<213> ORGANISM: Artificial Sequence
<220> FEATURE:
<223> OTHER INFORMATION: Description of Artificial Sequence: Synthetic
      binding motif oligonucleotide

<400> SEQUENCE: 200
gsgayarmgg amaaaaa                                                    17

<210> SEQ ID NO 201
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 201
trccgagryw nsssgcgs                                                   18

<210> SEQ ID NO 202
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 202
cgtccggcgc                                                            10

<210> SEQ ID NO 203
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other

<400> SEQUENCE: 203
aarwtsgarg nanncsaa                                                   18

<210> SEQ ID NO 204
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (11)..(12)
<223> OTHER INFORMATION: a, c, t, g, unknown or other

<400> SEQUENCE: 204
csnccaatgk nncs                                                       14

```
<210> SEQ ID NO 205
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other

<400> SEQUENCE: 205 gctnactaat                                                          10

<210> SEQ ID NO 206
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 206 cacgtgacya                                                          10

<210> SEQ ID NO 207
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 207
cayamrtgyn c                                                        11

<210> SEQ ID NO 208
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 208 tsgygrgasa                                                          10

<210> SEQ ID NO 209
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (6)..(8)
```

<223> OTHER INFORMATION: a, c, t, g, unknown or other

<400> SEQUENCE: 209
kncncnnnsc gctackgc                                         18

<210> SEQ ID NO 210
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 210
srnggcmcgg cnssg                                            15

<210> SEQ ID NO 211
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(8)
<223> OTHER INFORMATION: a, c, t, g, unknown or other

<400> SEQUENCE: 211
tacyacanca cawga                                            15

<210> SEQ ID NO 212
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 212
ccytgnaytt cwncttc                                          17

<210> SEQ ID NO 213
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (12)..(12)

```
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 213
gtgmaknmgr angng                                                      15

<210> SEQ ID NO 214
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 214
nttwacaycc rtacayny                                                   18

<210> SEQ ID NO 215
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other

<400> SEQUENCE: 215
aawnrtaaay arg                                                        13

<210> SEQ ID NO 216
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other

<400> SEQUENCE: 216
ggnaawangt aaacaa                                                     16

<210> SEQ ID NO 217
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 217
```

```
sastkcwctc ktcgt                                                        15

<210> SEQ ID NO 218
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 218
ttgcttgaac gsatgcca                                                     18

<210> SEQ ID NO 219
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (12)..(13)
<223> OTHER INFORMATION: a, c, t, g, unknown or other

<400> SEQUENCE: 219
cggmnnncwn ynncccg                                                      17

<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 220
rgargtsacg cakrttct                                                     18

<210> SEQ ID NO 221
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 221
ggaagctgaa acgymwrr                                                     18

<210> SEQ ID NO 222
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 222
aggtgatgga gtgctcag                                                     18
```

```
<210> SEQ ID NO 223
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 223
gkctrrnrgg agangm                                                     16

<210> SEQ ID NO 224
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 224
ngggsgntns ygtncga                                                    17

<210> SEQ ID NO 225
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 225
agnawgtttt tgwcaama                                                   18

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 226
kcksgcaggc wttkytct                                                   18
```

```
<210> SEQ ID NO 227
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 227
gnccsartng c                                                           11

<210> SEQ ID NO 228
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(10)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 228
sgcgmgggnn ccngaccg                                                    18

<210> SEQ ID NO 229
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 229
yctnattsgn cngs                                                        14

<210> SEQ ID NO 230
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
```

<222> LOCATION: (9)..(9)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 230
tnttsmttny tttccknc                                              18

<210> SEQ ID NO 231
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 231
ccacktksgs cctns                                                 15

<210> SEQ ID NO 232
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 232
crsgcywgkg c                                                     11

<210> SEQ ID NO 233
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 233
naaraagcng ggcacnc                                               17

<210> SEQ ID NO 234
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(12)
<223> OTHER INFORMATION: a, c, t, g, unknown or other

<400> SEQUENCE: 234
tyttcyagaa nnttcy                                                    16

<210> SEQ ID NO 235
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 235
cacacacaca cacacaca                                                  18

<210> SEQ ID NO 236
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 236
sckkcgckst ssttyaa                                                   17

<210> SEQ ID NO 237
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 237
gnngcatgtg aaaa                                                      14

<210> SEQ ID NO 238
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 238 cttttttyy tsgcc                                                      15

<210> SEQ ID NO 239
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(15)
<223> OTHER INFORMATION: a, c, t, g, unknown or other

<400> SEQUENCE: 239
gccggtmmcg sycnn                                                     15

<210> SEQ ID NO 240
<211> LENGTH: 15
<212> TYPE: DNA

```
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 240 annttttyt tkygc                                                         15

<210> SEQ ID NO 241
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 241
aaacntttat anataca                                                      17

<210> SEQ ID NO 242
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 242
caatntctnc k                                                            11

<210> SEQ ID NO 243
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
```

<400> SEQUENCE: 243
gnrrnanacg cgtnr                                                15

<210> SEQ ID NO 244
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 244
tttccnaawn rggaaa                                               16

<210> SEQ ID NO 245
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
cacacacccg ggatgatcag aaccgtccgt tatcaat                        37

<210> SEQ ID NO 246
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
cacacatcta gactctcttc tattcttaat tgccgcttcc actaaacggc aaagtctcca    60
cg                                                              62

<210> SEQ ID NO 247
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
atggtcatcc aagggaagag attggccgcc tcctctattc agc                 43

<210> SEQ ID NO 248
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
gtaggcgtca caggaaagac tgcgtacca                                 29

-continued

```
<210> SEQ ID NO 249
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
tatcaccaat gctggatgta aagaagtcgc g                                    31

<210> SEQ ID NO 250
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
aattgggcta ggaaaccggg gatgc                                           25

<210> SEQ ID NO 251
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
cggtctaatg acggcgcatg atatcatagc cgaaacggtc gag                       43

<210> SEQ ID NO 252
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
acttggctgg agtccatccc ttcggca                                         27

<210> SEQ ID NO 253
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ctgcccgagt ttgaagtatc tcaacttacc gccgacgcca tg                        42

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
tgagacgcgc tgcgcagggc                                                 20

<210> SEQ ID NO 255
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
cgaggtgatc gagacgcaga tgc                                            23

<210> SEQ ID NO 256
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
ttatgaagca ccagacatca gccccagc                                       28

<210> SEQ ID NO 257
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
gtactagtaa aaaaatggtc atccaaggga agagattggc cgcctcctct attcagc       57

<210> SEQ ID NO 258
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
gtcccgggct attatgaagc accagacatc agccccagc                           39

<210> SEQ ID NO 259
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
tacccgggct attagtgatg gtggtgatgg tgtgaagcac cagacatcag ccccagc       57

<210> SEQ ID NO 260
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
atgggttccg ttagtaggga acatgagtca atc                                 33

<210> SEQ ID NO 261
<211> LENGTH: 34
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 261
gttccttgtg tgagctcctg aataagactg catg                              34

<210> SEQ ID NO 262
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
ccatcaaaat cccctctat cacacgggca ctgggagcaa c                       41

<210> SEQ ID NO 263
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
cccacgcctt gcgcatctat aatcagg                                      27

<210> SEQ ID NO 264
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
tgtccgaata ttctcctcgt tgtaggtagt ggatt                             35

<210> SEQ ID NO 265
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
gcagtagtcg ataggtacac atccttgggg gttccatgac tgc                    43

<210> SEQ ID NO 266
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
agaggatcaa ggcattatac atgagtctgt ggaacttggg ctttcc                 46

<210> SEQ ID NO 267
<211> LENGTH: 25
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 267
ttccccgtcc tccatggcct tatgc					25

<210> SEQ ID NO 268
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
ggcctttgcg cgatacgctg gtctctcggg tcccat					36

<210> SEQ ID NO 269
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
tcacgccatt tgttgaagca gggaatg					27

<210> SEQ ID NO 270
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
gtactagtaa aaaatgggt tccgttagta gggaacatga gtcaatc					47

<210> SEQ ID NO 271
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gtgtttaaac ctatcacgcc atttgttgaa gcagggaatg					40

<210> SEQ ID NO 272
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ggtttaaacc tatcagtgat ggtggtgatg gtgcgccatt tgttgaagca gggaatgaa					59

<210> SEQ ID NO 273
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 273
atgacccaaa agactataca gcaggtccca aga                                33

<210> SEQ ID NO 274
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
tatggtgcat cgaatgttgt ttgcctgg                                      28

<210> SEQ ID NO 275
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
aaaatgcgtg agcactttgt ccagcgc                                       27

<210> SEQ ID NO 276
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
cgacgtaatt gacgttgtca acatgccg                                      28

<210> SEQ ID NO 277
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
catctcgggt tcccatcact ccctgagtat gac                                33

<210> SEQ ID NO 278
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
gacaaagaag ctggacaccg cagccttggg attccacgaa c                       41

<210> SEQ ID NO 279
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
```
gatctgcctt gtcggtggct atgacgacct tcagcctgag gagtca         46

<210> SEQ ID NO 280
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ttaacggatg atagaggcca acggccaaag acaccacttg cgtacac         47

<210> SEQ ID NO 281
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
cacacaacta gtaaaaaaat gacccaaaag actatacagc aggtcccaag a    51

<210> SEQ ID NO 282
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
tgtgtgcccg ggttaacgga tgatagaggc caacggccaa agacaccact tgcgtacac    59

<210> SEQ ID NO 283
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
tacccgggct attagtgatg gtggtgatgg tgacggatga tagaggccaa c    51

<210> SEQ ID NO 284
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
atgactccat caccgtttct cgatgctgt                             29

<210> SEQ ID NO 285
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
cacatgggta gcatcgttca ttgcccaaca caaagcgggc cagttaactc       50

-continued

<210> SEQ ID NO 286
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
gtcgagctaa gagtgactga tgccattggc                                        30

<210> SEQ ID NO 287
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
cgtaattcag cttctgaacc tgagcccagg                                        30

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
ctttgcccgg ccgtggttcg c                                                 21

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
cccccaagct cgacaacggg c                                                 21

<210> SEQ ID NO 290
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
ttctcaaaat gcaccggact gattacttgg a                                      31

<210> SEQ ID NO 291
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
cccattcctc tctcctgcgt gccctggccg gtaaagacgt at                          42

<210> SEQ ID NO 292

<210> SEQ ID NO 292
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
ccctccttcg atggacttgt ccgggcaaac gaccggttgc gaatggagat            50

<210> SEQ ID NO 293
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 293
ctacctattc tcttcaaccc gccgtaacag c                                31

<210> SEQ ID NO 294
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
cacacaacta gtaaaaaaat gactccatca ccgtttctcg atgctgt               47

<210> SEQ ID NO 295
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 295
tgtgtgcccg ggctacctat tctcttcaac ccgccgtaac agc                   43

<210> SEQ ID NO 296
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 296
tgtgtgcccg ggctatcagt gatggtggtg atggtgccta ttctcttcaa c          51

<210> SEQ ID NO 297
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 297
cacacagctc ttctagaatg gtcatccaag ggaagag                          37

<210> SEQ ID NO 298
<211> LENGTH: 28
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 298
agtatcgacg tcggctgact tgagacca                                      28

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
ccatcacatc cacagtggcg g                                             21

<210> SEQ ID NO 300
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
aaccaggcaa gttcgacata accggc                                        26

<210> SEQ ID NO 301
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
gtaggctatc cccgtctccc cgattatg                                      28

<210> SEQ ID NO 302
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
tgattgaggt caaggatgat ttgtccgaga                                    30

<210> SEQ ID NO 303
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
tcttcctatc tatgcggtca ttgccagct                                     29

<210> SEQ ID NO 304
<211> LENGTH: 39
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 304
cacacagctc ttccttttta tgaagcacca gacatcaac                              39

<210> SEQ ID NO 305
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
cacacagctc ttccttttta gtgatggtgg tgatggtgtg aagcaccaga catcaacccc       60
aacg                                                                    64

<210> SEQ ID NO 306
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
cacacagctc ttctagaatg ggttccgtta gtaggga                                37

<210> SEQ ID NO 307
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
caaatccttg atgacagaga tctgccagga                                        30

<210> SEQ ID NO 308
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
gctgggactt tgtcgctgcc gttgctcaag ctggat                                 36

<210> SEQ ID NO 309
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
actgctccta ctttctcgaa cttatagagc ccttg                                  35

<210> SEQ ID NO 310
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 310
atatccgacg atgagtctgt                                                 20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
atggacaatg ggacccgaga                                                 20

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
ggacttcttg caccgctacg                                                 20

<210> SEQ ID NO 313
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
cacacagctc ttccttttca cgccatttgt tgaagcaaag                           40

<210> SEQ ID NO 314
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
cacacagctc ttccttttca gtgatggtgg tgatggtgcg ccatttgttg aagca          55

<210> SEQ ID NO 315
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
gattactgca gcagtattag tcttc                                           25

<210> SEQ ID NO 316
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 316
gtcgaaaact tcatcggcaa ag                                                   22

<210> SEQ ID NO 317
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
cacgatatta tcgccacata cttc                                                 24

<210> SEQ ID NO 318
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
cgggacgatc gagatcgtgg atacg                                                25

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
caggatatta tcgccacata catc                                                 24

<210> SEQ ID NO 320
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
ctggacgatt gagcgcttgg atacg                                                25

<210> SEQ ID NO 321
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
cgtcttctcc atcgtttgcc caagag                                               26

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
ggtccctgac aaagttaccg agtg                                              24

<210> SEQ ID NO 323
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
cgtcttctcc atcgtttgct caggag                                            26

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
gatccaacac gacgttaccg agcg                                              24

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
ggtatgtcgt tgtgccagtg ttg                                               23

<210> SEQ ID NO 326
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
cccacgcttg ggttcttgga gtggtc                                            26

<210> SEQ ID NO 327
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
ggtatattgt tgtgcctgtg ttg                                               23

<210> SEQ ID NO 328
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
ccgacgcttg ggttcttgga gctgtc                                            26

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
ggaaggatga ggtggtgcag tac                                              23

<210> SEQ ID NO 330
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
gtcttgtgac aagtttggaa actc                                             24

<210> SEQ ID NO 331
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
gaaagaatga ggtggtgcaa tac                                              23

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
gtcctgtgac aagctaggga attc                                             24

<210> SEQ ID NO 333
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
ctatcgtggg atgtgatctg tgtcg                                            25

<210> SEQ ID NO 334
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
ctcgaatctc ttgacactga actcg                                            25

```
<210> SEQ ID NO 335
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
aacgacaaga ttagattggt tgaga                                        25

<210> SEQ ID NO 336
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
gtcgagtttg aagtgtgtgt ctaag                                        25

<210> SEQ ID NO 337
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
agatctcata tggctccatt tttgcccgac caggtcgact acaaacacgt c           51

<210> SEQ ID NO 338
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
atctggatcc tcattactac aacttggctt tggtcttcaa ggagtctgcc aaacctaac   59

<210> SEQ ID NO 339
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
acatctggat cctcattact acaacttggc cttggtct                          38

<210> SEQ ID NO 340
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
cacacagctc ttctagaatg gctccatttt tgcccgacca ggtcgac                47

<210> SEQ ID NO 341
<211> LENGTH: 50
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
cacacagctc ttcctttcta caacttggct ttggtcttca aggagtctgc                50

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
gtctactgat tcccctttgt c                                               21

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
ttctcgttgt acccgtcgca                                                 20

<210> SEQ ID NO 344
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
cacacacata tgcgacgggt acaacgagaa tt                                   32

<210> SEQ ID NO 345
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
cacacaacgc gtagacgaag ccgttcttca ag                                   32

<210> SEQ ID NO 346
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
atgatctgcc atgccgaact c                                               21

<210> SEQ ID NO 347
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 347
agcgagttcg gcatggcaga tcatcatg                                          28

<210> SEQ ID NO 348
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
cacacactgc agttgtccaa tgtaataatt tt                                     32

<210> SEQ ID NO 349
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
cacacatcta gacccgggct cttcttctga ataggcaatt gataaactta cttatc          56

<210> SEQ ID NO 350
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
gagcccgggt ctagatgtgt gctcttccaa agtacggtgt tgttgaca                   48

<210> SEQ ID NO 351
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
cacacacata tgaattctgt actggtagag ctaaatt                                37

<210> SEQ ID NO 352
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
gagctccaat tgtaatattt cggg                                              24

<210> SEQ ID NO 353
<211> LENGTH: 25
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 353
gtcgacctaa attcgcaact atcaa                                             25

<210> SEQ ID NO 354
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
gaattcacat ggctaatttg gcctcggttc cacaacgcac tcagcattaa aaa              53

<210> SEQ ID NO 355
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
gagctcccct gcaaacaggg aaacacttgt catctgattt                             40

<210> SEQ ID NO 356
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
cacctcgctc ttccagctgt catgtctatt caatgcttcg a                           41

<210> SEQ ID NO 357
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
cacacagcat gctaatgttt atatcgttga cggtgaaa                               38

<210> SEQ ID NO 358
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
cacaaagcgg aagagcaaat tttgtattct cagtaggatt tcatc                       45

<210> SEQ ID NO 359
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 359
cacacagcat gcaaacttaa gggtgttgta gatatccc                                    38

<210> SEQ ID NO 360
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
cacacacccg ggatcgacag tcgattacgt aatccatatt attt                             44

<210> SEQ ID NO 361
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
cacacagcat gcaaacttaa gggtgttgta gatatccc                                    38

<210> SEQ ID NO 362
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
cacacagagc tcacagtcga ttacgtaatc cat                                         33

<210> SEQ ID NO 363
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
cacatctaga gcatgcaaac ttaagggtgt tgta                                        34

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
ttaatgcctt ctcaagacaa                                                        20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
```

```
ggttttccca gtcacgacgt                                              20

<210> SEQ ID NO 366
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
ccttgctaat tttcttctgt atagc                                        25

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
ttctcgttgt acccgtcgca                                              20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
cacacaactt cagagttgcc                                              20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
tcgccacctc tgacttgagc                                              20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
aattgaacat cagaagagga                                              20

<210> SEQ ID NO 371
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
cctgaaattt ccaaatggtg tctaa                                        25
```

```
<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372 tttttttgtgc gcaagtacac                                              20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
caacttgacg tgagaaacct                                               20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
agatgctcgt tttacaccct                                               20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
acacagcttt gatgttctct                                               20

<210> SEQ ID NO 376
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
gatattattc caccttccct tcatt                                         25

<210> SEQ ID NO 377
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
ccgttaaaca aaaatcagtc tgtaaa                                        26

<210> SEQ ID NO 378
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
atgtccgacg acgagatagc aggaatagtc at                                     32

<210> SEQ ID NO 379
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
tcagaagagt aaatacaacg cactaaccaa gct                                    33

<210> SEQ ID NO 380
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
atgctgaaga gaaagagaca actcgacaag                                        30

<210> SEQ ID NO 381
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
gtggttatcg gactctacat aatgtcaacg                                        30

<210> SEQ ID NO 382
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
atgactcagg actataaaga cgatagtcct acgtccactg agttg                       45

<210> SEQ ID NO 383
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
ctattctaca atgtttaatt caacatcacc gtagccaaac ct                          42

<210> SEQ ID NO 384
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 384
atgtcgtctt taaagaacag aaaatc                                          26

<210> SEQ ID NO 385
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
ttataaattt atggcctcta ctatttct                                        28

<210> SEQ ID NO 386
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
cctacttcca cagctttaat ctactatcat                                      30

<210> SEQ ID NO 387
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
tttaagaaaa caactaagag aagccac                                         27

<210> SEQ ID NO 388
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
gatattattc caccttccct tcatt                                           25

<210> SEQ ID NO 389
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
ccgttaaaca aaaatcagtc tgtaaa                                          26

<210> SEQ ID NO 390
<211> LENGTH: 24
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 390
tgccatcctt ggtagtcagt tatt                                            24

<210> SEQ ID NO 391
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
ccgaaacaac cgtagatacc tttaatggct tgtccttggt gttga                     45

<210> SEQ ID NO 392
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
tcaacaccaa ggacaagcca ttaaaggtat ctacggttgt ttcgg                     45

<210> SEQ ID NO 393
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
tcctcgtcca tcttcaacaa gtcggtaccg agctctgcga att                       43

<210> SEQ ID NO 394
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
aattcgcaga gctcggtacc gacttgttga agatggacga gga                       43

<210> SEQ ID NO 395
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
tgtcgccatt caaccagtag at                                              22

<210> SEQ ID NO 396
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 396
ttgatccact gtcttaagat tgtcaa                                          26

<210> SEQ ID NO 397
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
ccgaaacaac cgtagatacc tttaaccaga acgaagtagc ggagaat                   47

<210> SEQ ID NO 398
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
attctccgct acttcgttct ggttaaaggt atctacggtt gtttcgg                   47

<210> SEQ ID NO 399
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
cgacagacct caccgacgta tggtaccgag ctctgcgaat t                         41

<210> SEQ ID NO 400
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
aattcgcaga gctcggtacc atacgtcggt gaggtctgtc g                         41

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
aggattttgc tgttggtggc                                                 20
```